United States Patent
Nacro

(10) Patent No.: US 10,280,168 B2
(45) Date of Patent: May 7, 2019

(54) BICYCLIC HETEROARYL DERIVATIVES AS MNK1 AND MNK2 MODULATORS AND USES THEREOF

(71) Applicant: Agency for Science, Technology and Research, Singapore (SG)

(72) Inventor: Kassoum Nacro, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 79 days.

(21) Appl. No.: 14/517,415

(22) Filed: Oct. 17, 2014

(65) Prior Publication Data

US 2015/0038506 A1    Feb. 5, 2015

Related U.S. Application Data

(63) Continuation-in-part of application No. 14/363,718, filed as application No. PCT/SG2013/000126 on Apr. 1, 2013, now Pat. No. 9,908,886.

(30) Foreign Application Priority Data

Mar. 30, 2012  (GB) .................................. 1205669.3

(51) Int. Cl.
| | |
|---|---|
| C07D 487/04 | (2006.01) |
| C07D 235/04 | (2006.01) |
| C07D 471/10 | (2006.01) |
| C07D 471/04 | (2006.01) |
| A61K 31/535 | (2006.01) |

(52) U.S. Cl.
CPC ......... *C07D 487/04* (2013.01); *C07D 235/04* (2013.01); *C07D 471/04* (2013.01); *C07D 471/10* (2013.01)

(58) Field of Classification Search
None
See application file for complete search history.

(56) References Cited

U.S. PATENT DOCUMENTS

| | | | |
|---|---|---|---|
| 9,908,886 | B2 | 3/2018 | Nacro et al. |
| 2012/0058997 | A1 | 3/2012 | Xu et al. |
| 2013/0029964 | A1 | 1/2013 | Aoki et al. |
| 2014/0256733 | A1 | 9/2014 | Goodfellow et al. |
| 2014/0371199 | A1 | 12/2014 | Nacro et al. |
| 2018/0208600 | A1 | 7/2018 | Nacro et al. |

FOREIGN PATENT DOCUMENTS

| | | |
|---|---|---|
| CN | 101454325 A | 6/2009 |
| CN | 101472912 A | 7/2009 |
| CN | 101600718 A | 12/2009 |
| CN | 101678026 A | 3/2010 |
| CN | 101679408 A | 3/2010 |
| EP | 1 746 099 A1 | 1/2007 |
| JP | 2009-502734 A | 1/2009 |
| JP | 2010-509242 A | 3/2010 |
| JP | 2010-526795 A | 8/2010 |
| JP | 2011-500623 A | 1/2011 |
| WO | WO 2007/025090 A2 | 3/2007 |
| WO | WO 2008/058126 * | 5/2008 |
| WO | WO 2008/078091 A1 | 7/2008 |
| WO | WO 2008/138889 A2 | 11/2008 |
| WO | WO 2010/055072 A2 | 5/2010 |
| WO | WO 2011/022439 A1 | 2/2011 |
| WO | WO 2011/104337 A1 | 9/2011 |
| WO | WO 2011/136264 A1 | 11/2011 |
| WO | WO 2012/013713 A2 | 2/2012 |
| WO | WO 2013/147711 A1 | 10/2013 |

OTHER PUBLICATIONS

Matthews et al. Design and evaluation of 3,6-di(hetero)aryl imidazo[1,2-a]pyrazines as inhibitors of checkpoint and other kinases. Bioorg. Med. Chem. Letters 20, pp. 4045-4049 (2010).*
Chinese Office Action, dated Oct. 16, 2015, in connection with Application No. 201380027654.7.
Extended European Search Report, dated Oct. 16, 2015, in connection with European Application No. 13768800.8.
International Search Report and Written Opinion, dated May 30, 2013, in connection with Application No. PCT/SG2013/000126.
International Preliminary Report on Patentability, completed May 15, 2014, in connection with Application No. PCT/SG2013/000126.
[No Author Listed], CAS RN 1022885-04-6. STN entry date May 27, 2008.
[No Author Listed], CAS RN 1134720-44-7. STN entry date Apr. 15, 2009.
[No Author Listed], CAS RN 1263282-04-7. STN entry date Feb. 21, 2011.
[No Author Listed], NCBI. Substance Record for SID 5446061. Entered Sep. 11, 2005. http://pubchem.ncbi.nlm.nhi.gov/substance/5446061. Last accessed on May 10, 2015. 5 pages.
Caballero et al., Docking and quantitative structure-activity relationship studies for imidazo[1,2-a]pyrazines as inhibitors of checkpoint kinase-1. Med Chem Res. Aug. 2012;21(8):1912-1920.
El Akkaoui et al., Direct Arylation of Imidazo[1,2-b]pyridazines: Microwave-Assisted One-Pot Suzuki Coupling/Pd-Catalysed Arylation. Eur J Org Chem. 2010;2010:862-871.

(Continued)

*Primary Examiner* — Jeffrey S Lundgren
*Assistant Examiner* — Michael J Schmitt
(74) *Attorney, Agent, or Firm* — Wolf, Greenfield & Sacks, P.C.

(57) ABSTRACT

The present invention relates to certain compounds (e.g., imidazopyrazine, imidazopyridine, imidazopyridazine and imidazopyrimidine compounds) that act as inhibitors of the MAP kinase interacting kinases MNK2a, MNK2b, MNK1a, and MNK1b. The present invention further relates to pharmaceutical compositions comprising these compounds, and to the use of the compounds for the preparation of a medicament for the prophylaxis and treatment of diseases (e.g., proliferative diseases (e.g., cancer), neurodegenerative diseases (e.g., Alzheimer's disease), metabolic diseases (e.g. diabetes), neurodevelopmental disorders (e.g. autism), or psychiatric disorders (e.g. schizophrenia or anxiety)) as well as methods of treating these diseases.

18 Claims, 8 Drawing Sheets

(56) References Cited

OTHER PUBLICATIONS

Kim et al., Design and Synthesis of Imidazopyridine Analogues as Inhibitors of Phosphoinositide 3-Kinase Signaling and Angiogenesis. J Med Chem. Mar. 2011;54(7):2455-2466.

Matthews et al., Design and evaluation of 3,6-di(hetero)aryl imidazo[1,2-a]pyrazines as inhibitors of checkpoint and other kinases. Bioorganic & Medicinal Chemistry Letters. Jul. 2010;20(14):4045-4049.

Wang et al., Inhibition of mammalian target of rapamycin induces phosphatidylinositol 3-kinase-dependent and Mnk-mediated eukaryotic translation initiation factor 4E phosphorylation. Mol Cell Biol. Nov. 2007;27(21):7405-13. Epub Aug. 27, 2007.

Zaki et al., The synthesis of imidazo[4,5-d]pyridines from a substituted imidazole and acyl or sulfonyl acetonitrile. Tetrahedron. Apr. 2007;63(18):3745-3753.

Singapore Written Opinion for Singapore Application No. SG 11201406207P dated Jul. 3, 2015.

Singapore Written Opinion for Singapore Application No. SG 11201406207P dated Nov. 20, 2015.

Singapore Written Opinion for Singapore Application No. SG 11201406207P dated Aug. 10, 2016.

Singapore Written Opinion for Singapore Application No. SG 11201406207P dated Jan. 23, 2017.

Singapore Examination Report for Singapore Application No. SG 11201406207P dated Jun. 9, 2017.

[No Author Listed], PubChem SID 5446061. Deposit Date Sep. 11, 2005. Accessed at www.pubchem.ncbi.nlm.nih.gov/substance/5446061#section=Identity.

Australian Examination Report dated Sep. 3, 2018 in connection with Australian Application No. 2017219039.

Extended European Search Report for European Application No. 17179630.3, dated Mar. 9, 2018.

Japanese Office Actoin dated Oct. 25, 2016 for Japanese Application No. 2015-503165.

Mohamed et al., Synthesis of some new pyridines, fused pyrimidines, and fused 1,2,4-triazines. J Heterocyclic Chem. May 2010;47:517-23.

[No Author Listed] CAS RN 1084951-22-3. STN entry date Dec. 15, 2008.

[No Author Listed] CAS RN 1268454-15-4. STN entry date Mar. 15, 2011.

\* cited by examiner

BICYCLIC HETEROARYL DERIVATIVES AS MNK1 AND MNK2 MODULATORS AND USES THEREOF

CROSS-REFERENCE TO RELATED APPLICATIONS

The present application is a continuation-in-part of and claims priority under 35 U.S.C. § 120 to U.S. Patent Application, U.S. Ser. No. 14/363,718, filed Jun. 6, 2014, which is a national stage filing under 35 U.S.C. § 371 of international PCT application, PCT/SG2013/000126, filed Apr. 1, 2013, which claims priority to British Patent Application No. 1205669.3, filed Mar. 30, 2012, each of which is incorporated herein by reference.

BACKGROUND OF THE INVENTION

The human MAP Kinase-interacting kinases, also known as MAP Kinase signal-integrating kinases, (MNKs[1]), are ubiquitously expressed protein-serine/threonine kinases that are directly activated by ERK or p38 MAP kinases.[2;3] They comprise a group of four proteins derived from two genes (gene symbols: MKNK1 and MKNK2) by alternative splicing. MNK1a/b and MNK2a/b proteins differ at their C-termini, in each case the a-form possessing a longer C-terminal region than the b-form which lacks the MAP Kinase-binding region. The N-termini of all forms contain a polybasic region which binds Importin α and the translation factor scaffold protein eukaryotic Initiation Factor (eIF4G). The catalytic domains of MNK1a/b and MNK2a/b share three unusual features, two short inserts and a DFD tripeptide feature where other kinases have DFG. Mnk isoforms differ markedly in their activity, regulation, and in subcellular localization. The best-characterized MNK substrate is eIF4E. Although the cellular role of eIF4E phosphorylation remains unclear, it may promote export of a defined set of mRNAs from the nucleus. Other Mnk substrates bind to AU-rich elements that modulate the stability/translation of specific mRNAs.[1] MNK1 is highly expressed in hematological malignancies[4;5] and both MNK1 and MNK2 are up-regulated in solid tumors such as gliomas and ovarian cancers.[6;7]

The Eukaryotic Initiation Factor-4 E (eIF4E) regulates the expression of genes involved in proliferation and survival as a cap dependent mRNA translation and mRNA export factor. eIF4E is dysregulated in several human cancers, including breast,[10] prostate,[11] and some leukemias,[12] and elevated levels of eIF4E are a marker of poor prognosis[12;13]. Moreover, overexpression and dysregulation of eIF4E leads to an increased tumor number, invasion, and metastases in mouse models[13] and transgenic expression of eIF4E leads to a variety of cancers.[13;14]

Overexpression of eIF4E results in a specific increase in the translation of these weakly competitive mRNAs, many of which encode products that stimulate cell growth and angiogenesis, e.g., fibroblast growth factor 2 and vascular endothelial growth factor,[15-17] cyclin D1,[18] and ribonucleotide reductase.[19] Several lines of evidence support the key role that eIF4E plays in cancer development and/or progression. First, overexpression of eIF4E can cause neoplastic transformation of cells or accentuate neoplastic features.[20;21] Second, reducing eIF4E with antisense RNA or reducing its function by overexpression of the inhibitory 4E-BP proteins can suppress the oncogenic properties of many cell lines.[10;22;23] Third, increased expression of eIF4E found in the most classes of solid tumors. These include bladder,[24] breast,[25;26] cervical,[27] head and neck,[28-30] and prostate tumors.[31] Finally, both the expression and activity of eIF4E are regulated at multiple levels by growth factors and oncogenes,[32] suggesting that the protein is a nexus of converging transformation signaling pathways. In addition, there is substantial evidence for de-regulated eIF4E function in neurodevelopmental and psychiatric disorders such as autism, FragileX syndrome and schizophrenia. Mutations in eIF4E and the 4E-BP protein CYFIP1 are associated with autism-spectrum disorders and schizophrenia[76-78] and transgenic expression of eIF4E in mice results in autism-related behavioral deficits[70]. Similarly, loss of 4E-BP2 or CYFIP1 is associated with autism-related phenotypes in mice[71-72].

eIF4E is phosphorylated by the MNK1/2 serine/threonine kinases in response to activation by mitogenic and stress signals downstream of ERK1/2 and p38 MAP kinase respectively.[2;3] eIF4E phosphorylation at serine 209 by MNK1/2 is required to promote its transformation activity.[33;34] Surprisingly, MNK1/2 double knock-out mice do not have any apparent phenotype,[35] calling into question whether phosphorylation by MNK has any impact on the functionality of the mammalian eIF4E.[36] Nevertheless, MNK phosphorylation of eIF4E on Ser-209 is believed to be critical to eIF4E oncogenic activity.[34]

Thus, inhibitors of MNK1/2, by preventing the phosphorylation of eIF4E could provide a viable therapeutic approach in high-eIF4E dependent cancers, neurodevelopmental disorders, and psychiatric disorders.

Studies have shown that overexpression of eIF4E, as well as eIF4E phosphorylation, promote cancer cell survival, at least in part through the elevation of the anti-apoptotic protein Mcl-1.[34] Mcl-1 is a Bcl2 family member with a very short half-life, and Mcl-1 mRNA translation highly depends on eIF4E. Thus, it is possible that the inhibition of eIF4E phosphorylation by Mnk might induce the death tumor cells, as shown for Myc-induced lymphoma.[34]

Blast crisis chronic myeloid leukemia (BC-CML) is characterized by an expansion of a population of granulocyte macrophage progenitor-like cells (GMPs) that have acquired self-renewal capacity,[37] a feature not seen in normal or chronic phase (CP) GMPs. The ability to self-renew is thought to be mediated by β-catenin activation, and may contribute to disease persistence, as well as activity as a reservoir for drug resistance. The mechanisms contributing to β-catenin activation remain obscure, and will need to be identified to improve the control of BC-CML. The role of the translation machinery in mediating β-catenin-mediated self-renewal was investigated, since prior work had implicated aberrant mRNA translation in drug-resistance and BC pathophysiology.[38-40] Using immunofluorescence (IF), it was confirmed that BC-GMPs have activated nuclear beta-catenin compared to GMPs isolated from normal cord blood, and that this was associated with increased eIF4E expression and phosphorylation at Ser209. Trough biochemical and genetic approaches in CML cell lines (K562 and KCL22), it was demonstrated that eIF4E overexpression was sufficient to increase beta-catenin activity (as measured by immunofluorescence for nuclear beta-catenin, beta-catenin reporter assays, and expression of beta-catenin-regulated genes). By expressing phospho-mutant forms of eIF4E (S209A, S209D), it was found that the increase in beta-catenin transcriptional activity is dependent on phosphorylation of at Ser209. In line with these observations, siRNA-mediated knockdown or inhibition of the MNK1/2 kinases (which mediate in vivo eIF4E phosphorylation) with small molecules prevented the increased beta-catenin activity induced by eIF4E overexpression. Mechanistically, eIF4E activates beta-catenin signaling via a two-step mechanism. First, eIF4E overexpression increased total cell beta-catenin and secondly, eIF4E phosphorylation facilitated beta-catenin nuclear translocation. The latter step was associated with increased beta-catenin phosphorylation at Ser552, a site known to be involved in nuclear translocation, and directly regulated by AKT. Consistent with this model, siRNA-mediated knockdown or small molecule inhibition of AKT (AKT inhibitor IV) prevented eIF4E-mediated increases in beta-catenin transcriptional activity. The importance of eIF4E phosphorylation on beta-catenin activation and the self-renewal capacity of primary BC GMPs cells was assessed. Treatment with CGP57380, but not imatinib or dasatinib, inhibited eIF4E phosphorylation, as well as prevents accumulation of active nuclear beta-catenin in BC GMPs. The effect of MNK1/2 inhibition was evaluated on the stem cell function of BC cells using both in vitro and in vivo assays. In an in vitro serial replating assay, it was shown that CGP57380 impaired the ability of CD34+ BC cells (including those carrying T315I mutation), but not normal CD34+ cells, to serially replate for more than 8 weeks in methylcellulose. Interestingly, treatment with either imatinib or dasatinib only partially impaired the ability of BC-CML to serially replate. In vitro treatment of BC CD34+ CML cells, but not normal cord blood CD34+ cells, with CGP57380 retarded their ability to engraft NSG mice. Finally, in vivo serial transplantation assay for assessing the leukemia stem cell (LSC) function of patient-derived BC-GMPs was developed. BC GMPs or BC CD34+ CML cells were injected intrafemorally into 8- to 10-week old sublethally irradiated NSG mice. Following engraftment, mice were treated with vehicle, CGP53780 (40 mg/kg/d), or dasatinib (5 mg/kg/d) for three consecutive weeks. Following treatment, human CD34+ cells were isolated from the mice, and transplanted into a second recipient mouse. At 16 weeks, it was found that in vivo treatment with CGP57380, but not dasatinib, prevented BC cells from serially transplanting NSG mice. In summary, these results demonstrate that: 1. eIF4E is overexpressed and phosphorylated at Ser209 in BC, but not in normal GMPs; 2. eIF4E phosphorylation activates beta-catenin signalling in BC GMPs; 3. MNK inhibition prevents eIF4E phosphorylation and beta-catenin signalling in BC GMPs; and 4. MNK inhibition prevents BC GMPs from functioning as leukemia stem cells. These studies suggest that pharmacologic inhibition of the MNK1/2 kinases may be therapeutically useful in BC CML.

The level of expression of eIF4E and the degree of eIF4E phosphorylation is regulated by pathways that include the P38 kinase, MAPK kinase and AKT/mTOR pathways[41] as shown in FIG. 4. Inhibitors of mTOR such as rapamycin, decrease the level of phosphorylated eIF4E.[42] mTOR inhibitors, as single agents, have proven efficacious in several cancer types such as transplant-associated lymphoma[43;44] and Kaposi sarcoma,[45;46] tuberous sclerosis-related astrocytoma,[47] and mantle cell and other non-Hodgkin lymphomas.[48] Two mTOR inhibitors are currently marketed for the treatment of the renal cell carcinoma.[49;50]

Inhibition of mTOR by rapamycin also suppresses mTOR catalyzed phosphorylation of EBP1 leading to an increased level eIF4E-EBP1. Consequently, rapamycin inhibits translation initiation by decreasing the phosphorylation of eIF4E-binding proteins, thus decreasing eIF4E availability to the initiation complex.

The treatment with rapalogs typically leads to the clinically stable disease or partial remission rather than the tumor elimination.[51] This suboptimal drug effect is likely due at least in part to the cytostatic rather than cytotoxic properties of the mTORC1 inhibitors. Therefore, there is a potential for a drug combination therapy that ideally would culminate in the complete remission of the cancer. However, most of the attempts to combine mTORC1 inhibitors with other drugs, typically the standard chemotherapeutic agents targeting DNA replication, have been disappointing, on occasion even leading to drug antagonism. Preclinical studies of mTOR combined with cis-platin[52] or methotrexate[53] show the most promise.

Combination therapy with MNK1/2 and mTOR kinases inhibitors could be a viable strategy to treat certain types of cancer.[54] WO 2010/055072 discloses MNK and mTOR combination therapy with small molecules, antibodies and siRNA for the treatment of cancer,[55] and recent findings support that MNK and mTOR combination induces apoptosis in cutaneous T cell lymphoma cells.[42]

Macrophages are major effectors of innate immunity, stimulated by a broad variety of bacterial products through specific TLRs on the cell surface to produce proinflammatory cytokines, such as TNF. E. coli LPS is a potent stimulus to macrophage gene expression, especially TNF, by engaging the TLR4 membrane signaling complex.[56] It was shown that TLR signaling pathways require Mnk expression through the use of a panel of commercial TLR agonist panel on macrophage. TNF production was increased as a response to Salmonella LPS (TLR4), ODN2006 (TLR9), HKLM (TLR2), FSL (TLR6/2) and imiquimod (TLR7) stimulation. In each case the production of TNF was inhibited by MNK kinases inhibitor CGP57380 in a dose dependant fashion[57] and the release of multiple innate proinflammatory cytokines were affected, supporting a central role for MNK in inflammation.[58]

It is reported that heterogeneous nuclear ribonucleoprotein A1 (hnRNPA1) when phosphorylated by MNK1/2 accumulates in the cytoplasmic stress granules (SGs) under stress related conditions. hnRNPA1 exit the nucleus bound to poly(A) mRNA and this complex is required for hnRNPA1 phosphorylation by MNK1/2 and for its relocalization to the cytoplasmic SGs. Phosphorylation of hnRNPA1 by MNK1/2 reduces its binding affinity to 3'UTR mRNA and consequently Mnk inhibition enhances hnRNAPA1 association with TNF mRNA. TNF gene transcript level is undetectable in unstimulated T Cell and greatly increased upon stimulation. MNK inhibition effect on TNF appears to be more at the translation level as MNK inhibition has no influence on the level of TNF mRNA.[59] Moreover, the formation of SG is reported to be prevented by MNK inhibition[60] thus removing the protection that was offered by the SGs where the phosphorylated hnRNPA1 bound mRNA could localize.

MNK inhibitors can regulate the innate immune response in macrophage. A compound with anti inflammatory properties will inhibit the release of pro-inflammatory cytokines.

It has been shown that CGP57380, a Mnk inhibitor, inhibits the release of TNF alpha by macrophage[61] (and not eIF4E). According to WO2005/003785 MNK kinases are promising targets for anti-inflammatory therapy.

MNK1/2 were also reported to phosphorylate a number of different proteins in addition to eIF4E. Three of these are hnRNPA1,[60] cPLA2 and Sprouty2.[62;63] Their role and function is still being investigated. Among these substrates, hnRNPA1 is overexpressed in colorectal cancer and it could contribute to maintenance of telomere repeats in cancer cells with enhanced cell proliferation.[64] It is also reported that the expression levels of hnRNPA/B is deregulated in non small cell lung cancer.[65]

MNK inhibitors are potentially useful in the treatment of cancers including breast,[66] protate,[11] hematological malignancies (e.g., CML, AML), head and neck, colon,[67] bladder, prostatic adenocarcinoma, lung, cervical, and lymphomas.[68;68;69]

SUMMARY OF THE INVENTION

In one aspect, the present invention relates to compounds that act as kinase inhibitors, in particular as inhibitors of the MAP kinase interacting kinases 1 and 2 (MNK1 and MNK2). In certain embodiments, a compound of the present invention is of Formula (I):

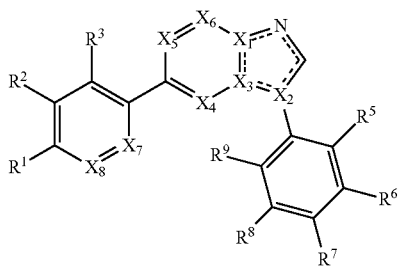

(I)

or a pharmaceutically acceptable form thereof, wherein $R^1$, $R^2$, $R^3$, $R^5$, $R^6$, $R^7$, $R^8$, $R^9$, $X_1$, $X_2$, $X_3$, $X_4$, $X_5$, $X_6$, $X_7$, and $X_8$ are as described herein.

In another aspect, the present invention relates to pharmaceutical compositions comprising these compounds and to their use for the preparation of a medicament for the prophylaxis and treatment diseases associated with a dysfunction linked to MNK1 and MNK2 pathway, where MNK1 and MNK2 play a role (MNK overexpression, eIF4E overexpression, P38 MAPK kinase pathway). The invention provides methods of treating proliferative diseases, neurodegenerative diseases, metabolic disorders, neurodevelopmental disorders, or psychiatric disorders with the compounds provided herein. In certain embodiments, the proliferative disease is cancer (e.g. blood and solid tumors). In certain embodiments, the proliferative disease is an inflammatory condition. In certain embodiments, neurodegenerative disease is Alzheimer's disease. In certain embodiments, the metabolic disorder is obesity or diabetes. In certain embodiments, the neurodevelopmental disorder is autism, FragileX Syndrome, neurofibromatosis, tuberous sclerosis complex, or Rett's Syndrome. In certain embodiments, the psychiatric disorder is schizophrenia or anxiety. In certain embodiments, the provided treatment comprises combination of the compounds provided herein with one or more additional agents. In some embodiments, an additional agent is a kinase inhibitor. In some embodiments, an additional agent is an mTOR inhibitor. Exemplary mTOR inhibitors include sirolimus, temsirolimus, everolimus, and ridaforolimus. In some embodiments, an additional agent is a PI3-kinase inhibitor. Exemplary PI3-kinase inhibitors include wortmannin, demethoxyviridin, LY294002, perifosine, CAL101, PX-886, BEZ235, SF1126, INK1117, INK1197, IPI-145, GDC-0941, BKM120, XL147, XL765, palomid 529, GSK1059615, ZSTK474, PWT33597, IC87114, TG100-115, CAL263, PI-103, GNE-477, CUDC-907, GSK 2126458, GDC-0980, PF-46915032, CAL263, SF1126 and PX-886. In some embodiments, the PI3-kinase inhibitor inhibits PI3K-α, PI3K-β, PI3K-γ, and/or PI3K-δ.

In yet another aspect, the present invention describes methods for the synthesis and isolation of a compound of Formula (I), such as, for example, substituted 3,6-diphenylimidazo[1,2-a]pyridine; 3,6-diphenylimidazo[1,2-a]pyrazine; 3,6-diphenylimidazo[1,2-b]pyridazine; 3,5-diphenylpyrazolo[1,5-a]pyrimidine; 1,6-diphenyl-1H-imidazo[4,5-c]pyridine; or 1,6-diphenyl-1H-benzo[d]imidazole.

DEFINITIONS

Chemical Definitions

Figure 1:
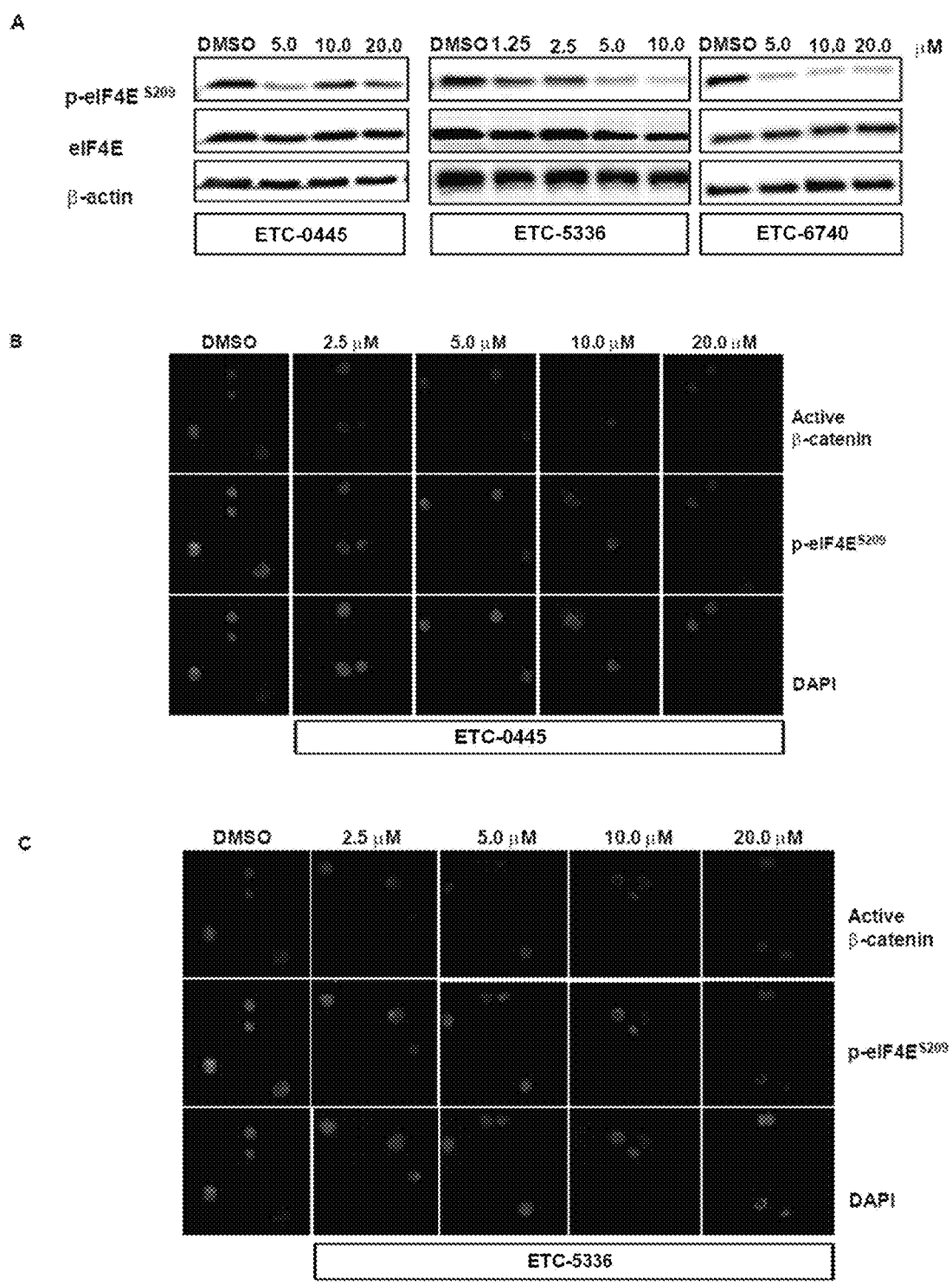
FIG. 1 demonstrates that Example 6 (ETC-10445-3), Example 1 (ETC-5336) and Example 2 (ETC-6740) prevent eIF4E phosphorylation in BC-CML cell lines and primary cells. (A) Western blot analysis of K562 cell lines treated with various concentrations of compounds for 24 h. (B-D) BC-CML cells were treated with various compounds for 48 h. 48 hours post drug treatment, cells were harvested for immunofluorescence analysis for nuclear active β-catenin and phosphor-eIF4E level.
Figure 1:
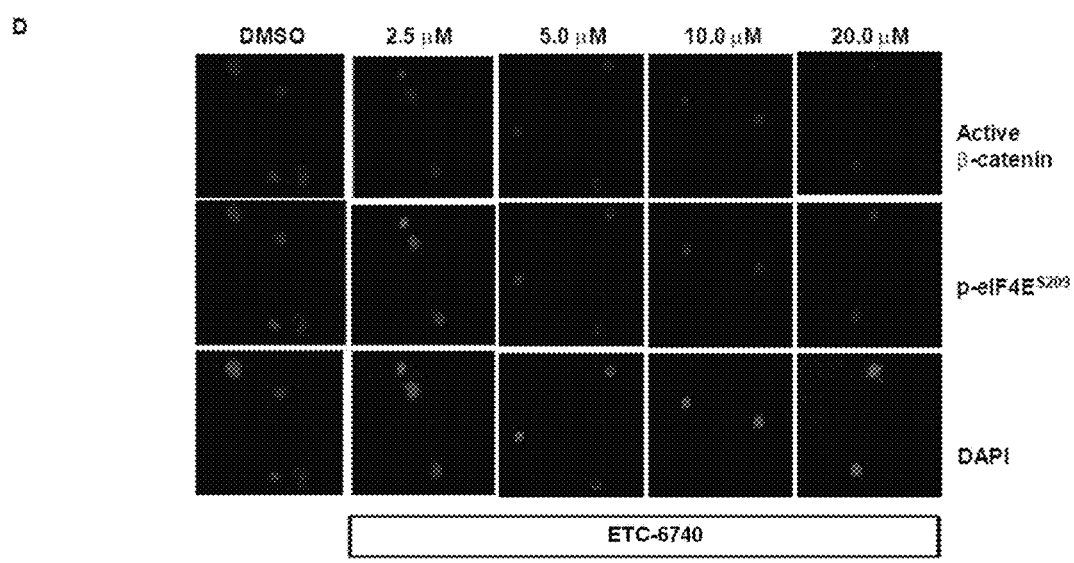

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

The term "aliphatic," as used herein, includes both saturated and unsaturated, nonaromatic, straight chain (i.e., unbranched), branched, acyclic, and cyclic (i.e., carbocyclic) hydrocarbons, and combinations thereof. In some embodiments, an aliphatic group is optionally substituted with one or more functional groups. As will be appreciated by one of ordinary skill in the art, "aliphatic" is intended herein to include, but is not limited to, alkyl, alkenyl, alkynyl, cycloalkyl, and cycloalkenyl moieties, and combinations thereof.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR)R$^{ee}$, —OC(=NR$^{ff}$) OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N (R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{1-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_6$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{aa}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6- chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

These and other exemplary substituents are described in more detail in the Detailed Description, Examples, and claims. The present invention is not intended to be limited in any manner by the above exemplary listing of substituents.

Other Definitions

The term "pharmaceutically acceptable form thereof" as used herein refers to pharmaceutically acceptable salts, solvates, hydrates, prodrugs, tautomers, isomers, enantiomers, diastereomers, and/or polymorphs of a compound of the present invention.

In certain embodiments, the pharmaceutically acceptable form is a pharmaceutically acceptable salt. The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate and aryl sulfonate.

In certain embodiments, the pharmaceutically acceptable form is a hydrate or solvate. The term "hydrate" as used herein refers to a compound non-covalently associated with one or more molecules of water. Likewise, the term "solvate" refers to a compound non-covalently associated with one or more molecules of an organic solvent.

In certain embodiments, the pharmaceutically acceptable form is a prodrug. The term "prodrug" as used herein refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. In recent years several types of bioreversible derivatives have been exploited for utilization in designing prodrugs. Using esters as a prodrug type for compounds containing a carboxyl or hydroxyl functionality is known in the art as described, for example, in *The Organic Chemistry of Drug Design and Drug Interaction* by Richard Silverman, published by Academic Press (1992).

In certain embodiments, the pharmaceutically acceptable form is a tautomer. The term "tautomer" as used herein includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

In certain embodiments, the pharmaceutically acceptable form is an isomer. The term "isomer" as used herein includes any and all geometric isomers and stereoisomers (e.g., enantiomers, diastereomers, etc.). For example, "isomer" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

In certain embodiments, the pharmaceutically acceptable form is a polymorph. The term "polymorph" as used herein refers to a crystalline compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys.

"Treat," "treating" and "treatment" encompasses an action that occurs while a subject is suffering from a condition (e.g., a "MNK1- or MNK2-related" disease, disorder, or condition, e.g., a disease, disorder, or condition in which MNK1 and/or MNK2 is known to play role) which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

As used herein "inhibition," "inhibiting," and "inhibit", refer to the ability of a compound to reduce, slow, halt or prevent activity of a particular biological process relative to vehicle. In certain embodiments, the biological process is in vitro (e.g., a biochemical or cellular assay). In certain embodiments, the biological process is in vivo.

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent. In some embodiments, a therapeutically effective amount is an amount effective to inhibit cell growth or induce cell death.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "kinase" represent transferase class enzymes that are able to transfer a phosphate group from a donor molecule to an acceptor molecule, e.g., an amino acid residue of a protein or a lipid molecule. Representative, non-limiting examples of kinases include Abl, ACK, Akt1/PKBα, Akt2/PKBβ, Akt3/PKBγ, ALK1, ALK2, Alk4, AMPKα1/β1/γ1, AMPKα1/β1/γ2, AMPKα1/β1/γ3, AMPKα1/β2/γ1, AMPKα2/β1/γ1, AMPKα2/β2/γ2, Abl2, ARKS, Ask1, Aurora A, Aurora B, Aurora C, Axl, BARK1, Blk, Bmx, B-Raf, Brk, BrSK1, BrSK2, Btk, CaMK1α, CaMK1β, CaMK1γ, CaMK1δ, CAMK2α, CaMK2β, CAMK2δ, CAMK2γ, CAMK4, CAMKK1, CAMKK2, CDK1, CDK2, CDK3, CDK4, CDK5, CDK6, CDK7, CDK9, CDK1/cyclin B, CDK2/cyclin A, CDK2/cyclin E, CDK3/cyclin E, CDK5/p25, CDK5/p35, CDK6/cyclinD3, CDK7/cyclin H/MAT1, CDK9/cyclin T1, CHK1, CHK2, CK1(γ), CK1δ, CK2α1, CK2α2, cKit, c-RAF, CLK1, CLK2, CLK3, COT, Csk, DAPK1, DAPK2, DAPK3, DCAMLK2, DDR2, DMPK, DRAK1, DYRK1A, DYRK2, DYRK3, eEF2K, EGFR, EPHA1, EPHA2, EPHA3, EPHA4, EPHA5, EPHA6, EPHA7, EPHA8, EphB1, EphB2, EphB3, EphB4, ErbB4, Erk1, Erk2, FAK, Fer, Fes, FGFR1, Flt2, Flt4, FLT3 D835Y, FGFR2, FGFR3, FGFR4, Fgr, Flt1, Flt3, Fms, FRK, FynA, GCK, GPRK5, GRK2, GRK4, GRK6, GRK7, GSK3α, GSK3β, Hck, HER2, HER4, HIPK1, HIPK2, HIPK3, HIPK4, IGF1R, IKKβ, IKKα, IKKε, IR, InsR, IRR, IRAK1, IRAK2, IRAK4, Itk, JAK2, JAK3, JNK1, JNK2, JNK3, KDR, KHS1, Kit, Lck, LIMK1, LKB1, LOK, LRRK2, Lyn A, Lyn B, MAPK1, MAPK2, MAPK12, MAPKAP-K2, MAPKAP-K3, MAPKAPK2, MAPKAPK3, MAPKAPK5, MARK1, MARK2, MARK3, MARK4, MELK, MEK1, MEK2, MEKK2, MEKK3, Mer, Met, MET M1250T, MINK, MKK4, MKK6, MKK7β, MLCK, MLK1, MLK3, MNK1, MNK2, MRCKα, MRCKβ, MSK1, MSK2, MSSK1, STK23, STK4, STK3, STK24, MST1, MST2, MST3, MST4, MUSK, mTOR, MYO3β, MYT1, NDR1, NEK11, NEK2, NEK3, NEK6, NEK7, NEK9, NLK, NUAK2, p38α, p38β, p38δ, p38γ, p70S6K, S6K, SRK, PAK1/CDC42, PAK2, PAK3, PAK4, PAK5, PAK6, PAR-1Bα, PASK, PBK, PDGFRα, PDGFRβ, PDK1, PEK, PHKG2, PI3Kα, PI3Kβ, PI3Kγ, PI3Kδ, Pim1, Pim2, PKAcα, PKAcβ, PKAcγ, PKA(b), PKA, PKBα, PKBβ, PKBγ, PKCα, PKCβ1, PKCβ2, PKCβ11, PKCδ, PKCε, PKCγ, PKCμ, PKCη, PKCι, PKCθ, PKCζ, PKD1, PKD2, PKD3, PKG1α, PKG1B, PKN1, PKN2, PKR, PLK1, PLK2, PLK3, PLK4, Polo, PRAK, PRK2, PrKX, PTK5, PYK2, QIK, Raf1, Ret, RIPK2, RIPK5, ROCK1, ROCK2, RON, ROS, Rse, RSK1, RSK2, RSK3, RSK4, SAPK2a, SAPK2b, SAPK3, SAPK4, SGK1, SGK2, SGK3, SIK, MLCK, SLK, Snk, Src, SRPK1, SRPK2, STK33, SYK, TAK1-TAB1, TAK1, TBK1, TAO1, TAO2, TAO3, TBK1, TEC, TESK1, TGFβR1, TGFβR2, Tie2, TLK2, TrkA, TrkB, TrkC, TSSK1, TSSK2, TTK, TXK, TYK2, TYRO3, ULK1, ULK2, WEE1, WNK2, WNK3, Yes1, YSK1, ZAK, ZAP70, ZC3, and ZIPK.

As used herein, the term "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

As used herein, the term "neurodegenerative diseases" refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease.

As used herein, the term "neurodevelopmental disorder" refers to impairments of the growth and development of the brain or central nervous system. A neurodevelopmental disorder also refers to a disorder of brain function that affects emotion, learning ability, self-control and memory and that unfolds as the individual grows. Disorders considered neurodevelopmental in origin, or that have neurodevelopmental consequences when they occur in infancy and childhood include, but are not limited to autism and autism spectrum disorders (e.g. Asperger syndrome or Mendelsohnn's Syndrome), fetal alcohol spectrum disorder, motor disorders (e.g. developmental coordination disorder, stereotypic movement disorder and the tic disorders including Tourette syndrome), traumatic brain injury (e.g. congenital injuries), genetic disorders (e.g. fragile-X syndrome, Neurofibromatosis, Tuberous Sclerosis, Rett's Syndrome, Timothy Syndrome, PTEN mutations, or Tourettes), Down syndrome, communication, speech and language disorders, eating disorders (e.g., anorexia nervosa and bulimia nervosa), adjustment disorder, attention-deficit/hyperactivity disorder, conduct disorder, oppositional defiant disorder, delirium, dementia, multi-infarct dementia, learning and memory disorders (e.g., amnesia and age-related memory loss). In certain embodiments, the neurodevelopmental disorder is autism, FragileX Syndrome, neurofibromatosis, tuberous sclerosis complex, or Rett's Syndrom.

As used herein, the term "psychiatric disorder," also called mental illness or mental disorder, refers to a mental or behavioral pattern or anomaly that causes either one suffering or an impaired ability to function in ordinary life (disability), and which is not developmentally or socially normative. Mental disorders are generally defined by a combination of how a person feels, acts, thinks or perceives. This may be associated with particular regions or functions of the brain or rest of the nervous system, often in a social context. As listed in the Diagnostic and Statistical Manual of Mental Disorders-Fourth Edition (DSM-IV), published by the American Psychiatric Association, Washington D. C. (1994), exemplary psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence). In certain embodiments, the psychiatric disorder is schizophrenia or anxiety.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type 1 diabetes, type 2 diabetes, gestational diabetes), hyperglycemia, hyperinsulinemia, insulin resistance, and obesity.

DETAILED DESCRIPTION OF CERTAIN EMBODIMENTS

In one aspect, the present invention provides a compound of Formula (I):

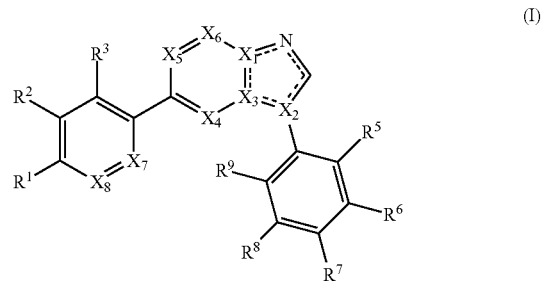

or a pharmaceutically acceptable form thereof, wherein
$X_1$, $X_2$, and $X_3$ are independently N or C;
$X_4$, $X_5$, $X_6$ are independently N or $CR^4$;
wherein at least one of $X_1$, $X_2$, $X_3$, $X_4$, $X_5$, and $X_6$ is N;
$X_7$ is N or $CR^{10}$;
$X_8$ is N or $CR^{11}$;
----- is a single or double bond, as valency allows;
$R^1$, $R^2$, $R^3$, $R^5$, $R^6$, $R^7$, $R^8$, $R^9$, $R^{10}$, and $R^{11}$ are independently hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)$_2$, —NO$_2$, —C(O)R, —CO$_2$R, —C(O)N(R)$_2$, —C(O)NROR, —S(O)R, —SO$_2$R, —SO$_2$N(R)$_2$, —OC(O)R, —NRC(O)R, —NRSO$_2$R, or —NRC(O)N(R)$_2$;

each R is independently hydrogen, optionally substituted $C_{1-6}$ aliphatic, optionally substituted aryl, optionally substituted carbocyclyl, optionally substituted heteroaryl, or optionally substituted heterocyclyl, optionally substituted acyl, or a nitrogen protecting group when attached to a nitrogen, or an oxygen protecting group when attached to oxygen; or two R groups on the same nitrogen may be taken together to form an optionally substituted heterocycle;

each $R^4$ is independently hydrogen, halogen, or optionally substituted $C_{1-6}$ aliphatic; and $R^1$ and $R^2$, $R^2$ and $R^3$, $R^3$ and $R^4$, $R^1$ and $R^{11}$, $R^{10}$ and $R^{11}$, $R^5$ and $R^6$, $R^6$ and $R^7$, $R^7$ and $R^8$, or $R^8$ and $R^9$ may be optionally taken together to form an optionally substituted 5-6 membered carbocyclic, aryl, heterocyclic, or heteroaryl ring.

As described generally above, $R^1$ is hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)$_2$, —NO$_2$, —C(O)R, —CO$_2$R, —C(O)N(R)$_2$, —C(O)NROR, —S(O)R, —SO$_2$R, —SO$_2$N(R)$_2$, —OC(O)R, —NRC(O)R, —NRSO$_2$R, or —NRC(O)N(R)$_2$. In some embodiments, $R^1$ is hydrogen. In some embodiments, $R^1$ is halogen. In some embodiments, $R^1$ is —CN, —CH$_2$OH, —CH$_2$NH$_2$, —C(O)R$_a$, —CH$_2$R$_b$, —CH(OH)R$_c$, or —SO$_2$R$_a$, wherein R$_a$, R$_b$, and R$_c$ are as described herein. In some embodiments, R¹ is —C(O)R, where R is optionally substituted heterocyclyl.

As described generally above, R² is hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)₂, —NO₂, —C(O)R, —CO₂R, —C(O)N(R)₂, —C(O)NROR, —S(O)R, —SO₂R, —SO₂N(R)₂, —OC(O)R, —NRC(O)R, —NRSO₂R, or —NRC(O)N(R)₂. In some embodiments, R² is hydrogen. In some embodiments, R² is halogen. In some embodiments, R² is —H, —F, —Cl, —CH₃, —CF₃, —CHF₂, —OH, —OC₁₋₆ alkyl, —SR, —NH₂, —NHCH₃, —N(CH₃)₂, —NHEt, —N(Et)₂, —NHi-Pr, —NC(O)R_c, SR_c, —S(O)R_e, —S(O)₂R_e, —CN, —CH₂OH, —CH₂NH₂, —N(R)₂, —NO₂, —CONH₂, —CONHR, —CONRR, —C(O)R, C(O)R_e, —C(O)OR_e, —C(O)NR_cR_f, —C(OH)RR, C₂-C₆ alkenyl, C₂-C₆ alkynyl, C₃-C₆ cycloalkyl, C₄-C₇ cycloalkyl, mono or polycyclic aryl, or mono or polycyclic heteroaryl. In some embodiments, R² is optionally substituted from 1 to 3 times with substitutents selected from the group consisting of halogen, —H, —OR_c, —C(O)R_b, —C(O)OR_c, —C(O)NR_fR_g, —NH₂, —NHR_d, —NR_dR_f, —SR_c, —S(O)R, —S(O)₂R, —CN, —NO₂, C₁-C₆ alkyl, C₂-C₆ alkenyl, C₂-C₆ alkynyl, C₃-C₆ cycloalkyl, C₄-C₇ cycloalkylalkyl, and mono or polycyclic aryl. In some embodiments, R² is —H, —F, —Cl, —CN, —CH₃, —CF₃, —CHF₂, —C(O)NH₂, —OH, —OC₁₋₄alkyl, or —OCF₃.

In some embodiments, R¹ and R² are taken together to form an optionally substituted 5-membered ring heterocyclic or heteroaryl moiety.

As described generally above, R³ is hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)₂, —NO₂, —C(O)R, —CO₂R, —C(O)N(R)₂, —C(O)NROR, —S(O)R, —SO₂R, —SO₂N(R)₂, —OC(O)R, —NRC(O)R, —NRSO₂R, or —NRC(O)N(R)₂. In some embodiments, R³ is hydrogen. In some embodiments, R³ is halogen. In some embodiments, R³ is —H, —F, —Cl, —CH₃, —CF₃, —CHF₂, —OH, or —OMe. In some embodiments, R³ is —H, —F, —Cl, —CN, —CH₃, —CF₃, —CHF₂, —C(O)NH₂, —OH, —OC₁₋₄alkyl, or —OCF₃.

As described generally above, each R⁴ is independently hydrogen, halogen, or optionally substituted C₁₋₆ aliphatic. In some embodiments, R⁴ is hydrogen. In some embodiments, R⁴ is halogen. In some embodiments, R⁴ is fluoro or chloro. In some embodiments, R⁴ is optionally substituted C₁₋₆ aliphatic. In some embodiments, R⁴ is optionally substituted C₁₋₆ alkyl. In some embodiments, R⁴ is unsubstituted C₁₋₆ alkyl. In some embodiments, R⁴ is H or Me.

As described generally above, R⁵ is hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)₂, —NO₂, —C(O)R, —CO₂R, —C(O)N(R)₂, —C(O)NROR, —S(O)R, —SO₂R, —SO₂N(R)₂, —OC(O)R, —NRC(O)R, —NRSO₂R, or —NRC(O)N(R)₂. In some embodiments, R⁵ is hydrogen. In some embodiments, R⁵ is —F, —Cl, Me, —CF₃, —OCF₃, —OH, —OMe, —CN, or —CONH₂.

As described generally above, R⁶ is hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)₂, —NO₂, —C(O)R, —CO₂R, —C(O)N(R)₂, —C(O)NROR, —S(O)R, —SO₂R, —SO₂N(R)₂, —OC(O)R, —NRC(O)R, —NRSO₂R, or —NRC(O)N(R)₂. In some embodiments, R⁶ is hydrogen. In some embodiments, R⁶ is halogen. In some embodiments, R⁶ is —F, —Cl, Me, —CF₃, —OCF₃, —OH, —OMe, —CN, or —CONH₂. In some embodiments, R⁶ is —H, —F, —Cl, —CN, —CH₃, —CF₃, —CHF₂, —C(O)NH₂, —OH, —OC₁₋₄alkyl, or —OCF₃.

As described generally above, R⁷ is hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)₂, —NO₂, —C(O)R, —CO₂R, —C(O)N(R)₂, —C(O)NROR, —S(O)R, —SO₂R, —SO₂N(R)₂, —OC(O)R, —NRC(O)R, —NRSO₂R, or —NRC(O)N(R)₂. In some embodiments, R⁷ is hydrogen. In some embodiments, R⁷ is halogen. In some embodiments, R⁷ is —H, —F, —Cl, Me, —CF₂H, —CF₃, —OH, —NH₂, —NHMe, —N(Me)₂, —CO₂H, —CONH₂, —CN, —OMe, alkyne, —CH₂OH, —CH₂NH₂, —NHCOCH₃, —CONHOH, —SO₂NH₂, —SO₂Me, morpholine, 1-methylpiperazine, carbocyclyl, heterocyclyl, aryl, heteroaryl, or substituted heteroaryl. In some embodiments, R⁷ is —CN. In some embodiments, R⁷ is —H, —F, —Cl, —CN, —CH₃, —CF₃, —CHF₂, —C(O)NH₂, —OH, —OC₁₋₄alkyl, or —OCF₃.

In some embodiments, R⁶ and R⁷ are taken together to form an optionally substituted 5- or 6-membered ring heterocyclic or heteroaryl moiety. In certain embodiments, a heterocyclic or heteroaryl moiety formed by R⁶ and R⁷ together with the benzene ring fused thereto is one of the following formulae:

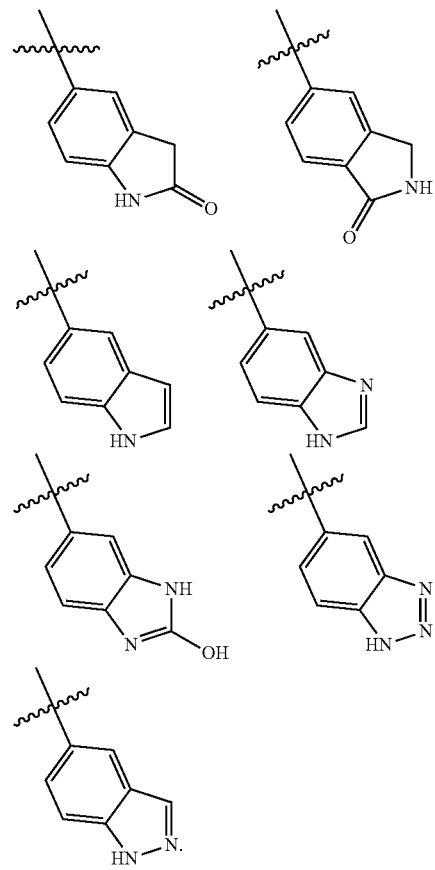

As described generally above, $R^8$ is hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)$_2$, —NO$_2$, —C(O)R, —CO$_2$R, —C(O)N(R)$_2$, —C(O)NROR, —S(O)R, —SO$_2$R, —SO$_2$N(R)$_2$, —OC(O)R, —NRC(O)R, —NRSO$_2$R, or —NRC(O)N(R)$_2$. In some embodiments, $R^8$ is hydrogen. In some embodiments, $R^8$ is halogen.

As described generally above, $R^9$ is hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)$_2$, —NO$_2$, —C(O)R, —CO$_2$R, —C(O)N(R)$_2$, —C(O)NROR, —S(O)R, —SO$_2$R, —SO$_2$N(R)$_2$, —OC(O)R, —NRC(O)R, —NRSO$_2$R, or —NRC(O)N(R)$_2$. In some embodiments, $R^9$ is hydrogen. In some embodiments, $R^9$ is halogen.

In some embodiments, each $R_a$ is independently —OR$_f$, NHR$_c$, NR$_c$R$_f$, optionally substituted alkyl, optionally substituted alkenyl, optionally substituted alkynyl, optionally substituted carbocyclyl, optionally substituted aryl, optionally substituted heteroaryl, or optionally substituted heterocyclyl. In some embodiments, each $R_a$ is independently —OR$_f$, NHR$_c$, NR$_c$R$_f$, alkyl, cycloalkyl, aryl, or optionally substituted 3- to 7-membered heterocyclyl having 1-2 heteroatoms independently selected from nitrogen, oxygen, and sulfur.

In some embodiments, each $R_b$ is independently —OR$_f$, —NHR$_c$, —NR$_c$R$_f$, optionally substituted alkyl, optionally substituted alkenyl, optionally substituted alkynyl, optionally substituted carbocyclyl, optionally substituted aryl, optionally substituted heteroaryl, optionally substituted heterocyclyl, —SR$_c$, —S(O)R$_c$, —S(O)$_2$R$_c$, C(O)R$_c$, —C(O)OR$_c$, or —C(O)NR$_c$R$_f$. In some embodiments, $R_b$ is optionally substituted 3- to 7-membered heterocyclyl having 1-2 heteroatoms independently selected from nitrogen, oxygen, and sulfur. In some embodiments, $R_b$ is $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl. In certain embodiments, $R_b$ is optionally substituted from 1 to 3 times with substituents independently selected from the group consisting of halogen, —H, —OR$_c$, —C(O)R$_b$, —C(O)OR$_c$, —C(O)NR$_c$R$_f$, —NHR$_d$, —NR$_d$R$_f$, —SR$_c$, —S(O)R, —S(O)$_2$R, —NH$_2$, —CN, —NO$_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, monocyclic aryl, and polycyclic aryl.

In some embodiments, each $R_c$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl. In some embodiments, $R_c$ is $C_{1-6}$ alkyl (e.g., methyl, ethyl, isopropyl, cyclopropyl, t-butyl), cycloalkyl, 3- to 7-membered heterocyclyl, aryl, or heteroaryl. In some embodiments, $R_c$ is optionally substituted phenyl. In some embodiments, $R_c$ is an optionally substituted 5- to 10-membered heteroaryl having 1-4 heteroatoms independently selected from nitrogen, oxygen, and sulfur.

In some embodiments, each $R_d$ is independently optionally substituted alkyl, optionally substituted alkenyl, optionally substituted alkynyl, —COR$_c$, S(O)R$_c$, S(O)$_2$R$_c$, optionally substituted alkylaryl, or optionally substituted aryl. In some embodiments, $R_d$ is alkyl, —COR$_c$, S(O)R$_c$, S(O)$_2$R$_c$, phenyl, benzyl, substituted benzyl, or aryl.

In some embodiments, each $R_e$ is independently hydrogen, halo, —OH, —OR$_c$, —NH$_2$, —NHR$_c$, —NHSO$_2$R$_c$, —NR$_f$SO$_2$R$_c$, —NR$_c$R$_f$, —CN, optionally substituted alkyl, optionally substituted alkenyl, optionally substituted alkynyl, optionally substituted aryl, optionally substituted heteroaryl, optionally substituted heterocyclyl, —COR$_c$, or —NHCOR$_c$. In some embodiments, $R_e$ is —H, —F, —OH, —OR$_c$, —NH$_2$, —NHR$_c$, —NHSO$_2$R$_c$, —NR$_c$R$_f$, —CN, aryl, heterocyclyl, trifluoroacetyl, acetyl, or NH-acetyl.

In some embodiments, each $R_f$ is independently —H or $C_{1-6}$ alkyl.

In some embodiments, each $R_g$ is independently hydrogen, halo, —OH, —OR$_c$, —NH$_2$, —NHR$_c$, —NHSO$_2$R$_c$, —NR$_f$SO$_2$R$_c$, —NR$_c$R$_f$, —CN, optionally substituted alkyl, optionally substituted alkenyl, optionally substituted alkynyl, optionally substituted aryl, optionally substituted heteroaryl, optionally substituted heterocyclyl, —COR$_c$, or —NHCOR$_c$. In some embodiments, $R_e$ is —H, —F, —OH, —OR$_c$, —NH$_2$, —NHR$_c$, —NHSO$_2$R$_c$, —NR$_c$R$_f$, —CN, aryl, heterocyclyl, trifluoroacetyl, acetyl, or NH-acetyl.

In some embodiments, $R_d$ and $R_e$ are each fluoro. In some embodiments, $R_d$ and $R_e$ are each methyl. In some embodiments, $R_d$ and $R_e$ are taken together to form =O. In some embodiments, $R_d$ and $R_e$ are taken together to form a 4-, 5-, or 6-membered spiro-fused heterocycle or carbocycle.

In some embodiments, $R_d$ and $R_g$ are each fluoro. In some embodiments, $R_d$ and $R_g$ are each methyl. In some embodiments, $R_d$ and $R_g$ are taken together to form =O. In some embodiments, $R_d$ and $R_g$ are taken together to form a 4-, 5-, or 6-membered spiro-fused heterocycle or carbocycle.

In some embodiments, $R^1$ is —CN or —SONH$_2$. In some embodiments, $R^1$ is one of the following:

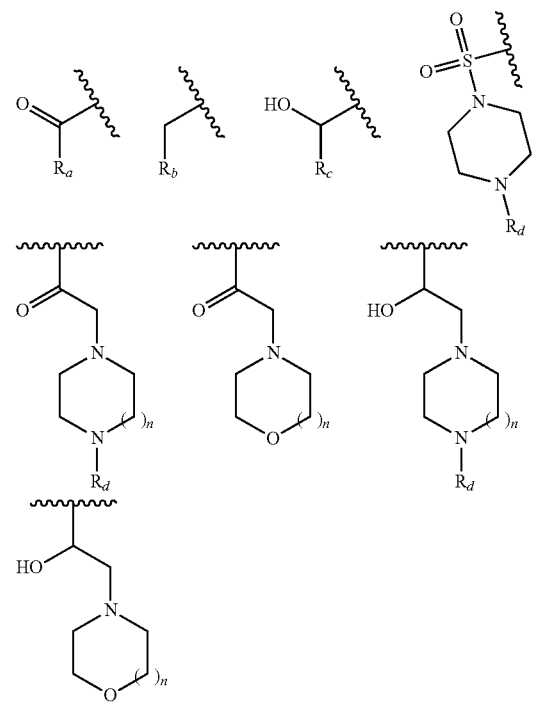

wherein $R_a$, $R_b$, $R_c$, and $R_d$ are described herein, and n is 0, 1, or 2.

In some embodiments, $R^1$ is —C(O)R, wherein R is optionally substituted heterocyclyl. In some embodiments, $R^1$ is —C(O)R, wherein R is

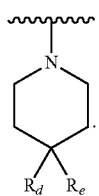
In some embodiments, $R^1$ is —C(O)R, wherein R is one of the following:
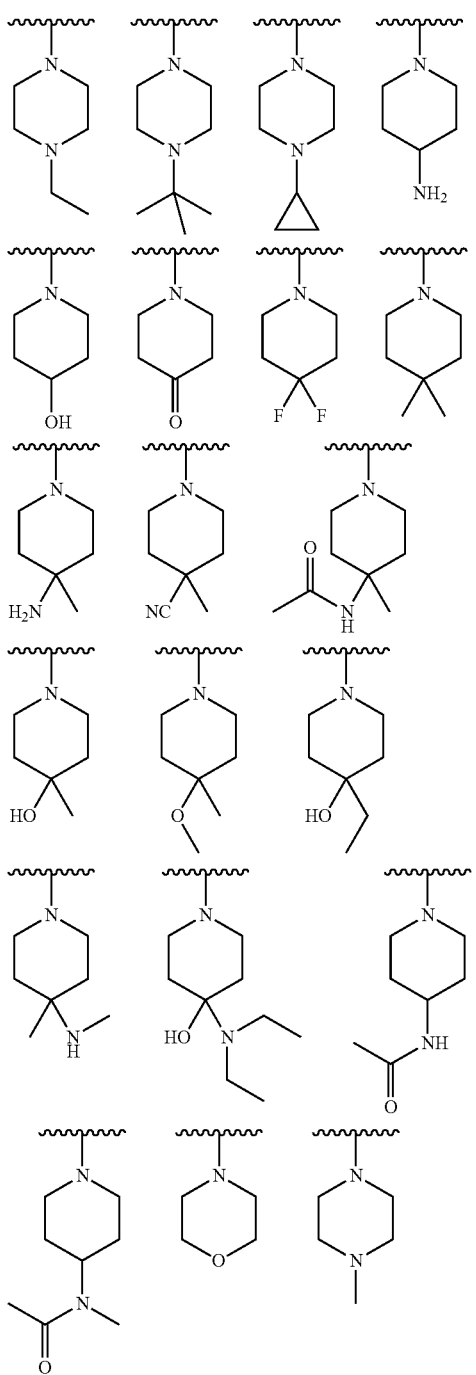
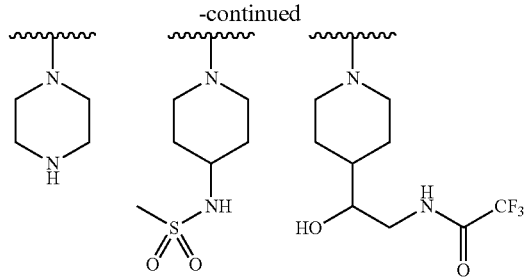
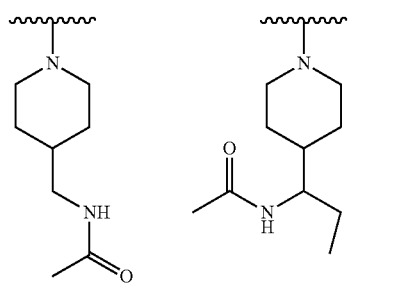
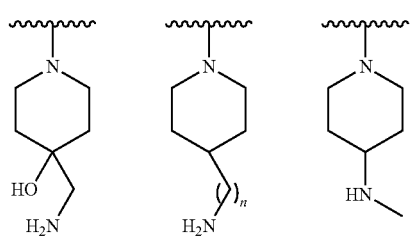
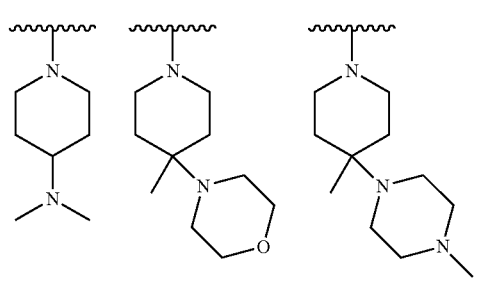
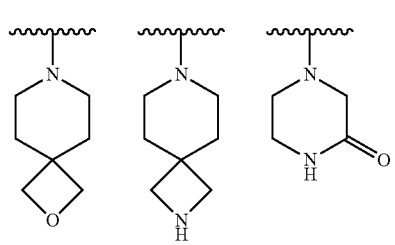
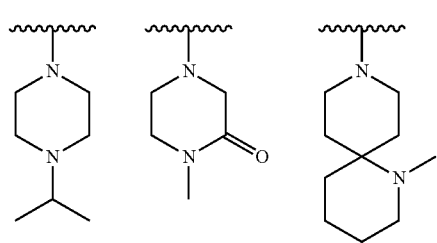

-continued
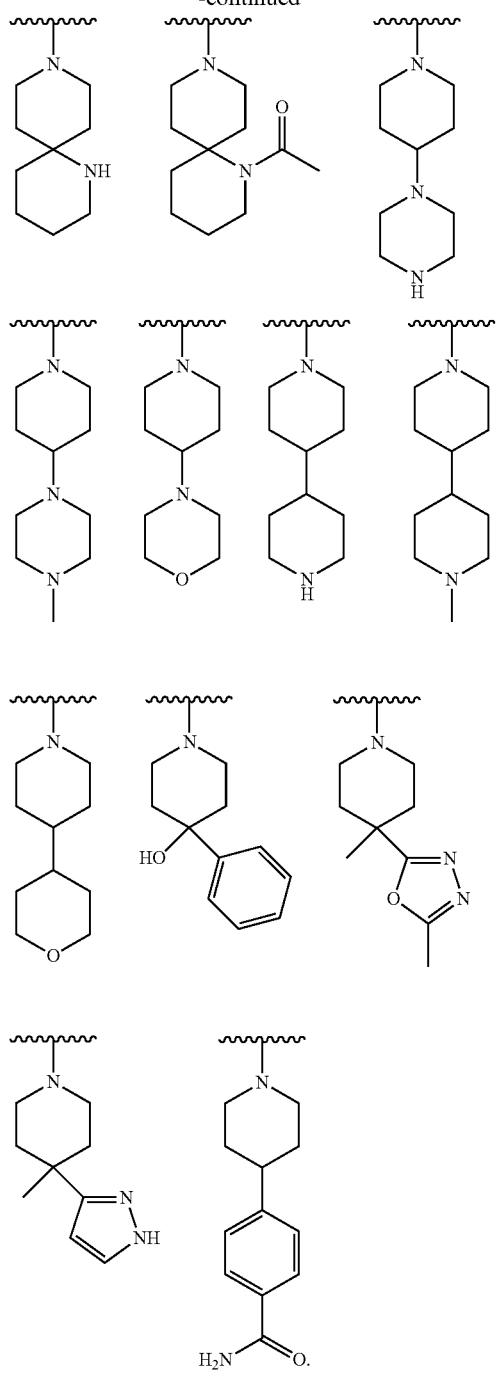
In some embodiments, $R_a$ is one of the following:
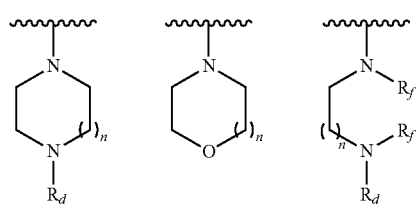
-continued
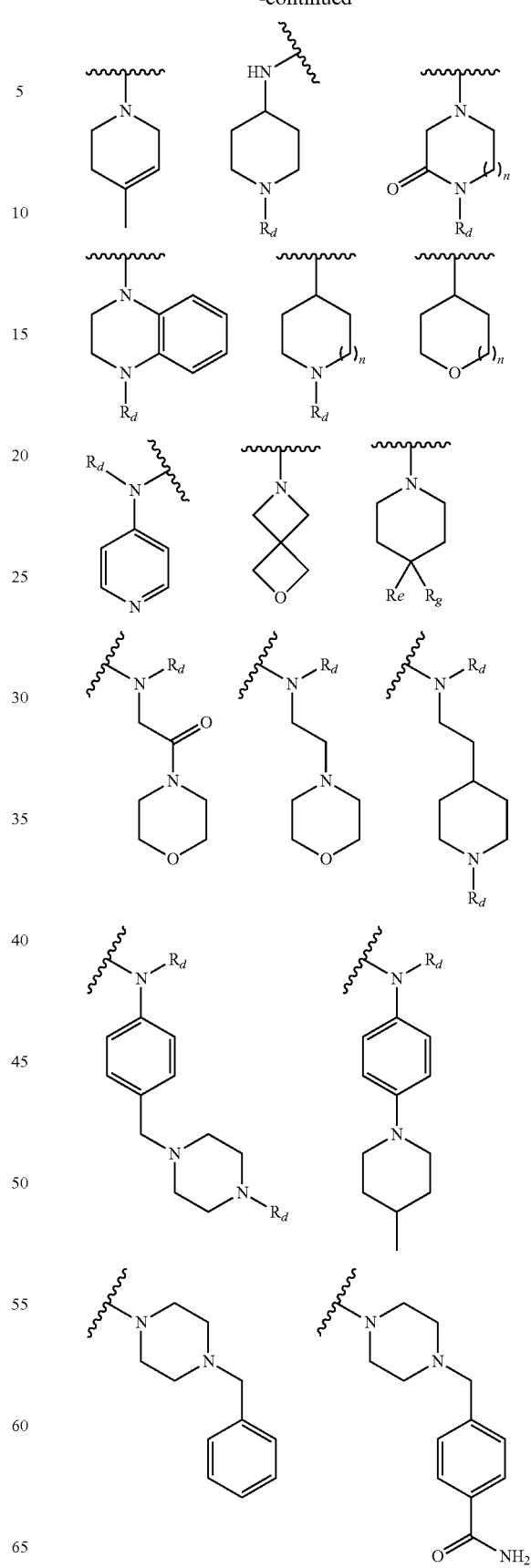

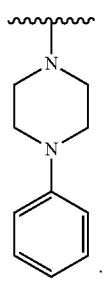
n=1, 2
In some embodiments, $R_a$ is one of the following:
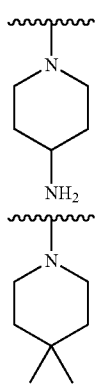 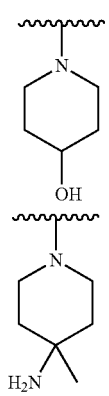 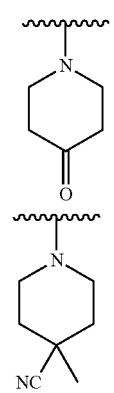 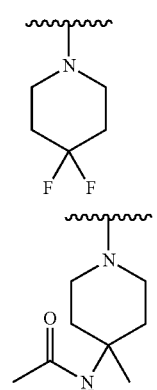
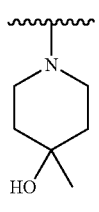 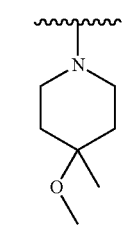 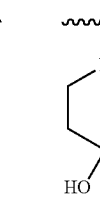
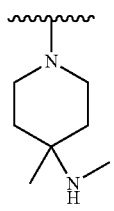 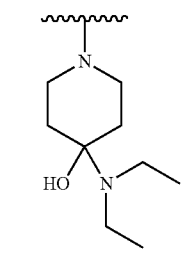 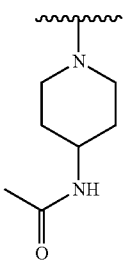
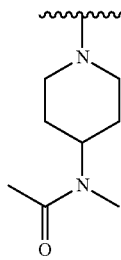 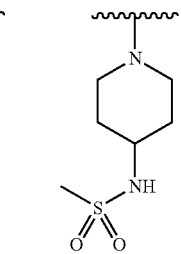
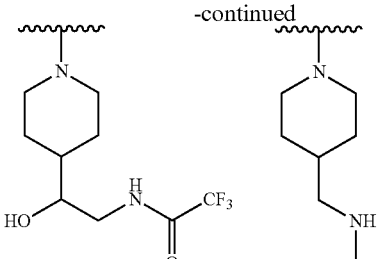
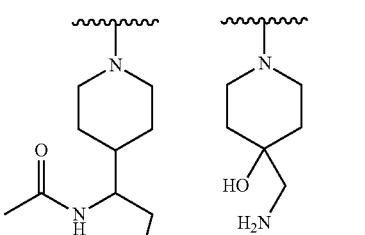
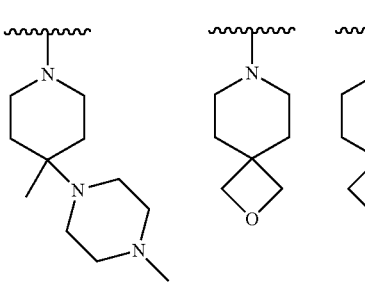
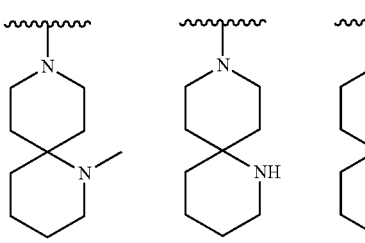
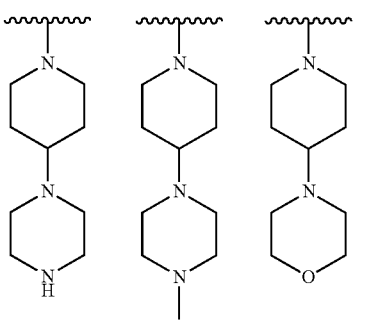

-continued

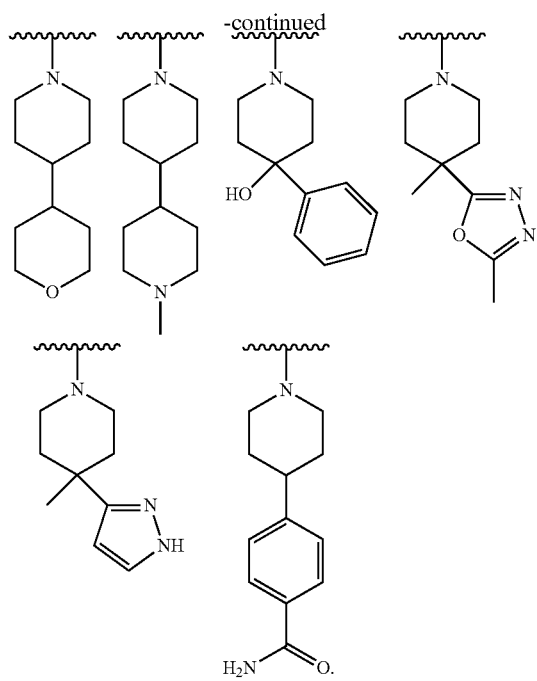

In some embodiments, $R_b$ is one of the following: OH, NH$_2$

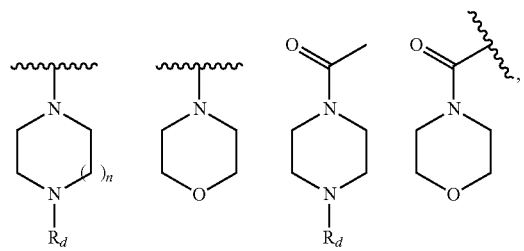

wherein n is 1 or 2.
In some embodiments, $R_c$ is one of the following:

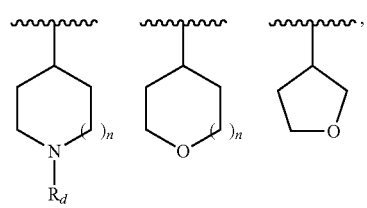

wherein n is 1 or 2.
In some embodiments, $R^1$ and $R^2$ are taken together to form:

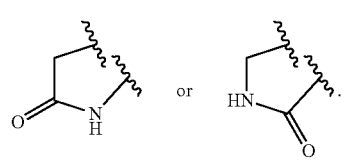 [SMILES: *CC(=O)N* ; *CNC(*)=O]

In some embodiments, $R^2$ is hydrogen, —OR$^O$, or —N(R$^N$)$_2$, wherein R$^O$ is hydrogen, optionally substituted C$_{1-6}$ aliphatic, optionally substituted acyl, or an oxygen protecting group; and each instance of R$^N$ is independently hydrogen, optionally substituted C$_{1-6}$ aliphatic, optionally substituted acyl, or an oxygen protecting group. In certain embodiments, R$^2$ is hydrogen. In certain embodiments, R$^2$ is —OR$^O$, wherein R$^O$ is as defined herein. In certain embodiments, R$^2$ is —OR$^O$, wherein R$^O$ is hydrogen. In certain embodiments, R$^2$ is —OR$^O$, wherein R$^O$ is an oxygen protecting group. In certain embodiments, R$^2$ is —N(R$^N$)$_2$, wherein R$^N$ is as defined herein. In certain embodiments, R$^2$ is —NHR$^N$, wherein R$^N$ is as defined herein. In certain embodiments, R$^2$ is —NHR$^N$, wherein R$^N$ is hydrogen. In certain embodiments, R$^2$ is —NHR$^N$, wherein R$^N$ is optionally substituted acyl. In certain embodiments, R$^2$ is —NHR$^N$, wherein R$^N$ is acetyl. In certain embodiments, R is —NHR$^N$, wherein R$^N$ is a nitrogen protecting group.

In some embodiments, R$^3$ is hydrogen. In some embodiments, R$^2$ and R$^3$ are both hydrogen. In some embodiments, R$^2$ is —OR$^O$ and R$^3$ is hydrogen. In some embodiments, R$^2$ is —OH and R$^3$ is hydrogen. In some embodiments, R$^2$ is —N(R$^N$)$_2$ and R$^3$ is hydrogen. In some embodiments, R$^2$ is —NHR$^N$ and R$^3$ is hydrogen. In some embodiments, R$^2$ is —NHC(=O)CH$_3$ and R$^3$ is hydrogen.

In some embodiments, R$^6$ is hydrogen. In some embodiments, R is CN. In some embodiments, R$^6$ is hydrogen and R is CN.

In some embodiments, R$^2$ is —H, —CN, —NH$_2$, —SO$_2$NH$_2$,

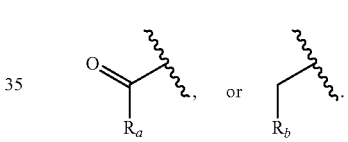

In some embodiments, R$^2$, R$^3$, R$^4$, R$^5$, R$^6$, R$^8$, and R$^9$ are each hydrogen.

In some embodiments, a provided compound is of Formula (Ia):

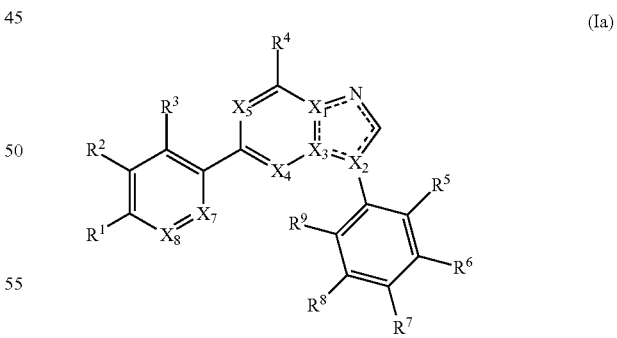

or a pharmaceutically acceptable form thereof, wherein
X$_1$, X$_2$, and X$_3$ are independently N or C;
X$_4$ and X$_5$ are independently N or CR$^4$;
wherein at least one of X$_1$, X$_2$, X$_3$, X$_4$, and X$_5$ is N;
X$_7$ is N or CR$^{10}$;
X$_8$ is N or CR$^{11}$;
----- is a single or double bond, as valency allows;
R$^1$, R$^2$, R$^3$, R$^5$, R$^6$, R$^7$, R$^8$, R$^9$, R$^{10}$, and R$^{11}$ are independently hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)$_2$, —NO$_2$, —C(O)R, —CO$_2$R, —C(O)N(R)$_2$, —C(O)NROR, —S(O)R, —SO$_2$R, —SO$_2$N(R)$_2$, —OC(O)R, —NRC(O)R, —NRSO$_2$R, or —NRC(O)N(R)$_2$;

each R is independently hydrogen, optionally substituted C$_{1-6}$ aliphatic, optionally substituted aryl, optionally substituted carbocyclyl, optionally substituted heteroaryl, or optionally substituted heterocyclyl, optionally substituted acyl, or a nitrogen protecting group when attached to a nitrogen, or an oxygen protecting group when attached to oxygen; or two R groups on the same nitrogen may be taken together to form an optionally substituted heterocycle;

each R$^4$ is independently hydrogen, halogen, or optionally substituted C$_{1-6}$ aliphatic; and R$^1$ and R$^2$, R$^2$ and R$^3$, R$^3$ and R$^4$, R$^1$ and R$^{11}$, R$^{10}$ and R$^{11}$, R$^5$ and R$^6$, R$^6$ and R$^7$, R$^7$ and R$^8$, or R$^8$ and R$^9$ may be optionally taken together to form an optionally substituted 5-6 membered carbocyclic, aryl, heterocyclic, or heteroaryl ring.

In some embodiments, a provided compound is of Formula (Ia-i):

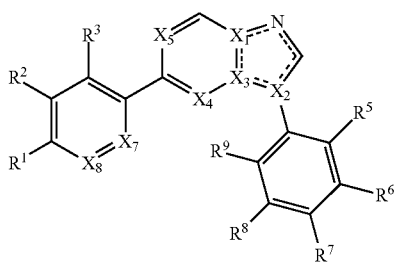

(Ia-i)

or a pharmaceutically acceptable form thereof, wherein
X$_1$, X$_2$, and X$_3$ are independently N or C;
X$_4$ and X$_5$ are independently N or CR$^4$;
wherein at least one of X$_1$, X$_2$, X$_3$, X$_4$, and X$_5$ is N;
X$_7$ is N or CR$^{10}$;
X$_8$ is N or CR$^{11}$;
- - - - is a single or double bond, as valency allows;
R$^1$, R$^2$, R$^3$, R$^5$, R$^6$, R$^7$, R$^8$, R$^9$, R$^{10}$, and R$^{11}$ are independently hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)$_2$, —NO$_2$, —C(O)R, —CO$_2$R, —C(O)N(R)$_2$, —C(O)NROR, —S(O)R, —SO$_2$R, —SO$_2$N(R)$_2$, —OC(O)R, —NRC(O)R, —NRSO$_2$R, or —NRC(O)N(R)$_2$;

each R is independently hydrogen, optionally substituted C$_{1-6}$ aliphatic, optionally substituted aryl, optionally substituted carbocyclyl, optionally substituted heteroaryl, or optionally substituted heterocyclyl, optionally substituted acyl, or a nitrogen protecting group when attached to a nitrogen, or an oxygen protecting group when attached to oxygen; or two R groups on the same nitrogen may be taken together to form an optionally substituted heterocycle;

each R$^4$ is independently hydrogen, halogen, or optionally substituted C$_{1-6}$ aliphatic; and R$^1$ and R$^2$, R$^2$ and R$^3$, R$^3$ and R$^4$, R$^1$ and R$^{11}$, R$^{10}$ and R$^{11}$, R$^5$ and R$^6$, R$^6$ and R$^7$, R$^7$ and R$^8$, or R$^8$ and R$^9$ may be optionally taken together to form an optionally substituted 5-6 membered carbocyclic, aryl, heterocyclic, or heteroaryl ring.

In some embodiments, a provided compound is of Formula (Ib):

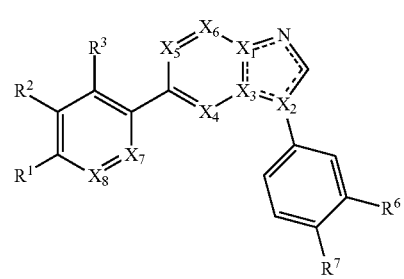

(Ib)

or a pharmaceutically acceptable form thereof, wherein
X$_1$, X$_2$, and X$_3$ are independently N or C;
X$_4$, X$_5$, X$_6$ are independently N or CR$^4$;
wherein at least one of X$_1$, X$_2$, X$_3$, X$_4$, X$_5$, and X$_6$ is N;
X$_7$ is N or CH;
X$_8$ is N or CH;
- - - - is a single or double bond, as valency allows;
R$^1$ is —C(O)R, wherein R is optionally substituted heterocyclyl;
R$^2$, R$^3$, R$^6$, and R$^7$ are independently —H, —F, —Cl, —CN, —CH$_3$, —CF$_3$, —CHF$_2$, —C(O)NH$_2$, —OH, —OC$_{1-4}$alkyl, or —OCF$_3$; or R$^6$ and R$^7$ are taken together to form a 5-6 membered fused heterocyclyl or heteroaryl moiety; and
each R$^4$ is independently hydrogen or C$_{1-6}$ alkyl.

In some embodiments, a provided compound is of Formula (Ib-i):

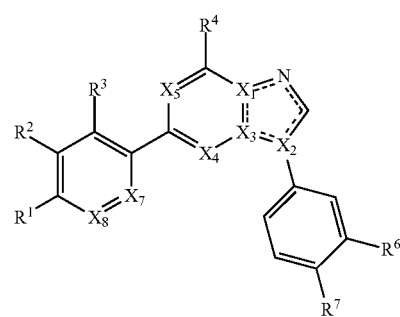

(Ib-i)

or a pharmaceutically acceptable form thereof, wherein
X$_1$, X$_2$, and X$_3$ are independently N or C;
X$_4$ and X$_5$ are independently N or CR$^4$;
wherein at least one of X$_1$, X$_2$, X$_3$, X$_4$, and X$_5$ is N;
X$_7$ is N or CH;
X$_8$ is N or CH;
- - - - is a single or double bond, as valency allows;
R$^1$ is —C(O)R, wherein R is optionally substituted heterocyclyl;
R$^2$, R$^3$, R$^6$, and R$^7$ are independently —H, —F, —Cl, —CN, —CH$_3$, —CF$_3$, —CHF$_2$, —C(O)NH$_2$, —OH, —OC$_{1-4}$alkyl, or —OCF$_3$; or R$^6$ and R$^7$ are taken together to form a 5-6 membered fused heterocyclyl or heteroaryl moiety; and
each R$^4$ is independently hydrogen or C$_{1-6}$ alkyl.

In some embodiments, $R^4$ is hydrogen.

In some embodiments, a provided compound is of Formula (Ib-ii):

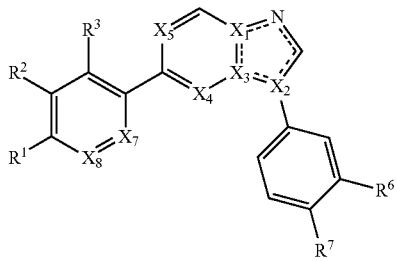

(Ib-ii)

or a pharmaceutically acceptable form thereof, wherein
$X_1$, $X_2$, and $X_3$ are independently N or C;
$X_4$ and $X_5$ are independently N or $CR^4$;
wherein at least one of $X_1$, $X_2$, $X_3$, $X_4$, and $X_5$ is N;
$X_7$ is N or CH;
$X_8$ is N or CH;
----- is a single or double bond, as valency allows;
$R^1$ is —C(O)R, wherein R is optionally substituted heterocyclyl;
$R^2$, $R^3$, $R^6$, and $R^7$ are independently —H, —F, —Cl, —CN, —CH$_3$, —CF$_3$, —CHF$_2$, —C(O)NH$_2$, —OH, —OC$_{1-4}$alkyl, or —OCF$_3$; or $R^6$ and $R^7$ are taken together to form a 5-6 membered fused heterocyclyl or heteroaryl moiety; and
each $R^4$ is independently hydrogen or $C_{1-6}$ alkyl.

In some embodiments, a provided compound is of Formula (Ic):

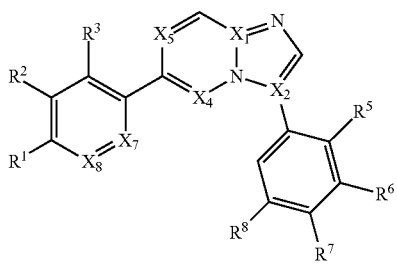

(Ic)

or a pharmaceutically acceptable form thereof, wherein
$X_1$, and $X_2$ are independently N or C;
$X_4$ and $X_5$ are independently N or $CR^4$;
$X_7$ is N or $CR^{10}$;
$X_8$ is N or $CR^{11}$;
$R^1$, $R^2$, $R^3$, $R^5$, $R^6$, $R^7$, $R^8$, $R^{10}$, and $R^{11}$ are independently hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)$_2$, —NO$_2$, —C(O)R, —CO$_2$R, —C(O)N(R)$_2$, —C(O)NROR, —S(O)R, —SO$_2$R, —SO$_2$N(R)$_2$, —OC(O)R, —NRC(O)R, —NRSO$_2$R, or —NRC(O)N(R)$_2$;
each R is independently hydrogen, optionally substituted $C_{1-6}$ aliphatic, optionally substituted aryl, optionally substituted carbocyclyl, optionally substituted heteroaryl, or optionally substituted heterocyclyl, optionally substituted acyl, or a nitrogen protecting group when attached to a nitrogen, or an oxygen protecting group when attached to oxygen; or two R groups on the same nitrogen may be taken together to form an optionally substituted heterocycle;
each $R^4$ is independently hydrogen, halogen, or optionally substituted $C_{1-6}$ aliphatic; and
$R^1$ and $R^2$, $R^2$ and $R^3$, $R^3$ and $R^4$, $R^1$ and $R^{11}$, $R^{10}$ and $R^{11}$, $R^5$ and $R^6$, $R^6$ and $R^7$, $R^7$ and $R^8$, or $R^8$ and $R^9$ may be optionally taken together to form an optionally substituted 5-6 membered carbocyclic, aryl, heterocyclic, or heteroaryl ring.

In some embodiments, a provided compound is of Formula (Ic-i):

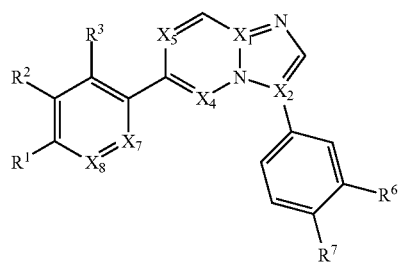

(Ic-i)

or a pharmaceutically acceptable form thereof, wherein
$X_1$, and $X_2$ are independently N or C;
$X_4$ and $X_5$ are independently N or $CR^4$;
$X_7$ is N or CH;
$X_8$ is N or CH;
$R^1$ is —C(O)R, wherein R is optionally substituted heterocyclyl;
$R^2$, $R^3$, $R^6$, and $R^7$ are independently —H, —F, —Cl, —CN, —CH$_3$, —CF$_3$, —CHF$_2$, —C(O)NH$_2$, —OH, —OC$_{1-4}$alkyl, or —OCF$_3$; or $R^6$ and $R^7$ are taken together to form a 5-6 membered fused heterocyclyl or heteroaryl moiety; and
each $R^4$ is independently hydrogen or $C_{1-6}$ alkyl.

In some embodiments, a provided compound is of Formula (Id):

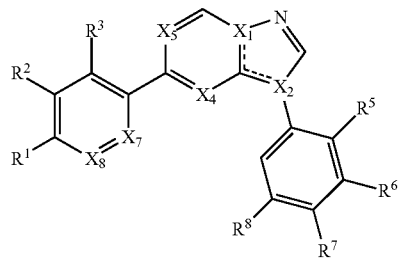

(Id)

or a pharmaceutically acceptable form thereof, wherein
$X_1$, and $X_2$ are independently N or C;
$X_4$ and $X_5$ are independently N or $CR^4$;
$X_7$ is N or $CR^{10}$;
$X_8$ is N or $CR^{11}$;
one ----- is a single bond, and the other ----- is a double bond;
$R^1$, $R^2$, $R^3$, $R^5$, $R^6$, $R^7$, $R^8$, $R^{10}$, and $R^{11}$ are independently hydrogen, halogen, optionally substituted aliphatic, optionally substituted aryl, optionally substituted carbocyclyl, optionally substituted heteroaryl, optionally substituted heterocyclyl, —CN, —OR, —SR, —N(R)$_2$, —NO$_2$, —C(O)R, —CO$_2$R, —C(O)N(R)$_2$, —C(O)NROR, —S(O)R, —SO$_2$R, —SO$_2$N(R)$_2$, —OC(O)R, —NRC(O)R, —NRSO$_2$R, or —NRC(O)N(R)$_2$;

each R is independently hydrogen, optionally substituted C$_{1-6}$ aliphatic, optionally substituted aryl, optionally substituted carbocyclyl, optionally substituted heteroaryl, or optionally substituted heterocyclyl, optionally substituted acyl, or a nitrogen protecting group when attached to a nitrogen, or an oxygen protecting group when attached to oxygen; or two R groups on the same nitrogen may be taken together to form an optionally substituted heterocycle;

each R$^4$ is independently hydrogen, halogen, or optionally substituted C$_{1-6}$ aliphatic; and R$^1$ and R$^2$, R$^2$ and R$^3$, R$^3$ and R$^4$, R$^1$ and R$^{11}$, R$^{10}$ and R$^{11}$, R$^5$ and R$^6$, R$^6$ and R$^7$, R$^7$ and R$^8$, or R$^8$ and R$^9$ may be optionally taken together to form an optionally substituted 5-6 membered carbocyclic, aryl, heterocyclic, or heteroaryl ring.

In some embodiments, a provided compound is of Formula (Id-i):

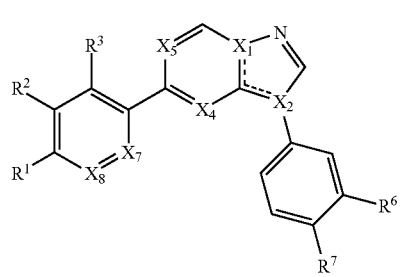

(Id-i)

or a pharmaceutically acceptable form thereof, wherein
X$_1$, and X$_2$ are independently N or C;
X$_4$ and X$_5$ are independently N or CR$^4$;
X$_7$ is N or CH;
X$_8$ is N or CH;
one ---- is a single bond, and the other ---- is a double bond;
R$^1$ is —C(O)R, wherein R is an optionally substituted heterocyclyl;
R$^2$, R$^3$, R$^6$, and R$^7$ are independently —H, —F, —Cl, —CN, —CH$_3$, —CF$_3$, —CHF$_2$, —C(O)NH$_2$, —OH, —OC$_{1-4}$alkyl, or —OCF$_3$; or R$^6$ and R$^7$ are taken together to form a 5-6 membered fused heterocyclyl or heteroaryl; and
each R$^4$ is independently hydrogen or C$_{1-6}$ alkyl.

In some embodiments, for any of the formulae described herein, X$_7$ and X$_8$ are each CH.

In some embodiments, a provided compound is of Formula (II), (III), (IV), (V), (VI), or (VII):

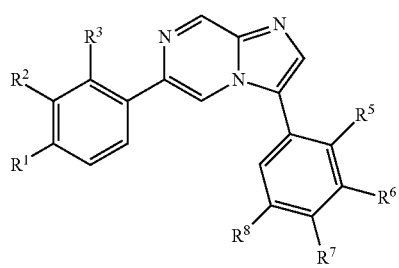

Formula II

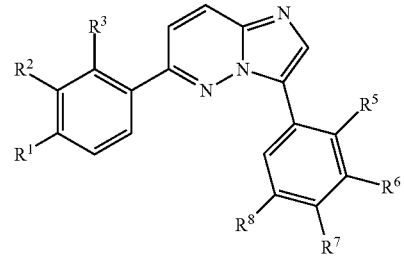

Formula III

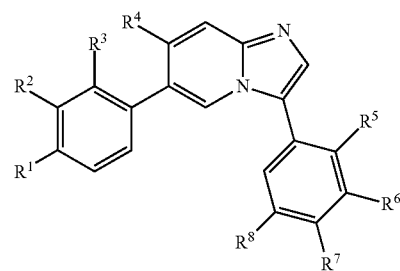

Formula IV

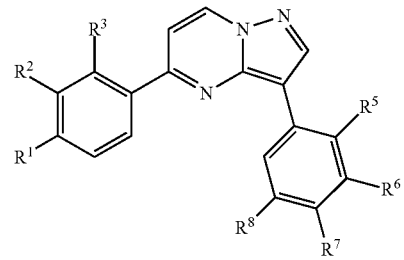

Formula V

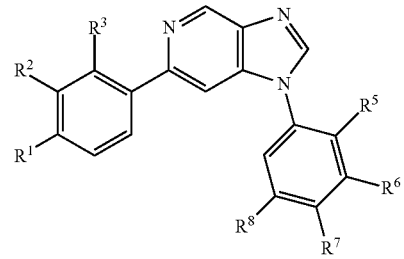

Formula VI

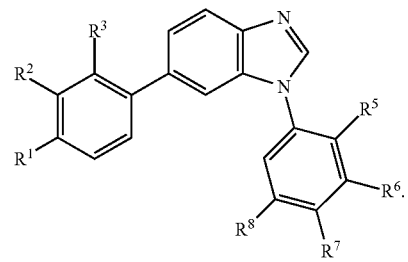

Formula VII

In some embodiments, for Formula (II), (III), (IV), (V), (VI), or (VII), R$^1$ is —C(O)R as described herein.

In some embodiments, a provided compound is of Formula (IIa), (IIIa), (IVa), (Va), (VIa), or (VIIa):

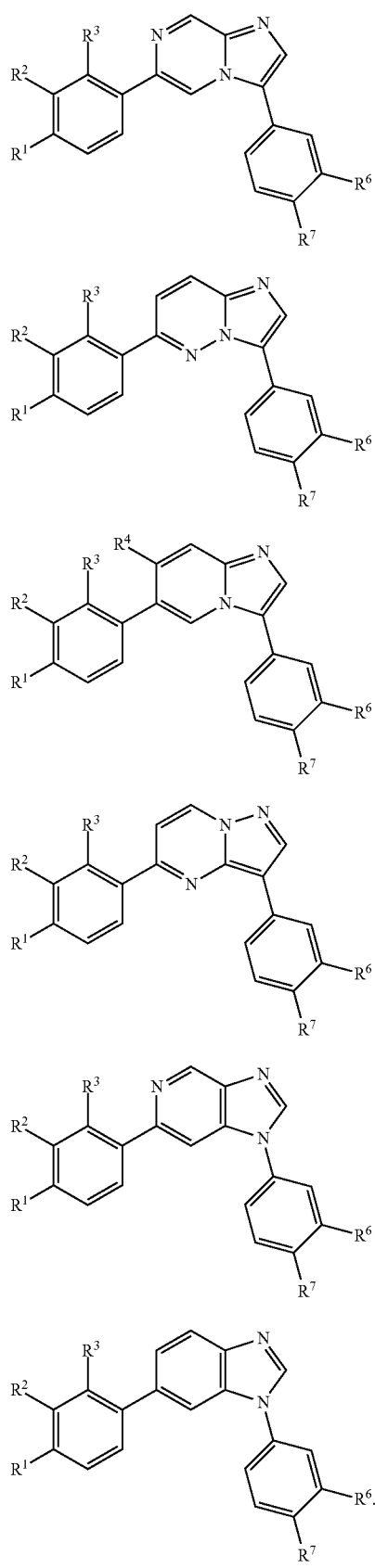
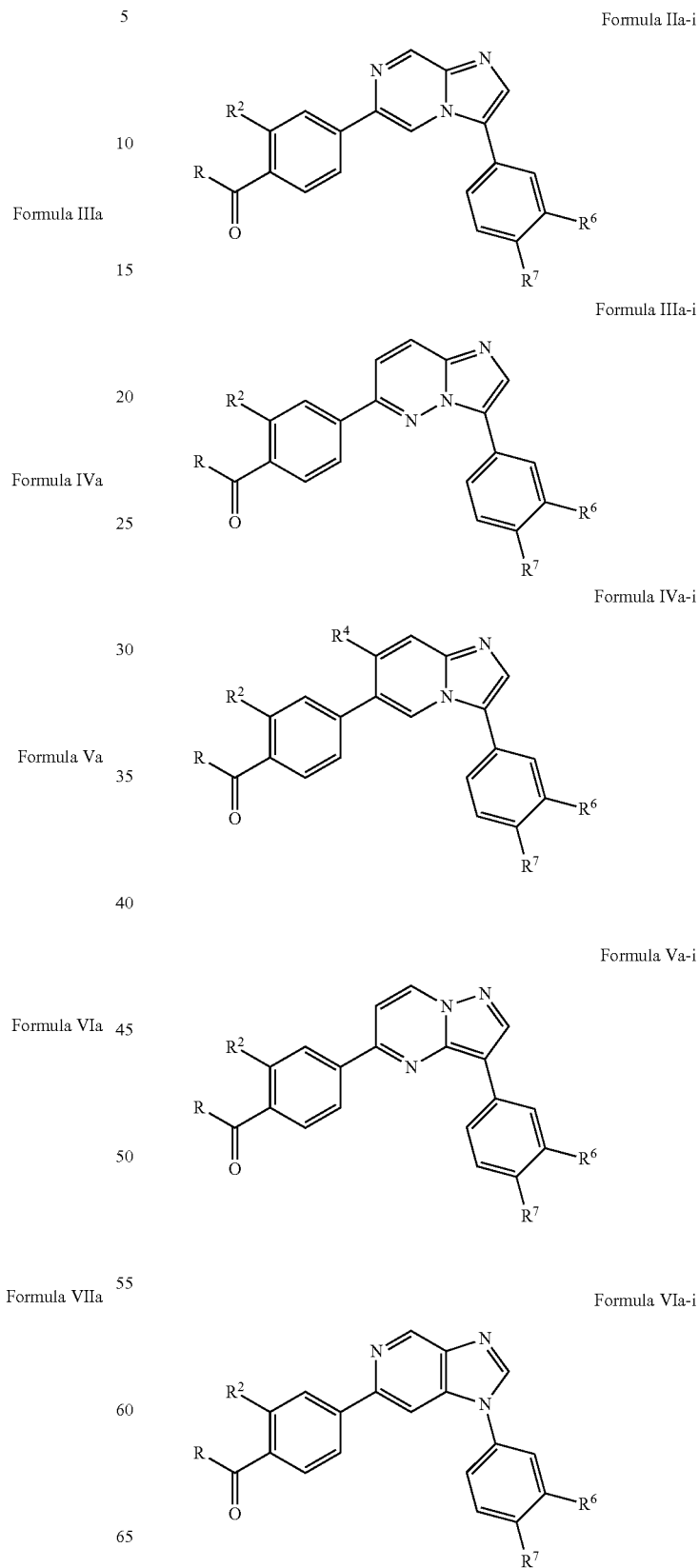
In some embodiments, a provided compound is of Formula (IIa-i), (IIIa-i), (IVa-i), (Va-i), (VIa-i), or (VIIa-i):

Formula VIIa-i
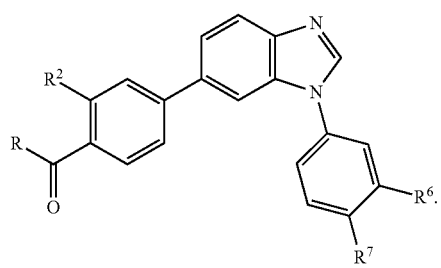
In some embodiments, a provided compound is of Formula (IIb), (IIIb), (IVb), (Vb), (VIb), or (VIIb):
Formula IIb
Formula IIIb
Formula IVb
Formula Vb
Formula VIb
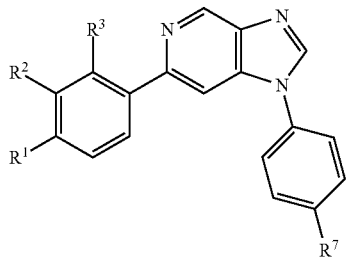
Formula VIIb
In some embodiments, a provided compound is of Formula (IIb-i), (IIIb-i), (IVb-i), (Vb-i), (VIb-i), or (VIIb-i):
Formula IIb-i
Formula IIIb-i
Formula IVb-i -continued
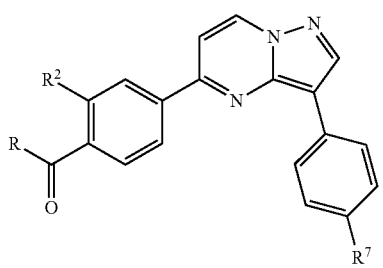
Formula Vb-i
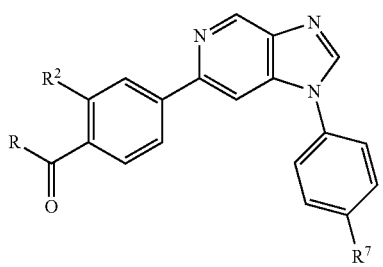
Formula VIb-i
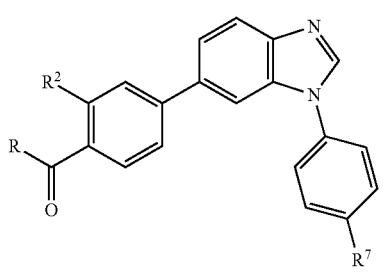
Formula VIIb-i
In some embodiments, a provided compound is of Formula (IIc), (IIIc), (IVc), (Vc), (VIc), or (VIIc):
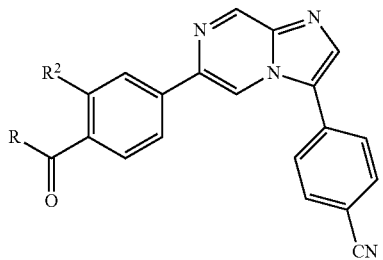
Formula IIc
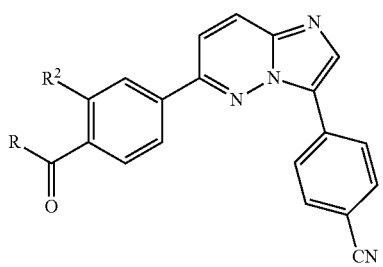
Formula IIIc
-continued
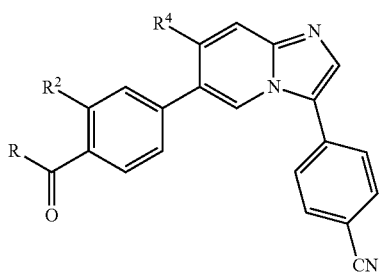
Formula IVc
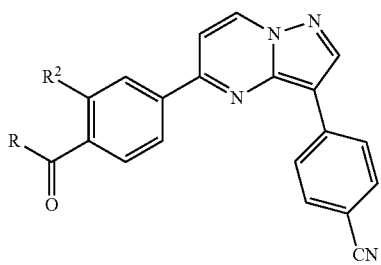
Formula Vc
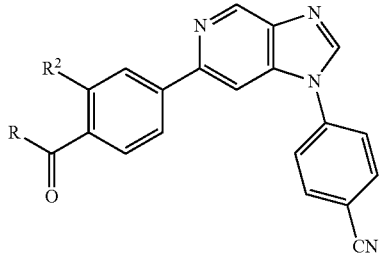
Formula VIc
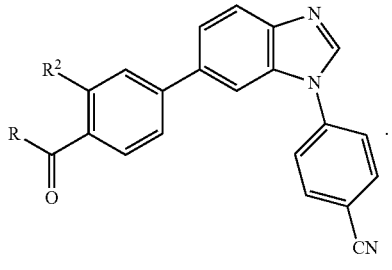
Formula VIIc
In some embodiments, R is optionally substituted heterocyclyl.
In some embodiments, a provided compound is one of the following:
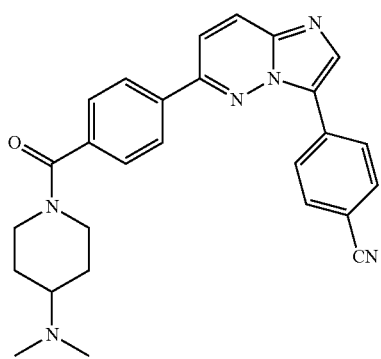

53
-continued
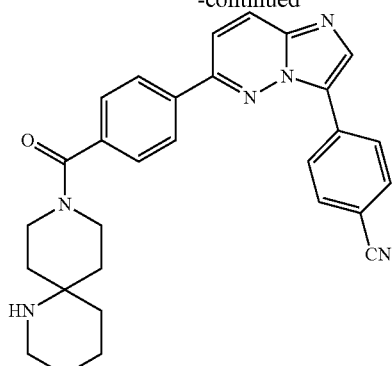
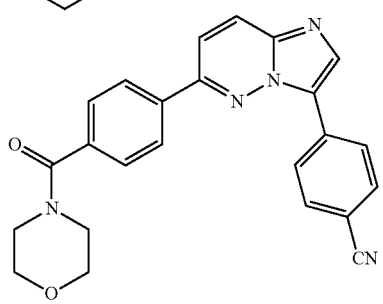
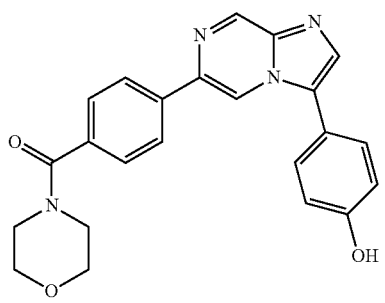
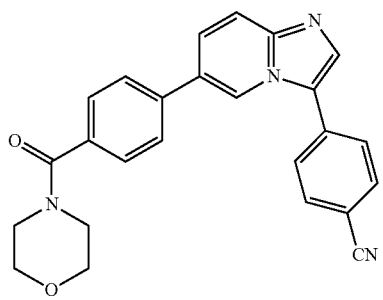
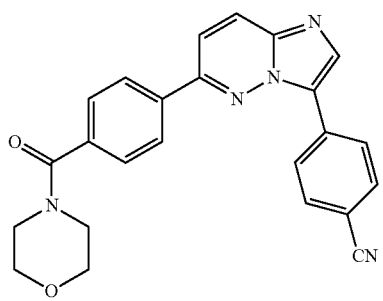
54
-continued
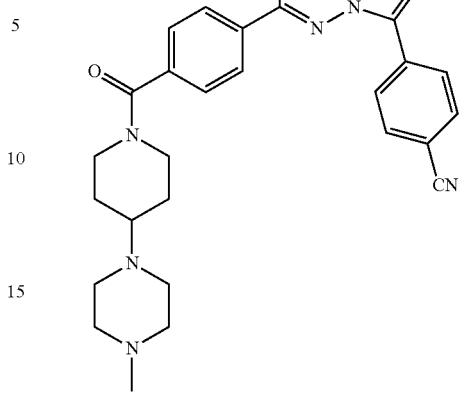
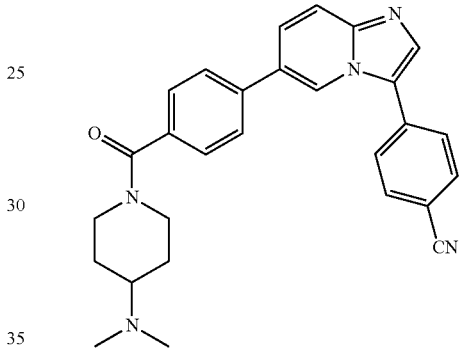
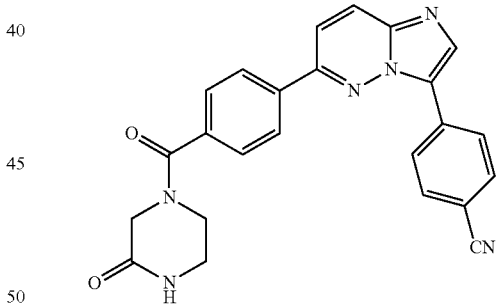
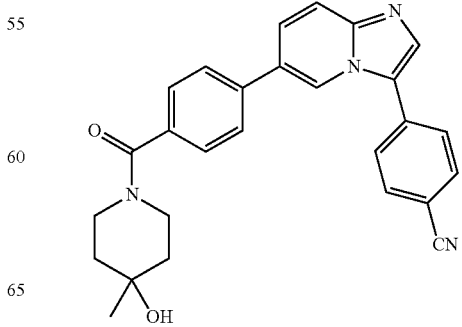

55
-continued
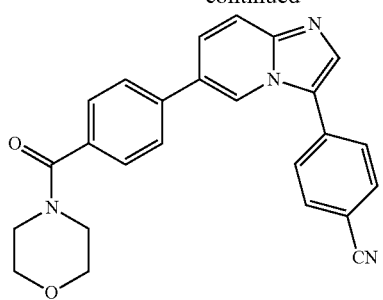
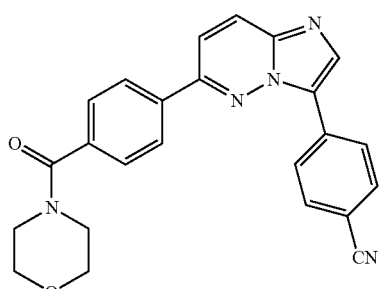
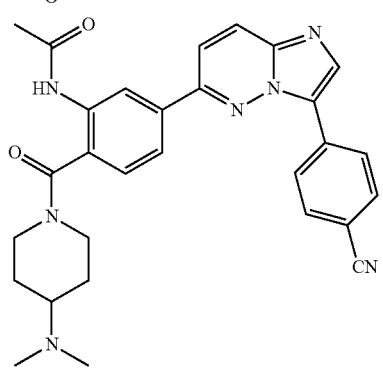
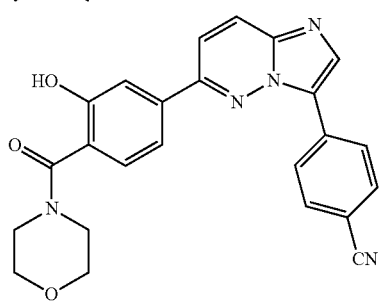
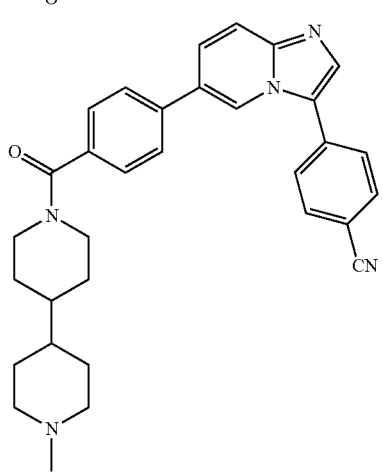
56
-continued
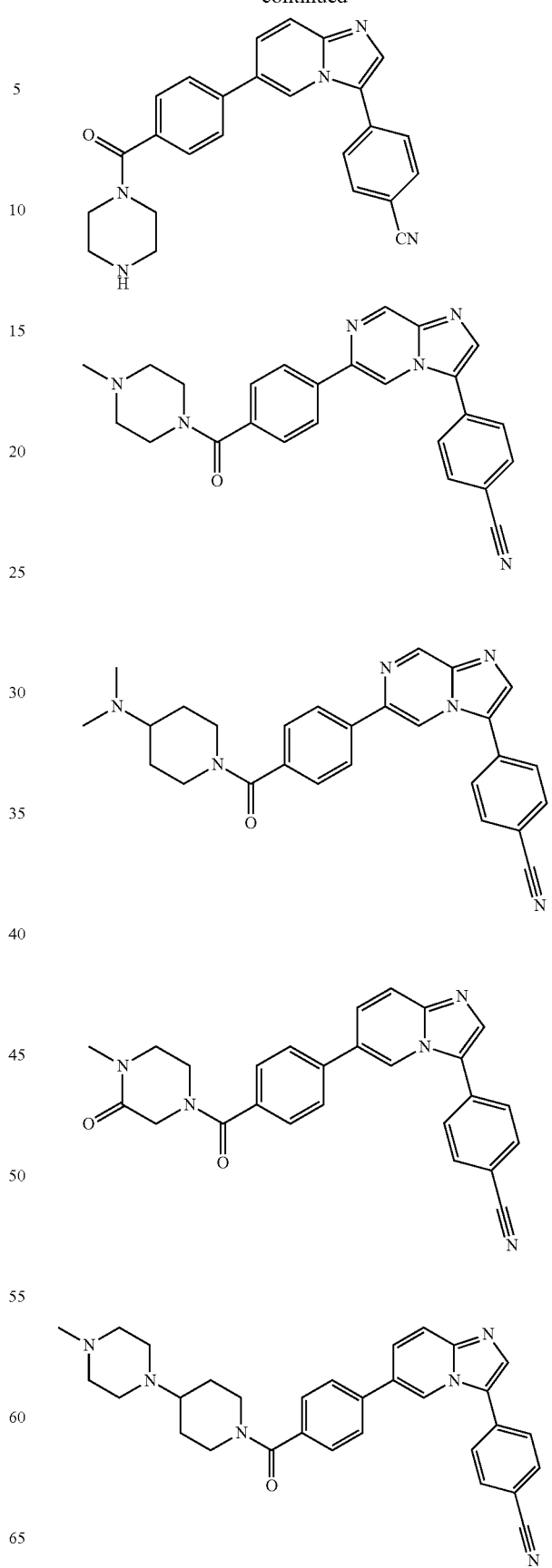

-continued

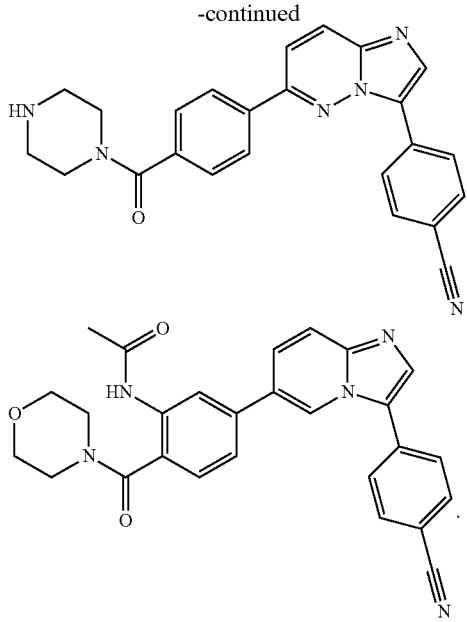

The present invention also provides pharmaceutical compositions comprising an effective amount of a compound described herein, or a pharmaceutically acceptable form (e.g., pharmaceutically acceptable salt or prodrug) thereof, and, optionally, a pharmaceutically acceptable excipient.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. CREMOPHOR), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer P188, cetrimonium bromide, cetylpyridinium chloride, benzalkonium chloride, docusate sodium, etc. and/ or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as CREMOPHOR, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquids to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered. by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Still further encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Optionally, a single container may comprise one or more compartments for containing an inventive pharmaceutical composition or compound, and/or a pharmaceutically acceptable excipient for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A kit may thus comprise such multi-compartment containers providing an inventive pharmaceutical composition or compound and one or more pharmaceutically acceptable excipients.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In some embodiments, an additional therapeutically active agent is a kinase inhibitor.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Compounds and compositions described herein are generally useful for the inhibition of one or more kinases. In certain embodiments, compounds and compositions described herein are generally useful for the inhibition of MNK1 and/or MNK2. In some embodiments, methods of treating kinase-related disorder in a subject are provided which comprise administering an effective amount of a compound described herein (e.g., a compound of Formula (I)), or a pharmaceutically acceptable form thereof), to a subject in need of treatment. In some embodiments, methods of treating MNK1- and/or MNK2-related disorder in a subject are provided which comprise administering an effective amount of a compound described herein (e.g., a compound of Formula (I)), or a pharmaceutically acceptable form thereof), to a subject in need of treatment. In certain embodiments, the effective amount is a therapeutically effective amount. In certain embodiments, the effective amount is a prophylactically effective amount. In certain embodiments, the subject is suffering from a MNK1-related disorder. In certain embodiments, the subject is susceptible to a MNK1-mediated disorder. In certain embodiments, the subject is suffering from a MNK2-related disorder. In certain embodiments, the subject is susceptible to a MNK2-mediated disorder.

As used herein, the term "kinase-related disorder" (e.g., "MNK1- and/or MNK2-related disorder") means any disease, disorder, or other pathological condition in which a kinase (e.g., MNK1 and/or MNK2) is known to play a role. In some embodiments, the present disclosure relates to treating or lessening the severity of one or more diseases in which MNK1 and/or MNK2 is known to play a role.

In certain embodiments, the kinase-related condition (e.g., MNK1- and/or MNK2-related condition) is selected from the group consisting of proliferative diseases, neurodegenerative diseases, autoimmune diseases, and inflammatory diseases.

In certain embodiments, a provided compound is useful for treating a proliferative disease, e.g., cancer. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer [e.g., squamous cell carcinoma (SCC), keratoacanthoma (KA), melanoma, basal cell carcinoma (BCC)]; small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In certain embodiments, a provided compound is useful for treating a neurodegenerative disease. Exemplary neurodegenerative diseases include, but are not limited to, Alzheimer's disease, Huntington's disease, progressive supranuclear palsy, corticobasal degeneration, frontotemporal lobar degeneration, Pick's disease, Parkinson's disease, Lewy body disease, and amyotropic lateral sclerosis (ALS).

In certain embodiments, a provided compound is useful for treating an autoimmune disease. Exemplary autoimmune diseases include, but are not limited to, rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic arthritis, juvenile arthritis, asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), Still's disease, myasthenia gravis, Hashimoto's thyroiditis, Ord's thyroiditis, Grave's disease, acute disseminated encephalomyelitis, Addison's disease, opsoclonus-myoclonus syndrome, antiphospholipid antibody syndrome, autoimmune hepatitis, celiac disease, Goodpasture's syndrome, optic neuritis, scleroderma, primary biliary cirrhosis, Reiter's syndrome, warm autoimmune hemolytic anemia, alopecia universalis, chronic fatigue, dysautonomia, neuromyotonia, vulvodynia and disorders ameliorated by a gastroprokinetic agent (e.g., ileus, postoperative ileus and ileus during sepsis; gastroesophageal reflux disease (GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, a provided compound is useful for treating an inflammatory disease. The term "inflammatory disease" refers to those conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory diseases include, but are not limited to inflammation associated with acne, asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis, and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, dry eye syndrome, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis), inflammatory bowel syndrome (IBS), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis, prostatistis, appendicitis, Blau syndrome, blepharitis, bronchiolitis, cervicitis, cholangitis, cholecystitis, chronic recurrent multifocal osteomyelitis (CRMO), cryopyrin associated periodic syndrome (CAPS), dacryoadenitis, dermatomyositis, dry eye syndrome, encephalitis, endocarditis, endometritis, enterocolitis, epicondylitis, epididymitis, familial cold-induced autoinflammatory syndrome, familial Mediterranean fever (FMF), fasciitis, fibrositis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, inflammatory osteolysis, otitis, pancreatitis, parotitis, pericarditis, peritonitis, pharyngitis, pleuritis, phlebitis, pneumonitis, pneumonia, proctitis, pulmonary fibrosis, pyelonephritis, pyoderma gangrenosum and acne syndrome (PAPA), pyogenic sterile arthritis, rhinitis, salpingitis, sinusitis, stomatitis, synovitis, TNF receptor associated periodic syndrome (TRAPS), tonsillitis, undifferentiated arthropathy, uveitis, vaginitis and vulvitis. In certain embodiments, the inflammatory condition is an acute inflammatory condition (e.g., inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

In certain embodiments, a provided compound is useful for treating or lessening the severity of arthropathies and osteopathological diseases including, but not limited to, rheumatoid arthritis, osteoarthritis, gout, polyarthritis, and psoriatic arthritis.

In certain embodiments, a provided compound is useful for treating or lessening the severity of acute and chronic inflammatory diseases including, but not limited to, ulcerative colitis, inflammatory bowel disease, Crohn's disease, dry eye syndrome, allergic rhinitis, allergic dermatitis, cystic fibrosis, chronic obstructive bronchitis, and asthma.

In certain embodiments, a provided compound is useful for treating or lessening the severity of hyperproliferative diseases including, but not limited to, psoriasis or smooth muscle cell proliferation including vascular proliferative disorders, atherosclerosis, and restenosis.

In certain embodiments, a provided compound is useful for treating or lessening the severity of endometriosis, uterine fibroids, endometrial hyperplasia, and benign prostate hyperplasia.

In some embodiments, a provided compound is useful for treating or lessening the severity of one or more diseases and conditions, wherein the disease or condition is selected from immune-related conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, a provided compound is useful for treating tumorogenesis.

In some embodiments, a provided compound is useful for treating a metabolic disorder (e.g., obesity, diabetes).

In some embodiments, a provided compound is useful for treating a neurodevelopmental disorder. Exemplary neurodevelopmental disorders include, but are not limited to, autism and autism spectrum disorders (e.g. Asperger syndrome or Mendelsohnn's Syndrome), fetal alcohol spectrum disorder, motor disorders (e.g. developmental coordination disorder, stereotypic movement disorder and the tic disorders including Tourette syndrome), traumatic brain injury (e.g. congenital injuries), genetic disorders (e.g. fragile-X syndrome, Neurofibromatosis, Tuberous Sclerosis, Rett's Syndrome, Timothy Syndrome, PTEN mutations, or Tourettes), Down syndrome, communication, speech and language disorders, eating disorders (e.g., anorexia nervosa and bulimia nervosa), adjustment disorder, attention-deficit/hyperactivity disorder, conduct disorder, oppositional defiant disorder, delirium, dementia, multi-infarct dementia, learning and memory disorders (e.g., amnesia and age-related memory loss). In certain embodiments, the neurodevelopmental disorder is autism, FragileX Syndrome, neurofibromatosis, tuberous sclerosis complex, or Rett's Syndrom.

In some embodiments, a provided compound is useful for treating a psychiatric disorder. Exemplary psychiatric disorders include, but are not limited to, anxiety disorders (e.g., acute stress disorder agoraphobia, generalized anxiety disorder, obsessive-compulsive disorder, panic disorder, post-traumatic stress disorder, separation anxiety disorder, social phobia, and specific phobia), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizo- phrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence). In certain embodiments, the psychiatric disorder is schizophrenia or anxiety.

In certain embodiments, the provided treatment comprises administration of a combination of the compounds provided herein with one or more additional therapeutic agents. In some embodiments, the additional therapeutic agent is a kinase inhibitor. In some embodiments, the additional therapeutic agent is an mTOR inhibitor. Exemplary mTOR inhibitors include sirolimus, temsirolimus, everolimus, and ridaforolimus. In some embodiments, an additional therapeutic agent is a PI3-kinase inhibitor. Exemplary PI3-kinase inhibitors include wortmannin, demethoxyviridin, LY294002, perifosine, CAL101, PX-886, BEZ235, SF1126, INK1117, INK1197, IPI-145, GDC-0941, BKM120, XL147, XL765, palomid 529, GSK1059615, ZSTK474, PWT33597, IC87114, TG100-115, CAL263, PI-103, GNE-477, CUDC-907, GSK 2126458, GDC-0980, PF-46915032, CAL263, SF1126 and PX-886. In some embodiments, the PI3-kinase inhibitor inhibits PI3K-$\alpha$, PI3K-$\beta$, PI3K-$\gamma$, and/or PI3K-$\delta$.

In some embodiments, the present disclosure provides a method of inhibiting MNK1 comprising contacting MNK1 with an effective amount of a compound described herein (e.g., a compound of Formula (I)), or a pharmaceutically acceptable form thereof. In some embodiments, the present disclosure provides a method of inhibiting MNK2 comprising contacting MNK2 with an effective amount of a compound described herein (e.g., a compound of Formula (I)), or a pharmaceutically acceptable form thereof. The MNK1 or MNK2 may be purified or crude, and may be present in a cell, tissue, or subject. Thus, such methods encompass both inhibition of in vitro and in vivo MNK1 or MNK2 activity. In certain embodiments, the method is an in vitro method, e.g., such as an assay method. It will be understood by one of ordinary skill in the art that inhibition of MNK1 or MNK2 does not necessarily require that all of the MNK1 or MNK2 be occupied by an inhibitor at once. Exemplary levels of inhibition of MNK1 or MNK2 include at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, and greater than 90% inhibition.

In some embodiments, provided is a method of inhibiting kinase activity in a subject in need thereof (e.g., a subject diagnosed as having a kinase-related disorder) comprising administering to the subject an effective amount of a compound described herein (e.g., a compound of Formula (I)), or a pharmaceutically acceptable form thereof, or a pharmaceutical composition thereof. In some embodiments, provided is a method of inhibiting MNK1 and/or MNK2 activity in a subject in need thereof (e.g., a subject diagnosed as having a MNK1- and/or MNK2-related disorder) comprising administering to the subject an effective amount of a compound described herein (e.g., a compound of Formula (I)), or a pharmaceutically acceptable form thereof, or a pharmaceutical composition thereof.

EXAMPLES

Compounds of formula (I) were synthesized and their ability to inhibit MNK1/2 kinase was evaluated both in enzymatic and in cell-based assays. In parallel, their ability to inhibit other kinases was also assessed. Enzymatic assays have shown that compounds of formula (I) are inhibitors of MNK1 and MNK2 with $IC_{50}$ values in the range of 1000 nM to lower than 10 nM. eIF4e phosphorylation inhibition in Hela cell line was found to have $IC_{50}$s in average 10 time higher than the enzymatic $IC_{50}$s. These cell-based $IC_{50}$s vary from as low as 40 nM to 3 µM.

To further evaluate the therapeutic potential of these bicyclic molecules, their ability to inhibit growth of several tumotype cell lines was assessed. Below are the technical descriptions of these assays.

Enzymatic and Cell-Based eIF4E Phosphorylation Assays and Thermal Shift Assay Biological Methods The compounds described in this invention bind to and inhibit the kinases MNK1 and MNK2. They were analyzed using both in vitro and in vivo assays that are known in the art.

Thermal Shift Assays

Thermal shift assays can be used to monitor the binding of small molecules to proteins by measuring the change in melting temperature that results from an increase in thermal stability of the protein on binding a compound. The thermally induced unfolding of the protein is monitored in the presence of a fluorescent dye, Sypro Orange using a real time PCR system. The innate fluorescence of Sypro Orange is quenched in an aqueous environment; however in a hydrophobic non-polar environment such as the exposed hydrophobic residues of an unfolding protein, the compound fluoresces profusely. This enables the unfolding of proteins to be monitored by measuring an increase in fluorescence. Melting temperature is defined as the temperature at which half the protein is in an unfolded state.

The increase in melting temperature of MNK1 and MNK2 on binding small molecular weight compounds was determined using recombinant full length human enzymes with N-terminal GST tags (glutathione-S-transferase). The proteins were expressed in E. coli and purified on glutathione sepharose using the Profinia Protein Purification System (BioRad, Hercules, Calif.) and the GST tag was removed using PreScission protease. Both recombinant enzymes were diluted in buffer A (10 mM Tris/HCl pH7.5, 50 mM NaCl, 1 mM DTT) to a concentration of 62.5 µM. The compounds to be analyzed were dissolved in 100% DMSO to a final concentration of 100 µM. The reaction mixture consisted of 5 µM enzyme (MNK1 or MNK2), 4 µM compound, 17 µl buffer A and 5 µl of 5× Sypro Orange in a final volume of 25 µl. The thermal analysis was performed on a BioRad CFX96 RTPCR instrument from 20° C. to 90° C. in 0.5° C. increments with a dwell time of 20 s.

The data is analyzed by plotting the fluorescent intensity as a function of temperature. Readings that occur before or after the sigmoidal region of the melt curve are discarded. The fluorescent values are normalized for each compound, 100 for the maximum reading (UL) and 0 for the minimum reading (LL). The curve is fitted to the Boltzmann equation using non-linear regression (GraphPad Prism, GraphPad Software Inc.). The inflection point of the transition curve, $T_m$ (V50) is calculated using the Boltzmann equation:

$$Y=[LL+(UL-LL)]/[1+\exp(T_m-t/\alpha)]$$

Where t=temperature, LL and UL are the minimum and maximum intensities respectively and α is the slope of the curve within $T_m$. The thermal shift is defined as the difference between the melting temperatures in the presence and absence of compound.

In Vitro MNK Kinase Assay

MNK1 and MNK2 inhibitor activity was determined using recombinant kinase domains expressed in E. coli. MNK1 and MNK2 were expressed as GST fusion proteins and the GST tag was removed using PreScission protease. After concentration to 10-15 mg/ml the proteins were flash frozen in liquid nitrogen and stored at −80° C. MNK1 and MNK2 were activated using recombinant ERK2 which was activated using a constitutively active mutant of MEK1, both ERK2 and MEK1 were expressed in E. coli as N-terminally his tagged proteins. Recombinant ERK2 was activated by incubating 11.3 µM of the kinase with 1 µM MEK1 and 100 µM ATP. This reaction mixture was then used immediately for the activation of the MNKs. The activation of the MNK1 was performed by incubating 5.0 µM of MNK1 with 0.3 µM of activated ERK2 and 500 µM ATP at 30° C. for 6 hours. The activation of MNK2 was performed by incubating 50 µM of MNK2 with 3.0 µM of activated ERK2 and 500 µM ATP at 30° C. for 2 hours. The activated MNKs were stored at −20° C. until required for assay.

Kinase assays were performed on the Caliper Life Sciences (Mountain View, Calif.) Microfluidics LabChip® Platform. Enzyme activity is analyzed by 'sipping' reactions from a microtitre plate into LabChip. The data signature is generated by the shift in mobility of non-phosphorylated peptide substrates and phosphorylated products by electrophoresis in the chip and detected by LED induced fluorescence. The magnitude of the fluorescent signal reveals the extent of the reaction. The data is analyzed by calculating the relative heights of the substrate and product peaks and the product/(product+substrate) peak ratio is reported.

The following buffers were used to assay kinase activity:

Reconstitution buffer: 10 mM HEPES/NaOH pH7.5, 0.003% Brij® L23, 0.004% TWEEN® 20.

Substrate buffer: 245 mM HEPES/NaOH pH7.5, 0.003% Brij® L23, 0.004% TWEEN® 20, 26 mM $MgCl_2$.

Termination buffer: 100 mM HEPES/NaOH pH7.3, 0.022% Brij® L23, 5.6% DMSO, 0.16% CR3, 11.2 mM EDTA pH8.0.

Separation buffer: 100 mM HEPES/NaOH pH7.3, 0.02% Brij® L23, 5% DMSO, 0.1% CR3, 1 mM EDTA pH8.0.

```
Peptide substrate (JH3):
  5-FAM-TATKSGSTTKNRFVV-CONH2.
```

The MNK1 assay was performed by adding 65 nM of activated MNK1 and 1 µl of test compound to a microtitre plate in a volume of 15 µl of reconstitution buffer. The plate was incubated at 22° C. for 15 minutes before the addition of 3.9 µM of JH3 and 3.12 mM ATP in 10 µl of substrate buffer and a further incubation period of 60 minutes at 28° C. The reaction was stopped by the addition of 45 µl of termination buffer. The final concentration of MNK1, JH3 peptide, ATP and compound in a 26 µl assay volume was 40 nM, 1.5 µM, 1.2 mM, and 1× respectively.

The MNK2 assay was performed by adding 32.5 nM of activated MNK1 and 1 µl of test compound to a microtitre plate in a volume of 15 µl of reconstitution buffer. The plate was incubated at 22° C. for 15 minutes before the addition of 3.9 µM of JH3 and 650 µM ATP in 10 µl of substrate buffer and a further incubation period of 60 minutes at 28° C. The reaction was stopped by the addition of 45 µl of termination buffer. The final concentration of MNK2, JH3 peptide, ATP and compound in a 26 µl assay volume was 20 nM, 1.5 µM, 250 µM, and 1× respectively.

Inhibition constants ($IC_{50}$) were determined by plotting kinase activity versus log compound concentration and fitting with a non-linear regression algorithm using GraphPad Prism (GraphPad Software Inc.).

MNK Cell-Based Assay

It has been reported that Ser209 of eIF4E is solely phosphorylated by the MNK enzymes. The ability of compounds to inhibit this process in Hela cells was investigated using the AlphaScreen SureFire® assay platform from Perkin Elmer (Waltham, Mass.). eIF4E phosphorylated on Ser209 is recognized by two antibodies, the first which is fused to a streptavidin coated donor bead binds to an epitope away from Ser209, the second which is fused to a protein A conjugated acceptor bead binds to phosphorylated Ser209. The phosphorylation of eIF4E on Ser209 brings the two antibodies into close proximity and when excited by a laser a singlet oxygen is released by the donor bead which excites the acceptor bead resulting in the emission of light. This enables the monitoring of eIF4E Ser209 phosphorylation and its inhibition in a cellular context.

Hela cells were seeded into microtitre plates (30,000 cells per well) in 100 µl of culture medium and incubated at 37° C. for 24 hours. The media was then removed by aspiration and the cells resuspended in 50 µl of serum free medium containing the test compound and incubated at 37° C. for 2 hours. The culture medium was again removed by aspiration and the cells resuspended in lysis buffer (provided in Perkin Elmer SureFire® Assay Kit). After agitation at 350 rpm for 20 minutes at 22° C., 4 µl was transferred to a 384 well OptiPlate™ (Perkin Elmer, Waltham, Mass.). To each well was added 5 µl of acceptor mix; the plate was sealed and agitated gently at 22° C. for 2 hours. Then, in subdued light, 2 µl of donor mix was added to each well, the plate was sealed, wrapped in aluminum foil and agitated gently at 22° C. for 2 hours. Emission was measured using the EnVision® plate reader (Perkin Elmer, Waltham, Mass.).

Inhibition constants ($IC_{50}$) were determined by plotting AlphaScreen signal versus log compound concentration and fitting with a non-linear regression algorithm using GraphPad Prism (GraphPad Software Inc.).

Cell Cytoxicity Assays

Methodology:

Cancer cell lines, MV-4-11 (leukemia), P116.c139 (acute T cell leukemia) and D1.1 (acute T cell leukemia), were purchased from ATCC and cultured according to supplier's recommendations. K562 cells (myelogenous leukemia) over-expressing eIF4E, were also used for the cytotoxicity assay. For cells treated for 48 hours, 5000 cells were seeded in 70 µl of growth medium in black, flat-bottom 96-well plate. For cells treated for six days, 1000 cells were seeded in 70 µl of growth medium in black, flat-bottom 96-well plate. The compounds, Cercosporamide, Example 176 (ETC-7114), Example 175 (ETC-7117), Example 133 (ETC-7165) and Example 62 (ETC-7168), were treated with doses ranging from 0.003 µM to 50 µM. 50 µl of the diluted compounds were added to the cells and incubated at 37° C. in 5% $CO_2$. After 48 hours or six days treatment, cell viability was determined by CellTiter-Glo Luminescent Cell Viability Assay (Promega, Madison, Wis.). 120 µl of the reagent was added to the cells and luminescence was measured using Tecan Safire Reader. Data was analysed with Graphpad Prism software and the figures represented indicate the half maximal inhibitory concentration ($IC_{50}$). Error bars denote standard deviation (SD).

Results:

TABLE 1

| | $IC_{50}$ (µM) after 48 hours of treatment | | | |
|---|---|---|---|---|
| | K562 | MV-4-11 | D1.1 | P116.c139 |
| Cercosporamide | >50 | >50 | 20.2 | >50 |
| ETC-7114 Example 176 | 14.2 | 1.0 | 1.0 | 0.4 |
| ETC-7117 Example 175 | 18.2 | 0.9 | 12.3 | 12.5 |
| ETC-7165 Example 133 | 23.0 | 2.8 | 15.8 | 10.9 |
| ETC-7168 Example 62 | 7.5 | 0.8 | 1.6 | 0.8 |

TABLE 2

| | $IC_{50}$ (µM) after 6 days of treatment | | | |
|---|---|---|---|---|
| | K562 | MV-4-11 | D1.1 | P116.c139 |
| Cercosporamide | 4.3 | 4.0 | 17.3 | 4.9 |
| ETC-7114 Example 176 | 3.4 | 0.4 | 0.8 | 0.1 |
| ETC-7117 Example 175 | 21.2 | 0.3 | 10.1 | 5.7 |
| ETC-7165 Example 133 | 16.0 | 1.5 | 11.2 | 4.0 |
| ETC-7168 Example 62 | 3.1 | 0.2 | 1.7 | 0.3 |

Discussion:

Generally, the $IC_{50}$ is lower in cells treated for 6 days than in the cells treated for 48 hours. Amongst the three test cell lines, the MV-4-11 cell line is the most sensitive to all test compounds.

Amongst the four compounds, Example 176 (ETC-7114 and Example 62 (ETC-7168) are the most cytotoxic. The $IC_{50}$ of example 176 (ETC-7114) and Example 62 (ETC-7168) is ≤1 µM and ≤2 µM, respectively, in the three test cell lines, regardless of the treatment duration. The $IC_{50}$ of example 176 (ETC-7114) and Example 62 (ETC-7168) in K562 cells over-expressing eIF4E were reduced by more than half when treatment duration was extended to 6 days. These data suggest that the cytotoxic effects of Example 176 (ETC-7114) and Example 62 (ETC-17168) are probably non-cell line specific.

The treatment duration affects the cytotoxic effects of compounds Example 175 (ETC-7117) and Example 133 (ETC-7165) in the test cell lines. The extended treatment duration from 48 hours to 6 days could decrease the $IC_{50}$ by more than half-fold in P116.c139 cells. However, the $IC_{50}$ of example 175 (ETC-7117) and example 133 (ETC-7165) in K562 cells over-expressing eIF4E and in D1.1 cells was not influenced by the treatment duration. These data suggests that the cytotoxic effects of Example 175 (ETC-7117) and Example 133 (ETC-7165) are probably more cell line specific.

Immunofluorescence and Serial Replating Assays

Methods

Cord Blood (CB) samples were purchased from the Singapore Cord Blood bank. CML samples were the Sin gapore General Hospital after signed informed consent under local IRB-approved procedures. MNCs were obtained using Ficoll separation, and CD34+ cells selected by immunomagnetic beads (Miltenyi Biotech, Germany).

Cell Culture and Generation of Cell Lines

K562 cell line was obtained from the ATCC, and grown in RPMI supplemented with 10% FCS, L-glutamine, and penicillin/streptomycin.

Serial Replating Assay

CD34-enriched CB and BC cells were thawed and allowed to recover overnight in serum-free StemPro media (Invitrogen, Carlsbad, Calif.), supplemented with human growth factors and 1× nutrient supplement (Invitrogen). Cells were then subjected to drug treatment for 48 hr, harvested, washed, and seeded in methylcellulose (H4434, STEMCELL Technologies, Canada). Colonies were enumerated after 2 weeks, individually picked, and replated in fresh methylcellulose in a 96-well format, and counted at 2 weeks. Three rounds of serial replating (representing >8 weeks in culture) were performed.

Immunofluorescence Analysis

Cells ($1\times10^5$) were cytospun onto glass slides, fixed with 4% paraformaldehyde, and stained with mouse monoclonal antibodies against activated β-catenin (clone 8E7, Millipore, UK), or rabbit monoclonal antibodies against phospho-eIF4E S209 (EP2151Y, Abcam, UK). Slides were then stained with either PE-conjugated anti-mouse or FITC-conjugated anti-rabbit antibodies. Images were obtained with the use of a fluorescence microscope (Olympus IX71S1F3) at 40× magnification.

Western Blotting

Figure 2:
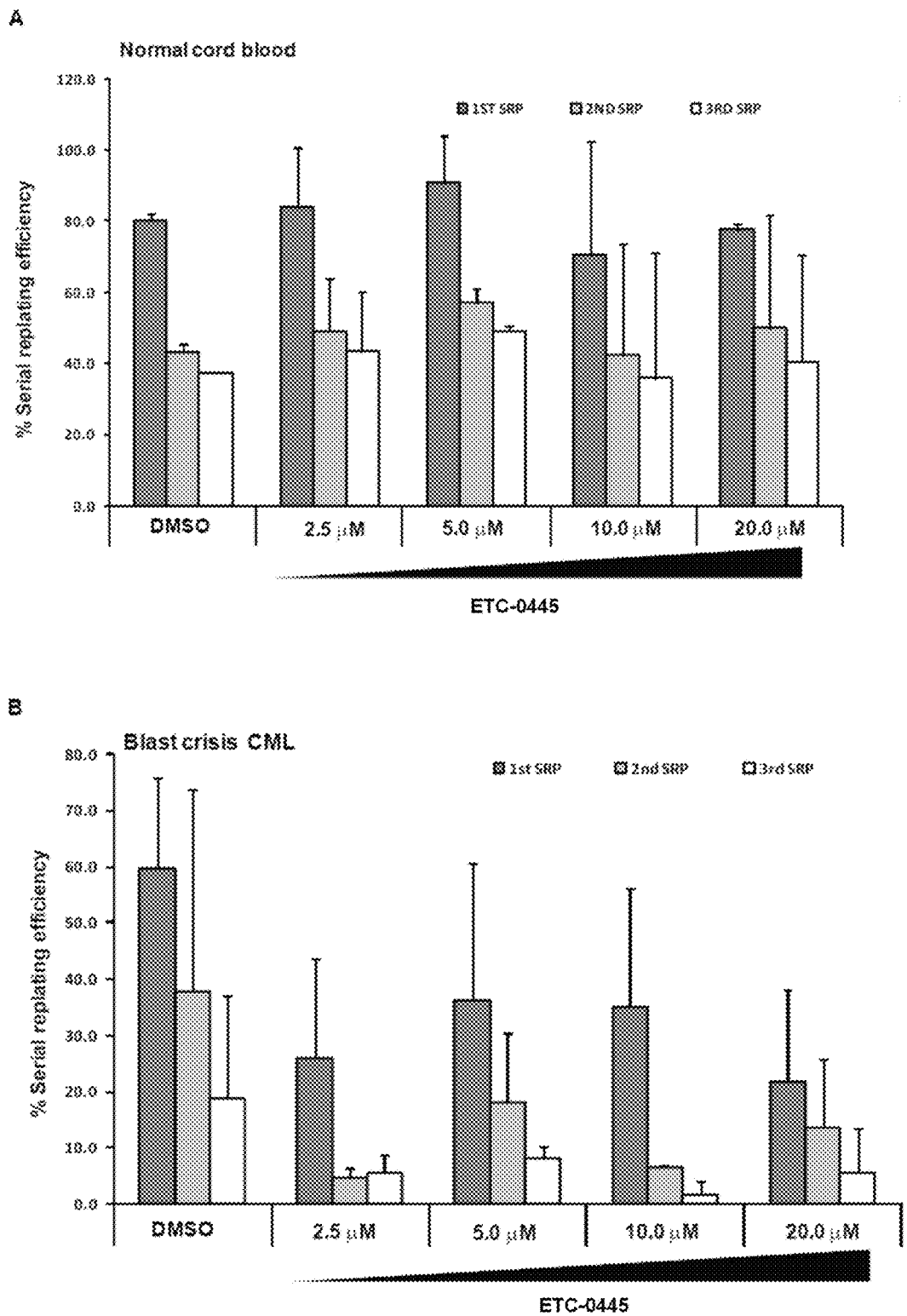
FIG. 2 shows the effects of Example 6 (ETC-0445-3), Example 1 (ETC-5336), and Example 2 (ETC-6740) on serial replating efficiency of BC-CML primary cells. Colony forming and serial replating assays were performed on normal and BC-CML primary samples. CD34+ cells from (A) cord blood and (B-D) BC CML cells were treated with compounds for 48 hr. Forty-eight hours post drug treatment, $1 \times 10^4$ cells were plated for colony-forming cell (CFC) assay; colonies were enumerated and individually picked for serial replating. The serial replating efficiency was assessed by the ability of individual clones to replate to the third plating over 8 weeks and displayed as percentage relative to the first colony forming assay readout.
Figure 2:
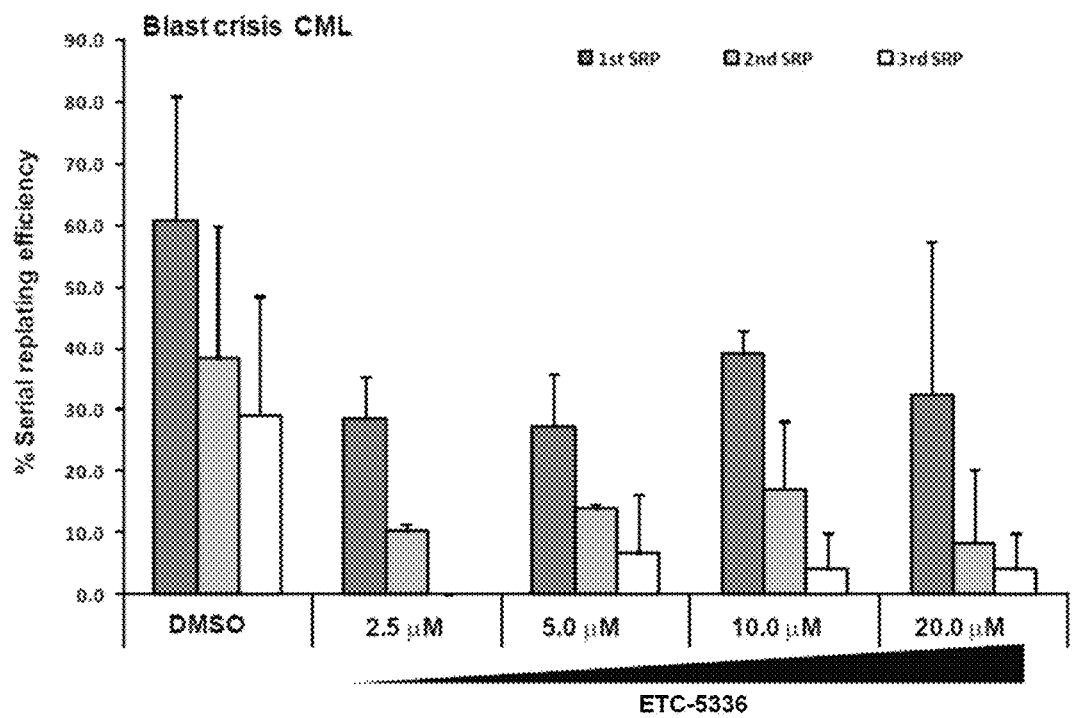
Figure 2:
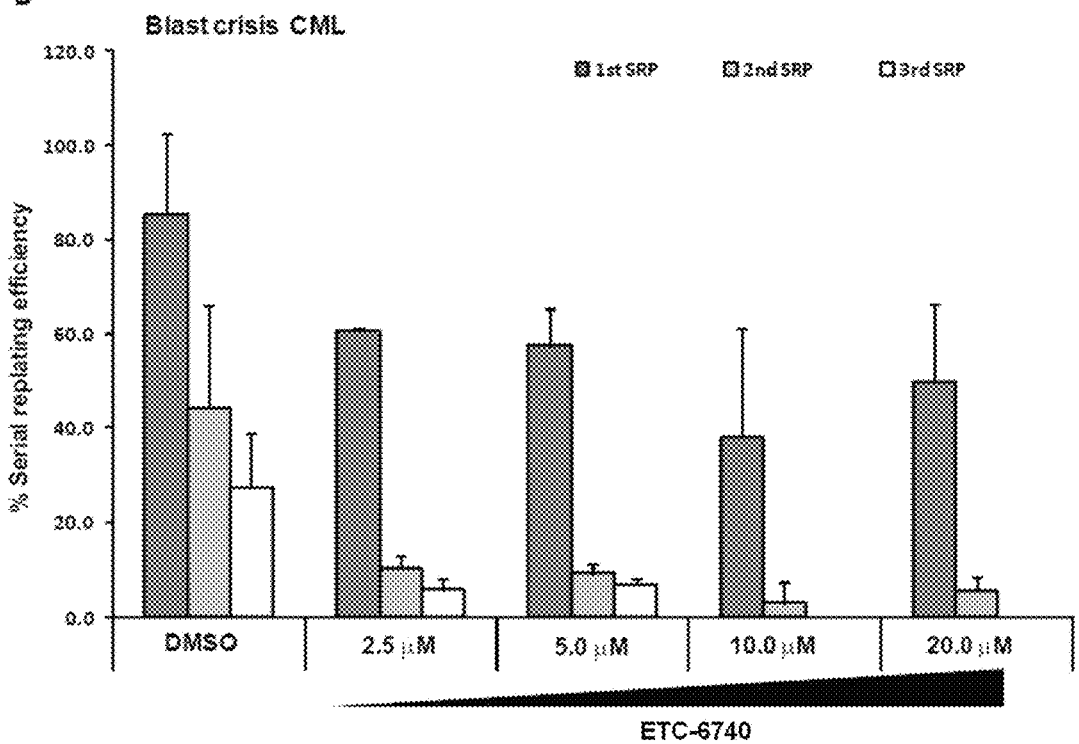
Figure 3:
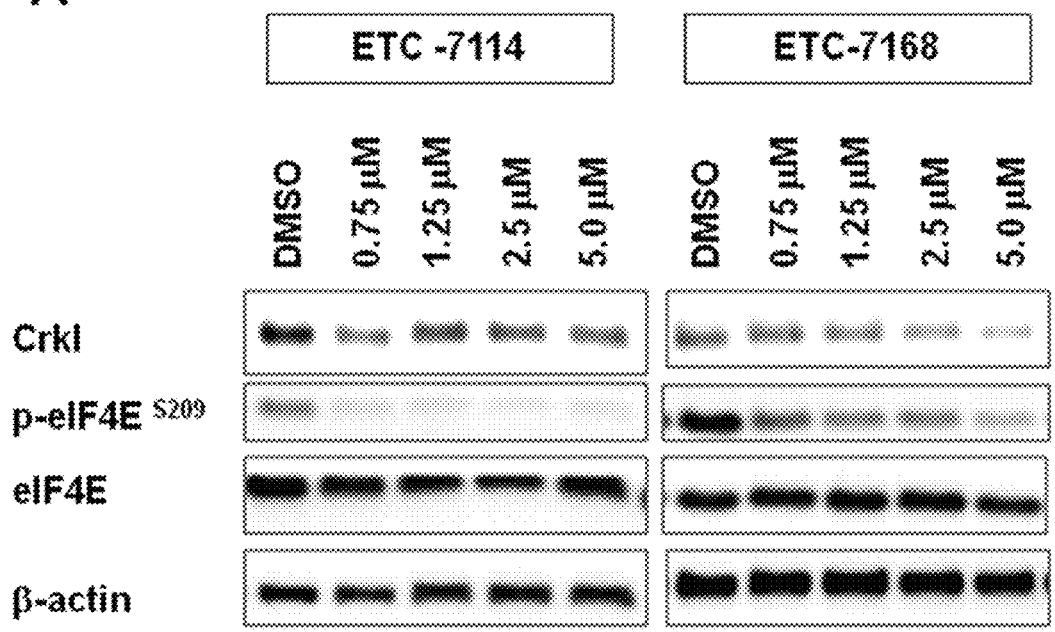
FIG. 3 demonstrates that Example 176 (ETC-7114) and Example 62 (ETC-7168) prevent eIF4E phosphorylation in BC-CML cell line. (A) Western blot analysis of K562 cell line treated with various concentration of compounds for 24 h. Samples from BC-CML patients were treated with various compounds for 24 h. 24 hours post drug treatment, cells were harvested for immunofluorescence analysis for nuclear active beta-catenin and phosphor-eIF4E level.
Figure 3:
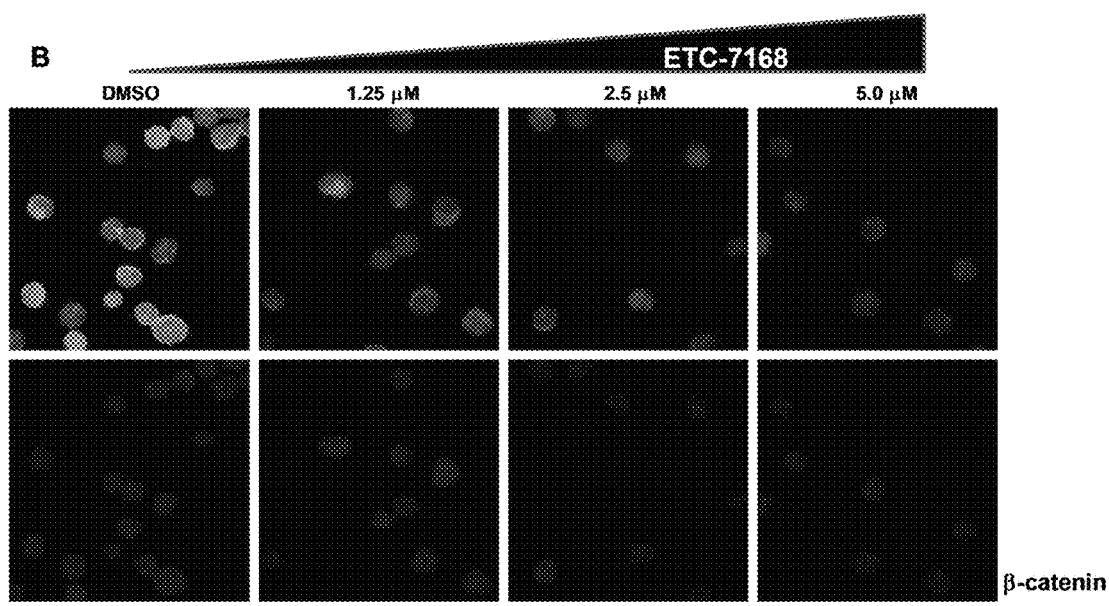
Figure 3:
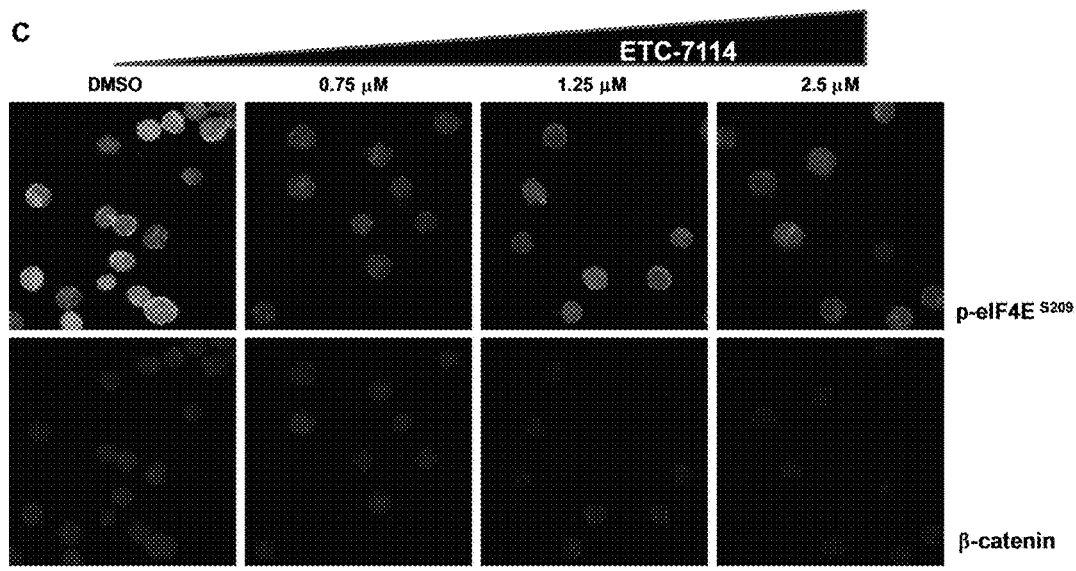
Figure 4:
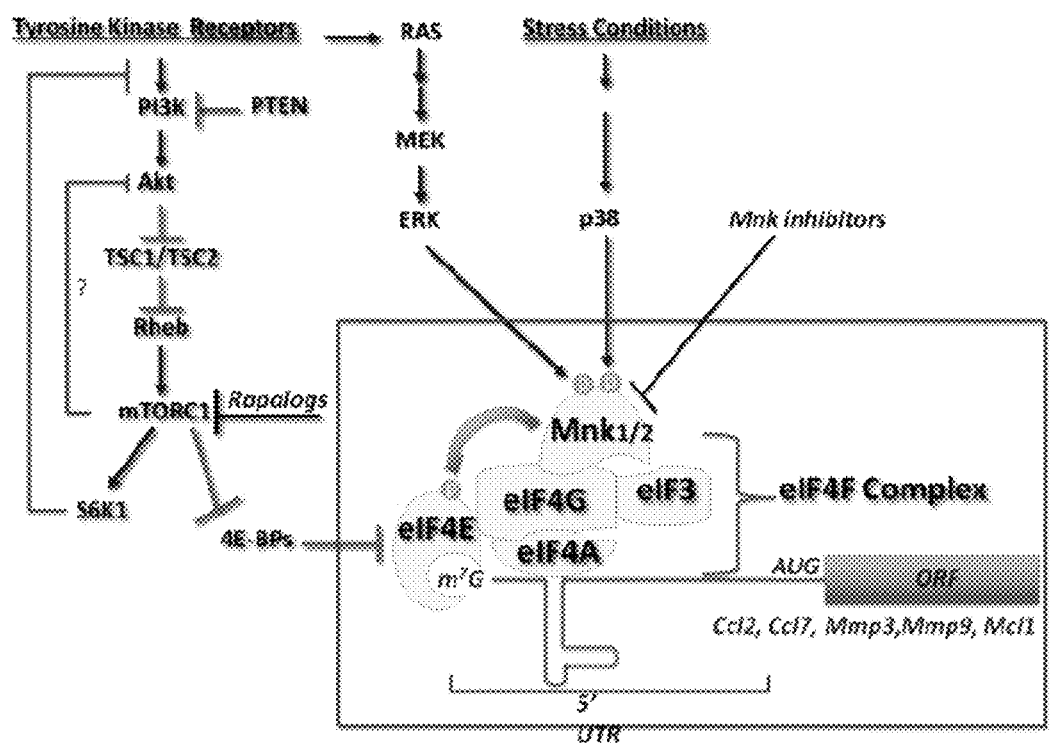
FIG. 4 shows the pathway connection between MNK and mTOR (PNAS 2010, 107 (32), 13975-13976).

Exponentially growing cells were plated at $2\times10^5$ cells/ml, and whole cell lysate processed for western blot analysis using antibodies recognizing eIF4E, phospho-eIF4E (Cell signaling Technology), Discussion As shown in FIG. 1A, treatment of K562 cells with increasing concentration of drugs causes a dose dependent decrease in eIF4E phosphorylation. Similar to what was observed in BC-CML cell lines, we showed that treatment of BC-CML primary cells with increasing dose of drugs also resulted in a dose dependent decrease in eIF4E phosphorylation as well as active beta-catenin (FIG. 1B-D). The functional consequence of decrease beta-catenin as well as eIF4E phosphorylation on the self renewal capacity of BC leukemia stem cells (LSCs) was assessed next. We performed a serial replating assay as previously described [4]. Importantly, the serial replating assay has been found to correlate well with beta-catenin-driven self-renewal in BC-GMPs, and also the in vivo serial-transplanting ability of a variety of fusion-gene driven LSCs [5]. Using normal CB CD34+ cells, we found that control treated cells were capable of serial replating up to three times (equivalent to >8 weeks in vitro). We also found that treatment with Example 6 (ETC-0445) did not significantly alter the serial replating efficiency compared to DMSO (FIG. 2A). In contrast, for CD34+ BC cells, treatment with increasing dose of Example 6 (ETC-0445) and Example 1 (ETC-5336) retards the serial replating efficiency as compared to DMSO (FIGS. 2B and 2C). Treatment of CD34+ BC cells with increasing dose of Example 2 (ETC-6740) not only retards serial replating efficiency, at 10.0 μM and 20.0 μM, it potently impaired the ability of BC cells to serial replate (FIG. 2D).

Behavioral and Biochemical Assays in Mouse Model for Autism

Methods

For biochemical analyses mice were sacrificed by $CO_2$ inhalation, the cerebellum dissected and rapidly placed in a vibratome chamber and sectioned at 300 μm in cold oxygenated aCSF (in mM: 125 NaCl, 2.5 KCl, 1 $MgCl_2$, 2 $CaCl_2$, 1.25 $NaH_2PO_4$, 20 Glucose, 26 $NaHCO_3$, 95% $O_2$/5% $CO_2$). Slices obtained were maintained at 33° C. in oxygenated aCSF and treated with 40 μM CGP57380 or 50 nM ETC7168 for 45 mins and tissues were subsequently snap frozen in liquid nitrogen. Tissues were lysed in 25 mM Tris-HCl, 150 mM NaCl, 1% Triton, 0.2% SDS, 5 mM EDTA, 2 mM DTT, 1 mM NaF, 1 mM $Na_3VO_4$ containing protease inhibitor cocktail. The soluble fractions were analyzed by immunoblotting with primary antibodies for 24 hrs at 4° C. followed by detection with secondary antibodies for enhanced chemoluminescent detection. Impact of MNK inhibitors on autism-related behavior was tested in a knock-out mouse model for autism. Nlgn3 knock-out mouse model a human mutation identified in patients with autism[73-74]. Compounds were applied in DMSO using intraperitoneal injection in adult male mice (2-4 months of age). Two injections were performed, the first 30 h and a second one 5 h before testing. Behavioral testing was performed using a well-accepted test for autism that consists of quantitative analysis of ultrasonic vocalizations emitted by male mice exposed to females in estrous[75]. The apparatus consisted of an arena (40 cm×20 cm) surrounded by 30-cm-high walls made of grey plastic and equipped with a microphone and a video camera. Prior to testing, the estrous cycle of each female mouse was assessed and only females in estrous were kept for testing. Male mice were acclimatized for 3 min in the chamber. Subsequently a female in estrous was introduced in the arena, and ultrasonic vocalizations were recorded for 3 min using the Avisoft system (Avisoft Bioacoustics) with a frequency bandwidth of 30 kHz to 100 kHz. The number and length of ultrasonic vocalizations were quantified. All animal experiments were approved by the cantonal veterinary office Basel-Stadt, Switzerland.

Discussion

Figure 5:
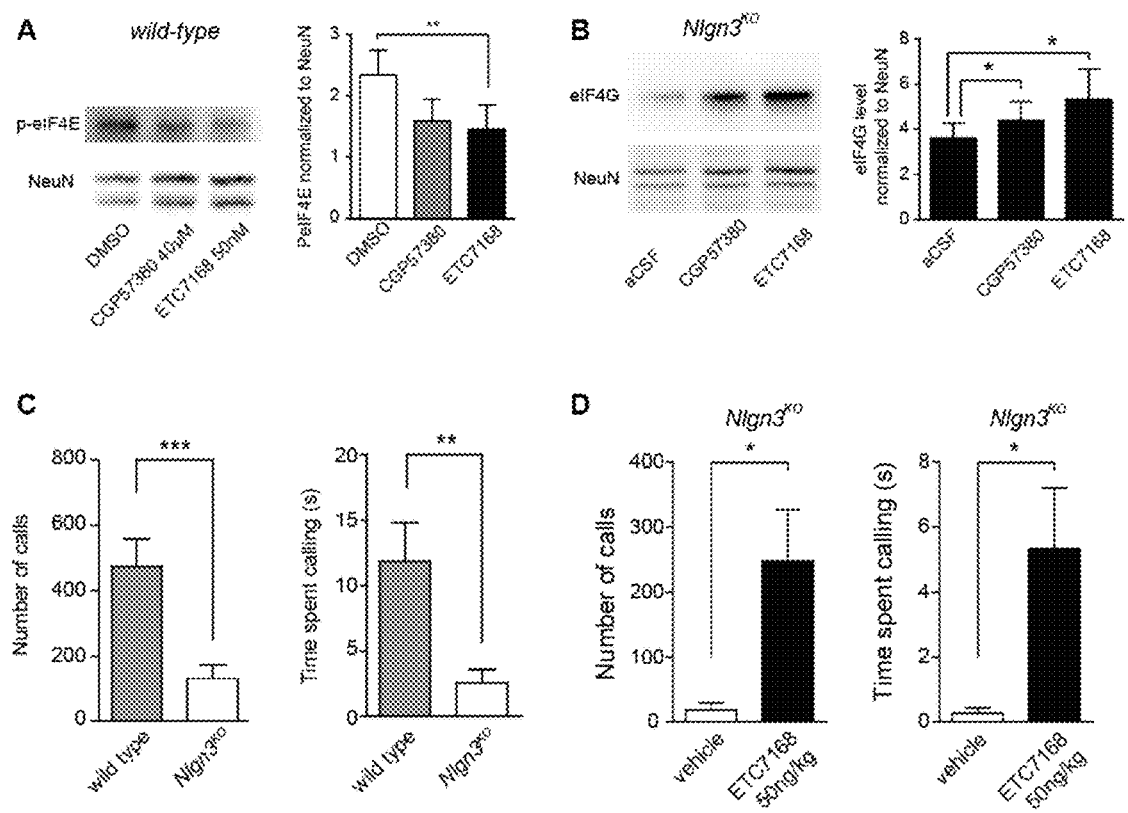
FIG. 5 demonstrates that Example 62 (ETC-7168) modifies eIF4E/eIF4G proteins and improves autism-relevant behavior in mice. (A) Brain slices derived from the mouse cerebellum were treated with CGP57380 or ETC-7168. One hour after treatment, phospho-eIF4E levels were assessed by immuno-blotting with eIF4E-phospho-Ser209 specific antibodies. (B) Brain slices from Nlgn3 knock-out mice were treated with CGP57380 or ETC-7168. One hour after treatment, eIF4G levels were assessed by immunoblotting. Both inhibitors elevated eIF4G levels in mouse cerebellar tissue. (C) Nlgn3 knock-out mice were tested in ultrasonic vocalization assays. Male mice were exposed to females in estrous and ultrasonic vocalizations recorded. Nlgn3 knock-out mice emit fewer calls and spend overall shorter time calling. (D) Nlgn3 knock-out male mice were intraperitonally injected with 50 microgram/kg of ETC-7168 30 hours before testing and a second time 5 hours before testing. Quantification of the number of ultrasonic vocalization calls and the time spent calling in response to a female in estrous was quantified.

As shown in FIG. 5A ECT7168 and the less specific CGP57380 inhibit eIF4E phosphorylation in cerebellar neurons in brain sections. Moreover, both Mnk inhibitors result in an elevation in eIF4G levels in brain sections from Nlgn3 knock-out mice (FIG. 5B). This highlights the possibility to modify eIF4F translation initiation complex function in brain cells by pharmacological inhibition with the novel compounds. The ability of ETC7168 to modify autism-related behaviors in mice was assessed using an ultrasonic vocalization assay. FIG. 5C demonstrates that Nlgn3 knock-out mice emit fewer ultrasonic vocalizations and spend less time calling. This represents a recognized autism-related behavioral phenotype in rodents. FIG. 5D demonstrates that treatment of Nlgn3 knock-out mice with 50 microgram/kg ETC7168 results in a robust elevation of ultrasonic vocalizations. Thus, there is a substantial amelioration of the autism-related phenotype.

Pharmacokinetics Assays
TABLE 3
Pharamacokinetics of Exemplified Compounds.
| Entry | Chemical Structure | Plasma Cmax (ng/mL) | Plasma AUC last (hr·ng/mL) | Plasma AUC inf (hr·ng/mL) | Plasma Tmax (hr) | Plasma T½ (hr) |
|---|---|---|---|---|---|---|
| 1 | 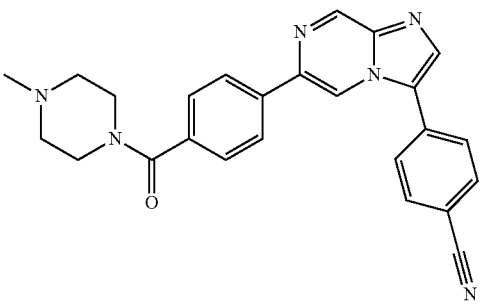 [SMILES: CN1CCN(C(=O)c2ccc(-c3cn4c(-c5ccc(C#N)cc5)cnc4cn3)cc2)CC1] | 2667 | 7423 | 7443 | 0.25 | 3.02 |
| 2 | 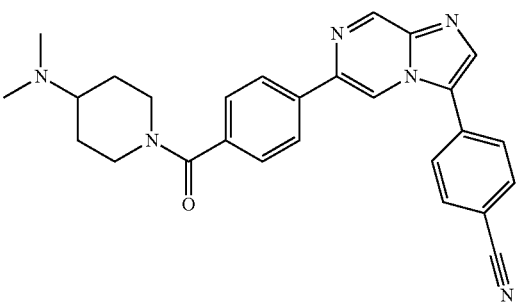 [SMILES: CN(C)C1CCN(C(=O)c2ccc(-c3cn4c(-c5ccc(C#N)cc5)cnc4cn3)cc2)CC1] | 227 | 527 | 536 | 0.25 | 2.06 |
| 3 | 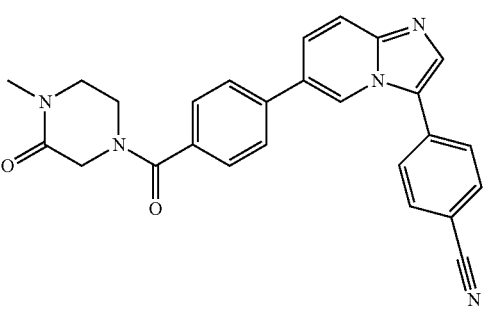 [SMILES: CN1CCN(C(=O)c2ccc(-c3ccc4ncc(-c5ccc(C#N)cc5)n4c3)cc2)CC1=O] | 3163 | 4124 | 4193 | 0.25 | 2.51 |
| 4 | 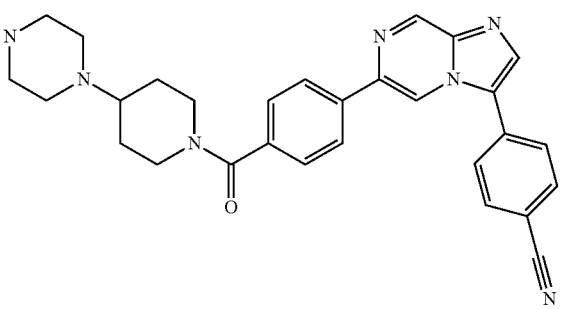 | 223 | 614 | 632 | 0.25 | 2.38 |

TABLE 3-continued

Pharamacokinetics of Exemplified Compounds.

| Entry | Chemical Structure | Plasma Cmax (ng/mL) | Plasma AUC last (hr·ng/mL) | Plasma AUC inf (hr·ng/mL) | Plasma Tmax (hr) | Plasma T½ (hr) |
|---|---|---|---|---|---|---|
| 5 | 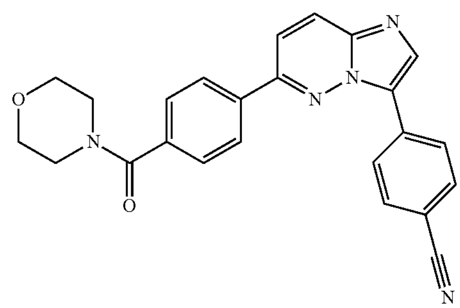 [SMILES: N#Cc1ccc(-c2cnc3ccc(-c4ccc(C(=O)N5CCOCC5)cc4)nn23)cc1] | 13384 | 74665 | 76457 | 0.5 | 4.33 |
| 6 | 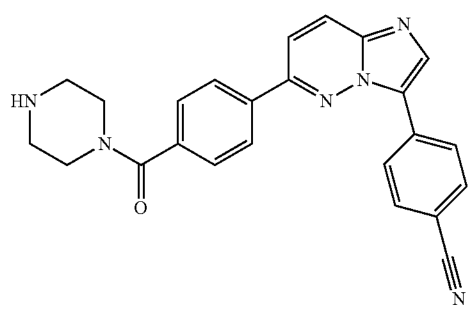 [SMILES: N#Cc1ccc(-c2cnc3ccc(-c4ccc(C(=O)N5CCNCC5)cc4)nn23)cc1] | 275 | 350 | 359 | 0.25 | 1.59 |
| 7 | 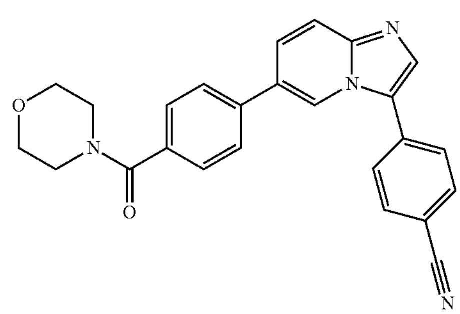 | 7356 | 25986 | 26028 | 0.25 | 2.94 |
| 8 | 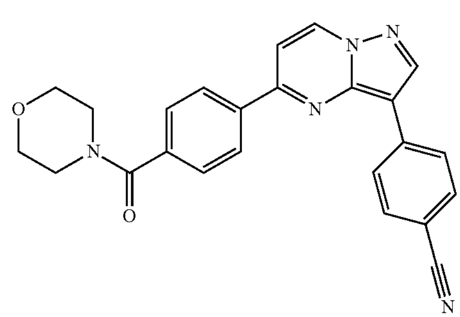 [SMILES: N#Cc1ccc(-c2cnn3ccc(-c4ccc(C(=O)N5CCOCC5)cc4)nc23)cc1] | 5968 | 54848 | 55149 | 0.5 | 2.78 |

TABLE 3-continued

Pharamacokinetics of Exemplified Compounds.

| Entry | Chemical Structure | Plasma Cmax (ng/mL) | Plasma AUC last (hr·ng/mL) | Plasma AUC inf (hr·ng/mL) | Plasma Tmax (hr) | Plasma T½ (hr) |
|---|---|---|---|---|---|---|
| 9 | 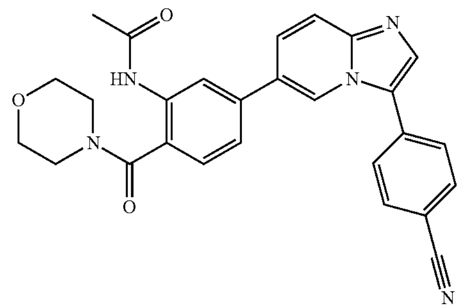 [SMILES: CC(=O)Nc1cc(-c2ccc3ncc(-c4ccc(C#N)cc4)n3c2)ccc1C(=O)N1CCOCC1] | 3858 | 5715 | 5725 | 0.25 | 1.47 |
| 10 | 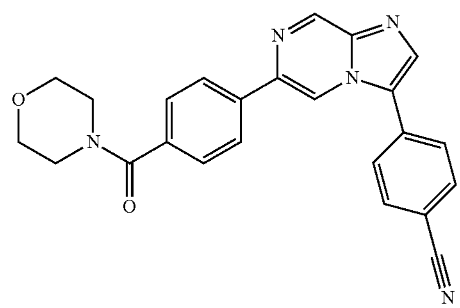 [SMILES: N#Cc1ccc(-c2cnc3cnc(-c4ccc(C(=O)N5CCOCC5)cc4)cn23)cc1] | 6397 | 12687 | 12755 | 0.5 | 1.11 |

TABLE 4

Pharmacokinetics of Exemplified Compounds.

| Entry | Chemical Structure | Brain Cmax (ng/g) | Brain AUC last (hr·ng/g) | Brain AUC inf (hr·ng/g) | Brain Tmax (hr) | Brain T½ (hr) | Plasma/Brain Ratio |
|---|---|---|---|---|---|---|---|
| 1 | 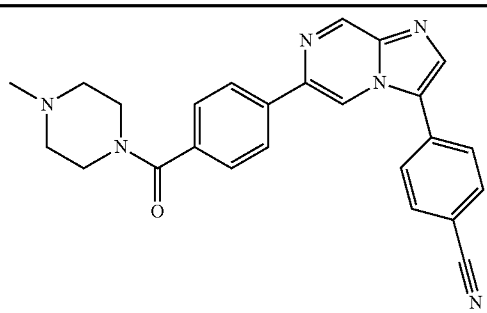 | 290 | 520 | 625 | 0.5 | 1.39 | 0.07 |
| 2 | 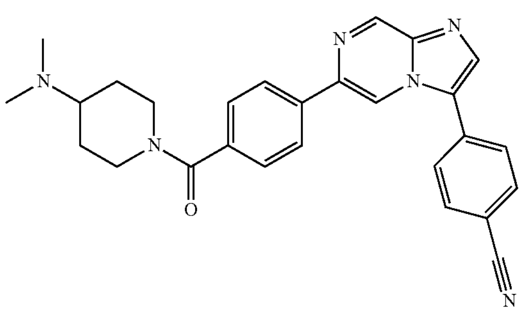 [SMILES: CN(C)C1CCN(C(=O)c2ccc(-c3cn4c(-c5ccc(C#N)cc5)cnc4cn3)cc2)CC1] | 14.6 | 71 | 99 | 0.25 | 4.11 | 0.13 |

TABLE 4-continued
Pharmacokinetics of Exemplified Compounds.
| Entry | Chemical Structure | Brain Cmax (ng/g) | Brain AUC last (hr·ng/g) | Brain AUC inf (hr·ng/g) | Brain Tmax (hr) | Brain T½ (hr) | Plasma/ Brain Ratio |
|---|---|---|---|---|---|---|---|
| 3 | 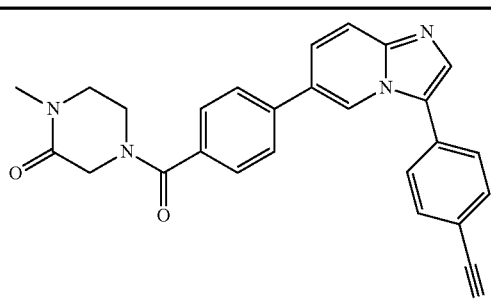 | 77.78 | 59 | 77 | 0.25 | 0.96 | 0.01 |
| 4 | 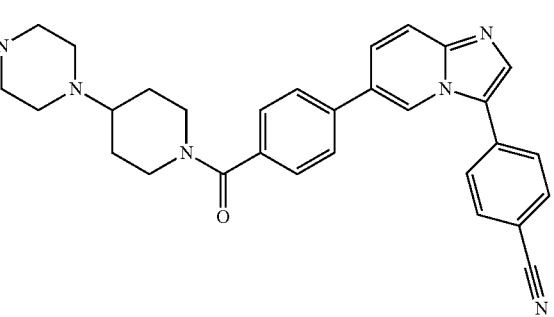 | 20 | 184 | nc | 8 | nc | 0.3 |
| 5 | 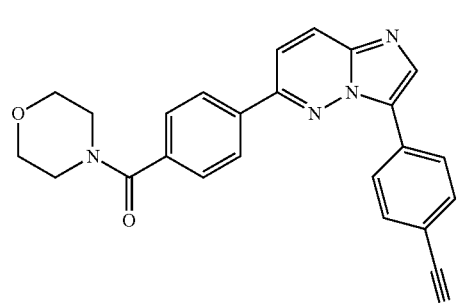 | 1724 | 8811 | 8951 | 0.5 | 4.28 | 0.12 |
| 6 | 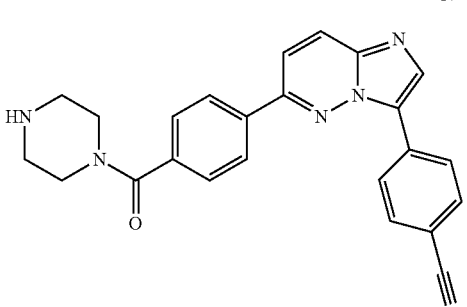 | 10 | 17 | nc | 0.25 | nc | 0.05 |
| 7 | 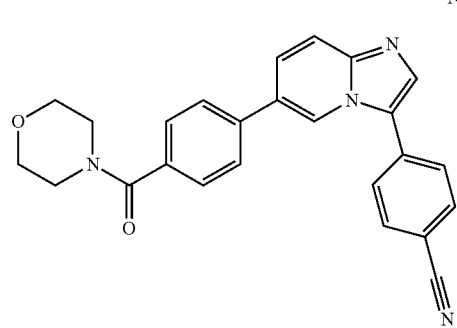 | 678 | 2474 | 2516 | 1 | 2.05 | 0.1 |

TABLE 4-continued

Pharmacokinetics of Exemplified Compounds.

| Entry | Chemical Structure | Brain Cmax (ng/g) | Brain AUC last (hr·ng/g) | Brain AUC inf (hr·ng/g) | Brain Tmax (hr) | Brain T½ (hr) | Plasma/ Brain Ratio |
|---|---|---|---|---|---|---|---|
| 8 | 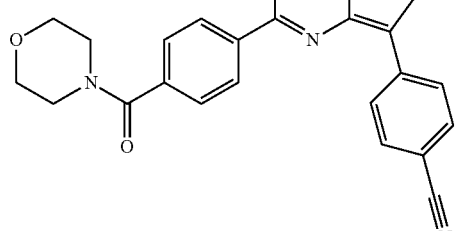 | 3967 | 29166 | 29267 | 2 | 2.63 | 0.53 |
| 9 | 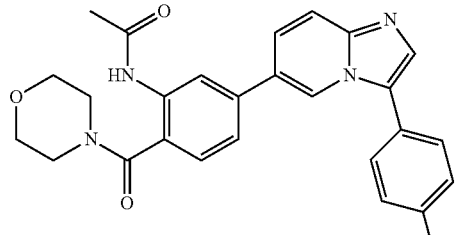 | 106 | 156 | 161 | 0.5 | 0.76 | 0.03 |
| 10 | 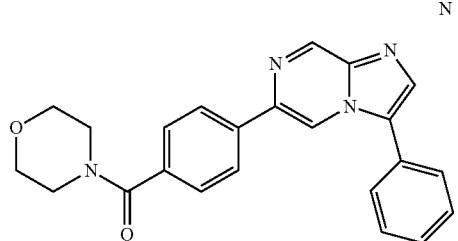 | 469 | 754 | 775 | 1 | 0.69 | 0.06 |

Treatment of K562 cells with of Example 176 (ETC-7114) or Example 62 (ETC-7168) cause a decrease in eIF4E phosphorylation (FIG. 1A); in addition to inhibition of eIF4E phosphorylation, a decrease in BCR-ABL activity is observed, as demonstrated by the decrease in phosphorylation of CrK1, an in vivo substrate of BCR-ABL[79-80]. The decrease in eIF4E phosphorylation is also accompanied by the decrease in nuclear beta-catenin accumulation as demonstrated using immunofluorescence analysis (FIGS. 1B and C).

Synthetic Examples

The following examples serve to illustrate the invention without limiting the scope thereof.

Abbreviations

CAN: acetonitrile
AcOEt: ethyl acetate
AcOH: acetic acid
AUC: area under the curve
Brine: saturated solution of NaCl in water
cat.: catalyst
d: day(s)
DCM: dichloromethane
DIEA: diisopropyl-ethyl-amine
DMF: N,N-dimethylformamide
DMSO: dimethylsulfoxide
DMSO-$d_6$: per-deuterated dimethylsulfoxide
dppf: 1,1'-Bis(diphenylphosphino)ferrocene
EDCI: 1-ethyl-3-(3-dimethylaminopropyl)carbodiimide)
Ether: diethylether
EtOH: ethanol
h: hour(s)
HATU: 2-(1H-7-Azabenzotriazol-1-yl)-1,1,3,3-tetramethyl uronium hexafluorophosphate Methanaminium
HBTU: O-Benzotriazole-N,N,N',N'-tetramethyl-uronium-hexafluoro-phosphate
hOBt: N-Hydroxybenzotriazole
HPLC: high pressure liquid chromatography
L: liter(s)
LC-MS: Liquid chromatography-mass spectrometry Me: methyl
MeOH: methanol
min: minute(s)
m.p.: melting point
MS: mass spectrometry
NBS: N-Bromosuccinimide
NEt$_3$: triethylamine
NIS: N-iodosuccinimide
NMM: N-methylmorpholine
NMR: Nuclear Magnetic Resonance
Pd(dppf)Cl$_2$: [1,1'-Bis(diphenylphosphino)ferrocene]dichloropalladium(II)
rt: room temperature
THF: tetrahydrofuran
TFA: trifluoroacetic acid
TLC: thin layer chromatography Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example those described by Larock, R. C., Comprehensive Organic Transformations, VCH publishers, (1989), which is hereby incorporated by reference in its entirety.

Formula 2

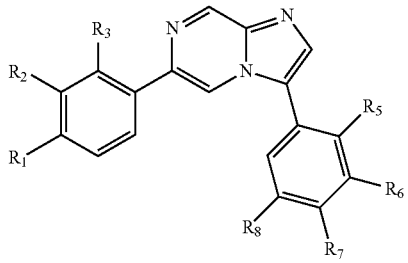

General Procedure A

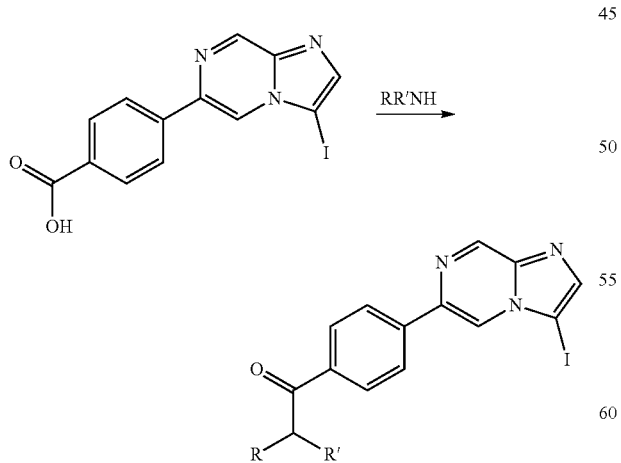

To a solution of 4-(3-iodoimidazo[1,2-a]pyrazin-6-yl) benzoic acid, N-methylmorpholine and HATU in DMF, was added the desired amine (RR'NH) and the resulting mixture was stirred for 10 h under nitrogen atmosphere. The reaction mixture was poured onto ice water and the precipitate was isolated by filtration and dried to afford the desired amide used as such or purified as indicated.

General Procedure B

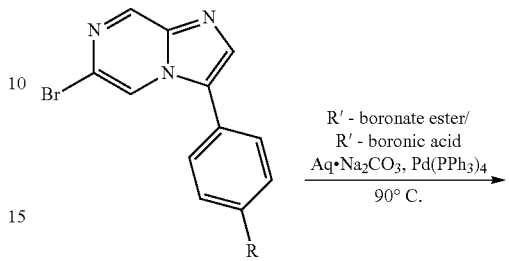

R' - boronate ester/
R' - boronic acid
Aq·Na$_2$CO$_3$, Pd(PPh$_3$)$_4$
90° C.

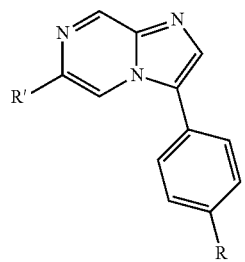

R = CONH$_2$
R = CN

To a solution of the halogenetated bicyclic derivative in 1,4-dioxane was added the boronic acid or the boronate ester derivative, K$_3$PO$_4$ and water and Pd(PPh$_3$)$_4$. The reaction mixture was heated at 90° C. for 12 h under argon atmosphere then, was filtered through celite and concentrated under reduced pressure. The residue was purified by flash column chromatography to afford the desired product.

Intermediate 1

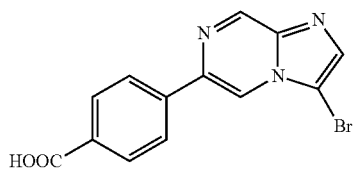

Intermediate 2

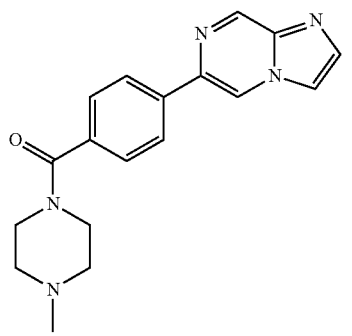

Intermediate 3

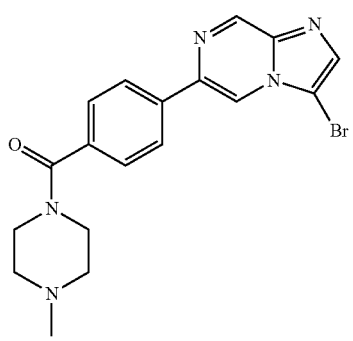

Intermediate 4

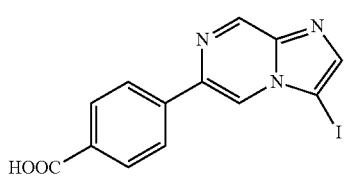

Intermediate 5

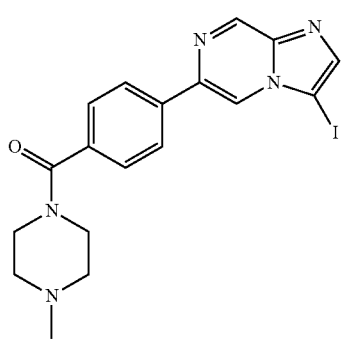

Intermediate 6

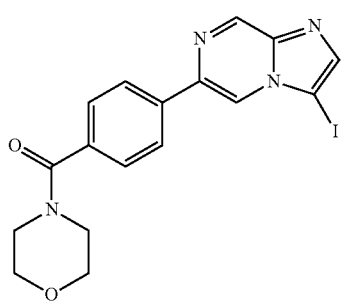

Intermediate 7

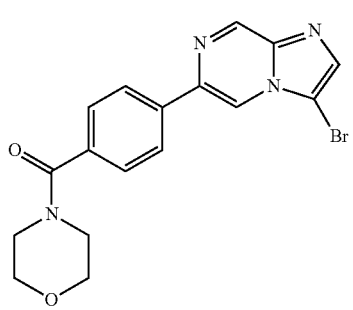

Intermediate 8

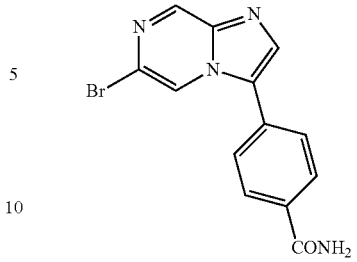

Intermediate 9

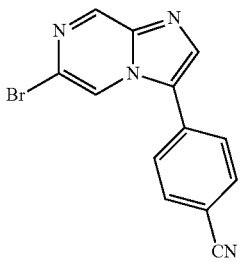

Intermediate 1: 4-(3-bromoimidazo[1,2-a]pyrazin-6-yl)benzoic Acid

Step 1: To a solution of 6-bromoimidazo[1,2-a]pyrazine (30 g, 151 mmol) in toluene (400 mL) were sequentially added Cs$_2$CO$_3$ (123 g, 378 mmol), 4-(ethoxycarbonyl)phenylboronic acid (35.2 g, 181 mmol) and Pd(dppf)$_2$Cl$_2$ (3.70 g, 4.50 mmol). The reaction mixture was stirred at 90° C. for 12 h under argon atmosphere then, was filtered through celite. The filtrate was concentrated and the residue was purified the by flash column chromatography (silica gel, eluent n-hexane/EtOAc 70:30) to afford ethyl 4-(imidazo[1,2-a]pyrazin-6-yl)benzoate (16 g, 39%) as yellow solid. $^1$H NMR (400 MHz, DMSO-d$_6$) δ: 9.35 (s, 1H), 9.17 (s, 1H), 8.15 (d, J=8.4 Hz, 2H), 8.03 (d, J=8.4 Hz, 2H), 7.88 (s, 1H), 7.79 (s, 1H), 4.32 (q, J=6.8 Hz, 2H), 1.44 (t, J=7.2 Hz 3H); MS (ESI) m/z 268 [C$_{15}$H$_{13}$N$_3$O$_2$+H]$^+$.

Step 2: To a solution of ethyl 4-(imidazo[1,2-a]pyrazin-6-yl)benzoate (16.0 g, 59.8 mmol) in CCl$_4$/CH$_3$OH (200/50 mL) was added N-bromosuccinamide (12.7 g, 71.8 mmol). The reaction mixture was stirred at room temperature for 30 min then, was filtered through celite. The filtrate was concentrated, resuspended in water and extracted with CH$_2$Cl$_2$. The organic phase was concentrated to afford ethyl 4-(3-bromoimidazo[1,2-a]pyrazin-6-yl)benzoate (18.0 g, 87%) as a yellow solid. $^1$H NMR (400 MHz, DMSO-d$_6$) δ: 9.17 (s, 1H), 8.78 (s, 1H), 8.28 (d, J=8.4 Hz, 2H), 8.09 (d, J=8.0 Hz, 2H), 7.94 (s, 1H), 4.34 (q, J=7.2 Hz, 2H), 1.35 (t, J=7.2 Hz, 3H); MS (ESI) m/z 345 [C$_{15}$H$_{12}$BrN$_3$O$_2$]$^+$ Step 3: To a solution of ethyl 4-(3-bromoimidazo[1,2-a]pyrazin-6-yl)benzoate (27.0 g, 77.9 mmol) in THF/CH$_3$OH (300/100 mL) were added LiOH (26.0 g, 623 mmol) and water (100 mL). The reaction mixture was stirred for 5 h at room temperature then, was concentrated, diluted with water (200 mL) and acidified with aqueous HCl solution till pH 3. The precipitate was isolated by filtration and dried to afford 4-(3-bromoimidazo[1,2-a]pyrazin-6-yl)benzoic acid (14.0 g, 56%) as white solid. $^1$H NMR (400 MHz, CDCl$_3$) δ: 9.17 (s, 1H), 8.68 (s, 1H), 8.25 (d, J=8.4 Hz 2H), 8.09 (d, J=8.0 Hz, 2H), 7.99 (s, 1H); MS (ESI) m/z 316 [C$_{13}$H$_8$BrN$_3$O$_2$]$^+$.

Intermediates 2 and 3: (4-(3-bromoimidazo[1,2-a]pyrazin-6-yl)phenyl)(4-methylpiperazin-1-yl)methanone

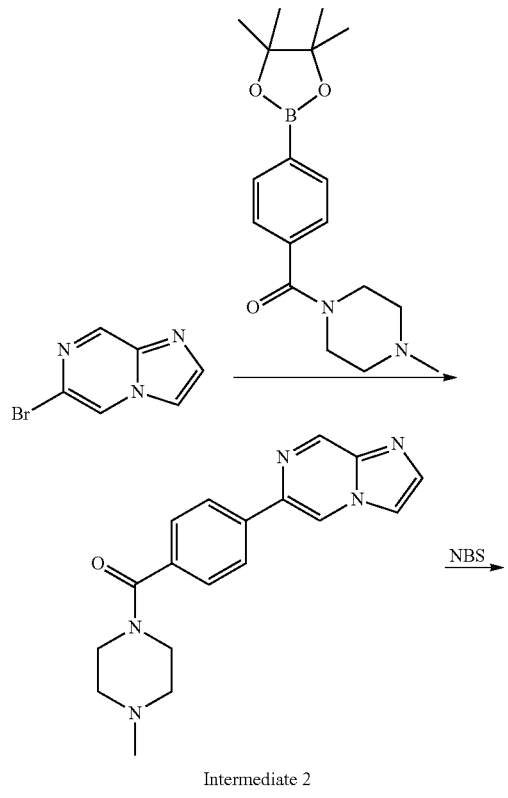

Intermediate 2

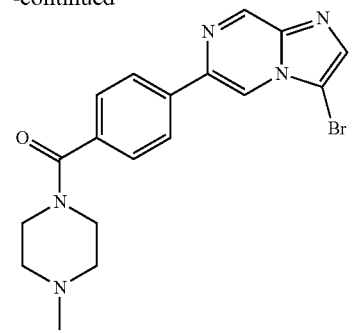

Intermediate 3

Step 1: To a solution of 6-bromoimidazo[1,2-a]pyrimidine (2.4 g, 12.1 mmol) in DMF, were sequentially added (4-methylpiperazin-1-yl)(4-(4,4,5,5-tetramethyl-1,3,2-dioxaborolan-2-yl)phenyl)methanone (80% of 4.1 g, 12.1 mmol), a solution of NaHCO$_3$ (3.1 g, 36.3 mmol) in water (30 mL), water (3 mL) and (A-Phos)$_2$PdCl$_2$ (400 mg, 0.60 mmol). The reaction mixture was heated at 90° C. for 4 h, then was diluted with water (100 mL) and extracted with EtOAc (3×100 mL). The combined organic layer was dried over Na$_2$SO$_4$, filtered and concentrated under reduced pressure. The residue was purified by flash column chromatography (silica gel, eluent CHCl$_3$/MeOH 95:5 to 85:15) to afford of (4-(imidazo[1,2-a]pyrazin-6-yl)phenyl)(4-methylpiperazin-1-yl)methanone (1.5 g, 65%). $^1$H NMR (400 MHz, CDCl$_3$) δ 8.60 (d, J=2.0 Hz, 1H), 8.10 (d, J=4.0, 1 H), 7.80 (d, J=8.0 Hz, 1H), 7.58 (m, 4H) 7.39 (d, J=8.0, 1H), 3.84 (br s, 2H), 3.50 (br s, 2H), 2.40 (br s, 4H), 2.35 (s, 3H); MS (ESI) m/z 322 [M+1]

Step 2: To a solution of ((4-(imidazo[1,2-a]pyrazin-6-yl)phenyl)(4-methylpiperazin-1-yl)methanone (1.4 g, 4.36 mmol) in ACN (15 mL) and DCM (5 mL) was added N-Bromosuccinimide (0.93 g, 5.23 mmol) at 0° C. The reaction mixture was stirred for 90 min while warming to room temperature. The reaction mixture was diluted with DCM and washed with water. The organic layer was dried over Na$_2$SO$_4$, filtered and concentrated under reduced pressure. The crude compound was purified by flash column chromatography (silica gel, eluent CHCl$_3$/MeOH 95:5 to 90:10) to afford ((4-(3-bromoimidazo[1,2-a]pyrazin-6-yl)phenyl)(4-methylpiperazin-1-yl)methanone (1.0 g, 83%) as a brown solid. $^1$H NMR (400 MHz, CDCl$_3$) δ 8.82 (d, J=4.0 Hz, 1H), 8.53 (d, J=4.0 Hz, 1H), 7.87 (s, 1H), 7.50 (m, 4H), 3.84 (bs, 2H), 3.50 (br s, 2H), 2.39 (bs, 4H), 2.34 (s, 3H); MS (ESI) m/z 400.

Intermediates 4 and 5: 4-(3-iodoimidazo[1,2-a]pyrazin-6-yl)benzoic Acid and (4-(3-iodoimidazo[1,2-a]pyrazin-6-yl)phenyl)(4-methylpiperazin-1-yl)methanone

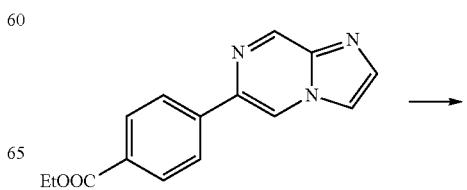

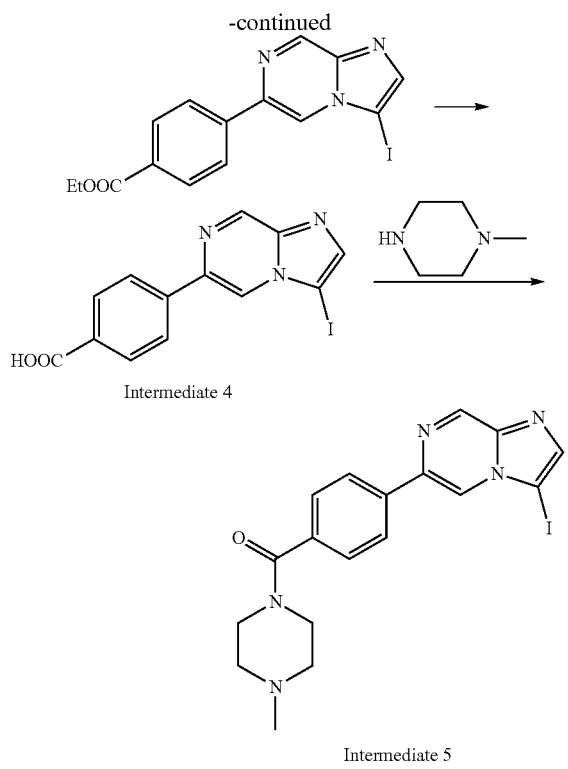

Intermediate 4

Intermediate 5

Step 1: To a solution of ethyl 4-(imidazo[1,2-a]pyrazin-6-yl)benzoate (8.00 g, 29.9 mmol) in DMF (200 mL), was added N-Iodosuccinimide (8.10 g, 36.0 mmol) and the mixture was heated at 60° C. for 2 h and poured onto ice water. The precipitate was isolated by filtration and dried to afford ethyl 4-(3-iodoimidazo[1,2-a]pyrazin-6-yl)benzoate (11 g, 94%) as yellow solid. $^1$H NMR (400 MHz, DMSO-$d_6$) δ 9.13 (s, 1H), 8.80 (s, 1H), 8.29 (d, J=8.4 Hz, 2H), 8.07 (d, J=8.4 Hz, 2H), 8.00 (s, 1H), 4.37-4.31 (m, 2H), 1.34 (t, J=7.2 Hz, 3H); MS (ESI) m/z 393 $[C_{15}H_{12}IN_3O_2]^+$.

Step 2: A solution of ethyl 4-(3-iodoimidazo[1,2-a]pyrazin-6-yl)benzoate (11 g, 30.5 mmol) and LiOH.H$_2$O (5.00 g, 121 mmol) in THF/CH$_3$OH/H$_2$O (200/50/50 mL) was stirred for 12 h. The reaction mixture was concentrated, diluted with water (20 mL) and acidified with an aqueous solution of HCl till pH 2. The precipitate was isolated by filtration and dried to afford 4-(3-iodoimidazo[1,2-a]pyrazin-6-yl)benzoic acid (8.00 g, 72%) as off white solid. $^1$H NMR (400 MHz, DMSO-$d_6$) δ: 9.12 (s, 1H), 8.78 (s, 1H), 8.26 (d, J=8.4 Hz, 2H), 8.06 (d, J=8.4 Hz, 2H), 8.05 (s, 1H); MS (ESI) m/z 366 $[C_{13}H_8IN_3O_2+H]^+$.

Step 3: N-methylmorpholine (6.90 mL, 54.64 mmol), HATU (15.58 g, 40.98 mmol) and N-methylpiperazine (4.15 mL, 40.98 mmol) were added sequentially to a solution of 4-(3-iodoimidazo[1,2-a]pyrazin-6-yl)benzoic acid (10.0 g, 27.32 mmol) in DMF (50 mL). The resulting mixture was stirred at room temperature for 3 h under nitrogen atmosphere and, was diluted with water (100 mL). The precipitate was isolated by filtration and dried to afford (4-(3-iodoimidazo[1,2-a]pyrazin-6-yl)phenyl)(morpholino)methanone (10.5 g, 86%) as off-white solid. $^1$H NMR (400 MHz, CDCl$_3$) δ: 9.15 (d, J=1.2 Hz, 1H), 8.44 (d, J=1.2 Hz, 1H), 8.05 (d, J=8.0 Hz, 2H), 7.83 (s, 1H), 7.57 (d, J=8.0 Hz, 2H), 3.85 (bs, 2H), 3.51 (bs, 2H), 2.53 (bs, 2H), 2.41 (bs, 2H), 2.35 (s, 3H); MS (ESI) m/z 447 $[C_{18}H_{18}IN_5O]^+$.

Intermediate 6: Synthesis of (4-(3-iodoimidazo[1,2-a]pyrazin-6-yl)phenyl) (morpholino) methanone N-methyl-morpholine (3.0 mL, 7.5 mmol), HATU (7.5 g, 27 mmol) and morpholine (1.26 g, 14.85 mmol) were added sequentially to a solution of 4-(3-iodoimidazo[1,2-a]pyrazin-6-yl)benzoic acid (5.0 g, 3.25 mmol) in DMF (10 mL) and the resulting mixture was stirred at room temperature for 3 h under nitrogen atmosphere. The reaction mixture was diluted with water (50 mL) and the precipitate that has formed was filtered off and dried to afford (4-(3-iodoimidazo[1,2-a]pyrazin-6-yl)phenyl)(morpholino)methanone (2.0 g, 65%) as off-white solid. $^1$H NMR (400 MHz, CDCl$_3$) δ 9.10 (s, 1H), 8.50 (s, 1H), 8.10 (d, 2H), 7.90 (s, 1H), 7.60 (d, 2H), 3.4-3.9 (m, 8H); MS (ESI) m/z 434 $[C_{17}H_{15}IN_4O_2+H]^+$.

Intermediate 7: (4-(3-bromoimidazo[1,2-a]pyrazin-6-yl)phenyl)(morpholino)methanone To a solution of 4-(3-bromoimidazo[1,2-a]pyrazin-6-yl) benzoic acid (8.00 g, 25.14 mmol) in DMF (70 mL), were added sequentially N-methyl-morpholine (5.5 mL, 50.28 mmol), HATU (14.4 g, 37.71 mmol) and Morpholine (3.32 mL, 37.71 mmol). The reaction mixture was stirred at room temperature for 3 h under nitrogen atmosphere then, was diluted with water (50 mL). The precipitate was isolated by filtration and dried to afford compound (4-(3-bromoimidazo[1,2-a]pyrazin-6-yl)phenyl)(morpholino) methanone (6.40 g, 66%) as off-white solid. $^1$H NMR (400 MHz, CDCl$_3$) δ 9.15 (d, J=1.2 Hz, 1H), 8.44 (d, J=1.2 Hz, 1H), 8.05 (d, J=8.0 Hz, 2H), 7.83 (s, 1H), 7.57 (d, J=8.0 Hz, 2H), 3.85 (bs, 2H), 3.51 (bs, 2H), 2.53 (bs, 2H), 2.41 (bs, 2H); MS (ESI) m/z 387 $[C_{17}H_{15}BrN_4O_2+H]^+$.

Intermediate 8: (6-bromoimidazo[1,2-a]pyrazin-3-yl)benzamide 5a and 4-(6-bromoimidazo[1,2-a]pyrazin-3-yl)benzonitrile To a solution of 3-bromo-6-iodoimidazo[1,2-a]pyrazine (500 mg, 1.50 mmol) in DMF (20.0 mL) was added 4-carbamoylphenylboronic acid (305 mg, 1.84 mmol), Na$_2$CO$_3$ (408 mg, 3.84 mmol), water (2.00 mL) and Pd(PPh$_3$)$_4$ (36 mg, 0.03 mmol). The mixture was heated at 90° C. for 2 h and diluted with water. The precipitate was isolated by filtration and dried under vacuum to afford 4-(6-bromoimidazo[1,2-a]pyrazin-3-yl)benzamide (300 mg, 61%) as an off white solid. $^1$H NMR (400 MHz, CDCl$_3$) δ: 9.04 (s, 1H), 8.82 (s, 1H), 8.20 (s, 1H), 8.12 (s, 1H), 8.05 (d, J=8.4 Hz, 2H), 7.86 (d, J=8.4 Hz, 2H), 7.50 (s, 1H); MS (ESI) m/z 317 $[C_{13}H_9BrN_4O]^+$.

Intermediate 9: 4-(6-bromoimidazo[1,2-a]pyrazin-3-yl)benzonitrile

To a solution of 6-bromo-3-iodoimidazo[1,2-a]pyrazine (3 g, 9.26 mmol) in DMF (50 mL), were added 4-cyanophenylboronic acid 3 (1.632 g, 11.1 mmol), K$_3$PO$_4$ (4.91 g, 23.15 mmol), Pd(PPh$_3$)$_4$ (0.534 mg, 0.46 mmol) and water (5 mL). The reaction mixture was heated at 90° C. for 1 h and water was added to the mixture to induce precipitation. The precipitate was isolated by filtration and was purified by column chromatography (silica gel, eluent petroleum ether/EtOAc 1:1) to afford of 4-(6-bromoimidazo[1,2-a]pyrazin-3-yl)benzonitrile (2.5 g, 90%) as an off-white solid. $^1$H NMR (400 MHz, DMSO-$d_6$) δ 9.88 (s, 1H), 8.90 (s, 1H), 8.27 (s, 1H), 8.05-7.99 (m, 4H); MS (ESI) m/z 301.1 $[C_{13}H_7BrN_4+2]^+$.

Example 1: (4-(3-(4-hydroxyphenyl)imidazo[1,2-a]pyrazin-6-yl)phenyl)(4-methylpiperazin-1-yl)methanone

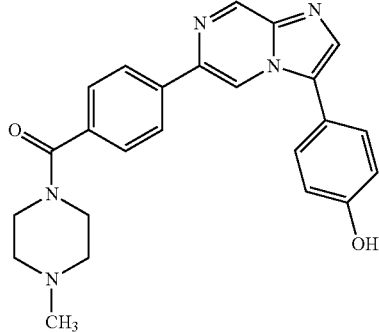 [SMILES: CN1CCN(C(=O)c2ccc(-c3cn4c(-c5ccc(O)cc5)cnc4cn3)cc2)CC1]

The title was prepared following General procedure B using (4-(3-bromoimidazo[1,2-a]pyrazin-6-yl)phenyl)(4-methylcyclohexyl)methanone (intermediate 7) and 4-hydroxyphenylboronic acid as starting materials. The reaction crude product was purified by flash column chromatography (silica gel, eluent $CH_2Cl_2/CH_3OH$ 95:5) to afford (4-(3-(4-hydroxyphenyl)imidazo[1,2-a]pyrazin-6-yl)phenyl)(4-methylpiperazin-1-yl)methanone (930 mg, 40%, AUC HPLC 98.2%) as an off-white solid. $^1$H NMR (400 MHz, $CDCl_3$) δ 9.21 (s, 1H), 8.54 (s, 1H), 7.96 (d, J=8.4 Hz, 2H), 7.83 (s, 1H), 7.54 (d, J=8.4 Hz, 2H), 7.43 (d, J=8.4 Hz, 2H), 7.06 (d, J=8.8 Hz, 2H), 3.86 (bs, 2H), 3.51 (bs, 2H), 2.53 (bs, 2H), 2.41 (bs, 2H), 2.35 (s, 3H); MM (ESI) m/z 414 $[C_{24}H_{23}N_5O_2+H]^+$.

Example 2: (4-(3-(4-hydroxyphenyl)imidazo[1,2-a]pyrazin-6-yl)phenyl)(morpholino)methanone

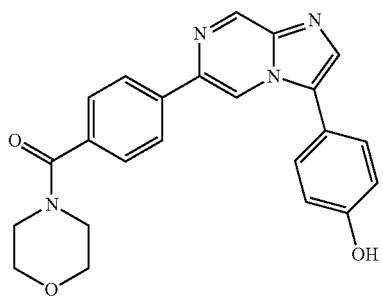 [SMILES: O=C(c1ccc(-c2cn3c(-c4ccc(O)cc4)cnc3cn2)cc1)N1CCOCC1]

The title compound was prepared following General procedure B using ((4-(3-bromoimidazo[1,2-a]pyrazin-6-yl)phenyl)(morpholino) methanone (intermediate 7) and 4-hydroxyphenylboronic acid as starting materials. The reaction crude product was purified by flash column chromatography (silica gel, 100-200 eluent $CH_2Cl_2/CH_3OH$ 95:5) to afford 4-(3-(4-hydroxyphenyl)imidazo[1,2-a]pyrazin-6-yl)phenyl)(morpholino)methanone (150 mg, 32%, AUC HPLC 97.6%) as an off-white solid. $^1$H NMR (400 MHz, $CD_3OD$) δ 9.88 (s, 1H), 9.21 (s, 1H), 8.83 (s, 1H), 8.11 (d, J=8.0 Hz, 2H), 7.94 (s, 1H), 7.61 (d, J=8.4 Hz, 2H), 7.51 (d, J=8.4 Hz, 2H), 6.97 (d, J=8.4 Hz, 2H), 3.60 (bs, 8H); MS (ESI) m/z 401 $[C_{23}H_{20}N_4O_3+H]^+$.

Example 3: 4-(6-(4-(4,4-dimethylpiperidine-1-carbonyl)phenyl)imidazo[1,2-a]pyrazin-3-yl)benzamide

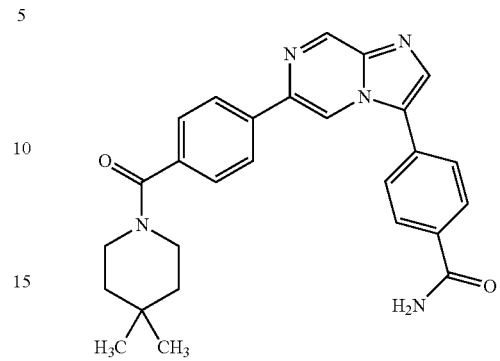

Step 1: The title compound was prepared following General procedure A and the reaction crude product was used without further purification in the next step.

$^1$H NMR (400 MHz, $CDCl_3$) δ: 9.08 (s, 1H), 8.41 (s, 1H), 8.04 (d, J=8.4 Hz, 2H), 7.90 (s, 1H), 7.56 (d, J=8.4 Hz, 2H), 3.75 (bs, 2H), 3.40 (bs, 2H), 1.51 (bs, 2H), 1.34 (s, 2H), 1.02 (s, 6H); MS (ESI) m/z 460 $[C_{20}H_{21}IN_4O]^+$.

Step 2: The title was prepared following General procedure B with (4,4-dimethylpiperidin-1-yl)(4-(3-iodoimidazo[1,2-a]pyrazin-6-yl)phenyl)methanone and 4-carbamoylphenylboronic acid as starting materials. The reaction crude product was purified by column chromatography (silica gel, 100-200 eluent $CH_2Cl_2/CH_3OH$ 90:10) to afford 6-(4-(4,4-dimethylpiperidine-1-carbonyl)phenyl)imidazo[1,2-a]pyrazin-3-yl)benzamide (130 mg, 34%, AUC HPLC 95.4%) as an off-white solid. $^1$H NMR (400 MHz, $CDCl_3$) δ: 9.26 (s, 1H), 8.62 (s, 1H), 8.06 (d, J=8.4 Hz, 2H), 7.96 (s, 1H), 7.95 (d, J=4.8 Hz, 2H), 7.73 (d, J=8.4 Hz, 2H), 7.52 (d, J=8.0 Hz, 2H), 6.25 (bs, 1H), 5.74 (bs, 1H), 3.75 (bs, 2H), 3.39 (bs, 2H), 1.49 (bs, 2H), 1.32 (bs, 2H), 1.02 (s, 6H); MS (ESI) m/z 453 $[C_{27}H_{27}N_5O_2+H]^+$.

Intermediate 10: 4-(3-(4-carbamoylphenyl)imidazo[1,2-a]pyrazin-6-yl)benzoic Acid Intermediate 10

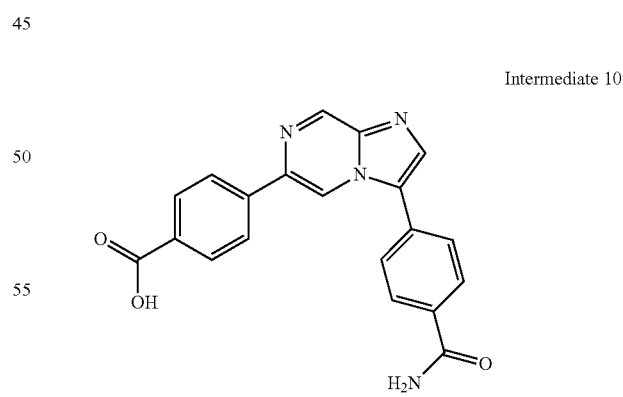

Step 1: To a solution of 4-(6-bromoimidazo[1,2-a]pyrazin-3-yl)benzamide (2.00 g, 6.30 mmol) in a mixture of 1,4-dioxane (25 mL) and water (5 mL), were sequentially added 4-(ethoxycarbonyl)phenylboronic acid (1.30 g, 6.90 mmol), $Na_2CO_3$ (3.30 g, 6.90 mmol) and $Pd(PPh_3)_4$ (363 mg, 0.31 mmol). The reaction mixture was heated at 90° C. for 16 h under argon atmosphere then, was filtered through a short pad of celite. The filtrate was concentrated under reduced pressure and the residue was purified by flash column chromatography (silica gel, eluent $CH_2Cl_2/CH_3OH$ 95:5) to afford ethyl 4-(3-(4-carbamoylphenyl)imidazo[1,2-a]pyrazin-6-yl)benzoate (1.50 g, 62%) as yellow solid. MS (ESI) m/z 387 $[C_{22}H_{18}N_4O_3+H]^+$.

Step 2: To a solution of ethyl 4-(3-(4-carbamoylphenyl)imidazo[1,2-a]pyrazin-6-yl)benzoate (1.50 g, 12.7 mmol) in THF/$CH_3OH$ (20/10 mL) was added $LiOH \cdot H_2O$ (870 mg, 20.7 mmol). The mixture was stirred at rt for 5 h then was concentrated under reduced pressure to a smaller volume. The residue was diluted with water (20 mL) and acidified till pH 3 with an aqueous 2M HCl solution. The precipitate was isolated by filtration and dried to afford 4-(3-(4-carbamoylphenyl)imidazo[1,2-a]pyrazin-6-yl)benzoic acid (750 mg, 93%) as an off-white solid. $^1$H NMR (400 MHz, $CDCl_3$) δ 9.30 (s, 1H), 9.06 (s, 1H), 8.17 (d, J=8.4 Hz, 2H), 8.14 (s, 1H), 8.10 (d, J=8.4 Hz, 2H), 8.03 (d, J=8.4 Hz, 2H), 7.93 (d, J=8.4 Hz, 3H), 7.49 (bs, 1H); MS (ESI) m/z 359 $[C_{20}H_{14}N_4O_3+H]^+$.

Example 4: 4-(6-(4-(4-aminopiperidine-1-carbonyl)phenyl)imidazo[1,2-a]pyrazin-3-yl)benzamide Hydrochloride

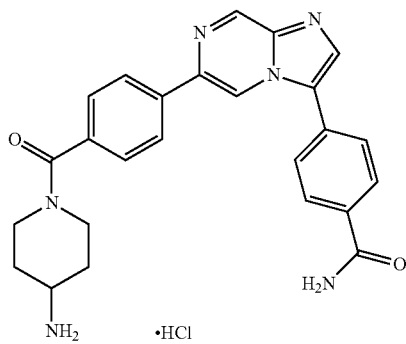 [SMILES: NC(=O)c1ccc(-c2cnc3cnc(-c4ccc(C(=O)N5CCC(N)CC5)cc4)cn23)cc1 ; Cl]

Step 1: tert-butyl 1-(4-(3-(4-carbamoylphenyl)imidazo[1,2-a]pyrazin-6-yl)benzoyl)piperidin-4-ylcarbamate was prepared following General procedure A using tert-butyl piperidin-4-ylcarbamate and tert-butyl piperidin-4-ylcarbamate as starting materials. The reaction crude product was purified by column chromatography (silica gel, eluent $CH_2Cl_2/CH_3OH$ 95:5) to afford the boc protected intermediate. $^1$H NMR (400 MHz, DMSO-$d_6$) δ 9.28 (s, 1H), 9.00 (s, 1H), 8.16-8.13 (m, 3H), 8.08 (d, J=8 Hz, 2H), 7.93 (d, J=8.4 Hz, 2H), 7.49-7.45 (m, 3H), 6.89 (s, 1H), 4.30-4.20 (m, 1H), 3.55-3.46 (m, 2H), 3.15-3.10 (m, 4H), 1.79-1.71 (m, 2H), 1.23 (s, 9H); MS (ESI) m/z 541 $[C_{30}H_{32}N_6O_4+H]^+$.

Step 2: To a solution of tert-butyl 1-(4-(3-(4-carbamoylphenyl)imidazo[1,2-a]pyrazin-6-yl)benzoyl)piperidin-4-ylcarbamate (500 mg, 0.98 mmol) in $CH_2Cl_2$ (5 mL) was added a 20% HCl solution in 1,4-dioxane (0.15 mL, 0.82 mmol). The reaction mixture was stirred at room temperature for 2 h then, was concentrated under reduced pressure to afford 4-(6-(4-(4-aminopiperidine-1-carbonyl)phenyl)imidazo[1,2-a]pyrazin-3-yl)benzamide hydrochloride salt (90 mg, 15%, AUC HPLC 96%) as yellow solid. $^1$H NMR (400 MHz, DMSO-$d_6$) δ 9.54 (s, 1H), 9.09 (s, 1H), 8.48 (s, 1H), 8.23-8.18 (m, 4H), 7.96 (d, J=8.0 Hz, 2H), 7.60 (d, J=8.0 Hz, 2H), 4.80 (bs, 1H), 3.89-3.85 (m, 2H), 3.10-3.00 (m, 2H), 2.10-2.00 (m, 2H), 1.59-1.50 (m, 2H); MS (ESI) m/z 477 $[C_{25}H_{24}N_6O_2+H]^+$.

Example 5: 4-(6-(4-(4-tert-butylpiperazine-1-carbonyl)phenyl)imidazo[1,2-a]pyrazin-3-yl)benzamide

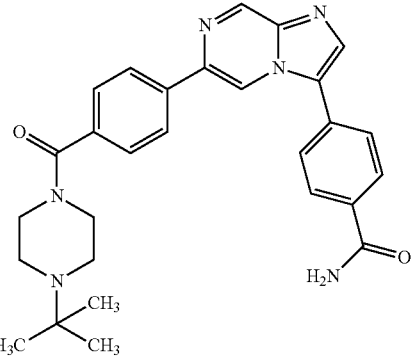

The title compound was prepared following General procedure A using N-t-butyl piperazine. The reaction crude product was purified by column chromatography (silica gel, 100-200 eluent $CH_2Cl_2/CH_3OH$ 97:3) to afford 4-(6-(4-(4-tert-butylpiperazine-1-carbonyl)phenyl)imidazo[1,2-a]pyrazin-3-yl)benzamide (158 mg, 70%, AUC HPLC 96%) as an off-white solid. $^1$H NMR (400 MHz, $CDCl_3$) δ 9.28 (s, 1H), 9.00 (s, 1H), 8.16 (d, J=8.0 Hz, 2H), 8.13 (s, 1H), 8.08 (d, J=8.0 Hz, 2H), 7.94 (d, J=8.0 Hz, 2H), 7.52 (d, J=8.0 Hz, 3H), 7.45 (bs, 1H), 3.65 (bs, 1H), 2.82 (bs, 1H), 2.70-2.65 (m, 3H), 1.80 (bs, 3H), 1.54 (s, 9H); MS (ESI) m/z 483 $[C_{28}H_{30}N_6O_2+H]^+$.

Example 6: 4-(6-(4-(4-methylpiperazine-1-carbonyl)phenyl)imidazo[1,2-a]pyrazin-3-yl)benzonitrile

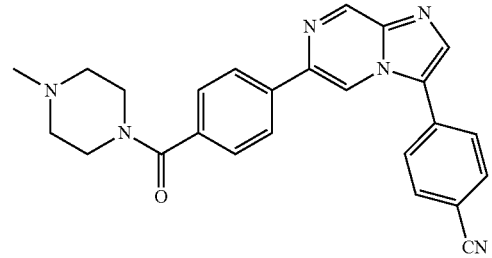 [SMILES: CN1CCN(C(=O)c2ccc(-c3cn4c(-c5ccc(C#N)cc5)cnc4cn3)cc2)CC1]

To a solution of (4-(3-bromoimidazo[1,2-a]pyrazin-6-yl)phenyl)(4-methylpiperazin-1-yl)methanone (200 mg, 0.50 mmol) in toluene (4 mL) and Ethanol (2 ml) under inert atmosphere, was added $K_2CO_3$ (138 mg, 1.00 mmol), 4-cyanophenylboronic acid (110 mg, 0.75 mmol) and $Pd(PPh_3)_4$ (58 mg, 0.05 mmol). The resulting mixture was heated in a microwave oven at 140° C. for 15 min, and then was concentrated under reduced pressure. The residue was purified by column chromatography (silica gel, eluent $CH_2Cl_2$/MeOH 95:5 to 90:10) to afford 4-(6-(4-(4-methylpiperazine-1-carbonyl)phenyl)imidazo[1,2-a]pyrazin-3-yl)benzonitrile (154.7 mg, 73%, AUC HPLC 99%) as a yellow solid. $^1$H NMR (300 MHz, DMSO-$d_6$) δ 9.31 (s, 1H), 9.04 (s, 1H), 8.25 (s, 1H), 8.16 (d, J=8.1 Hz, 2H), 8.11-8.04 (m, 4H), 7.51 (d, J=8.1 Hz, 2H), 3.63 (bs, 2H), 3.46-3.20 (m, 2H), 2.32 (bs, 4H), 2.20 (s, 3H); MS (ESI) m/z 423 $[C_{25}H_{21}N_6O+H]^+$.

Example 7: 4-(6-(4-(morpholine-4-carbonyl)phenyl)imidazo[1,2-a]pyrazin-3-yl)benzonitrile

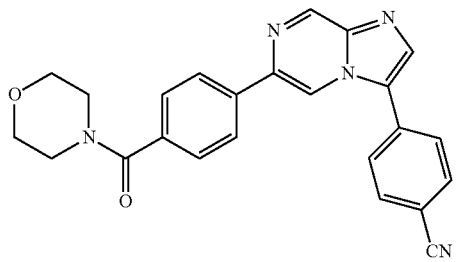 [SMILES: N#Cc1ccc(-c2cnc3cnc(-c4ccc(C(=O)N5CCOCC5)cc4)cn23)cc1]

To a solution of (4-(3-iodoimidazo[1,2-a]pyrazin-6-yl)phenyl)(morpholino)methanone (200 mg, 0.52 mmol) in a mixture toluene (3 mL) and water (1.5 ml) under inert atmosphere was successively added $K_2CO_3$ (127 g, 0.92 mmol), 4-cyanophenylboronic acid (111 mg, 0.52 mmol) and $Pd(PPh_3)_4$ (53 mg, 0.05 mmol). The resulting mixture was microwaved at 140° C. for 15 min then was concentrated under reduced pressure. The residue was purified by column chromatography (silica gel, eluent DCM/MeOH 95:5) to afford 4-(6-(4-(morpholine-4-carbonyl)phenyl)imidazo[1,2-a]pyrazin-3-yl)benzonitrile (100 mg, 53%, AUC HPLC 95%), yellow solid. $^1$H NMR (400 MHz, $CD_3OD$) δ 9.17 (d, J=0.7 Hz, 1H), 8.55 (d, J=1.0 Hz, 1H), 7.95-7.86 (m, 3H), 7.80 (d, J=8.3 Hz, 2H), 7.72 (d, J=8.3 Hz, 2H), 7.43 (d, J=8.2 Hz, 2H), 3.88-3.22 (m, 8H); MS (ESI) m/z 410 $[C_{24}H_{19}N_5O_2+H]^+$.

Example 8: 2-(6-(4-(4-methylpiperazine-1-carbonyl)phenyl)imidazo[1,2-a]pyrazin-3-yl)benzonitrile

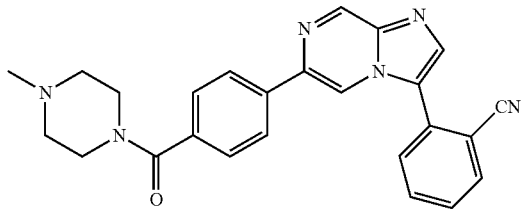 [SMILES: CN1CCN(C(=O)c2ccc(-c3cn4c(-c5ccccc5C#N)cnc4cn3)cc2)CC1]

To a solution of (4-(3-iodoimidazo[1,2-a]pyrazin-6-yl)phenyl)(4-methylpiperazin-1-yl)methanone (400 mg, 0.89 mmol) in a mixture of toluene (8 mL) and ethanol (4 ml) under inert atmosphere, was added $K_2CO_3$ (247 mg, 1.79 mmol), 2-cyanophenylboronic acid (197 mg, 1.34 mmol) and $Pd(PPh_3)_4$ (103 mg, 0.089 mmol). The resulting mixture was heated in a microwave oven at 140° C. for 15 min, and then was concentrated under reduced pressure. The residue was purified by column chromatography (silica gel, eluent $CH_2Cl_2$/MeOH 95:5 to 90:10) to afford 2-(6-(4-(4-methylpiperazine-1-carbonyl)phenyl)imidazo[1,2-a]pyrazin-3-yl)benzonitrile (134 mg, 35%, AUC HPLC 99%) as a yellow solid. $^1$H NMR (400 MHz, $CD_3OD$) δ 9.13 (d, J=0.8 Hz, 1H), 8.65 (d, J=0.8 Hz, 1H), 8.06 (s, 1H), 8.03-7.98 (m, 3H), 7.91-7.84 (m, 2H), 7.73-7.68 (m, 1H), 7.46 (d, J=8.2 Hz, 2H), 3.77 (bs, 2H), 3.48 (bs, 2H), 2.52-2.42 (m, 4H), 2.33 (s, 3H); $^{13}$C NMR (100 MHz, $CD_3OD$) δ 171.99, 143.89, 141.99, 140.85, 139.26, 137.46, 136.94, 135.46, 135.09, 132.04, 131.99, 131.26, 128.72, 127.97, 125.66, 55.96, 55.53, 46.01, 43.00; MS (ESI) m/z 423 $[C_{25}H_{22}N_6O+H]^+$.

Example 9: 4-(6-(4-(4-(methylamino)piperidine-1-carbonyl)phenyl)imidazo[1,2-a]pyrazin-3-yl)benzonitrile

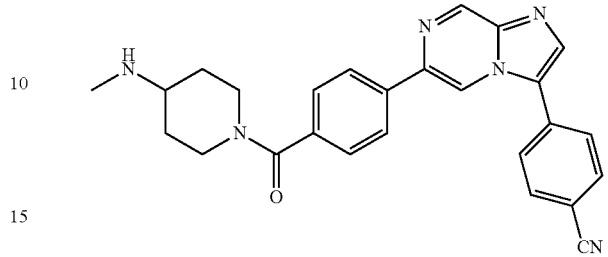

Step 1: To a solution of 4-(3-(4-cyanophenyl)imidazo[1,2-a]pyrazin-6-yl)benzoic acid (100 mg, 0.294 mmol) in DMF (10.0 mL), were added HATU (168 mg, 0.441 mmol), N-methyl morpholine (59 mg, 0.588 mmol) and tert-butyl methyl(piperidin-4-yl)carbamate (126 mg, 0.588 mmol). The reaction mixture was stirred at room temperature under inert atmosphere for 16 h, and then was diluted with water (20 mL) and extracted with DCM (3×20 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford the boc-protected derivative as a yellow solid. MS (ESI) m/z 537 $[C_{31}H_{32}N_6O_3+H]^+$.

Step 2: To a solution of tert-butyl 1-(4-(3-(4-cyanophenyl)imidazo[1,2-a]pyrazin-6-yl)benzoyl)piperidin-4-yl(methyl)carbamate (0.294 mmol) in methanol (3 mL) and dioxane (3 mL), was added a solution of 4M HCl in dioxane (3 mL). The resulting mixture was stirred at room temperature for 18 h and then was concentrated under reduced pressure. The residue was purified by preparative HPLC (C18, eluent ACN/$H_2O$/HCOOH 0.01%) to afford 4-(6-(4-(4-(methylamino)piperidine-1-carbonyl)phenyl)imidazo[1,2-a]pyrazin-3-yl)benzonitrile (63.3 mg, 50%, AUC HPLC 96%) as a yellow solid. $^1$H NMR (400 MHz, $CD_3OD$) δ 9.22 (s, 1H), 8.97 (s, 1H), 8.17 (d, J=8.2 Hz, 2H), 8.13 (s, 1H), 8.03-7.98 (m, 4H), 7.57 (d, J=8.2 Hz, 2H), 4.75-4.72 (m, 1H), 3.91 (bs, 1H), 3.17-3.11 (m, 2H), 3.01-2.98 (m, 1H), 2.64 (s, 3H), 2.19-2.05 (m, 2H), 1.51 (bs, 2H); $^{13}$C NMR (100 MHz, $CD_3OD$) δ 172.10, 144.07, 142.39, 141.09, 139.45, 137.02, 136.83, 134.47, 133.68, 129.78, 128.56, 128.03, 119.37, 115.42, 113.53, 57.32, 31.51; MS (ESI) m/z 437 $[C_{26}H_{24}N_6O+H]^+$.

Example 10: 4-(6-(4-(4-(2-aminoethyl)piperidine-1-carbonyl)phenyl)imidazo[1,2-a]pyrazin-3-yl)benzonitrile

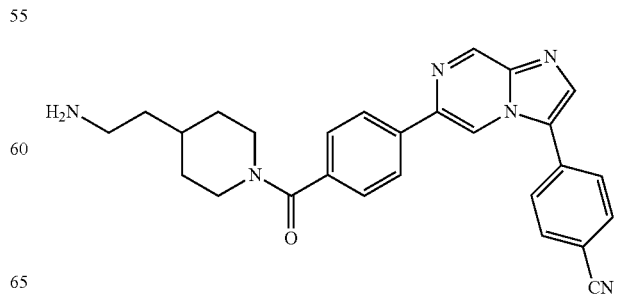

Step 1: To a solution of 4-(3-(4-cyanophenyl)imidazo[1,2-a]pyrazin-6-yl)benzoic acid (50 mg, 0.147 mmol) in DMF (5.0 mL) were added HATU (84 mg, 0.221 mmol), N-methyl morpholine (30 mg, 0.294 mmol) and tert-butyl 2-(piperidin-4-yl)ethylcarbamate (67 mg, 0.294 mmol). The reaction mixture was stirred at room temperature under inert atmosphere for 16 h and then diluted with water (10 mL) and extracted with DCM (3×10 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford the carbamate derivative as a yellow solid. MS (ESI) m/z 551 $[C_{32}H_{34}N_6O_3+H]^+$.

Step 2: To a solution of tert-butyl 2-(1-(4-(3-(4-cyanophenyl)imidazo[1,2-a]pyrazin-6-yl)benzoyl)piperidin-4-yl)ethylcarbamate (0.147 mmol) in DCM (1 mL) was added TFA (1 mL). The reaction mixture was stirred at room temperature for 18 h and then concentrated under reduced pressure. The residue was purified by preparative HPLC (C18, eluent ACN/$H_2O$/HCOOH 0.01%) to afford 4-(6-(4-(4-(2-aminoethyl)piperidine-1-carbonyl)phenyl)imidazo[1,2-a]pyrazin-3-yl)benzonitrile (15.9 mg, 22%, AUC HPLC 99%) as a yellow solid. $^1$H NMR (400 MHz, $CD_3OD$) δ 9.19 (d, J=1.3 Hz, 1H), 8.93 (d, J=1.3 Hz, 1H), 8.13-8.11 (m, 3H), 8.01-7.96 (m, 4H), 7.53 (d, J=8.4 Hz, 2H), 4.69-4.66 (m, 1H), 3.82-3.80 (m, 1H), 3.18-3.15 (m, 1H), 3.04-3.00 (m, 2H), 2.91 (bs, 1H), 1.89 (bs, 1H), 1.75-1.64 (m, 4H), 1.30-1.27 (m, 2H); $^{13}$C NMR (100 MHz, $CD_3OD$) δ 171.92, 167.39, 144.03, 142.35, 141.11, 139.14, 137.48, 136.83, 134.46, 133.65, 129.74, 128.50, 127.94, 119.39, 115.32, 113.48, 43.46, 38.38, 34.93, 34.58, 33.46, 32.58; MS (ESI) m/z 451 $[C_{27}H_{26}N_6O+H]^+$.

Example 11: 4-(6-(4-(4-methyl-1,2,3,6-tetrahydropyridine-1-carbonyl)phenyl)imidazo[1,2-a]pyrazin-3-yl)benzonitrile

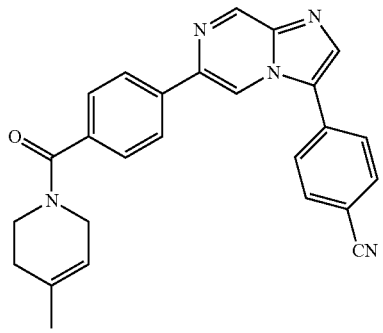 [SMILES: CC1=CCN(C(=O)c2ccc(-c3cn4c(-c5ccc(C#N)cc5)cnc4cn3)cc2)CC1]

To a solution of 4-(3-(4-carbamoylphenyl)imidazo[1,2-a]pyrazin-6-yl)benzoic acid (100 mg, 0.279 mmol) in DMF (0.56 mL) was added phosphorus oxychloride (51 μl, 0.558 mmol) dropwise. The reaction mixture was stirred at room temperature under inert atmosphere for 4 h, followed by the addition of 4-methylpiperidin-4-ol (43 mg, 0.279 mmol) and anhydrous pyridine (1 mL). The reaction mixture was cooled to 0° C., and phosphorus oxychloride (28 μl, 0.307 mmol) was added dropwise. The reaction mixture was stirred at 0° C. for at least 30 min, and allowed to warm to room temperature overnight. The reaction mixture was then diluted with water (25 mL) and extracted with EtOAc (3×25 mL). The combined organic layer was dried over $Na_2SO_4$ and was concentrated under reduced pressure. The crude residue was purified by column chromatography (silica gel, eluent $CH_2Cl_2$/MeOH 95:5) to afford 4-(6-(4-(4-methyl-1,2,3,6-tetrahydropyridine-1-carbonyl)phenyl)imidazo[1,2-a]pyrazin-3-yl)benzonitrile (36 mg, 31%, AUC HPLC 93%) as a yellow solid. $^1$H NMR (400 MHz, $CDCl_3$) δ 9.29 (s, 1H), 8.59 (s, 1H), 7.98-7.95 (m, 3H), 7.91-7.88 (m, 2H), 7.77-7.75 (m, 2H), 7.56-7.54 (m, 2H), 5.48-5.23 (br s, 1H), 4.17 (bs., 1H), 3.88 (bs., 2H), 3.50 (bs., 1H), 2.16-2.07 (m, 2H), 1.74 (s., 3H); $^{13}$C NMR (400 MHz, $CDCl_3$) δ 144.12, 141.20, 140.31, 137.37, 136.99, 136.25, 133.45, 132.49, 128.18, 126.49, 125.66, 118.13, 112.69, 112.38, 23.10; MS (ESI) m/z 420 $[C_{26}H_{21}N_5O+H]^+$.

Example 12: 4-(6-(4-(4-ethylpiperazine-1-carbonyl)phenyl)imidazo[1,2-a]pyrazin-3-yl)benzonitrile

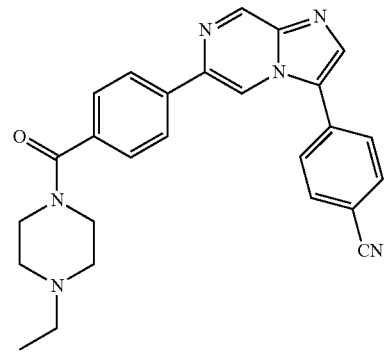 [SMILES: CCN1CCN(C(=O)c2ccc(-c3cn4c(-c5ccc(C#N)cc5)cnc4cn3)cc2)CC1]

Step 1: (4-ethylpiperazin-1-yl)(4-(3-iodoimidazo[1,2-a]pyrazin-6-yl)phenyl)methanone was prepared following General procedure A and the reaction crude product was used without further purification in the next step. $^1$H NMR (400 MHz, $CDCl_3$) δ 9.11 (s, 1H), 8.72 (s, 1H), 8.10 (s, 1H), 8.19 (d, J=8.0 Hz, 2H), 7.51 (d, J=8.0 Hz, 2H), 3.61 (bs, 2H), 3.51 (bs, 4H), 2.39 (bs, 2H), 2.34 (m, 2H), 1.00 (s, 3H); MS (ESI) m/z 461 $[C_{19}H_{20}IN_5O]^+$ Step 2: The title compound was prepared following General procedure B with (4-ethylpiperazin-1-yl)(4-(3-iodoimidazo[1,2-a]pyrazin-6-yl)phenyl)methanone and 4-cyanophenylboronic acid as starting materials. The reaction crude product was purified by column chromatography (silica gel, 100-200 eluent $CH_2Cl_2$/$CH_3OH$ 95:5) to afford 4-(6-(4-(4-ethylpiperazine-1-carbonyl)phenyl)imidazo[1,2-a]pyrazin-3-yl)benzonitrile (95 mg, 20%, AUC HPLC 95.7%) as a light green solid. $^1$H NMR (400 MHz, DMSO-$d_6$) δ 9.30 (s, 1H), 8.60 (s, 1H), 7.99 (s, 1H), 7.97 (d, J=8 Hz, 2H), 7.91 (d, J=8.4 Hz, 2H), 7.77 (d J=8 Hz, 2H), 7.55 (d, J=8 Hz, 2H), 3.86-3.80 (m, 2H), 3.50-3.43 (m, 2H), 2.60-2.40 (m, 6H), 1.10 (t, J=5.4 Hz, 3H); MS (ESI) m/z 437 $[C_{26}H_{24}N_6O+H]^+$.

Example 13: 4-(6-(4-(4-isopropylpiperazine-1-carbonyl)phenyl)imidazo[1,2-a]pyrazin-3-yl)benzonitrile

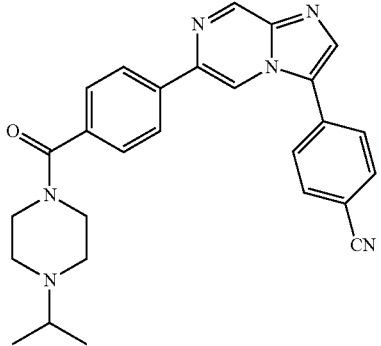 [SMILES: CC(C)N1CCN(C(=O)c2ccc(-c3cn4c(-c5ccc(C#N)cc5)cnc4cn3)cc2)CC1]

Step 1: (4-(3-iodoimidazo[1,2-a]pyrazin-6-yl)phenyl)(4-isopropylpiperazin-1-yl)methanone was prepared following General procedure A and the reaction crude product was used without further purification in the next step.

$^1$H NMR (400 MHz, CDCl$_3$) δ 9.15 (d, J=1.2 Hz, 1H), 8.44 (d, J=1.2 Hz, 1H), 8.05 (d, J=8.0 Hz, 2H), 7.83 (s, 1H), 7.57 (d, J=8.0 Hz, 2H), 3.85 (bs, 2H), 3.51 (bs, 2H), 2.53 (bs, 2H), 2.41 (bs, 2H), 2.05-2.00 (m, 1H), 1.35 (d, J=8.0 Hz, 6H); MS (ESI) m/z 475 $[C_{20}H_{22}IN_5O]^+$.

Step 2: 4-(6-(4-(4-isopropylpiperazine-1-carbonyl)phenyl)imidazo[1,2-a]pyrazin-3-yl)benzonitrile was prepared following General procedure B with (4-(3-iodoimidazo[1,2-a]pyrazin-6-yl)phenyl)(4-isopropylpiperazin-1-yl)methanone and 4-cyanophenylboronic acid as starting materials. The reaction crude product was purified by column chromatography (silica gel, 100-200 eluent CH$_2$Cl$_2$/CH$_3$OH 98:2) to afford 4-(6-(4-(4-isopropylpiperazine-1-carbonyl)phenyl)imidazo[1,2-a]pyrazin-3-yl)benzonitrile (60 mg, 23%, AUC HPLC>99%) as an off-white solid. $^1$H NMR (400 MHz, DMSO-d$_6$) δ 9.30 (s, 1H), 9.03 (s, 1H), 8.23 (s, 1H), 8.14 (d, J=8.0 Hz, 2H), 8.03-8.09 (m, 4H), 7.50 (d, J=8.4 Hz, 2H), 3.60 (bs, 4H), 2.66-2.72 (m, 1H), 2.49 (bs, 4H), 0.96 (d, J=6.4 Hz, 6H); MS (ESI) m/z 451 $[C_{27}H_{26}N_6O+H]^+$.

Example 14: 4-(6-(4-(4-cyclopropylpiperazine-1-carbonyl)phenyl)imidazo[1,2-a]pyrazin-3-yl)benzonitrile

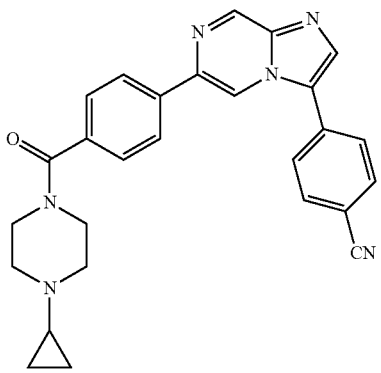 [SMILES: N#Cc1ccc(-c2cnc3cnc(-c4ccc(C(=O)N5CCN(C6CC6)CC5)cc4)cn23)cc1]

Step 1: (4-cyclopropylpiperazin-1-yl)(4-(3-iodoimidazo[1,2-a]pyrazin-6-yl)phenyl) methanone was prepared following General procedure A and the reaction crude product was used without further purification in the next step.

$^1$H NMR (400 MHz, DMSO-d$_6$) δ 9.21 (s, 1H), δ 8.89 (s, 1H), 7.96 (d, J=8.0 Hz, 2H), 7.83 (s, 1H), 7.55 (d, J=8.0 Hz, 2H), 3.75 (bs, 4H), 3.53 (bs, 4H), 2.84-2.90 (m, 1H), 1.10 (s, 2H), 0.77 (d, J=8.0 Hz, 2H); MS (ESI) m/z 473 $[C_{20}H_{20}IN_5O+H]^+$.

Step 2: The title compound was prepared following General procedure B with (4-cyclopropylpiperazin-1-yl)(4-(3-iodoimidazo[1,2-a]pyrazin-6-yl)phenyl) methanone and 4-cyanophenylboronic acid as starting materials. The reaction crude product was purified by column chromatography (silica gel, eluent CH$_2$Cl$_2$/CH$_3$OH 97:3) to afford 4-(6-(4-(4-cyclopropylpiperazine-1-carbonyl)phenyl)imidazo[1,2-a]pyrazin-3-yl)benzonitrile (65 mg, 28%, AUC HPLC 96.9%) as an off-white solid. $^1$H NMR (400 MHz, DMSO-d$_6$) δ 9.30 (s, 1H), 9.03 (s, 1H), 8.23 (s, 1H), 8.15 (d, J=8.0 Hz, 2H), 8.03-8.09 (m, 4H), 7.50 (d, J=8.0 Hz, 2H), 3.58 (bs, 4H), 2.62 (bs, 4H), 1.64-1.67 (m, 1H), 0.32 (d, J=8.0 Hz, 2H), 0.42 (d, J=8.0 Hz, 2H); MS (ESI) m/z 449 $[C_{27}H_{24}N_6O+H]^+$.

Example 15: 4-(6-(4-(4-hydroxypiperidine-1-carbonyl)phenyl)imidazo[1,2-a]pyrazin-3-yl)benzonitrile

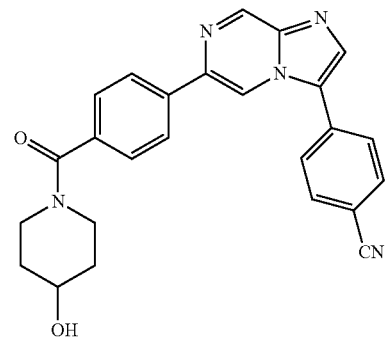 [SMILES: N#Cc1ccc(-c2cnc3cnc(-c4ccc(C(=O)N5CCC(O)CC5)cc4)cn23)cc1]

Step 1: 1-(4-(3-iodoimidazo[1,2-a]pyrazin-6-yl)benzoyl)piperidin-4-one was prepared following General procedure A and the reaction crude product was used without further purification in the next step.

$^1$H NMR (400 MHz, CDCl$_3$) δ 9.15 (d, J=1.2 Hz, 1H), 8.44 (d, J=1.2 Hz, 1H), 8.05 (d, J=8.0 Hz, 2H), 7.83 (s, 1H), 7.57 (d, J=8.0 Hz, 2H), 3.85 (bs, 2H), 3.51 (bs, 2H), 2.53 (bs, 2H), 2.41 (bs, 2H); MS (ESI) m/z 446 $[C_{18}H_{15}IN_4O_2+H]^+$.

Step 2: 4-(6-(4-(4-oxopiperidine-1-carbonyl)phenyl)imidazo[1,2-a]pyrazin-3-yl)benzonitrile was prepared following General procedure B with 1-(4-(3-iodoimidazo[1,2-a]pyrazin-6-yl)benzoyl)piperidin-4-one and 4-cyanophenylboronic acid as starting materials. The reaction crude product was purified by column chromatography (silica gel, 100-200 eluent CH$_2$Cl$_2$/CH$_3$OH 97:3) to afford 4-(6-(4-(4-oxopiperidine-1-carbonyl)phenyl)imidazo[1,2-a]pyrazin-3-yl)benzonitrile (20 mg, 24%, AUC HPLC 96.9%) as an off-white solid; $^1$H NMR (400 MHz, DMSO-d$_6$) δ 9.31 (s, 1H), 9.05 (s, 1H), 8.24 (s, 1H), 8.18 (d, J=8.4 Hz, 2H), 8.04-8.09 (m, 4H), 7.61 (d, J=8.4 Hz, 2H), 3.75 (bs, 8H); MS (ESI) m/z 422 $[C_{25}H_{19}N_5O_2+H]^+$.

Step 3: To a solution of 4-(6-(4-(4-oxopiperidine-1-carbonyl)phenyl)imidazo[1,2-a]pyrazin-3-yl)benzonitrile (140 mg, 0.34 mmol) in methanol (5 mL) was added sodium borohydride (19 mg, 0.5 mmol). The reaction mixture was stirred at room temperature for 1 h and was concentrated under reduced pressure. The residue was purified by flash column chromatography (silica gel, eluent $CH_2Cl_2/CH_3OH$ 90:10) to afford 4-(6-(4-(4-hydroxypiperidine-1-carbonyl)phenyl)imidazo[1,2-a]pyrazin-3-yl)benzonitrile (65 mg, 50%, AUC HPLC>99%) as gray solid. $^1$H NMR (400 MHz, DMSO-$d_6$) δ 9.30 (s, 1H), 9.03 (s, 1H), 8.23 (s, 2H), 8.03-8.09 (m, 5H), 7.48 (d, J=8.4 Hz, 2H), 4.10 (d, J=8.0 Hz, 1H), 1.22 (bs, 8H); MS (ESI) m/z 424 $[C_{25}H_{21}N_5O_2+H]^+$.

Intermediate 11: ethyl 4-(3-(4-cyanophenyl)imidazo[1,2-a]pyrazin-6-yl)benzoate

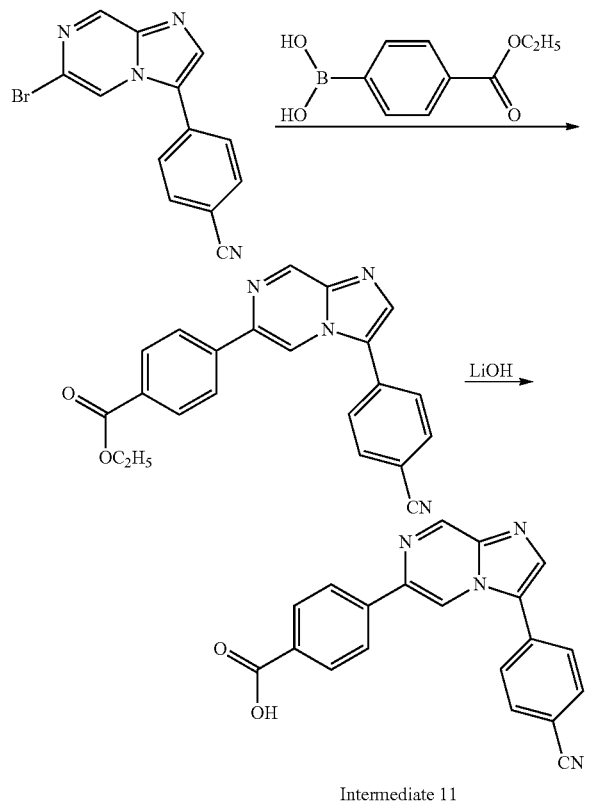

Intermediate 11

Step 1: To a solution of 4-(6-bromoimidazo[1,2-a]pyrazin-3-yl)benzonitrile (5.00 g, 16.7 mmol) in DMF (100 mL), were added 4-(ethoxycarbonyl)phenylboronic acid (4.90 g, 25.2 mmol), $Na_2CO_3$ (4.40 g, 41.5 mmol), water (5.0 mL) and Pd(PPh$_3$)$_4$ (386 mg, 0.33 mmol). The reaction mixture was heated at 90° C. for 2 h under argon atmosphere then, was diluted with water. The precipitate was isolated by filtration and dried under vacuum to afford ethyl 4-(3-(4-cyanophenyl)imidazo[1,2-a]pyrazin-6-yl)benzoate (2.80 g, 46%) as off white solid. $^1$H NMR (400 MHz, DMSO-$d_6$) δ 9.28 (s, 1H), 9.07 (s, 1H), 8.25 (s, 1H), 8.22 (d, J=6.0 Hz, 2H), 8.08-8.02 (m, 6H), 4.38-4.33 (m, 2H), 1.36 (t, J=7.2 Hz, 3H); MS (ESI) m/z 369 $[C_{22}H_{16}N_4O_2+H]^+$ Step 2: To a solution of ethyl 4-(3-(4-cyanophenyl)imidazo[1,2-a]pyrazin-6-yl)benzoate (2.80 g, 7.61 mmol) in THF/CH$_3$OH/H$_2$O (50/20/20 mL) was added LiOH.H$_2$O (1.25 g, 30.5 mmol). The reaction mixture was stirred at rt for 12 h and was concentrated to a smaller volume. The residue was diluted with water (20 mL) and acidified till pH 2. The precipitate was filtered off and dried to afford 4-(3-(4-cyanophenyl)imidazo[1,2-a]pyrazin-6-yl)benzoic acid (2.00 g, 80%) as off white solid. $^1$H NMR (400 MHz, DMSO-$d_6$) δ: 9.30 (s, 1H), 9.08 (s, 1H), 8.22 (d, J=9.6 Hz, 3H), 8.06-8.02 (m, 6H); MS (ESI) m/z 341 $[C_{20}H_{12}N_4O_2+H]^+$.

Example 16: 4-(6-(4-(4-hydroxy-4-methylpiperidine-1-carbonyl)phenyl)imidazo[1,2-a]pyrazin-3-yl)benzonitrile

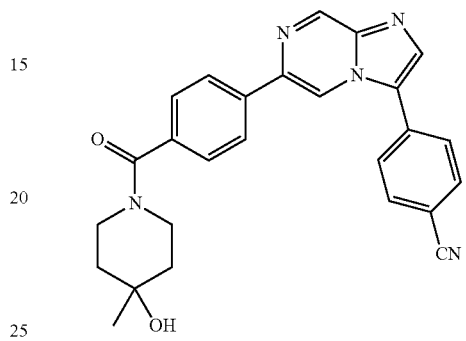

To a solution of 4-(3-(4-cyanophenyl)imidazo[1,2-a]pyrazin-6-yl)benzoic acid (100 mg, 0.294 mmol) in DMF (1.5 mL) was added HATU (168 mg, 0.442 mmol) and N-methyl morpholine (130 μl, 1.178 mmol). The reaction mixture was stirred at room temperature under inert atmosphere for 1 h, followed by the addition of 4-methylpiperidin-4-ol hydrochloride (89 mg, 0.587 mmol). The reaction mixture was left to stir for 18 h, then was diluted with water (25 mL) and extracted with EtOAc (3×25 mL). The combined organic layer was dried over $Na_2SO_4$ and was concentrated under reduced pressure. The crude residue was purified by column chromatography (silica gel, eluent $CH_2Cl_2$/MeOH 95:5) to afford 4-(6-(4-(4-hydroxy-4-methylpiperidine-1-carbonyl)phenyl)imidazo[1,2-a]pyrazin-3-yl)benzonitrile (73 mg, 57%, AUC HPLC 97%) as a white solid. $^1$H NMR (400 MHz, CDCl$_3$) δ 9.28 (s, 1H), 8.59 (s, 1H), 7.98-7.94 (m, 3H), 7.90-7.88 (m, 2H), 7.77-7.75 (m, 2H), 7.53 (d, J=8.4 Hz, 2H), 4.35 (bs, 1H), 3.51-3.38 (m., 3H), 1.70-1.55 (m, 4H), 1.32 (s, 3H); $^{13}$C NMR (400 MHz, CDCl$_3$) δ 169.70, 144.12, 141.20, 140.29, 137.33, 136.86, 136.24, 133.45, 132.47, 128.19, 127.70, 126.54, 125.68, 118.13, 112.70, 112.39, 68.13, 30.41; MS (ESI) m/z 438 $[C_{26}H_{23}N_5O_2+H]^+$.

Example 17: 4-(6-(4-(4-methyl-1,4-diazepane-1-carbonyl)phenyl)imidazo[1,2-a]pyrazin-3-yl)benzonitrile

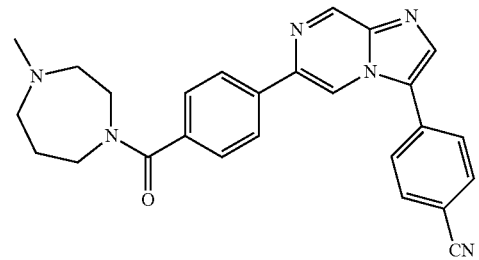 [SMILES: CN1CCCN(C(=O)c2ccc(-c3cn4c(-c5ccc(C#N)cc5)cnc4cn3)cc2)CC1]

The title compound was prepared according to general procedure A using 4-(3-(4-cyanophenyl)imidazo[1,2-a]pyrazin-6-yl)benzoic acid and 1-methyl-homopiperazine as starting materials. The reaction mixture was stirred at room temperature under inert atmosphere for 18 h, then it was diluted with water (10 mL) and extracted with EtOAc (3×30 mL). The combined organic layer was dried over Na$_2$SO$_4$ and was concentrated under reduced pressure. The residue was purified by preparative HPLC (C18, eluent ACN, water, formic acid 0.1%) to afford 4-(6-(4-(4-methyl-1,4-diazepane-1-carbonyl)phenyl)imidazo[1,2-a]pyrazin-3-yl)benzonitrile (11 mg, 17%, AUC HPLC 99%) as a white solid. $^1$H NMR (400 MHz, DMSO-d$_6$) δ 9.30 (d, J=1.2 Hz, 1H), 9.03 (d, J=1.2 Hz, 1H), 8.24 (s, 1H), 8.15 (d, J=8.4 Hz, 2H), 8.11-8.01 (m, 4H), 7.50 (d, J=7.2 Hz, 2H), 3.70-3.60 (m, 4H), 2.70-2.64 (m, 1H), 2.61-2.55 (m, 1H), 2.60-2.50 (m, 2H), 2.29 (d, J=26.0 Hz, 3H), 1.91-1.82 (m, 1H), 1.80-1.70 (m, 1H); MS (ESI) m/z 437 [C$_{26}$H$_{24}$N$_6$O+H]$^+$.

Example 18: 4-(6-(4-(4-aminopiperidine-1-carbonyl)phenyl)imidazo[1,2-a]pyrazin-3-yl)benzonitrile Hydrochloride

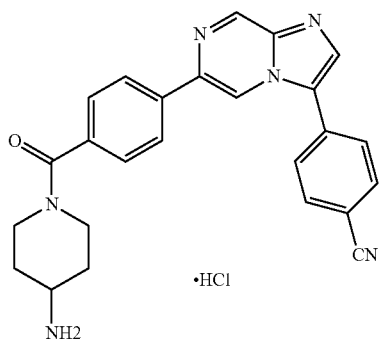 [SMILES: N#Cc1ccc(-c2cnc3cnc(-c4ccc(C(=O)N5CCC(N)CC5)cc4)cn23)cc1 ; Cl]

Step 1: tert-butyl 1-(4-(3-(4-cyanophenyl)imidazo[1,2-a]pyrazin-6-yl)benzoyl)piperidin-4-ylcarbamate was prepared following General procedure A and the reaction crude product was purified by column chromatography (silica gel, 100-200 eluent CH$_2$Cl$_2$/CH$_3$OH 97:3). $^1$H NMR (400 MHz, CDCl$_3$) δ 9.30 (s, 1H), 8.61 (s, 1H), 8.02 (bs, 1H), 8.00 (s, 1H), 7.98 (d, J=8.4 Hz, 2H), 7.96 (d, J=8.0 Hz, 2H), 7.79 (d, J=8.4 Hz, 2H), 7.53 (d, J=8.0 Hz, 2H), 4.30-4.25 (m, 1H), 3.74-3.70 (m, 4H), 2.10-2.06 (m, 4H), 1.45 (bs, 9H); MS (ESI) m/z 523 [C$_{30}$H$_{30}$N$_6$O$_3$+H]$^+$.

Step 2: A solution of tert-butyl 1-(4-(3-(4-cyanophenyl)imidazo[1,2-a]pyrazin-6-yl)benzoyl)piperidin-4-ylcarbamate (100 mg, 0.90 mmol) in a mixture of CH$_2$Cl$_2$ (5 mL), and 20% HCl solution in 1,4-dioxan (0.15 mL, 0.82 mmol) was stirred at room temperature for 2 h. The reaction mixture was concentrated to afford 4-(6-(4-(4-aminopiperidine-1-carbonyl)phenyl)imidazo[1,2-a]pyrazin-3-yl)benzonitrile Hydrochloride (52 mg, 59%, AUC HPLC 98.0%) as a yellow solid. $^1$H NMR (400 MHz, CDCl$_3$) δ 9.32 (s, 1H), 9.04 (s, 1H), 8.3 (bs, 1H), 8.26 (s, 1H), 8.18-8.16 (m, 3H), 8.07-8.04 (m, 4H), 7.48 (d, J=8.0 Hz, 2H), 3.30-3.20 (m, 2H), 2.01-1.96 (m, 4H), 1.49-1.39 (m, 2H); MS (ESI) m/z 458 [C$_{25}$H$_{22}$N$_6$O+H]$^+$.

Example 19: 4-(6-(4-(4,4-dimethylpiperidine-1-carbonyl)phenyl)imidazo[1,2-a]pyrazin-3-yl)benzonitrile

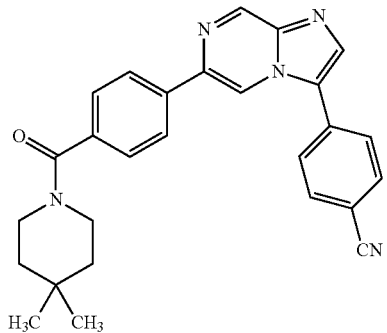 [SMILES: CC1(C)CCN(C(=O)c2ccc(-c3cn4c(-c5ccc(C#N)cc5)cnc4cn3)cc2)CC1]

The title compound was prepared following General procedure A with 4,4-dimethylpiperidine as starting material. The reaction crude product was purified by flash column chromatography (silica gel, 100-200 eluent CH$_2$Cl$_2$/CH$_3$OH 95:5) to afford 4-(6-(4-(4,4-dimethylpiperidine-1-carbonyl)phenyl)imidazo[1,2-a]pyrazin-3-yl)benzonitrile (35 mg, 14%, AUC HPLC 95%) as a light brown solid. $^1$H NMR (400 MHz, CDCl$_3$) δ 9.29 (s, 1H), 8.59 (s, 1H), 7.99-7.89 (m, 5H), 7.77 (d, J=8.4 Hz, 2H), 7.53 (d, J=8.4 Hz, 2H), 3.75 (bs, 2H), 3.39 (bs, 2H), 1.49 (bs, 2H), 1.32 (bs, 2H), 1.01 (s, 6H); MS (ESI) m/z 436 [C$_{27}$H$_{25}$N$_5$O+H]$^+$.

Example 20: 4-(6-(4-(4-(aminomethyl)-4-hydroxypiperidine-1-carbonyl)phenyl) imidazo[1,2-a]pyrazin-3-yl)benzonitrile

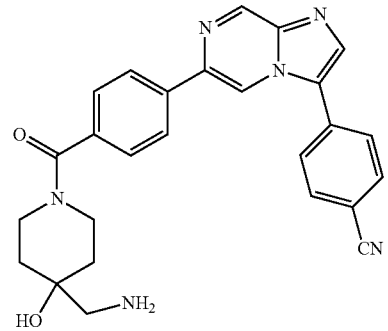 [SMILES: N#Cc1ccc(-c2cnc3cnc(-c4ccc(C(=O)N5CCC(O)(CN)CC5)cc4)cn23)cc1]

Step 1: To a solution of t-butyl-4-(aminomethyl)-4-hydroxypiperidine-1-carboxylate (2.0 g, 8.69 mmol) in THF, were added DMAP (110 mg, 0.86 mmol) and ethyl 2,2,2-trifluoroacetate (1.5 g, 10.43 mmol). The reaction mixture was heated at 70° C. and stirred for 6 h then was diluted with ethyl acetate. The organic layer was washed in turn with 1N HCl (2×10 mL) and brine then, dried over Na$_2$SO$_4$, filtered and concentrated. The residue was purified by flash column chromatography (silica gel, eluent n-Hexane/EtOAc 70:30) to afford tert-butyl 4-hydroxy-4-((2,2,2-trifluoroacetamido)methyl)piperidine-1-carboxylate (2.00 g, 84%) as an oil. $^1$H NMR (400 MHz, CDCl$_3$) δ 6.90 (bs, 1H), 3.79 (bs, 2H), 3.41 (bs, 2H), 3.25-3.18 (m, 4H), 1.57 (bs, 4H), 1.48 (s, 9H); MS (ESI) m/z 327 [C$_{13}$H$_{21}$F$_3$N$_2$O$_4$+H]$^+$.

Step 2: A solution of tert-butyl 4-hydroxy-4-((2,2,2-trifluoroacetamido)methyl)piperidine-1-carboxylate (500 mg, 8.69 mmol) in a mixture of 1,4-dioxane and 30% HCl solution in 1,4-dioxane (10 mL). The reaction mixture was stirred for 3 h at room temperature and was concentrated to afford 2,2,2-trifluoro-N-((4-hydroxypiperidin-4-yl)methyl)acetamide (400 mg, 90%) as an oil. $^1$H NMR (400 MHz, DMSO-$d_6$) δ 5.08 (bs, 1H), 3.37 (bs, 2H), 3.20 (d, J=6.4 Hz, 2H), 3.10-3.07 (m, 2H), 3.01-2.94 (m, 2H), 1.72-1.64 (m, 2H), 1.57-1.54 (m, 2H); MS (ESI) m/z 227 $[C_8H_{14}ClF_3N_2O_2+H]^+$.

Step 3: To a solution of 4-(3-(4-hydroxyphenyl)-1-(tetrahydro-2H-pyran-2-yl)-1H-indazol-5-yl)benzoic acid (300 mg, 0.88 mmol) in DMF (5 mL) were added N-methylmorpholine (270 mg, 3.57 mmol), HATU (503 mg, 1.32 mmol) and 2,2,2-trifluoro-N-((4-hydroxypiperidin-4-yl)methyl)acetamide (350 mg, 3.57 mmol). The reaction mixture was stirred for 10 h at room temperature and was quenched by adding water. The aqueous phase was extracted with $CH_2Cl_2$ and the organic layer was washed with brine solution, dried over $Na_2SO_4$, filtered and concentrated. The crude compound was purified by flash column chromatography (silica gel, eluent $CH_2Cl_2/CH_3OH$ 95:5) to afford N-((1-(4-(3-(4-cyanophenyl)imidazo[1,2-a]pyrazin-6-yl)benzoyl)-4-hydroxypiperidin-4-yl)methyl)-2,2,2-trifluoroacetamide (70 mg, 20%) as an off white solid. $^1$H NMR (400 MHz, DMSO-$d_6$) δ 9.29 (s, 2H), 9.03 (s, 1H), 8.23 (s, 1H), 8.14 (d, J=8.4 Hz, 2H), 8.09-8.03 (m, 4H), 7.49 (d, J=8.0 Hz, 2H), 4.78 (s, 1H), 4.20 (bs, 1H), 3.40 (bs, 1H), 3.28 (bs, 1H), 3.22 (d, J=6.0 Hz, 2H), 3.15 (bs, 1H), 1.52-1.40 (m, 4H); MS (ESI) m/z 549 $[C_{28}H_{23}F_3N_6O_3+H]^+$.

Step 4: To a solution of N-((1-(4-(3-(4-cyanophenyl)imidazo[1,2-a]pyrazin-6-yl)benzoyl)-4-hydroxypiperidin-4-yl)methyl)-2,2,2-trifluoroacetamide (100 mg, 0.17 mmol) in methanol (5 mL) was added $K_2CO_3$ (97 mg, 0.44 mmol) was added. The reaction mixture was stirred for 5 h then was concentrated under reduced pressure. The residue was purified by flash column chromatography (silica gel, eluent $CH_2Cl_2/CH_3OH$ 90:10) to afford 4-(6-(4-(4-(aminomethyl)-4-hydroxypiperidine-1-carbonyl)phenyl) imidazo[1,2-a]pyrazin-3-yl)benzonitrile (50 mg, 40%, AUC HPLC 96.7%) as a light yellow solid. $^1$H NMR (400 MHz, DMSO-$d_6$) δ 9.20 (s, 1H), 8.95 (s, 1H), 8.15-8.11 (m, 3H), 8.02-7.96 (m, 4H), 7.55 (d, J=8.4 Hz, 2H), 4.41 (bs, 2H), 3.65-3.49 (bs, 2H), 3.35 (s, 2H), 2.94 (s, 2H), 1.77-1.63 (m, 4H); MS (ESI) m/z 453 $[C_{26}H_{24}N_6O_2+H]^+$.

Example 21: 4-(6-(4-(4-(dimethylamino)piperidine-1-carbonyl)phenyl)imidazo[1,2-a]pyrazin-3-yl)benzonitrile The title compound was prepared following General procedure A using 4-(3-(4-cyanophenyl)imidazo[1,2-a]pyrazin-6-yl)benzoic acid and NN-dimethyl-4-aminopiperidine as starting materials. The reaction crude product was purified by column chromatography (silica gel, eluent $CH_2Cl_2/CH_3OH$ 96:4) to afford 4-(6-(4-(4-(dimethylamino)piperidine-1-carbonyl)phenyl)imidazo[1,2-a]pyrazin-3-yl)benzonitrile (65 mg, 22%, AUC HPLC 96%) as an off-white solid. $^1$H NMR (400 MHz, DMSO-$d_6$) δ 9.31 (s, 1H), 9.03 (s, 1H), 8.24 (s, 1H), 8.16 (d, J=8.0 Hz, 2H), 8.04-8.09 (m, 4H), 7.52 (d, J=8.0 Hz, 2H), 3.55 (bs, 4H), 3.08-3.16 (m, 1H), 2.85 (t, 6H), 2.25 (bs, 4H); MS (ESI) m/z 451 $[C_{27}H_{26}N_6O+H]^+$.

Example 22: N-(1-(4-(3-(4-cyanophenyl)imidazo[1,2-a]pyrazin-6-yl)benzoyl)piperidin-4-yl)acetamide

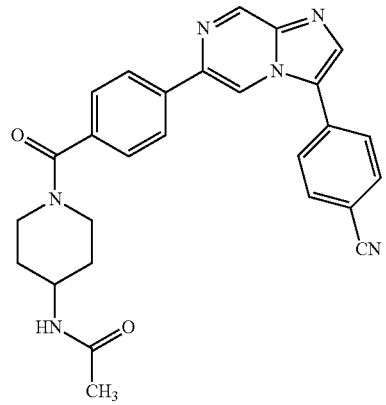 [SMILES: CC(=O)NC1CCN(C(=O)c2ccc(-c3cn4c(-c5ccc(C#N)cc5)cnc4cn3)cc2)CC1]

The title compound was prepared following General procedure A using 4-(3-(4-cyanophenyl)imidazo[1,2-a]pyrazin-6-yl)benzoic acid and 4-N-acetamido-piperidine as starting materials. The reaction crude production was purified by column chromatography (silica gel, eluent $CH_2Cl_2/CH_3OH$ 93:7) to afford N-(1-(4-(3-(4-cyanophenyl)imidazo[1,2-a]pyrazin-6-yl)benzoyl)piperidin-4-yl)acetamide (80 mg, 29%, AUC HPLC 96%) as an off-white solid. $^1$H NMR (400 MHz, CD$_3$OD) δ 9.21 (s, 1H), 8.96 (s, 1H), 8.14 (d, J=8.4 Hz, 2H), 8.11 (s, 1H), 8.02-7.96 (m, 4H), 7.54 (d, J=8.0 Hz, 2H), 3.96 (bs, 1H), 3.72 (s, 3H), 3.09 (bs, 1H), 2.51 (bs, 2H), 4.59 (bs, 1H), 2.02 (bs, 1H), 1.94 (s, 3H), 1.88 (bs, 1H); MS (ESI) m/z 465 $[C_{27}H_{24}N_6O_2+H]^+$.

Example 23: 4-(6-(4-(4-amino-4-methylpiperidine-1-carbonyl)phenyl)imidazo[1,2-a]pyrazin-3-yl)benzonitrile Hydrochloride Salt

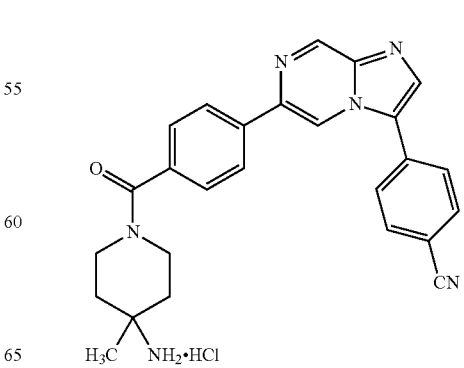

Step 1: tert-butyl 1-(4-(3-(4-cyanophenyl)imidazo[1,2-a]pyrazin-6-yl)benzoyl)-4-methylpiperidin-4-ylcarbamate was prepared following General procedure A using 4-(3-(4-cyanophenyl)imidazo[1,2-a]pyrazin-6-yl)benzoic acid and tert-butyl 4-methylpiperidin-4-ylcarbamate as starting materials. The reaction crude production was purified by column chromatography (silica gel, eluent CH$_2$Cl$_2$/CH$_3$OH 95:5). $^1$H NMR (400 MHz, CDCl$_3$) δ 9.30 (s, 1H), 9.03 (s, 1H), 8.23 (s, 1H), 8.12 (d, J=8.0 Hz, 2H), 8.09-8.03 (m, 4H), 7.49 (d, J=8.0 Hz, 2H), 6.62 (bs, 1H), 3.39-3.35 (m, 1H), 3.21 (bs, 3H), 2.10-1.96 (m, 3H), 1.37-1.30 (m, 13H); MS (ESI) m/z 537 [C$_{31}$H$_{32}$N$_6$O$_3$+H]$^+$.

Step 2: A solution of tert-butyl 1-(4-(3-(4-cyanophenyl)imidazo[1,2-a]pyrazin-6-yl)benzoyl)-4-methylpiperidin-4-ylcarbamate (150 mg, 0.27 mmol) in a mixture of CH$_2$Cl$_2$ (5 mL) and 20% HCl solution in 1,4-dioxane (0.15 mL, 0.82 mmol) was stirred at room temperature for 2 h. The reaction mixture was concentrated to afford 4-(6-(4-(4-amino-4-methylpiperidine-1-carbonyl)phenyl)imidazo[1,2-a]pyrazin-3-yl)benzonitrile hydrochloride salt (76 mg, 60%, AUC HPLC 97%) as an off-white solid. $^1$H NMR (400 MHz, CDCl$_3$) δ 9.32 (s, 1H), 9.04 (s, 1H), 8.26 (s, 1H), 8.24 (bs, 1H), 8.17 (d, J=12.0 Hz, 2H), 8.09-8.04 (m, 4H), 7.49 (d, J=8.0 Hz, 2H), 3.39-3.29 (m, 3H), 1.76-1.58 (m, 4H), 1.39 (bs, 3H); MS (ESI) m/z 473 [C$_{26}$H$_{24}$N$_6$O+H]$^+$.

Example 24: 4-(6-(4-(2-oxa-7-azaspiro[3.5]nonane-7-carbonyl)phenyl)imidazo[1,2-a]pyrazin-3-yl)benzonitrile

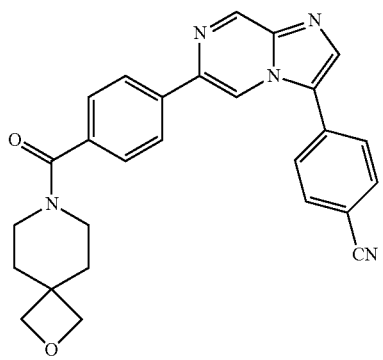 [SMILES: N#Cc1ccc(-c2cnc3cnc(-c4ccc(C(=O)N5CCC6(CC5)COC6)cc4)cn23)cc1]

The title compound was prepared following General procedure A using 4-(3-(4-cyanophenyl)imidazo[1,2-a]pyrazin-6-yl)benzoic acid and 2-oxa-7-azaspiro[3.5]nonane as starting materials. The reaction crude product was purified by column chromatography (silica gel, eluent CH$_2$Cl$_2$/CH$_3$OH 95:5) to afford 4-(6-(4-(2-oxa-7-azaspiro[3.5]nonane-7-carbonyl)phenyl)imidazo[1,2-a]pyrazin-3-yl)benzonitrile (58 mg, 25%, AUC HPLC 96%) as an off-white solid. $^1$H NMR (400 MHz, CDCl$_3$) δ 9.30 (s, 1H), 9.04 (s, 1H), 8.24 (s, 1H), 8.14 (d, J=8.0 Hz, 2H), 8.09-8.03 (m, 4H), 7.27 (d, J=8.0 Hz, 2H), 4.33 (bs, 4H), 3.53 (bs, 2H), 3.28 (bs, 2H), 1.78-1.72 (m, 4H); MS (ESI) m/z 450 [C$_{27}$H$_{23}$N$_5$O$_2$+H]$^+$.

Example 25: 4-(6-(4-(2-oxa-6-azaspiro[3.3]heptane-6-carbonyl)phenyl)imidazo[1,2-a]pyrazin-3-yl)benzonitrile

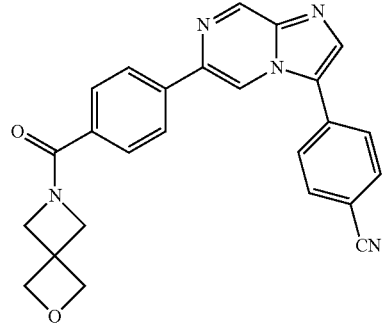 [SMILES: N#Cc1ccc(-c2cnc3cnc(-c4ccc(C(=O)N5CC6(COC6)C5)cc4)cn23)cc1]

The title compound was prepared following General procedure A using 4-(3-(4-cyanophenyl)imidazo[1,2-a]pyrazin-6-yl)benzoic acid and 2-oxa-6-azaspiro[3.3]heptane as starting material. The reaction crude product was purified be column chromatography (silica gel, eluent CH$_2$Cl$_2$/CH$_3$OH 93:7) to afford 4-(6-(4-(2-oxa-6-azaspiro[3.3]heptane-6-carbonyl)phenyl)imidazo[1,2-a]pyrazin-3-yl)benzonitrile (40 mg, 33%, AUC HPLC 96%) as an off-white solid. $^1$H NMR (400 MHz, CDCl$_3$) δ 9.30 (s, 1H), 9.09 (s, 1H), 8.25 (s, 1H), 8.12 (d, J=8.4 Hz, 2H), 8.01-8.10 (m, 4H), 7.27 (d, J=8.0 Hz, 2H), 4.70 (bs, 4H), 4.50 (bs, 2H), 4.20 (bs, 2H); MS (ESI) m/z 422 [C$_{25}$H$_{19}$N$_5$O$_2$+H]$^+$.

Example 26: 4-(6-(4-(4-tert-butylpiperazine-1-carbonyl)phenyl)imidazo[1,2-a]pyrazin-3-yl)benzonitrile

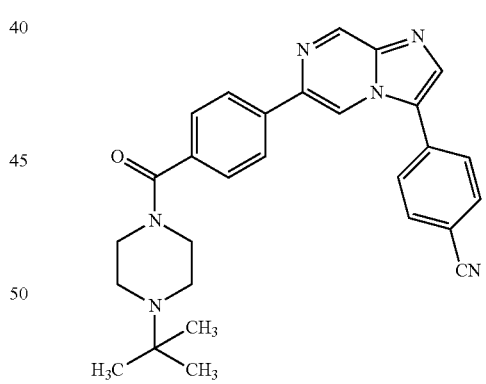

The title compound was prepared following General procedure A using 4-(3-(4-cyanophenyl)imidazo[1,2-a]pyrazin-6-yl)benzoic acid and N-t-butyl piperazine as starting materials. The reaction crude product was purified by column chromatography (silica gel, eluent CH$_2$Cl$_2$/CH$_3$OH 95:5) to afford 4-(6-(4-(4-tert-butylpiperazine-1-carbonyl)phenyl)imidazo[1,2-a]pyrazin-3-yl)benzonitrile (137 mg, 27%, AUC HPLC 98%) as an off-white solid. $^1$H NMR (400 MHz, CDCl$_3$) δ 9.29 (s, 1H), 9.02 (s, 1H), 8.21 (s, 1H), 8.14 (d, J=8.0 Hz, 2H), 8.13-8.03 (m, 4H), 7.49 (d, J=8.0 Hz, 2H), 3.59 (bs, 2H), 2.49-2.43 (m, 6H), 1.02 (s, 9H); MS (ESI) m/z 465 [C$_{28}$H$_{28}$N$_6$O+H]$^+$.

Example 27: 4-(6-(4-(4-aminopiperidine-1-carbonyl)-3-methylphenyl)imidazo[1,2-a]pyrazin-3-yl)benzonitrile

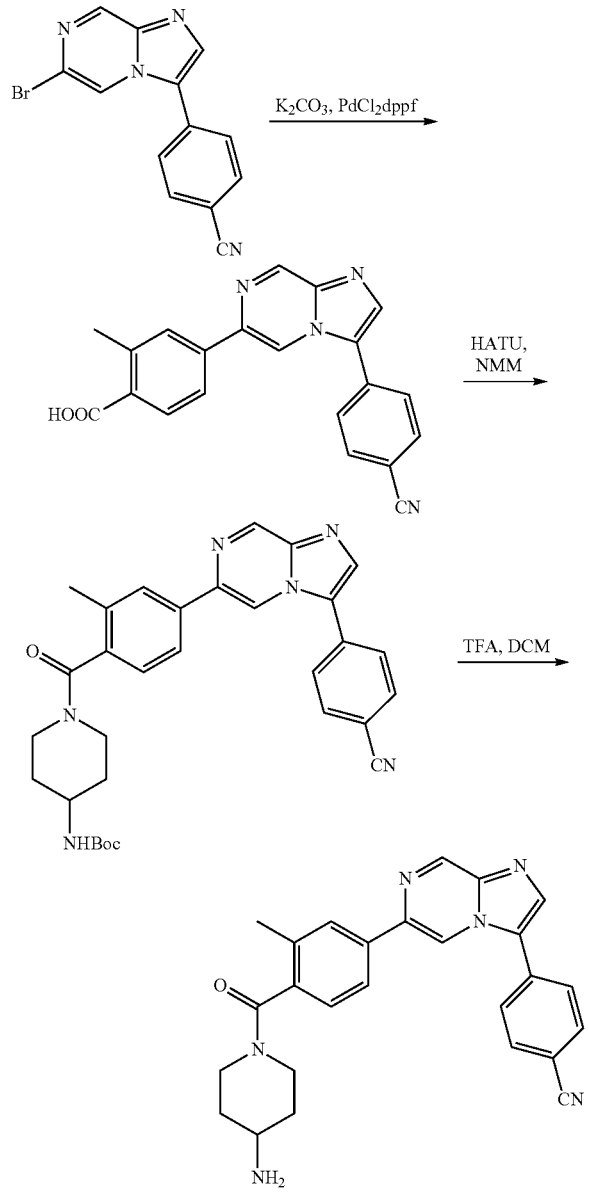

Step 1: To a solution of 6-bromo-3-iodoimidazo[1,2-a]pyrazine (5.00 g, 15.4 mmol) in DMF (60 mL) under inert atmosphere, was added Na$_2$CO$_3$ (4.08 g, 38.6 mmol), 4-cyanophenylboronic acid (2.66 g, 16.9 mmol) and Pd(PPh$_3$)$_4$ (356 mg, 0.31 mmol). The resulting mixture was stirred at 80° C. for 48 h, then was concentrated under reduced pressure. The residue was purified by column chromatography (silica gel, eluent hexane/EtOAc 3:2) to afford the crude 4-(6-bromoimidazo[1,2-a]pyrazin-3-yl)benzonitrile (1.51 g, 33%) as a pink solid. $^1$H NMR (400 MHz, CD$_3$OD) δ 9.07 (d, J=1.2 Hz, 1H), 8.88 (d, J=1.2 Hz, 1H), 8.27 (s, 1H), 8.02 (q, J=7.8 Hz, 4H); MS (ESI) m/z 301 [C$_{13}$H$_7$BrN$_4$+H]$^+$.

Step 2: 4-borono-2-methylbenzoic acid (100 mg, 0.55 mmol), K$_2$CO$_3$ (138 mg, 1.00 mmol) and Pd(dppf)Cl$_2$ (73.1 mg, 0.01 mmol) were added sequentially to a solution of 4-(6-bromoimidazo[1,2-a]pyrazin-3-yl)benzonitrile (150 mg, 0.50 mmol) in DMF at room temperature under inert atmosphere. The reaction mixture was refluxed for 18 h, then was diluted with water (10 mL) and extracted with DCM (3×10 mL). The combined organic layers were dried over Na$_2$SO$_4$, filtered and concentrated under reduced pressure to afford 4-(3-(4-cyanophenyl)imidazo[1,2-a]pyrazin-6-yl)-2-methylbenzoic acid (105 mg, 83%) as a brown solid. $^1$H NMR (400 MHz, DMSO-d$_6$) 12.87 (bs, 1H), 9.31 (s, 1H), 9.07 (s, 1H), 8.24 (s, 1H), 8.10-8.04 (m, 5H), 8.02 (d, J=8.2 Hz, 1H), 7.94 (d, J=8.2 Hz, 1H), 2.62 (s, 3H); MS (ESI) m/z 355 [C$_{21}$H$_{14}$N$_4$O$_2$+H]$^-$ Step 3: To a solution of 4-(3-(4-cyanophenyl)imidazo[1,2-a]pyrazin-6-yl)-2-methylbenzoic acid (50 mg, 0.14 mmol) in DMF (3 mL), were added HATU (80 mg, 0.21 mmol), N-methyl morpholine (57 mg, 0.56 mmol) and tert-butyl piperidin-4-ylcarbamate hydrochloride (56 mg, 0.30 mmol). The reaction mixture was stirred at room temperature under inert atmosphere for 18 h, then was diluted with water (10 mL) and extracted with DCM (3×10 mL). The combined organic layers were dried over Na$_2$SO$_4$, filtered and concentrated under reduced pressure. The crude residue was purified by column chromatography (silica gel, eluent EtOAc) to afford tert-butyl 1-(4-(3-(4-cyanophenyl)imidazo[1,2-a]pyrazin-6-yl)-2-methylbenzoyl)piperidin-4-ylcarbamate (63 mg, 83%) as off-white powder. MS (ESI) m/z 437 [C$_{26}$H$_{24}$N$_6$O+H]$^+$.

Step 4: A solution of tert-butyl 1-(4-(3-(4-cyanophenyl)imidazo[1,2-a]pyrazin-6-yl)-2-methylbenzoyl)piperidin-4-ylcarbamate in DCM (3 mL) and TFA (3 mL) was stirred 18 h at room temperature. The reaction mixture was concentrated under reduced pressure and the residue was purified by preparative HPLC (C18, eluent ACN/H$_2$O/HCOOH 0.01%) to afford 4-(6-(4-(4-aminopiperidine-1-carbonyl)-3-methylphenyl)imidazo[1,2-a]pyrazin-3-yl)benzonitrile (38 mg, 94%, AUC HPLC 98%) as a white solid. $^1$H NMR (400 MHz, CD$_3$OD) δ 9.16 (d, J=1.4 Hz, 1H), 8.89 (d, J=1.4 Hz, 1H), 8.08 (s, 1H), 8.00-7.88 (m, 6H), 7.33 (t, J=8.6 Hz, 1H), 4.78 (s, 1H), 3.60 (bs, 1H), 3.43 (t, J=11.3 Hz, 1H), 3.21 (t, J=11.9 Hz, 1H), 2.97 (bs, 3H), 2.38 (d, J=3.8 Hz, 3H), 2.17 (d, J=12.3 Hz, 1H), 1.97 (bs, 1H), 1.71-1.42 (m, 2H); $^{13}$C NMR (400 MHz, CD$_3$OD) δ 171.84, 163.22, 163.88, 162.53, 143.96, 142.33, 141.26, 138.66, 137.22, 136.79, 134.45, 133.65, 129.74, 127.91, 127.57, 127.21, 125.59, 119.72, 119.38, 115.20, 113.47, 46.00, 40.81, 31.85, 31.36, 30.84, 19.05; MS (ESI) m/z 437 [C$_{26}$H$_{24}$N$_6$O+H]$^+$.

Example 28: 4-(6-(4-(4-amino-4-methylpiperidine-1-carbonyl)-3-methylphenyl)imidazo[1,2-a]pyrazin-3-yl)benzonitrile

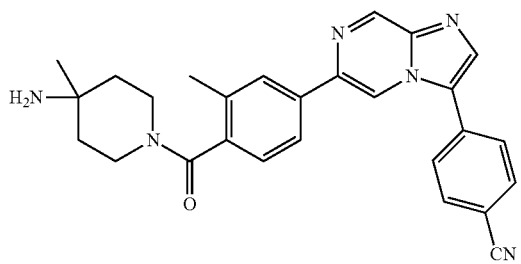 [SMILES: Cc1cc(-c2cn3c(-c4ccc(C#N)cc4)cnc3cn2)ccc1C(=O)N1CCC(C)(N)CC1]

Step 1: To a solution of 4-(3-(4-cyanophenyl)imidazo[1,2-a]pyrazin-6-yl)-2-methylbenzoic acid (55 mg, 0.15 mmol)

in DMF (3 mL), were added HATU (86 mg, 0.30 mmol), N-methyl morpholine (31 mg, 0.30 mmol) and tert-butyl piperidin-4-ylcarbamate hydrochloride (65 mg, 0.30 mmol). The reaction mixture was stirred at room temperature under inert atmosphere for 18 h, then was diluted with water (10 mL) and the aqueous phase was extracted with DCM (3×10 mL). The combined organic layers were dried over $Na_2SO_4$, filtered and concentrated under reduced pressure. The crude residue was purified by column chromatography (silica gel, eluent EtOAc) to afford tert-butyl 1-(4-(3-(4-cyanophenyl)imidazo[1,2-a]pyrazin-6-yl)-2-methylbenzoyl)-4-methylpiperidin-4-ylcarbamate, 7 (36 mg, 83%) as an off-white powder. MS (ESI) m/z 437 $[C_{26}H_{24}N_6O+H]^+$.

Step 2: A solution of tert-butyl 1-(4-(3-(4-cyanophenyl)imidazo[1,2-a]pyrazin-6-yl)-2-methylbenzoyl)-4-methylpiperidin-4-ylcarbamate in DCM (3 mL) and TFA (3 mL) was stirred 18 h at room temperature. The reaction mixture was concentrated under reduced pressure and the residue was purified by preparative HPLC (C18, eluent $ACN/H_2O/$HCOOH 0.01%) to afford 4-(6-(4-(4-amino-4-methylpiperidine-1-carbonyl)-3-methylphenyl)imidazo[1,2-a]pyrazin-3-yl)benzonitrile (37 mg, 54%, AUC HPLC 99%) as a white solid. $^1$H NMR (400 MHz, $CD_3OD$) 9.18 (d, J=1.4 Hz, 1H), 8.91 (d, J=1.4 Hz, 1H), 8.10 (s, 1H), 8.05-7.86 (m, 6H), 7.32 (d, J=8.0 Hz, 1H), 4.37-3.90 (m, 2H), 3.78-3.51 (m, 1H), 3.61-3.32 (m, 1H), 2.98 (t, J=8.6 Hz, 3H), 1.93-1.64 (m, 2H), 1.61 (bs, 2H), 1.36 (s, 3H); $^{13}$C NMR (400 MHz, $CD_3OD$) δ 170.32, 142.54, 140.94, 139.92, 137.19, 136.04, 135.36, 134.88, 132.27, 128.43, 126.51, 124.11, 117.95, 113.77, 112.07, 37.45, 36.95, 36.30, 17.72; MS (ESI) m/z 451 $[C_{27}H_{26}N_6O+H]^+$.

Example 29: 4-(6-(4-(4-aminopiperidine-1-carbonyl)-3-fluorophenyl)imidazo[1,2-a]pyrazin-3-yl)benzonitrile

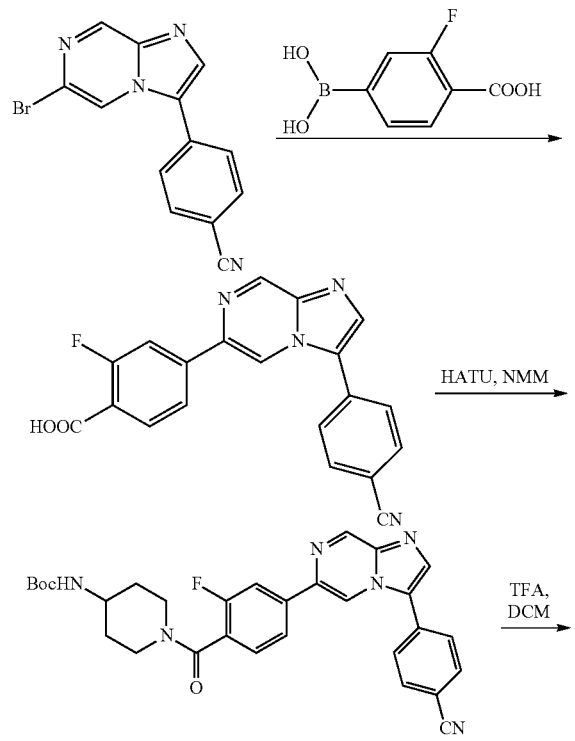

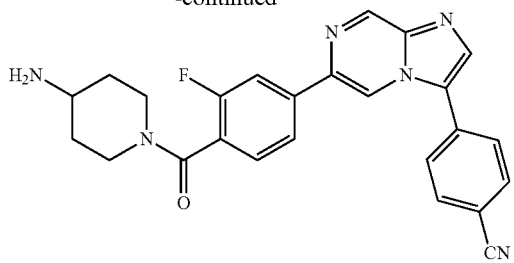

Step 1: 4-borono-2-Fluorobenzoic acid (102 mg, 0.55 mmol), $K_2CO_3$ (138 mg, 1.00 mmol) and $Pd(dppf)Cl_2$ (73.1 mg, 0.01 mmol) were added sequentially to a solution of 4-(6-bromoimidazo[1,2-a]pyrazin-3-yl)benzonitrile (150 mg, 0.50 mmol) in DMF under inert atmosphere. The reaction mixture was refluxed for 18 h, then was diluted with water (10 mL) and extracted with DCM (3×10 mL). The combined organic layers were dried over $Na_2SO_4$, filtered and concentrated under reduced pressure to afford the crude-(3-(4-cyanophenyl)imidazo[1,2-a]pyrazin-6-yl)-2-fluorobenzoic acid (161 mg, 67%) as brown solid. MS (ESI) m/z 359 $[C_{20}H_{11}FN_4O_2+H]^+$.

Step 2: To a solution of 4-(3-(4-cyanophenyl)imidazo[1,2-a]pyrazin-6-yl)-2-fluorobenzoic acid (60 mg, 0.17 mmol) in DMF (3 mL), were successively added HATU (95 mg, 0.25 mmol), N-methylmorpholine (67 mg, 0.67 mmol) and tert-butyl piperidin-4-ylcarbamate hydrochloride (67 mg, 0.34 mmol). The reaction mixture was stirred at room temperature under inert atmosphere for 18 h, and then was diluted with water (10 mL) and the aqueous phase was extracted with DCM (3×10 mL). The combined organic layers were dried over $Na_2SO_4$, filtered and concentrated under reduced pressure. The residue was purified by column chromatography (silica gel, eluent EtOAc) to afford 1-(4-(3-(4-cyanophenyl)imidazo[1,2-a]pyrazin-6-yl)-2-fluorobenzoyl)piperidin-4-ylcarbamate (70 mg, 76%) as an off-white powder. MS (ESI) m/z 441 $[C_{25}H_{21}FN_6O+H]^+$.

Step 3: A solution of tert-butyl 1-(4-(3-(4-cyanophenyl)imidazo[1,2-a]pyrazin-6-yl)-2-fluorobenzoyl)piperidin-4-ylcarbamate (70 mg, 0.13 mmol) in DCM (3 mL) and TFA (3 mL) was stirred 18 h at room temperature. The reaction mixture was concentrated under reduced pressure and the residue was purified by preparative HPLC (C18, eluent $ACN/H_2O/HCOOH$ 0.01%) to afford 4-(6-(4-(4-aminopiperidine-1-carbonyl)-3-fluorophenyl)imidazo[1,2-a]pyrazin-3-yl)benzonitrile (39 mg, 53%, AUC HPLC 98%) as a white solid. $^1$H NMR (400 MHz, $CD_3OD$) δ 9.20 (d, J=1.4 Hz, 1H), 9.00 (d, J=1.4 Hz, 1H), 8.11 (s, 1H), 8.07-7.91 (m, 6H), 7.50 (t, J=7.5 Hz, 1H), 4.75 (d, J=13.7 Hz, 1H), 3.69 (d, J=12.6 Hz, 1H), 3.39-3.18 (m, 2H), 2.98 (t, J=11.7 Hz, 1H), 2.11 (d, J=12.1 Hz, 1H), 1.97 (d, J=11.7 Hz, 1H), 1.97-1.45 (m, 2H); $^{13}$C NMR (400 MHz, $CD_3OD$) δ 170.23, 166.98, 161.24, 158.80, 144.16, 142.48, 141.84, 139.82, 136.98, 134.49, 133.61, 130.45, 129.86, 128.20, 125.04, 124.85, 124.06, 124.03, 119.40, 115.980, 115.24, 115.01, 113.61, 46.78, 41.45, 32.61, 31.88; MS (ESI) m/z 441 $[C_{25}H_{21}FN_6O+H]^+$.

Example 30: 4-(6-(4-(4-amino-4-methylpiperidine-1-carbonyl)-3-fluorophenyl)imidazo[1,2-a]pyrazin-3-yl)benzonitrile

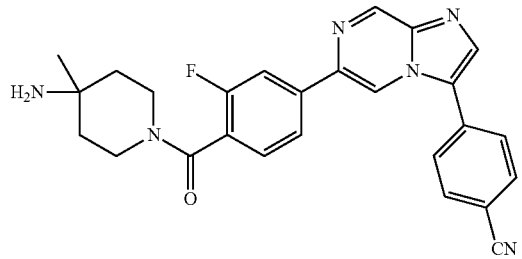 [SMILES: CC1(N)CCN(C(=O)c2ccc(-c3cn4c(-c5ccc(C#N)cc5)cnc4cn3)cc2F)CC1]

Step 1: To a solution of 4-(3-(4-cyanophenyl)imidazo[1,2-a]pyrazin-6-yl)-2-fluorobenzoic acid (90 mg, 0.25 mmol) in DMF (3 mL), was successively added HATU (95 mg, 0.25 mmol), N-methylmorpholine (55 mg, 0.50 mmol) and tert-butyl piperidin-4-ylcarbamate hydrochloride (106 mg, 0.50 mmol). The reaction mixture was stirred under inert atmosphere for 18 h at room temperature, then was diluted with water (10 mL) and the aqueous phase was extracted with DCM (3×10 mL). The combined organic layers were dried over $Na_2SO_4$, filtered and concentrated under reduced pressure. The crude residue was purified by column chromatography (silica gel, eluent EtOAc) to afford tert-butyl 1-(4-(3-(4-cyanophenyl)imidazo[1,2-a]pyrazin-6-yl)-2-fluorobenzoyl)-4-methylpiperidin-4-ylcarbamate as off-white powder. MS (ESI) m/z 455 $[C_{26}H_{23}FN_6O+H]^+$.

Step 2: A solution of tert-butyl 1-(4-(3-(4-cyanophenyl)imidazo[1,2-a]pyrazin-6-yl)-2-fluorobenzoyl)-4-methylpiperidin-4-ylcarbamate in DCM (3 mL) and TFA (3 mL) was stirred 18 h at room temperature. The reaction mixture was concentrated under reduced pressure and the residue was purified by preparative HPLC (C18, eluent $ACN/H_2O$/HCOOH 0.01%) to afford 4-(6-(4-(4-amino-4-methylpiperidine-1-carbonyl)-3-fluorophenyl)imidazo[1,2-a]pyrazin-3-yl)benzonitrile (42 mg, 37% over 2 steps, AUC HPLC 99%) as a white solid. $^1$H NMR (400 MHz, $CD_3OD$) δ 9.20 (d, J=1.4 Hz, 1H), 8.99 (d, J=1.4 Hz, 1H), 8.11 (s, 1H), 8.02-7.94 (m, 6H), 7.50 (t, J=5.0 Hz, 1H), 4.41 (d, J=14.1 Hz, 1H), 3.60 (d, J=14.5 Hz, 1H), 3.49-3.34 (m, 2H), 2.05-1.76 (m, 4H), 1.50 (s, 3H); $^{13}$C NMR (400 MHz, $CD_3OD$) δ 165.53, 159.80, 157.35, 142.70, 140.99, 140.55, 140.47, 138.36, 138.33, 135.50, 133.03, 132.13, 129.03, 128.40, 126.75, 123.36, 123.18, 122.60, 117.94, 114.54, 113.81, 113.57, 11.16, 52.22, 42.86, 37.46, 35.17, 34.42, 20.74; MS (ESI) m/z 455 $[C_{26}H_{23}FN_6O+H]^+$.

Example 31: 4-(6-(4-(4-aminopiperidine-1-carbonyl)-3-chlorophenyl)imidazo[1,2-a]pyrazin-3-yl)benzonitrile

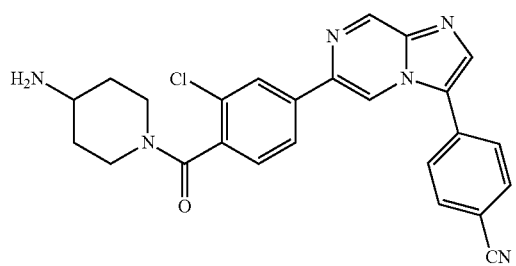 [SMILES: N#Cc1ccc(-c2cnc3cnc(-c4ccc(C(=O)N5CCC(N)CC5)c(Cl)c4)cn23)cc1]

Step 1: 4-borono-2-Chlorobenzoic acid (110 mg, 0.55 mmol), $K_2CO_3$ (138 mg, 1.00 mmol) and $Pd(dppf)Cl_2$ (73.1 mg, 0.01 mmol) were added sequentially to a solution of 4-(6-bromoimidazo[1,2-a]pyrazin-3-yl)benzonitrile (150 mg, 0.50 mmol) in DMF under inert atmosphere. The reaction mixture was stirred at 80° C. for 18 h then was diluted with water (10 mL) and extracted with DCM (3×10 mL). The combined organic layers were dried over $Na_2SO_4$, filtered and concentrated under reduced pressure to afford the 4-(3-(4-cyanophenyl)imidazo[1,2-a]pyrazin-6-yl)-2-chlorobenzoic acid (127 mg, 68%) as brown solid. MS (ESI) m/z 375 $[C_{20}H_{11}ClN_4O_2+H]^+$.

Step 2: To a solution of 4-(3-(4-cyanophenyl)imidazo[1,2-a]pyrazin-6-yl)-2-chlorobenzoic acid (53 mg, 0.14 mmol) in DMF (3 mL) under inert atmosphere, was added HATU (80 mg, 0.21 mmol), N-methyl morpholine (57 mg, 0.56 mmol) and tert-butyl piperidin-4-ylcarbamate hydrochloride (56 mg, 0.28 mmol). The reaction mixture was stirred at room temperature for 18 h, then was diluted with water (10 mL) and extracted with DCM (3×10 mL). The combined organic layer was dried over $Na_2SO_4$, filtered and concentrated under reduced pressure. The crude residue was purified by column chromatography (silica gel, eluent EtOAc) to afford tert-butyl 1-(4-(3-(4-cyanophenyl)imidazo[1,2-a]pyrazin-6-yl)-2-chlorobenzoyl)piperidin-4-ylcarbamate (70 mg, 89%) as off-white powder. $^1$H NMR (400 MHz, $CDCl_3$) δ 9.26 (s, 1H), 8.61 (s, 1H), 8.23 (d, J=2.7 Hz, 1H), 8.07-7.96 (m, 2H), 7.93-7.81 (m, 4H), 7.35 (m, J=9.8 Hz, 1H), 4.64 (s, 2H), 3.72 (s, 1H), 3.44 (t, J=12.5 Hz, 1H), 3.18 (t, J=11.5 Hz, 1H), 3.00-2.94 (m, 3H), 2.08 (d, J=10.6 Hz, 1H), 1.93 (t, J=10.3 Hz, 1H), 1.45 (s, 9H); MS (ESI) m/z 457 $[C_{23}H_{21}ClN_6O+H]^+$.

Step 3: To a solution of tert-butyl 1-(4-(3-(4-cyanophenyl)imidazo[1,2-a]pyrazin-6-yl)-2-fluorobenzoyl)piperidin-4-ylcarbamate (70 mg, 0.13 mmol) in DCM (5 mL) were added TFA (5 mL) and the resulting mixture stirred 18 h at room temperature. The reaction mixture was concentrated under reduced pressure and purified by preparative HPLC (C18, eluent $ACN/H_2O$/HCOOH 0.01%) to afford 4-(6-(4-(4-aminopiperidine-1-carbonyl)-3-chlorophenyl)imidazo[1,2-a]pyrazin-3-yl)benzonitrile (15 mg, 26%, AUC HPLC 97%) as white solid. $^1$H NMR (400 MHz, $CD_3OD$) δ 9.20 (d, J=1.4 Hz, 1H), 8.93 (d, J=1.2 Hz, 1H), 8.23 (d, J=2.7 Hz, 1H), 8.04-8.15 (m, 2H), 7.98 (m, J=7.6 Hz, 4H), 7.45 (m, J=9.7 Hz, 1H), 4.73 (t, J=14.9 Hz, 1H), 3.53 (t, J=12.5 Hz, 1H), 3.11-3.27 (m, 2H), 2.98 (m, J=6.5 Hz, 1H), 2.09 (d, J=14.2 Hz, 1H), 1.93 (t, J=13.0 Hz, 1H), 1.70-1.45 (m, 2H); $^{13}$C NMR (100 MHz, $CD_3OD$) δ 167.27, 167.15, 142.72, 140.99, 139.16, 139.04, 138.33, 135.51, 135.34, 135.21, 133.03, 132.15, 130.59, 130.50, 128.42, 127.91, 127.49, 127.44, 126.75, 125.32, 125.27, 114.50, 112.14, 45.44, 44.87, 39.84, 39.03, 31.72, 31.13, 30.85; MS (ESI) m/z 457 $[C_{23}H_{21}ClN_6O+H]^+$.

Example 32: 4-(6-(4-(4-amino-4-methylpiperidine-1-carbonyl)-3-chlorophenyl)imidazo[1,2-a]pyrazin-3-yl)benzonitrile

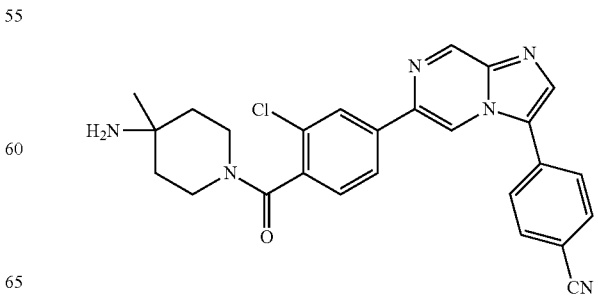

Step 1: To a solution of 4-(3-(4-cyanophenyl)imidazo[1,2-a]pyrazin-6-yl)-2-chlorobenzoic acid (75 mg, 0.20 mmol) in DMF (2 mL), were successively added HATU (114 mg, 0.30 mmol), N-methyl morpholine (61 mg, 0.40 mmol) and tert-butyl 4-methylpiperidin-4-ylcarbamate hydrochloride (86 mg, 0.40 mmol). The reaction mixture was stirred at room temperature under inert atmosphere for 18 h, then was diluted with water (10 mL) and the aqueous layer was extracted with DCM (3×10 mL). The combined organic layers were dried over $Na_2SO_4$, filtered and concentrated under reduced pressure. The crude residue was purified by column chromatography (silica gel, eluent EtOAc) to afford tert-butyl 1-(2-chloro-4-(3-(4-cyanophenyl)imidazo[1,2-a]pyrazin-6-yl)benzoyl)-4-methylpiperidin-4-ylcarbamate as an off-white powder. MS (ESI) m/z 471 $[C_{26}H_{23}ClN_6O+H]^+$.

Step 2: A solution of tert-butyl 1-(2-chloro-4-(3-(4-cyanophenyl)imidazo[1,2-a]pyrazin-6-yl)benzoyl)-4-methylpiperidin-4-ylcarbamate in DCM (3 mL) and TFA (3 mL) was stirred at room temperature for 18 h. The reaction mixture was concentrated under reduced pressure and the residue was purified by preparative HPLC (C18, eluent ACN/$H_2O$/HCOOH 0.01%) to afford 4-(6-(4-(4-amino-4-methylpiperidine-1-carbonyl)-3-chlorophenyl)imidazo[1,2-a]pyrazin-3-yl)benzonitrile (11 mg, 13% over 2 steps, AUC HPLC 99%), white solid. $^1$H NMR (400 MHz, $CD_3OD$) δ 9.20 (d, J=1.3 Hz, 1H), 8.99 (d, J=1.3 Hz, 1H), 8.24 (s, 1H), 8.21-7.88 (m, 2H), 7.98 (m, J=5.7 Hz, 4H), 7.46 (d, J=8.0 Hz, 1H), 4.32-4.00 (m, 1H), 3.71-3.51 (m, 1H), 3.50-3.30 (m, 2H), 1.93-1.51 (m, 4H), 1.37 (d, J=4.0 Hz, 3H); $^{13}$C NMR (100 MHz, $CD_3OD$) δ 170.32, 142.54, 140.94, 139.92, 137.19, 136.04, 135.36, 134.88, 132.27, 128.43, 126.51, 124.11, 117.95, 113.77, 112.07, 43.01, 37.45, 36.95, 36.3, 17.72; MS (ESI) m/z 471 $[C_{26}H_{23}ClN_6O+H]^+$.

Example 33: 4-(6-(3-methoxy-4-(piperazine-1-carbonyl)phenyl)imidazo[1,2-a]pyrazin-3-yl)benzonitrile

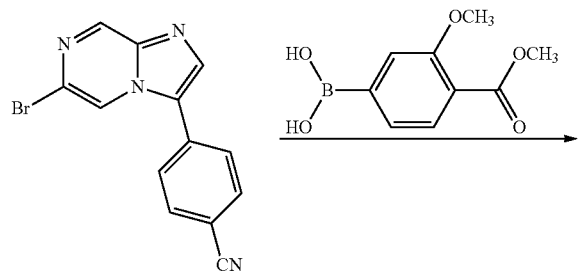

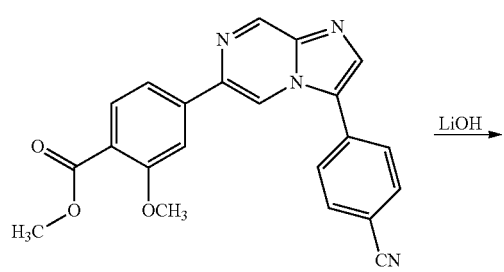

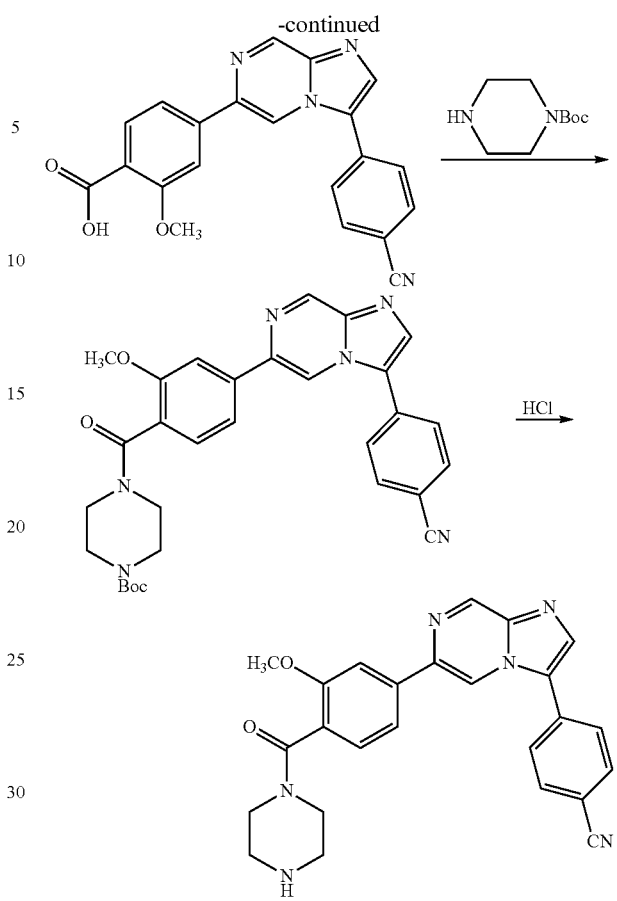

Step 1: To a solution of 4-(6-bromoimidazo[1,2-a]pyrazin-3-yl)benzonitrile (2.00 g, 6.91 mmol) in 1,4-dioxane, were added 3-methoxy-4-(methoxycarbonyl)phenylboronic acid (1.76 g, 8.7 mmol), an aqueous solution of $Na_2CO_3$ (1.46 g, 13.8 mmol) in water and $Pd(PPh_3)_4$ (498 mg, 0.43 mmol). The reaction mixture heated for 3 h at 90° C. under argon atmosphere and was filtered through celite. The filtrate was concentrated and the residue was purified the compound by flash column chromatography (silica gel, eluent $CH_2Cl_2$/$CH_3OH$ 98:2) to afford methyl 4-(3-(4-cyanophenyl)imidazo[1,2-a]pyrazin-6-yl)-2-methoxybenzoate (1.20 g, 44%) as yellow solid. $^1$H NMR (400 MHz, DMSO-$d_6$) δ: 9.87 (s, 1H), 9.22 (s, 1H), 8.89 (s, 1H), 7.95 (s, 1H), 7.80 (s, 1H), 7.73 (s, 1H), 7.61 (d, J=8.0 Hz, 2H), 6.98 (d, J=8.0 Hz, 2H), 3.91 (s, 3H), 3.79 (s, 3H); MS (ESI), m/z 385 $[C_{22}H_{16}N_4O_3+H]^+$.

Step 2: To a solution of methyl 4-(3-(4-cyanophenyl)imidazo[1,2-a]pyrazin-6-yl)-2-methoxybenzoate (1.20 g, 3.20 mmol) in THF/$CH_3OH$ (40/10 mL) was added a solution of LiOH (440 mg, 9.7 mmol) in water (10 mL). The reaction mixture was stirred at room temperature for 5 h and was concentrated in vacuo. The residue was first diluted with water (10 mL) and then was acidified till pH 3 using an aqueous solution of 2N HCl. The yellow precipitated was isolated by filtration and washed with water then was dried under vacuum to afford 4-(3-(4-cyanophenyl)imidazo[1,2-a]pyrazin-6-yl)-2-methoxybenzoic acid (800 mg, 80%) as light yellow solid. $^1$H NMR (400 MHz, DMSO-$d_6$) δ: 9.91 (s, 1H), 9.23 (s, 1H), 8.89 (s, 1H), 7.97 (s, 1H), 7.73 (d, J=8.0 Hz, 2H), 7.61 (d, J=8.0 Hz, 2H), 6.98 (d, J=8.0 Hz, 2H), 3.91 (s, 3H); MS (ESI), m/z 371 $[C_{21}H_{14}N_4O_3+H]^+$.

Step 3: To a stirred solution of 4-(3-(4-cyanophenyl)imidazo[1,2-a]pyrazin-6-yl)-2-methoxybenzoic acid (300 mg, 0.81 mmol) in DMF (5 mL) were added N-methylmorpholine (250 mg, 2.43 mmol), HATU (465 mg, 1.22 mmol) and tert-butyl piperazine-1-carboxylate (230 mg, 1.22 mmol). The reaction mixture was stirred for 10 h at room temperature, and was diluted with water followed by an extraction with $CH_2Cl_2$. The organic layer was washed with brine, dried over $Na_2SO_4$, filtered and concentrated. The residue was purified by flash column chromatography (silica gel, eluent $CH_2Cl_2/CH_3OH$ 97:3) to afford tert-butyl 4-(4-(3-(4-cyanophenyl)imidazo[1,2-a]pyrazin-6-yl)-2-methoxybenzoyl)piperazine-1-carboxylate (100 mg, 30%) as off-white solid. $^1$H NMR (400 MHz, DMSO-$d_6$) δ 9.29 (s, 1H), 9.02 (s, 1H), 8.17 (s, 1H), 8.08 (d, J=8.4 Hz, 2H), 7.94 (d, J=8.4 Hz, 2H), 7.75 (s, 1H), 7.69 (d, J=8.0 Hz, 1H), 7.30 (d, J=7.6 Hz, 1H), 3.89 (s, 3H), 3.62-3.56 (m, 2H), 3.46-3.41 (m, 2H), 3.37-3.29 (m, 4H), 1.39 (s, 9H); MS (ESI) m/z 539 $[C_{30}H_{30}N_6O_4+H]^+$.

Step 4: A solution of tert-butyl 4-(4-(3-(4-cyanophenyl)imidazo[1,2-a]pyrazin-6-yl)-2-methoxybenzoyl)piperazine-1-carboxylate (50 mg, 0.09 mmol) in a mixture of 1,4-dioxane and 30% HCl solution in 1,4-dioxane (1 mL) was stirred at room temperature for 3 h and was concentrated under reduced pressure. The residue was purified by flash column chromatography (silica gel, eluent 10% $CH_2Cl_2$/$CH_3OH$ 90:10) to afford 4-(6-(3-methoxy-4-(piperazine-1-carbonyl)phenyl)imidazo[1,2-a]pyrazin-3-yl)benzonitrile (25 mg, 30%, AUC HPLC 88%) as a light yellow solid. $^1$H NMR (400 MHz, DMSO-$d_6$) δ 9.21 (bs, 1H), 8.97 (s, 1H), 8.12 (bs, 1H), 8.02-7.96 (m, 4H), 7.81 (s, 1H), 7.69 (d, J=7.6 Hz, 1H), 7.39 (d, J=8.0 Hz, 1H), 3.99 (s, 3H), 3.89-3.84 (m, 2H), 3.52-3.43 (m, 2H), 3.14 (bs, 2H), 3.03 (bs, 2H); MS (ESI) m/z 439 $[C_{25}H_{22}N_6O_2+H]^+$.

Example 34: 4-(6-(2-fluoro-4-(4-methylpiperazine-1-carbonyl)phenyl)imidazo[1,2-a]pyrazin-3-yl)benzonitrile

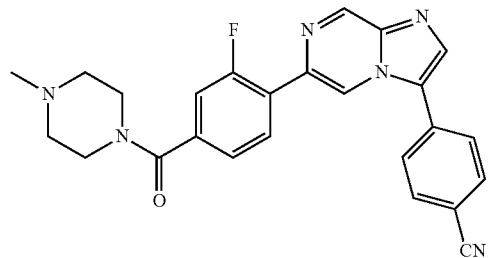 [SMILES: CN1CCN(C(=O)c2ccc(-c3cn4c(-c5ccc(C#N)cc5)cnc4cn3)c(F)c2)CC1]

Step 1: To a solution of 4-(6-bromoimidazo[1,2-a]pyrazin-3-yl)benzonitrile (50 mg, 0.167 mmol) in a mixture of DMF (2 mL) and water (1.3 mL), was added $Na_2CO_3$ (35 mg, 0.334 mmol), 4-borono-3-fluorobenzoic acid (33 mg, 0.183 mmol) and Pd(PPh$_3$)$_4$ (19 mg, 0.016 mmol). The resulting mixture was heated in a microwave reactor at 140° C. for 0.5 h and was filtered through celite. The filtrate was concentrated under reduced pressure and the residue was purified by column chromatography to afford 4-(3-(4-cyanophenyl)imidazo[1,2-a]pyrazin-6-yl)-3-fluorobenzoic acid (25.0 mg, 42.3%, AUC HPLC 99%) as a off white solid. $^1$H NMR (600 MHz, DMSO-$d_6$) δ 9.33 (s, 1H), 8.97 (s, 1H), 8.26 (s, 1H), 8.10-8.01 (m, 5H), 7.84 (d, J=8.4 Hz, 2H), 7.72 (d, J=12.6 Hz, 2H); MS (ESI) m/z 359 $[C_{20}H_{11}FN_4O_2+H]^+$.

Step 2: To a solution of 4-(3-(4-cyanophenyl)imidazo[1,2-a]pyrazin-6-yl)-3-fluorobenzoic acid (30 mg, 0.083 mmol) in a mixture of $CH_2Cl_2$ (2 mL) and DMF (1, 3 mL) was added sequentially DIPEA (60 μL, 0.351 mmol), HOBt (23 mg, 0.175 mmol), EDCI.HCl (33 mg, 0.175 mmol) and N-methyl piperazine (14 μL, 0.125 mmol). The reaction mixture was stirred at room temperature under inert atmosphere for 16 h, and then solvents were removed under vacuum. The crude residue was purified by column chromatography to afford 4-(6-(2-fluoro-4-(4-methylpiperazine-1-carbonyl)phenyl)imidazo[1,2-a]pyrazin-3-yl)benzonitrile (16 mg, 45%, AUC HPLC 99%) as an white solid. $^1$H NMR (600 MHz, DMSO-$d_6$) δ 9.36 (s, 1H), 9.01 (s, 1H), 8.30 (s, 1H), 8.14 (t, J=7.8 Hz, 1H), 8.15-8.03 (m, 4H), 7.44 (d, J=11.4 Hz, 1H), 7.39 (d, J=9.6 Hz, 1H), 3.64-3.62 (m, 2H), 2.40-2.26 (m, 4H), 2.20 (s, 3H); MS (ESI) m/z 441 $[C_{25}H_{21}N_6O+H]^+$.

Example 35: 3-fluoro-4-(6-(4-(4-methylpiperazine-1-carbonyl)phenyl)imidazo[1,2-a]pyrazin-3-yl)benzonitrile

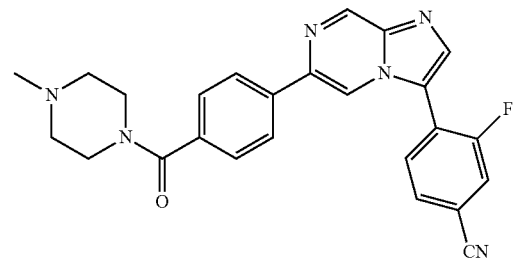 [SMILES: CN1CCN(C(=O)c2ccc(-c3cn4c(-c5ccc(C#N)cc5F)cnc4cn3)cc2)CC1]

To a solution of (4-(3-iodoimidazo[1,2-a]pyrazin-6-yl)phenyl)(4-methylpiperazin-1-yl)methanone (200 mg, 0.45 mmol) in a mixture of toluene (4 mL) and ethanol (2 ml) under inert atmosphere, was added $K_2CO_3$ (124 mg, 0.89 mmol), 4-cyano-2-fluorophenylboronic acid (88 mg, 0.54 mmol) and Pd(PPh$_3$)$_4$ (52 mg, 0.045 mmol). The resulting mixture was heated in a microwave reactor at 140° C. for 15 min, and then was concentrated under reduced pressure. The residue was purified by column chromatography (silica gel, eluent $CH_2Cl_2$/MeOH 95:5 to 90:10) to afford 3-fluoro-4-(6-(4-(4-methylpiperazine-1-carbonyl)phenyl)imidazo[1,2-a]pyrazin-3-yl)benzonitrile (18.1 mg, 9%, AUC HPLC 96%) as a yellow solid. $^1$H NMR (400 MHz, CD$_3$OD) δ 9.21 (s, 1H), 8.74 (d, J=1.5 Hz, 1H), 8.12 (d, J=8.2 Hz, 2H), 8.10 (s, 1H), 8.00-7.96 (m, 1H), 7.89-7.87 (m, 1H), 7.82 (d, J=8.0 Hz, 1H), 7.54 (d, J=8.2 Hz, 2H), 3.81 (bs, 2H), 3.53 (bs, 2H), 2.55-2.52 (m, 4H), 2.36 (s, 3H); $^{13}$C NMR (100 MHz, CD$_3$OD) δ 171.97, 160.63, 143.81, 142.39, 140.94, 139.19, 138.00, 136.99, 133.17, 130.43, 128.75, 127.91, 122.44, 122.00, 121.61, 118.25, 116.42, 115.57, 55.98, 55.58, 46.01; MS (ESI) m/z 441 $[C_{25}H_{21}N_6O+H]^+$.

Example 36: 4-(6-(6-(4-methylpiperazine-1-carbonyl)pyridin-3-yl)imidazo[1,2-a]pyrazin-3-yl)benzonitrile

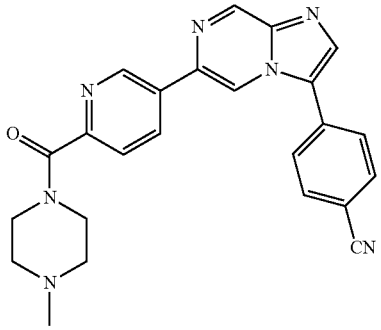 [SMILES: CN1CCN(C(=O)c2ccc(-c3cn4c(-c5ccc(C#N)cc5)cnc4cn3)cn2)CC1]

Example 37: 4-(6-(5-(4-methylpiperazine-1-carbonyl)pyridin-2-yl)imidazo[1,2-a]pyrazin-3-yl)benzonitrile

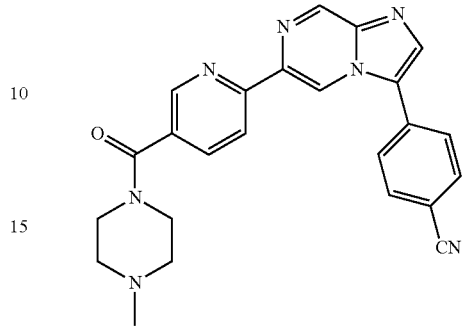

Step: 1 To a solution of 4-(6-bromoimidazo[1,2-a]pyrazin-3-yl)benzonitrile (140 mg, 0.468 mmol) and methyl 5-(4,4,5,5-tetramethyl-1,3,2-dioxaborolan-2-yl)picolinate (246 mg, 0.936 mmol) in a mixture of DMF/$H_2O$ (6:1, 3.5 mL) was added $Na_2CO_3$ (148 mg, 1.40 mmol). The suspension was stirred vigorously whilst de-gassing with $N_2$ for 5 min before adding Pd(PPh$_3$)$_4$ (54 mg, 0.046 mmol). The mixture was heated to 100° C. for 3 h and then, concentrated under reduced pressure. The crude residue was purified by column chromatography to afford methyl 5-(3-(4-cyanophenyl) imidazo[1,2-a]pyrazin-6-yl)picolinate (120 mg, 72%) as an off white solid. $^1$H NMR (600 MHz, DMSO-d$_6$) δ 9.42 (s, 1H), 9.35 (s, 1H), 9.25 (s, 1H), 8.66 (d, J=10.8 Hz, 1H), 8.28 (s, 1H), 8.18 (d, J=8.4 Hz, 1H), 8.12-8.05 (m, 4H), 3.92 (s, 3H); MS (ESI) m/z 356 [$C_{20}H_{13}N_5O_2$+H]$^+$.

Step: 2 A solution of methyl 5-(3-(4-cyanophenyl) imidazo[1,2-a]pyrazin-6-yl)picolinate (60 mg, 0.169 mmol) and a 5N sodium hydroxide solution (135 μL, 0.676 mmol) in methanol (3 ml) was stirred at room temperature for 1 hr. 5N hydrochloric acid (319 μL) was added to the reaction solution at room temperature, followed by extraction with ethyl acetate. The extract was dried over $Na_2SO_4$, concentrated under reduced pressure. To a solution of the crude acid (50 mg, 0.146 mmol) in DMF (1.5 mL) was added sequentially N-methyl piperizine (41 μL, 0.366 mmol), HBTU (139 mg, 0.366 mmol), HOBt (38 mg, 0.278 mmol) and DIPEA (127 μL, 0.733 mmol). The reaction mixture was stirred at room temperature under inert atmosphere for 12 h, then it was diluted with water (3 mL) and extracted with $CH_2Cl_2$ (3×10 mL). The combined organic layer was dried over $Na_2SO_4$ and was concentrated under reduced pressure. The crude residue was purified by column chromatography to afford 4-(6-(6-(4-methylpiperazine-1-carbonyl)pyridin-3-yl)imidazo[1,2-a]pyrazin-3-yl)benzonitrile (35 mg, 56%, AUC HPLC 96%), light brown solid. $^1$H NMR (600 MHz, DMSO-d$_6$) δ 9.33 (s, 1H), 9.28 (s, 1H), 9.27 (s, 1H), 8.57 (d, J=10.2 Hz, 1H), 8.26 (s, 1H), 8.13-8.02 (m, 4H), 7.70 (d, J=8.4 Hz, 1H), 3.71-3.64 (m, 2H), 3.50-3.42 (m, 2H), 2.45-2.37 (m, 2H), 2.34-2.26 (m, 2H), 2.20 (s, 3H); MS (ESI) m/z 424 [$C_{24}H_{21}N_7O$+H]$^+$.

Step 1: A mixture of 4-(6-bromoimidazo[1,2-a]pyrazin-3-yl)benzonitrile (50 mg, 0.167 mmol), ethyl 6-bromonicotinate (39 mg, 0.167 mmol), PdCl$_2$(PPh$_3$)$_2$ (12 mg, 0.016 mmol), and hexamethylditin (35 μL, 0.167 mmol) in anhydrous DMF (0.5 mL) was heated at 100° C. for 3 h, and then cooled to room temperature and solvents were removed under vacuum. The crude residue was purified by column chromatography to afford methyl 6-(3-(4-cyanophenyl) imidazo[1,2-a]pyrazin-6-yl)nicotinate (29.6 mg, 48%) as an off white solid. $^1$H NMR (600 MHz, DMSO-d$_6$) δ 9.42 (s, 1H), 9.36 (s, 1H), 9.16 (s, 1H), 8.53-8.46 (m, 2H), 8.29 (s, 1H), 8.14 (d, J=8.4 Hz, 2H), 8.05 (d, J=8.4 Hz, 2H), 4.38 (q, J=7.2 Hz, 2H), 1.36 (t, J=7.2 Hz, 2H); MS (ESI) m/z 370 [$C_{21}H_{15}N_5O_2$+H]$^+$.

Step 2: A solution of methyl 6-(3-(4-cyanophenyl) imidazo[1,2-a]pyrazin-6-yl)nicotinate (20 mg, 0.054 mmol) and a 5N sodium hydroxide solution (43 μL, 0.216 mmol) in ethanol (1 ml) was stirred at room temperature for 1 hr. 5N hydrochloric acid (101 μL) was added to the reaction solution at room temperature, followed by extraction with ethyl acetate. The extract was dried over $Na_2SO_4$, filtered and concentrated under reduced pressure and directly used in the next step without further purification.

To a solution of above acid (15 mg, 0.043 mmol) in DMF (0.5 mL) was added sequentially N-methylpiperazine (12 μL, 0.109 mmol), HBTU (42 mg, 0.109 mmol), HOBt (12 mg, 0.083 mmol) and DIPEA (13 μL, 0.073 mmol). The reaction mixture was stirred at room temperature under inert atmosphere for 12 h, then was diluted with water (1 mL) and extracted with EtOAc (3×5 mL). The combined organic layer was dried over $Na_2SO_4$ and was concentrated under reduced pressure. The crude residue was purified by column chromatography to afford 4-(6-(5-(4-methylpiperazine-1-carbonyl)pyridin-2-yl)imidazo[1,2-a]pyrazin-3-yl)benzonitrile (12 mg, 66%, AUC HPLC 93.6%) as a light brown solid. $^1$H NMR (600 MHz, DMSO-d$_6$) δ 9.34 (d, J=12.0 Hz, 2H), 8.68 (s, 1H), 8.40 (d, J=7.8 Hz, 2H), 8.26 (s, 1H), 8.12 (d, J=8.4 Hz, 2H), 8.05-7.98 (m, 3H), 3.68-3.63 (m, 2H), 2.40-2.35 (m, 4H), 2.20 (s, 3H); MS (ESI) m/z 424 [$C_{24}H_{21}N_7O$+H]$^+$.

Example 38: 4-(6-(2-hydroxy-4-(4-methylpiperazine-1-carbonyl)phenyl)imidazo[1,2-a]pyrazin-3-yl)benzonitrile

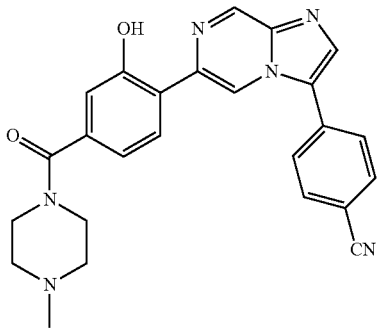 [SMILES: CN1CCN(C(=O)c2ccc(-c3cn4c(-c5ccc(C#N)cc5)cnc4cn3)c(O)c2)CC1]

Step 1: To a solution of 3-methoxy-4-bromobenzoic acid (500 mg, 2.16 mmol) in DMF (5 mL) was added NMM (0.44 g, 4.32 mmol) followed by addition of HATU (1.23 g, 3.24 mmol) at rt and stirred for 30 min. 1-methylpiperazine (0.24 g, 2.38 mmol) was added and stirred at rt for 16 h. The reaction mixture was diluted with EtOAc and washed with water and brine solution. The organic layer was dried over anhydrous $Na_2SO_4$ and concentrated under reduced pressure to obtain 350 mg (83%) of (4-bromo-3-methoxyphenyl)(4-methylpiperazin-1-yl)methanone (AUC LC-MS 83%) as a brown solid.

Step 2: To a solution of (4-bromo-3-methoxyphenyl)(4-methylpiperazin-1-yl)methanone (350 mg) 1,4-dioxane (10 mL), were added bis(pinacolato)diboron (0.30 g, 1.19 mmol), KOAc (330 mg, 3.36 mmol), $PdCl_2dppf$ (24 mg, 0.03 mmol) and dppf (18 mg, 0.033 mmol). The reaction mixture was heated at 90° C. for 16 h, was diluted with EtOAc and washed with water, the organic layer was dried over anhydrous $Na_2SO_4$ and concentrated under reduced pressure to afford 350 mg of (3-methoxy-4-(4,4,5,5-tetramethyl-1,3,2-dioxaborolan-2-yl)phenyl)(4-methylpiperazin-1-yl)methanone as a brown liquid which was used in next step without further purification.

Step 3: To a mixture of 4-(6-bromoimidazo[1,2-a]pyridin-3-yl)benzonitrile (232 mg), (3-methoxy-4-(4,4,5,5-tetramethyl-1,3,2-dioxaborolan-2-yl)phenyl) (4-methylpiperazin-1-yl)methanone (350 mg), $K_3PO_4$ (412 mg, 1.94 mmol) in 1,4-dioxane (5 mL) and water (5 mL) was added $Pd(PPh_3)_4$ (56 mg, 0.048 mmol). The reaction mixture was heated at 90° C. for 16 h under argon atmosphere, was diluted with water and extracted with EtOAc. The organic phase was washed in turn with water, brine solution, dried over anhydrous $Na_2SO_4$ filtered and concentrated under reduced. The residue was purified by column chromatography to allord 4-(6-(3-methoxy-4-(4-methylpiperazine-1-carbonyl)phenyl)imidazo[1,2-a]pyridin-3-yl)benzonitrile give (80 mg, 30%, AUC HPLC 99.3%) as an off-white solid; m.p. 311-318° C. $^1$H NMR (400 MHz, DMSO-$d_6$) δ (ppm): 9.27 (s, 1H), 9.14 (s, 1H), 8.19 (d, J=8.0 Hz, 1H), 7.99 (s, 1H), 7.88 (d, J=8.0 Hz, 2H), 7.79 (d, J=8.0 Hz, 2H), 7.14-7.12 (m, 2H), 3.95 (s, 3H), 3.84 (bs, 2H), 3.54 (bs, 2H), 2.54 (s, 2H), 2.36 (bs, 2H), 2.34 (s, 3H); MS (ESI) m/z 453.32 $[C_{26}H_{24}N_6O_2+H]^+$.

Step 4: A solution of 4-(6-(3-methoxy-4-(4-methylpiperazine-1-carbonyl)phenyl)imidazo[1,2-a]pyridin-3-yl)benzonitrile (150 mg) in anhydrous DCM (5 mL) was treated with $BBr_3$ at rt for 3 h. After the completion of reaction as indicated by TLC, the reaction mixture was washed with $NaHCO_3$. The organic layer was dried over $Na_2SO_4$ filtered and concentrated. The residue was purified by preparative HPLC to afford 4-(6-(2-hydroxy-4-(4-methylpiperazine-1-carbonyl)phenyl)imidazo[1,2-a]pyrazin-3-yl)benzonitrile (50 mg, 34%, AUC HPLC 97%) as an off white solid; m.p. 237-241° C. $^1$H NMR (400 MHz, DMSO-$d_6$) δ (ppm): 11.15 (s, 1H), 9.43 (s, 1H), 9.31 (s, 1H), 8.26 (s, 1H), 8.16 (d, J=12.0 Hz, 1H), 8.09-8.01 (m, 4H), 6.95 (s, 2H), 3.59 (bs, 2H), 3.34 (bs, 2H), 2.49 (bs, 2H), 2.27 (bs, 2H), 2.19 (s, 3H); MS (ESI) m/z 439.2 $[C_{25}H_{22}N_6O_2+H]^+$.

Example 39: 4-(6-(3-methoxy-4-(4-methylpiperazine-1-carbonyl)phenyl)imidazo[1,2-a]pyrazin-3-yl)benzonitrile

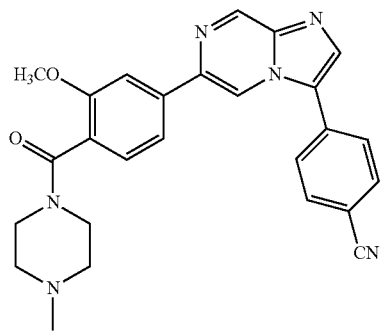 [SMILES: COc1cc(-c2cn3c(-c4ccc(C#N)cc4)cnc3cn2)ccc1C(=O)N1CCN(C)CC1]

Step: 1 To a solution of 4-bromo-2-methoxy benzoic acid (1 g, 4.34 mmol) in DMF (15 mL) was added NMM (0.876 mL, 8.68 mmol) followed by HATU (2.08 g, 6.51 mmol) at rt and stirred for 30 min. 1-Methylpiperazine (0.478 mg, 4.78 mmol) was added and stirred at rt for 16 h. The reaction mixture was diluted with EtOAc, washed with water and brine solution. The organic layer was dried over anhydrous $Na_2SO_4$ and concentrated under reduced pressure. The residue was purified by column chromatography (silica gel, Petroleum ether/EtOAc 100:0 to 50:50) to afford (4-bromo-2-methoxyphenyl)(4-methylpiperazin-1-yl)methanone (1.1 g, 81%) of as an off white solid. $^1$H NMR (400 MHz, $CDCl_3$) δ 7.33 (s, 1H), 7.25-7.19 (m, 2H), 3.84 (s, 3H), 3.6-2.9 (m, 8H), 2.83 (s, 3H); MS (ESI) m/z 315.10 $[C_{13}H_{17}BrN_2O_2+2]^+$.

Step 2: A mixture of (4-bromo-2-methoxyphenyl)(4-methylpiperazin-1-yl)methanone (1.1 g, 3.52 mmol), Bis(pinacolato)diboron (1.07 g, 4.23 mmol), KOAc (1.03 g, 10.56 mmol) in 1,4-dioxane (20 mL) was degassed with argon for 30 min. $PdCl_2dppf$ (75 mg, 0.1 mmol), dppf (56 mg, 0.1 mmol) was added and again degassed with argon for 30 min and the reaction mixture was heated at 90° C. for 16 h. The reaction mixture was diluted with EtOAc and washed with water. The organic layer was dried over anhydrous $Na_2SO_4$ and concentrated under reduced pressure to afford 800 mg of (2-methoxy-4-(4,4,5,5-tetramethyl-1,3,2-dioxaborolan-2-yl)phenyl)(4-methylpiperazin-1-yl)methanone as a dark brown liquid which was used in next step without purification.

Step 3: To a mixture of 2-methoxy-4-(4,4,5,5-tetramethyl-1,3,2-dioxaborolan-2-yl)phenyl)(4-methylpiperazin-1-yl)methanone (678 mg, 1.88 mmol), 4-(6-bromoimidazo[1,2-a]pyrazin-3-yl)benzonitrile (400 mg, 1.34 mmol), $K_3PO_4$ (568.1 mg, 2.68 mmol) in 1,4-dioxane (20 mL) and water (5 mL) was added $Pd(PPh_3)_4$ (77 mg, 0.05 mmol). The reaction mixture was heated at 90° C. for 1 h and was diluted with water and extracted with EtOAc. The organic phase was washed with water and brine, dried over anhydrous Na$_2$SO$_4$, filtered and concentrated under reduced pressure. The residue was purified by Preparative HPLC to afford 4-(6-(3-methoxy-4-(4-methylpiperazine-1-carbonyl)phenyl)imidazo[1,2-a]pyrazin-3-yl)benzonitrile (180 mg, 30%, AUC HPLC 96.7%) as a pale brown solid; m.p. 188-192° C. $^1$H NMR (400 MHz, CD$_3$OD) δ (ppm): 9.19 (s, 1H), 8.94 (s, 1H), 8.89 (s, 1H), 8.00-7.94 (m, 4H), 7.78 (s, 1H), 7.64 (d, J=8.0 Hz, 1H), 7.32 (d, J=8.0 Hz, 1H), 3.95 (s, 3H), 3.80 (bs, 2H), 3.34 (bs, 2H), 2.54 (s, 2H), 2.45 (bs, 1H), 2.38 (bs, 1H), 2.33 (s, 3H); MS (ESI) m/z 453.30 [C$_{26}$H$_{24}$N$_6$O$_2$+H]$^+$.

Example 40: 4-(6-(4-(4-methylpiperazin-1-ylsulfonyl)phenyl)imidazo[1,2-a]pyrazin-3-yl)benzonitrile

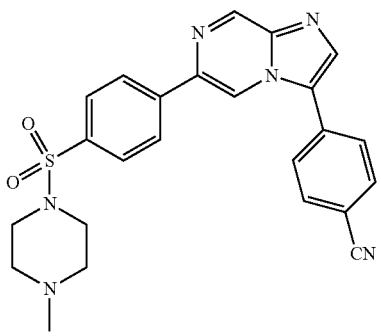 [SMILES: CN1CCN(S(=O)(=O)c2ccc(-c3cn4c(-c5ccc(C#N)cc5)cnc4cn3)cc2)CC1]

1-methyl-4-(4-(4,4,5,5-tetramethyl-1,3,2-dioxaborolan-2-yl)phenylsulfonyl)piperazine (240 mg, 0.656 mmol), K$_3$PO$_4$ (212 mg, 1 mmol) and Pd(PPh$_3$)$_4$ (28 mg, 0.025 mmol) were added sequentially to a solution of 4-(6-bromoimidazo[1,2-a]pyrazin-3-yl)benzonitrile (150 mg, 0.5 mmol) in a mixture of 1,4-dioxane/H$_2$O (10:1 mL) at room temperature under argon atmosphere. The reaction mixture was refluxed for 6 h and was diluted with water (10 mL) and extracted with EtOAc (3×50 mL). The combined organic layer was dried over Na$_2$SO$_4$, filtered and concentrated under reduced pressure. The residue was purified by column chromatography (silica gel, eluent CHCl$_3$/MeOH 95:5) to afford 4-(6-(4-(4-methylpiperazin-1-ylsulfonyl)phenyl)imidazo[1,2-a]pyrazin-3-yl)benzonitrile (80 mg, 36%, AUC HPLC 99.1%) as an off-white solid; m.p. 220-228° C. $^1$H NMR (400 MHz, CDCl$_3$) δ (ppm): 9.30 (s, 1H), 8.61 (s, 1H), 8.08 (d, J=8.8 Hz, 2H), 8.00 (s, 1H), 7.92-7.85 (m, 4H), 7.77 (d, J=8.4 Hz, 2H), 3.08 (bs, 4H), 2.50-2.48 (m, 4H), 2.27 (s, 3H); MS (ESI) m/z 459.27 [C$_{24}$H$_{22}$N$_6$O$_2$S+H]$^+$.

Example 41: (4-(3-(4-chlorophenyl)imidazo[1,2-a]pyrazin-6-yl)phenyl)(4-methylpiperazin-1-yl)methanone

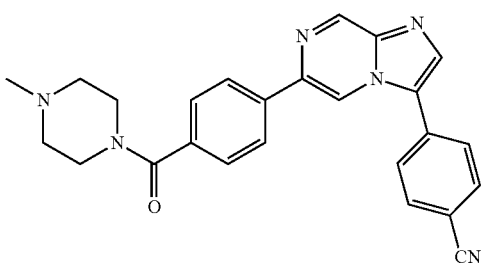 [SMILES: CN1CCN(C(=O)c2ccc(-c3cn4c(-c5ccc(C#N)cc5)cnc4cn3)cc2)CC1]

To a solution of (4-(3-iodoimidazo[1,2-a]pyrazin-6-yl)phenyl)(4-methylpiperazin-1-yl)methanone (150 mg, 0.34 mmol) in a mixture of toluene (4 mL) and ethanol (2 ml) under inert atmosphere, was added K$_2$CO$_3$ (93 mg, 0.67 mmol), 4-chlorophenylboronic acid (79 mg, 0.50 mmol) and Pd(PPh$_3$)$_4$ (39 mg, 0.034 mmol). The resulting mixture was heated in a microwave reactor at 140° C. for 15 min, and then was concentrated under reduced pressure. The residue was purified by column chromatography (silica gel, eluent CH$_2$Cl$_2$/MeOH 95:5 to 90:10) to afford (4-(3-(4-chlorophenyl)imidazo[1,2-a]pyrazin-6-yl)phenyl) (4-methylpiperazin-1-yl)methanone (128.4 mg, 66%, AUC HPLC 99%) as a yellow solid. $^1$H NMR (400 MHz, CDCl$_3$) δ 9.24 (d, J=1.4 Hz, 1H), 8.54 (d, J=1.4 Hz, 1H), 7.95 (d, J=8.4 Hz, 2H), 7.89 (s, 1H), 7.60-7.55 (m, 4H), 7.52 (d, J=8.4 Hz, 2H), 3.82 (bs, 2H), 3.49 (s, 2H), 2.50-2.33 (m, 7H); $^{13}$C NMR (100 MHz, CDCl$_3$) δ 169.78, 143.84, 140.70, 139.63, 137.76, 136.14, 135.34, 135.33, 129.98, 129.36, 127.84, 126.45, 126.41, 126.24, 112.54, 55.27, 54.79, 46.03; MS (ESI) m/z 432 [C$_{24}$H$_{22}$ClN$_5$O+H]$^+$.

Example 42: 4-(3-(4-chlorophenyl)imidazo[1,2-a]pyrazin-6-yl)benzamide

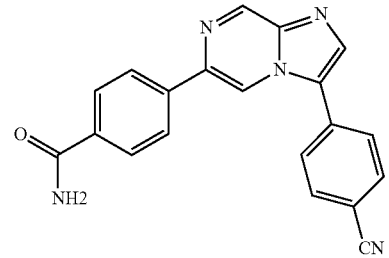 [SMILES: N#Cc1ccc(-c2cnc3cnc(-c4ccc(C(N)=O)cc4)cn23)cc1]

To a solution of 6-bromo-3-(4-chlorophenyl)imidazo[1,2-a]pyrazine (200 mg, 0.65 mmol) in a mixture of toluene (3 mL) and EtOH (1.5 mL) under inert atmosphere, was consecutively added K$_2$CO$_3$ (180 mg, 1.30 mmol), 4-carbamoylphenylboronic acid (117 mg, 0.71 mmol) and Pd(PPh$_3$)$_4$ (75 mg, 0.06 mmol). The resulting mixture was heated in a microwave reactor at 140° C. for 30 min and was concentrated under reduced pressure. The residue was purified by column chromatography (silica gel, eluent hexane/EtOAc 3:2) to afford 4-(3-(4-chlorophenyl)imidazo[1,2-a]pyrazin-6-yl)benzamide (31 mg, 83%, AUC HPLC 97%) as white solid. $^1$H NMR (400 MHz, DMSO-d$_6$) δ 9.26 (s, 1H), 8.97 (s, 1H), 8.16 (d, J=8.2 Hz, 2H), 8.13-8.02 (m, 2H), 7.99 (d, J=8.2 Hz, 2H), 7.87 (d, J=8.2 Hz, 2H), 7.66 (d, J=8.3 Hz, 2H), 7.42 (m, 1H); $^{13}$C NMR (100 MHz, DMSO-d$_6$) δ 167.43, 142.93, 140.29, 138.83, 187.92, 135.55, 133.99, 133.30, 129.74, 129.38, 127.87, 126.43, 126.21, 126.01, 114.30; MS (ESI) m/z 390 [C$_{19}$H$_{13}$ClN$_4$O+H]$^+$.

Example 43: 1-(4-(3-(4-chlorophenyl)imidazo[1,2-a]pyrazin-6-yl)benzoyl)piperidin-4-one

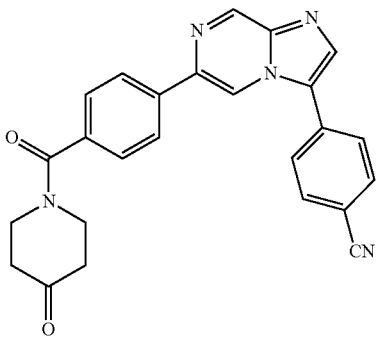 [SMILES: N#Cc1ccc(-c2cnc3cnc(-c4ccc(C(=O)N5CCC(=O)CC5)cc4)cn23)cc1]

Step 1: To a solution of 6-bromo-3-iodoimidazo[1,2-a]pyrazine (3.00 g, 9.26 mmol) in DMF (20 mL), was added Na$_2$CO$_3$ (2.46 g, 23.2 mmol), 4-chlorophenylboronic acid (1.60 g, 10.2 mmol) and Pd(PPh$_3$)$_4$ (214 mg, 0.18 mmol). The resulting mixture was stirred at 80° C. for 18 h under inert atmosphere and was concentrated under reduced pressure. The residue was purified by column chromatography (silica gel, eluent Hex/EtOAc 3:2) to afford 6-bromo-3-(4-chlorophenyl)imidazo[1,2-a]pyrazine (930 mg, 32%) as a yellow solid. $^1$H NMR (400 MHz, CDCl$_3$) δ 9.03 (d, J=1.2 Hz, 1H), 8.36 (d, J=1.2 Hz, 1H), 7.91 (s, 1H), 7.54 (q, J=12.3 Hz, 4H); MS (ESI) m/z 308 [C$_{13}$H$_7$BrN$_4$+H]$^+$.

Step 2: To a solution of 6-bromo-3-(4-chlorophenyl)imidazo[1,2-a]pyrazine (2.78 g, 9.03 mmol) in a mixture of DMF (24 mL) and water (4.8 mL) under inert atmosphere, was added K$_2$CO$_3$ (2.50 g, 18.1 mmol), 4-boronobenzoic acid (1.65 mg, 9.94 mmol) and PdCl$_2$dppf (1.32 g, 1.81 mmol). The resulting mixture was heated in a microwave reactor at 140° C. for 30 min then, was concentrated under reduced pressure. The residue was purified by column chromatography (silica gel, eluent CH$_2$Cl$_2$/MeOH 9:1) to afford 4-(3-(4-chlorophenyl)imidazo[1,2-a]pyrazin-6-yl)benzoic acid 5 (326 mg, 11%) as a brown solid. $^1$H NMR (400 MHz, DMSO-d$_6$) δ 13.02 (bs, 1H), 9.28 (d, J=1.3 Hz, 1H), 9.00 (d, J=1.4 Hz, 1H), 8.22 (d, J=8.5 Hz, 2H), 8.11 (s, 1H), 8.04 (d, J=8.5 Hz, 2H), 7.88 (d, J=8.5 Hz, 2H), 7.67 (d, J=8.5 Hz, 2H); $^{13}$C NMR (100 MHz, DMSO-d$_6$) δ 167.05, 142.99, 140.33, 140.30, 137.64, 135.62, 133.35, 130.56, 129.81, 129.66, 129.40, 126.42, 126.31, 114.72; MS (ESI) m/z 350[C$_{19}$H$_{12}$ClN$_3$O$_2$+H]$^+$.

Step 3: To a solution of 4-(3-(4-chlorophenyl)imidazo[1,2-a]pyrazin-6-yl)benzoic acid (45 mg, 0.13 mmol) in DMF (5 mL), were sequentially added HATU (73 mg, 0.19 mmol), N-methyl morpholine (52 mg, 0.51 mmol) and piperidin-4-one (45 mg, 0.40 mmol). The reaction mixture was stirred at room temperature under inert atmosphere for 18 h, then was diluted with water (10 mL) and extracted with DCM (3×10 mL). The combined organic layers were dried over Na$_2$SO$_4$, filtered and concentrated under reduced pressure. The crude residue was purified by preparative HPLC (C18, eluent ACN/H$_2$O/HCOOH 0.01%) to afford 1-(4-(3-(4-chlorophenyl)imidazo[1,2-a]pyrazin-6-yl)benzoyl)piperidin-4-one (41 mg, 75%, AUC HPLC 99%) as brown solid. $^1$H NMR (400 MHz, CD$_3$OD) δ 9.11 (s, 1H), 8.74-8.79 (m, 1H), 8.00-8.08 (m, 2H), 7.96 (s, 1H), 7.71 (d, J=8.5 Hz, 2H), 7.59 (d, J=8.5 Hz, 2H), 7.48 (d, J=8.4 Hz, 2H), 4.12-3.61 (m, 3H), 3.45 (bs, 1H), 2.70-2.36 (m, 1H), 1.91-1.62 (m, 3H); $^{13}$C NMR (100 MHz, CD$_3$OD) δ 208.88, 1.72.48, 171.94, 164.41, 143.52, 143.47, 141.05, 140.96, 139.31, 138.96, 137.41, 137.35, 136.89, 136.40, 135.00, 134.92, 130.90, 128.70, 128.53, 127.89, 127.84, 127.22, 115.16, 115.09, 99.62, 96.49, 46.52, 40.93, 36.99, 36.14; MS (ESI) m/z 431 [C$_{24}$H$_{19}$ClN$_4$O$_2$+H]$^+$.

Example 44: (4-(3-(4-chlorophenyl)imidazo[1,2-a]pyrazin-6-yl)phenyl) (4-hydroxypiperidin-1-yl)methanone

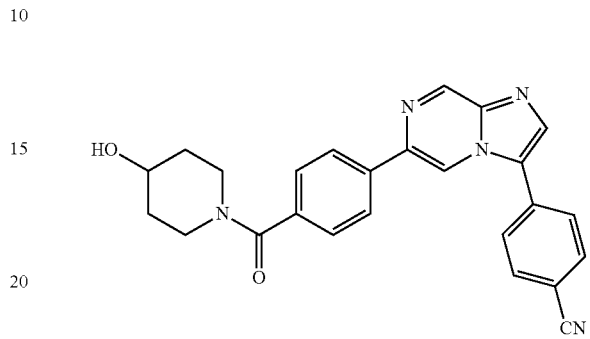

To a solution of 1-(4-(3-(4-chlorophenyl)imidazo[1,2-a]pyrazin-6-yl)benzoyl)piperidin-4-one (22 mg, 0.05 mmol) in MeOH (3 mL) was added NaBH$_4$ (5 mg, 0.13 mmol) and the reaction mixture was stirred at room temperature for 18 h. The reaction was quenched by adding water (10 mL) dropwise, and the aqueous solution was extracted with DCM (3×10 mL). The combined organic layers were dried over Na$_2$SO$_4$ and were concentrated under reduced pressure. The crude residue was purified by preparative HPLC (C18, eluent ACN/H$_2$O/0.01% HCOOH) to afford (4-(3-(4-chlorophenyl)imidazo[1,2-a]pyrazin-6-yl)phenyl) (4-hydroxypiperidin-1-yl)methanone (10 mg, 45%, AUC HPLC>99%) as a white solid. $^1$H NMR (400 MHz, CD$_3$OD) δ 9.15 (d, J=1.3 Hz, 1H), 8.82 (d, J=1.3 Hz, 1H), 8.08 (d, J=8.4 Hz, 2H), 7.98 (s, 1H), 7.75 (d, J=8.6 Hz, 2H), 7.63 (d, J=8.6 Hz, 2H), 7.51 (d, J=8.4 Hz, 2H), 4.19 (bs, 1H), 3.91 (m, J=4.0 Hz, 1H), 3.68 (bs, 1H), 3.46-3.19 (m, 2H), 2.04-1.74 (m, 2H), 1.67-1.39 (m, 2H); $^{13}$C NMR (400 MHz, CD$_3$OD) δ 172.00, 143.69, 141.66, 140.95, 139.15, 137.42, 136.35, 135.43, 130.89, 128.56, 128.46, 127.44, 115.12, 67.64, 46.48, 40.87, 35.45, 34.75; MS (ESI) m/z 433 [C$_{24}$H$_{21}$ClN$_4$O$_2$+H]$^+$.

Example 45: (4-(3-(4-chlorophenyl)imidazo[1,2-a]pyrazin-6-yl)phenyl)(4-ethylpiperazin-1-yl)methanone

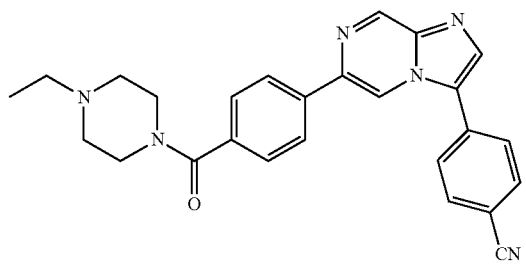 [SMILES: CCN1CCN(C(=O)c2ccc(-c3cn4c(-c5ccc(C#N)cc5)cnc4cn3)cc2)CC1]

To a solution of 4-(3-(4-chlorophenyl)imidazo[1,2-a]pyrazin-6-yl)benzoic acid (50 mg, 0.14 mmol) in DCM (5 mL) at 0° C., was added oxalyl chloride (36 mg, 0.29 mmol) and the mixture thus obtained was stirred to room temperature for 3 h. The reaction mixture was concentrated under reduced vacuum and to the residue, was added DMF (5 mL), 1-ethylpiperazine (92 mg, 0.23 mmol) and a solution of KOH (0.10 ml, 13 M in THF). The resulting mixture was stirred at room temperature for 18 h, then was diluted with water (10 mL) and extracted with DCM (3×10 mL). The combined organic layers were dried over $Na_2SO_4$ and concentrated under reduced pressure. The crude residue was purified by preparative HPLC (C18, eluent ACN/$H_2O$/HCOOH 0.01%) to afford (4-(3-(4-chlorophenyl)imidazo[1,2-a]pyrazin-6-yl)phenyl)(4-ethylpiperazin-1-yl)methanone (28 mg, 44%, AUC HPLC 99%) as brown solid. $^1$H NMR (400 MHz, DMSO-$d_6$) δ 9.08 (d, J=1.0 Hz, 1H), 8.76 (d, J=1.1 Hz, 1H), 8.05 (d, J=8.3 Hz, 2H), 7.93 (s, 1H), 7.71 (d, J=8.5 Hz, 2H), 7.60 (d, J=8.5 Hz, 2H), 7.52 (d, J=8.3 Hz, 2H), 3.80 (bs, 4H), 3.10-2.79 (m, 6H), 1.25 (t, J=7.2 Hz, 3H); $^{13}$C NMR (100 MHz, DMSO-$d_6$) δ 171.92, 143.84, 141.82, 140.56, 139.58, 136.24, 136.22, 135.84, 130.88, 130.81, 128.89, 128.46, 127.86, 127.49, 115.11, 53.17, 52.79, 10.67; MS (ESI) m/z 446 $[C_{25}H_{24}ClN_5O+H]^+$.

Example 46: (4-(3-(4-chlorophenyl)imidazo[1,2-a]pyrazin-6-yl)phenyl)(piperazin-1-yl)methanone 2,2,2-trifluoroacetate Salt

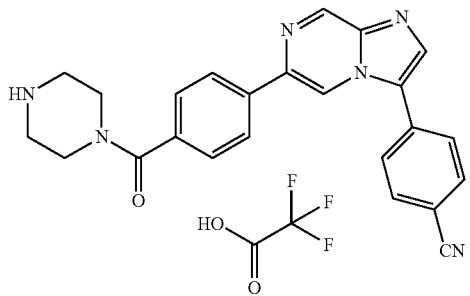 [SMILES: N#Cc1ccc(-c2cnc3cnc(-c4ccc(C(=O)N5CCNCC5)cc4)cn23)cc1 ; O=C(O)C(F)(F)F]

Step 1: To a solution of 4-(3-(4-chlorophenyl)imidazo[1,2-a]pyrazin-6-yl)benzoic acid (50 mg, 0.14 mmol) in DMF (5 mL) were added HATU (82 mg, 0.22 mmol), N-methyl morpholine (29 mg, 0.29 mmol) and tert-butyl piperazine-1-carboxylate (54 mg, 0.29 mmol). The reaction mixture was stirred at room temperature under inert atmosphere for 18 h, then was diluted with water (10 mL) and extracted with DCM (3×10 mL). The combined organic layer was dried over $Na_2SO_4$, filtered and concentrated under reduced pressure. The crude residue was purified by preparative HPLC (C18, eluent ACN/$H_2O$/HCOOH 0.01%) to afford tert-butyl 4-(4-(3-(4-chlorophenyl)imidazo[1,2-a]pyrazin-6-yl)benzoyl)piperazine-1-carboxylate (23 mg, 31%, AUC HPLC 100%) as a brown solid. $^1$H NMR (400 MHz, CDCl$_3$) δ 9.33 (s, 1H), 8.54 (s, 1H), 7.96 (d, J=8.0 Hz, 2H), 7.91 (s, 1H), 7.57 (d, J=7.5 Hz, 4H), 7.51 (d, J=8.0 Hz, 2H), 3.84-3.60 (bs, 2H), 3.60-3.28 (bs, 6H), 1.46 (s, 9H); $^{13}$C NMR (100 MHz, CDCl$_3$) δ 169.97, 162.65, 154.55, 143.07, 140.40, 139.28, 137.46, 136.05, 135.90, 133.08, 129.61, 127.89, 126.69, 125.36, 112.64, 80.47, 28.36; MS (ESI) m/z 518 $[C_{28}H_{28}ClN_5O_3+H]^+$.

Step 2: A solution of tert-butyl 4-(4-(3-(4-chlorophenyl)imidazo[1,2-a]pyrazin-6-yl)benzoyl)piperazine-1-carboxylate (66 mg, 0.65 mmol) in a mixture of DCM (5 mL) and TFA (5 mL) was stirred at room temperature for 18 h, then was concentrated under reduced pressure to afford (4-(3-(4-chlorophenyl)imidazo[1,2-a]pyrazin-6-yl)phenyl)(piperazin-1-yl)methanone as a TFA salt (24 mg, 69%, AUC HPLC 98%) as a brown solid. $^1$H NMR (400 MHz, CDCl$_3$) δ 9.29 (d, J=1.3 Hz, 1H), 8.96 (d, J=1.3 Hz, 1H), 8.18 (d, J=8.4 Hz, 2H), 8.12 (s, 1H), 7.88 (d, J=8.5 Hz, 2H), 7.67 (d, J=8.5 Hz, 2H), 7.58 (d, J=8.4 Hz, 2H), 3.68 (s, 5H), 3.20 (s, 4H); $^{13}$C NMR (100 MHz, CDCl$_3$) δ 170.01, 142.99, 140.34, 138.97, 138.12, 136.21, 134.45, 132.67, 130.23, 129.65, 127.99, 126.99, 126.88, 125.02, 112.75, 43.42, 29.69; MS (ESI) m/z 418 $[C_{23}H_{20}ClN_5O+H]^+$.

Example 47: (4-aminopiperidin-1-yl)(4-(3-(4-chlorophenyl)imidazo[1,2-a]pyrazin-6-yl)phenyl)methanone 2,2,2-trifluoroacetate Salt

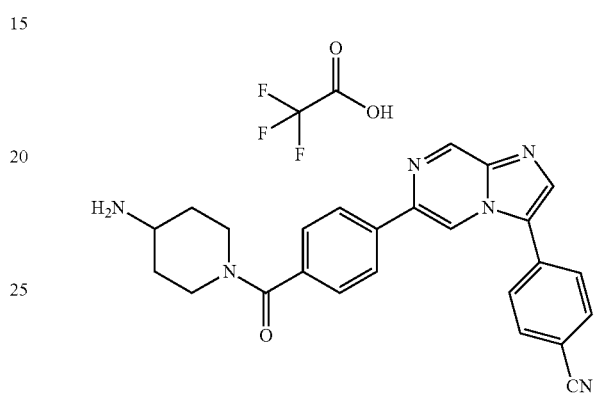

Step 1: To a solution of 4-(3-(4-chlorophenyl)imidazo[1,2-a]pyrazin-6-yl)benzoic acid (70 mg, 0.20 mmol) in DMF (5 mL), was successively added HATU (114 mg, 0.30 mmol), N-methyl morpholine (41 mg, 0.40 mmol) and tert-butyl piperidin-4-ylcarbamate (80 mg, 0.40 mmol). The reaction mixture was stirred at room temperature under inert atmosphere for 18 h, then was diluted with water (10 mL) and extracted with DCM (3×10 mL). The combined organic layers were dried over $Na_2SO_4$, filtered and concentrated under reduced pressure. The crude residue was purified by preparative (C18, eluent ACN/$H_2O$/0.01% HCOOH acid) to afford tert-butyl 1-(4-(3-(4-chlorophenyl)imidazo[1,2-a]pyrazin-6-yl)benzoyl)piperidin-4-ylcarbamate (47 mg, 44%, AUC HPLC 98%) as a brown solid. $^1$H NMR (400 MHz, CDCl$_3$) δ 9.30 (s, 1H), 8.53 (s, 1H), 7.92 (t, J=7.3 Hz, 3H), 7.56 (d, J=1.2 Hz, 4H), 7.47 (d, J=8.1 Hz, 2H), 4.58 (d, J=7.1 Hz, 2H), 3.69 (bs, 2H), 3.21-2.83 (m, 2H), 1.97 (bs, 2H), 1.43 (s, 9H); $^{13}$C NMR (100 MHz, CDCl$_3$) δ 169.72, 162.92, 155.09, 143.03, 140.39, 139.36, 137.27, 136.51, 135.80, 133.20, 130.09, 129.59, 127.64, 126.66, 126.60, 125.44, 112.64, 79.67, 47.92, 46.55, 41.22, 33.10, 32.15, 28.39; MS (ESI) m/z 532 $[C_{29}H_{30}ClN_5O_3+H]^+$.

Step 2: A solution of tert-butyl 1-(4-(3-(4-chlorophenyl)imidazo[1,2-a]pyrazin-6-yl)benzoyl)piperidin-4-ylcarbamate (40 mg, 0.08 mmol) in a mixture of DCM (5 mL) and TFA (5 mL) was stirred at room temperature for 18 h, then was concentrated under reduced pressure to afford (4-aminopiperidin-1-yl)(4-(3-(4-chlorophenyl)imidazo[1,2-a]pyrazin-6-yl)phenyl)methanone as a TFA salt (54 mg, >99%, AUC HPLC 96%) as a brown solid. $^1$H NMR (400 MHz, CD$_3$OD) δ 9.22 (s, 1H), 8.83 (s, 1H), 8.07 (d, J=7.8 Hz, 3H), 7.73 (d, J=8.2 Hz, 2H), 7.62 (d, J=8.2 Hz, 2H), 7.51 (d, J=8.0 Hz, 2H), 4.71 (bs, 1H), 3.85 (bs, 1H), 3.45 (m, J=3.4 Hz, 1H), 3.30-2.85 (m, 2H), 2.28-1.91 (m, 2H), 1.62 (bs, 2H); $^{13}$C NMR (100 MHz, CD$_3$OD) δ 172.04, 143.03, 141.45, 140.50, 139.00, 137.041, 136.68, 133.66, 131.50, 131.04, 130.94, 130.58, 128.76, 128.60, 128.02, 126.78, 117.47, 115.32, 114.65, 47.09, 41.61, 32.74, 31.48, 30.76; MS (ESI) m/z 432 [C$_{23}$H$_{20}$ClN$_5$O+H]$^+$.

Example 48: N-(1-(4-(3-(4-chlorophenyl)imidazo[1,2-a]pyrazin-6-yl)benzoyl)piperidin-4-yl)-2,2,2-trifluoroacetamide

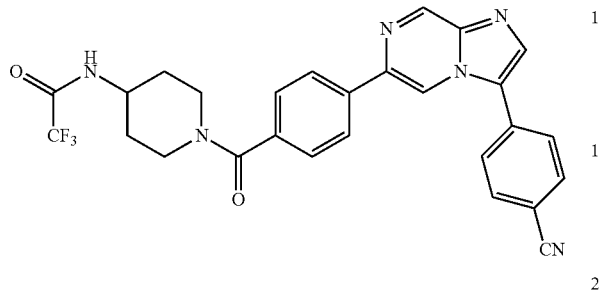

To a solution of (4-aminopiperidin-1-yl)(4-(3-(4-chlorophenyl)imidazo[1,2-a]pyrazin-6-yl)phenyl)methanone (16 mg, 0.04 mmol) in DMF (3 mL) were added pyridine (0.05 mL) and 2,2,2-trifluoroacetic anhydride (0.3 mL). The reaction mixture was stirred at room temperature for 18 h and was concentrated under reduced pressure. The crude residue was purified by preparative HPLC (C18, eluent ACN/H$_2$O/0.01% HCOOH) to afford N-(1-(4-(3-(4-chlorophenyl)imidazo[1,2-a]pyrazin-6-yl)benzoyl)piperidin-4-yl)-2,2,2-trifluoroacetamide (13 mg, 63%, AUC HPLC 99%) as yellow solid. $^1$H NMR (400 MHz, CD$_3$OD) δ 9.12 (d, J=1.3 Hz, 1H), 8.80 (d, J=1.3 Hz, 1H), 8.08 (d, J=8.4 Hz, 2H), 7.96 (s, 1H), 7.74 (d, J=8.6 Hz, 2H), 7.61 (d, J=8.6 Hz, 2H), 7.51 (d, J=8.4 Hz, 2H), 4.65 (bs, 1H), 4.05 (m, J=5.7 Hz, 1H), 3.80 (bs, 1H), 3.25 (bs, 1H), 3.00 (bs, 1H), 2.00 (bs, 1H), 1.88 (bs, 1H), 1.58 (bs, 2H); $^{13}$C NMR (100 MHz, CD$_3$OD) δ 170.63, 157.09, 156.35, 142.41, 140.45, 139.30, 137.92, 135.67, 134.86, 134.86, 134.38, 129.44, 127.09, 126.46, 126.11, 120.32, 117.47, 114.62, 113.69, 111.77, 46.44, 40.91, 31.11, 30.32; MS (ESI) m/z 528 [C$_{26}$H$_{21}$ClF$_3$N$_5$O+H]$^+$.

Example 49: N-(1-(4-(3-(4-chlorophenyl)imidazo[1,2-a]pyrazin-6-yl)benzoyl)piperidin-4-yl)-2,2,2-acetamide

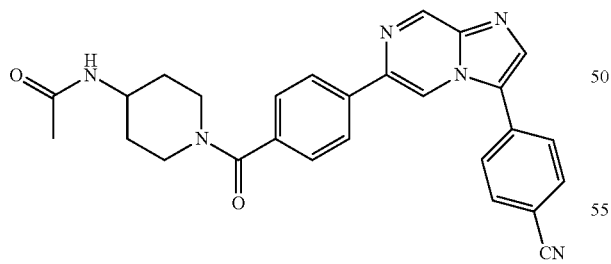

To a solution of (4-aminopiperidin-1-yl)(4-(3-(4-chlorophenyl)imidazo[1,2-a]pyrazin-6-yl)phenyl)methanone (16 mg, 0.04 mmol) in DMF (3 mL), were successively added pyridine (0.05 mL) and acetic anhydride (0.3 mL, 3.18 mmol). The reaction mixture was stirred at room temperature for 18 h and was concentrated under reduced pressure. The crude residue was purified by preparative HPLC (C18, eluent ACN/H$_2$O/0.01% HCOOH) to afford N-(1-(4-(3-(4-chlorophenyl)imidazo[1,2-a]pyrazin-6-yl)benzoyl)piperidin-4-yl)-2,2,2-acetamide (11 mg, 61%, AUC HPLC>99%) as white solid. $^1$H NMR (400 MHz, CD$_3$OD) δ 9.13 (d, J=1.3 Hz, 1H), 8.81 (d, J=1.3 Hz, 1H), 8.07 (d, J=8.4 Hz, 2H), 7.96 (s, 1H), 7.74 (d, J=8.6 Hz, 2H), 7.62 (d, J=8.6 Hz, 2H), 7.51 (d, J=8.4 Hz, 2H), 4.55 (bs, 1H), 3.95 (d, J=5.3 Hz, 1H), 3.74 (bs, 1H), 3.24 (bs, 1H), 3.07 (bs, 1H), 2.03-1.81 (m, 5H), 1.32-1.60 (m, 2H); $^{13}$C NMR (400 MHz, CD$_3$OD) δ 172.61, 172.03, 143.83, 141.86, 140.75, 139.39, 137.21, 136.27, 135.79, 130.87, 128.49, 127.87, 127.54, 115.10, 42.30, 42.30, 33.22, 32.31, 22.66; MS (ESI) m/z 474 [C$_{26}$H$_{24}$ClN$_5$O$_2$+H]$^+$.

Example 50: (4-(3-(4-(2H-tetrazol-5-yl)phenyl)imidazo[1,2-a]pyrazin-6-yl)phenyl)(4-methylpiperazin-1-yl)methanone

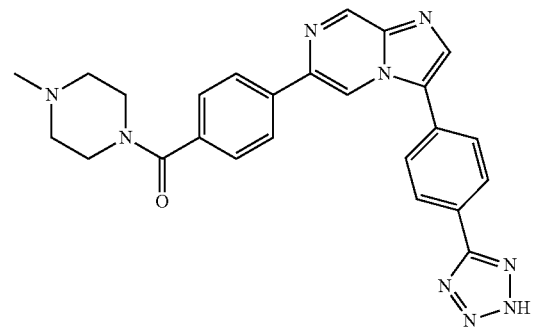 [SMILES: CN1CCN(C(=O)c2ccc(-c3cn4c(-c5ccc(-c6nn[nH]n6)cc5)cnc4cn3)cc2)CC1]

To a solution of 4-(6-(4-(4-methylpiperazine-1-carbonyl)phenyl)imidazo[1,2-a]pyrazin-3-yl)benzonitrilemethanone (100 mg, 0.16 mmol) in DMF (3 mL), was added NH$_4$Cl (30 mg, 0.56 mmol) and NaN$_3$ (30 mg, 0.46 mmol). The resulting mixture was heated at 100° C. for 18 h and was concentrated under reduced pressure. The residue was purified by preparative HPLC (C18, eluent ACN/H$_2$O/0.01% HCOOH) to afford (4-(3-(4-(2H-tetrazol-5-yl)phenyl)imidazo[1,2-a]pyrazin-6-yl)phenyl)(4-methylpiperazin-1-yl)methanone (25 mg, 33%, AUC HPLC 99%) as a white solid. $^1$H NMR (400 MHz, CD$_3$OD) δ 9.15 (d, J=1.2 Hz, 1H), 9.91 (d, J=1.2 Hz, 1H), 8.29 (d, J=8.4 Hz, 2H), 8.13 (t, J=8.7 Hz, 3H), 8.06 (s, 1H), 7.91 (d, J=8.4 Hz, 2H), 7.60 (d, J=8.3 Hz, 2H), 3.86 (m, 4H), 3.19 (m, 4H), 2.84 (s, 3H); $^{13}$C NMR (100 MHz, CD$_3$OD) δ 172.09, 165.22, 160.86, 143.88, 141.92, 140.60, 139.91, 135.96, 135.77, 130.35, 129.80, 129.15, 127.98, 115.40, 54.60, 44.2; MS (ESI) m/z 366 [C$_{25}$H$_{23}$N$_9$O+H]$^+$.

Example 51: (4-methylpiperazin-1-yl)(4-(3-(4-(trifluoromethyl)phenyl)imidazo[1,2-a]pyrazin-6-yl)phenyl)methanone

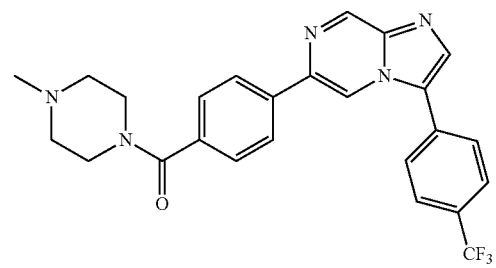 [SMILES: CN1CCN(C(=O)c2ccc(-c3cn4c(-c5ccc(C(F)(F)F)cc5)cnc4cn3)cc2)CC1]

To a solution of (4-(3-iodoimidazo[1,2-a]pyrazin-6-yl)phenyl)(4-methylpiperazin-1-yl)methanone (200 mg, 0.45 mmol) in a mixture of toluene (4 mL) and ethanol (2 ml) under inert atmosphere, was added $K_2CO_3$ (124 mg, 0.89 mmol), 4-(trifluoromethyl)phenylboronic acid (101 mg, 0.54 mmol) and $Pd(PPh_3)_4$ (52 mg, 0.045 mmol). The resulting mixture was heated in a microwave reactor at 140° C. for 15 min then, was concentrated under reduced pressure. The residue was purified by column chromatography (silica gel, eluent $CH_2Cl_2$/MeOH 95:5 to 90:10) to afford (4-methylpiperazin-1-yl)(4-(3-(4-(trifluoromethyl)phenyl)imidazo[1,2-a]pyrazin-6-yl)phenyl)methanone (150 mg, 72%, AUC HPLC 97%) as a yellow solid. $^1$H NMR (400 MHz, $CD_3OD$) δ 9.18 (s, 1H), 8.91 (s, 1H), 8.11 (d, J=8.2 Hz, 2H), 8.08 (s, 1H), 8.00 (d, J=8.2 Hz, 2H), 7.94 (d, J=8.2 Hz, 2H), 7.54 (d, J=8.3 Hz, 2H), 3.81 (bs, 2H), 3.54 (bs, 2H), 2.55-2.47 (m, 4H), 2.36 (s, 3H); $^{13}$C NMR (100 MHz, $CD_3OD$) δ 172.00, 143.96, 142.16, 140.93, 139.31, 136.90, 136.43, 132.89, 131.85, 129.77, 128.75, 128.19, 127.90, 127.57, 125.52, 115.24, 45.99; MS (ESI) m/z 466 $[C_{25}H_{22}F_3N_5O+H]^+$.

Example 52: N-hydroxy-4-(6-(4-(4-methylpiperazine-1-carbonyl)phenyl)imidazo[1,2-a]pyrazin-3-yl)benzamide

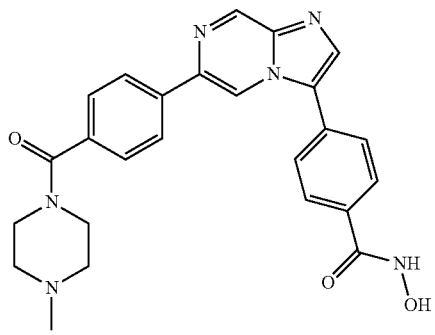 [SMILES: CN1CCN(C(=O)c2ccc(-c3cn4c(-c5ccc(C(=O)NO)cc5)cnc4cn3)cc2)CC1]

Step 1: To a solution of (4-(3-bromoimidazo[1,2-a]pyrazin-6-yl)phenyl)(4-methylcyclohexyl)methanone (1.00 g, 2.5 mmol) in 1,4-dioxane (25 mL), were added 4-(ethoxycarbonyl)phenylboronic acid (970 mg, 5.0 mmol), $K_3PO_4$ (1.06 g, 5.0 mmol), water (5 mL) and $Pd(PPh_3)_4$ (580 mg, 0.5 mmol). The reaction mixture was heated at 90° C. for 12 h under argon atmosphere then, was cooled and filtered through a pad of celite. The filtrate was concentrated under reduce pressure and the residue was purified by flash column chromatography (eluent $CHCl_3$/MeOH 94:6) to afford ethyl 3-(6-(4-(4-methylpiperazine-1-carbonyl)phenyl)imidazo[1,2-a]pyrazin-3-yl)benzoate (600 mg, 55%) as a off-white solid. $^1$H NMR (400 MHz, $CD_3OD$) δ 9.28-9.27 (d, J=1.2 Hz, 1H), δ 8.64-8.64 (d, J=1.2 Hz, 1H), 8.29-8.27 (d, J=8.0 Hz, 2H), 7.99-7.98 (d, J=2.0 Hz, 2H), 7.96 (s, 1H), 7.74-7.72 (d, J=8.4 Hz, 2H), 7.55-7.53 (d, J=8.4 Hz, 2H), 4.48-4.43 (q, J=7.2 Hz, 2H), 3.84 (bs, 2H), 3.50 (bs, 2H), 2.53 (bs, 2H), 2.39 (bs, 2H), 2.35 (s, 3H), 1.47-1.44 (t, J=7.2 Hz, 3H); MS (ESI) m/z 470 $[C_{27}H_{27}N_5O_3+H]^+$.

Step 2: A solution of ethyl 3-(6-(4-(4-methylpiperazine-1-carbonyl)phenyl)imidazo[1,2-a]pyrazin-3-yl)benzoate (600 mg, 1.28 mmol) and LiOH (107 mg, 2.56 mmol) in THF/MeOH/$H_2O$ (6/2.5/2 20 mL) was stirred at room temperature for 5 h. The reaction mixture was evaporated and diluted with $H_2O$ (200 mL) and acidified with aqueous HCl till pH 3. The white precipitate was isolated by filtration and dried to afford the 3-(6-(4-(4-methylpiperazine-1-carbonyl)phenyl)imidazo[1,2-a]pyrazin-3-yl)benzoic acid as a white solid (450 mg, 80%). $^1$H NMR (400 MHz, DMSO-$d_6$) δ 9.28 (s, 1H), 9.01 (s, 1H), 8.17-8.11 (m, 5H), 7.94-7.92 (d, J=8.0 Hz, 2H), 7.50-7.48 (d, J=8.0 Hz, 2H), 3.61 (bs, 4H), 2.32 (bs, 4H), 2.19 (s, 3H); MS (ESI) m/z 440 $[C_{25}H_{23}N_5O_3-H]^+$.

Step 3: To a solution of acid (50 mg, 0.113 mmol) in $CH_2Cl_2$: DMF (3:1, 4 mL) was added sequentially DIPEA (83 µL, 0.476 mmol), HOBt (32 mg, 0.238 mmol), EDCI·HCl (45 mg, 0.238 mmol) and $NH_2$—OTHP (26 mg, 0.226 mmol). The reaction mixture was stirred at room temperature under inert atmosphere for 12 h, then it was diluted with water (3 mL) and extracted with $CH_2Cl_2$ (3×10 mL). The combined organic layer was dried over $Na_2SO_4$ and was concentrated under reduced pressure. The crude residue was purified by column chromatography to afford 4-(6-(4-(4-methylpiperazine-1-carbonyl)phenyl)imidazo[1,2-a]pyrazin-3-yl)-N-(tetrahydro-2H-pyran-2-yloxy)benzamide (44.6 mg, 73%, AUC HPLC 94.5%) as a white solid. $^1$H NMR (600 MHz, DMSO-$d_6$) δ 11.81 (bs, 1H), 9.30 (s, 1H), 9.00 (s, 1H), 8.19 (s, 1H), 8.16 (d, J=12 Hz, 2H), 7.99 (dd, J=10.6, 8.3 Hz, 4H), 7.51 (d, J=12 Hz, 2H), 5.08-5.04 (m, 1H), 4.13-4.06 (m, 1H), 3.70-3.53 (m, 3H), 2.43-2.27 (m, 4H), 2.22 (s, 3H), 1.79-1.73 (m, 3H), 1.63-1.53 (m, 3H); MS (ESI) m/z 541 $[C_{30}H_{32}N_6O_4+H]^+$.

Step 4: To a solution of protected hydroxamate (10 mg, 0.018 mmol) in a $CH_3CN$: MeOH (1:1, 0.6 mL) was added 1M aqueous HCl (0.111 mL) at room temperature. After stirring for 4 h, the solution was concentrated in vacuo. The solid was triturated in hexane dried to yield N-hydroxy-4-(6-(4-(4-methylpiperazine-1-carbonyl)phenyl)imidazo[1,2-a]pyrazin-3-yl)benzamide (5.3 mg, 63%, AUC HPLC 99%), light yellow solid. $^1$H NMR (600 MHz, DMSO-$d_6$) δ 11.39 (bs, 1H), 9.35 (s, 1H), 9.04 (s, 1H), 8.26 (s, 1H), 8.20 (d, J=8.4 Hz, 2H), 8.00 (d, J=7.8 Hz, 2H), 7.95 (d, J=8.4 Hz, 2H), 7.59 (d, J=8.4 Hz, 2H), 4.39-3.60 (m, 6H), 3.05-3.15 (m, 2H), 2.77 (s, 3H); MS (ESI) m/z 457 $[C_{25}H_{24}N_6O_3+H]^+$.

Example 53: (4-(3-(4-(difluoromethyl)phenyl)imidazo[1,2-a]pyrazin-6-yl)phenyl)(4-methylpiperazin-1-yl)methanone

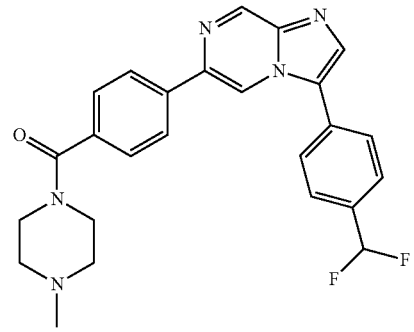 [SMILES: CN1CCN(C(=O)c2ccc(-c3cn4c(-c5ccc(C(F)F)cc5)cnc4cn3)cc2)CC1]

To a mixture of 2-(4-(difluoromethyl)phenyl)-4,4,5,5-tetramethyl-1,3,2-dioxaborolane (200 mg, 0.5 mmol), (4-(3-bromoimidazo[1,2-a]pyrazin-6-yl)phenyl)(4-methylpiperazin-1-yl)methanone (317 mg, 1.25 mmol), $K_3PO_4$ (212 mg, 1 mmol) in 1,4-Dioxane (10 mL) and water (1 mL) was added $Pd(PPh_3)_4$ (30 mg) and the reaction mixture was heated at 90° C. for 1 h. Water was added to the reaction mixture and extracted with EtOAc. The organic layer was dried over anhydrous Na$_2$SO$_4$, filtered and concentrated under reduced pressure. The residue was purified by column chromatography (silica gel, eluent CHCl$_3$/MeO 96.5:3.5%) and by preparative HPLC to give (4-(3-(4-(difluoromethyl)phenyl)imidazo[1,2-a]pyrazin-6-yl)phenyl)(4-methylpiperazin-1-yl)methanone (50 mg, 23%, AUC HPLC 99.59%) as an off-white solid; m.p. 73-86° C. $^1$H NMR (400 MHz, CDCl$_3$) δ (ppm): 9.26 (s, 1H), 8.60 (s, 1H), 7.96-7.94 (m, 3H), 7.77-7.71 (m, 4H), 7.52 (d, J=8.0 Hz, 2H), 6.76 (t, J=5.6 Hz, 1H), 3.82 (bs, 2H), 3.47 (bs, 2H), 2.51 (bs, 2H), 2.34 (bs, 2H), 2.33 (s, 3H); MS (ESI) m/z 448.46 [C$_{25}$H$_{23}$F$_2$N$_5$O+H]$^+$.

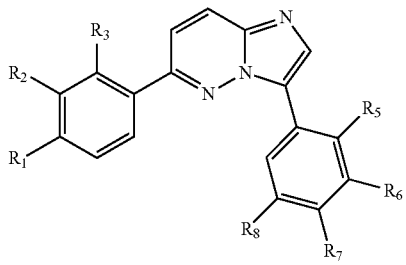

Formula 3

Intermediate 12: 4-(3-(4-cyanophenyl)imidazo[1,2-b]pyridazin-6-yl)benzoic Acid

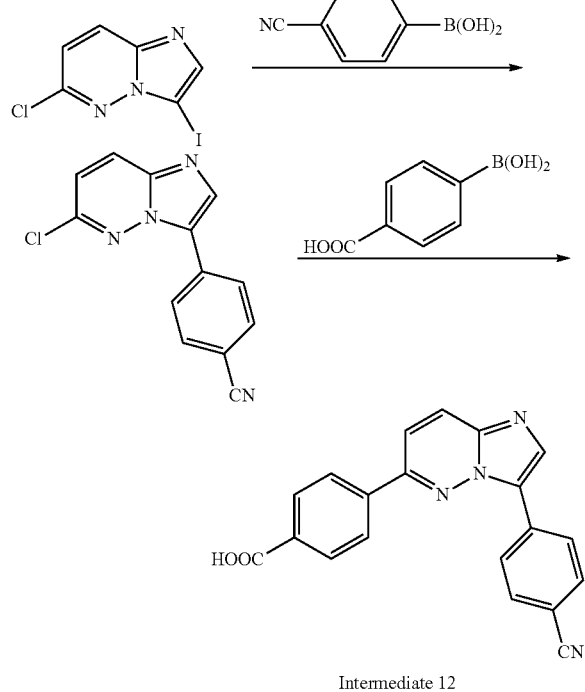

Intermediate 12

Step 1: To a solution of 6-chloro-3-iodoimidazo[1,2-b]pyridazine (1.00 g, 3.58 mmol) in a mixture of DMF (20 mL) and water (1 mL) under inert atmosphere, were added Na$_2$CO$_3$ (759 mg, 7.16 mmol), 4-cyanophenylboronic acid (885 mg, 5.37 mmol) and Pd(PPh$_3$)$_4$ (414 mg, 0.358 mmol). The resulting mixture was stirred at 90° C. for 18 h and quenched with ice water. The precipitate was isolated by filtration and dried in vacuo to afford 4-(6-chloroimidazo[1,2-b]pyridazin-3-yl)benzonitrile (897 mg, 98%) as a yellow solid. $^1$H NMR (400 MHz, CDCl$_3$) δ 8.24-8.21 (m, 2H), 8.18 (s, 1H), 8.02 (d, J=9.4 Hz, 1H), 7.81-7.79 (m, 2H), 7.45 (d, J=9.4 Hz, 1H); MS (ESI) m/z 255 [C$_{13}$H$_7$ClN$_4$+H]$^+$.

Step 2: To a solution of 4-(6-chloroimidazo[1,2-b]pyridazin-3-yl)benzonitrile (484 mg, 1.9 mmol) in DMF (20 mL) and water (4 mL) under inert atmosphere were added Cs$_2$CO$_3$ (1.24 g, 3.8 mmol), 4-boronobenzoic acid (473 mg, 2.85 mmol) and Pd(dppf)$_2$Cl$_2$ (278 mg, 0.38 mmol). The resulting mixture was heated at 90° C. for 18 h, and then was diluted with water (20 mL) and extracted with DCM (3×40 mL). The combined organic layer was dried over Na$_2$SO$_4$, filtered and concentrated under reduced pressure. The residue was purified by column chromatography (silica gel, eluent CH$_2$Cl$_2$/MeOH 95:5 to 90:10) to afford 4-(3-(4-cyanophenyl)imidazo[1,2-b]pyridazin-6-yl)benzoic acid (310 mg, 48%) as a brown solid. $^1$H NMR (400 MHz, DMSO-d$_6$) δ 8.54 (s, 1H), 8.51 (d, J=8.6 Hz, 2H), 8.40 (d, J=9.6 Hz, 1H), 8.26 (d, J=8.4 Hz, 2H), 8.13 (d, J=8.4 Hz, 2H), 8.03 (d, J=8.6 Hz, 2H), 8.02 (d, J=9.6 Hz, 1H); MS (ESI) m/z 341 [C$_{20}$H$_{12}$N$_4$O$_2$+H]$^+$.

Intermediate 13: 4-(3-bromoimidazo[1,2-b]pyridazin-6-yl)benzoic Acid

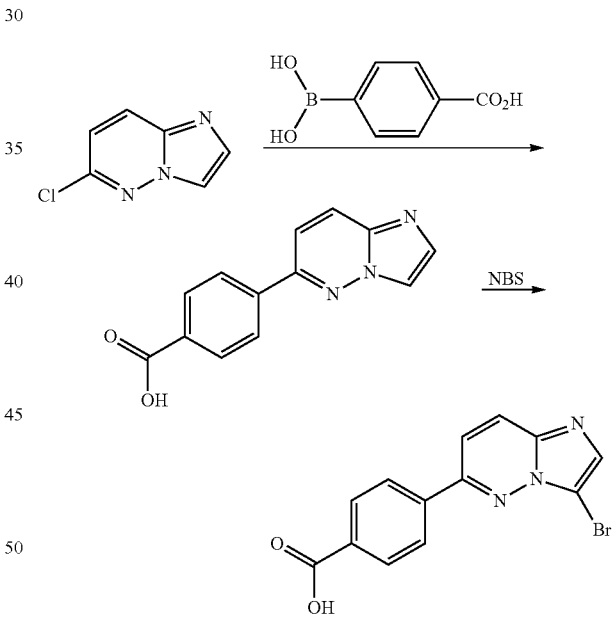

Intermediate 13

Step 1: 4-boronobenzoic acid (11.88 g, 71.61 mmol), K$_3$PO$_4$ (27.60 g, 13.02 mmol) and Pd(PPh$_3$)$_4$ (3.75 g, 3.25 mmol) were added sequentially to a solution of 6-chloroimidazo[1,2-b]pyridazine (10 g, 65.10 mmol) in a mixture of 1,4-dioxane/H$_2$O (250:50 mL) at room temperature under argon atmosphere. The reaction mixture was refluxed for 6 h and was diluted with water (100 mL) and extracted with EtOAc (3×100 mL). The combined aqueous layer was acidified to pH 2 using citric acid. The precipitate was isolated by filtration and dried under reduced pressure to afford 4-(imidazo[1,2-b]pyridazin-6-yl)benzoic acid (4.5 g, 57%) as an off-white solid. $^1$H NMR (400 MHz, DMSO-d$_6$)

δ 13.01 (bs, 1H), 8.04 (s, 1H), 8.3-8.01 (m, 5H), 7.85 (d, J=7.2 Hz, 2H); MS (ESI) m/z 240 [M+H]⁺.

Step 2: To a solution of 4-(imidazo[1,2-b]pyridazin-6-yl)benzoic acid (4.5 g, 18.82 mmol) in DCM (25 mL) and ACN (55 mL) was added NBS (3.68 g, 20.71 mmol) and stirred at 0° C. for 3 h. The reaction mixture was filtered, washed with water and dried to afford 4-(3-bromoimidazo[1,2-b]pyridazin-6-yl)benzoic acid (5.5 g, 93%) as a yellow solid. ¹H NMR (400 MHz, DMSO-d₆) δ 13.01 (bs, 1H), 8.3-8.01 (m, 5H), 7.85 (d, J=7.2 Hz, 2H); MS (ESI) m/z 317 [M]⁺.

Example 54: (4-(3-(4-chlorophenyl)imidazo[1,2-b]pyridazin-6-yl)phenyl)(4-methylpiperazin-1-yl)methanone

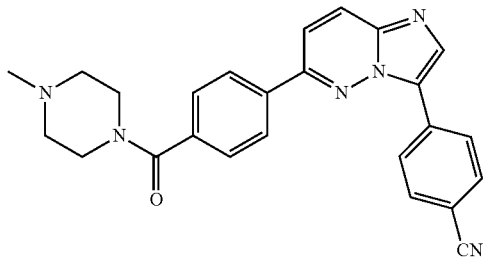 [SMILES: CN1CCN(C(=O)c2ccc(-c3ccc4ncc(-c5ccc(C#N)cc5)n4n3)cc2)CC1]

Step 1: To a solution of 6-chloro-3-iodoimidazo[1,2-b]pyridazine (1.00 g, 3.58 mmol) in a mixture of DMF (20 mL) and water (1 mL) under inert atmosphere, were added Na₂CO₃ (759 mg, 7.16 mmol), 4-cyanophenylboronic acid (885 mg, 5.37 mmol) and Pd(PPh₃)₄ (414 mg, 0.358 mmol). The resulting mixture was stirred at 90° C. for 18 h and quenched with ice water. The precipitate was isolated by filtration and dried in vacuo to afford 4-(6-chloroimidazo[1,2-b]pyridazin-3-yl)benzonitrile (897 mg, 98%) as a yellow solid. ¹H NMR (400 MHz, CDCl₃) δ 8.24-8.21 (m, 2H), 8.18 (s, 1H), 8.02 (d, J=9.4 Hz, 1H), 7.81-7.79 (m, 2H), 7.45 (d, J=9.4 Hz, 1H); MS (ESI) m/z 255 [C₁₃H₇ClN₄+H]⁺.

Step 2: To a solution of 4-(6-chloroimidazo[1,2-b]pyridazin-3-yl)benzonitrile (200 mg, 0.785 mmol) in toluene (3 mL) and ethanol (1.5 mL) under inert atmosphere were added K₂CO₃ (347 mg, 2.51 mmol), 4-(4-methylpiperazine-1-carbonyl)phenylboronic acid hydrochloride (268 mg, 0.942 mmol) and Pd(PPh₃)₄ (91 mg, 0.079 mmol). The resulting mixture was heated in a microwave reactor at 140° C. for 15 min and then was concentrated under reduced pressure. The residue was purified by column chromatography (silica gel, eluent CH₂Cl₂/MeOH 95:5 to 90:10) to afford 4-(6-(4-(4-methylpiperazine-1-carbonyl)phenyl)imidazo[1,2-b]pyridazin-3-yl)benzonitrile (91.2 mg, 43%, AUC HPLC 99%) as a yellow solid. ¹H NMR (400 MHz, CDCl₃) δ 8.30 (d, J=8.6 Hz, 2H), 8.23-8.21 (m, 2H), 8.06 (d, J=8.4 Hz, 2H), 7.81 (d, J=8.6 Hz, 2H), 7.66-7.61 (m, 3H), 7.31 (bs, 1H), 3.97-3.74 (m, 4H), 2.84 (bs, 4H), 2.56 (s, 3H); ¹³C NMR (100 MHz, CDCl₃) δ 169.57, 165.35, 151.41, 140.15, 137.01, 136.67, 134.25, 132.82, 132.60, 128.12, 127.49, 127.05, 126.70, 126.54, 118.75, 116.71, 111.15, 53.78, 44.43; MS (ESI) m/z 423 [C₂₅H₂₂N₆O+H]⁺.

Example 55: 4-(6-(4-(4-hydroxypiperidine-1-carbonyl)phenyl)imidazo[1,2-b]pyridazin-3-yl)benzonitrile

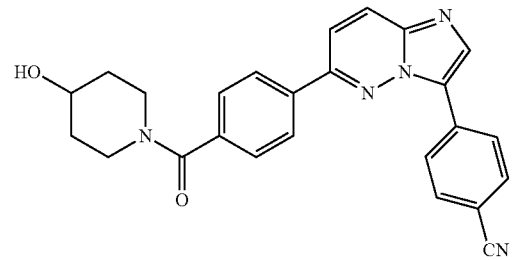 [SMILES: N#Cc1ccc(-c2cnc3ccc(-c4ccc(C(=O)N5CCC(O)CC5)cc4)nn23)cc1]

To a solution (4-hydroxypiperidin-1-yl) (4-(4,4,5,5-tetramethyl-1,3,2-dioxaborolan-2-yl)phenyl)methanone (94 mg, ~0.28 mmol) in a mixture of DMF (8 mL) and water (2 mL) blanketed with nitrogen, was successively added K₂CO₃ (217 mg, 1.58 mmol), Pd(dppf)Cl₂ (114 mg, 0.08 mmol) and 4-(6-chloroimidazo[1,2-b]pyridazin-3-yl)benzonitrile (200 mg, 0.78 mmol). The reaction mixture was stirred at 80° C. for 18 h, then was diluted with water (10 mL) and extracted with DCM (3×10 mL). The combined organic layers were dried over Na₂SO₄, filtered and concentrated under reduced pressure. The crude residue was purified by preparative HPLC (C18, eluent ACN/H₂O/0.01% HCOOH) to afford 4-(6-(4-(4-hydroxypiperidine-1-carbonyl)phenyl)imidazo[1,2-b]pyridazin-3-yl)benzonitrile (52 mg, 61%, AUC HPLC 99%) as yellow solid. ¹H NMR (400 MHz, DMSO-d₆) δ 8.51-8.47 (m, 3H), 8.37 (d, J=8.0 Hz, 1H) 8.19 (d, J=8.0 Hz, 2H), 8.02-7.96 (m, 3H), 7.59 (d, J=8.0 Hz, 2H), 4.82 (s, 1H), 4.03 (s, 1H), 3.77 (s, 1H), 3.54 (s, 1H), 3.37-3.20 (m, 2H), 1.82-1.74 (m, 2H), 1.40 (s, 2H); ¹³C NMR (100 MHz, DMSO-d₄) ppm 168.14, 150.88, 140.10, 138.02, 135.60, 135.37, 132.84, 132.64, 127.37, 127.17, 126.58, 126.22, 125.87, 118.79, 116.89, 109.47, 65.32, 44.49, 34.391, 33.63; MS (ESI) m/z 424 [C₂₅H₂₁N₅O₂+H]⁺.

Example 56: 4-(6-(4-(4-aminopiperidine-1-carbonyl)phenyl)imidazo[1,2-b]pyridazin-3-yl)benzonitrile

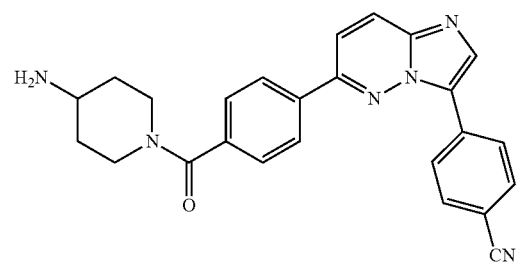 [SMILES: N#Cc1ccc(-c2cnc3ccc(-c4ccc(C(=O)N5CCC(N)CC5)cc4)nn23)cc1]

Step 1: To a solution of 4-(3-(4-cyanophenyl)imidazo[1,2-b]pyridazin-6-yl)benzoic acid (100 mg, 0.294 mmol) in DMF (10 mL) were added HATU (168 mg, 0.441 mmol), N-methyl morpholine (59 mg, 0.588 mmol) and tert-butyl piperidin-4-ylcarbamate (126 mg, 0.588 mmol). The reaction mixture was stirred at room temperature under inert atmosphere for 18 h, and then was diluted with water (10 mL) and extracted with DCM (3×10 mL). The combined organic layer was dried over Na$_2$SO$_4$, filtered and concentrated under reduced pressure. The crude residue was purified by column chromatography (silica gel, eluent CH$_2$Cl$_2$/MeOH 95:5 to 90:10) to afford title compound as a yellow solid. MS (ESI) m/z 523 [C$_{30}$H$_{30}$N$_6$O$_3$+H]$^+$.

Step 2: To a solution of tert-butyl 1-(4-(3-(4-cyanophenyl) imidazo[1,2-b]pyridazin-6-yl)benzoyl)piperidin-4-ylcarbamate (0.294 mmol) in DCM (1 mL) was added TFA (1 mL). The resulting mixture was stirred at room temperature for 18 h and was concentrated under reduced pressure. The residue was purified by preparative HPLC (C18, eluent ACN/H$_2$O/0.01% HCOOH) to afford 4-(6-(4-(4-aminopiperidine-1-carbonyl)phenyl)imidazo[1,2-b]pyridazin-3-yl) benzonitrile (20.5 mg, 15%, AUC HPLC 98%) as a yellow solid. $^1$H NMR (400 MHz, CD$_3$OD) δ 8.30 (d, J=8.4 Hz, 2H), 8.21 (bs, 1H), 8.14-8.10 (m, 3H), 7.83 (d, J=9.4 Hz, 1H), 7.76 (d, J=8.4 Hz, 2H), 7.62 (d, J=8.2 Hz, 2H), 4.78 (bs, 1H), 3.89 (bs, 1H), 3.51-3.45 (m, 1H), 3.32-3.22 (m, 1H), 3.07-2.99 (m, 1H), 2.18-2.05 (m, 2H), 1.67 (bs, 2H); $^{13}$C NMR (100 MHz, CD$_3$OD) δ 171.72, 167.66, 152.79, 141.68, 138.46, 138.03, 135.25, 134.11, 133.59, 128.88, 128.64, 128.17, 127.68, 127.07, 119.71, 118.50, 111.88, 47.10, 41.61, 31.59, 30.85; MS (ESI) m/z 423 [C$_{25}$H$_{22}$N$_6$O+H]$^+$.

Example 57: N-(1-(4-(3-(4-cyanophenyl)imidazo[1,2-b]pyridazin-6-yl)benzoyl)piperidin-4-yl)acetamide

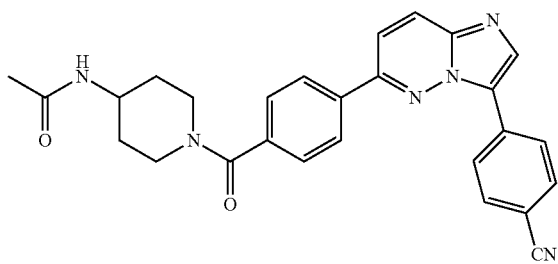 [SMILES: CC(=O)NC1CCN(C(=O)c2ccc(-c3ccc4ncc(-c5ccc(C#N)cc5)n4n3)cc2)CC1]

To a solution of 4-(3-(4-cyanophenyl)imidazo[1,2-b]pyridazin-6-yl)benzoic acid (100 mg, 0.294 mmol) in DMF (10 mL) were added HATU (224 mg, 0.588 mmol), N-methyl morpholine (89 mg, 0.882 mmol) and N-(piperidin-4-yl)acetamide (125 mg, 0.882 mmol). The reaction mixture was stirred at room temperature under inert atmosphere for 18 h, and then diluted with water (10 mL) and extracted with DCM (3×10 mL). The combined organic layer was dried over Na$_2$SO$_4$, filtered and concentrated under reduced pressure. The crude residue was purified by column chromatography (silica gel, eluent CH$_2$Cl$_2$/MeOH 95:5 to 90:10) to afford N-(1-(4-(3-(4-cyanophenyl)imidazo [1,2-b]pyridazin-6-yl)benzoyl)piperidin-4-yl)acetamide, (33 mg, 24%, AUC HPLC 98%) as a yellow solid. $^1$H NMR (400 MHz, DMSO-d$_6$) δ 8.53-8.49 (m, 3H), 8.39 (d, J=9.6 Hz, 1H), 8.22 (d, J=8.3 Hz, 2H), 8.03-7.98 (m, 3H), 7.86 (d, J=7.6 Hz, 1H), 7.59 (d, J=8.3 Hz, 2H), 4.34 (bs, 1H), 3.85-3.83 (m, 1H), 3.59 (bs, 1H), 3.19-3.03 (m, 2H), 1.89-1.70 (m, 5H), 1.35-1.34 (m, 2H); $^{13}$C NMR (100 MHz, DMSO-d$_6$) δ 168.31, 168.23, 150.88, 140.12, 137.83, 135.71, 135.38, 132.85, 132.67, 127.39, 127.23, 126.61, 126.27, 125.91, 118.79, 116.93, 109.49, 45.48, 22.63; MS (ESI) m/z 465 [C$_{27}$H$_{24}$N$_6$O$_2$+H]$^+$.

Example 58: 4-(6-(4-(4-amino-4-methylpiperidine-1-carbonyl)phenyl)imidazo[1,2-b]pyridazin-3-yl) benzonitrile

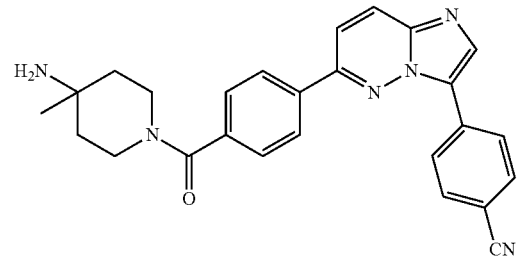 [SMILES: CC1(N)CCN(C(=O)c2ccc(-c3ccc4ncc(-c5ccc(C#N)cc5)n4n3)cc2)CC1]

Step 1: To a solution of 4-(3-(4-cyanophenyl)imidazo[1,2-b]pyridazin-6-yl)benzoic acid (100 mg, 0.294 mmol) in DMF (10 mL) were added HATU (168 mg, 0.441 mmol), N-methyl morpholine (59 mg, 0.588 mmol) and tert-butyl 4-methylpiperidin-4-ylcarbamate (126 mg, 0.588 mmol). The reaction mixture was stirred at room temperature under inert atmosphere for 18 h, and then was diluted with water (10 mL) and extracted with DCM (3×10 mL). The combined organic layer was dried over Na$_2$SO$_4$, filtered and concentrated under reduced pressure. The crude residue was purified by column chromatography (silica gel, eluent CH$_2$Cl$_2$/MeOH 95:5 to 90:10) to afford tert-butyl 1-(4-(3-(4-cyanophenyl)imidazo[1,2-b]pyridazin-6-yl)benzoyl)-4-methylpiperidin-4-ylcarbamate as a yellow solid. MS (ESI) m/z 537 [C$_{31}$H$_{32}$N$_6$O$_3$+H]$^+$.

Step 2: To a solution of tert-butyl 1-(4-(3-(4-cyanophenyl) imidazo[1,2-b]pyridazin-6-yl)benzoyl)-4-methylpiperidin-4-ylcarbamate (0.294 mmol) in DCM (1 mL) was added TFA (1 mL). The resulting mixture was stirred at room temperature for 18 h and concentrated under reduced pressure. The residue was purified by preparative HPLC (C18, eluent ACN/H$_2$O/0.01% HCOOH) to afford 4-(6-(4-(4-amino-4-methylpiperidine-1-carbonyl)phenyl)imidazo[1,2-b]pyridazin-3-yl)benzonitrile (23.5 mg, 17%, AUC HPLC 99%) as a yellow solid. $^1$H NMR (400 MHz, CD$_3$OD) δ 8.28 (d, J=8.4 Hz, 2H), 8.18 (bs, 1H), 8.12-8.08 (m, 3H), 7.82 (d, J=9.4 Hz, 1H), 7.74 (d, J=8.4 Hz, 2H), 7.61 (d, J=8.0 Hz, 2H), 4.36 (bs, 1H), 3.73 (bs, 1H), 3.50-3.47 (m, 2H), 1.94-1.85 (m, 4H), 1.53 (s, 3H); $^{13}$C NMR (100 MHz, CD$_3$OD) δ 171.70, 152.75, 138.42, 137.99, 135.25, 134.08, 133.58, 128.89, 128.62, 128.10, 127.63, 127.06, 119.72, 118.48, 111.84, 53.50, 44.88, 39.31, 36.73, 36.01, 22.66; MS (ESI) m/z 437 [C$_{26}$H$_{24}$N$_6$O+H]$^+$.

Example 59: 4-(6-(4-(4-isopropylpiperazine-1-carbonyl)phenyl)imidazo[1,2-b]pyridazin-3-yl)benzonitrile

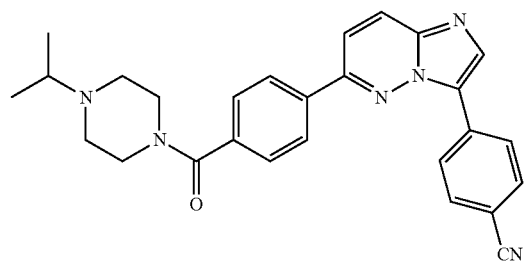 [SMILES: CC(C)N1CCN(C(=O)c2ccc(-c3ccc4ncc(-c5ccc(C#N)cc5)n4n3)cc2)CC1]

To a solution of 4-(3-(4-cyanophenyl)imidazo[1,2-b]pyridazin-6-yl)benzoic acid (55 mg, 0.162 mmol) in DMF (10 mL) were added HATU (123 mg, 0.324 mmol), N-methyl morpholine (49 mg, 0.486 mmol) and 1-isopropylpiperazine (62 mg, 0.486 mmol). The reaction mixture was stirred at room temperature under inert atmosphere for 18 h, and then was diluted with water (10 mL) and extracted with DCM (3×20 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford 4-(6-(4-(4-isopropylpiperazine-1-carbonyl)phenyl)imidazo[1,2-b]pyridazin-3-yl)benzonitrile (32 mg, 44%, AUC HPLC 98%) as a yellow solid. $^1H$ NMR (400 MHz, DMSO-$d_6$) δ 8.53-8.49 (m, 3H), 8.39 (d, J=9.5 Hz, 1H), 8.22 (d, J=8.3 Hz, 2H), 8.03-8.01 (m, 3H), 7.64 (d, J=8.2 Hz, 2H), 3.90-3.59 (m, 3H), 2.99-2.92 (m, 2H), 2.75 (bs, 4H), 1.08 (d, J=6.3 Hz, 6H); $^{13}C$ NMR (100 MHz, DMSO-$d_6$) δ 168.14, 150.84, 137.18, 135.92, 135.42, 132.85, 132.66, 127.79, 127.18, 126.64, 126.28, 125.93, 118.79, 116.92, 109.50, 47.54, 17.43; MS (ESI) m/z 451 $[C_{27}H_{26}N_6O+H]^+$.

Example 60: 4-(6-(4-(4-(methylamino)piperidine-1-carbonyl)phenyl)imidazo[1,2-b]pyridazin-3-yl)benzonitrile

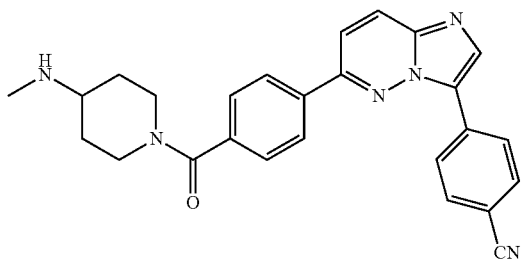 [SMILES: CNC1CCN(C(=O)c2ccc(-c3ccc4ncc(-c5ccc(C#N)cc5)n4n3)cc2)CC1]

Step 1: To a solution of 4-(3-(4-cyanophenyl)imidazo[1,2-b]pyridazin-6-yl)benzoic acid (55 mg, 0.162 mmol) in DMF (10 mL) were added HATU (123 mg, 0.324 mmol), N-methyl morpholine (49 mg, 0.486 mmol) and tert-butyl piperidin-4-ylcarbamate (104 mg, 0.486 mmol). The reaction mixture was stirred at room temperature under inert atmosphere for 18 h, and then was diluted with water (10 mL) and extracted with DCM (3×10 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford tert-butyl 1-(4-(3-(4-cyanophenyl)imidazo[1,2-b]pyridazin-6-yl)benzoyl)piperidin-4-yl(methyl)carbamate as a yellow solid. MS (ESI) m/z 537 $[C_{31}H_{32}N_6O_3+H]^+$.

Step 2: To a solution of tert-butyl 1-(4-(3-(4-cyanophenyl)imidazo[1,2-b]pyridazin-6-yl)benzoyl)piperidin-4-yl(methyl)carbamate (0.162 mmol) in DCM (1 mL) was added TFA (1 mL). The resulting mixture was stirred at room temperature for 18 h and concentrated under reduced pressure. The residue was purified by preparative HPLC (C18, eluent $ACN/H_2O$/0.01% HCOOH) to afford 4-(6-(4-(4-(methylamino)piperidine-1-carbonyl)phenyl)imidazo[1,2-b]pyridazin-3-yl)benzonitrile (29.8 mg, 42%, AUC HPLC 99%) as a yellow solid. $^1H$ NMR (400 MHz, $CD_3OD$) δ 8.29 (d, J=8.4 Hz, 2H), 8.19 (bs, 1H), 8.13-8.09 (m, 3H), 7.82 (d, J=9.4 Hz, 1H), 7.75 (d, J=8.4 Hz, 2H), 7.62 (d, J=8.0 Hz, 2H), 3.94 (bs, 1H), 3.40 (bs, 1H), 3.34-3.20 (m, 2H), 3.01 (bs, 1H), 2.77 (s, 3H), 2.37-2.16 (m, 2H), 1.66 (bs, 2H); $^{13}C$ NMR (100 MHz, $CD_3OD$) δ 171.69, 152.76, 138.39, 138.02, 135.24, 134.09, 133.59, 128.91, 128.62, 128.12, 127.65, 127.06, 119.72, 118.49, 111.84, 57.16, 47.09, 41.58, 30.66, 29.87, 29.16; MS (ESI) m/z 437 $[C_{26}H_{24}N_6O+H]^+$.

Example 61: 4-(6-(4-(4-(methylamino)piperidine-1-carbonyl)phenyl)imidazo[1,2-b]pyridazin-3-yl)benzonitrile

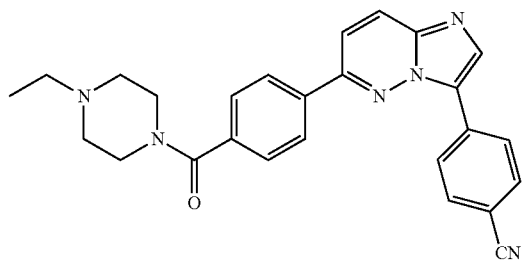 [SMILES: CCN1CCN(C(=O)c2ccc(-c3ccc4ncc(-c5ccc(C#N)cc5)n4n3)cc2)CC1]

To a solution of 4-(3-(4-cyanophenyl)imidazo[1,2-b]pyridazin-6-yl)benzoic acid (120 mg, 0.353 mmol) in DMF (10 mL) were added HATU (402 mg, 1.06 mmol), N-methyl morpholine (143 mg, 1.41 mmol) and 1-ethylpiperazine (181 mg, 1.41 mmol). The reaction mixture was stirred at room temperature under inert atmosphere for 18 h before diluted with water (10 mL) and extracted with DCM (3×10 mL). The combined organic layer was dried over $Na_2SO_4$, filtered and concentrated under reduced pressure. The crude residue was purified by column chromatography (silica gel, eluent $CH_2Cl_2$/MeOH 95:5-90:10) to afford 4-(6-(4-(4-(methylamino)piperidine-1-carbonyl)phenyl)imidazo[1,2-b]pyridazin-3-yl)benzonitrile (64.6 mg, 42%, AUC HPLC 99%) as yellow solid. $^1H$ NMR (400 MHz, DMSO-$d_6$) δ 8.54 (s, 1H), 8.51 (d, J=8.7 Hz, 2H), 8.42 (d, J=9.6 Hz, 1H), 8.25 (d, J=8.4 Hz, 2H), 8.03-8.00 (m, 3H), 7.69 (d, J=8.2 Hz, 2H), 3.44-3.22 (m, 4H), 3.17-3.04 (m, 6H), 1.24-1.20 (m, 3H); $^{13}C$ NMR (100 MHz, DMSO-$d_6$) δ 168.45, 162.96, 150.86, 140.21, 136.40, 135.54, 132.93, 132.73, 128.01, 127.34, 126.77, 126.39, 126.02, 118.86, 117.00, 109.62, 51.01, 50.26, 9.12; MS (ESI) m/z 437 $[C_{26}H_{24}N_6O+H]^+$.

Example 62: 4-(6-(4-(morpholine-4-carbonyl)phenyl)imidazo[1,2-b]pyridazin-3-yl)benzonitrile

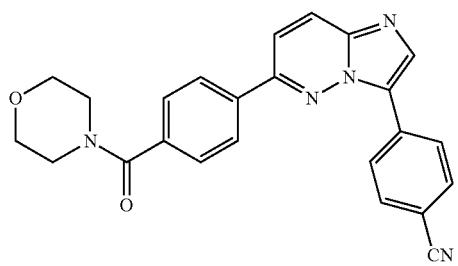 [SMILES: N#Cc1ccc(-c2cnc3ccc(-c4ccc(C(=O)N5CCOCC5)cc4)nn23)cc1]

To a solution of 4-(6-chloroimidazo[1,2-b]pyridazin-3-yl)benzonitrile (150 mg, 0.59 mmol) in DMF (2.5 mL) and water (0.5 mL) under inert atmosphere were added $Cs_2CO_3$ (384 mg, 1.18 mmol), morpholino(4-(4,4,5,5-tetramethyl-1,3,2-dioxaborolan-2-yl)phenyl)methanone (279 mg, 0.88 mmol) and Pd(dppf)$_2Cl_2$ (86 mg, 0.118 mmol). The resulting mixture was heated in a microwave reactor at 140° C. for 30 min, and then was diluted with water (10 mL) and extracted with DCM (3×15 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford 4-(6-(4-(morpholine-4-carbonyl)phenyl)imidazo[1,2-b]pyridazin-3-yl)benzonitrile (72.1 mg, 35%, AUC HPLC 96%) as a yellow solid. $^1$H NMR (400 MHz, $CDCl_3$) δ 8.31-8.25 (m, 4H), 8.06-8.05 (m, 2H), 7.82-7.81 (m, 2H), 7.70-7.61 (m, 3H), 3.78-3.53 (m, 8H); $^{13}$C NMR (100 MHz, $CDCl_3$) δ 169.39, 151.86, 137.43, 136.45, 133.24, 132.63, 132.52, 128.14, 128.08, 127.47, 127.26, 126.86, 126.30, 118.66, 117.32, 111.39, 66.87, 48.21, 42.67; MS (ESI) m/z 410 $[C_{24}H_{19}N_5O_2+H]^+$.

Example 63: 4-(6-(4-(4-(dimethylamino)piperidine-1-carbonyl)phenyl)imidazo[1,2-b]pyridazin-3-yl)benzonitrile

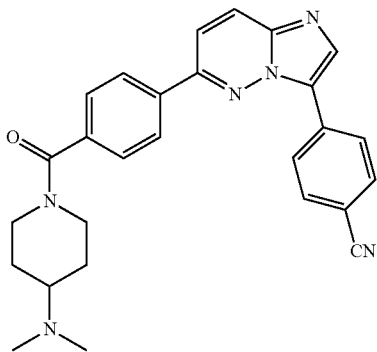 [SMILES: CN(C)C1CCN(C(=O)c2ccc(-c3ccc4ncc(-c5ccc(C#N)cc5)n4n3)cc2)CC1]

Step 1: To a solution of 4-(3-bromoimidazo[1,2-b]pyridazin-6-yl)benzoic acid (500 mg, 1.57 mmol) in DMF (5 mL) was added NMM (317 mg, 3.14 mmol) followed by HATU (754.7 mg, 2.35 mmol) and the solution was stirred for 30 min at rt. N,N-dimethylpiperidin-4-amine (221 mg, 1.72 mmol) was added to the reaction mixture and stirred for an additional 16 h. The reaction mixture was diluted with EtOAc and washed with water and brine. The organic layer was dried over anhydrous $Na_2SO_4$ and concentrated under reduced pressure to obtain crude product. The crude residue was purified by column chromatography (silica gel, eluent $CH_2Cl_2$/MeOH 95:5) to afford (4-(3-bromoimidazo[1,2-b]pyridazin-6-yl)phenyl)(4-(dimethylamino)piperidin-1-yl)methanone (350 mg, 52%) as an off-white solid. $^1$H NMR (400 MHz, DMSO-$d_6$) δ 13.01 (bs, 1H), 8.3-8.01 (m, 5H), 7.85 (d, J=7.2 Hz, 2H); MS (ESI) m/z 317 $[M]^+$.

Step 2: To a mixture of (4-(3-bromoimidazo[1,2-b]pyridazin-6-yl)phenyl)(4-(dimethylamino)piperidin-1-yl)methanone (350 mg, 0.817 mmol), 4-cyanophenylboronic acid (144 mg, 0.981 mmol), $K_3PO_4$ (346 mg, 1.63 mmol) in 1,4-dioxne (25 mL) and water (5 mL) was added $Pd(PPh_3)_4$ (47 mg, 0.04 mmol). The reaction mixture was heated at 90° C. for 6 h under argon atmosphere then, was diluted with water (200 mL). The precipitate was isolated by filtration and was purified by column chromatography (silica gel, eluent $CHCl_3$/MeOH 95:5) to afford 4-(6-(4-(4-(dimethylamino)piperidine-1-carbonyl)phenyl)imidazo[1,2-b]pyridazin-3-yl)benzonitrile (150 mg, 41%, AUC HPLC 98.9%) as a yellow solid; $^1$H NMR (400 MHz, $CDCl_3$) δ (ppm): 8.78 (d, J=8.77 Hz, 1H), 8.52 (s, 1H), 8.30 (d, J=8.2 Hz, 2H), 8.23 (d, J=8.2 Hz, 2H), 7.76 (d, J=7.7 Hz, 2H), 7.62 (d, J=7.6 Hz, 2H), 7.41 (d, J=7.4 Hz, 1H), 4.9 (bs, 1H), 3.9 (bs, 1H), 3.17 (bs, 1H), 2.91 (bs, 1H), 2.45 (bs, 1H), 2.38 (bs, 6H), 2.08 (bs, 1H), 1.95 (bs, 1H), 1.52 (b. s, 2H); MS (ESI) m/z 451.2 $[C_{27}H_{26}N_6O+H]^+$.

Example 64: 4-(6-(4-(1,4-oxazepane-4-carbonyl)phenyl)imidazo[1,2-b]pyridazin-3-yl)benzonitrile

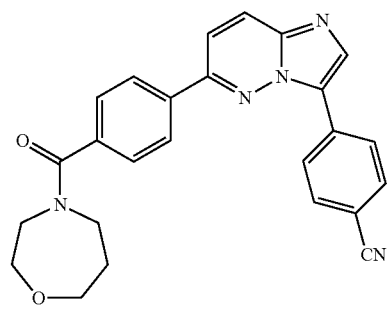 [SMILES: N#Cc1ccc(-c2cnc3ccc(-c4ccc(C(=O)N5CCCOCC5)cc4)nn23)cc1]

To a solution of 4-(3-(4-cyanophenyl)imidazo[1,2-b]pyridazin-6-yl)benzoic acid (200 mg, 0.588 mmol) in DMF (5 mL) was added NMM (118.8 mg, 1.176 mmol) followed by HATU (376.3 mg, 1.17 mmol) and the solution was stirred at rt for 30 min. 1,4-oxazepane (65 mg, 0.646 mmol) was added to the reaction mixture which was stirred for an additional for 16 h. The reaction mixture was diluted with EtOAc and washed with water and brine. The organic layer was dried over anhydrous $Na_2SO_4$ and concentrated under reduced pressure to obtain crude product. The crude product was purified by column chromatography (silica gel, eluent $CH_2Cl_2$/MeOH 95:5) to afford 4-(6-(4-(1,4-oxazepane-4-carbonyl)phenyl)imidazo[1,2-b]pyridazin-3-yl)benzonitrile (120 mg, 50%, AUC HPLC 99.42%) as a pale-yellow solid; 1H NMR (400 MHz, $CDCl_3$) δ 8.33 (d, J=7.9 Hz, 2H), 8.21 (s, 1H), 8.16 (d, J=9.7 Hz, 1H), 8.05 (d, J=7.5 Hz, 2H), 7.82 (d, J=8.3 Hz, 2H), 7.63-7.59 (m, 3H), 3.9 (m, 5H), 3.7 (bs, 1H), 3.59 (bs, 2H), 2.17 (bs, 1H), 1.87 (bs, 1H); MS (ESI) m/z 424.31 $[C_{25}H_{21}N_5O_2+H]^+$.

Example 65: 4-(6-(4-(piperazine-1-carbonyl)phenyl)imidazo[1,2-b]pyridazin-3-yl)benzonitrile

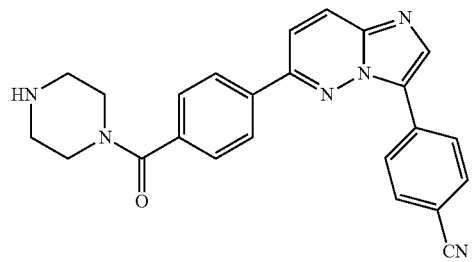 [SMILES: N#Cc1ccc(-c2cnc3ccc(-c4ccc(C(=O)N5CCNCC5)cc4)nn23)cc1]

Step 1: To a solution of 4-(3-(4-cyanophenyl)imidazo[1,2-b]pyridazin-6-yl)benzoic acid (120 mg, 0.353 mmol) in DMF (10 mL) were added HATU (402 mg, 1.06 mmol), N-methyl morpholine (143 mg, 1.41 mmol) and tert-butyl piperazine-1-carboxylate (263 mg, 1.41 mmol). The reaction mixture was stirred at room temperature under inert atmosphere for 18 h, and then was diluted with water (10 mL) and extracted with DCM (3×20 mL). The combined organic layer was dried over Na$_2$SO$_4$, filtered and concentrated under reduced pressure. The crude residue was purified by column chromatography (silica gel, eluent CH$_2$Cl$_2$/MeOH 95:5 to 90:10) to afford tert-butyl 4-(4-(3-(4-cyanophenyl)imidazo[1,2-b]pyridazin-6-yl)benzoyl)piperazine-1-carboxylate as a yellow solid. MS (ESI) m/z 509 [C$_{29}$H$_{28}$N$_6$O+H]$^+$.

Step 2: To a solution of tert-butyl 4-(4-(3-(4-cyanophenyl)imidazo[1,2-b]pyridazin-6-yl)benzoyl)piperazine-1-carboxylate (0.353 mmol) in DCM (1 mL) was added TFA (1 mL). The resulting mixture was stirred at room temperature for 18 h and concentrated under reduced pressure. The residue was purified by preparative HPLC (C18, eluent ACN/H$_2$O/0.01% HCOOH) to afford 4-(6-(4-(piperazine-1-carbonyl)phenyl)imidazo[1,2-b]pyridazin-3-yl)benzonitrile (15.4 mg, 11%, AUC HPLC 92%) as a yellow solid. $^1$H NMR (400 MHz, CD$_3$OD) δ 8.45 (d, J=8.6 Hz, 2H), 8.34 (s, 1H), 8.26-8.22 (m, 3H), 7.95 (d, J=9.6 Hz, 1H), 7.89 (d, J=8.6 Hz, 2H), 7.71 (d, J=8.4 Hz, 2H), 3.87 (bs, 4H), 3.27 (bs, 4H); $^{13}$C NMR (100 MHz, CD$_3$OD) δ 171.80, 152.88, 138.46, 137.54, 135.28, 134.19, 133.64, 129.23, 129.11, 128.72, 128.27, 127.85, 127.14, 119.70, 118.58, 112.00, 44.56; MS (ESI) m/z 409 [C$_{24}$H$_{20}$N$_6$O+H]$^+$.

Example 66: N-(1-(4-(3-(4-cyanophenyl)imidazo[1,2-b]pyridazin-6-yl)benzoyl)-4-ethylpiperidin-4-yl)acetamide

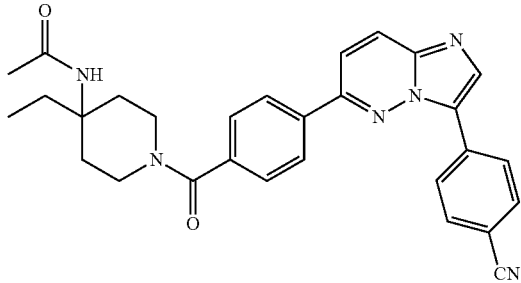 [SMILES: CCC1(NC(C)=O)CCN(C(=O)c2ccc(-c3ccc4ncc(-c5ccc(C#N)cc5)n4n3)cc2)CC1]

Step 1: To a solution of 4-(3-(4-cyanophenyl)imidazo[1,2-b]pyridazin-6-yl)benzoic acid (120 mg, 0.353 mmol) in DMF (10 mL) were added HATU (402 mg, 1.06 mmol), N-methyl morpholine (143 mg, 1.41 mmol) and tert-butyl 4-ethylpiperidin-4-ylcarbamate (322 mg, 1.41 mmol). The reaction mixture was stirred at room temperature under inert atmosphere for 18 h, and then was diluted with water (10 mL) and extracted with DCM (3×20 mL). The combined organic layer was dried over Na$_2$SO$_4$, filtered and concentrated under reduced pressure. The crude residue was purified by column chromatography (silica gel, eluent CH$_2$Cl$_2$/MeOH 95:5 to 90:10) to afford tert-butyl 1-(4-(3-(4-cyanophenyl)imidazo[1,2-b]pyridazin-6-yl)benzoyl)-4-ethylpiperidin-4-ylcarbamate as a yellow solid. MS (ESI) m/z 509 [C$_{29}$H$_{28}$N$_6$O+H]$^+$.

Step 2: To a solution of tert-butyl 1-(4-(3-(4-cyanophenyl)imidazo[1,2-b]pyridazin-6-yl)benzoyl)-4-ethylpiperidin-4-ylcarbamate (0.353 mmol) in DCM (1 mL) was added TFA (1 mL). The reaction mixture was stirred at room temperature for 18 h and was concentrated under reduced pressure. The crude compound was carried forth to the next step without further purification. MS (ESI) m/z 409 [C$_{27}$H$_{26}$N$_6$O+H]$^+$.

Step 3: To a solution of 4-(6-(4-(4-amino-4-ethylpiperidine-1-carbonyl)phenyl)imidazo[1,2-b]pyridazin-3-yl)benzonitrile (0.353 mmol) in DCM (1 mL) were added acetic anhydride (0.1 mL, 1.06 mmol) and triethylamine (0.15 mL, 1.06 mmol). The resulting mixture was stirred at room temperature for 1 h and concentrated under reduced pressure. The crude residue was purified by column chromatography (silica gel, eluent CH$_2$Cl$_2$/MeOH 95:5 to 90:10) and preparative HPLC (C18, eluent ACN/H$_2$O/0.01% HCOOH) to afford N-(1-(4-(3-(4-cyanophenyl)imidazo[1,2-b]pyridazin-6-yl)benzoyl)-4-ethylpiperidin-4-yl)acetamide (44.2 mg, 25%, AUC HPLC 96%) as a yellow solid. $^1$H NMR (400 MHz, CD$_3$OD) δ 8.20 (d, J=8.3 Hz, 2H), 8.02-7.98 (m, 3H), 7.72 (d, J=9.5 Hz, 1H), 7.67 (d, J=8.3 Hz, 2H), 7.55-7.53 (m, 3H), 4.39-4.36 (m, 1H), 3.58-3.55 (m, 1H), 3.37-3.34 (m, 1H), 3.24-3.18 (m, 1H), 2.31-2.29 (m, 2H), 2.01 (s, 3H), 1.86-1.77 (m, 2H), 1.55-1.50 (m, 2H), 0.86 (t, J=7.4 Hz, 3H); $^{13}$C NMR (100 MHz, CD$_3$OD) δ 171.50, 171.37, 152.67, 138.98, 137.55, 135.19, 133.98, 133.59, 133.54, 128.83, 128.45, 127.49, 126.93, 119.70, 118.35, 111.80, 56.18, 45.30, 39.55, 35.26, 34.54, 31.58, 23.64, 7.70; MS (ESI) m/z 493 [C$_{29}$H$_{28}$N$_6$O$_2$+H]$^+$.

Example 67: N-((1-(4-(3-(4-cyanophenyl)imidazo[1,2-b]pyridazin-6-yl)benzoyl)piperidin-4-yl)methyl)acetamide

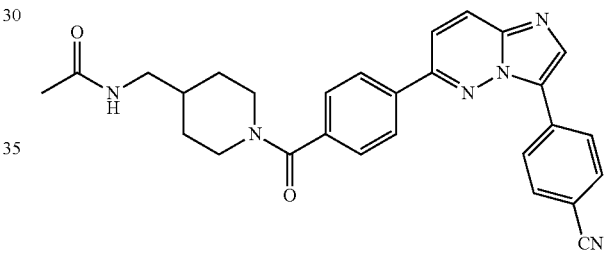

Step 1: To a solution of 4-(3-(4-cyanophenyl)imidazo[1,2-b]pyridazin-6-yl)benzoic acid (120 mg, 0.353 mmol) in DMF (10 mL) were added HATU (402 mg, 1.06 mmol), N-methylmorpholine (143 mg, 1.41 mmol) and tert-butyl piperidin-4-ylmethylcarbamate (302 mg, 1.41 mmol). The reaction mixture was stirred at room temperature under inert atmosphere for 18 h, and then was diluted with water (10 mL) and extracted with DCM (3×20 mL). The combined organic layer was dried over Na$_2$SO$_4$, filtered and concentrated under reduced pressure. The crude residue was purified by column chromatography (silica gel, eluent CH$_2$Cl$_2$/MeOH 95:5 to 90:10) to afford tert-butyl (1-(4-(3-(4-cyanophenyl)imidazo[1,2-b]pyridazin-6-yl)benzoyl)piperidin-4-yl)methylcarbamate as a yellow solid. MS (ESI) m/z 537 [C$_{31}$H$_{32}$N$_6$O$_3$+H]$^+$.

Step 2: A solution of tert-butyl (1-(4-(3-(4-cyanophenyl)imidazo[1,2-b]pyridazin-6-yl)benzoyl)piperidin-4-yl)methylcarbamate (0.353 mmol) in DCM (1 mL) and TFA (1 mL) was stirred at room temperature for 18 h and concentrated under reduced pressure. The crude compound was used for next step without further purification. MS (ESI) m/z 437 [C$_{26}$H$_{24}$N$_6$O+H]$^+$.

Step 3: To a solution of 4-(6-(4-(4-(aminomethyl)piperidine-1-carbonyl)phenyl)imidazo[1,2-b]pyridazin-3-yl)benzonitrile (0.353 mmol) in DCM (1 mL) were added acetic anhydride (0.1 mL, 1.06 mmol) and triethylamine (0.15 mL, 1.06 mmol). The resulting mixture was stirred at room temperature for 1 h and concentrated under reduced pressure. The crude residue was purified by column chromatography (silica gel, eluent CH₂Cl₂/MeOH 95:5 to 90:10) and preparative HPLC (C18, eluent ACN/H₂O/0.01% HCOOH) to afford N-((1-(4-(3-(4-cyanophenyl)imidazo[1,2-b]pyridazin-6-yl)benzoyl)piperidin-4-yl)methyl)acetamide (40.3 mg, 24%, AUC HPLC 96%) as a yellow solid. $^1$H NMR (400 MHz, CD₃OD) δ 8.42 (d, J=8.6 Hz, 2H), 8.29 (bs, 1H), 8.18 (d, J=8.6 Hz, 3H), 7.90 (d, J=9.6 Hz, 1H), 7.86 (d, J=8.6 Hz, 2H), 7.60 (d, J=8.4 Hz, 2H), 4.68-4.65 (m, 1H), 3.79-3.76 (m, 1H), 3.13 (bs, 3H), 2.93-2.87 (m, 1H), 1.95 (s, 3H), 1.88-1.79 (m, 2H), 1.73-1.70 (m, 1H), 1.28-1.24 (m, 2H); $^{13}$C NMR (100 MHz, CD₃OD) δ 173.51, 171.60, 153.21, 139.20, 137.96, 135.24, 134.37, 133.75, 128.78, 128.69, 128.60, 128.07, 127.62, 127.17, 119.75, 118.77, 45.65, 43.39, 37.59, 31.55, 30.70, 29.07, 22.56; MS (ESI) m/z 479 [C₂₈H₂₆N₆O₂+H]⁺.

Example 68: 4-(6-(4-(3-oxopiperazine-1-carbonyl)phenyl)imidazo[1,2-b]pyridazin-3-yl)benzonitrile

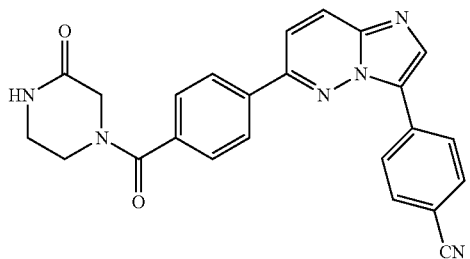

To a solution of 4-(3-(4-cyanophenyl)imidazo[1,2-b]pyridazin-6-yl)benzoic acid (50 mg, 0.147 mmol) in DMF (0.74 mL) were added HATU (84 mg, 0.221 mmol), N-methyl morpholine (65 μL, 0.588 mmol) and 2-oxopiperazine (18 mg, 0.177 mmol). The reaction mixture was stirred at room temperature under inert atmosphere for 18 h, then was diluted with water (15 mL) and extracted with EtOAc (3×30 mL). The combined organic layer was dried over Na₂SO₄, filtered and concentrated under reduced pressure. The residue was purified by column chromatography (silica gel, eluent CHCl₃/MeOH 92:8) to afford 4-(6-(4-(3-oxopiperazine-1-carbonyl)phenyl)imidazo[1,2-b]pyridazin-3-yl)benzonitrile (28 mg, 45%, AUC HPLC 99%) as a yellow solid. $^1$H NMR (400 MHz, DMSO-d₆) δ 8.53-8.46 (m, 3H), 8.38 (d, J=9.6 Hz, 1H), 8.22 (d, J=8.4 Hz, 2H), 8.15 (s, 1H), 8.03-7.96 (m, 3H), 7.67 (d, J=8.4 Hz, 2H), 4.20-4.05 (m, 1H), 4.05-3.90 (m, 1H), 3.90-3.70 (m, 1H), 3.60-3.50 (m, 1H), 3.30-3.20 (m, 2H); $^{13}$C NMR (100 MHz, DMSO-d₆) δ 168.44, 150.95, 140.24, 137.06, 136.24, 135.51, 132.94, 132.79, 127.93, 127.36, 126.74, 126.39, 126.04, 118.92, 117.07, 109.62, 30.70; MS (ESI) m/z 423 [C₂₄H₁₈N₆O₂+H]⁺.

Example 69: 4-(6-(4-(4-methyl-3-oxopiperazine-1-carbonyl)phenyl)imidazo[1,2-b]pyridazin-3-yl)benzonitrile

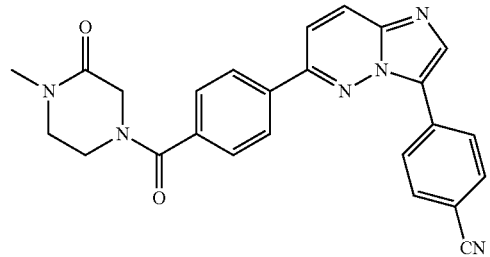 [SMILES: CN1CCN(C(=O)c2ccc(-c3ccc4ncc(-c5ccc(C#N)cc5)n4n3)cc2)CC1=O]

To a solution of 4-(3-(4-cyanophenyl)imidazo[1,2-b]pyridazin-6-yl)benzoic acid (50 mg, 0.147 mmol) in DMF (0.74 mL) were added HATU (84 mg, 0.221 mmol), N-methyl morpholine (65 μL, 0.588 mmol) and 1-methyl-2-oxopiperazine hydrochloride (27 mg, 0.177 mmol). The reaction mixture was stirred at room temperature under inert atmosphere for 18 h, then was diluted with water (15 mL) and extracted with EtOAc (3×30 mL). The combined organic layer was dried over Na₂SO₄, filtered and concentrated under reduced pressure. The residue was purified by column chromatography (silica gel, eluent CHCl₃/MeOH 92:8), followed by preparative HPLC (C18, eluent ACN, water, formic acid 0.1%) to afford 4-(6-(4-(4-methyl-3-oxopiperazine-1-carbonyl)phenyl)imidazo[1,2-b]pyridazin-3-yl)benzonitrile (16 mg, 24%, AUC HPLC 99%) as a yellow solid. $^1$H NMR (400 MHz, DMSO-d₆) δ 8.52-8.47 (m, 3H), 8.39 (d, J=9.6 Hz, 1H), 8.23 (d, J=8.4 Hz, 2H), 8.04-7.97 (m, 3H), 7.67 (d, J=8.4 Hz, 2H), 4.25-3.95 (m, 2H), 3.95-3.75 (m, 1H), 3.75-3.55 (m, 1H), 3.50-3.20 (m, 2H), 2.88 (s, 3H); MS (ESI) m/z 437 [C₂₅H₂₀N₆O₂+H]⁺.

Example 70: 4-(6-(4-(4-(4-methylpiperazin-1-yl)piperidine-1-carbonyl)phenyl)imidazo[1,2-b]pyridazin-3-yl)benzonitrile

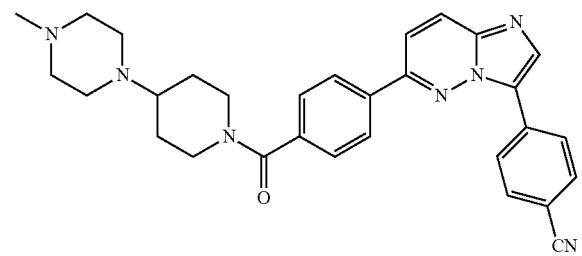

To a solution of 4-(3-(4-cyanophenyl)imidazo[1,2-b]pyridazin-6-yl)benzoic acid (50 mg, 0.147 mmol) in DMF (0.74 mL) were added HATU (84 mg, 0.221 mmol), N-methyl morpholine (65 μL, 0.588 mmol) and 1-methyl-4-(piperidin-4-yl)piperazine (32 mg, 0.177 mmol). The reaction mixture was stirred at room temperature under inert atmosphere for 18 h, then was diluted with water (15 mL) and extracted with EtOAc (3×30 mL). The combined organic layer was dried over Na₂SO₄, filtered and concentrated under reduced pressure. The residue was purified by column chromatography (silica gel, eluent CHCl₃/MeOH 90:10) to afford 4-(6-(4-(4-(4-(4-methylpiperazin-1-yl)piperidine-1-carbonyl)phenyl)imidazo[1,2-b]pyridazin-3-yl)benzonitrile (17 mg, 23%, AUC HPLC 99%) as a yellow solid. $^1$H NMR (400 MHz, DMSO-$d_6$) δ 8.53-8.47 (m, 3H), 8.38 (d, J=9.6 Hz, 1H), 8.20 (d, J=8.4 Hz, 2H), 8.04-7.96 (m, 3H), 7.60 (d, J=8.4 Hz, 2H), 4.55-4.40 (m, 1H), 3.70-3.60 (m, 1H), 3.50-3.20 (m, 4H), 3.15-3.00 (m, 1H), 2.90-2.75 (m, 1H), 2.55-2.40 (m, 2H), 2.40-2.20 (m, 3H), 2.13 (s, 3H), 1.95-1.65 (m, 2H), 1.50-1.35 (m, 2H); $^{13}$C NMR (100 MHz, DMSO-$d_6$) δ 168.18, 151.03, 140.24, 138.08, 135.75, 135.47, 132.97, 132.80, 127.56, 127.29, 126.73, 126.41, 126.04, 118.92, 117.07, 109.61, 60.71, 55.16, 48.50, 45.75, 30.70; MS (ESI) m/z 506 $[C_{30}H_{31}N_7O+H]^+$.

Example 71: 4-(6-(4-(1,9-diazaspiro[5.5]undecane-9-carbonyl)phenyl)imidazo[1,2-b]pyridazin-3-yl)benzonitrile

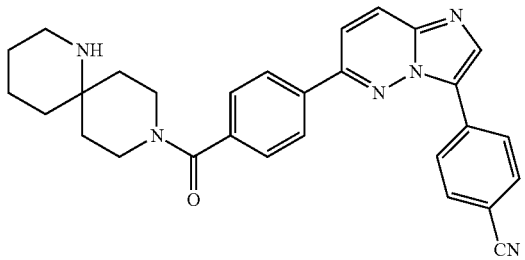 [SMILES: N#Cc1ccc(-c2cnc3ccc(-c4ccc(C(=O)N5CCC6(CCCCN6)CC5)cc4)nn23)cc1]

Step 1: To a solution of 4-(3-(4-cyanophenyl)imidazo[1,2-b]pyridazin-6-yl)benzoic acid (100 mg, 0.294 mmol) in DMF (1.47 mL) were added HATU (168 mg, 0.441 mmol), tert-butyl 1,9-diazaspiro[5.5]undecane-1-carboxylate hydrochloride (103 mg, 0.353 mmol) and N-methylmorpholine (162 µl, 1.47 mmol). The reaction mixture was stirred at room temperature under inert atmosphere for 18 h, then it was diluted with H$_2$O (15 mL) and extracted with EtOAc (3×30 mL). The combined organic layer was dried over Na$_2$SO$_4$ and was concentrated under reduced pressure. The residue was purified by column chromatography (silica gel, eluent CHCl$_3$/MeOH 96:4) to afford tert-butyl 9-({4-[3-(4-cyanophenyl)imidazo[1,2-b]pyridazin-6-yl]phenyl}carbonyl)-1,9-diazaspiro[5.5]undecane-1-carboxylate (70 mg, 41%) as a yellow solid. MS (ESI) m/z 577 $[C_{34}H_{36}N_6O_3+H]^+$.

Step 2: To tert-butyl 9-(4-(3-(4-cyanophenyl)imidazo[1,2-b]pyridazin-6-yl)benzoyl)-1,9-diazaspiro[5.5]undecane-1-carboxylate (50 mg, 0.131 mmol) was added 20% TFA in CH$_2$Cl$_2$ (5 mL). The reaction mixture was stirred at room temperature for 20 min then concentrated under reduced pressure. To the residue was added saturated sodium bicarbonate (10 mL) and extracted with EtOAc (3×30 mL). The combined organic was dried over Na$_2$SO$_4$, filtered and concentrated under reduced pressure. The residue was purified by preparative HPLC (C18, eluent ACN, water, formic acid 0.1%) to afford 4-(6-(4-(1,9-diazaspiro[5.5]undecane-9-carbonyl)phenyl)imidazo[1,2-b]pyridazin-3-yl)benzonitrile (37 mg, 89%, AUC HPLC 99%) as a yellow solid. $^1$H NMR (400 MHz, DMSO-$d_6$) δ 8.54-8.48 (m, 3H), 8.38 (d, J=9.6 Hz, 1H), 8.28 (s, 1H), 8.21 (d, J=8.0 Hz, 2H), 8.04-7.97 (m, 3H), 7.59 (d, J=8.0 Hz, 2H), 3.75-3.60 (m, 3H), 2.85-2.70 (m, 2H), 1.80-1.40 (m, 11H); $^{13}$C NMR (100 MHz, DMSO-$d_6$) δ 168.36, 164.63, 151.10, 140.29, 138.00, 135.87, 135.50, 133.01, 132.86, 127.61, 127.40, 126.79, 126.49, 126.11, 118.99, 117.14, 109.68, 30.76, 24.82, 18.89; MS (ESI) m/z 477 $[C_{29}H_{28}N_6O+H]^+$.

Example 72: 4-(6-(3-chloro-4-(4-methylpiperazine-1-carbonyl)phenyl)imidazo[1,2-b]pyridazin-3-yl)benzonitrile

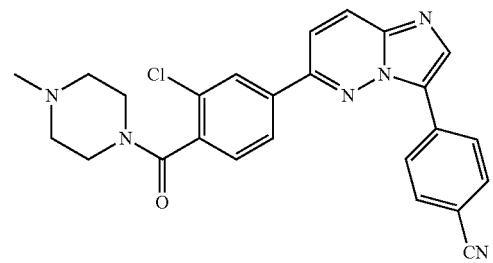 [SMILES: CN1CCN(C(=O)c2ccc(-c3ccc4ncc(-c5ccc(C#N)cc5)n4n3)cc2Cl)CC1]

Step 1: To a solution of 4-(6-chloroimidazo[1,2-b]pyridazin-3-yl)benzonitrile (100 mg, 0.39 mmol) in a mixture of DMF (4 mL) and water (1 mL) under inert atmosphere, was successively added K$_2$CO$_3$ (108 mg, 0.78 mmol), Pd(dppf)Cl$_2$ (57 mg, 0.08 mmol) and 4-borono-2-chlorobenzoic acid (78 mg, 0.39 mmol) were added at room temperature. The reaction mixture was stirred at 80° C. for 18 h, then was diluted with water (10 mL) and extracted with DCM (3×10 mL). The combined organic layers were dried over Na$_2$SO$_4$, filtered and concentrated under reduced pressure to afford the crude 2-chloro-4-(3-(4-cyanophenyl)imidazo[1,2-b]pyridazin-6-yl)benzoic acid as a black solid. MS (ESI) m/z 375 $[C_{20}H_{11}ClN_4O_2+H]^+$.

Step 2: To a solution of 2-chloro-4-(3-(4-cyanophenyl)imidazo[1,2-b]pyridazin-6-yl)benzoic acid in DMF (5 mL) was successively added HATU (223 mg, 0.59 mmol), N-methyl morpholine (80 mg, 0.78 mmol) and 1-methylpiperazine (78 mg, 0.78 mmol). The reaction mixture was stirred at room temperature under inert atmosphere for 18 h, then was diluted with water (10 mL) and the aqueous phase extracted with DCM (3×10 mL). The combined organic layer was dried over Na$_2$SO$_4$, filtered and concentrated under reduced pressure. The crude residue was purified by preparative HPLC (C18, eluent ACN/H$_2$O/HCOOH 0.01%) to afford 4-(6-(3-chloro-4-(4-methylpiperazine-1-carbonyl)phenyl)imidazo[1,2-b]pyridazin-3-yl)benzonitrile (50 mg, 28%, AUC HPLC 95%) as yellow solid. $^1$H NMR (400 MHz, CD$_3$OD) δ 8.06-7.97 (m, 3H), 7.96-7.85 (m, 3H), 7.64 (d, J=9.5 Hz, 1H), 7.58 (d, J=8.4 Hz, 2H), 7.49 (d, J=8.0 Hz, 1H), 3.97 (s, 2H), 3.48 (s, 2H), 2.93 (s, 2H), 2.85 (s, 2H), 2.60 (s, 3H); $^{13}$C NMR (100 MHz, CD$_3$OD) δ 168.03, 151.17, 141.47, 138.71, 137.81, 135.52, 133.65, 132.25, 130.16, 130.01, 129.61, 128.93, 128.01, 127.73, 127.23, 127.17, 127.11, 119.65, 117.95, 111.78, 55.23, 54.75, 48.42, 46.57, 45.08, 41.43, 30.75; MS (ESI) m/z 457 $[C_{25}H_{21}ClN_6O+H]^+$.

Example 73: 4-(6-(3-fluoro-4-(4-methylpiperazine-1-carbonyl)phenyl)imidazo[1,2-b]pyridazin-3-yl)benzonitrile

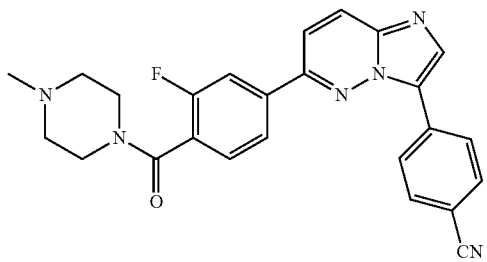 [SMILES: CN1CCN(C(=O)c2ccc(-c3ccc4ncc(-c5ccc(C#N)cc5)n4n3)cc2F)CC1]

Step 1: To a solution of 4-(6-chloroimidazo[1,2-b]pyridazin-3-yl)benzonitrile (100 mg, 0.39 mmol) in a mixture of DMF (4 mL) and water (1 mL) at room temperature, was successively added $K_2CO_3$ (108 mg, 0.78 mmol), Pd(dppf)Cl$_2$ (57 mg, 0.08 mmol) and 4-borono-2-fluorobenzoic acid (72 mg, 0.39 mmol) under inert atmosphere. The reaction mixture was stirred at 80° C. for 18 h and was diluted with water (10 mL). The aqueous phase was extracted with DCM (3×10 mL) and the combined organic layers were dried over $Na_2SO_4$, filtered and concentrated under reduced pressure to afford the crude 4-(3-(4-cyanophenyl)imidazo[1,2-b]pyridazin-6-yl)-2-fluorobenzoic acid as black solid. MS (ESI) m/z 359 $[C_{20}H_{11}FN_4O_2+H]^+$.

Step 2: To a solution of 4-(3-(4-cyanophenyl)imidazo[1,2-b]pyridazin-6-yl)-2-fluorobenzoic acid (~0.39 mmol) in DMF (5 mL) was added HATU (223 mg, 0.59 mmol), N-methyl morpholine (80 mg, 0.78 mmol) and 1-methylpiperazine (78 mg, 0.78 mmol). The reaction mixture was stirred at room temperature under inert atmosphere for 18 h, was diluted with water (10 mL) and extracted with DCM (3×10 mL). The combined organic layer was dried over $Na_2SO_4$, filtered and was concentrated under reduced pressure. The crude residue was purified by preparative HPLC (C18, eluent ACN/H$_2$O/0.01% HCOOH) to afford 4-(6-(3-fluoro-4-(4-methylpiperazine-1-carbonyl)phenyl)imidazo[1,2-b]pyridazin-3-yl)benzonitrile (35 mg, 20%, AUC HPLC 97%) as a yellow solid. $^1$H NMR (400 MHz, CD$_3$OD) δ 8.07-8.33 (m, 3H), 8.02 (d, J=9.0 Hz, 1H), 7.87 (d, J=7.6 Hz, 1H), 7.63-7.82 (m, 4H), 7.58 (t, J=7.2 Hz, 1H), 3.99 (bs, 2H), 3.61 (bs, 2H), 3.03 (bs, 2H), 2.93 (bs, 2H), 2.67 (s, 3H); $^{13}$C NMR (100 MHz, CD$_3$OD) δ 167.15, 166.38, 161.13, 158.67, 151.44, 141.60, 140.24, 140.16, 135.51, 133.56, 135.51, 133.80, 133.56, 131.29, 131.19, 130.15, 127.97, 127.44, 127.15, 126.08, 125.90, 124.73, 124.70, 119.67, 118.14, 115.68, 115.45, 111.89, 55.11, 54.66, 46.59, 44.77, 41.44; MS (ESI) m/z 441 $[C_{25}H_{21}N_6O+H]^+$.

Example 74: 4-(6-(3-methyl-4-(4-methylpiperazine-1-carbonyl)phenyl)imidazo[1,2-b]pyridazin-3-yl)benzonitrile

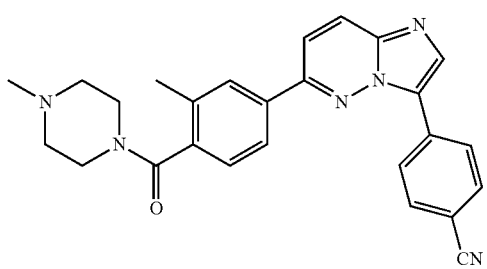 [SMILES: Cc1cc(-c2ccc3ncc(-c4ccc(C#N)cc4)n3n2)ccc1C(=O)N1CCN(C)CC1]

Step 1: To a solution of 4-(6-chloroimidazo[1,2-b]pyridazin-3-yl)benzonitrile (200 mg, 0.67 mmol) in a mixture of DMF (4 mL) and water (1 mL) blanketed with nitrogen, was successively added $K_2CO_3$ (185 mg, 1.34 mmol), Pd(dppf)Cl$_2$ (98 mg, 0.13 mmol) and 4-borono-2-methylbenzoic acid (131 mg, 0.73 mmol). The reaction mixture was stirred at 80° C. for 18 h, then was diluted with water (10 mL) and extracted with DCM (3×10 mL). The combined organic layers were dried over $Na_2SO_4$, filtered and concentrated under reduced pressure to afford the crude 4-(3-(4-cyanophenyl)imidazo[1,2-b]pyridazin-6-yl)-2-methylbenzoic acid (271 mg) as black solid which was used carried forth to the next step without further purification. MS (ESI) m/z 355 $[C_{21}H_{14}FN_4O_2+H]^+$.

Step 2: To a solution of 4-(3-(4-cyanophenyl)imidazo[1,2-b]pyridazin-6-yl)-2-methylbenzoic acid (90 mg, crude) in DMF (5 mL), was added HATU (142 mg, 0.38 mmol), N-methyl morpholine (52 mg, 0.50 mmol) and 1-methylpiperazine (51 mg, 0.50 mmol). The reaction mixture was stirred at room temperature under inert atmosphere for 18 h, then was diluted with water (10 mL) and extracted with DCM (3×10 mL). The combined organic layers were dried over $Na_2SO_4$, filtered and concentrated under reduced pressure. The crude residue was purified by preparative HPLC (C18, eluent ACN/H$_2$O/0.01% HCOOH) to afford 4-(6-(3-methyl-4-(4-methylpiperazine-1-carbonyl)phenyl)imidazo[1,2-b]pyridazin-3-yl)benzonitrile (30 mg, 28%, AUC HPLC 99%) as a brown solid. $^1$H NMR (400 MHz, CD$_3$OD) δ 8.12 (s, 1H), 8.02 (d, J=9.5 Hz, 1H), 7.91-7.82 (m, 2H), 7.75 (d, J=9.5 Hz, 3H), 7.70 (d, J=8.4 Hz, 2H), 7.39 (d, J=7.9 Hz, 1H), 4.09-3.85 (m, 2H), 3.48 (s, 2H), 2.95 (s, 2H), 2.79 (s, 2H), 2.60 (s, 3H), 2.41 (s, 3H); $^{13}$C NMR (100 MHz, CD$_3$OD) δ 169.86, 165.89, 151.43, 140.16, 136.98, 135.48, 133.71, 132.62, 132.10, 128.96, 126.58, 126.51, 126.08, 125.48, 124.59, 118.29, 117.07, 110.36, 53.90, 53.46, 45.20, 43.59, 39.84, 17.97; MS (ESI) m/z 437 $[C_{26}H_{24}N_6O+H]^+$.

Example 75: 4-(6-(3-isopropoxy-4-(4-methylpiperazine-1-carbonyl)phenyl) imidazo[1,2-b]pyridazin-3-yl)benzonitrile

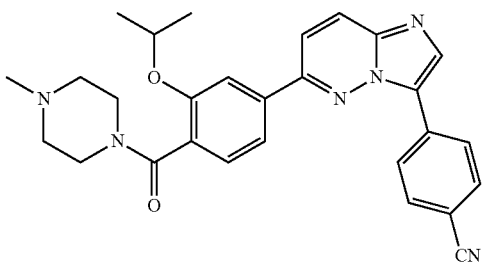 [SMILES: CC(C)Oc1cc(-c2ccc3ncc(-c4ccc(C#N)cc4)n3n2)ccc1C(=O)N1CCN(C)CC1]

To a solution of 4-(6-chloroimidazo[1,2-a]pyrazin-3-yl)benzonitrile (100 mg, 0.39 mmol) in a mixture of DMF (4 mL) and water (1 mL) blanketed with nitrogen, was sequentially added $K_2CO_3$ (108 mg, 0.78 mmol), Pd(dppf)Cl$_2$ (57 mg, 0.08 mmol) and (2-isopropoxy-4-(4,4,5,5-tetramethyl-1,3,2-dioxaborolan-2-yl)phenyl)(4-methylpiperazin-1-yl)methanone (200 mg, 0.39 mmol). The reaction mixture was stirred at 80° C. for 18 h, then was diluted with water (10 mL) and extracted with DCM (3×10 mL). The combined organic layers were dried over $Na_2SO_4$, filtered and concentrated under reduced pressure. The crude residue was purified by preparative HPLC (C18, eluent ACN/H$_2$O/0.01% HCOOH) to afford 4-(6-(3-isopropoxy-4-(4-methylpiperazine-1-carbonyl)phenyl) imidazo[1,2-b]pyridazin-3-yl)benzonitrile (74 mg, 40%, AUC HPLC 99%) as yellow solid. $^1$H NMR (400 MHz, CD$_3$OD) δ ppm 8.00-8.14 (m, 3H), 7.95 (d, J=8.16 Hz, 1H) 7.66-7.74 (m, 1H), 7.51-7.60 (m, 4H), 7.40 (d, J=6.90 Hz, 1H), 4.69-4.82 (m, 1H) 3.82-4.20 (m, 2H), 3.57 (s, 2H), 2.90-3.18 (m, 4H), 2.74 (s, 3H), 1.31-1.49 (m, 6H); $^{13}$C NMR (100 MHz, CD$_3$OD) δ ppm 169.42, 155.57, 152.50, 138.95, 135.28, 133.94, 130.30, 129.05, 128.73, 127.23, 126.91, 120.88, 119.67, 118.36, 112.90, 111.70, 72.498, 55.09, 55.092, 54.63, 48.42, 46.06, 44.56, 40.80, 22.52, 22.36; MS (ESI) m/z 481 [C$_{28}$H$_{28}$N$_6$O$_2$+H]$^+$.

Example 76: 4-(6-(3-isopropoxy-4-(4-methylpiperazine-1-carbonyl)phenyl) imidazo[1,2-b]pyridazin-3-yl)benzonitrile

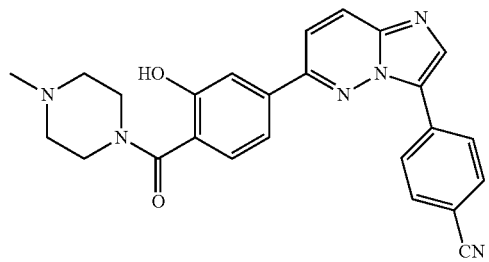 [SMILES: CN1CCN(C(=O)c2ccc(-c3ccc4ncc(-c5ccc(C#N)cc5)n4n3)cc2O)CC1]

Boron tribromide (195 mg, 0.78 mmol) was added slowly to a solution of 4-(6-(3-isopropoxy-4-(4-methylpiperazine-1-carbonyl)phenyl) imidazo[1,2-b]pyridazin-3-yl)benzonitrile (237 mg, 0.49 mmol) in DCM (10 ml) at −78° C. then the reaction mixture was stirred at room temperature for 6 h. The reaction mixture was quenched by adding MeOH and concentrated under vacuum. The crude residue was purified by preparative HPLC (C18, eluent ACN/H$_2$O/0.01% HCOOH) to afford 4-(6-(3-isopropoxy-4-(4-methylpiperazine-1-carbonyl)phenyl) imidazo[1,2-b]pyridazin-3-yl)benzonitrile (18 mg, 11%, AUC HPLC 95%) as yellow solid. $^1$H NMR (400 MHz, CD$_3$OD) δ ppm 8.29 (d, J=8.0 Hz, 3H), 8.19 (s, 1H), 8.00-8.12 (m, 1H), 7.70-7.82 (m, 3H), 7.49-7.63 (m, 2H), 7.40 (d, J=8.0 Hz, 1H), 3.48-4.11 (m, 4H), 3.01 (s, 4H), 2.64-2.74 (m, 3H); $^{13}$C NMR (100 MHz, CD$_3$OD) δ ppm 169.82, 167.16, 155.65, 152.74, 141.68, 139.22, 135.16, 134.13, 133.71, 133.58, 130.52, 128.06, 127.66, 126.91, 126.42, 125.79, 119.83, 119.72, 118.45, 115.15, 111.86, 54.97, 44.70, 40.47; MS (ESI) m/z 439 [C$_{25}$H$_{22}$N$_6$O$_2$+H]$^+$ Example 77: 4-(6-(3-hydroxy-4-(morpholine-4-carbonyl)phenyl)imidazo[1,2-b]pyridazin-3-yl)benzonitrile

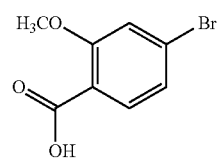

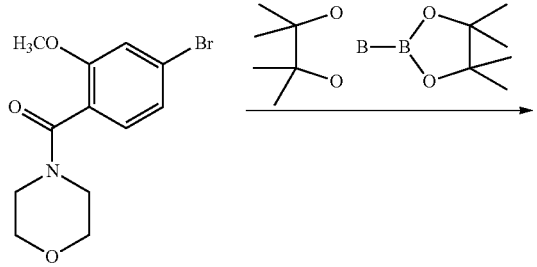

-continued

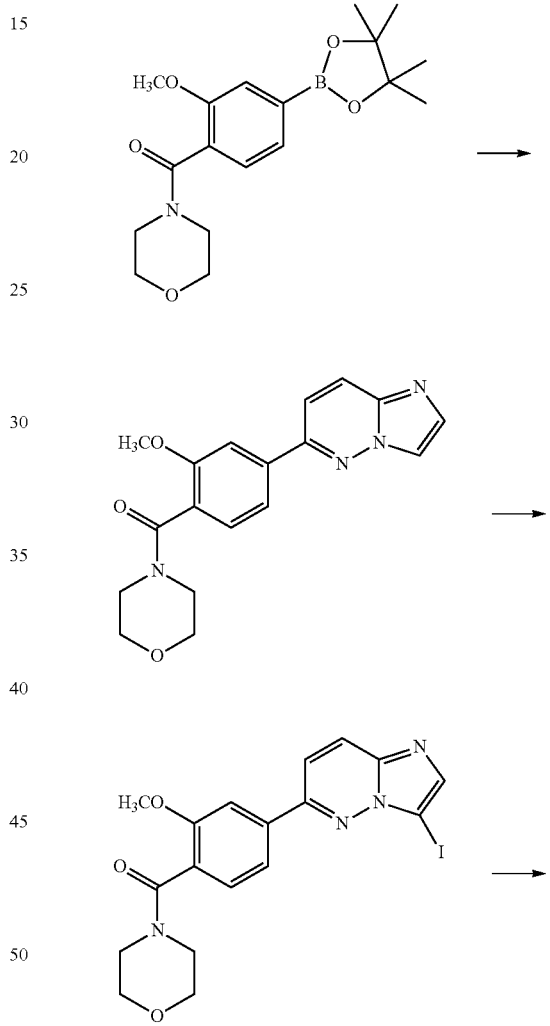

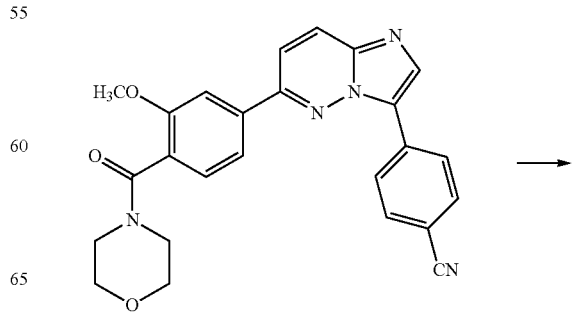

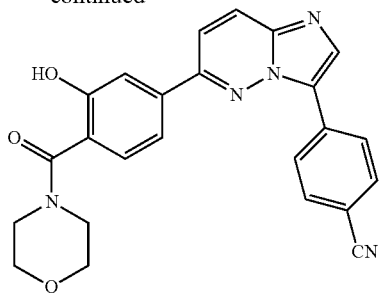

Step 1: To a solution of 4-bromo-2-methoxybenzoic acid (2 g, 8.66 mmol) in DMF (20 mL) were added HATU (4.94 g, 12.99 mmol), N-methyl morpholine (1.75 g, 17.32 mmol) and morpholine (0.83 g, 0.95 mmol). The reaction mixture was stirred at 0° C. to rt for 16 h, then was diluted with H$_2$O (15 mL) and extracted with EtOAc (3×25 mL). The combined organic layer was dried over Na$_2$SO$_4$ and was concentrated under reduced pressure to afford (4-bromo-2-methoxyphenyl)(morpholino)methanone (1.4 g, 54%). $^1$H NMR: (400 MHz, CDCl$_3$) δ (ppm) 7.07-7.04 (m, 2H), 6.99 (s, 1H), 3.78 (s, 3H), 3.74-3.71 (bs, 4H), 3.69-3.52 (bs, 2H), 3.19-3.66 (bs, 2H); MS (ESI) m/z 301 [C$_{12}$H$_{14}$BrNO$_3$+H]$^+$.

Step 2: To a mixture of (4-bromo-2-methoxyphenyl)(morpholino)methanone (1.19 g, 3.96 mmol), bis(pinacolato)diboron (1.07 g, 402 mmol), KOAc (1.16 g, 11.89 mmol) in 1,4-dioxane (18 mL) was added PdCl$_2$dppf (87.08 mg, 0.12 mmol), dppf (65.97 mg, 0.12 mmol) and the reaction mixture was heated at 90° C. for 16 h under argon. The reaction mixture was diluted with EtOAc and washed with water, the organic layer was dried over anhydrous Na$_2$SO$_4$ and concentrated under reduced pressure to afford (2-methoxy-4-(4,4,5,5-tetramethyl-1,3,2-dioxaborolan-2-yl)phenyl)(morpholino)methanone (1.23 g, 90%) as a brown liquid which was used in next step without purification. Direct mass indicated desired m/z 345

Step 3: To a mixture of (2-methoxy-4-(4,4,5,5-tetramethyl-1,3,2-dioxaborolan-2-yl)phenyl)(morpholino)methanone 2 (1.23 g, 3.54 mmol), 6-chloroimidazo[1,2-b]pyridazine (0.43 g, 2.84 mmol), K$_3$PO$_4$ (1.5 g, 7.08 mmol) in 1,4-dioxane (18 mL) and water (3 mL) was added Pd(PPh$_3$)$_4$ (204 mg, 0.17 mmol) and the reaction mixture was heated at 90° C. for 16 h under argon. The reaction mixture was diluted with water and extracted with EtOAc and washed with water and brine solution. The organic layer was dried over anhydrous Na$_2$SO$_4$ and concentrated under reduced pressure to obtain the crude product. The crude product was purified by column chromatography (silica gel, eluent CH$_2$Cl$_2$/MeOH 97:3) to afford (4-(imidazo[1,2-b]pyridazin-6-yl)-2-methoxyphenyl)(morpholino)methanone (0.7 g, 58.8%, LC-MS 85%) as a light yellow solid. $^1$H NMR: (400 MHz, CDCl$_3$) δ (ppm) 8.04 (d, J=6.8 Hz, 2H), 7.82 (s, 1H), 7.59 (s, 1H), 7.49-7.40 (m, 3H), 3.98 (s, 3H), 3.87-3.65 (m, 4H), 3.61-3.33 (m, 2H), 3.29 (bs, 2H); MS (ESI) m/z 339.14 [C$_{18}$H$_{18}$N$_4$O$_3$+H]$^+$.

Step 4: To a solution of (4-(imidazo[1,2-b]pyridazin-6-yl)-2-methoxyphenyl)(morpholino)methanone (0.66 g, 1.95 mmol) in ACN (10 mL) was added NIS (0.52 g, 2.34 mmol) and stirred at 70° C. for 3 h. The reaction mixture was diluted with EtOAc and washed with water, the organic layer was dried over anhydrous Na$_2$SO$_4$ and concentrated under reduced pressure to afford (4-(3-iodoimidazo[1,2-b]pyridazin-6-yl)-2-methoxyphenyl)(morpholino)methanone (0.88 g, 97%, LC-MS 65%) as a green solid. $^1$H NMR: (400 MHz, CDCl$_3$) δ (ppm) 7.99 (d, J=9.2 Hz, 1H), 7.88 (s, 1H), 7.71 (s, 1H), 7.60 (d, J=7.6 Hz, 1H), 7.54 (d, J=9.2 Hz, 1H), 7.42 (d, J=8.0 Hz, 1H), 3.99 (s, 3H), 3.83-3.80 (m, 4H), 3.61-3.59 (m, 2H), 3.39-3.33 (m, 2H); MS (ESI) m/z 465 [C$_{18}$H$_{17}$N$_4$O$_3$+H]$^+$.

Step 5: To a mixture of (4-(3-iodoimidazo[1,2-b]pyridazin-6-yl)-2-methoxyphenyl)(morpholino)methanone (0.86 g, 1.85 mmol), 4-cyanophenylboronic acid (0.33 g, 2.22 mmol), K$_3$PO$_4$ (0.78 g, 3.7 mmol) in 1,4-dioxane (14 mL) and water (2 mL) was added Pd(PPh$_3$)$_4$ (106.8 mg, 0.09 mmol) and the reaction mixture was heated at 90° C. for 16 h under argon. The reaction mixture was diluted with water and extracted with EtOAc and washed with water and brine solution. The organic layer was dried over anhydrous Na$_2$SO$_4$ and concentrated under reduced pressure to obtain the crude product. The crude product was purified by column chromatography (silica gel, eluent CH$_2$Cl$_2$/MeOH 97:3) to afford 4-(6-(3-methoxy-4-(morpholine-4-carbonyl)phenyl)imidazo[1,2-b]pyridazin-3-yl)benzonitrile (0.35 g, 43.2%, LC-MS 99%) as a light yellow solid.

Step 6: To a solution of 4-(6-(3-methoxy-4-(morpholine-4-carbonyl)phenyl)imidazo[1,2-b]pyridazin-3-yl)benzonitrile (0.25 g, 0.57 mmol) in CH$_2$Cl$_2$ (10 mL) cooled to 0° C. was added BBr$_3$ (2 mL). The reaction mixture was stirred at room temperature for 2 h. The reaction mixture was cooled to 0° C. and quenched by drop wise addition of a saturated aqueous NaHCO$_3$ (10 mL) and extracted with CH$_2$Cl$_2$ (3×30 mL). The organic layer was washed with water and brine, dried over anhydrous Na$_2$SO$_4$, filtered and concentrated under reduced pressure. The crude compound was purified by column chromatography (silica gel, eluent MeOH/CHCl$_3$ 3:97) followed by preparative TLC to afford 4-(6-(3-hydroxy-4-(morpholine-4-carbonyl)phenyl)imidazo[1,2-b]pyridazin-3-yl)benzonitrile (80 mg, 33%, AUC HPLC 98.2%) as an pale yellow solid, m.p: 149-153° C. $^1$H NMR (400 MHz, CDCl$_3$) δ (ppm) 9.86 (s, 1H), 8.39 (d, J=8.4 Hz, 2H), 8.14 (d, J=9.2 Hz, 1H), 7.81 (d, J=8.4 Hz, 2H), 7.61 (t, J=10 Hz, 2H), 7.52 (d, J=8.0, 1H), 7.42 (d, J=8.2 Hz, 1H), 3.81 (bs, 8H); MS (ESI) m/z 426 [C$_{24}$H$_{19}$N$_5$O$_3$+H]$^+$.

Example 78: 4-(6-(2-methoxy-4-(4-methylpiperazine-1-carbonyl)phenyl)imidazo[1,2-b]pyridazin-3-yl)benzonitrile

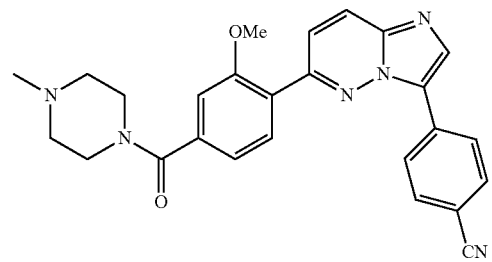 [SMILES: COc1cc(C(=O)N2CCN(C)CC2)ccc1-c1ccc2ncc(-c3ccc(C#N)cc3)n2n1]

To a solution of (4-bromo-3-methoxyphenyl)(4-methylpiperazin-1-yl)methanone (312 mg, 1.00 mmol) in DMF (10 mL) under inert atmosphere, were added 4,4,4',4',5,5,5',5'-octamethyl-2,2'-bi1,3,2-dioxaborolane) (280 mg, 1.10 mmol), KOAc (295 mg, 3.00 mmol) and PdCl$_2$dppf (22 mg, 0.03 mmol). The resulting mixture was stirred at 100° C. for 2 h after which time the reaction mixture was diluted with DMF (8 mL) and water (2 mL) prior to the addition of 4-(6-chloroimidazo[1,2-a]pyrazin-3-yl)benzonitrile (100 mg, 0.39 mmol), K$_2$CO$_3$ (108 mg, 0.78 mmol) and additional PdCl$_2$dppf (57 mg, 0.08 mmol). The reaction mixture thus obtained was heated to reflux for 3 h and was concentrated under reduced pressure. The residue was purified by preparative HPLC (C18, eluent, ACN/H$_2$O/0.01% HCOOH) to afford 4-(6-(2-methoxy-4-(4-methylpiperazine-1-carbonyl)phenyl)imidazo[1,2-b]pyridazin-3-yl)benzonitrile (30 mg, AUC HPLC 97%) as yellow solid. $^1$H NMR (400 MHz, CD$_3$OD) δ ppm 8.33 (s, 1H), 8.27 (d, J=8.2 Hz, 2H), 8.18 (s, 1H), 8.01 (d, J=9.5 Hz, 1H), 7.66-7.78 (m, 4H), 7.16 (d, J=7.7 Hz, 1H), 3.65-4.00 (m, 7H), 2.83-3.01 (m, 4H), 2.57-2.67 (m, 3H); $^{13}$C NMR (100 MHz, CD$_3$OD) δ ppm 171.45, 167.58, 159.10, 152.89, 141.44, 139.44, 134.71, 134.21, 133.41, 132.29, 130.47, 129.04, 127.95, 127.76, 127.58, 125.35, 122.63, 120.58, 119.73, 111.91, 111.69, 56.66, 54.99, 444.92; MS (ESI) m/z 453 [C$_{26}$H$_{24}$N$_6$O$_2$+H]$^+$.

Example 79: 4-(6-(4-(4-methylpiperazine-1-carbonyl)-3-nitrophenyl)imidazo[1,2-b]pyridazin-3-yl)benzonitrile Step 1: To a solution of 2-nitro-4-bromobenzoic acid (9.3 mmol) in DMF (6 mL) was added NMM (1.87 g, 18.6 mmol) followed by addition of HATU (5.3 g, 13.95 mmol) and the mixture was stirred at rt for 30 min. 1-Methylpiperazine (1.39 g, 13.95 mmol) was added and stirred at rt for an additional 16 h. The reaction mixture was diluted with EtOAc and washed with water and brine. The organic layer was dried over anhydrous Na$_2$SO$_4$, filtered and concentrated under reduced pressure to give ((4-bromo-2-methylphenyl)(4-methylpiperazin-1-yl)methanone (1.9 g, 70%, AUC HPLC 98%) as a brown solid. $^1$H NMR (400 MHz, CDCl$_3$): δ 8.4 (s, 1H), 8.01 (d, J=6.2 Hz, 1H), 7.4 (d, J=8.3 Hz, 1H) 3.8 (bs, 2H), 2.3-2.5 (s, 7H).

Step 2: To a solution of (4-bromo-2-nitrophenyl)(4-methylpiperazin-1-yl)methanone 6 (328 mg, 1.00 mmol) in DMF (10 mL) under inert atmosphere, was added 4,4,4',4',5,5,5',5'-octamethyl-2,2'-bi1,3,2-dioxaborolane) (280 mg, 1.10 mmol), KOAc (295 mg, 3.00 mmol) and PdCl$_2$dppf (22 mg, 0.03 mmol). The resulting mixture was stirred at 100° C. for 2 h after which time, it was diluted with DMF (8 mL) and water (2 mL) prior to the addition of 4-(6-chloroimidazo[1,2-a]pyrazin-3-yl)benzonitrile 3 (200 mg, 0.78 mmol), K$_2$CO$_3$ (217 mg, 1.58 mmol) and additional PdCl$_2$dppf (114 mg, 0.08 mmol). The reaction mixture thus obtained was heat to reflux for 3 h and was concentrated under reduced pressure. The residue was purified by preparative HPLC (C18, eluent ACN/H$_2$O/0.01% HCOOH) to afford 4-(6-(4-(4-methylpiperazine-1-carbonyl)-3-nitrophenyl)imidazo[1,2-b]pyridazin-3-yl)benzonitrile (129 mg, 36% over 2 steps, AUC HPLC 97%) as yellow solid. $^1$H NMR (400 MHz, CD$_3$OD) 8.94 (d, J=1.6 Hz, 1H), 8.56 (dd, J=8.0, 1.63 Hz, 1H), 8.43 (d, J=8.5 Hz, 2H), 8.36 (s, 1H), 8.28 (d, J=9.5 Hz, 1H), 8.02 (d, J=9.5 Hz, 1H), 7.89 (d, J=8.5 Hz, 2H), 7.72 (d, J=7.9 Hz, 1H), 3.71-4.05 (m, 2H), 3.41 (s, 2H), 2.70 (t, J=5.0 Hz, 2H), 2.53 (s, 2H), 2.42 (s, 3H); $^{13}$C NMR (100 MHz, CD$_3$OD) δ ppm 168.22, 151.26, 147.63, 141.86, 139.15, 135.75, 134.46, 134.18, 133.78, 130.40, 128.68, 128.24, 127.63, 124.68, 119.67, 118.41, 112.39, 55.35, 54.99, 47.61, 45.88, 42.47; MS (ESI) m/z 468 [C$_{25}$H$_{21}$N$_7$O$_3$+H]$^+$.

Example 80: N-(5-(3-(4-cyanophenyl)imidazo[1,2-b]pyridazin-6-yl)-2-(morpholine-4-carbonyl)phenyl)acetamide

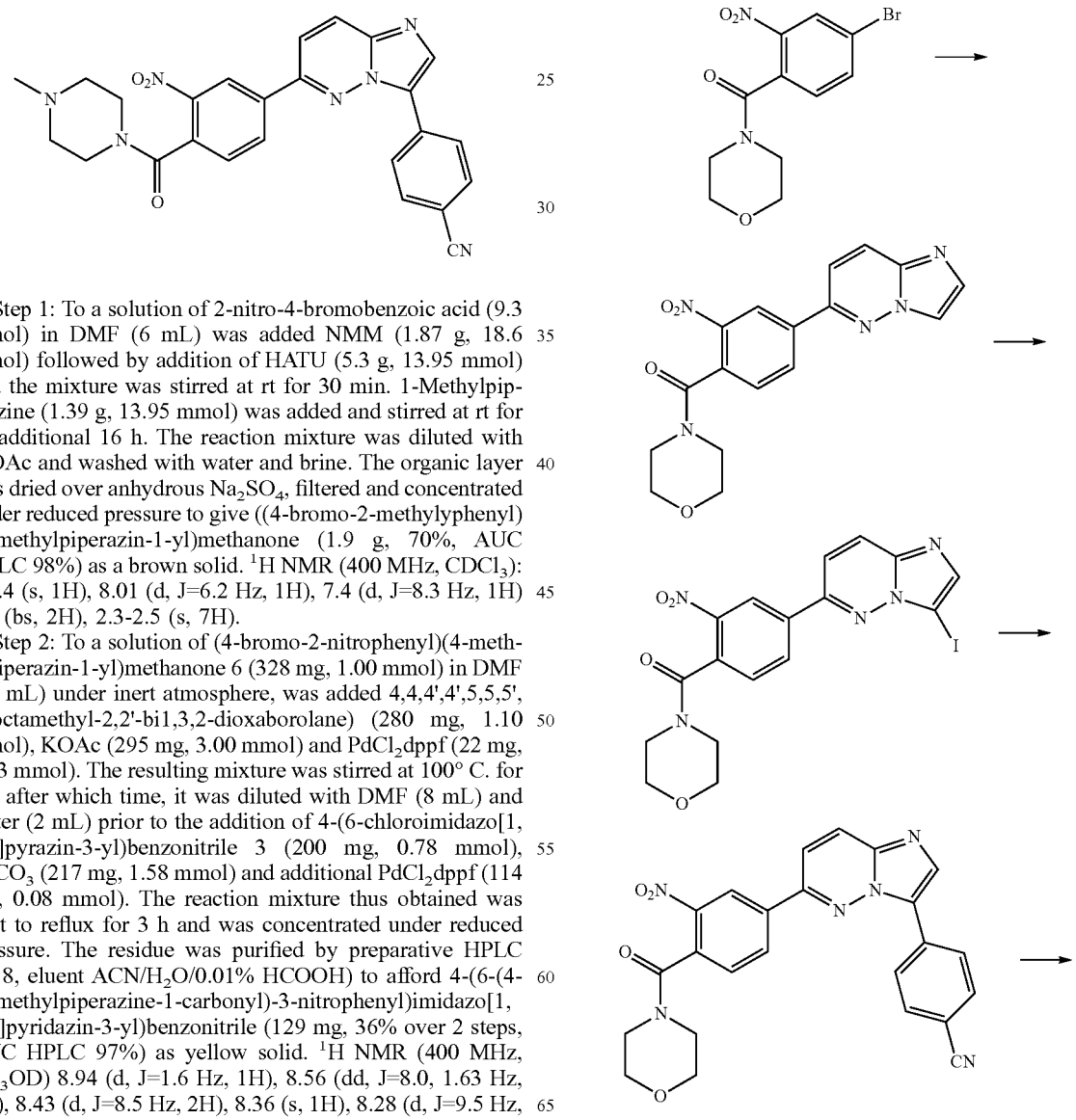

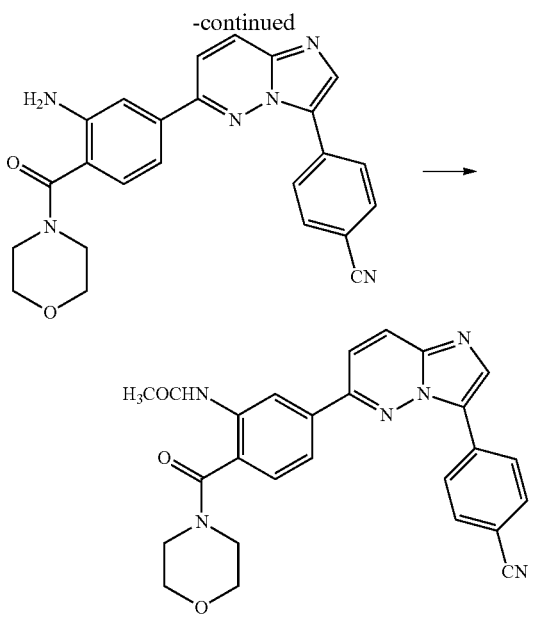

Step 1: To a solution of 4-bromo-2-nitrobenzoic acid (2.5 g, 10.16 mmol) in DMF (15 mL) were added HATU (5.79 g, 15.24 mmol), N-methyl morpholine (2.05 g, 20.32 mmol) and morpholine (0.97 g, 11.18 mmol). The reaction mixture was stirred at 0° C. to room temperature for 16 h, then it was diluted with H$_2$O (30 mL) and extracted with EtOAc (3×100 mL). The combined organic layer was dried over Na$_2$SO$_4$ and was concentrated under reduced pressure to afford (4-bromo-2-nitrophenyl)(morpholino)methanone (4.2 g, 91.8%, LC-MS 69.8%). $^1$H NMR (400 MHz, DMSO-d$_6$) δ (ppm) 8.40 (s, 1H), 8.08 (d, J=8.4 Hz, 1H), 7.54 (d, J=8.0 Hz, 1H), 3.67-3.51 (m, 4H), 3.51 (bs, 2H), 3.21 (bs, 2H); MS (ESI) m/z 316 [C$_{11}$H$_{11}$BrN$_2$O$_4$+H]$^+$.

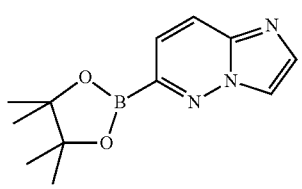 [SMILES: CC1(C)OB(c2ccc3nccn3n2)OC1(C)C]

Step 2: To a mixture of 6-chloroimidazo[1,2-b]pyridazine (1.5 g, 9.76 mmol), Bis(pinacolato)diboron (2.65 g, 10.45 mmol), KOAc (2.87 g, 29.29 mmol) in 1,4-dioxane (15 mL) was added PdCl$_2$dppf (214 mg, 0.29 mmol) and dppf (162.4 mg, 0.29 mmol) and the reaction mixture was heated at 90° C. for 16 h under argon. The reaction mixture was diluted with EtOAc and washed with water, the organic layer was dried over anhydrous Na$_2$SO$_4$ and concentrated under reduced pressure to afford 6-(4,4,5,5-tetramethyl-1,3,2-dioxaborolan-2-yl)imidazo[1,2-b]pyridazine (2.15 g, 90%) as a brown liquid which was used in next step without purification. MS (ESI) m/z 246 [C$_{12}$H$_{16}$BN$_3$O$_2$+H]$^+$.

Step 3: To a mixture of (4-bromo-2-nitrophenyl)(morpholino)methanone (2 g, 7.32 mmol), 6-(4,4,5,5-tetramethyl-1,3,2-dioxaborolan-2-yl)imidazo[1,2-b]pyridazine (2.15 g, 8.78 mmol), K$_3$PO$_4$ (3.1 g, 14.64 mmol) in 1,4-dioxane (30 mL) and water (4 mL) was added Pd(PPh$_3$)$_4$ (423 mg, 0.36 mmol) and the reaction mixture was heated at 90° C. for 16 h under argon. The reaction mixture was diluted with water and extracted with EtOAc and washed with water and brine solution. The organic layer was dried over anhydrous Na$_2$SO$_4$ and concentrated under reduced pressure to obtain the crude product. The crude product was purified by column chromatography (silica gel, eluent CH$_2$Cl$_2$/MeOH 97:3) to afford (4-(imidazo[1,2-b]pyridazin-6-yl)-2-nitrophenyl)(morpholino)methanone (1.25 g, 55.8%, LC-MS 96.5%) as a light yellow solid. $^1$H NMR: (400 MHz, DMSO-d$_6$) δ (ppm) 8.84 (s, 1H), 8.54 (d, J=6.0 Hz, 1H), 8.46 (s, 1H), 8.32 (d, J=9.6 Hz, 1H), 7.98 (d, J=9.6 Hz, 1H), 7.89 (s, 1H), 7.77 (d, J=8.0 Hz, 1H), 3.7 (bs, 4H), 3.55 (bs, 2H), 3.17 (bs, 2H); MS (ESI) m/z 354 [C$_{17}$H$_{15}$N$_5$O$_4$+H]$^+$.

Step 4: To a solution of (4-(imidazo[1,2-b]pyridazin-6-yl)-2-nitrophenyl)(morpholino)methanone (1.24 g, 3.51 mmol) in ACN (18 mL) was added N-iodosuccinimide (0.95 g, 4.2 mmol). The reaction mixture was stirred at 80° C. for 2 h and was diluted with EtOAc and washed with water. The organic layer was dried over anhydrous Na$_2$SO$_4$ and concentrated under reduced pressure to afford (4-(3-iodoimidazo[1,2-b]pyridazin-6-yl)-2-nitrophenyl)(morpholino)methanone (1.7 g, 94%, LC-MS 93.3%) as a green solid. $^1$H NMR: (400 MHz, CDCl$_3$) δ (ppm) 8.84 (s, 1H), 8.45 (d, J=8.0 Hz, 1H), 8.08 (d, J=9.6 Hz, 1H), 7.94 (s, 1H), 7.59 (d, J=8.0 Hz, 1H), 3.85-3.66 (m, 6H), 3.29 (bs, 2H); MS (ESI) m/z 480 [C$_{17}$H$_{14}$IN$_5$O$_4$+H]$^+$.

Step 5: To a mixture of (4-(3-iodoimidazo[1,2-b]pyridazin-6-yl)-2-nitrophenyl)(morpholino)methanone (1.7 g, 3.54 mmol), 4-cyanophenylboronic acid (0.62 g, 4.25 mmol), K$_3$PO$_4$ (1.5 g, 7.08 mmol) in 1,4-dioxane (18 mL) and water (2.5 mL) was added Pd(PPh$_3$)$_4$ (204 mg, 0.17 mmol) and the reaction mixture was heated at 90° C. for 16 h under argon. The reaction mixture was diluted with water and extracted with EtOAc and washed with water and brine solution. The organic layer was dried over anhydrous Na$_2$SO$_4$ and concentrated under reduced pressure to obtain the crude product. The crude product was purified by column chromatography (silica gel, eluent CH$_2$Cl$_2$/MeOH 97:3) to afford 4-(6-(4-(morpholine-4-carbonyl)-3-nitrophenyl)imidazo[1,2-b]pyridazin-3-yl)benzonitrile (1.1 g, 68.7%, LC-MS 91%) as a light yellow solid. $^1$H NMR (400 MHz, CDCl$_3$) δ (ppm) 8.80 (s, 1H), 8.67 (d, J=8.0 Hz, 1H), 8.55-8.23 (m, 4H), 7.83 (d, J=8.4 Hz, 2H), 7.67 (d, J=9.6 Hz, 1H), 7.61 (d, J=8.0, 1H), 3.86-3.67 (m, 4H), 3.66 (bs, 2H), 3.31 (t, J=4.4 Hz, 2H); MS (ESI) m/z 455 [C$_{24}$H$_{18}$N$_6$O$_4$+H]$^+$.

Step 6: To a solution of 4-(6-(4-(morpholine-4-carbonyl)-3-nitrophenyl)imidazo[1,2-b]pyridazin-3-yl)benzonitrile (0.6 g, 1.32 mmol) in ethanol (10 mL) was added SnCl$_2$.2H$_2$O (0.89 g, 3.96 mmol) and concentrated HCl (1 mL). The reaction mixture was stirred at 90° C. for 3 h. The solvent was evaporated under reduced pressure and basified with a saturated aq. NaHCO$_3$ and extracted with EtOAc (3×30 mL). The organic layer was washed with water and brine, dried over anhydrous Na$_2$SO$_4$, filtered and concentrated under reduced pressure to afford 4-(6-(3-amino-4-(morpholine-4-carbonyl)phenyl)imidazo[1,2-b]pyridazin-3-yl)benzonitrile (250 mg, 45%, LC-MS 77%) as a yellow solid.

Step 7: To a solution of 4-(6-(3-amino-4-(morpholine-4-carbonyl)phenyl)imidazo[1,2-b]pyridazin-3-yl)benzonitrile (0.24 g, 0.56 mmol) in dichloromethane (10 mL) were added TEA (0.15 mL, 1.13 mmol) and acetyl chloride (0.06 mL, 0.85 mmol). The reaction mixture was stirred for 2 h at room temperature. The reaction mixture was diluted with H$_2$O (20 mL), basified with saturated aqueous NaHCO$_3$ and extracted with CHCl$_3$ (3×50 mL). The combined organic layer was concentrated under reduced pressure to afford crude compound. The crude product was purified by column chromatography (silica gel, eluent CHCl$_3$/MeOH 97:3) to afford N-(5-(3-(4-cyanophenyl)imidazo[1,2-b]pyridazin-6-yl)-2-(morpholine-4-carbonyl)phenyl)acetamide (100 mg, 38%, AUC HPLC 98.09%) as an pale yellow solid, m.p: 226-229° C. NMR: (400 MHz, CDCl$_3$) δ (ppm) 9.12 (d, J=11.6 Hz, 2H), 8.39 (d, J=8.4 Hz, 2H), 8.22 (s, 1H), 8.14 (d, J=9.1 Hz, 1H), 7.84 (d, J=8.0 Hz, 2H), 7.75 (d, J=8.0 Hz, 1H), 7.66 (d, J=9.2 Hz, 1H), 7.39 (d, J=7.6 Hz, 1H), 3.76 (bs, 8H), 2.26 (s, 3H); MS (ESI) m/z 467 [C$_{26}$H$_{22}$N$_6$O$_3$+H]$^+$.

Example 81: N-(5-(3-(4-cyanophenyl)imidazo[1,2-b]pyridazin-6-yl)-2-(4-(dimethylamino)piperidine-1-carbonyl)phenyl)acetamide

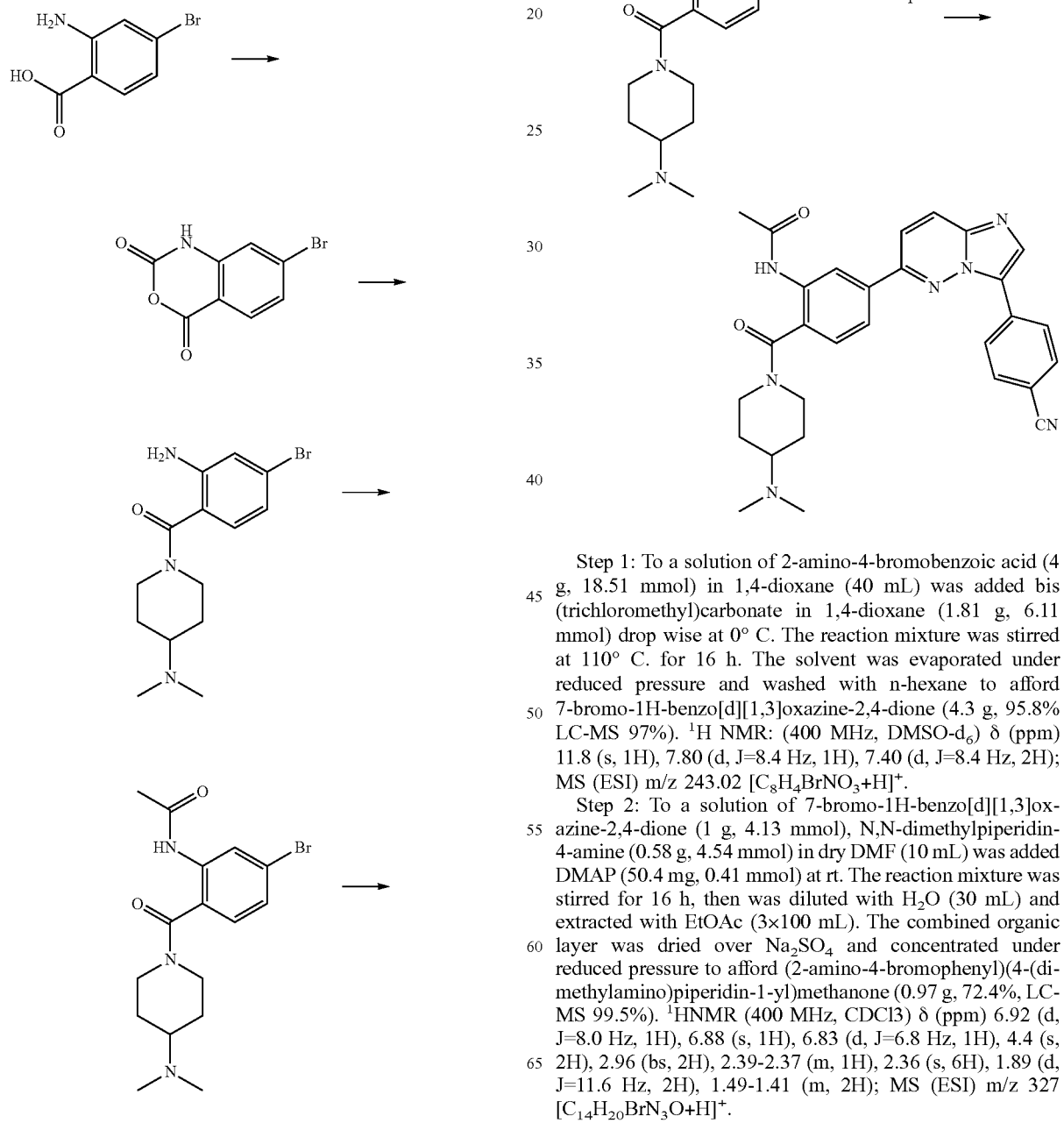

Step 1: To a solution of 2-amino-4-bromobenzoic acid (4 g, 18.51 mmol) in 1,4-dioxane (40 mL) was added bis(trichloromethyl)carbonate in 1,4-dioxane (1.81 g, 6.11 mmol) drop wise at 0° C. The reaction mixture was stirred at 110° C. for 16 h. The solvent was evaporated under reduced pressure and washed with n-hexane to afford 7-bromo-1H-benzo[d][1,3]oxazine-2,4-dione (4.3 g, 95.8% LC-MS 97%). $^1$H NMR: (400 MHz, DMSO-d$_6$) δ (ppm) 11.8 (s, 1H), 7.80 (d, J=8.4 Hz, 1H), 7.40 (d, J=8.4 Hz, 2H); MS (ESI) m/z 243.02 [C$_8$H$_4$BrNO$_3$+H]$^+$.

Step 2: To a solution of 7-bromo-1H-benzo[d][1,3]oxazine-2,4-dione (1 g, 4.13 mmol), N,N-dimethylpiperidin-4-amine (0.58 g, 4.54 mmol) in dry DMF (10 mL) was added DMAP (50.4 mg, 0.41 mmol) at rt. The reaction mixture was stirred for 16 h, then was diluted with H$_2$O (30 mL) and extracted with EtOAc (3×100 mL). The combined organic layer was dried over Na$_2$SO$_4$ and concentrated under reduced pressure to afford (2-amino-4-bromophenyl)(4-(dimethylamino)piperidin-1-yl)methanone (0.97 g, 72.4%, LC-MS 99.5%). $^1$HNMR (400 MHz, CDCl3) δ (ppm) 6.92 (d, J=8.0 Hz, 1H), 6.88 (s, 1H), 6.83 (d, J=6.8 Hz, 1H), 4.4 (s, 2H), 2.96 (bs, 2H), 2.39-2.37 (m, 1H), 2.36 (s, 6H), 1.89 (d, J=11.6 Hz, 2H), 1.49-1.41 (m, 2H); MS (ESI) m/z 327 [C$_{14}$H$_{20}$BrN$_3$O+H]$^+$.

Step 3: To a solution of (2-amino-4-bromophenyl)(4-(dimethylamino)piperidin-1-yl)methanone (0.5 g, 1.53 mmol) in dichloromethane (10 mL) were added triethylamine (0.63 mL, 4.59 mmol) and acetyl chloride (0.16 mL, 2.29 mmol). The reaction mixture was stirred for 3 h at rt. The reaction mixture was diluted with $H_2O$ (20 mL), basified with saturated aqueous solution of $NaHCO_3$ and extracted with $CHCl_3$ (3×50 mL). The combined organic layer was concentrated under reduced pressure to afford N-(5-bromo-2-(4-(dimethylamino)piperidine-1-carbonyl)phenyl)acetamide (0.6 g, 88.23%, LC-MS 83%). $^1$H NMR: (400 MHz, $CDCl_3$) δ (ppm) 9.01 (s, 1H), 8.53 (s, 1H), 7.42 (d, J=8.4 Hz, 1H), 7.06 (d, J=7.6 Hz, 1H), 4.6 (bs, 1H), 2.95 (bs, 3H), 2.41 (m, 1H), 2.32 (s, 6H), 2.08 (s, 3H), 1.95 (bs, 2H), 1.52 (bs, 2H); MS (ESI) m/z 369.07 $[C_{16}H_{22}BrN_3O_2+H]^+$.

Step 4: To a mixture of N-(5-bromo-2-(4-(dimethylamino)piperidine-1-carbonyl)phenyl)acetamide (0.52 g, 1.42 mmol), 6-(4,4,5,5-tetramethyl-1,3,2-dioxaborolan-2-yl)imidazo[1,2-b]pyridazine (416.3 mg, 1.69 mmol), $K_3PO_4$ (602 mg, 2.84 mmol) in 1,4-dioxane (10 mL) and water (2 mL) was added $Pd(PPh_3)_4$ (82 mg, 0.07 mmol) and the reaction mixture was heated at 90° C. for 6 h. The reaction mixture was filtered through celite bed and washed with 10% MeOH in $CHCl_3$ and dried over anhydrous $Na_2SO_4$ and concentrated under reduced pressure to obtain the crude product. The crude product was purified by column chromatography (silica gel, eluent $CHCl_3$/MeOH/$NH_3$ 90:10:1) to afford N-(2-((4-(dimethylamino)piperidin-1-yl]carbonyl)-5-(imidazo(1,2-a)pyridazin-6-yl)phenyl)acetamide (0.5 g, 70%, LC-MS 81%) as a light yellow solid. NMR: (400 MHz, $CDCl_3$) δ (ppm) 9.07 (s, 1H), 8.91 (s, 1H), 8.02 (d, J=8.8 Hz, 2H), 7.76 (s, 1H), 7.75 (d, J=6.4 Hz, 1H), 7.42 (d, J=1.6 Hz, 1H), 4.75 (bs, 1H), 3.95 (bs, 1H), 3.15-2.95 (m, 2H), 2.41 (m, 1H), 2.25 (s, 6H), 2.19 (s, 3H), 1.98 (bs, 1H), 1.75 (bs, 2H), 1.25 (s, 3H); MS (ESI) m/z 406.16 $[C_{23}H_{27}N_5O_2+H]^+$.

Step 5: To a solution of N-(2-(4-(dimethylamino)piperidine-1-carbonyl)-5-(imidazo[1,2-a]pyridin-6-yl)phenyl)acetamide (0.49 g, 1.21 mmol) in ACN (10 mL) was added N-iodosuccinimide (0.32 g, 1.45 mmol) and stirred at 80° C. for 3 h. The reaction mixture was diluted with EtOAc and washed with water, the organic layer was dried over anhydrous $Na_2SO_4$ and concentrated under reduced pressure to afford N-(2-((4-(dimethylamino)piperidin-1-yl)carbonyl)-5-(3-iodoimidazo[1,2-a]pyridazin-6-yl)phenyl)acetamide (0.3 g, 46.7%) as a green solid. The crude product was used in the next step without purification.

Step 6: To a mixture of N-(2-(4-(dimethylamino)piperidine-1-carbonyl)-5-(3-iodoimidazo[1,2-a]pyridazin-6-yl)phenyl)acetamide (0.3 g, 0.56 mmol), 4-cyanophenylboronic acid (99.4 mg, 0.67 mmol), $K_3PO_4$ (237 mg, 101 mmol) in 1,4-dioxane (10 mL) and water (2 mL) was added $Pd(PPh_3)_4$ (32.3 mg, 0.03 mmol) and the reaction mixture was heated at 90° C. for 16 h. The reaction mixture was filtered through celite and washed with 10% MeOH in $CHCl_3$ and dried over anhydrous $Na_2SO_4$ and concentrated under reduced pressure. The residue was purified by preparative HPLC to afford N-(5-(3-(4-cyanophenyl)imidazo[1,2-b]pyridazin-6-yl)-2-(4-(dimethylamino)piperidine-1-carbonyl)phenyl)acetamide (50 mg, 17.4%, LC-MS 95%) as a yellow solid. m.p: 141-146° C. $^1$H NMR: (400 MHz, $CDCl_3$) δ (ppm) 9.13 (s, 1H), 9.08 (s, 1H), 8.39 (d, J=8.4 Hz, 2H), 8.22 (s, 1H), 8.13 (d, J=9.2 Hz, 1H), 7.85 (d, J=8.4 Hz, 2H), 7.75 (d, J=7.6, 1H), 6.67 (d, J=9.6 Hz, 1H), 7.40 (d, J=8.4 Hz, 1H), 4.75 (bs, 1H), 3.95 (bs, 1H), 3.15-2.95 (m, 2H), 2.41 (m, 1H), 2.3 (s, 6H), 2.21 (s, 3H), 1.95 (bs, 2H), 1.65 (bs, 2H); MS (ESI) m/z 508.16 $[C_{29}H_{29}N_7O_2+H]^+$.

Example 82: (4-(3-(4-chlorophenyl)imidazo[1,2-b]pyridazin-6-yl)phenyl)(4-methylpiperazin-1-yl)methanone

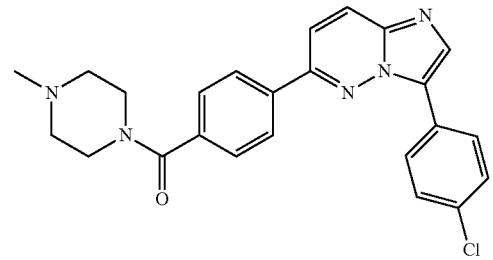 [SMILES: CN1CCN(C(=O)c2ccc(-c3ccc4ncc(-c5ccc(Cl)cc5)n4n3)cc2)CC1]

Step 1: To a solution of 3-bromo-6-chloroimidazo[1,2-b]pyridazine (500 mg, 2.15 mmol) in 1,4-dioxane (4.5 mL) under inert atmosphere were added aqueous $Na_2CO_3$ solution (3.76 mL, 2 M), 4-chlorophenylboronic acid (336 mg, 2.15 mmol) and $Pd(dppf)_2Cl_2$ (124 mg, 0.108 mmol). The resulting mixture was heated to reflux for 18 h, and then diluted with water (20 mL) and extracted with DCM (3×30 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford 6-chloro-3-(4-chlorophenyl)imidazo[1,2-b]pyridazine (243 mg, 43%) as a yellow solid. $^1$H NMR (400 MHz, $CDCl_3$) δ 8.06 (s, 1H), 8.01-7.96 (m, 3H), 7.50-7.47 (m, 2H), 7.11 (d, J=12 Hz, 1H); MS (ESI) m/z 264 $[C_{12}H_7C_{12}N_3+H]^+$.

Step 2: To a solution of 6-chloro-3-(4-chlorophenyl)imidazo[1,2-b]pyridazine (200 mg, 0.757 mmol) in toluene (3 mL) and ethanol (1.5 mL) under inert atmosphere were added $K_2CO_3$ (335 mg, 2.4 mmol), 4-(4-methylpiperazine-1-carbonyl)phenylboronic acid hydrochloride (259 mg, 0.909 mmol) and $Pd(PPh_3)_4$ (88 mg, 0.076 mmol). The resulting mixture was heated in a microwave reactor at 140° C. for 15 min, and then was concentrated under reduced pressure. The residue was purified by column chromatography (silica gel, eluent $CH_2Cl_2$/MeOH 95:5 to 90:10) to afford (4-(3-(4-chlorophenyl)imidazo[1,2-b]pyridazin-6-yl)phenyl)(4-methylpiperazin-1-yl)methanone (41 mg, 17%, AUC HPLC 99%) as a yellow solid. $^1$H NMR (400 MHz, $CDCl_3$) δ 8.19 (d, J=9.5 Hz, 1H), 8.11-8.06 (m, 5H), 7.62-7.58 (m, 3H), 7.54-7.51 (m, 2H), 3.94-3.67 (m, 4H), 2.72-2.66 (m, 4H), 2.49 (s, 3H); $^{13}$C NMR (100 MHz, $CDCl_3$) δ 169.59, 165.33, 150.94, 139.36, 137.12, 136.71, 133.88, 132.95, 129.00, 128.02, 127.98, 127.90, 127.36, 126.89, 126.24, 115.76, 54.12, 44.83; MS (ESI) m/z 432 $[C_{24}H_{22}ClN_5O+H]^+$.

Example 83: (4-(3-(4-chlorophenyl)imidazo[1,2-b]pyridazin-6-yl)-2-methylphenyl)(4-methylpiperazin-1-yl)methanone

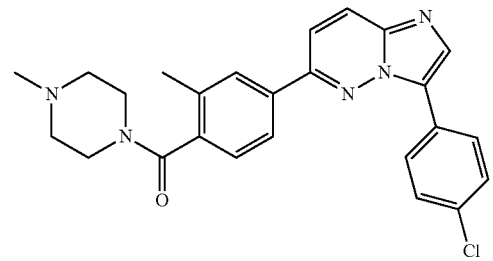

Step 1: To a solution of 6-chloro-3-(4-chlorophenyl)imidazo[1,2-b]pyridazine (308 mg, 1.00 mmol) in a mixture of DMF (4 mL) and water (1 mL), were successively added K$_2$CO$_3$ (138 mg, 1.00 mmol), Pd(dppf)Cl$_2$ (146 mg, 0.20 mmol) and 4-borono-2-methylbenzoic acid (198 mg, 1.10 mmol). The reaction mixture was stirred at 80° C. for 18 h under inert atmosphere, then was diluted with water (10 mL) and extracted with DCM (3×10 mL). The combined organic layers were dried over Na$_2$SO$_4$, filtered and concentrated under vacuum to afford the crude 4-(3-(4-chlorophenyl)imidazo[1,2-b]pyridazin-6-yl)-2-methylbenzoic acid (724 mg) as black solid. MS (ESI) m/z 364 [C$_{20}$H$_{14}$ClN$_3$O$_2$+H]$^+$.

Step 2: To a solution of 4-(3-(4-chlorophenyl)imidazo[1,2-b]pyridazin-6-yl)-2-methylbenzoic acid (363 mg, ~1.00 mmol) in DMF (5 mL), was successively added HATU (1.14 g, 3.00 mmol), N-methyl morpholine (400 mg, 4.00 mmol) and 1-methylpiperazine (200 mg, 2.00 mmol). The reaction mixture was stirred at room temperature under inert atmosphere for 18 h, then was diluted with water (10 mL) and extracted with DCM (3×10 mL). The combined organic layer was dried over Na$_2$SO$_4$, filtered and concentrated under reduced pressure. The crude residue was purified by preparative HPLC (C18, eluent ACN/H$_2$O/0.01% HCOOH) to afford (4-(3-(4-chlorophenyl)imidazo[1,2-b]pyridazin-6-yl)-2-methylphenyl) (4-methylpiperazin-1-yl)methanone (24 mg, 5%, AUC HPLC 99%) as yellow solid. $^1$H NMR (400 MHz, CD$_3$OD) δ 8.05-7.93 (m, 4H), 7.89-7.82 (m, 2H), 7.67 (d, J=9.5 Hz, 1H), 7.39 (d, J=8.6 Hz, 3H), 4.18-3.83 (m, 2H), 3.50 (s, 2H), 3.08 (s, 2H), 2.91 (s, 2H), 2.70 (s, 3H), 2.39 (s, 3H); $^{13}$C NMR (100 MHz, CD$_3$OD) δ 171.40, 166.86, 152.68, 140.84, 138.16, 137.71, 136.82, 134.77, 133.56, 130.39, 129.87, 129.14, 128.97, 128.33, 127.93, 126.71, 126.03, 117.84, 55.26, 54.85, 46.54, 44.94, 41.19, 19.34; MS (ESI) m/z 446 [C$_{25}$H$_{24}$ClN$_6$O+H]$^+$.

Example 84: (4-(3-(1H-indol-5-yl)imidazo[1,2-b]pyridazin-6-yl)phenyl)(4-methylpiperazin-1-yl)methanone

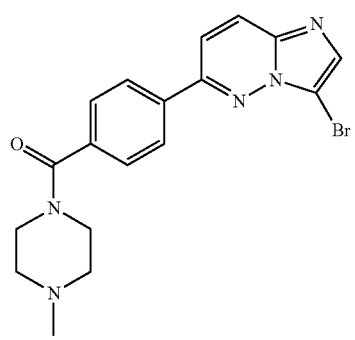 [SMILES: CN1CCN(C(=O)c2ccc(-c3ccc4ncc(Br)n4n3)cc2)CC1]

Step 1: To a solution of 4-(3-bromoimidazo[1,2-b]pyridazin-6-yl)benzoic acid (100 mg, 0.314 mmol) in DMF (1.5 mL) was added HATU (179 mg, 0.471 mmol) and N-methyl morpholine (138 μl, 1.257 mmol). The reaction mixture was stirred at room temperature under inert atmosphere for 1 h, followed by the addition of 1-methylpiperazine (70 μl, 0.628 mmol). The reaction mixture was left to stir for 18 h, then it was diluted with H$_2$O (25 mL) and extracted with EtOAc (3×25 mL). The combined organic layer was dried over Na$_2$SO$_4$ and was concentrated under reduced pressure. The crude residue was purified by column chromatography (silica gel, eluent CH$_2$Cl$_2$/MeOH 95:5) to afford the product as a yellow solid (127 mg, 99%). $^1$H NMR (400 MHz, CDCl$_3$) δ 8.09 (d, J=8.0 Hz, 2H), 8.02 (d, J=9.2 Hz, 1H), 7.81 (s, 1H), 7.59-7.54 (m, 3H), 3.84 (bs, 2H), 3.49 (bs, 3H), 2.50-2.34 (m, 6H); MS (ESI) m/z 400 [C$_{18}$H$_{18}$BrN$_5$O+H]$^+$.

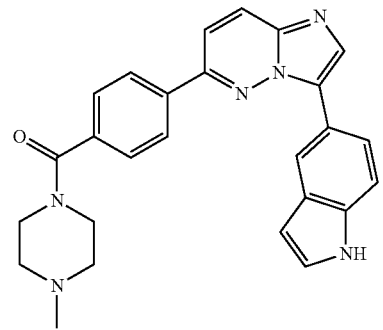 [SMILES: CN1CCN(C(=O)c2ccc(-c3ccc4ncc(-c5ccc6[nH]ccc6c5)n4n3)cc2)CC1]

Step 2: (4-(3-bromoimidazo[1,2-b]pyridazin-6-yl)phenyl)(4-methylpiperazin-1-yl)methanone (100 mg, 0.250 mmol), 1H-indol-5-ylboronic acid (48 mg, 0.300 mmol), Pd(PPh$_3$)$_4$ (29 mg, 0.025 mmol) and Cs$_2$CO$_3$ (163 mg, 0.50 mmol) was dissolved in dioxane (2.0 mL) and water (0.5 mL). The resulting mixture was heated in a microwave reactor for 30 min at 110° C., then was diluted with water (25 mL) and extracted with EtOAc (3×25 mL). The combined organic layer was filtered through celite, dried over Na$_2$SO$_4$ and was concentrated under reduced pressure. The crude residue was purified by column chromatography (silica gel, eluent CH$_2$Cl$_2$/MeOH 95:5) to afford (4-(3-(1H-indol-5-yl)imidazo[1,2-b]pyridazin-6-yl)phenyl)(4-methylpiperazin-1-yl)methanone (51 mg, 47%, AUC HPLC 97%) as a yellow solid. $^1$H NMR (400 MHz, CDCl$_3$) δ 8.45 (s, 1H), 8.32 (bs, 1H), 8.10-8.07 (m, 4H), 7.91 (d, J=8.4 Hz, 1H), 7.57-7.50 (m, 4H), 7.29 (t, J=2.8 Hz, 1H), 6.67 (s, 1H), 3.83 (bs, 2H), 3.49 (bs, 2H), 2.50-2.33 (m, 7H); $^{13}$C NMR (100 MHz, CDCl$_3$): 169.67, 150.44, 138.93, 137.35, 137.10, 135.61, 133.08, 130.37, 128.11, 127.80, 127.27, 126.09, 125.00, 121.77, 120.35, 119.87, 114.56, 111.32, 103.30, 46.06; MS (ESI) m/z 437 [C$_{26}$H$_{24}$N$_6$O+H]$^+$ Example 85: 5-(6-(4-(4-methylpiperazine-1-carbonyl)phenyl)imidazo[1,2-b]pyridazin-3-yl)indolin-2-one

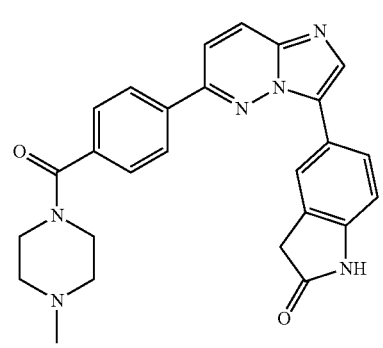 [SMILES: CN1CCN(C(=O)c2ccc(-c3ccc4ncc(-c5ccc6c(c5)CC(=O)N6)n4n3)cc2)CC1]

(4-(3-bromoimidazo[1,2-b]pyridazin-6-yl)phenyl)(4-methylpiperazin-1-yl)methanone (100 mg, 0.250 mmol), 5-(4,4,5,5-tetramethyl-1,3,2-dioxaborolan-2-yl)indolin-2- one (78 mg, 0.300 mmol), Pd(PPh$_3$)$_4$ (29 mg, 0.025 mmol) and Cs$_2$CO$_3$ (163 mg, 0.500 mmol) was dissolved in dioxane (2.0 mL) and water (0.5 mL). The reaction mixture was heated in a microwave reactor for 30 min at 110° C., then was diluted with water (25 mL) and extracted with EtOAc (3×25 mL). The combined organic layer was filtered through celite, dried over Na$_2$SO$_4$ and was concentrated under reduced pressure. The crude residue was purified by column chromatography (silica gel, eluent CH$_2$Cl$_2$/MeOH 95:5) to afford 5-(6-(4-(4-methylpiperazine-1-carbonyl)phenyl)imidazo[1,2-b]pyridazin-3-yl)indolin-2-one (33 mg, 29%, AUC HPLC 98%) as a yellow solid. $^1$H NMR (400 MHz, CDCl$_3$) δ 8.12 (d, J=9.2 Hz, 1H), 8.06-8.04 (m, 4H), 7.99 (s, 1H), 7.60 (d, J=8.4 Hz, 3H), 7.55 (d, J=9.6 Hz, 1H), 7.04 (d, J=8.0 Hz, 1H), 3.85 (bs, 2H), 3.68 (s, 2H), 3.52 (bs, 2H), 2.53-2.36 (m, 7H); $^{13}$C NMR (100 MHz, CDCl$_3$) δ 176.79, 169.52, 150.82, 142.26, 139.19, 137.34, 137.08, 132.93, 128.78, 127.89, 127.25, 127.00, 126.29, 125.78, 123.54, 123.03, 115.13, 109.71, 46.04, 36.22; MS (ESI) m/z 453 [C$_{26}$H$_{24}$N$_6$O$_2$+H]$^+$.

Example 86: (4-(3-(1H-indazol-5-yl)imidazo[1,2-b]pyridazin-6-yl)phenyl)(4-methylpiperazin-1-yl)methanone

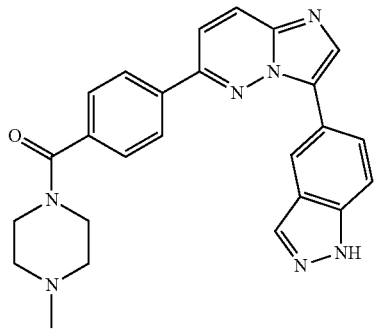 [SMILES: CN1CCN(C(=O)c2ccc(-c3ccc4ncc(-c5ccc6[nH]ncc6c5)n4n3)cc2)CC1]

(4-(3-bromoimidazo[1,2-b]pyridazin-6-yl)phenyl)(4-methylpiperazin-1-yl)methanone (100 mg, 0.250 mmol), 1H-indazol-5-ylboronic acid (49 mg, 0.300 mmol), Pd(PPh$_3$)$_4$ (29 mg, 0.025 mmol) and Cs$_2$CO$_3$ (163 mg, 0.500 mmol) was dissolved in dioxane (2.0 mL) and water (0.5 mL). The reaction mixture was heated in a microwave reactor for 30 min at 110° C., then it was diluted with water (25 mL) and extracted with EtOAc (3×25 mL). The combined organic layer was filtered through celite, dried over Na$_2$SO$_4$ and was concentrated under reduced pressure. The crude residue was purified by preparative HPLC (C18, eluent ACN, water, formic acid 0.1%) to afford (4-(3-(1H-indazol-5-yl)imidazo[1,2-b]pyridazin-6-yl)phenyl)(4-methylpiperazin-1-yl)methanone (21 mg, 19%, AUC HPLC 99%) as a yellow solid. $^1$H NMR (400 MHz, CDCl$_3$) δ 8.62 (s, 1H), δ 8.20 (s, 1H), 8.13-8.05 (m, 5H), 7.66 (d, J=8.8 Hz, 1H), 7.59-7.53 (m, 3H), 3.84 (bs, 2H), 3.50 (bs, 2H), 2.51-2.34 (m, 7H); MS (ESI) m/z 438 [C$_{25}$H$_{23}$N$_7$O+H]$^+$.

Example 87: (4-(3-(1H-benzo[d]imidazol-5-yl)imidazo[1,2-b]pyridazin-6-yl)phenyl)(4-methylpiperazin-1-yl)methanone

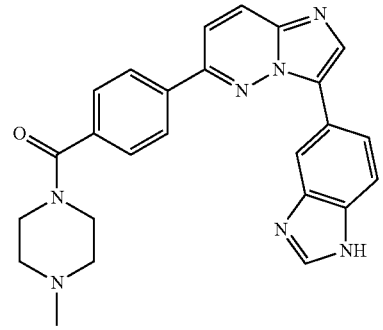 [SMILES: CN1CCN(C(=O)c2ccc(-c3ccc4ncc(-c5ccc6[nH]cnc6c5)n4n3)cc2)CC1]

(4-(3-bromoimidazo[1,2-b]pyridazin-6-yl)phenyl)(4-methylpiperazin-1-yl)methanone (50 mg, 0.125 mmol), 1H-benzo[d]imidazol-5-ylboronic acid (22 mg, 0.137 mmol) and Pd(PPh$_3$)$_4$ (22 mg, 0.019 mmol) was dissolved in dioxane (0.6 mL) and saturated NaHCO$_3$ solution (0.6 mL) was added. The reaction mixture was heated at 150° C. in a microwave reactor for 10 min, then was diluted with water (25 mL) and extracted with EtOAc (3×25 mL). The combined organic layer was filtered over celite, dried over Na$_2$SO$_4$ and was concentrated under reduced pressure. The crude residue was purified by preparative HPLC (C18, eluent ACN, water, formic acid 0.1%) to afford (4-(3-(1H-benzo[d]imidazol-5-yl)imidazo[1,2-b]pyridazin-6-yl)phenyl)(4-methylpiperazin-1-yl)methanone (15 mg, 27%, AUC HPLC 95%) as a yellow solid. $^1$H NMR (400 MHz, CDCl$_3$) δ 8.55 (s, 1H), 8.18-8.15 (m, 2H), 8.12 (t, J=4.8 Hz, 2H), 8.03 (d, J=8.0 Hz, 2H), 7.95-7.92 (m, 1H), 7.82-7.80 (m, 1H), 7.56-7.49 (m, 3H), 3.89 (bs, 2H), 3.55 (bs, 2H), 2.60-2.50 (m, 4H), 2.39 (s, 3H); MS (ESI) m/z 438 [C$_{25}$H$_{23}$N$_7$O+H]$^+$.

Example 88 (4-(3-(1H-benzo[d][1,2,3]triazol-5-yl)imidazo[1,2-b]pyridazin-6-yl)phenyl)(4-methylpiperazin-1-yl)methanone

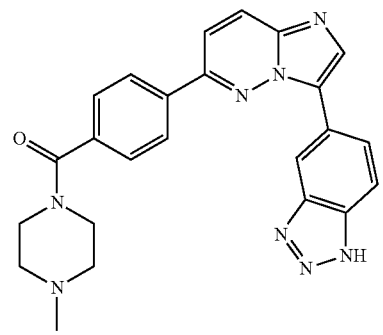 [SMILES: CN1CCN(C(=O)c2ccc(-c3ccc4ncc(-c5ccc6[nH]nnc6c5)n4n3)cc2)CC1]

A mixture of (4-(3-bromoimidazo[1,2-b]pyridazin-6-yl)phenyl)(4-methylpiperazin-1-yl)methanone (53 mg, 0.132 mmol), 1H-benzo[d][1,2,3]triazol-5-ylboronic acid (24 mg, 0.146 mmol) and Tetrakis (23 mg, 0.020 mmol) in 1,4-dioxane (0.65 mL) and saturated NaHCO$_3$ solution (0.65 mL), was heated in a microwave reactor for 10 min at 150°

C., then it was diluted with H₂O (25 mL) and washed with EtOAc (3×25 mL). The crude product remained in the aqueous layer, hence it was concentrated under reduced pressure, dissolved in methanol and filtered over celite and the filtrate was concentrated under reduced pressure. The residue was then purified by preparative HPLC (C18, eluent ACN, water, formic acid 0.1%) to afford (4-(3-(1H-benzo[d][1,2,3]triazol-5-yl)imidazo[1,2-b]pyridazin-6-yl)phenyl)(4-methylpiperazin-1-yl)methanone (13 mg, 23%, AUC HPLC 98%) as a yellow solid. ¹H NMR (400 MHz, CDCl₃) δ 8.91 (s, 1H), 8.21-8.14 (m, 3H), 8.06-8.03 (m, 4H), 7.61 (d, J=8.4 Hz, 2H), 7.55 (d, J=8.8 Hz, 1H), 3.95 (bs, 2H), 3.63 (bs, 2H), 2.68-2.60 (m, 4H), 2.43 (s, 3H); MS (ESI) m/z 439 [C₂₄H₂₂N₈O+H]⁺.

Example 89: 5-(6-(4-(4-(4-methylpiperazin-1-yl)piperidine-1-carbonyl)phenyl)imidazo[1,2-b]pyridazin-3-yl)indolin-2-one

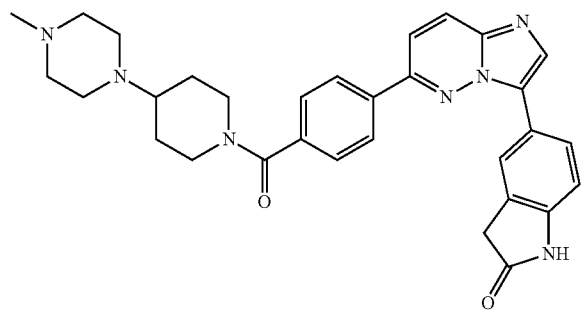 [SMILES: CN1CCN(C2CCN(C(=O)c3ccc(-c4ccc5ncc(-c6ccc7c(c6)CC(=O)N7)n5n4)cc3)CC2)CC1]

Step 1: To a solution of 4-(3-bromoimidazo[1,2-b]pyridazin-6-yl)benzoic acid (200 mg, 0.589 mmol) in DMF (3.0 mL) was added HATU (336 mg, 0.884 mmol) and N-methyl morpholine (259 μl, 2.357 mmol). The reaction mixture was stirred at room temperature under inert atmosphere for 1 h, followed by the addition of 1-methyl-4-(piperidin-4-yl)piperazine (162 mg, 0.884 mmol). The reaction mixture was stirred for 18 h then, was diluted with water (25 mL) and extracted with EtOAc (3×25 mL). The combined organic layer was dried over Na₂SO₄ and was concentrated under reduced pressure. The crude residue was purified by column chromatography (silica gel, eluent CH₂Cl₂/MeOH/NH₄OH 94:5:1) to afford a light yellow solid (128 mg, 45%). ¹H NMR (400 MHz, CD₃OD) δ 8.25 (d, J=8.4 Hz, 2H), 8.14 (d, J=9.6 Hz, 1H), 7.92 (d, J=9.6 Hz, 1H), 7.86 (s, 1H), 7.63 (d, J=8.4 Hz, 2H), 4.73 (bs, 1H), 4.58 (bs, 1H), 3.85 (bs, 1H), 3.15 (bs, 1H), 2.93 (bs, 1H), 2.68-2.57 (m, 8H), 2.32 (s, 3H), 2.09-1.92 (m, 2H), 1.51 (bs, 2H); MS (ESI) m/z 483 [C₂₃H₂₇BrN₆O+H]⁺.

Step 2: (4-(3-bromoimidazo[1,2-b]pyridazin-6-yl)phenyl)(4-(4-methylpiperazin-1-yl)piperidin-1-yl)methanone (125 mg, 0.258 mmol), 5-(4,4,5,5-tetramethyl-1,3,2-dioxaborolan-2-yl)indolin-2-one (81 mg, 0.310 mmol), Pd(PPh₃)₄ (30 mg, 0.026 mmol) and Cs₂CO₃ (169 mg, 0.517 mmol) was dissolved in dioxane (2.0 mL) and water (0.5 mL). The reaction mixture was heated in a microwave reactor for 30 min at 110° C., diluted with water (25 mL) and washed with EtOAc (3×25 mL). The aqueous layer was concentrated under reduced pressure. The crude residue was dissolved in dichloromethane and filtered through a pad of celite. The filtrate was purified by preparative HPLC (C18, eluent ACN, water, formic acid 0.1%) to afford 5-(6-(4-(4-(4-methylpiperazin-1-yl)piperidine-1-carbonyl)phenyl)imidazo[1,2-b]pyridazin-3-yl)indolin-2-one (15 mg, 11%, AUC HPLC 98%) as a yellow solid. ¹H NMR (400 MHz, CD₃OD) δ 8.21 (d, J=8.4 Hz, 2H), 8.16 (d, J=9.6 Hz, 1H), 8.10-8.07 (m, 3H), 7.86 (d, J=9.6 Hz, 1H), 7.63 (d, J=8.4 Hz, 2H), 7.08 (d, J=8.0 Hz, 1H), 4.69-4.58 (m, 2H), 3.86 (bs, 1H), 3.32-3.20 (m, 3H), 2.94-2.62 (m, 9H), 2.45 (s, 3H), 2.05-1.89 (m, 2H), 1.55 (bs, 2H); MS (ESI) m/z 536 [C₃₁H₃₃N₇O₂+H]⁺.

Example 90: 5-(6-(4-(1,9-diazaspiro[5.5]undecane-9-carbonyl)phenyl)imidazo[1,2-b]pyridazin-3-yl)indolin-2-one

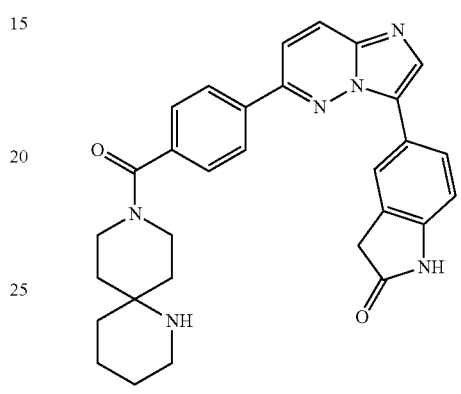

Step 1: tert-butyl 9-(4-(3-(2-oxoindolin-5-yl)imidazo[1,2-b]pyridazin-6-yl)benzoyl)-1,9-diazaspiro[5.5]undecane-1-carboxylate was prepared following General procedure A using 4-(3-bromoimidazo[1,2-b]pyridazin-6-yl)benzoic acid and tert-butyl 1,9-diazaspiro[5.5]undecane-1-carboxylate as starting materials. Purification by column chromatography (silica gel, eluent EtOAc/Hexane 60:40) to afford a light yellow solid (330 mg). MS (ESI) m/z 554 [C₂₇H₃₂BrN₅O₃+H]⁺.

Step 2: tert-butyl 9-(4-(3-bromoimidazo[1,2-b]pyridazin-6-yl)benzoyl)-1,9-diazaspiro[5.5]undecane-1-carboxylate (340 mg, 0.521 mmol), 5-(4,4,5,5-tetramethyl-1,3,2-dioxaborolan-2-yl)indolin-2-one (162 mg, 0.625 mmol), Pd(PPh₃)₄ (60 mg, 0.052 mmol) and Cs₂CO₃ (340 mg, 1.042 mmol) was dissolved in dioxane (4.0 mL) and water (1.0 mL). The reaction mixture was heated in a microwave reactor for 30 min at 110° C., then it was diluted with H₂O (25 mL) and extracted with EtOAc (3×25 mL). The combined organic layer was filtered over celite, dried over Na₂SO₄, filtered and concentrated under reduced pressure. The crude residue was purified by column chromatography (silica gel, eluent CH₂Cl₂/MeOH 95:5) to afford a yellow solid (144 mg). MS (ESI) m/z 607 [C₃₅H₃₈N₆O₄+H]⁺.

Step 3: To a solution of tert-butyl 9-(4-(3-(2-oxoindolin-5-yl)imidazo[1,2-b]pyridazin-6-yl)benzoyl)-1,9-diazaspiro[5.5]undecane-1-carboxylate (142 mg, 0.234 mmol) in DCM (3.0 mL) was added trifluoroacetic acid (1.0 mL). The reaction mixture was stirred at room temperature under inert atmosphere for 30 min, then it was neutralized with NaHCO₃, and diluted with water (25 mL) and washed with EtOAc (3×25 mL). The crude product remained in the aqueous layer; hence it was concentrated under reduced pressure. The residue was dissolved in dichloromethane, filtered, and was concentrated under reduced pressure. The residue was purified by preparative HPLC (C18, eluent ACN, water, formic acid 0.1%) to afford 5-(6-(4-(1,9-diazaspiro[5.5]undecane-9-carbonyl)phenyl)imidazo[1,2-b]

pyridazin-3-yl)indolin-2-one (85 mg, 79%, AUC HPLC 99%) as a yellow solid. $^1$H NMR (400 MHz, CD$_3$OD) δ 8.23 (d, J=8.4 Hz, 2H), 8.17 (d, J=9.6 Hz, 1H), 8.09-8.06 (m, 3H), 7.86 (d, J=9.6 Hz, 1H), 7.64 (d, J=8.4 Hz, 2H), 7.08 (d, J=8.0 Hz, 1H), 4.57-4.38 (m, 2H), 3.73-3.44 (m., 4H), 3.23 (bs, 2H), 2.15-1.79 (m, 10H); $^{13}$C NMR (400 MHz, CD$_3$OD) δ 179.83, 171.80, 152.36, 144.81, 140.39, 138.61, 138.07, 132.82, 130.46, 128.81, 128.58, 128.01, 127.56, 126.70, 124.44, 123.70, 117.22, 110.84, 56.81, 40.76, 30.79, 23.56, 18.69; MS (ESI) m/z 507 [C$_{30}$H$_{30}$N$_6$O$_2$+H]$^+$.

Example 91: 5-(6-(4-(4-(dimethylamino)piperidine-1-carbonyl)phenyl)imidazo[1,2-b]pyridazin-3-yl)isoindolin-1-one

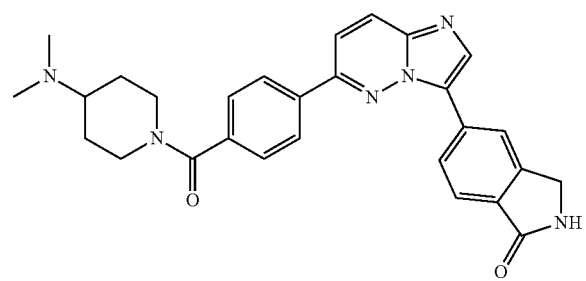 [SMILES: CN(C)C1CCN(C(=O)c2ccc(-c3ccc4ncc(-c5ccc6c(c5)CNC6=O)n4n3)cc2)CC1]

Step 1: To a solution of 4-(3-bromoimidazo[1,2-b]pyridazin-6-yl)benzoic acid (200 mg, 0.63 mmol) in DMF (5 mL) were added HATU (479 mg, 1.26 mmol), N-methyl morpholine (191 mg, 1.89 mmol) and N,N-dimethylpiperidin-4-amine (242 mg, 1.89 mmol). The reaction mixture was stirred at room temperature under inert atmosphere for 18 h, and then was diluted with water (10 mL) and extracted with DCM (3×20 mL). The combined organic layer was dried over Na$_2$SO$_4$, filtered and concentrated under reduced pressure. The crude residue was purified by column chromatography (silica gel, eluent CH$_2$Cl$_2$/MeOH 95:5 to 90:10) to afford (4-(3-bromoimidazo[1,2-b]pyridazin-6-yl)phenyl)(4-(dimethylamino)piperidin-1-yl)methanone as a yellow solid. MS (ESI) m/z 428 [C$_{20}$H$_{22}$BrN$_5$O+H]$^+$.

Step 2: To a solution of tert-butyl 4-(4-(3-bromoimidazo[1,2-b]pyridazin-6-yl)benzoyl)piperazine-1-carboxylate (0.63 mmol) in DMF (4 mL) and water (0.8 mL) under inert atmosphere were added Cs$_2$CO$_3$ (411 mg, 1.26 mmol), 5-(4,4,5,5-tetramethyl-1,3,2-dioxaborolan-2-yl)indolin-2-one (245 mg, 0.945 mmol) and Pd(dppf)$_2$Cl$_2$ (92 mg, 0.126 mmol). The resulting mixture was stirred and heated to 90° C. for 18 h, and then was diluted with water (20 mL) and extracted with DCM (3×40 mL). The combined organic layer was dried over Na$_2$SO$_4$, filtered and concentrated under reduced pressure. The crude residue was purified by column chromatography (silica gel, eluent CH$_2$Cl$_2$/MeOH 95:5 to 90:10) to afford 5-(6-(4-(4-(dimethylamino)piperidine-1-carbonyl)phenyl)imidazo[1,2-b]pyridazin-3-yl)isoindolin-1-one (66 mg, 22%, AUC HPLC 96%) as yellow solid. $^1$H NMR (400 MHz, DMSO-d$_6$) δ 10.56 (s, 1H), 8.30-8.02 (m, 6H), 7.88-7.86 (m, 1H), 7.60-7.58 (m, 2H), 7.02-7.00 (m, 1H), 4.47 (bs, 1H), 3.62 (bs, 3H), 3.06 (bs, 1H), 2.83 (bs, 1H), 2.35 (bs, 1H), 2.18 (s, 6H), 1.84-1.71 (m, 2H), 1.37 (bs, 2H); $^{13}$C NMR (100 MHz, DMSO-d$_6$) δ 176.28, 168.12, 150.21, 143.46, 138.61, 137.72, 135.92, 132.61, 128.02, 127.43, 126.97, 126.28, 126.24, 125.99, 122.76, 121.43, 115.21, 109.19, 61.09, 54.80, 41.32, 35.81; MS (ESI) m/z 481 [C$_{28}$H$_{28}$N$_6$O$_2$+H]$^+$.

Example 92: 5-(6-(4-(piperazine-1-carbonyl)phenyl)imidazo[1,2-b]pyridazin-3-yl)indolin-2-one

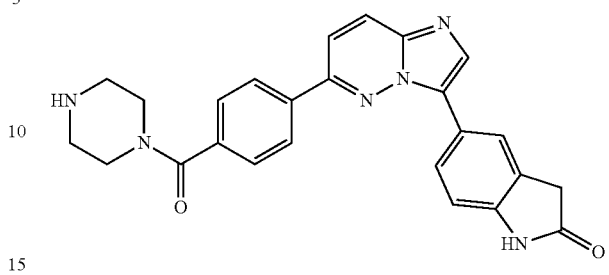

Step 1: To a solution of 4-(3-bromoimidazo[1,2-b]pyridazin-6-yl)benzoic acid (200 mg, 0.63 mmol) in DMF (5 mL), were added HATU (479 mg, 1.26 mmol), N-methyl morpholine (191 mg, 1.89 mmol) and tert-butyl piperazine-1-carboxylate (352 mg, 1.89 mmol). The reaction mixture was stirred at room temperature under inert atmosphere for 18 h, and then was diluted with water (10 mL) and extracted with DCM (3×20 mL). The combined organic layer was dried over Na$_2$SO$_4$, filtered and concentrated under reduced pressure. The residue was purified by column chromatography (silica gel, eluent CH$_2$Cl$_2$/MeOH 95:5 to 90:10) to afford tert-butyl 4-(4-(3-bromoimidazo[1,2-b]pyridazin-6-yl)benzoyl)piperazine-1-carboxylate as a yellow solid. MS (ESI) m/z 486 [C$_{22}$H$_{24}$BrN$_5$O$_3$+H]$^+$.

Step 2: To a solution of tert-butyl 4-(4-(3-bromoimidazo[1,2-b]pyridazin-6-yl)benzoyl)piperazine-1-carboxylate (0.63 mmol) in DMF (4 mL) and water (0.8 mL) under inert atmosphere were added Cs$_2$CO$_3$ (411 mg, 1.26 mmol), 5-(4,4,5,5-tetramethyl-1,3,2-dioxaborolan-2-yl)indolin-2-one (245 mg, 0.945 mmol) and Pd(dppf)$_2$Cl$_2$ (92 mg, 0.126 mmol). The resulting mixture was stirred and heated at 90° C. for 18 h, and then was diluted with water (20 mL) and extracted with DCM (3×40 mL). The combined organic layer was dried over Na$_2$SO$_4$, filtered and concentrated under reduced pressure. The crude residue was purified by column chromatography (silica gel, eluent CH$_2$Cl$_2$/MeOH 95:5 to 90:10) to afford tert-butyl 4-(4-(3-(2-oxoindolin-5-yl)imidazo[1,2-b]pyridazin-6-yl)benzoyl)piperazine-1-carboxylate. MS (ESI) m/z 539 [C$_{30}$H$_{30}$N$_6$O$_4$+H]$^+$ Step 3: To a solution of tert-butyl 4-(4-(3-(2-oxoindolin-5-yl)imidazo[1,2-b]pyridazin-6-yl)benzoyl)piperazine-1-carboxylate (0.63 mmol) in DCM (1 mL) was added TFA (1 mL). The resulting mixture was stirred at room temperature for 18 h and was concentrated under reduced pressure. The crude residue was purified by column chromatography (silica gel, eluent CH$_2$Cl$_2$/MeOH 95:5 to 90:10) and preparative HPLC (C18, eluent ACN/H$_2$O/0.01% HCOOH) to afford 5-(6-(4-(piperazine-1-carbonyl)phenyl)imidazo[1,2-b]pyridazin-3-yl)indolin-2-one (71 mg, 26%, AUC HPLC 99%) as a yellow solid. $^1$H NMR (400 MHz, DMSO-d$_6$) δ 10.56 (s, 1H), 8.29 (d, J=9.6 Hz, 1H), 8.19-8.17 (m, 3H), 8.09 (d, J=8.0 Hz, 1H), 8.02 (s, 1H), 7.87 (d, J=9.5 Hz, 1H), 7.58 (d, J=7.7 Hz, 2H), 7.01 (d, J=8.0 Hz, 1H), 3.62-3.51 (m, 7H), 2.75-2.69 (m, 4H); $^{13}$C NMR (100 MHz, DMSO-d$_6$) δ176.29, 168.24, 150.21, 143.46, 138.61, 137.56, 135.92, 132.60, 128.02, 127.60, 126.97, 126.28, 126.24, 126.00, 122.76, 121.43, 115.20, 109.20, 54.79, 45.71, 35.81; MS (ESI) m/z 439 [C$_{25}$H$_{22}$N$_6$O$_2$+H]$^+$.

Example 93: 5-(6-(4-(1,4-diazepane-1-carbonyl)phenyl)imidazo[1,2-b]pyridazin-3-yl)isoindolin-1-one

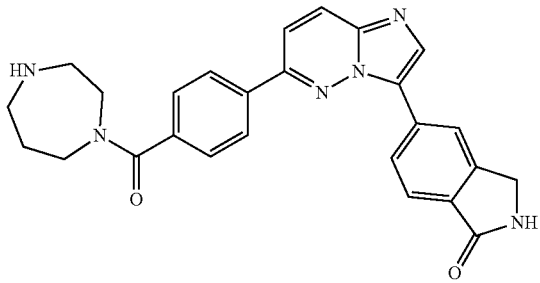 [SMILES: O=C1NCc2cc(-c3cnc4ccc(-c5ccc(C(=O)N6CCCNCC6)cc5)nn34)ccc21]

Step 1: To a solution of 4-(3-bromoimidazo[1,2-b]pyridazin-6-yl)benzoic acid (200 mg, 0.63 mmol) in DMF (5 mL) were added HATU (479 mg, 1.26 mmol), N-methyl morpholine (191 mg, 1.89 mmol) and tert-butyl 1,4-diazepane-1-carboxylate (379 mg, 1.89 mmol). The reaction mixture was stirred at room temperature under inert atmosphere for 18 h, and then was diluted with water (10 mL) and extracted with DCM (3×20 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford tert-butyl 4-(4-(3-bromoimidazo[1,2-b]pyridazin-6-yl)benzoyl)-1,4-diazepane-1-carboxylate as a yellow solid. MS (ESI) m/z 500 $[C_{23}H_{26}BrN_5O_3+H]^+$.

Step 2: To a solution of tert-butyl 4-(4-(3-bromoimidazo[1,2-b]pyridazin-6-yl)benzoyl)-1,4-diazepane-1-carboxylate (0.63 mmol) in DMF (4 mL) and water (0.8 mL) under inert atmosphere were added $Cs_2CO_3$ (411 mg, 1.26 mmol), 5-(4,4,5,5-tetramethyl-1,3,2-dioxaborolan-2-yl)indolin-2-one (245 mg, 0.945 mmol) and Pd(dppf)$_2$Cl$_2$ (92 mg, 0.126 mmol). The resulting mixture was stirred and heated to 90° C. for 18 h, and then was diluted with water (20 mL) and extracted with DCM (3×40 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford tert-butyl 4-(4-(3-(2-oxoindolin-5-yl)imidazo[1,2-b]pyridazin-6-yl)benzoyl)-1,4-diazepane-1-carboxylate 5 (310 mg, 48%) as a brown solid. MS (ESI) m/z 553 $[C_{31}H_{32}N_6O_4+H]^+$ Step 3: A solution of tert-butyl 4-(4-(3-(2-oxoindolin-5-yl)imidazo[1,2-b]pyridazin-6-yl)benzoyl)-1,4-diazepane-1-carboxylate (0.63 mmol) in a mixture of DCM (1 mL) and TFA (1 mL), was stirred at room temperature for 18 h and was concentrated under reduced pressure. The crude residue was purified by column chromatography (silica gel, eluent $CH_2Cl_2$/MeOH 95:5 to 90:10) and preparative HPLC (C18, eluent ACN/$H_2O$/0.01% HCOOH) to afford 5-(6-(4-(1,4-diazepane-1-carbonyl)phenyl)imidazo[1,2-b]pyridazin-3-yl)isoindolin-1-one (46 mg, 16%, AUC HPLC 98%) as a yellow solid. $^1$H NMR (400 MHz, DMSO-d$_6$) δ 10.55 (s, 1H), 8.29 (d, J=9.5 Hz, 1H), 8.19-8.17 (m, 3H), 8.09 (d, J=8.2 Hz, 1H), 8.03 (s, 1H), 7.87 (d, J=9.4 Hz, 1H), 7.58 (d, J=8.0 Hz, 2H), 7.01 (d, J=8.2 Hz, 1H), 3.68-3.62 (m, 4H), 3.41-3.38 (m, 2H), 3.17 (d, J=5.2 Hz, 2H), 2.91-2.85 (m, 1H), 2.81-2.74 (m, 3H), 1.78-1.72 (m, 1H), 1.63-1.56 (m, 1H); $^{13}$C NMR (100 MHz, DMSO-d$_6$) 176.28, 169.60, 150.24, 143.46, 138.61, 135.56, 128.02, 127.27, 127.01, 126.92, 126.28, 126.24, 126.00, 122.76, 121.45, 115.20, 109.20, 48.49, 44.53, 35.80; MS (ESI) m/z 453 $[C_{26}H_{24}N_6O_2+H]^+$.

Example 94: 5-(6-(4-(4-morpholinopiperidine-1-carbonyl)phenyl)imidazo[1,2-b]pyridazin-3-yl)indolin-2-one

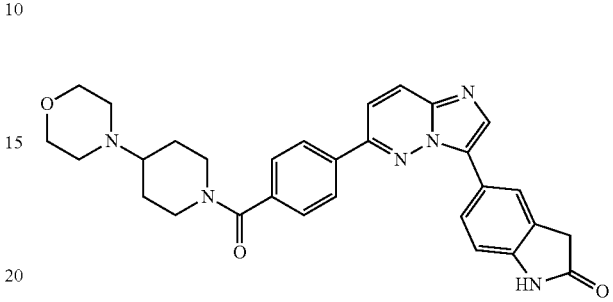

Step 1: To a solution of 4-(3-bromoimidazo[1,2-b]pyridazin-6-yl)benzoic acid (200 mg, 0.63 mmol) in DMF (5 mL) were added HATU (479 mg, 1.26 mmol), N-methyl morpholine (191 mg, 1.89 mmol) and 4-(piperidin-4-yl)morpholine (321 mg, 1.89 mmol). The reaction mixture was stirred at room temperature under inert atmosphere for 18 h, and then was diluted with water (10 mL) and extracted with DCM (3×20 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford (4-(3-bromoimidazo[1,2-b]pyridazin-6-yl)phenyl)(4-morpholinopiperidin-1-yl)methanone as a yellow solid. MS (ESI) m/z 470 $[C_{22}H_{24}BrN_5O_2+H]^+$.

Step 2: To a solution of (4-(3-bromoimidazo[1,2-b]pyridazin-6-yl)phenyl)(4-morpholinopiperidin-1-yl)methanone (0.63 mmol) in DMF (4 mL) and water (0.8 mL) under inert atmosphere were added $Cs_2CO_3$ (411 mg, 1.26 mmol), 5-(4,4,5,5-tetramethyl-1,3,2-dioxaborolan-2-yl)indolin-2-one (245 mg, 0.945 mmol) and Pd(dppf)$_2$Cl$_2$ (92 mg, 0.126 mmol). The resulting mixture was heated to 90° C. for 18 h, and then was diluted with water (20 mL) and extracted with DCM (3×40 mL). The combined organic layer was dried over $Na_2SO_4$, filtered and concentrated under reduced pressure. The crude residue was purified by column chromatography (silica gel, eluent $CH_2Cl_2$/MeOH 95:5 to 90:10) to afford 5-(6-(4-(4-morpholinopiperidine-1-carbonyl)phenyl)imidazo[1,2-b]pyridazin-3-yl)indolin-2-one (16.2 mg, 5%, AUC HPLC 98%) as a yellow solid. $^1$H NMR (400 MHz, DMSO-d$_6$) δ 10.56 (s, 1H), 8.29 (d, J=9.5 Hz, 1H), 8.19-8.17 (m, 3H), 8.09 (d, J=8.0 Hz, 1H), 8.02 (s, 1H), 7.88 (d, J=9.6 Hz, 1H), 7.59 (d, J=8.2 Hz, 2H), 7.01 (d, J=8.1 Hz, 1H), 4.48-4.46 (m, 1H), 3.62-3.56 (m, 7H), 3.08 (bs, 1H), 2.84 (bs, 1H), 2.44-2.41 (m, 5H), 1.91-1.76 (m, 2H), 1.05-1.03 (m, 2H); $^{13}$C NMR (100 MHz, DMSO-d$_6$) δ176.85, 168.69, 150.78, 144.04, 139.19, 138.27, 136.50, 133.18, 128.59, 128.00, 127.54, 126.85, 126.82, 126.57, 123.33, 122.01, 115.78, 109.76, 67.03, 61.41, 49.87, 36.38; MS (ESI) m/z 523 $[C_{30}H_{30}N_6O_3+H]^+$.

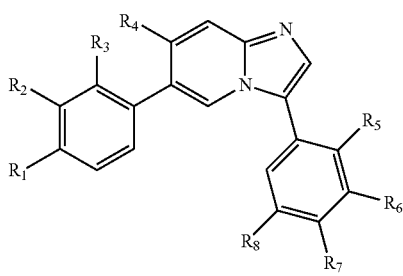

Formula 4

Intermediate 14: Synthesis of 6-bromo-3-(4-chlorophenyl)imidazo[1,2-a]pyridine

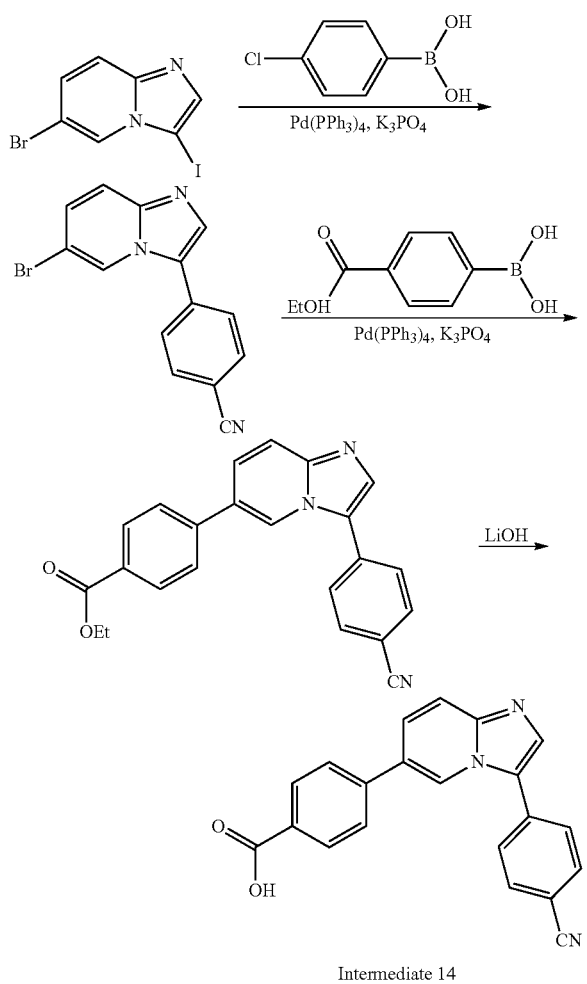

Intermediate 14

Step 1: To a solution of 6-bromo-3-iodoimidazo[1,2-a]pyridine (21 g, 65.4 mmol), 4-Chlorophenylboronic acid (11.22 g, 71.9 mmol), $K_3PO_4$ (27.7 g, 130.8 mmol) in a mixture of DMF (100 mL) and water (15 mL), was added $Pd(PPh_3)_4$ (3.77 g, 3.27 mmol). The reaction mixture was heated at 90° C. for 6 h under argon atmosphere prior to the addition of water (200 mL). The precipitate was isolated by filtration and was purified by column chromatography (silica gel, eluent $CHCl_3$/MeOH 95:5) to afford of 6-bromo-3-(4-chlorophenyl)imidazo[1,2-a]pyridine (10.6 g, 52%) as a yellowish green solid. $^1$H NMR (400 MHz, $CDCl_3$) δ 8.38 (s, 1H), 7.69 (s, 1H), 7.60 (d, J=8.0 Hz, 2H), 7.82 (t, J=9.2 Hz, 1H), 7.58 (q, J=5.2 Hz, 4H), MS (ESI) m/z 309 $[C_{13}H_8BrN_2Cl+2H]^+$.

Step 2: 4-(ethoxycarbonyl)phenylboronic acid (3.81 g, 19.67 mmol), $K_3PO_4$ (6.95 g, 32.78 mmol) and $Pd(PPh_3)_4$ (0.56 g, 0.49 mmol) were added sequentially to a solution of ethyl 4-(6-bromoimidazo[1,2-a]pyridin-3-yl)benzonitrile (5 g, 16.39 mmol) in a mixture of 1,4-dioxane (50 mL) and water (5 mL) at room temperature. The reaction mixture was refluxed for 6 h under argon atmosphere, and was diluted with water (100 mL) and extracted with EtOAc (3×100 mL). The combined organic layer was dried over $Na_2SO_4$, filtered and concentrated under reduced pressure. The residue was purified by column chromatography (silica gel, eluent petroleum ether/EtOAc 1:1) to afford ethyl 4-(3-(4-cyanophenyl)imidazo[1,2-a]pyridin-6-yl)benzoate (2.7 mg, 45%) as an off-white solid. $^1$H NMR (400 MHz, $CD_3OD$) δ 9.21 (s, 1H), 8.54 (s, 1H), 8.16 (d, J=8.4 Hz, 2H), 7.85-7.44 (m, 9H), 4.44 (q, J=7.2 Hz, 2H), 1.42 (t, J=7.2 Hz, 3H); MS (ESI) m/z 369 $[M+H]^+$.

Step 3: To a solution of ethyl 4-(3-(4-cyanophenyl)imidazo[1,2-a]pyridin-6-yl)benzoate (2.7 g, 7.18 mmol) in THF (40 mL) was added a solution of LiOH (0.9 g, 21.54 mmol) in water (10 mL) and MeOH (10 mL). The reaction mixture was stirred for 5 h at rt and was concentrated under reduced pressure to afford 4-(3-(4-cyanophenyl)imidazo[1,2-a]pyridin-6-yl)benzoic acid (900 mg, 37%) of as an off white solid which was used in the next step without purification. $^1$H NMR (400 MHz, DMSO-$d_6$) δ (ppm): 8.88 (s, 1H), 8.13-8.03 (m, 6H), 7.92-7.90 (m, 4H); MS (ESI) m/z 340 $[C_{21}H_{13}N_3O_2+H]^+$.

Example 95: 4-(6-(4-(4-Methylpiperazine-1-carbonyl)phenyl)imidazo[1,2-a]pyridin-3-yl)benzonitrile

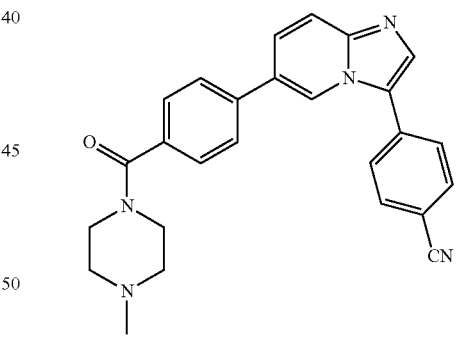

To a solution of 4-(6-bromoimidazo[1,2-a]pyridin-3-yl)benzonitrile (210 mg, 0.9 mmol), (4-methylpiperazin-1-yl) (4-(4,4,5,5-tetramethyl-1,3,2-dioxaborolan-2-yl)phenyl) methanone (388 mg, 1.17 mmol), $NaHCO_3$ (228 mg, 2.71 mmol) in a mixture of DMF (11 mL) and water (2 mL) was added (A-Phos)$_2$PdCl$_2$ (31 mg, 0.04 mmol). The reaction mixture was heated at 90° C. for 1 h under argon atmosphere then, was diluted with water and extracted with EtOAc. The organic phase was washed with water and brine solution, dried over anhydrous $Na_2SO_4$, filtered and concentrated under reduced pressure. The residue was purified by Preparative TLC to afford of 4-(6-(4-(4-methylpiperazine-1-carbonyl)phenyl)imidazo[1,2-a]pyridin-3-yl)benzonitrile (130 mg, 45%, AUC HPLC purity 98.4%) as a pale yellow solid; m.p. 106-116° C. $^1$H NMR (400 MHz, CDCl$_3$) δ (ppm): 8.50 (s, 1H), 7.85-7.79 (m, 4H), 7.74 (d, J=8.0 Hz, 2H), 7.60-7.52 (m, 5H), 3.83 (bs, 2H), 3.50 (bs, 2H), 2.51 (bs, 2H), 2.37 (bs, 2H), 2.34 (s, 3H). $^{13}$C NMR (75 MHz, CDCl$_3$) δ (ppm): 169.5, 146.3, 138.5, 135.6, 134.8, 133.8, 133.2, 128.1, 127.8, 127.2, 127.1, 125.6, 124.5, 120.6, 118.7, 118.4, 111.5, 55.3, 47.7, 46.0; MS (ESI) m/z 422.30 [C$_{26}$H$_{23}$N$_5$O+H]$^+$.

Example 96: 4-(6-(4-(morpholine-4-carbonyl)phenyl)imidazo[1,2-a]pyridin-3-yl)benzonitrile

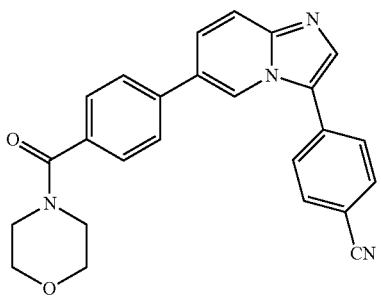 [SMILES: N#Cc1ccc(-c2cnc3ccc(-c4ccc(C(=O)N5CCOCC5)cc4)cn23)cc1]

To a solution of 4-(3-(4-cyanophenyl)imidazo[1,2-a]pyridin-6-yl)benzoic acid (0.2 g, 0.58 mmol) in DMF (5 mL) were added HATU (0.33 g, 0.88 mmol), N-methyl morpholine (0.18 g, 1.76 mmol) and morpholine (60 mg, 0.70 mmol). The reaction mixture was stirred at room temperature under inert atmosphere for 16 h then, was diluted with water (15 mL) and extracted with EtOAc (3×25 mL). The combined organic layer was dried over Na$_2$SO$_4$, filtered concentrated under reduced pressure. The crude residue was first purified by column chromatography (silica gel, eluent CH$_2$Cl$_{2\,1}$MeOH 95:5) and by Prep-HPLC to afford 4-(6-(4-(morpholine-4-carbonyl)phenyl)imidazo[1,2-a]pyridin-3-yl)benzonitrile (39 mg, 16.2%, AUC HPLC>99) as an off white solid; m.p. 117-130° C. $^1$H NMR (400 MHz, CDCl$_3$) δ (ppm): 8.49 (s, 1H), 7.84-7.71 (m, 5H), 7.60-7.50 (m, 5H), 3.72 (m, 8H); MS (ESI) m/z 409.19 [C$_{25}$H$_{20}$N$_4$O$_2$+H]$^+$.

Example 97: 4-(6-(4-(1,4-oxazepane-4-carbonyl)phenyl)imidazo[1,2-a]pyridin-3-yl)benzonitrile

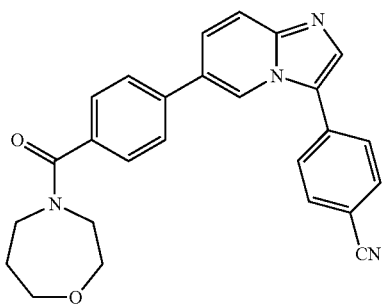 [SMILES: N#Cc1ccc(-c2cnc3ccc(-c4ccc(C(=O)N5CCCOCC5)cc4)cn23)cc1]

To a solution of 4-(3-(4-cyanophenyl)imidazo[1,2-a]pyridin-6-yl)benzoic acid (0.2 g, 0.58 mmol) in DMF (5 mL) at 0° C., were added HATU (0.33 g, 0.88 mmol), N-methyl morpholine (0.18 g, 1.76 mmol) and 1,4-oxazepane (64 mg, 0.638 mmol). The reaction mixture was allowed to warm to rt and stirred under inert atmosphere for 16 h, then was diluted with water (15 mL) and extracted with EtOAc (3×25 mL). The combined organic layer was dried over Na$_2$SO$_4$, filtered and concentrated under reduced pressure. The crude residue was purified by column chromatography (silica gel, eluent CH$_2$Cl$_2$/MeOH 95:5) and followed by preparative HPLC (C18, ACN/H$_2$O/10 mM NH$_4$HCO$_3$) to afford 4-(6-(4-(morpholine-4-carbonyl)phenyl)imidazo[1,2-a]pyridin-3-yl)benzonitrile (130 mg, 54%, AUC HPLC 99.85%) as an off-white solid; m.p. 107-112° C. $^1$H NMR (400 MHz, CDCl$_3$) δ (ppm): 8.49 (s, 1H), 7.84-7.71 (m, 5H), 7.60-7.50 (m, 5H), 4.09-3.8 (m, 5H), 3.7 (bs, 1H), 3.67 (b. s, 2H), 2.1 (bs, 1H); 1.9 (bs, 1H); MS (ESI) m/z 423.32 [C$_{26}$H$_{22}$N$_4$O$_2$+H]$^+$.

Example 98: 4-(6-(4-(4-ethylpiperazine-1-carbonyl)phenyl)imidazo[1,2-a]pyridin-3-yl)benzonitrile

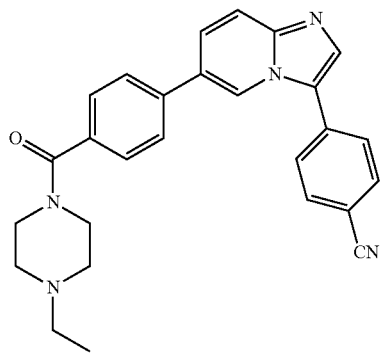 [SMILES: CCN1CCN(C(=O)c2ccc(-c3ccc4ncc(-c5ccc(C#N)cc5)n4c3)cc2)CC1]

To a solution of 4-(3-(4-cyanophenyl)imidazo[1,2-a]pyridin-6-yl)benzoic acid 1 (100 mg, 0.295 mmol) in DMF (1.5 mL) was added HATU (168 mg, 0.442 mmol) and N-methyl morpholine (130 μl, 1.178 mmol). The reaction mixture was stirred at room temperature under inert atmosphere for 1 h, followed by the addition of 1-ethylpiperazine (75 μl, 0.589 mmol). The reaction mixture was left to stir for 18 h, then was diluted with water (25 mL) and extracted with EtOAc (3×25 mL). The combined organic layer was dried over Na$_2$SO$_4$, filtered and concentrated under reduced pressure. The crude residue was purified by column chromatography (silica gel, eluent CH$_2$Cl$_2$/MeOH 95:5) to afford 4-(6-(4-(4-ethylpiperazine-1-carbonyl)phenyl)imidazo[1,2-a]pyridin-3-yl)benzonitrile (93 mg, 73%, AUC HPLC 99%) as a white solid. $^1$H NMR (400 MHz, DMSO-d$_6$) δ 8.80 (s, 1H), 8.03-7.98 (m, 5H), 7.84-7.81 (m, 3H), 7.74-7.72 (m, 1H), 7.50 (d, J=8.0 Hz, 2H), 3.62-3.38 (m, 4H), 2.37 (s, 6H), 1.01 (t, J=6.8 Hz, 3H); $^{13}$C NMR (100 MHz, DMSO-d$_6$) δ 168.49, 145.73, 137.74, 135.24, 135.08, 133.49, 133.15, 127.73, 127.66, 127.02, 125.73, 125.51, 124.40, 121.82, 118.78, 117.76, 109.77, 51.40, 11.69; MS (ESI) m/z 436 [C$_{27}$H$_{25}$N$_5$O+H]$^+$.

Example 99: N-(1-(4-(3-(4-cyanophenyl)imidazo[1,2-a]pyridin-6-yl)benzoyl)-4-methylpiperidin-4-yl)acetamide

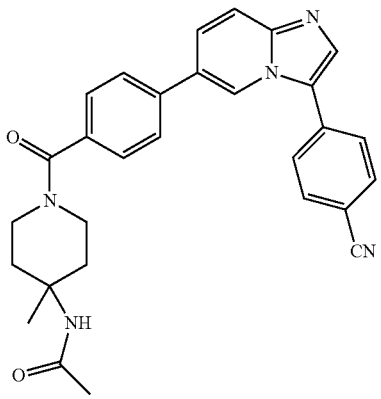 [SMILES: CC(=O)NC1(C)CCN(C(=O)c2ccc(-c3ccc4ncc(-c5ccc(C#N)cc5)n4c3)cc2)CC1]

Step 1: To a solution of 4-(3-(4-cyanophenyl)imidazo[1,2-a]pyridin-6-yl)benzoic acid (1 g, 2.9 mmol) in DMF (15.0 mL) were added HATU (1.65 g, 4.38 mmol), N-methyl morpholine (0.641 mL, 5.8 mmol) and tert-butyl 4-methyl-piperidin-4-ylcarbamate (691 mg, 3.24 mmol). The reaction mixture was stirred at room temperature under inert atmosphere for 16 h, then was diluted with water (15 mL) and extracted with EtOAc (3×25 mL). The combined organic layer was dried over $Na_2SO_4$ and was concentrated under reduced pressure. The crude residue was purified by column chromatography (silica gel, eluent $CH_2Cl_2$/MeOH 95:5) to afford tert-butyl 1-(4-(3-(4-cyanophenyl)imidazo[1,2-a]pyridin-6-yl)benzoyl)-4-methylpiperidin-4-ylcarbamate (800 mg, 53%) as an off-white solid. $^1$H NMR (400 MHz, $CD_3OD$) δ (ppm): 8.47 (s, 1H), 7.88 (d, J=7.6 Hz, 2H), 7.83 (s, 1H), 7.78 (d, J=8.0 Hz, 2H), 7.72 (d, J=9.2 Hz, 1H), 7.60 (d, J=8.0 Hz, 2H), 7.51 (d, J=7.6 Hz, 2H), 4.42 (bs, 1H), 4.19 (bs, 1H), 3.55-3.32 (m, 3H), 2.07-1.95 (m, 4H), 1.44 (s, 9H), 1.40 (s, 3H); MS (ESI) m/z 536.2 $[C_{32}H_{33}N_5O_3+H]^+$.

Step 2: To a solution of tert-butyl 1-(4-(3-(4-cyanophenyl)imidazo[1,2-a]pyridin-6-yl)benzoyl)-4-methylpiperidin-4-ylcarbamate (800 mg, 1.49 mmol) in DCM (10 mL) were added TFA (3 mL) in DCM (5 mL). The reaction mixture was stirred for 4 h at rt. The reaction mixture was diluted with water (100 mL), $NaHCO_3$ (2×100 mL) and extracted with $CH_2Cl_2$ (2×50 mL). The combined organic layer was concentrated to dryness under reduced pressure to afford 4-(6-(4-(4-amino-4-methylpiperidine-1-carbonyl)phenyl)imidazo[1,2-a]pyridin-3-yl)benzonitrile (600 mg, 61%, AUC HPLC>99%) as an off white solid; m.p. 233-235° C. $^1$H NMR (400 MHz, $CD_3OD$) δ (ppm): 8.75 (s, 1H), 7.92 (m, 3H), 7.87 (s, 1H), 7.79-7.76 (m, 4H), 7.52 (d, J=11.2 Hz, 2H), 3.8 (bs, 2H), 3.62 (m, 2H), 1.72-1.41 (m, 4H), 1.20 (s, 3H); MS (ESI) m/z 436.2 $[C_{27}H_{25}N_5O+H]^+$.

Step 3: To a solution of 4-(6-(4-(4-amino-4-methylpiperidine-1-carbonyl)phenyl)imidazo[1,2-a]pyridin-3-yl)benzonitrile (200 mg, 046 mmol) in DCM (10 mL) were added TEA (0.13 mL, 0.92 mmol) and acetyl chloride (0.05 mL, 0.596 mmol). The reaction mixture was stirred at room temperature under inert atmosphere for 4 h, then was diluted with cold water (10 mL) and extracted with EtOAc (3×25 mL). The combined organic layer was washed with $NaHCO_3$ (2×10 mL), dried over $Na_2SO_4$, filtered and concentrated under reduced pressure. The crude residue was purified by column chromatography (silica gel, eluent $CH_2Cl_2$/MeOH 95:5) and by preparative HPLC to afford N-(1-(4-(3-(4-cyanophenyl)imidazo[1,2-a]pyridin-6-yl)benzoyl)-4-methylpiperidin-4-yl)acetamide (100 mg, 47%, AUC HPLC 98.1%) as an off white solid; m.p. 188-210° C. $^1$H NMR (100 MHz, DMSO-$d_6$) δ (ppm): 8.79 (s, 1H), 8.02-7.96 (m, 5H), 7.81 (d, J=8.0 Hz, 2H), 7.72 (d, J=12.0 Hz, 2H), 7.50-7.45 (m, 3H), 4.12 (bs, 1H), 3.23 (bs, 2H), 2.09 (bs, 2H), 1.82 (s, 3H), 1.44 (bs, 2H), 1.29 (s, 3H); MS (ESI) m/z 478.39 $[C_{29}H_{27}N_5O_2+H]^+$.

Example 100: 4-(6-(4-(4-(diethylamino)-4-methylpiperidine-1-carbonyl)phenyl)imidazo[1,2-a]pyridin-3-yl)benzonitrile

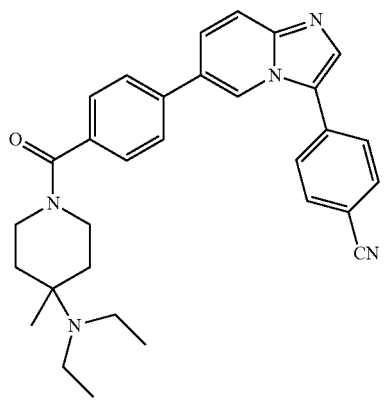 [SMILES: CCN(CC)C1(C)CCN(C(=O)c2ccc(-c3ccc4ncc(-c5ccc(C#N)cc5)n4c3)cc2)CC1]

To a solution of 4-(6-(4-(4-amino-4-methylpiperidine-1-carbonyl)phenyl)imidazo[1,2-a]pyridin-3-yl)benzonitrile (200 mg, 0.46 mmol) in methanol (15.0 mL) were added acetaldehyde (40 mg, 0.92 mmol), catalytic amount of acetic acid (0.5 mL). The reaction mixture was stirred at 0° C. under inert atmosphere for 2 h, then was slowly added $NaBH_3CN$ (97 mg, 1.38 mmol) then the reaction was slowly warmed to rt and stirred for 24 h. Reaction mixture was diluted with water and extracted with EtOAc (3×25 mL). The combined organic layer was dried over $Na_2SO_4$ and was concentrated under reduced pressure. The crude residue was purified by column chromatography (silica gel, eluent $CH_2Cl_2$/MeOH 95:5 to afford followed by preparative HPLC to afford 4-(6-(4-(4-(diethylamino)-4-methylpiperidine-1-carbonyl)phenyl) imidazo[1,2-a]pyridin-3-yl)benzonitrile (100 mg, 46%, AUC HPLC 97.2%) as an off white solid; m.p. 204-208° C. $^1$H NMR (400 MHz, DMSO-$d_6$) δ (ppm): 8.49 (s, 1H), 7.84-7.71 (m, 6H), 7.60-7.50 (m, 5H), 3.85-3.59 (m, 3H), 3.33 (bs, 1H), 2.57-2.49 (m, 4H), 1.90 (bs, 1H), 1.74 (bs, 1H), 1.42-1.30 (m, 2H), 1.06-1.01 (m, 9H); MS (ESI) m/z 492.34 $[C_{31}H_{33}N_5O+H]^+$.

Example 101: 4-(3-(4-cyanophenyl)imidazo[1,2-a]pyridin-6-yl)-N-methyl-N-(2-morpholino-2-oxoethyl)benzamide

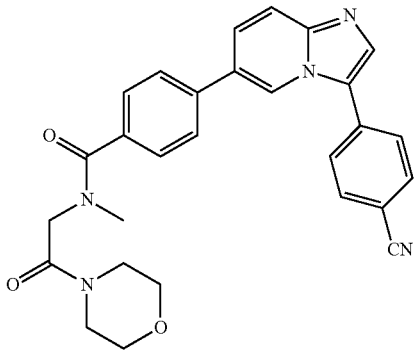 [SMILES: CN(CC(=O)N1CCOCC1)C(=O)c1ccc(-c2ccc3ncc(-c4ccc(C#N)cc4)n3c2)cc1]

To a solution of 4-(3-(4-cyanophenyl)imidazo[1,2-a]pyridin-6-yl)benzoic acid (100 mg, 0.295 mmol) in DMF (1.5 mL) was added HATU (168 mg, 0.442 mmol) and N-methyl morpholine (130 µl, 1.178 mmol). The reaction mixture was stirred at room temperature under inert atmosphere for 1 h, followed by the addition of 2-(methylamino)-1-morpholinoethanone hydrochloride (115 mg, 0.589 mmol). The reaction mixture was stirred for 18 h, then was diluted with water (25 mL) and extracted with EtOAc (3×25 mL). The combined organic layer was dried over Na$_2$SO$_4$ and was concentrated under reduced pressure. The crude residue was purified by column chromatography (silica gel, eluent CH$_2$Cl$_2$/MeOH 97:3) to afford 4-(3-(4-cyanophenyl)imidazo[1,2-a]pyridin-6-yl)-N-methyl-N-(2-morpholino-2-oxoethyl)benzamide (87 mg, 61%, AUC HPLC 97%) as a white solid. $^1$H NMR (400 MHz, CDCl$_3$) δ 8.50 (s, 1H), 7.84-7.79 (m, 4H), 7.75-7.73 (m, 2H), 7.63-7.52 (m, 5H), 4.36 (s, 2H), 3.73-3.54 (m, 8H), 3.11 (s, 3H); $^{13}$C NMR (100 MHz, DMSO-d$_6$) δ 170.16, 166.08, 145.71, 137.68, 135.54, 135.04, 133.49, 133.16, 127.75, 127.60, 126.95, 125.75, 124.42, 121.83, 118.78, 117.76, 109.80, 66.06, 52.21, 48.37, 44.53, 41.68, 34.39; MS (ESI) m/z 480 [C$_{28}$H$_{25}$N$_5$O$_3$+H]$^+$.

Example 102: 4-(6-(4-(3-oxopiperazine-1-carbonyl)phenyl)imidazo[1,2-a]pyridin-3-yl)benzonitrile

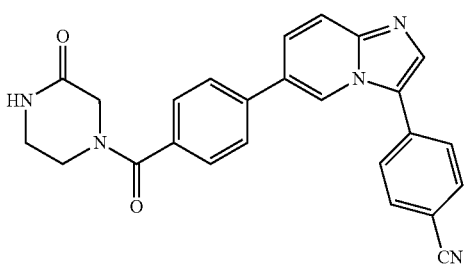 [SMILES: N#Cc1ccc(-c2cnc3ccc(-c4ccc(C(=O)N5CCNC(=O)C5)cc4)cn23)cc1]

To a solution of 4-(3-(4-cyanophenyl)imidazo[1,2-a]pyridin-6-yl)benzoic acid (70 mg, 0.206 mmol) in DMF (1.0 mL) were added HATU (117 mg, 0.309 mmol), N-methyl morpholine (90 µL, 0.824 mmol) and 2-oxopiperazine (25 mg, 0.247 mmol). The reaction mixture was stirred at room temperature under inert atmosphere for 18 h, then was diluted with water (15 mL) and extracted with EtOAc (3×30 mL). The combined organic layer was dried over Na$_2$SO$_4$ and was concentrated under reduced pressure. The residue was purified by column chromatography (silica gel, eluent CHCl$_3$/MeOH 95:5) to afford 4-(6-(4-(3-oxopiperazine-1-carbonyl)phenyl)imidazo[1,2-a]pyridin-3-yl)benzonitrile (80 mg, 92%, AUC HPLC 98%) as a white solid. $^1$H NMR (400 MHz, DMSO-d$_6$) δ 8.81 (s, 1H), 8.13 (bs, 1H), 7.95-8.05 (m, 5H), 7.78-7.89 (m, 3H), 7.70-7.78 (m, 1H), 7.57 (d, J=8.53 Hz, 2H), 4.09 (bs, 2H), 3.72 (bs., 1H), 3.55 (bs, 1H), 3.26 (bs, 2H); $^{13}$C NMR (100 MHz, DMSO-d$_6$) δ 168.65, 145.74, 138.12, 135.06, 133.48, 133.17, 127.75, 128.00, 125.69, 125.55, 124.44, 121.93, 118.79, 117.76, 109.79; MS (ESI) m/z 422 [C$_{25}$H$_{19}$N$_5$O$_2$+H]$^+$.

Example 103: 4-(6-(4-(4-methyl-1,4-diazepane-1-carbonyl)phenyl)imidazo[1,2-a]pyridin-3-yl)benzonitrile

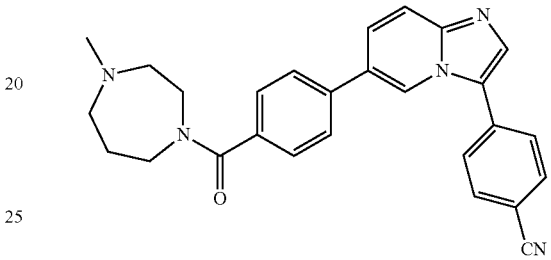

To a solution of 4-(3-(4-cyanophenyl)imidazo[1,2-a]pyridin-6-yl)benzoic acid (70 mg, 0.206 mmol) in DMF (1.0 mL) were added HATU (117 mg, 0.309 mmol), N-methyl morpholine (90 µL, 0.824 mmol) and N-methylhomopiperazine (31 µl, 0.247 mmol). The reaction mixture was stirred at room temperature under inert atmosphere for 18 h, then was diluted with water (15 mL) and extracted with EtOAc (3×30 mL). The combined organic layer was dried over Na$_2$SO$_4$ and was concentrated under reduced pressure. The residue was purified by column chromatography (silica gel, eluent CHCl$_3$/MeOH 90:10) to afford 4-(6-(4-(4-methyl-1,4-diazepane-1-carbonyl)phenyl)imidazo[1,2-a]pyridin-3-yl)benzonitrile (47 mg, 52%, AUC HPLC 98%) as a white solid. $^1$H NMR (400 MHz, CD$_3$OD) δ 8.76 (s, 1H), 7.90-7.97 (m, 4H), 7.88 (s, 1H), 7.74-7.82 (m, 4H), 7.56 (d, J=8.2 Hz, 2H), 3.80-3.83 (m, 1H), 3.74-3.80 (m, 1H), 3.56-3.62 (m, 1H), 3.52-3.56 (m, 1H), 2.95 (s, 1H), 2.86 (bs, 1H), 2.70-2.76 (m, 1H), 2.64-2.70 (m, 2H), 2.42 (d, J=0.8 Hz, 3H), 1.86-1.94 (m, 1H); $^{13}$C NMR (100 MHz, DMSO-d$_6$) δ 169.94, 145.78, 135.10, 133.55, 133.22, 127.81, 127.47, 127.03, 125.80, 125.59, 124.47, 121.81, 118.84, 117.83, 109.84, 47.98; MS (ESI) m/z 436 [C$_{27}$H$_{25}$N$_5$O+H]$^+$.

Example 104: 4-(6-(4-(4-(piperazin-1-yl)piperidine-1-carbonyl)phenyl)imidazo[1,2-a]pyridin-3-yl)benzonitrile

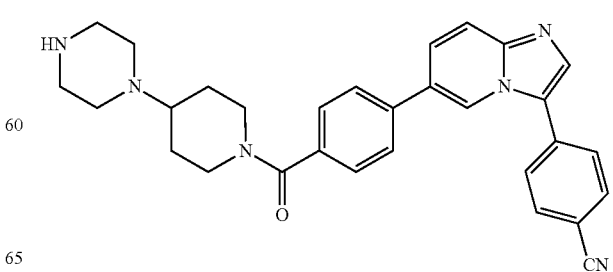

Step 1: To a solution of 4-(3-(4-cyanophenyl)imidazo[1,2-a]pyridin-6-yl)benzoic acid (100 mg, 0.294 mmol) in DMF (1.5 mL) were added HATU (168 mg, 0.441 mmol), N-methyl morpholine (129 µL, 1.18 mmol) and 1-Boc-4-(piperidin-4-yl)piperazine (95 mg, 0.353 mmol). The reaction mixture was stirred at room temperature under inert atmosphere for 18 h, then was diluted with water (15 mL) and extracted with EtOAc (3×30 mL). The combined organic layer was dried over $Na_2SO_4$ and was concentrated under reduced pressure. The residue was purified by column chromatography (silica gel, eluent $CHCl_3$/MeOH 96:4) to afford tert-butyl 4-(1-(4-(3-(4-cyanophenyl)imidazo[1,2-a]pyridin-6-yl)benzoyl)piperidin-4-yl)piperazine-1-carboxylate (57 mg, 33%, AUC HPLC 98%) as a white solid. $^1$H NMR (400 MHz, $CD_3OD$) δ 8.76 (bs., 1H), 7.96-7.88 (m, 5H), 7.83-7.77 (m, 4H), 7.56 (d, J=8.0 Hz, 2H), 4.00-3.85 (m, 1H), 3.65-3.55 (m, 4H), 3.25-3.10 (m, 2H), 3.10-3.00 (m, 4H), 3.00-2.70 (m, 2H), 2.25-1.95 (m, 2H), 1.75-1.55 (m, 2H), 1.47 (s, 9H); $^{13}$C NMR (100 MHz, DMSO-$d_6$) δ 171.93, 155.72, 140.09, 136.30, 134.67, 134.40, 134.25, 129.50, 129.96, 128.76, 128.55, 128.10, 122.92, 119.49, 118.30, 112.80, 82.11, 64.13, 28.53; MS (ESI) m/z 591 $[C_{35}H_{38}N_6O_3+H]^+$.

Step 2: A solution of tert-butyl 4-(1-(4-(3-(4-cyanophenyl)imidazo[1,2-a]pyridin-6-yl)benzoyl)piperidin-4-yl)piperazine-1-carboxylate (56 mg, 0.095 mmol) was added 20% TFA in $CH_2Cl_2$ (5 mL). The reaction mixture was stirred at room temperature for 20 min then, was concentrated under reduced pressure. To the residue was added saturated sodium bicarbonate (10 mL) and extracted with EtOAc (3×30 mL). The combined organic was dried over $Na_2SO_4$ and concentrated under reduced pressure. The residue was purified by preparative HPLC (C18, eluent ACN, water, formic acid 0.1%) to afford 4-(6-(4-(4-(piperazin-1-yl)piperidine-1-carbonyl)phenyl)imidazo[1,2-a]pyridin-3-yl)benzonitrile (47 mg, 99%, AUC HPLC 99%) as a yellow solid. $^1$H NMR (400 MHz, $CD_3OD$) δ 8.88 (s, 1H), 8.36-8.30 (m, 2H), 8.11 (d, J=9.6 Hz, 1H), 8.05-7.98 (m, 4H), 7.84 (d, J=8.4 Hz, 2H), 7.59 (d, J=8.0 Hz, 2H), 4.75-4.65 (m, 1H), 3.90-3.75 (m, 1H), 3.35-3.25 (m, 1H), 3.25-3.15 (m, 1H), 3.10-3.00 (m, 4H), 3.00-2.85 (m, 2H), 2.15-1.85 (m, 2H), 1.70-1.50 (m, 2H), 1.40-1.20 (m, 2H), 1.00-0.85 (m, 1H) $^{13}$C NMR (100 MHz, DMSO-$d_6$) δ 168.47, 158.52, 158.19, 136.84, 135.75, 133.25, 131.81, 128.85, 127.55, 127.38, 125.16, 122.92, 118.59, 117.87, 115.44, 114.92, 111.09, 61.85, 45.27; MS (ESI) m/z 491 $[C_{30}H_{30}N_6O+H]^+$.

Example 105: 4-(6-(4-(1'-methyl-4,4'-bipiperidine-1-carbonyl)phenyl)imidazo[1,2-a]pyridin-3-yl)benzonitrile

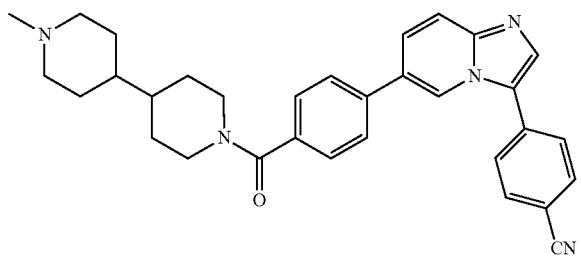

To a solution of 4-(3-(4-cyanophenyl)imidazo[1,2-a]pyridin-6-yl)benzoic acid (100 mg, 0.294 mmol) in DMF (1.5 mL) were added HATU (168 mg, 0.441 mmol), N-methyl morpholine (129 µL, 1.18 mmol) and, 1-methyl-4,4'-bipiperidine (64 mg, 0.353 mmol). The reaction mixture was stirred at room temperature under inert atmosphere for 18 h, then it was diluted with water (15 mL) and extracted with EtOAc (3×30 mL). The combined organic layer was dried over $Na_2SO_4$ and was concentrated under reduced pressure. The residue was purified by column chromatography (silica gel, eluent $CHCl_3$/MeOH 96:4), followed by cold $CH_3OH$/$CH_3CN$ wash to afford 4-(6-(4-(1'-methyl-4,4'-bipiperidine-1-carbonyl)phenyl)imidazo[1,2-a]pyridin-3-yl)benzonitrile (131 mg, 89%, AUC HPLC 97%) as a white solid. $^1$H NMR (400 MHz, DMSO-$d_6$) δ 8.80 (s, 1H), 8.04-7.98 (m, 5H), 7.87-7.79 (m, 3H), 7.77-7.70 (m, 1H), 7.50 (d, J=8.0 Hz, 2H), 4.60-4.40 (m, 1H), 3.75-3.60 (m, 1H), 3.45-3.35 (m, 1H), 3.15-2.70 (m, 9H), 2.65-2.55 (m, 1H), 2.50-2.35 (m, 2H), 1.90-1.65 (m, 2H), 1.50-1.30 (m, 2H), 1.30-1.10 (m, 1H); $^{13}$C NMR (100 MHz, DMSO-$d_6$) δ 168.39, 145.66, 137.60, 135.02, 133.44, 133.09, 127.69, 127.41, 126.94, 125.67, 125.46, 124.34, 121.74, 118.71, 117.71, 109.72, 53.11, 45.67; MS (ESI) m/z 505 $[C_{32}H_{33}N_5O+H]^+$.

Example 106: 4-(6-(4-(4-hydroxy-4-methylpiperidine-1-carbonyl)phenyl)imidazo[1,2-a]pyridin-3-yl)benzonitrile

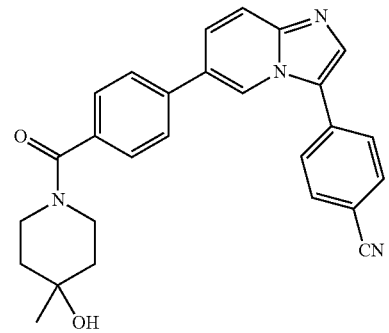

To a solution of 4-(3-(4-cyanophenyl)imidazo[1,2-a]pyridin-6-yl)benzoic acid (200 mg, 0.58 mmol) in DMF (15.0 mL) were added HATU (335 mg, 0.88 mmol), N-methyl morpholine (0.21 mL, 1.17 mmol) and 4-methylpiperidin-4-ol hydrochloride (115 mg, 0.76 mmol). The reaction mixture was stirred at room temperature under inert atmosphere for 16 h, then it was diluted with water (25 mL) and extracted with EtOAc (3×25 mL). The combined organic layer was dried over $Na_2SO_4$ and was concentrated under reduced pressure. The crude residue was purified by column chromatography (silica gel, eluent $CH_2Cl_2$/MeOH 95:5) followed by preparative HPLC to afford 4-(6-(4-(4-hydroxy-4-methylpiperidine-1-carbonyl)phenyl) imidazo[1,2-a]pyridin-3-yl)benzonitrile (100 mg, 40%, AUC HPLC>99%) as an off white solid; m.p. 149-154° C. $^1$H NMR (400 MHz, DMSO-$d_6$) δ (ppm): 8.80 (bs, 1H), 8.03-7.97 (m, 5H), 7.82-7.71 (m, 4H), 7.48 (d, J=8.0 Hz, 2H), 4.45 (s, 1H), 4.11 (bs, 1H), 3.41 (bs, 1H), 3.27 (bs, 2H), 1.53-1.44 (m, 4H), 1.16 (s, 3H); MS (ESI) m/z 437.26 $[C_{27}H_{24}N_4O_2+H]^+$.

Example 107: 4-(6-(4-(1,4-diazepane-1-carbonyl) phenyl)imidazo[1,2-a]pyridin-3-yl)benzonitrile

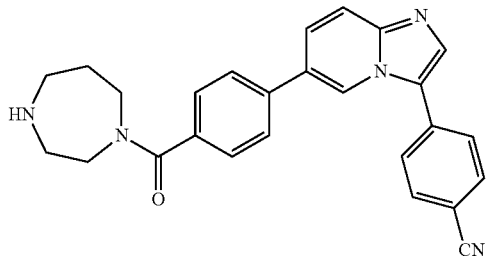 [SMILES: N#Cc1ccc(-c2cnc3ccc(-c4ccc(C(=O)N5CCCNCC5)cc4)cn23)cc1]

Step 1: To a solution of 4-(3-(4-cyanophenyl) imidazo[1, 2-a]pyridin-6-yl)benzoic acid (100 mg, 0.29 mmol) in DMF (3 mL) were added HATU (165 mg, 0.44 mmol), N-methyl morpholine (117 mg, 1.16 mmol) and tert-butyl 1,4-diazepane-1-carboxylate (118 mg, 0.59 mmol). The reaction mixture was stirred at room temperature under inert atmosphere for 18 h before being diluted with water (10 mL) and extracted with DCM (3×10 mL). The combined organic layer was dried over $Na_2SO_4$ and was concentrated under reduced pressure. The residue was purified by column chromatography (silica gel, eluent DCM/MeOH 7:3) to afford tert-butyl 4-(4-(3-(4-cyanophenyl)imidazo[1,2-a] pyridin-6-yl)benzoyl)-1,4-diazepane-1-carboxylate (120 mg, 79%, AUC HPLC 98%) as white solid. MS (ESI) m/z 522 $[C_{31}H_{31}N_5O_3+H]^+$.

Step 2: To a solution of tert-butyl 4-(4-(3-(4-cyanophenyl) imidazo[1,2-a]pyridin-6-yl)benzoyl)-1,4-diazepane-1-carboxylate in DCM (3 mL) was added TFA (3 mL). The reaction mixture was stirred at room temperature for 18 h then, was concentrated under reduced pressure and the residue was purified by preparative HPLC (C18, eluent ACN/$H_2O$/0.01% HCOOH) to afford 4-(6-(4-(1,4-diazepane-1-carbonyl)phenyl)imidazo[1,2-a]pyridin-3-yl)benzonitrile (78 mg, 64%, AUC HPLC 98%) as white solid. $^1$H NMR (400 MHz, $CD_3OD$) δ 8.75 (s, 1H), 7.93 (s, 4H), 7.89 (s, 1H), 7.81 (d, J=8.2 Hz, 2H), 7.77 (s, 2H), 7.61 (d, J=8.2 Hz, 2H), 4.05-3.60 (m, 4H), 3.50-3.32 (m, 4H), 2.27-2.00 (m, 2H); $^{13}$C NMR (400 MHz, $CD_3OD$) δ 173.64, 166.40, 147.45, 140.31, 136.31, 134.85, 134.72, 134.43, 129.51, 129.00, 128.59, 127.84, 126.63, 122.92, 119.53, 118.53, 112.79, 46.73, 45.87, 43.46, 27.48; MS (ESI) m/z 422 $[C_{26}H_{23}N_5O+H]^+$.

Example 108: 4-(6-(4-(4-(piperidin-4-yl)piperazine-1-carbonyl)phenyl)imidazo[1,2-a]pyridin-3-yl)benzonitrile

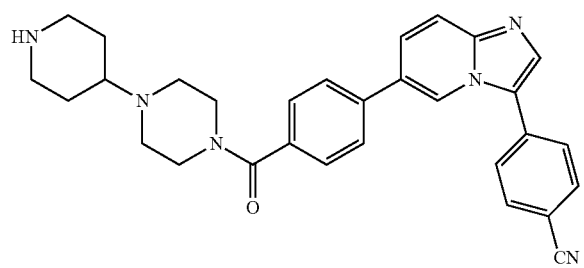 [SMILES: N#Cc1ccc(-c2cnc3ccc(-c4ccc(C(=O)N5CCN(C6CCNCC6)CC5)cc4)cn23)cc1]

Step 1: To a solution of 4-(3-(4-cyanophenyl) imidazo[1, 2-a]pyridin-6-yl)benzoic acid (200 mg, 0.58 mmol) in DMF (3 mL), were sequentially added HATU (330 mg, 0.87 mmol), N-methyl morpholine (235 mg, 2.32 mmol) and tert-butyl 4-(piperazin-1-yl)piperidine-1-carboxylate (312 mg, 1.16 mmol). The reaction mixture was stirred at room temperature under inert atmosphere for 18 h then, was diluted with water (10 mL) and extracted with DCM (3×15 mL). The combined organic layer was dried over $Na_2SO_4$, filtered and concentrated under reduced pressure. The residue was purified by column chromatography (silica gel, eluent DCM/MeOH 9:1) to afford tert-butyl 4-(4-(4-(3-(4-cyanophenyl)imidazo[1,2-a]pyridin-6-yl)benzoyl)piperazin-1-yl)piperidine-1-carboxylate (239 mg, 69%, AUC HPLC 95%) as an off-white solid. $^1$H NMR (400 MHz, $CD_3OD$) δ 8.64 (s, 1H), 7.84 (s, 4H), 7.80 (s, 1H), 7.20-7.65 (m, 4H), 7.49 (d, J=8.0 Hz, 2H), 4.72 (s, 1H), 4.00-3.69 (s, 1H), 3.55-3.36 (m, 4H), 3.29-2.75 (m, 2H), 2.65-2.49 (m, 5H), 2.19-1.59 (m, 2H), 1.59-1.38 (m, 11H); MS (ESI) m/z 591 $[C_{35}H_{38}N_6O_3+H]^+$.

Step 2: To a solution of tert-butyl 4-(4-(4-(3-(4-cyanophenyl)imidazo[1,2-a]pyridin-6-yl)benzoyl)piperazin-1-yl) piperidine-1-carboxylate in DCM (3 mL), was added TFA (3 mL). The reaction mixture was stirred at room temperature for 18 h then, was concentrated under reduced pressure and the residue was purified by column chromatography (silica gel, eluent DCM/MeOH 4:1) to afford 4-(6-(4-(4-(piperidin-4-yl)piperazine-1-carbonyl)phenyl)imidazo[1,2-a]pyridin-3-yl)benzonitrile (141 mg, 48%, AUC HPLC 99%) as pink solid. $^1$H NMR (400 MHz, $CD_3OD$) δ 8.79 (s, 1H), 8.09-8.03 (s, 1H), 8.02-7.98 (m, 1H), 7.96 (s, 4H), 7.94-7.88 (m, 1H), 7.80 (d, J=8.0 Hz, 2H), 7.55 (d, J=8.0 Hz, 2H), 4.66 (s, 1H), 3.82 (s, 1H), 3.28-3.06 (m, 5H), 3.00-2.83 (m, 5H), 2.76 (m, J=5.5 Hz, 1H), 2.08-1.74 (m, 2H), 1.67-1.40 (m, 2H); $^{13}$C NMR (100 MHz, $CD_3OD$) δ 171.78, 163.59, 163.24, 162.90, 162.56, 145.15, 139.22, 137.14, 135.65, 134.53, 133.45, 130.87, 130.28, 130.20, 129.37, 128.96, 128.86, 128.73, 127.23, 123.65, 119.75, 119.36, 116.94, 113.75, 62.66, 47.18, 45.13, 44.43, 42.58, 29.70, 28.94; MS (ESI) m/z 491 $[C_{35}H_{30}N_6O+H]^+$

Example 109: 4-(6-(4-(4-aminopiperidine-1-carbonyl)phenyl)imidazo[1,2-a]pyridin-3-yl)benzonitrile

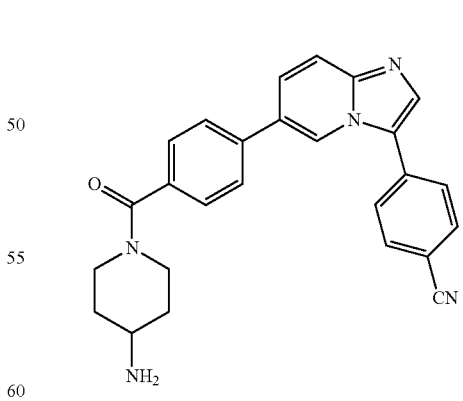

Step 1: To a solution of 4-(3-(4-cyanophenyl)imidazo[1, 2-a]pyridin-6-yl)benzoic acid (300 mg, 0.88 mmol) in DMF (2 mL) was added NMM (134 mg, 1.33 mmol) followed by addition of HATU (504 mg, 1.33 mmol) at rt and stirred for 30 min. tert-butyl piperidin-4-ylcarbamate (195 mg, 0.97 mmol) was added and stirred at rt for 1 h. The reaction mixture was diluted with water and filtered to obtain of tert-butyl 1-(4-(3-(4-cyanophenyl)imidazo[1,2-a]pyridin-6-yl)benzoyl)piperidin-4-ylcarbamate (325 mg, 55%, LC-MS 78.5%) as a pale yellow solid. MS (ESI) m/z: 522.2 (M+H).

Step 2: Trifluoroacetic acid (3.5 mL) in CH$_2$Cl$_2$ (15 mL) was added to a solution of tert-butyl 1-(4-(3-(4-cyanophenyl)imidazo[1,2-a]pyridin-6-yl)benzoyl)piperidin-4-ylcarbamate (325 mg, 0.624 mmol) in CH$_2$Cl$_2$ at 0° C. and stirred at rt for 1 h. Reaction mixture was diluted with water and basified with sat.Na$_2$CO$_3$ solution. The aqueous layer was extracted with EtOAc, dried and concentrated under reduced pressure to give crude product which, was purified by preparative HPLC to afford 4-(6-(4-(4-aminopiperidine-1-carbonyl)phenyl)imidazo[1,2-a]pyridin-3-yl)benzonitrile (30 mg, 21%, AUC HPLC 97.3%) as an off-white solid; m.p. 129-138° C. $^1$H NMR (400 MHz, DMSO-d$_6$) δ (ppm): 8.80 (s, 1H), 8.03-7.97 (m, 5H), 7.82 (d, J=11.0 Hz, 2H), 7.72 (d, J=14.0 Hz, 2H), 7.46 (d, J=11.0 Hz, 2H), 4.29 (bs, 1H), 3.57 (bs, 1H), 3.07-2.84 (m, 3H), 2.27-2.18 (m, 2H), 1.76 (bs, 2H), 1.23 (bs, 2H); MS (ESI) m/z 422.24 [C$_{26}$H$_{23}$N$_5$O+H]$^+$.

Example 110: N-(1-(4-(3-(4-cyanophenyl)imidazo [1,2-a]pyridin-6-yl)benzoyl)piperidin-4-yl)-2,2,2-trifluoroacetamide

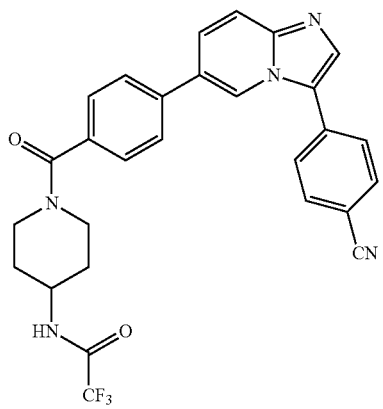 [SMILES: N#Cc1ccc(-c2cnc3ccc(-c4ccc(C(=O)N5CCC(NC(=O)C(F)(F)F)CC5)cc4)cn23)cc1]

To a solution of 4-(6-(4-(4-aminopiperidine-1-carbonyl)phenyl)imidazo[1,2-a]pyridin-3-yl)benzonitrile (300 mg, 0.71 mmol) in dichloromethane (10 mL) were added trifluoroacetic anhydride (0.12 mL, 0.85 mmol) and triethyl amine (0.2 mL, 1.42 mmol) in dichloromethane. The reaction mixture was stirred for 2 h at rt. The reaction mixture was diluted with H$_2$O (100 mL), NaHCO$_3$ (100 mL) and extracted with CH$_2$Cl$_2$ (2×50 mL). The combined organic layer was concentrated to dryness under reduced pressure to afford crude compound. The crude product was purified by Prep-HPLC (C18, ACN/H$_2$O/10 mM NH$_4$HCO$_3$) to afford N-(1-(4-(3-(4-cyanophenyl)imidazo[1,2-a]pyridin-6-yl)benzoyl)piperidin-4-yl)-2,2,2-trifluoroacetamide (120 mg, 33%, AUC HPLC 97.7%) as a white solid; $^1$H NMR (400 MHz, DMSO-d$_6$) δ (ppm): 9.40 (d, J=9.3 Hz, 1H), 8.80 (s, 1H), 8.03-7.97 (m, 5H), 7.86-7.82 (m, 4H), 7.50 (d, J=7.48 Hz, 2H), 4.47 (s, 1H), 3.97 (q, J=3.2 Hz, 1H), 3.69-3.36 (m, 1H), 3.31-3.28 (m, 1H), 2.97-2.93 (m, 1H), 2.07-1.77 (m, 2H), 1.51-1.49 (m, 2H); MS (ESI) m/z 518.31 [C$_{28}$H$_{22}$F$_3$N$_5$O$_2$+H]$^+$.

Example 111: N-(1-(4-(3-(4-cyanophenyl)imidazo [1,2-a]pyridin-6-yl)benzoyl)piperidin-4-yl)methanesulfonamide

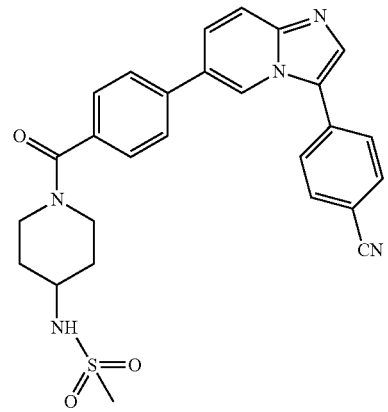 [SMILES: CS(=O)(=O)NC1CCN(C(=O)c2ccc(-c3ccc4ncc(-c5ccc(C#N)cc5)n4c3)cc2)CC1]

To a solution of 4-(6-(4-(4-aminopiperidine-1-carbonyl)phenyl)imidazo[1,2-a]pyridin-3-yl)benzonitrile (130 mg, 0.30 mmol) in dichloromethane (10 mL) were added TEA (0.12 mL, 0.91 mmol) and MsCl (0.42 mL, 0.37 mmol). The reaction mixture was stirred for 2 h at ambient temperature and diluted with H$_2$O (100 mL), NaHCO$_3$ (100 mL) and extracted with CH$_2$Cl$_2$ (2×50 mL). The combined organic layer was concentrated to dryness under reduced pressure to afford crude compound. The crude product was purified by preparative HPLC to afford N-(1-(4-(3-(4-cyanophenyl)imidazo[1,2-a]pyridin-6-yl)benzoyl)piperidin-4-yl)methanesulfonamide (60 mg, 42%, AUC HPLC 99.02%) as an off-white solid; mp 211-215° C., $^1$H NMR (400 MHz, CDCl$_3$) δ (ppm): 8.50 (s, 1H), 7.84-7.80 (m, 4H), 7.73 (d, J=8.4 Hz, 2H), 7.59 (d, J=8.0 Hz, 2H), 7.53-7.50 (m, 3H), 4.60 (bs, 1H), 4.29 (d, J=7.6 Hz, 1H), 3.85 (bs, 1H), 3.63-3.60 (m, 1H), 3.15 (bs, 2H), 3.09 (s, 3H), 2.03 (bs, 2H), 1.45 (bs, 2H); MS (ESI) m/z 500 [C$_{27}$H$_{25}$N$_5$O$_3$S+H]$^+$.

Example 112: 4-(6-(4-(4-(dimethylamino)piperidine-1-carbonyl)phenyl)imidazo[1,2-a]pyridin-3-yl)benzonitrile

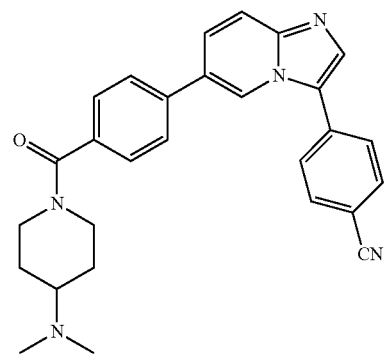

To a solution of 4-(3-(4-cyanophenyl)imidazo[1,2-a]pyridin-6-yl)benzoic acid (0.2 g, 0.58 mmol) in DMF (5 mL) were added HATU (0.33 g, 0.88 mmol), N-methyl morpholine (0.18 g, 1.76 mmol) and N,N-dimethylpiperidin-4- amine (81 mg, 0.70 mmol). The reaction mixture was stirred at 0° C. to room temperature under inert atmosphere for 16 h, then it was diluted with water (15 mL) and extracted with EtOAc (3×25 mL). The combined organic layer was dried over Na$_2$SO$_4$ and was concentrated under reduced pressure. The crude residue was purified by column chromatography (silica gel, eluent CH$_2$Cl$_2$/MeOH 95:5) to afford 4-(6-(4-(4-(dimethylamino)piperidine-1-carbonyl)phenyl)imidazo[1,2-a]pyridin-3-yl)benzonitrile (140 mg, 57%, AUC HPLC>99%) as an off-white solid; m.p. 128-132° C. $^1$H NMR (400 MHz, CDCl$_3$) δ (ppm): 8.49 (s, 1H), 7.84-7.71 (m, 5H), 7.60-7.50 (m, 5H), 7.80 (m, 3H), 7.71 (m, 1H), 7.45 (q, 2H), 4.45 (bs, 1H), 3.65 (bs, 1H), 3.15-2.8 (m, 2H), 2.39 (m, 1H), 2.22 (bs, 6H), 1.9-1.6 (m, 2H), 1.35 (m, 2H); MS (ESI) m/z 450.3 [C$_{28}$H$_{27}$N$_5$O+H]$^+$.

Example 113: 4-(6-(4-(4-amino-4-ethylpiperidine-1-carbonyl)phenyl)imidazo[1,2-a]pyridin-3-yl)benzonitrile

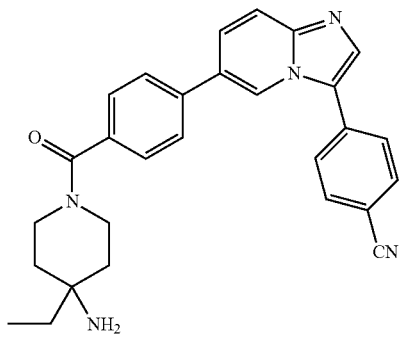 [SMILES: CCC1(N)CCN(C(=O)c2ccc(-c3ccc4ncc(-c5ccc(C#N)cc5)n4c3)cc2)CC1]

Step 1: To a solution of 4-(3-(4-cyanophenyl)imidazo[1,2-a]pyridin-6-yl)benzoic acid (100 mg, 0.294 mmol) in DMF (1.5 mL) was added HATU (168 mg, 0.442 mmol) and N-methyl morpholine (130 μl, 1.178 mmol). The reaction mixture was stirred at room temperature under inert atmosphere for 1 h, followed by the addition of tert-butyl 4-ethylpiperidin-4-ylcarbamate (134 mg, 0.589 mmol). The reaction mixture was stirred for 18 h, then was diluted with water (25 mL) and extracted with EtOAc (3×25 mL). The combined organic layer was dried over Na$_2$SO$_4$ and was concentrated under reduced pressure. The crude residue was purified by column chromatography (silica gel, eluent CH$_2$Cl$_2$/MeOH 95:5) to afford a white solid (45 mg, 28%, AUC HPLC 96%); MS (ESI) m/z 550 [C$_{33}$H$_{35}$N$_5$O$_3$+H]$^+$.

Step 2: To a solution of tert-butyl 1-(4-(3-(4-cyanophenyl)imidazo[1,2-a]pyridin-6-yl)benzoyl)-4-ethylpiperidin-4-ylcarbamate (45 mg, 0.082 mmol) in DCM (1.0 mL) was added trifluoroacetic acid (1 mL). The reaction mixture was stirred at room temperature under inert atmosphere for 30 min, then was neutralized with NaHCO$_3$, diluted with water (25 mL) and extracted with EtOAc (3×25 mL). The combined organic layer was dried over Na$_2$SO$_4$ and was concentrated under reduced pressure. The crude residue was purified by column chromatography (silica gel, eluent CH$_2$Cl$_2$/MeOH/NH$_4$OH 90:9:1) to afford 4-(6-(4-(4-amino-4-ethylpiperidine-1-carbonyl)phenyl)imidazo[1,2-a]pyridin-3-yl)benzonitrile (6 mg, 16%, AUC HPLC 98%) as a white solid. $^1$H NMR (400 MHz, CD$_3$OD) δ 8.77 (s, 1H), 7.97-7.90 (m, 5H), 7.82-7.79 (m, 4H), 7.55 (d, J=8.4 Hz, 2H), 3.90-3.54 (m, 4H), 1.75-1.51 (m, 6H), 0.98 (t, J=7.6 Hz, 3H); MS (ESI) m/z 451 [C$_{28}$H$_{27}$N$_5$O+H]$^+$.

Example 114: 4-(6-(4-(2,7-diazaspiro[3.5]nonane-7-carbonyl)phenyl)imidazo[1,2-a]pyridin-3-yl)benzonitrile

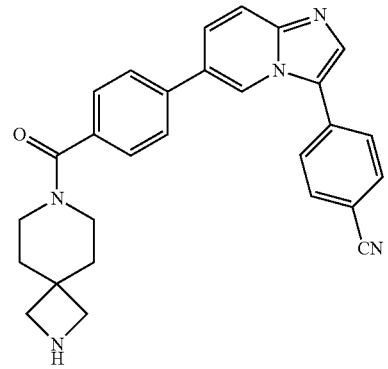 [SMILES: N#Cc1ccc(-c2cnc3ccc(-c4ccc(C(=O)N5CCC6(CC5)CNC6)cc4)cn23)cc1]

Step 1: To a solution of 4-(3-iodoimidazo[1,2-a]pyridin-6-yl)benzoic acid (500 mg, 1.37 mmol) in DMF (15.0 mL) were added HATU (782.9 mg, 2.05 mmol), N-methyl morpholine (0.03 mL, 2.74 mmol) and 1-methylpiperazine (340 mg, 1.5 mmol). The reaction mixture was stirred at room temperature under inert atmosphere for 16 h, then it was diluted with water (25 mL) and extracted with EtOAc (3×25 mL). The combined organic layer was dried over Na$_2$SO$_4$ and was concentrated under reduced pressure. The crude product was purified by column chromatography (silica gel, eluent CH$_2$Cl$_2$/MeOH 95:5) to afford tert-butyl 7-(4-(3-(4-cyanophenyl)imidazo[1,2-a]pyridin-6-yl)benzoyl)-2,7-diazaspiro[3.5]nonane-2-carboxylate (440 mg, 56%) as an off-white solid. $^1$H NMR (400 MHz, DMSO-d$_6$) δ (ppm): 8.45 (s, 1H), 7.94-7.67 (m, 5H), 4.08 (s, 1H), 3.98 (s, 1H), 3.79 (s, 1H), 3.29 (m, 4H), 2.89 (s, 3H), 1.77-1.70 (m, 4H), 1.38 (s, 9H); MS (ESI) m/z 573.1 [C$_{26}$H$_{29}$IN$_4$O$_3$+H]$^+$.

Step 2: 4-cyanophenylboronic acid (135 mg, 0.92 mmol), K$_3$PO$_4$ (326 mg, 1.53 mmol), and Pd(PPh$_3$)$_4$ (66 mg, 0.04 mmol) were added sequentially to a solution of tert-butyl 7-(4-(3-(4-cyanophenyl)imidazo[1,2-a]pyridin-6-yl)benzoyl)-2,7-diazaspiro[3.5]nonane-2-carboxylate (440 mg, 0.769 mmol) in a mixture of 1,4-Dioxane/H$_2$O (30:10 mL) at room temperature under argon atmosphere. The reaction mixture was refluxed for 6 h and was diluted with water (50 mL) and extracted with EtOAc (3×50 mL). The combined organic layer was dried over Na$_2$SO$_4$, filtered and concentrated under reduced pressure. The residue was purified by column chromatography (silica gel, eluent CHCl$_3$/MeOH 95:5) to afford 4-(6-(4-(2,7-diazaspiro[3.5]nonane-7-carbonyl)phenyl)imidazo[1,2-a]pyridin-3-yl)benzonitrile (250 mg, 59%). $^1$H NMR (400 MHz, DMSO-d$_6$) δ (ppm): 8.80 (s, 1H), 8.01 (s, 4H), 7.85-7.73 (m, 6H), 4.06 (s, 1H), 3.78 (s, 1H), 3.34 (m, 4H), 1.66 (bs, 4H), 1.38 (s, 9H); MS (ESI) m/z 548 [C$_{33}$H$_{33}$N$_5$O$_3$+H]$^+$ Step 3: To a solution of 4-(6-(4-(2,7-diazaspiro[3.5]nonane-7-carbonyl)phenyl)imidazo[1,2-a]pyridin-3-yl)benzonitrile (150 mg, 0.274 mmol) in dichloromethane (10 mL) were added TFA (3 mL) in dichloromethane (5 mL). The reaction mixture was stirred for 4 h at rt. The reaction mixture was diluted with water (100 mL), NaHCO$_3$ (100 mL) and extracted with CH$_2$Cl$_2$ (2×50 mL). The combined organic layer was concentrated to dryness under reduced pressure to afford crude compound. The crude product was purified by preparative HPLC (C18, ACN/H$_2$O/10 mM NH$_4$HCO$_3$) to afford (4-amino-4-methylpiperidin-1-yl)(4-(3-(4-chlorophenyl)imidazo[1,2-a]pyridin-6-yl)phenyl)methanone (80 mg, 16%, AUC HPLC 97.23%) as a brown solid; ¹H NMR (400 MHz, CDCl₃) δ (ppm): 8.81 (s, 1H), 8.01 (m, 5H), 7.85-7.82 (d, J=7.83 Hz, 3H), 7.76-7.73 (d, J=7.74 Hz, 3H), 4.01 (bs, 2H), 3.73 (bs, 2H), 2.50 (m, 4H), 1.60 (m, 4H); MS (ESI) m/z 448.26 [C₂₈H₂₅N₅O+H]⁺.

Example 115: 4-(3-(4-cyanophenyl)imidazo[1,2-a]pyridin-6-yl)-N-(2-morpholino-2-oxoethyl)benzamide

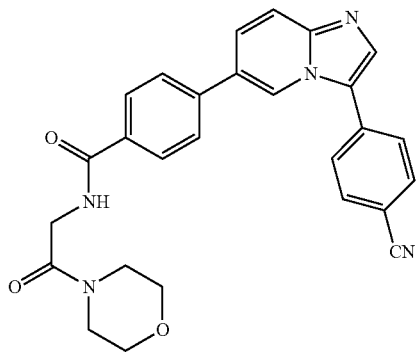 [SMILES: N#Cc1ccc(-c2cnc3ccc(-c4ccc(C(=O)NCC(=O)N5CCOCC5)cc4)cn23)cc1]

To a solution of 4-(3-(4-cyanophenyl)imidazo[1,2-a]pyridin-6-yl)benzoic acid (100 mg, 0.295 mmol) in DMF (1.5 mL) was added HATU (168 mg, 0.442 mmol) and N-methyl morpholine (130 μl, 1.178 mmol). The reaction mixture was stirred at room temperature under inert atmosphere for 1 h, followed by the addition of 2-amino-1-morpholinoethanone (106 mg, 0.589 mmol). The reaction mixture was left to stir for 18 h, then it was diluted with water (25 mL) and extracted with EtOAc (3×25 mL). The combined organic layer was dried over Na₂SO₄ and was concentrated under reduced pressure. The crude residue was purified by column chromatography (silica gel, eluent CH₂Cl₂/MeOH 97:3) to afford 4-(3-(4-cyanophenyl)imidazo[1,2-a]pyridin-6-yl)-N-(2-morpholino-2-oxoethyl)benzamide (84 mg, 61%, AUC HPLC 98%) as a white solid. ¹H NMR (400 MHz, DMSO-d₆) δ 8.84 (s, 1H), 8.65 (t, J=5.6 Hz, 1H), 8.04-7.98 (m, 7H), 7.89-7.87 (m, 2H), 7.84-7.75 (m, 2H), 4.16 (d, J=5.6 Hz, 2H), 3.61-3.57 (m, 4H), 3.51-3.46 (m, 4H); ¹³C NMR (100 MHz, DMSO-d₆) δ 167.20, 165.82, 145.76, 139.39, 135.11, 133.49, 133.28, 133.17, 127.92, 127.75, 126.88, 125.57, 125.52, 124.46, 121.97, 118.79, 117.76, 109.79, 66.04, 44.61, 41.78, 40.81; MS (ESI) m/z 466 [C₂₇H₂₃N₅O₃+H]⁺.

Example 116: 4-(3-(4-cyanophenyl)imidazo[1,2-a]pyridin-6-yl)-N-(2-morpholinoethyl)benzamide

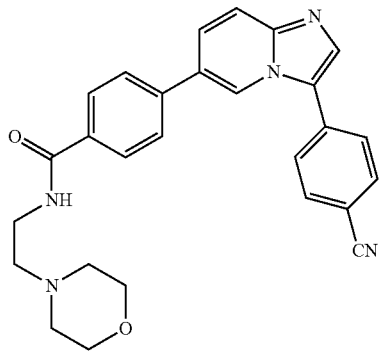 [SMILES: N#Cc1ccc(-c2cnc3ccc(-c4ccc(C(=O)NCCN5CCOCC5)cc4)cn23)cc1]

To a solution of 4-(3-(4-cyanophenyl)imidazo[1,2-a]pyridin-6-yl)benzoic acid (100 mg, 0.295 mmol) in DMF (1.5 mL) was added HATU (168 mg, 0.442 mmol) and N-methyl morpholine (130 μl, 1.178 mmol). The reaction mixture was stirred at room temperature under inert atmosphere for 1 h, followed by the addition of 2-morpholinoethanamine (77 μl, 0.589 mmol). The reaction mixture was left to stir for 18 h, then it was diluted with water (25 mL) and extracted with EtOAc (3×25 mL). The combined organic layer was dried over Na₂SO₄ and was concentrated under reduced pressure. The crude residue was purified by column chromatography (silica gel, eluent CH₂Cl₂/MeOH 95:5) to afford 4-(3-(4-cyanophenyl)imidazo[1,2-a]pyridin-6-yl)-N-(2-morpholinoethyl)benzamide (90 mg, 67%, AUC HPLC 98%) as a white solid. ¹H NMR (400 MHz, CDCl₃) δ 8.52 (s, 1H), 7.90-7.88 (m, 2H), 7.84-7.80 (m, 4H), 7.75-7.73 (m, 2H), 7.64-7.61 (m, 2H), 7.56-7.53 (m, 1H), 3.74 (t, J=4.4 Hz, 4H), 3.61-3.57 (m, 2H), 2.64 (t, J=6.0 Hz, 2H), 2.53 (s, 4H); ¹³C NMR (100 MHz, DMSO-d₆) δ 165.59, 145.69, 139.17, 135.05, 133.54, 133.42, 133.09, 127.75, 127.65, 126.77, 125.51, 125.44, 124.37, 121.85, 118.71, 117.69, 109.72, 65.92, 57.09, 53.04; MS (ESI) m/z 452 [C₂₇H₂₅N₅O₂+H]⁺.

Example 117: 4-(6-(4-(1,9-diazaspiro[5.5]undecane-9-cane-9-carbonyl)phenyl)imidazo[1,2-a]pyridin-3-yl)benzonitrile

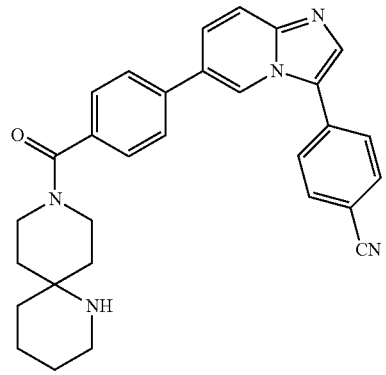 [SMILES: N#Cc1ccc(-c2cnc3ccc(-c4ccc(C(=O)N5CCC6(CCCCN6)CC5)cc4)cn23)cc1]

Step 1: To a solution of 4-(3-(4-cyanophenyl)imidazo[1,2-a]pyridin-6-yl)benzoic acid (120 mg, 0.353 mmol) in DMF (1.7 mL) was added HATU (201 mg, 0.530 mmol) and N-methyl morpholine (155 μl, 1.41 mmol). The reaction mixture was stirred at room temperature under inert atmosphere for 1 h, followed by the addition of tert-butyl 1,9-diazaspiro[5.5]undecane-1-carboxylate hydrochloride (205 mg, 0.707 mmol). The reaction mixture was left to stir for 18 h, then it was diluted with water (25 mL) and extracted with EtOAc (3×25 mL). The combined organic layer was dried over Na₂SO₄ and was concentrated under reduced pressure. The crude residue was purified by column chromatography (silica gel, eluent CH₂Cl₂/MeOH 95:5) to afford tert-butyl 9-(4-(3-(4-cyanophenyl)imidazo[1,2-a]pyridin-6-yl)benzoyl)-1,9-diazaspiro[5.5]undecane-1-carboxylate (192 mg, 94%, AUC HPLC 96%) as a white solid. ¹H NMR (400 MHz, DMSO-d₆) δ 8.81 (s, 1H), 8.03-7.98 (m, 5H), 7.84-7.81 (m, 3H), 7.75-7.72 (m, 1H), 7.49-7.47 (m, 2H), 3.42-3.31 (m, 5H), 1.70-1.51 (m, 9H), 1.40 (bs, 11H); MS (ESI) m/z 576 [C₃₅H₃₇N₅O₃+H]⁺.

Step 2: To a solution of tert-butyl 9-(4-(3-(4-cyanophenyl)imidazo[1,2-a]pyridin-6-yl)benzoyl)-1,9-diazaspiro[5.5]undecane-1-carboxylate (183 mg, 0.318 mmol) in DCM (1.0 mL) was added trifluoroacetic acid (1.0 mL). The reaction mixture was stirred at room temperature under inert atmosphere for 30 min, then was neutralized with solid NaHCO$_3$, then diluted with water (25 mL) and extracted with EtOAc (3×25 mL). The combined organic layer was dried over Na$_2$SO$_4$ and was concentrated under reduced pressure. The crude residue was purified by column chromatography (silica gel, eluent CH$_2$Cl$_2$/MeOH 92:8) to afford 4-(6-(4-(1,9-diazaspiro[5.5]undecane-9-carbonyl)phenyl)imidazo[1,2-a]pyridin-3-yl)benzonitrile (96 mg, 64%, AUC HPLC 99%) as a white solid. $^1$H NMR (400 MHz, DMSO-d$_6$) δ 8.80 (s, 1H), 8.03-7.98 (m, 5H), 7.86-7.82 (m, 3H), 7.75-7.72 (m, 1H), 7.49-7.47 (m, 2H), 3.50-3.31 (m, 4H), 2.98 (bs, 2H), 1.69-1.58 (m, 10H); $^{13}$C NMR (100 MHz, DMSO-d$_6$) δ 168.64, 145.73, 137.80, 135.26, 135.08, 133.49, 133.16, 127.75, 127.44, 127.09, 125.71, 125.51, 124.42, 121.81, 118.78, 117.78, 115.76, 109.79, 53.66, 22.92, 17.80; MS (ESI) m/z 476 [C$_{30}$H$_{29}$N$_5$O+H]$^+$.

Example 118: 4-(6-(4-(1-acetyl-1,9-diazaspiro[5.5]undecane-9-carbonyl)phenyl)imidazo[1,2-a]pyridin-3-yl)benzonitrile

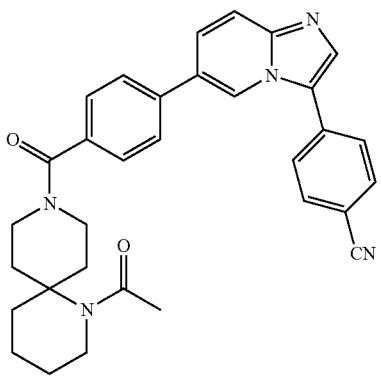 [SMILES: CC(=O)N1CCCCC12CCN(C(=O)c1ccc(-c3ccc4ncc(-c5ccc(C#N)cc5)n4c3)cc1)CC2]

To a solution of 4-(6-(4-(1,9-diazaspiro[5.5]undecane-9-carbonyl)phenyl)imidazo[1,2-a]pyridin-3-yl)benzonitrile (30 mg, 0.063 mmol) in DCM (0.5 mL) at 0° C. was added triethylamine (26 µl, 0.189 mmol), followed by acetyl chloride (10 µl, 0.126 mmol). The reaction mixture was stirred at 0° C. under inert atmosphere and allowed to warm to room temperature over 30 minutes. The reaction mixture was then diluted with water (25 mL) and extracted with EtOAc (3×25 mL). The combined organic layer was dried over Na$_2$SO$_4$ and was concentrated under reduced pressure. The crude residue was purified by column chromatography (silica gel, eluent CH$_2$Cl$_2$/MeOH/NH$_4$OH 90:9:1) to afford 4-(6-(4-(1-acetyl-1,9-diazaspiro[5.5]undecane-9-carbonyl)phenyl)imidazo[1,2-a]pyridin-3-yl)benzonitrile (14 mg, 43%, AUC HPLC 99%) as a white solid. $^1$H NMR (400 MHz, CDCl$_3$) δ 8.49 (s, 1H), 7.85-7.82 (m, 4H), 7.81-7.78 (m, 2H), 7.75-7.73 (m, 5H), 3.96-3.40 (m, 6H), 3.09-2.96 (m, 2H), 2.13 (s, 3H), 1.76-1.69 (m, 6H), 1.42 (bs, 2H); MS (ESI) m/z 518 [C$_{32}$H$_{31}$N$_5$O$_2$+H]$^+$.

Example 119: 4-(6-(4-(1-methyl-1,9-diazaspiro[5.5]undecane-9-carbonyl)phenyl)imidazo[1,2-a]pyridin-3-yl)benzonitrile

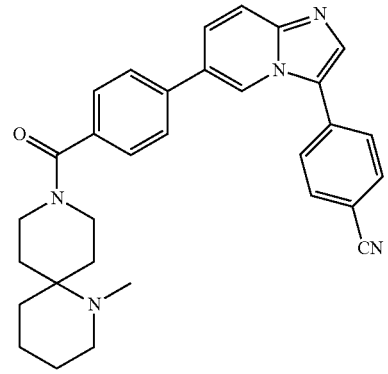 [SMILES: CN1CCCCC12CCN(C(=O)c1ccc(-c3ccc4ncc(-c5ccc(C#N)cc5)n4c3)cc1)CC2]

A mixture of 4-(6-(4-(1,9-diazaspiro[5.5]undecane-9-carbonyl)phenyl)imidazo[1,2-a]pyridin-3-yl)benzonitrile (104 mg, 0.219 mmol) and paraformaldehyde (70 mg) in acetonitrile (3 mL) and acetic acid (1.7 mL) was treated with sodium borohydride (35 mg). The reaction mixture was left to stir for 24 h, then it was diluted with saturated NaHCO$_3$ (25 mL) and extracted with EtOAc (3×25 mL). The combined organic layer was dried over Na$_2$SO$_4$ and was concentrated under reduced pressure. The crude residue was purified by column chromatography (silica gel, eluent CH$_2$Cl$_2$/MeOH/NH$_4$OH 90:9:1) to afford 4-(6-(4-(1-methyl-1,9-diazaspiro[5.5]undecane-9-carbonyl)phenyl)imidazo[1,2-a]pyridin-3-yl)benzonitrile (49 mg, 45%, AUC HPLC 93%) as a white solid. $^1$H NMR (400 MHz, CDCl$_3$) δ 8.52 (s, 1H), 7.86-7.82 (m, 4H), 7.77-7.74 (m, 2H), 7.61-7.59 (m, 2H), 7.55-7.53 (m, 3H), 4.45 (bs, 1H), 3.77 (bs, 1H), 3.24 (bs, 2H), 2.94 (bs, 2H), 2.56 (bs, 3H), 2.01-1.52 (m, 10H); $^{13}$C NMR (100 MHz, CDCl$_3$) δ 169.72, 146.34, 138.62, 134.78, 133.79, 133.25, 127.95, 127.84, 127.23, 127.19, 125.68, 124.52, 120.61, 118.73, 118.43, 111.60, 50.03, 35.99, 22.12, 21.78, 18.94; MS (ESI) m/z 490 [C$_{31}$H$_{31}$N$_5$O+H]$^+$.

Example 120: 4-(6-(4-(4-hydroxy-4-phenylpiperidine-1-carbonyl)phenyl)imidazo[1,2-a]pyridin-3-yl)benzonitrile

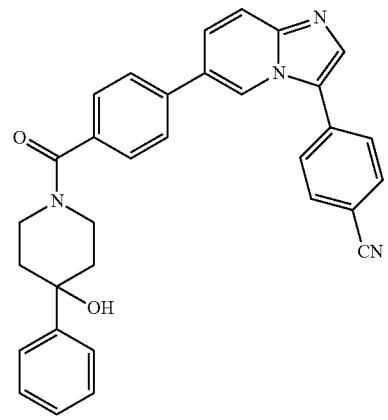 [SMILES: N#Cc1ccc(-c2cnc3ccc(-c4ccc(C(=O)N5CCC(O)(c6ccccc6)CC5)cc4)cn23)cc1]

To a solution of 4-(3-(4-cyanophenyl)imidazo[1,2-a]pyridin-6-yl)benzoic acid (100 mg, 0.295 mmol) in DMF (1.5 mL) was added HATU (168 mg, 0.442 mmol) and N-methyl morpholine (130 µl, 1.178 mmol). The reaction mixture was stirred at room temperature under inert atmosphere for 1 h, followed by the addition of 4-phenylpiperidin-4-ol (105 mg, 0.589 mmol). The reaction mixture was left to stir for 18 h, then was diluted with water (25 mL) and extracted with EtOAc (3×25 mL). The combined organic layer was dried over $Na_2SO_4$ and was concentrated under reduced pressure. The crude residue was purified by preparative HPLC (C18, eluent ACN, water, formic acid 0.1%) to afford 4-(6-(4-(4-hydroxy-4-phenylpiperidine-1-carbonyl)phenyl)imidazo[1,2-a]pyridin-3-yl)benzonitrile (52 mg, 35%, AUC HPLC 99%) as a white solid. $^1$H NMR (400 MHz, DMSO-$d_6$) δ 8.80 (s, 1H), 8.03-7.98 (m, 5H), 7.84-7.81 (m, 3H), 7.75-7.72 (m, 1H), 7.58-7.53 (m, 4H), 7.35-7.31 (m, 2H), 7.24-7.21 (m, 1H), 5.18 (s, 1H), 4.46 (bs, 1H), 3.53 (br s, 2H), 3.31 (bs, 1H), 1.96 (bs, 2H), 1.72-1.58 (m, 2H); $^{13}$C NMR (100 MHz, DMSO-$d_6$) δ 168.44, 149.11, 145.66, 137.42, 135.80, 134.99, 133.44, 133.08, 127.79, 127.66, 127.47, 126.91, 126.32, 125.74, 125.49, 124.69, 124.33, 121.71, 118.71, 117.67, 109.69, 70.07; MS (ESI) m/z 499 $[C_{32}H_{26}N_4O_2+H]^+$.

Example 121: 4-(3-(4-cyanophenyl)imidazo[1,2-a]pyridin-6-yl)-N-(2-(1-methylpiperidin-4-yl)ethyl)benzamide

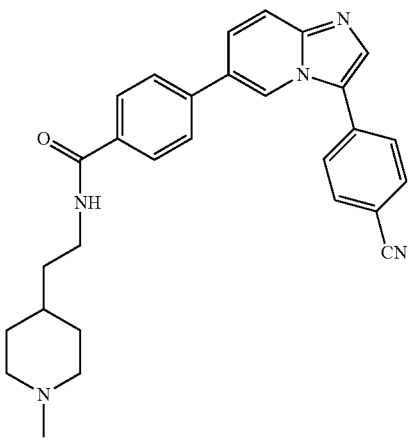 [SMILES: CN1CCC(CCNC(=O)c2ccc(-c3ccc4ncc(-c5ccc(C#N)cc5)n4c3)cc2)CC1]

To a solution of 4-(3-(4-cyanophenyl)imidazo[1,2-a]pyridin-6-yl)benzoic acid (100 mg, 0.295 mmol) in DMF (1.5 mL) was added HATU (168 mg, 0.442 mmol) and N-methyl morpholine (130 µl, 1.178 mmol). The reaction mixture was stirred at room temperature under inert atmosphere for 1 h, followed by the addition of 2-(1-methylpiperidin-4-yl)ethanamine (84 mg, 0.589 mmol). The reaction mixture was left to stir for 18 h, then it was diluted with water (25 mL) and extracted with EtOAc (3×25 mL). The combined organic layer was dried over $Na_2SO_4$ and was concentrated under reduced pressure. The crude residue was washed with MeOH (3×25 mL) and dried under vacuum to afford 4-(3-(4-cyanophenyl)imidazo[1,2-a]pyridin-6-yl)-N-(2-(1-methylpiperidin-4-yl)ethyl)benzamide (36 mg, 26%, AUC HPLC 97%) as a white solid. $^1$H NMR (400 MHz, DMSO-$d_6$) δ 8.82 (s, 1H), 8.49 (br s, 1H), 8.03-7.99 (m, 5H), 7.96-7.94 (m, 2H), 7.88-7.82 (m, 3H), 7.76-7.74 (m, 1H), 3.41 (b. s, 3H), 3.02-2.56 (m., 11H), 2.32 (m, 2H); $^{13}$C NMR (100 MHz, DMSO-$d_6$) δ 145.68, 139.25, 135.05, 133.42, 133.09, 127.76, 127.67, 126.78, 125.49, 125.44, 124.37, 121.84, 118.71, 117.71, 109.75, 55.77, 52.67, 49.48, 20.65; MS (ESI) m/z 465 $[C_{29}H_{29}N_5O+H]^+$.

Example 122: 4-(3-(4-cyanophenyl)imidazo[1,2-a]pyridin-6-yl)-N-methyl-N-(pyridin-4-yl)benzamide

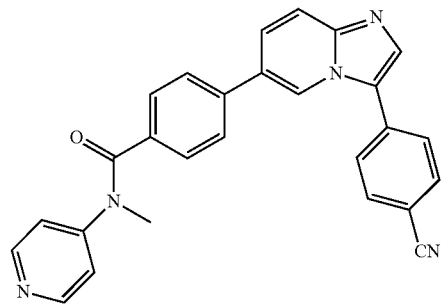 [SMILES: CN(C(=O)c1ccc(-c2ccc3ncc(-c4ccc(C#N)cc4)n3c2)cc1)c1ccncc1]

To a solution of 4-(3-(4-cyanophenyl)imidazo[1,2-a]pyridin-6-yl)benzoic acid (100 mg, 0.295 mmol) in DMF (1.5 mL) was added HATU (168 mg, 0.442 mmol) and N-methyl morpholine (130 µl, 1.178 mmol). The reaction mixture was stirred at room temperature under inert atmosphere for 1 h, followed by the addition of N-methylpyridin-4-amine (64 mg, 0.589 mmol). The reaction mixture was stirred for 18 h, then it was diluted with water (25 mL) and extracted with EtOAc (3×25 mL). The combined organic layer was dried over $Na_2SO_4$ and was concentrated under reduced pressure. The crude residue was purified by preparative HPLC (C18, eluent ACN/water/formic acid 0.1%) to afford 4-(3-(4-cyanophenyl)imidazo[1,2-a]pyridin-6-yl)-N-methyl-N-(pyridin-4-yl)benzamide (20 mg, 16%, AUC HPLC 97%) as a white solid. $^1$H NMR (400 MHz, DMSO-$d_6$) δ 8.77 (s, 1H), 8.45-8.43 (m, 2H), 7.99-7.98 (m, 5H), 7.79-7.68 (m, 4H), 7.45-7.43 (m, 2H), 7.24-7.23 (m, 2H), 3.43 (s, 3H); $^{13}$C NMR (100 MHz, DMSO-$d_6$) δ 169.33, 151.39, 150.40, 145.72, 138.18, 135.09, 134.83, 133.45, 133.15, 129.10, 127.76, 126.53, 125.32, 125.22, 124.69, 121.88, 120.50, 118.78, 117.72, 109.79, 37.04; MS (ESI) m/z 430 $[C_{27}H_{19}N_5O+H]^+$.

Example 123: 4-(6-(4-(4-(aminomethyl)piperidine-1-carbonyl)phenyl)imidazo[1,2-a]pyridin-3-yl)benzonitrile

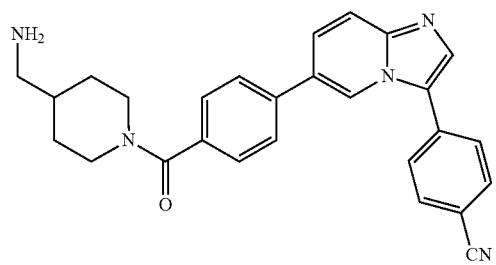 [SMILES: N#Cc1ccc(-c2cnc3ccc(-c4ccc(C(=O)N5CCC(CN)CC5)cc4)cn23)cc1]

Step 1: To a solution of 4-(3-(4-cyanophenyl)imidazo[1,2-a]pyridin-6-yl)benzoic acid (100 mg, 0.294 mmol) in DMF (1.5 mL) were added HATU (168 mg, 0.441 mmol), N-methyl morpholine (129 µL, 1.18 mmol) and 4-(boc-aminomethyl)piperidine (95 mg, 0.441 mmol). The reaction mixture was stirred at room temperature under inert atmosphere for 18 h, then it was diluted with water (10 mL) and extracted with EtOAc (3×20 mL). The combined organic layer was dried over $Na_2SO_4$ and was concentrated under reduced pressure. The residue was purified by column chromatography (silica gel, eluent $CHCl_3$/MeOH 96:4) to afford tert-butyl (1-(4-(3-(4-cyanophenyl)imidazo[1,2-a]pyridin-6-yl)benzoyl)piperidin-4-yl)methylcarbamate (157 mg, 99%, AUC HPLC 99%) as a white solid. $^1$H NMR (400 MHz, DMSO-$d_6$) δ 8.80 (s, 1H), 8.03-7.98 (m, 5H), 7.84-7.80 (m, 3H), 7.75-7.70 (m, 1H), 7.48 (d, J=8.4 Hz, 2H), 6.90-6.85 (m, 1H), 4.55-4.35 (m, 1H), 3.70-3.55 (m, 1H), 3.10-2.95 (m, 1H), 2.90-2.70 (m, 4H), 1.75-1.55 (m, 2H), 1.37 (s, 9H), 1.15-1.00 (m, 2H); MS (ESI) m/z 536 $[C_{32}H_{33}N_5O_3+H]^+$.

Step 2: To tert-butyl (1-(4-(3-(4-cyanophenyl)imidazo[1,2-a]pyridin-6-yl)benzoyl)piperidin-4-yl)methylcarbamate (70 mg, 0.131 mmol) was added 20% TFA in $CHCl_3$ (3 mL). The reaction mixture was stirred at room temperature for 20 min then concentrated under reduced pressure. To the residue was added saturated sodium bicarbonate (10 mL) and extracted with EtOAc (3×30 mL). The combined organic was dried over $Na_2SO_4$ and concentrated under reduced pressure. The residue was purified by preparative HPLC (C18, eluent ACN/$H_2O$/formic acid 0.1%) to afford 4-(6-(4-(4-(aminomethyl)piperidine-1-carbonyl)phenyl)imidazo[1,2-a]pyridin-3-yl)benzonitrile (26 mg, 46%, AUC HPLC 99%) as a white solid. $^1$H NMR (400 MHz, $CD_3OD$) δ 8.76 (s, 1H), 8.55 (s, 1H), 7.95-7.90 (m, 4H), 7.89 (s, 1H), 7.81-7.76 (m, 3H), 7.54 (d, J=8.4 Hz, 2H), 4.80-4.65 (m, 1H), 3.90-3.75 (m, 1H), 3.30-3.15 (m, 1H), 3.00-2.85 (m, 1H), 2.86 (d, J=6.8 Hz, 2H), 2.00-1.85 (m, 2H), 1.85-1.70 (m, 1H), 1.40-1.20 (m, 2H); $^{13}$C NMR (100 MHz, $CD_3OD$): δ 171.96, 147.44, 140.03, 136.66, 134.84, 134.72, 134.39, 129.44, 128.84, 128.61, 128.50, 127.80, 126.56, 122.83, 119.50, 118.48, 112.72, 45.70, 36.32; MS (ESI) m/z 436 $[C_{27}H_{25}N_5O+H]^+$.

Example 124: 4-(6-(4-(4-(2-aminoethyl)piperidine-1-carbonyl)phenyl)imidazo[1,2-a]pyridin-3-yl)benzonitrile

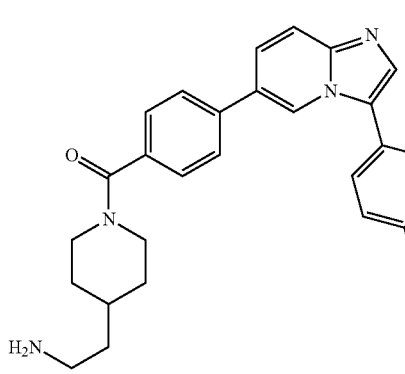

Step 1: To a solution of 4-(3-(4-cyanophenyl)imidazo[1,2-a]pyridin-6-yl)benzoic acid (100 mg, 0.294 mmol) in DMF (1.5 mL) were added HATU (168 mg, 0.441 mmol), N-methyl morpholine (129 μL, 1.18 mmol) and tert-butyl 2-(piperidin-4-yl)ethylcarbamate (101 mg, 0.441 mmol). The reaction mixture was stirred at room temperature under inert atmosphere for 18 h, then it was diluted with water (10 mL) and extracted with EtOAc (3×20 mL). The combined organic layer was dried over $Na_2SO_4$ and was concentrated under reduced pressure. The residue was purified by column chromatography (silica gel, eluent $CHCl_3$/MeOH 97:3) to afford tert-butyl 2-(1-(4-(3-(4-cyanophenyl)imidazo[1,2-a]pyridin-6-yl)benzoyl)piperidin-4-yl)ethylcarbamate (79 mg, 49%, AUC HPLC 98%) as a white solid. $^1$H NMR (400 MHz, DMSO-$d_6$): δ 8.70 (s, 1H), 8.05-7.97 (m, 4H), 7.85-7.78 (m, 3H), 7.75-7.70 (m, 1H), 7.48 (d, J=8.0 Hz, 2H), 6.80-6.73 (m, 1H), 4.55-4.35 (bs, 1H), 3.70-3.50 (bs, 1H), 3.10-2.90 (m, 3H), 2.85-2.70 (bs, 1H), 1.85-1.50 (m, 3H), 1.37 (s, 9H), 1.35-1.30 (m, 2H), 1.20-1.00 (m, 3H); MS (ESI) m/z 550 $[C_{33}H_{35}N_5O_3+H]^+$.

Step 2: To tert-butyl 2-(1-(4-(3-(4-cyanophenyl)imidazo[1,2-a]pyridin-6-yl)benzoyl)piperidin-4-yl)ethylcarbamate (70 mg, 0.127 mmol) was added 20% TFA in $CHCl_3$ (3 mL). The reaction mixture was stirred at room temperature for 20 min then it was concentrated under reduced pressure. To the residue was added saturated sodium bicarbonate (10 mL) and extracted with EtOAc (3×30 mL). The combined organic was dried over $Na_2SO_4$ and concentrated under reduced pressure. The residue was purified by preparative HPLC (C18, eluent ACN/water/formic acid 0.1%) to afford 4-(6-(4-(4-(2-aminoethyl)piperidine-1-carbonyl)phenyl)imidazo[1,2-a]pyridin-3-yl)benzonitrile (16 mg, 29%, AUC HPLC 99%) as a white solid. $^1$H NMR (400 MHz, $CD_3OD$) δ 8.75 (s, 1H), 8.55 (s, 1H), 7.95-7.90 (m, 4H), 7.89 (s, 1H), 7.81-7.76 (m, 3H), 7.53 (d, J=8.4 Hz, 2H), 4.75-4.60 (m, 1H), 3.90-3.75 (m, 1H), 3.25-3.10 (m, 1H), 3.00-2.80 (m, 3H), 1.95-1.80 (m, 1H), 1.80-1.65 (m, 2H), 1.65-1.60 (m, 2H), 1.40-1.15 (m, 2H); $^{13}$C NMR (400 MHz, $CD_3OD$) δ 171.89, 147.44, 139.93, 136.82, 134.84, 134.71, 134.39, 129.43, 128.81, 128.64, 128.48, 127.81, 126.55, 122.81, 119.50, 118.47, 112.71, 38.53, 35.50, 34.61; MS (ESI) m/z 450 $[C_{28}H_{27}N_5O+H]^+$.

Example 125: 4-(6-(4-(4-(pyridin-4-yl)piperazine-1-carbonyl)phenyl)imidazo[1,2-a]pyridin-3-yl)benzonitrile

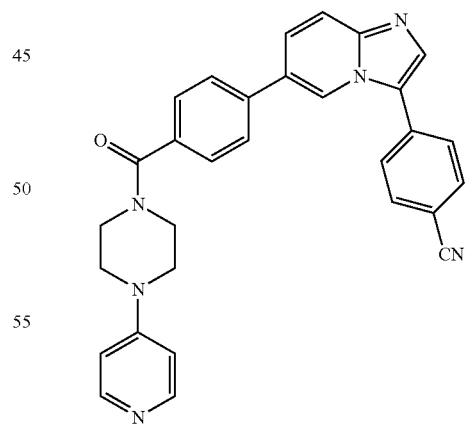

To a solution of 4-(3-(4-cyanophenyl)imidazo[1,2-a]pyridin-6-yl)benzoic acid (100 mg, 0.294 mmol) in DMF (1.5 mL) were added HATU (168 mg, 0.441 mmol), N-methyl morpholine (129 μL, 1.18 mmol) and 1-(4-pyridinyl)-piperazine (58 mg, 0.441 mmol). The reaction mixture was stirred at room temperature under inert atmosphere for 18 h then, was diluted with water (15 mL) and extracted with EtOAc (3×30 mL). The combined organic layer was dried over Na$_2$SO$_4$ and was concentrated under reduced pressure. The residue was purified by column chromatography (silica gel, eluent CHCl$_3$/MeOH 92:8) to afford 4-(6-(4-(4-(pyridin-4-yl)piperazine-1-carbonyl)phenyl)imidazo[1,2-a]pyridin-3-yl)benzonitrile (34 mg, 24%, AUC HPLC 96%) as a white solid. $^1$H NMR (400 MHz, DMSO-d$_6$) δ 8.77 (s, 1H), 8.17 (d, J=7.2 Hz, 2H), 7.96-7.90 (m, 4H), 7.90 (s, 1H), 7.83 (d, J=8.0 Hz, 2H), 7.79 (s, 2H), 7.63 (d, J=8.0 Hz, 2H), 7.08 (d, J=7.2 Hz, 2H) 3.95-3.68 (m, 8H); $^{13}$C NMR (400 MHz, DMSO-d$_6$): δ 168.98, 156.53, 145.76, 140.38, 138.13, 135.11, 134.76, 133.51, 133.19, 127.91, 127.79, 127.10, 125.70, 125.55, 124.46, 121.92, 118.81, 117.81, 109.83, 107.56; MS (ESI) m/z 485 [C$_{30}$H$_{24}$N$_6$O+H]$^+$.

Example 126: 4-(6-(4-(4-benzoylpiperazine-1-carbonyl)phenyl)imidazo[1,2-a]pyridin-3-yl)benzonitrile

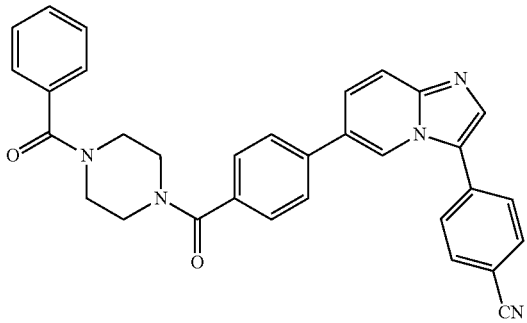 [SMILES: N#Cc1ccc(-c2cnc3ccc(-c4ccc(C(=O)N5CCN(C(=O)c6ccccc6)CC5)cc4)cn23)cc1]

To a solution of 4-(3-(4-cyanophenyl)imidazo[1,2-a]pyridin-6-yl)benzoic acid (100 mg, 0.294 mmol) in DMF (1.5 mL) were added HATU (168 mg, 0.441 mmol), N-methyl morpholine (129 μL, 1.18 mmol) and 1-benzoylpiperazine (67 mg, 0.441 mmol). The reaction mixture was stirred at room temperature under inert atmosphere for 18 h then, was diluted with water (15 mL) and extracted with EtOAc (3×30 mL). The combined organic layer was dried over Na$_2$SO$_4$ and was concentrated under reduced pressure. The residue was purified by column chromatography (silica gel, eluent CHCl$_3$/MeOH 92:8) to afford 4-(6-(4-(4-benzoylpiperazine-1-carbonyl)phenyl)imidazo[1,2-a]pyridin-3-yl)benzonitrile (75 mg, 50%, AUC HPLC 99%) as a white solid. $^1$H NMR (400 MHz, DMSO-d$_6$) δ 8.75 (s, 1H), 7.95-7.89 (m, 4H), 7.88 (s, 1H), 7.82-7.55 (m, 4H), 7.59 (d, J=8.0 Hz, 2H), 7.63-7.43 (m, 5H), 4.00-3.40 (m, 8H); $^{13}$C NMR (100 MHz, CD$_3$OD): δ 172.90, 172.34, 147.49, 140.29, 136.50, 136.11, 134.87, 134.76, 134.43, 131.43, 129.87, 129.48, 129.22, 128.63, 128.59, 128.21, 127.85, 126.61, 122.92, 119.55, 118.51, 112.76; MS (ESI) m/z 512 [C$_{32}$H$_{25}$N$_5$O+H]$^+$.

Example 127: 4-(3-(4-cyanophenyl)imidazo[1,2-a]pyridin-6-yl)-N-(4-(4-methylpiperidin-1-yl)phenyl)benzamide

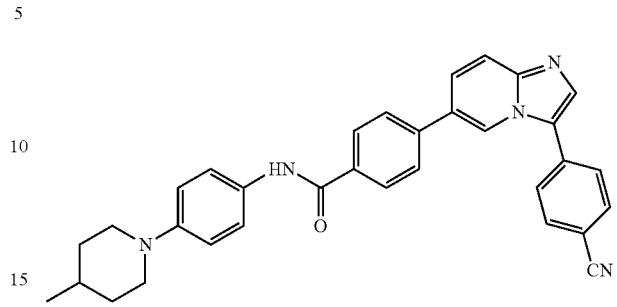

To a solution of 4-(3-(4-cyanophenyl)imidazo[1,2-a]pyridin-6-yl)benzoic acid (70 mg, 0.206 mmol) in DMF (1.0 mL) were added HATU (117 mg, 0.309 mmol), N-methyl morpholine (90 μL, 0.824 mmol) and 4-(4-methylpiperidin-1-yl)aniline (47 mg, 0.309 mmol). The reaction mixture was stirred at room temperature under inert atmosphere for 18 h then, was diluted with water (15 mL) and extracted with EtOAc (3×30 mL). The combined organic layer was dried over Na$_2$SO$_4$ and was concentrated under reduced pressure. The residue was washed with cold CHCl$_3$/MeOH mixture and the precipitates obtained were further washed with cold CH$_3$CN to afford 4-(3-(4-cyanophenyl)imidazo[1,2-a]pyridin-6-yl)-N-(4-(4-methylpiperidin-1-yl)phenyl)benzamide (17 mg, 17%, AUC HPLC 96%) as a white solid. $^1$H NMR (400 MHz, CD$_3$OD) δ 8.80 (s, 1H), 8.07 (d, J=8.4 Hz, 2H), 7.98-7.91 (m, 4H), 7.90 (s, 1H), 7.85 (d, J=8.4 Hz, 2H), 7.80 (s, 2H), 7.69 (d, J=8.4 Hz, 2H), 7.30 (d, J=8.4 Hz, 2H), 3.60-3.45 (m, 2H), 3.13 (bs, 1H), 3.10-2.95 (m, 2H), 2.85 (s, 3H), 2.20-2.05 (m, 2H), 2.03-1.85 (m, 2H); $^{13}$C NMR (400 MHz, DMSO-d$_6$): δ 164.93, 145.82, 139.73, 139.29, 137.63, 135.20, 134.03, 133.53, 133.21, 128.37, 127.78, 126.95, 126.70, 125.55, 124.51, 122.08, 120.67, 118.82, 117.85, 109.86. 37.72; MS (ESI) m/z 512 [C$_{33}$H$_{29}$N$_5$O+H]$^+$.

Example 128: 4-(3-(4-cyanophenyl)imidazo[1,2-a]pyridin-6-yl)-N-(4-((4-methylpiperazin-1-yl)methyl)phenyl)benzamide

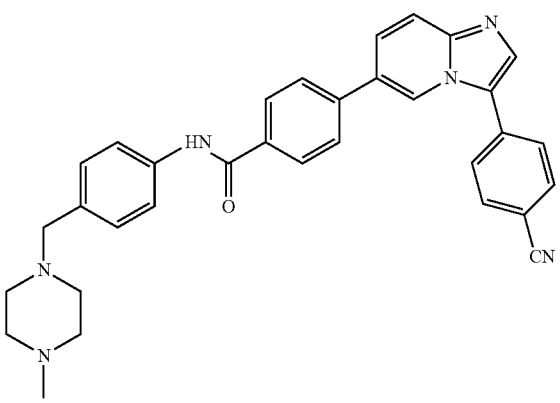 [SMILES: CN1CCN(Cc2ccc(NC(=O)c3ccc(-c4ccc5ncc(-c6ccc(C#N)cc6)n5c4)cc3)cc2)CC1]

To a solution of 4-(3-(4-cyanophenyl)imidazo[1,2-a]pyridin-6-yl)benzoic acid (70 mg, 0.206 mmol) in DMF (1.0 mL) were added HATU (117 mg, 0.309 mmol), N-methyl morpholine (90 μL, 0.824 mmol) and 4-((4-methylpiperazin-1-yl)methyl)aniline (51 mg, 0.309 mmol). The reaction mixture was stirred at room temperature under inert atmosphere for 18 h, then it was diluted with water (15 mL) and extracted with EtOAc (3×30 mL). The combined organic layer was dried over Na$_2$SO$_4$ and was concentrated under reduced pressure. The residue was purified by preparative HPLC (C18, eluent ACN, water, formic acid 0.1%) to afford 4-(3-(4-cyanophenyl)imidazo[1,2-a]pyridin-6-yl)-N-(4-((4-methylpiperazin-1-yl)methyl)phenyl)benzamide (40 mg, 37%, AUC HPLC 99%) as a white solid. $^1$H NMR (400 MHz, CD$_3$OD) δ 8.78 (s, 1H), 8.05 (d, J=8.4 Hz, 2H), 7.96-7.90 (m, 4H), 7.84 (s, 1H), 7.83 (d, J=8.4 Hz, 2H), 7.80-7.76 (m, 2H), 7.68 (d, J=8.8 Hz, 2H), 7.34 (d, J=8.4 Hz, 2H), 3.56 (s, 2H), 2.70-2.40 (m, 8H), 2.36 (s, 3H); $^{13}$C NMR (100 MHz, CD$_3$OD): δ 168.12, 147.47, 141.62, 139.17, 135.76, 134.82, 134.74, 134.53, 134.40, 131.08, 129.56, 129.44, 128.49, 128.30, 127.79, 126.61, 122.95, 122.18, 119.51, 118.48, 112.72, 63.14, 55.55, 53.15, 45.65; MS (ESI) m/z 527 [C$_{33}$H$_{30}$N$_6$O+H]$^+$.

Example 129: 4-((4-(4-(3-(4-cyanophenyl)imidazo[1,2-a]pyridin-6-yl)benzoyl)piperazin-1-yl)methyl)benzamide

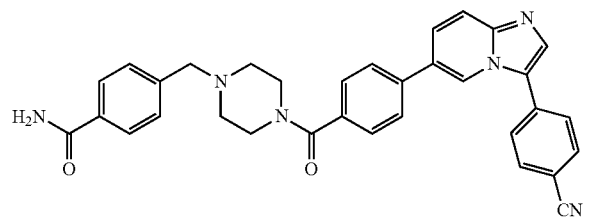 [SMILES: N#Cc1ccc(-c2cnc3ccc(-c4ccc(C(=O)N5CCN(Cc6ccc(C(N)=O)cc6)CC5)cc4)cn23)cc1]

To a solution of 4-(3-(4-cyanophenyl)imidazo[1,2-a]pyridin-6-yl)benzoic acid (70 mg, 0.206 mmol) in DMF (1.0 mL) were added HATU (117 mg, 0.309 mmol), N-methyl morpholine (113 μL, 0.824 mmol) and 4-(1-piperazinylmethyl)benzamide dihydrochloride (72 mg, 0.247 mmol). The reaction mixture was stirred at room temperature under inert atmosphere for 18 h, then it was diluted with water (15 mL) and extracted with EtOAc (3×30 mL). The combined organic layer was dried over Na$_2$SO$_4$ and was concentrated under reduced pressure. The residue was purified by preparative HPLC (C18, eluent ACN, water, formic acid 0.1%) to afford 4-((4-(4-(3-(4-cyanophenyl)imidazo[1,2-a]pyridin-6-yl)benzoyl)piperazin-1-yl)methyl)benzamide (7 mg, 7%, AUC HPLC 99%) as a white solid. $^1$H NMR (400 MHz, DMSO-d$_6$) δ 8.80 (s, 1H), 8.03-7.97 (m, 5H), 7.95 (bs, 1H), 7.90-7.80 (m, 5H), 7.96-7.71 (m, 1H), 7.51 (d, J=7.6 Hz, 2H), 7.43 (bs, 2H), 7.34 (bs, 1H), 3.80-3.40 (m, 8H), 2.69 (s, 2H); MS (ESI) m/z 541 [C$_{33}$H$_{28}$N$_6$O$_2$+H]$^+$.

Example 130: 4-(6-(4-(4-methyl-3-oxopiperazine-1-carbonyl)phenyl)imidazo[1,2-a]pyridin-3-yl)benzonitrile

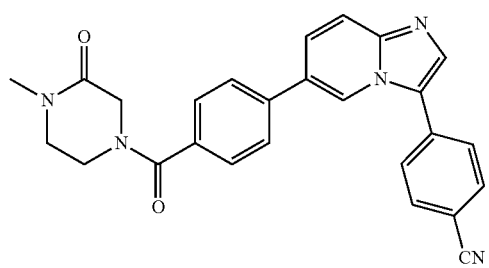 [SMILES: CN1CCN(C(=O)c2ccc(-c3ccc4ncc(-c5ccc(C#N)cc5)n4c3)cc2)CC1=O]

To a solution of 4-(3-(4-cyanophenyl)imidazo[1,2-a]pyridin-6-yl)benzoic acid (70 mg, 0.206 mmol) in DMF (1.0 mL) were added HATU (117 mg, 0.309 mmol), N-methyl morpholine (90 μL, 0.824 mmol) and 1-methylpiperazin-2-one (37 mg, 0.247 mmol). The reaction mixture was stirred at room temperature under inert atmosphere for 18 h, then it was diluted with water (15 mL) and extracted with EtOAc (3×30 mL). The combined organic layer was dried over Na$_2$SO$_4$ and concentrated under reduced pressure. The residue was purified by column chromatography (silica gel, eluent CHCl$_3$/MeOH 96:4) to afford 4-(6-(4-(4-methyl-3-oxopiperazine-1-carbonyl)phenyl)imidazo[1,2-a]pyridin-3-yl)benzonitrile (64 mg, 57%, AUC HPLC 98%) as a white solid. $^1$H NMR (400 MHz, CD$_3$OD) δ 8.76 (bs, 1H), 7.97-7.89 (m, 4H), 7.88 (s, 1H), 7.84-7.78 (m, 2H), 7.77 (d, J=1.2 Hz, 2H), 7.64-7.57 (m, 2H), 4.40-4.10 (m, 2H), 4.10-3.60 (m, 2H), 3.57-3.42 (m, 2H), 3.01 (s, 3H); $^{13}$C NMR (100 MHz, CD$_3$OD): δ 171.72, 147.44, 140.53, 135.51, 134.81, 134.72, 134.38, 129.42, 129.27, 128.56, 128.52, 127.79, 126.58, 122.93, 119.50, 118.47, 112.70, 34.68; MS (ESI) m/z 436 [C$_{26}$H$_{21}$N$_5$O$_2$+H]$^+$.

Example 131: 4-(6-(4-(4-phenylpiperazine-1-carbonyl)phenyl)imidazo[1,2-a]pyridin-3-yl)benzonitrile

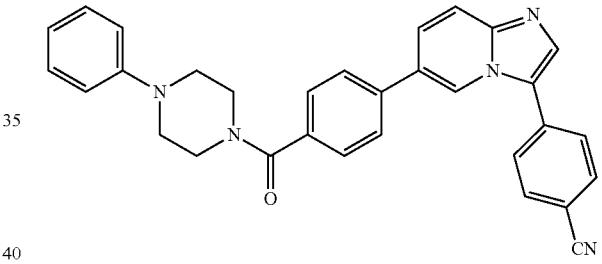

To a solution of 4-(3-(4-cyanophenyl)imidazo[1,2-a]pyridin-6-yl)benzoic acid (70 mg, 0.206 mmol) in DMF (1.0 mL) were added HATU (117 mg, 0.309 mmol), N-methyl morpholine (90 μL, 0.824 mmol) and 4-phenylpiperazine (38 μL, 0.247 mmol). The reaction mixture was stirred at room temperature under inert atmosphere for 18 h then, was diluted with water (15 mL) and extracted with EtOAc (3×30 mL). The combined organic layer was dried over Na$_2$SO$_4$ and was concentrated under reduced pressure. The residue was purified by column chromatography (silica gel, eluent EtOAc) to afford 4-(6-(4-(4-phenylpiperazine-1-carbonyl)phenyl)imidazo[1,2-a]pyridin-3-yl)benzonitrile (83 mg, 84%, AUC HPLC 98%) as a white solid. $^1$H NMR (400 MHz, DMSO-d$_6$) δ 8.81 (s, 1H), 8.04-7.98 (m, 5H), 7.88-7.80 (m, 3H), 7.66-7.62 (m, 1H), 7.56 (d, J=8.0 Hz, 2H), 7.37-7.20 (m, 2H), 6.96 (d, J=8.0 Hz, 2H), 6.83-6.79 (m, 1H), 3.90-3.45 (m, 4H), 3.30-3.10 (m, 4H); $^{13}$C NMR (100 MHz, DMSO-d$_6$): δ 168.66, 150.74, 145.77, 137.86, 135.18, 135.10, 133.52, 133.19, 128.99, 127.79, 127.77, 127.09, 125.77, 125.57, 124.45, 121.88, 119.40, 118.81, 117.79, 115.94, 109.81; MS (ESI) m/z 484 [C$_{31}$H$_{25}$N$_5$O+H]$_+$.

Example 132: 4-(6-(4-(4-benzylpiperazine-1-carbonyl)phenyl)imidazo[1,2-a]pyridin-3-yl)benzonitrile

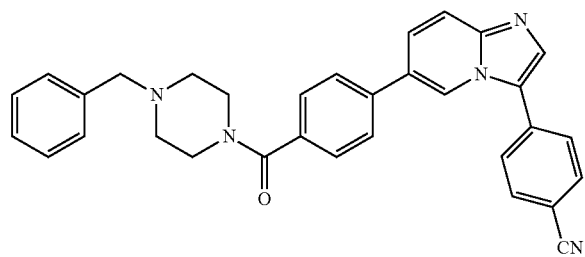 [SMILES: N#Cc1ccc(-c2cnc3ccc(-c4ccc(C(=O)N5CCN(Cc6ccccc6)CC5)cc4)cn23)cc1]

To a solution of 4-(3-(4-cyanophenyl)imidazo[1,2-a]pyridin-6-yl)benzoic acid (70 mg, 0.206 mmol) in DMF (1.0 mL) were added HATU (117 mg, 0.309 mmol), N-methyl morpholine (90 μL, 0.824 mmol) and 4-benzylpiperazine (43 μL, 0.247 mmol). The reaction mixture was stirred at room temperature under inert atmosphere for 18 h, then it was diluted with water (15 mL) and extracted with EtOAc (3×30 mL). The combined organic layer was dried over $Na_2SO_4$ and was concentrated under reduced pressure. The residue was purified by column chromatography (silica gel, eluent $CHCl_3$/MeOH 96:4) to afford 4-(6-(4-(4-benzylpiperazine-1-carbonyl)phenyl)imidazo[1,2-a]pyridin-3-yl)benzonitrile (48 mg, 47%, AUC HPLC 97%) as a white solid. $^1$H NMR (400 MHz, DMSO-$d_6$) δ 8.79 (bs, 1H), 8.03-7.96 (m, 5H), 7.84-7.78 (m, 3H), 7.74-7.69 (m, 1H), 7.49 (d, J=8.4 Hz, 2H), 7.36-7.28 (m, 4H), 7.28-7.22 (m, 1H), 3.75-3.55 (m, 2H), 3.51 (s, 2H), 3.50-3.33 (m, 2H), 2.49-2.30 (m, 4H); $^{13}$C NMR (100 MHz, DMSO-$d_6$): δ 168.54, 145.75, 137.77, 137.74, 135.28, 135.09, 133.51, 133.18, 128.89, 128.21, 127.76, 127.70, 127.04, 125.75, 125.54, 124.43, 121.83, 118.81, 117.79, 109.80, 61.83; MS (ESI) m/z 498 $[C_{32}H_{27}N_5O+H]^+$.

Example 133: 4-(6-(4-(4-(4-methylpiperazin-1-yl)piperidine-1-carbonyl)phenyl)imidazo[1,2-a]pyridin-3-yl)benzonitrile

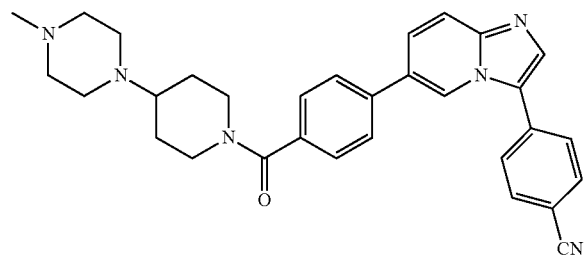

To a solution of 4-(3-(4-cyanophenyl)imidazo[1,2-a]pyridin-6-yl)benzoic acid (70 mg, 0.206 mmol) in DMF (1.0 mL) were added HATU (117 mg, 0.309 mmol), N-methyl morpholine (90 μL, 0.824 mmol) and 1-methyl-4-(piperidin-4-yl)piperazine (45 mg, 0.247 mmol). The reaction mixture was stirred at room temperature under inert atmosphere for 18 h then, was diluted with water (15 mL) and extracted with EtOAc (3×30 mL). The combined organic layer was dried over $Na_2SO_4$ and was concentrated under reduced pressure. The residue was purified by preparative HPLC (C18, eluent ACN, water, formic acid 0.1%) to afford 4-(6-(4-(4-(4-methylpiperazin-1-yl)piperidine-1-carbonyl)phenyl)imidazo[1,2-a]pyridin-3-yl)benzonitrile (23 mg, 22%, AUC HPLC 99%) as a white solid. $^1$H NMR (400 MHz, $CD_3OD$) δ 8.76 (br s, 1H), 7.97-7.90 (m, 4H), 7.89 (s, 1H), 7.81-7.76 (m, 4H), 7.54 (d, J=8.4 Hz, 2H), 4.75-4.60 (m, 1H), 3.90-3.75 (m, 1H), 3.25-3.10 (m, 1H), 3.00-2.85 (m, 1H), 2.80-2.55 (m, 9H), 2.40 (s, 3H), 2.10-1.95 (m, 1H), 1.95-1.80 (m, 1H), 1.65-1.40 (m, 2H); $^{13}$C NMR (100 MHz, $CD_3OD$): δ 171.87, 140.01, 136.75, 134.89, 134.75, 134.44, 129.48, 128.89, 128.71, 128.53, 127.89, 122.89, 119.56, 118.51, 112.75, 62.65, 55.83, 45.55; MS (ESI) m/z 505 $[C_{31}H_{32}N_6O+H]^+$.

Example 134: 4-(6-(4-(4-morpholinopiperidine-1-carbonyl)phenyl)imidazo[1,2-a]pyridin-3-yl)benzonitrile

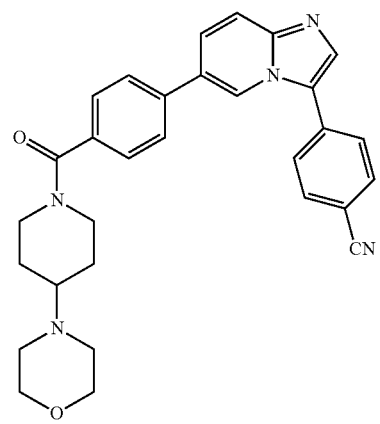 [SMILES: N#Cc1ccc(-c2cnc3ccc(-c4ccc(C(=O)N5CCC(N6CCOCC6)CC5)cc4)cn23)cc1]

To a solution of 4-(3-(4-cyanophenyl)imidazo[1,2-a]pyridin-6-yl)benzoic acid (0.2 g, 0.58 mmol) in DMF (5 mL) were added HATU (0.33 g, 0.88 mmol), N-methyl morpholine (0.18 g, 1.76 mmol) and 4-(piperidin-4-yl)morpholine (108.4 mg, 0.70 mmol). The reaction mixture was stirred at 0° C. to room temperature under inert atmosphere for 16 h, then it was diluted with water (15 mL) and extracted with EtOAc (3×25 mL). The combined organic layer was dried over $Na_2SO_4$ and was concentrated under reduced pressure. The crude residue was purified by column chromatography (silica gel, eluent $CH_2Cl_2$/MeOH 95:5) and followed by preparative HPLC (C18, ACN/$H_2O$/10 mM $NH_4HCO_3$) to afford 4-(6-(4-(4-morpholinopiperidine-1-carbonyl)phenyl)imidazo[1,2-a]pyridin-3-yl)benzonitrile (140 mg, 50%, AUC HPLC 98.7%) as a white solid; m.p. 131-141° C. $^1$H NMR (400 MHz, $CDCl_3$) δ (ppm): 8.6 (s, 1H), 8.05-7.91 (m, 5H), 7.80 (m, 2H), 7.48 (m, 1H), 4.45 (bs, 1H), 3.65-3.56 (m, 5H), 3.01-2.82 (m, 2H), 2.46-2.39 (m, 5H), 1.85-1.75 (m, 2H), 1.38 (bs, 2H); MS (ESI) m/z 492.23 $[C_{30}H_{29}N_5O_2+H]^+$.

Example 135: 4-(6-(4-(4-methyl-4-(5-methyl-1,3,4-oxadiazol-2-yl)piperidine-1-carbonyl)phenyl)imidazo[1,2-a]pyridin-3-yl)benzonitrile

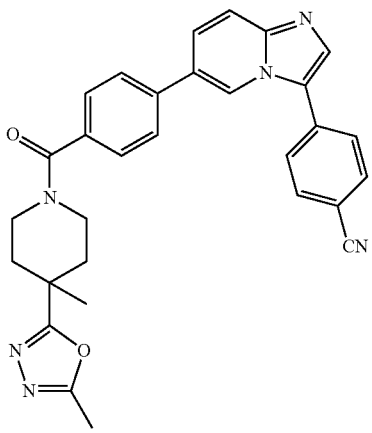 [SMILES: Cc1nnc(C2(C)CCN(C(=O)c3ccc(-c4ccc5ncc(-c6ccc(C#N)cc6)n5c4)cc3)CC2)o1]

To a solution of 4-(3-(4-cyanophenyl)imidazo[1,2-a]pyridin-6-yl)benzoic acid (150 mg, 0.44 mmol) and 2-methyl-5-(4-methylpiperidin-4-yl)-1,3,4-oxadiazole B (105 mg, 0.48 mmol) in DMF (5 mL) was added HATU (250 mg, 0.66 mmol) followed by NMM (0.09 mL, 0.88 mmol) and the reaction mixture was stirred at rt for 16 h. The reaction mixture was diluted with EtOAc and washed with water and brine solution. The organic layer was dried over anhydrous $Na_2SO_4$ and concentrated under reduced pressure to obtain 4-(6-(4-(4-methyl-4-(5-methyl-1,3,4-oxadiazol-2-yl)piperidine-1-carbonyl)phenyl)imidazo[1,2-a]pyridin-3-yl)benzonitrile (60 mg, 27%, AUC HPLC 95.3%) as a white solid, m.p: 150-160° C. $^1$H NMR (400 MHz, $CDCl_3$) δ (ppm): 8.80 (s, 1H), 8.03-7.98 (m, 5H), 7.82 (d, J=7.9 Hz, 4H), 7.51 (d, J=8.3 Hz, 2H), 4.08 (bs, 1H), 3.54 (bs, 1H), 3.31 (bs, 2H), 2.48 (s, 3H), 2.07 (bs, 2H), 1.70 (bs, 2H), 1.35 (s, 3H); MS (ESI) m/z 503.34 $[C_{30}H_{26}N_6O_2+H]^+$:

Example 136: 4-(6-(4-(4-methyl-4-(1H-pyrazol-3-yl)piperidine-1-carbonyl)phenyl)imidazo[1,2-a]pyridin-3-yl)benzonitrile

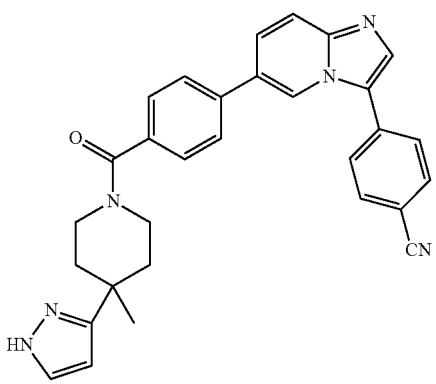 [SMILES: CC1(c2cc[nH]n2)CCN(C(=O)c2ccc(-c3ccc4ncc(-c5ccc(C#N)cc5)n4c3)cc2)CC1]

To a solution of 4-(3-(4-cyanophenyl)imidazo[1,2-a]pyridin-6-yl)benzoic acid (150 mg, 0.442 mmol) in DMF (5.0 mL) were added HATU (251 mg, 0.663 mmol), N-methyl morpholine (0.17 mL, 1.547 mmol) and tert-butyl 4-methyl-4-(1H-pyrazol-3-yl)piperidine hydrochloride (126 mg, 0.53 mmol). The reaction mixture was stirred at room temperature under inert atmosphere for 16 h, then was diluted with $H_2O$ (15 mL) and extracted with EtOAc (3×25 mL). The combined organic layer was dried over $Na_2SO_4$ and was concentrated under reduced pressure. The crude product was purified by column chromatography (silica gel, eluent $CH_2Cl_2$/MeOH 95:5) to afford 4-(6-(4-(4-methyl-4-(1H-pyrazol-3-yl)piperidine-1-carbonyl)phenyl)imidazo[1,2-a]pyridin-3-yl)benzonitrile (80 mg, 38%, AUC HPLC 97.2%) as an white solid; mp. 223-226° C. $^1$H NMR (400 MHz, $CDCl_3$) δ (ppm): 8.50 (s, 1H), 7.83-7.73 (m, 6H), 7.57-7.50 (m, 6H), 6.18 (s, 1H), 4.21 (s, 1H), 3.58 (s, 1H), 3.38 (s, 2H), 2.22-2.16 (m, 2H), 1.85-1.77 (m, 2H), 1.32 (s, 3H); MS (ESI) m/z 487.5 $[C_{30}H_{26}N_6O+H]^+$.

Example 137: 4-(6-(4-(4-amino-4-methylpiperidine-1-carbonyl)phenyl)-7-methylimidazo[1,2-a]pyridin-3-yl)benzonitrile

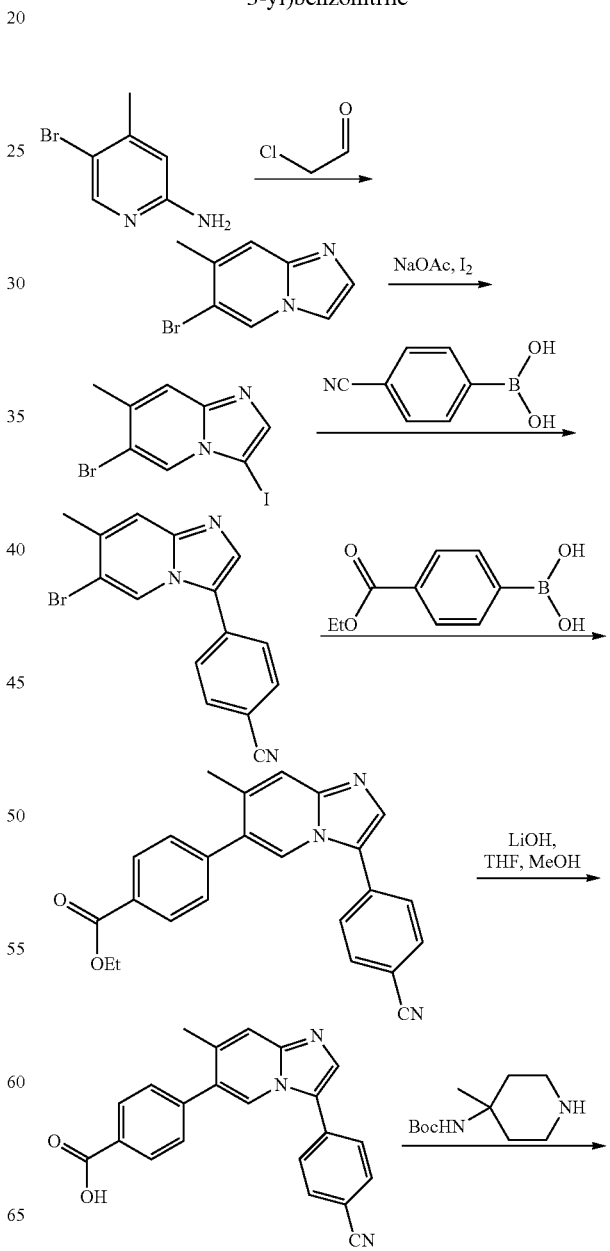

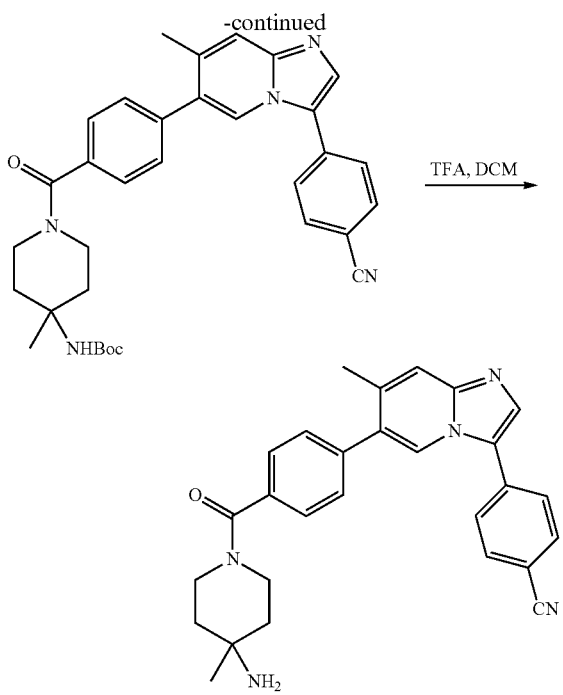

Step 1: A solution of 5-bromo-4-methylpyridin-2-amine (8 g, 42.78 mmol) and chloroacetaldehyde (approx. 50% wt) solution in water (27.52 ml, 214 mmol) in ethanol (50 ml) was heated at 100° C. under $N_2$ for 16 h. The solvent was removed and the residue was dissolved in EtOAc (100 ml). The organic layer was washed with sat.NaHCO$_3$ (2×50 ml), water (2×50 ml), brine (2×100 ml), dried over Na$_2$SO$_4$ and the solvent was removed completely under vacuum to afford 6-bromo-7-methylimidazo[1,2-a]pyridine (8.5 g, 94%) as a brown solid. $^1$H NMR (400 MHz, DMSO-d$_6$) δ 8.93 (s, 1H), 7.85 (s, 1H), 7.57 (d, J=7.56 Hz, 2H), 2.38 (s, 3H); LC-MS (95%) m/z 211 [C$_8$H$_7$BrN$_2$+H]$^+$.

Step 2: To a solution of 6-bromo-7-methylimidazo(1,2-a)pyridine (9 g, 43.0 mmol) and anhydrous sodium acetate (9.52 g, 116.1 mmol) in MeOH (100 mL) at 0° C. was added iodine (12.0 g, 47.3 mmol). The reaction mixture was stirred at rt for 20 h. The precipitate was collected by filtration and washed with MeOH to afford 6-bromo-3-iodo-7-methylimidazo[1,2-a]pyridine (6 g, 41%) as a light grey solid. $^1$H NMR (400 MHz, CDCl$_3$) δ 8.30 (s, 1H), 7.64 (s, 1H) 7.49 (s, 1H) 2.50 (s, 3H); MS (ESI) m/z 336.7 [M+H]$^+$.

Step 3: To mixture of 6-bromo-3-iodo-7-methylimidazo[1,2-a]pyridine (5 g, 14.9 mmol), 4-cyanophenylboronic acid (2.41 g, 16.4 mmol) and K$_3$PO$_4$ (6.32 g, 29.8 mmol) in 1,4-dioxane (200 mL) and water (50 mL) was added Pd(PPh$_3$)$_4$ (860 mg, 0.74 mmol). The reaction mixture was heated at 90° C. for 1 h. The reaction mixture was diluted with water and extracted with EtOAc (2×100 ml) and washed with water (2×50 ml) and brine solution (2×50 ml). The organic layer was dried over anhydrous Na$_2$SO$_4$ and concentrated under reduced pressure to obtain the crude product. The crude product was purified by column chromatography (silica gel, eluent CHCl$_3$/MeOH 95:5) to give 4-(6-bromo-7-methylimidazo[1,2-a]pyridin-3-yl)benzonitrile (2.72 g, 59%). $^1$H NMR (400 MHz, CDCl$_3$) δ 8.52 (s, 1H), 7.83 (d, J=7.82 Hz, 2H), 7.74 (s, 1H), 7.68 (d, J=7.6 Hz, 2H), 2.49 (s, 3H); MS (ESI) m/z 312 [M+H]$^+$.

Step 4: To a mixture of 4-(6-bromo-7-methylimidazo[1,2-a]pyridin-3-yl)benzonitrile (2.7 g, 8.68 mmol), 4-(ethoxycarbonyl)phenylboronic acid (1.85 g, 9.54 mmol), K$_3$PO$_4$ (3.68 g, 17.36 mmol) in 1,4-dioxane (200 mL) and water (50 mL), was added Pd(PPh$_3$)$_4$ (501 mg, 0.43 mmol). The reaction mixture was heated at 90° C. for 1 h and was diluted with water, extracted with EtOAc (2×100 ml) and washed with water (2×50 ml) and brine solution (2×50 ml). The organic layer was dried over anhydrous Na$_2$SO$_4$ and concentrated under reduced pressure. The residue was purified by column chromatography (silica gel, eluent CHCl$_3$/MeOH 95:5) to 1.6 g (50%) of ethyl 4-(3-(4-cyanophenyl)-7-methylimidazo[1,2-a]pyridin-6-yl)benzoate. $^1$H NMR (400 MHz, CD$_3$OD) δ 9.21 (s, 1H), 8.95 (s, 1H), 8.21 (s, 1H), 8.17-8.12 (m, 5H), 8.08 (s, 1H), 7.91 (d, J=8.0 Hz, 1H), 7.82 (t, J=8.4 Hz, 1H), 4.03 (q, J=7.2 Hz, 2H), 2.39 (s, 3H) 2.1-2.23 (t, J=7.2 Hz, 3H); MS (ESI) m/z 353 [M+H]$^+$.

Step 5: To a solution of 4-(3-(4-cyanophenyl)-7-methylimidazo[1,2-a]pyridin-6-yl)benzoate (1.6 g, 3.26 mmol) in THF (20 mL) was added LiOH (0.411 g, 9.79 mmol) in water (15 mL) and MeOH (15 ml) at rt and stirred for 16 h. TLC indicated absence of SM and formation of a polar spot. The reaction mixture was concentrated under reduced pressure to afford 4-(3-(4-cyanophenyl)-7-methylimidazo[1,2-a]pyridin-6-yl)benzoic acid (900 mg, 64%) as an off white solid which was used in the next step with out purification. $^1$H NMR (400 MHz, CD$_3$OD) δ 9.21 (s, 1H), 8.95 (s, 1H), 8.21 (s, 1H), 8.17-8.12 (m, 5H), 8.08 (s, 1H), 7.91 (d, J=8.0 Hz, 1H), 7.82 (t, J=8.4 Hz, 1H), 4.03 (q, J=7.2 Hz, 2H), 2.39 (s, 3H) 2.1-2.23 (t, J=7.2 Hz, 3H); MS (ESI) m/z 353 [M+H]$^+$.

Step 6: To a solution of 4-(3-(4-cyanophenyl)-7-methylimidazo[1,2-a]pyridin-6-yl)benzoic acid (250 mg, 0.7 mmol) in DMF (15.0 mL) were added HATU (400 mg, 1.05 mmol), N-methyl morpholine (0.155 mL, 1.4 mmol) and tert-butyl 4-methylpiperidin-4-ylcarbamate (165 mg, 0.77 mmol). The reaction mixture was stirred at room temperature under inert atmosphere for 16 h then, was diluted with water (25 mL) and extracted with EtOAc (3×25 mL). The combined organic layer was dried over Na$_2$SO$_4$ and was concentrated under reduced pressure. The crude product was purified by column chromatography (silica gel, eluent CH$_2$Cl$_2$/MeOH 95:5) to afford tert-butyl 1-(4-(3-(4-cyanophenyl)-7-methylimidazo[1,2-a]pyridin-6-yl)benzoyl)-4-methylpiperidin-4-ylcarbamate (300 mg, 77%, LC-MS 92%) as an off-white solid. $^1$H NMR (400 MHz, DMSO-d$_6$) δ (ppm): 8.41 (s, 1H), 7.95-7.94 (m, 5H), 7.67 (s, 1H), 7.54 (d, J=12.0 Hz, 2H), 7.44 (d, J=12.0 Hz, 2H), 3.79 (bs, 2H), 3.45 (bs, 3H), 2.29 (s, 3H), 1.58-1.24 (m, 6H), 1.09 (s, 9H); MS (ESI) m/z 510 [M+H]$^+$.

Step 7: To a solution of tert-butyl 1-(4-(3-(4-cyanophenyl)-7-methylimidazo[1,2-a]pyridin-6-yl)benzoyl)-4-methylpiperidin-4-ylcarbamate (300 mg, 0.546 mmol) in dichloromethane (10 mL) was added TFA (3 mL) in dichloromethane (5 mL). The reaction mixture was stirred for 4 h at rt. The reaction mixture was diluted with water (100 mL) and NaHCO$_3$ (100 mL) and extracted with CH$_2$Cl$_2$ (2×50 mL). The combined organic layer was concentrated to dryness under reduced pressure to afford 4-(6-(4-(4-amino-4-methylpiperidine-1-carbonyl)phenyl)-7-methylimidazo[1,2-a]pyridin-3-yl)benzonitrile (100 mg, 46%, AUC HPLC 95.5%) as an off-white solid; m.p. 124-132° C. $^1$H NMR (400 MHz, DMSO-d$_6$) δ (ppm): 8.41 (s, 1H), 7.95-7.94 (m, 5H), 7.67 (s, 1H), 7.54 (d, J=12.0 Hz, 2H), 7.44 (d, J=12.0 Hz, 2H), 3.79 (bs, 2H), 3.45 (bs, 3H), 2.29 (s, 3H), 1.58-1.24 (m, 6H), 1.09 (s, 3H); MS (ESI) m/z 450.31 [C$_{28}$H$_{27}$N$_5$O+H]$^+$.

Example 138: 4-(7-methyl-6-(4-(4-methylpipera-zine-1-carbonyl)phenyl)imidazo[1,2-a]pyridin-3-yl) benzonitrile

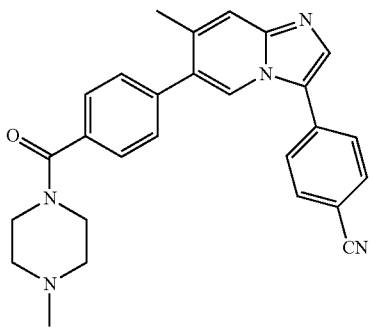 [SMILES: Cc1cc2ncc(-c3ccc(C#N)cc3)n2cc1-c1ccc(C(=O)N2CCN(C)CC2)cc1]

To a solution of 4-(3-(4-cyanophenyl)-7-methylimidazo[1,2-a]pyridin-6-yl)benzoic acid (200 mg, 0.566 mmol) in DMF (10.0 mL) were added HATU (322 mg, 0.849 mmol), N-methyl morpholine (0.158 mL, 1.132 mmol) and 1-methylpiperazin (0.068 mL, 0.623 mmol). The reaction mixture was stirred at room temperature under inert atmosphere for 16 h, then it was diluted with water (25 mL) and extracted with EtOAc (3×25 mL). The combined organic layer was dried over $Na_2SO_4$ and was concentrated under reduced pressure. The crude residue was purified by column chromatography (silica gel, eluent $CH_2Cl_2$/MeOH 95:5) and followed by preparative HPLC to afford 4-(7-methyl-6-(4-(4-methylpiperazine-1-carbonyl)phenyl)imidazo[1,2-a]pyridin-3-yl)benzonitrile (100 mg, 50%, AUC HPLC 97.6%) as an off-white solid; m.p. 162-164° C. $^1$H NMR (400 MHz, $CD_3OD$) δ (ppm): 8.47 (s, 1H), 7.85-7.81 (m, 5H), 7.57-7.53 (m, 5H), 3.83 (bs, 2H), 3.53 (bs, 2H), 2.54-2.34 (bm, 4H), 2.34 (s, 3H), 2.33 (s, 3H); MS (ESI) m/z 436.27 $[C_{27}H_{25}N_5O+H]^+$.

Example 139: 4-(6-(2-methyl-4-(4-methylpipera-zine-1-carbonyl)phenyl)imidazo[1,2-a]pyridin-3-yl) benzonitrile

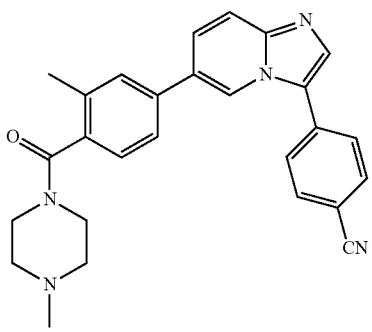 [SMILES: Cc1cc(-c2ccc3ncc(-c4ccc(C#N)cc4)n3c2)ccc1C(=O)N1CCN(C)CC1]

Step 1: To a solution of 2-methyl-4-bromobenzoic acid (2 g, 9.30 mmol) in DMF (6 mL) was added NMM (1.87 g, 18.604 mmol) followed by addition of HATU (5.3 g, 13.95 mmol) at rt and stirred for 30 min. 1-methylpiperazine (1.39 g, 13.95 mmol) was added and stirred at rt for 16 h. The reaction mixture was diluted with EtOAc and washed with water and brine solution. The organic layer was dried over anhydrous $Na_2SO_4$ and concentrated under reduced pressure to obtain (4-bromo-2-methylyphenyl)(4-methylpiperazin-1-yl)methanone (1.9 g, 70%, AUC LC-MS 98%) as a brown solid.

Step 2: A mixture of (4-bromo-2-methylphenyl)(4-methylpiperazin-1-yl)methanone (1.9 g, 6.39 mmol), Bis(pinacolato)diboron (1.74 g, 6.84 mmol), KOAc (41.88 g, 19.19 mmol) in 1,4-dioxane (30 mL) was degassed with argon for 30 min. $PdCl_2dppf$ (140.5 mg, 0.19 mmol) and dppf (106.4 mg, 0.19 mmol) were added and again degassed with argon for 30 min and the reaction mixture was heated at 90° C. for 16 h. The reaction mixture was diluted with EtOAc and washed with water, the organic layer was dried over anhydrous $Na_2SO_4$ and concentrated under reduced pressure to afford the crude (2-methyl-4-(4,4,5,5-tetramethyl-1,3,2-dioxaborolan-2-yl)phenyl)(4-methylpiperazin-1-yl)methanone (~1.3 g) as a brown liquid which was used in next step without further purification. MS (ESI) m/z 345.

Step 3: To a mixture of 4-(6-bromoimidazo[1,2-a]pyridin-3-yl)benzonitrile (3.95 g, 13.33 mmol), (2-methyl-4-(4,4,5,5-tetramethyl-1,3,2-dioxaborolan-2-yl)phenyl)(4-methylpiperazin-1-yl)methanone (1.3 g, 3.78 mmol), $K_3PO_4$ (1.6 g, 7.56 mmol) in 1,4-dioxane (30 mL) and water (6 mL) was added $Pd(PPh_3)_4$ (218 mg, 0.188 mmol). The reaction mixture was heated at 90° C. for 1 h and was diluted with water and extracted with EtOAc and washed with water and brine solution. The organic layer was dried over anhydrous $Na_2SO_4$ and concentrated under reduced pressure to obtain the crude product. The crude product was purified by column chromatography followed by preparative HPLC to afford 4-(6-(2-methyl-4-(4-methylpiperazine-1-carbonyl)phenyl)imidazo[1,2-a]pyridin-3-yl)benzonitrile (45 mg, AUC HPLC>99%); White solid; m.p. 169-173° C. $^1$H NMR (400 MHz, $CDCl_3$) δ (ppm): 8.46 (s, 1H), 7.85-7.80 (m, 3H), 7.77-7.72 (m, 2H), 7.52-7.48 (m, 1H), 7.39-7.37 (m, 2H), 7.28 (s, 1H), 3.86 (bs, 2H), 3.31 (bs, 2H), 2.51 (bs, 2H), 2.39 (s, 3H), 2.33 (s, 5H); MS (ESI) m/z 436 $[C_{27}H_{25}N_5O+H]^+$.

Example 140: 4-(6-(2-fluoro-4-(4-methylpiperazine-1-carbonyl)phenyl)imidazo[1,2-a]pyridin-3-yl)ben-zonitrile

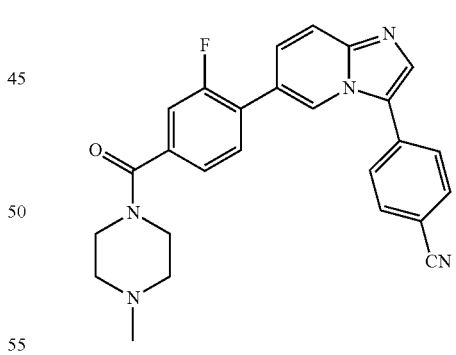

Step 1: To a solution of 2-fluoro-4-bromobenzoic acid (1 g, 4.56 mmol) in DMF (3 mL) was added NMM (922 mg, 9.13 mmol) followed by addition of HATU (2.6 g, 6.85 mmol) at rt and stirred for 30 min. 1-Methylpiperazine (684 mg, 6.85 mmol) was added and stirred at rt for 16 h. The reaction mixture was diluted with EtOAc and washed with water and brine solution. The organic layer was dried over anhydrous $Na_2SO_4$ and concentrated under reduced pressure to obtain (4-bromo-2-fluoroyphenyl)(4-methylpiperazin-1-yl)methanone (1.6 g, 100%, LC-MS 87%) as a brown solid. MS (ESI) m/z 302.

Step 2: A mixture of (4-bromo-3-fluorophenyl)(4-methylpiperazin-1-yl)methanone (1.6 g, 5.31 mmol), Bis(pinacolato)diboron (1.45 g, 5.68 mmol), KOAc (1.56 g, 15.95 mmol) in 1,4-dioxane (30 mL) was degassed with argon for 30 min. PdCl$_2$dppf (116 mg, 0.159 mmol) and dppf (88.4 mg, 0.159 mmol) were added and again degassed with argon for 30 min and the reaction mixture was heated at 90° C. for 16 h. The reaction mixture was diluted with EtOAc and washed with water, the organic layer was dried over anhydrous Na$_2$SO$_4$ and concentrated under reduced pressure to afford 2-fluoro-4-(4-methylpiperazine-1-carbonyl)phenylboronic acid (900 mg, LC-MS 55%) as a brown liquid which was used in next step without purification.

Step 3: To a solution of 4-(6-bromoimidazo[1,2-a]pyridin-3-yl)benzonitrile (400 mg, 1.342 mmol), 2-fluoro-4-(4-methylpiperazine-1-carbonyl)phenylboronic acid (900 mg, 3.30 mmol), K$_3$PO$_4$ (711 mg, 3.35 mmol) in a mixture of 1,4-dioxane (12 mL) and water (3 mL) was added Pd(PPh$_3$)$_4$ (77.5 mg, 0.067 mmol). The reaction mixture was heated at 90° C. for 1 h, was diluted with water, extracted with EtOAc and the organic phase was washed with water and brine solution, dried over anhydrous Na$_2$SO$_4$, filtered and concentrated under reduced. The residue was purified by preparative HPLC to give 4-(6-(2-methyl-4-(4-methylpiperazine-1-carbonyl)phenyl)imidazo[1,2-a]pyridin-3-yl)benzonitrile (35 mg, AUC HPLC 99.56%); m.p. 170-174° C. $^1$H NMR (400 MHz, CD$_3$OD) δ (ppm): 8.77 (s, 1H), 7.91 (m, 5H), 7.79-7.66 (m, 3H), 7.38-7.36 (m, 2H), 3.80 (bs, 2H), 3.54 (bs, 2H), 2.61 (bs, 4H), 2.40 (s, 3H); MS (ESI) m/z 440.40 [C$_{26}$H$_{22}$FN$_5$O+H]$^+$.

Example 141: 4-(6-(3-chloro-4-(4-methylpiperazine-1-carbonyl)phenyl)imidazo[1,2-a]pyridin-3-yl)benzonitrile

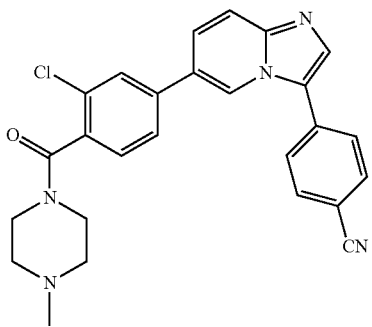 [SMILES: CN1CCN(C(=O)c2ccc(-c3ccc4ncc(-c5ccc(C#N)cc5)n4c3)cc2Cl)CC1]

Step 1: To a mixture of 4-(6-bromoimidazo[1,2-a]pyridin-3-yl)benzonitrile (436 mg, 1.46 mmol), 3-chloro-4-(ethoxycarbonyl)phenylboronic acid (500 mg, 1.61 mmol), K$_3$PO$_4$ (775 mg, 3.65 mmol) in 1,4-dioxane (14 mL) and water (3.5 mL), was added Pd(PPh$_3$)$_4$ (85 mg, 0.0736 mmol). The reaction mixture was heated at 90° C. for 1 h, then was diluted with water and extracted with EtOAc. The organic layer and washed in turn with water and brine then was dried over anhydrous Na$_2$SO$_4$ and concentrated under reduced pressure to obtain ethyl 2-chloro-4-(3-(4-cyanophenyl)imidazo[1,2-a]pyridin-6-yl)benzoate (1 g, 90%). The product was used in the next step without further purification.

Step 2: To a solution of ethyl 2-chloro-4-(3-(4-cyanophenyl)imidazo[1,2-a]pyridin-6-yl)benzoate (1 g, 2.49 mmol) in THF (10 mL) and MeOH (10 mL) was added LiOH (261 mg, 6.23 mmol) in water (4 mL). The reaction mixture was stirred for 16 h at rt and was concentrated under reduced pressure then diluted with water and acidified with potassium bisulphate. The aqueous layer was extracted with EtOAc, which was dried and concentrated under reduced pressure to give 300 mg (38%) of 2-chloro-4-(3-(4-cyanophenyl)imidazo[1,2-a]pyridin-6-yl)benzoic acid (LC-MS 68%) as a yellow solid.

Step 3: To a solution of 2-chloro-4-(3-(4-cyanophenyl)imidazo[1,2-a]pyridin-6-yl)benzoic acid (300 mg, 0.80 mmol) in DMF (2 mL) was added NMM (162 mg, 1.60 mmol) followed by addition of HATU (458 mg, 1.20 mmol) at rt and stirred for 30 min. 1-Methylpiperazine (120 mg, 1.21 mmol) was added and stirred at rt for 16 h. The reaction mixture was diluted with water and filtered to obtain a solid which was further purified by preparative HPLC to afford 4-(6-(3-chloro-4-(4-methylpiperazine-1-carbonyl)phenyl)imidazo[1,2-a]pyridin-3-yl)benzonitrile (60 mg, 24%) as an off white solid; m.p. 143-157° C. $^1$H NMR (400 MHz, CDCl$_3$) δ (ppm): 8.46 (s, 1H), 7.85-7.79 (m, 4H), 7.73-7.71 (m, 2H), 7.56 (s, 1H), 7.49-7.38 (m, 3H), 3.88-3.83 (m, 2H), 3.34 (bs, 2H), 2.51-2.41 (m, 4H), 2.33 (s, 3H); MS (ESI) m/z 456.32 [C$_{26}$H$_{22}$ClN$_5$O+H]$^+$.

Example 142: 4-(6-(3-fluoro-4-(4-methylpiperazine-1-carbonyl)phenyl)imidazo[1,2-a]pyridin-3-yl)benzonitrile

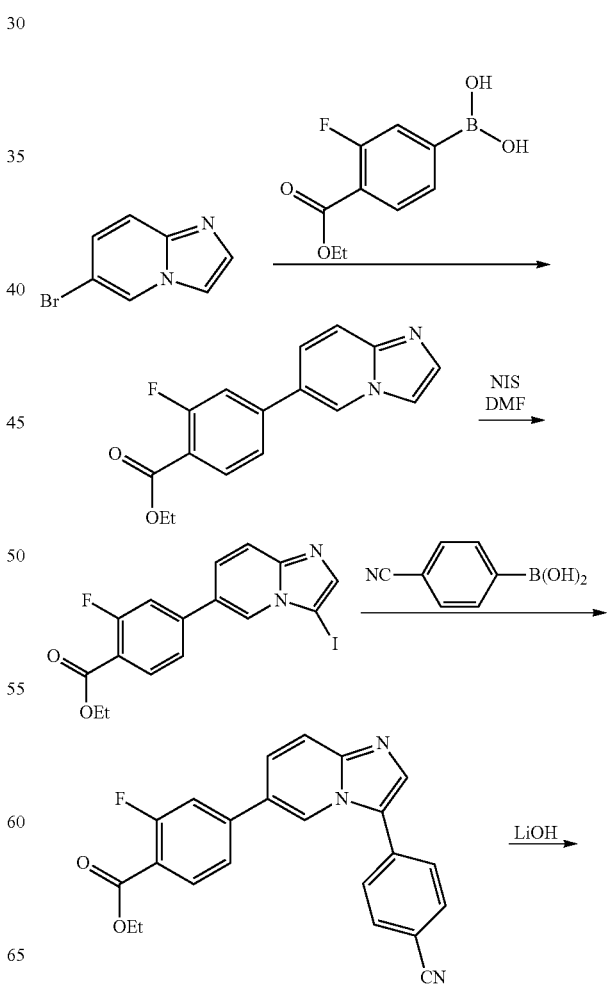

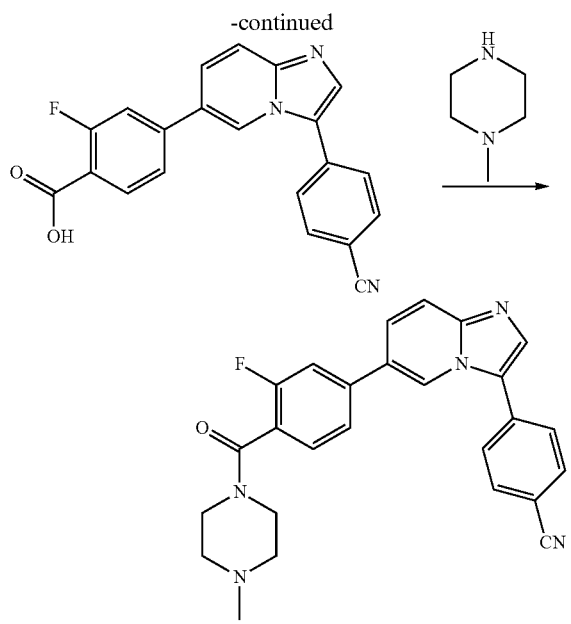

Step 1: To a solution of 4-(ethoxycarbonyl)-3-fluorophenylboronic acid (1.29 g, 6.091 mmol), K$_3$PO$_4$ (3.22 g, 15.22 mmol) in 1,4-dioxane (20 mL), and water (3 mL) was added 6-bromoimidazo[1,2-a]pyridine (1 g, 5.07 mmol) and degassed with argon for 30 min. (A-Phos)$_2$PdCl$_2$ (293 mg, 0.25 mmol) was added and again degassed with argon for 30 min and the reaction mixture was heated at 90° C. for overnight. The reaction mixture was washed with water. The organic layer was concentrated and the crude product was purified by column chromatography (silica gel, eluent CHCl$_3$/MeOH 96.5:3.5) to afford 2-fluoro-4-(imidazo[1,2-a]pyridin-6-yl)benzoate (1.16 g, 81%, AUC LC-MS 84%). $^1$H NMR (300 MHz, DMSO-d$_6$) ppm δ 9.1 (s, 1H), 7.9 (m, 2H), 7.6 (m, 5H), 4.3 (q, J=6.9 Hz, 2H), 1.3 (t, J=6.9 Hz, 3H); MS (ESI) m/z 285 (M+1).

Step 2: To a solution of 2-fluoro-4-(imidazo[1,2-a]pyridin-6-yl)benzoate (1.16 g, 4.10 mmol) in DMF (20 mL) and added to NIS (1.10 g, 4.92 mmol). The reaction mixture stirred for 3 h at 100° C. Water was added to the reaction mixture to induce precipitation of the product which was filtered and dried under reduced pressure to give ethyl 2-fluoro-4-(3-iodoimidazo[1,2-a]pyridin-6-yl)benzoate (1.2 g, 75%, AUC LC-MS 92.5%). $^1$H NMR (300 MHz, DMSO-d$_6$) δ 8.5 (s, 1H), 7.8 (m, 6H), 4.3 (q, J=6.9 Hz, 2H), 1.3 (t, J=6.9 Hz, 3H); MS (ESI) m/z 410 (M+1).

Step 3: To a solution of ethyl 2-fluoro-4-(3-iodoimidazo[1,2-a]pyridin-6-yl)benzoate (900 mg, 2.23 mmol) and 4-cyanophenylboronic acid (394 mg, 2.68 mmol), K$_3$PO$_4$ (949 mg, 4.47 mmol) in 1,4-dioxane (10 mL), and water (1 mL) was degassed with argon for 30 min. (A-Phos)$_2$PdCl$_2$ (129 mg, 0.111 mmol) was added and again degassed with argon for 30 min and the reaction mixture was heated at 90° C. for overnight. TLC indicated absence of SM. The reaction mixture was washed with water. The organic layer was concentrated and purified by column chromatography (silica gel, eluent CHCl$_3$/MeOH 96.5:3.5) to afford ethyl4-(3-(4-cyanophenyl)imidazo[1,2-a]pyridin-6-yl)-2-fluorobenzoate (600 mg, 71%). $^1$H NMR (300 MHz, DMSO-d$_6$) ppm δ 8.9 (s, 1H), 7.8 (m, 6H), 4.3 (q, J=6.9 Hz, 2H), 1.3 (t, J=6.9 Hz, 3H); MS (ESI) m/z 386 (M+1).

Step 4: To a solution of ethyl 4-(3-(4-cyanophenyl)imidazo[1,2-a]pyridin-6-yl)-2-fluorobenzoate (600 mg, 1.55 mmol) dissolved in THF (5 mL), water (5 mL), EtOH (5 mL) was added LiOH (130 mg, 3.11 mmol). The reaction mixture was stirred for 1 h. After completion of the reaction as indicated by TLC, the reaction mixture was added to citric acid and washed with water and extracted with EtOAc. The organic layer was washed with water and brine, dried over anhydrous Na$_2$SO$_4$, filtered and concentrated under reduced pressure. The crude compound was purified by recrystallization to afford 4-(3-(4-cyanophenyl)imidazo[1,2-a]pyridin-6-yl)-2-fluorobenzoic acid (450 mg, 81%, AUC LC-MS 83.2%). $^1$H NMR (300 MHz, DMSO-d$_6$) ppm δ 8.07 (s, 1H), 7.6 (d, J=8.0 Hz, 2H), 7.5 (m, 2H), 7.4 (m, 4H), 7.3 (d, J=11.2 Hz, 2H); MS (ESI) m/z 358 (M+1).

Step 5: To a solution of 4-(3-(4-cyanophenyl)imidazo[1,2-a]pyridin-6-yl)-2-fluorobenzoic acid (450 mg, 1.26 mmol) in DMF (5 mL) was added NMM (0.28 mL, 2.52 mmol) followed by addition of HATU (957 mg, 2.52 mmol) at rt and stirred for 20 min. 1-Methylpiperazine (0.138 mL, 1.38 mmol) was added and stirred at rt for 16 h. The reaction mixture was diluted with EtOAc and washed with water and brine solution. The organic layer was dried over anhydrous Na$_2$SO$_4$ and concentrated under reduced pressure to obtain 4-(6-(3-fluoro-4-(4-methylpiperazine-1-carbonyl)phenyl)imidazo[1,2-a]pyridin-3-yl)benzonitrile (150 mg, 27.1%, AUC HPLC 97.4%) as an off white solid; m.p. 176-185° C. $^1$H NMR (400 MHz, DMSO-d$_6$) δ (ppm): 8.86 (s, 1H), 8.01 (m, 5H), 7.84-7.67 (m, 4H), 7.49 (t, J=8.0 Hz, 1H), 3.65 (bs, 2H), 3.26 (bs, 4H), 2.37 (bs, 2H), 2.27 (bs, 4H), 2.20 (s, 3H); MS (ESI) m/z 440 [C$_{26}$H$_{22}$FN$_5$O+H]$^+$.

Example 143: 4-(6-(2-hydroxy-4-(4-methylpiperazine-1-carbonyl)phenyl)imidazo[1,2-a]pyridin-3-yl)benzonitrile

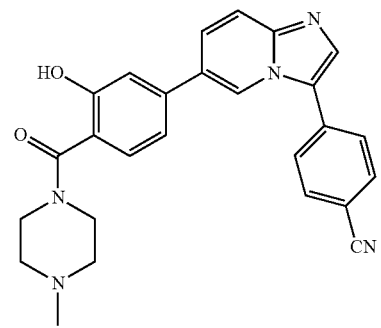 [SMILES: CN1CCN(C(=O)c2ccc(-c3ccc4ncc(-c5ccc(C#N)cc5)n4c3)cc2O)CC1]

Step 1: To a mixture of 4-(6-bromoimidazo[1,2-a]pyridin-3-yl)benzonitrile (3.95 g, 13.33 mmol), (2-methoxy-4-(4,4,5,5-tetramethyl-1,3,2-dioxaborolan-2-yl)phenyl) (4-methylpiperazin-1-yl)methanone (4.9 g, 13.61 mmol), K$_3$PO$_4$ (5.8 g, 27.22 mmol) in 1,4-dioxane (80 mL) and water (20 mL) was added Pd(PPh$_3$)$_4$ (785.9 mg, 0.68 mmol). The reaction mixture was heated at 90° C. for 1 h. The reaction mixture was diluted with water and extracted with EtOAc and washed with water and brine solution. The organic layer was dried over anhydrous Na$_2$SO$_4$ and concentrated under reduced pressure to obtain crude product. The crude product was purified by column chromatography and by preparative HPLC of 4-(6-(3-methoxy-4-(4-methylpiperazine-1-carbonyl)phenyl)imidazo[1,2-a]pyridin-3-yl)benzonitrile (54 mg, AUC HPLC 98.1%) as an off-white solid; m.p. 121-134° C. $^1$H NMR (400 MHz, CDCl$_3$) δ (ppm): 8.46 (s, 1H), 7.84-7.71 (m, 4H), 7.49 (d, J=15.0 Hz, 1H), 7.34 (d, J=10.4 Hz, 1H), 7.13 (d, J=10.4 Hz, 1H), 7.01 (s, 1H), 3.90 (s, 3H), 3.85 (bs, 2H), 3.32 (bs, 2H), 2.61-2.40 (m, 4H), 2.32 (s, 3H); MS (ESI) m/z 452 [C$_{27}$H$_{25}$N$_5$O$_2$+H]$^+$.

Step 2: A solution of 4-(6-(3-methoxy-4-(4-methylpiperazine-1-carbonyl)phenyl)imidazo[1,2-a]pyridin-3-yl)benzonitrile (600 mg, 1.33 mmol) in CH$_2$Cl$_2$ (10 mL) was cooled to 0° C. followed by the addition of BBr$_3$ (738 mg, 2.2 mmol). The reaction mixture was stirred at rt for 2 h. The reaction mixture was cooled to 0° C. and quenched by dropwise addition of a saturated aqueous solution of NaHCO$_3$ (100 mL) followed by extraction with EtOAc (3×100 mL). The organic layer was washed in turn with water and brine then, was dried over anhydrous Na$_2$SO$_4$, filtered and concentrated under reduced pressure. The crude compound was purified by column chromatography (silica gel, eluent CHCl$_3$/MeOH 99/1 to 97/3) and by purification by preparative HPLC to afford 4-(6-(3-hydroxy-4-(4-methylpiperazine-1-carbonyl)phenyl)imidazo[1,2-a]pyridin-3-yl)benzonitrile (80 mg, 20%, AUC HPLC 98.7%) as an off-white solid; $^1$H NMR (400 MHz, DMSO-d$_6$) δ (ppm): 8.69 (s, 1H), 8.28 (s, 1H), 8.00 (m, 4H), 7.82-7.79 (m, 1H), 7.64-7.61 (m, 1H), 7.21-7.15 (m, 3H), 3.39 (bs, 4H), 2.29 (bs, 2H), 2.18 (s, 3H); MS (ESI) m/z 438.2 [C$_{26}$H$_{23}$N$_5$O$_2$+H]$^+$.

Example 144: 4-(6-(3-hydroxy-4-(4-methylpiperazine-1-carbonyl)phenyl)imidazo[1,2-a]pyridin-3-yl)benzonitrile

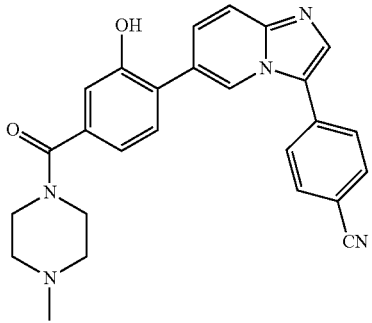 [SMILES: CN1CCN(C(=O)c2ccc(-c3ccc4ncc(-c5ccc(C#N)cc5)n4c3)c(O)c2)CC1]

Step 1: A mixture of 4-(6-bromoimidazo[1,2-a]pyridin-3-yl)benzonitrile (2.38 g, 8 mmol), (3-methoxy-4-(4,4,5,5-tetramethyl-1,3,2-dioxaborolan-2-yl)phenyl) (4-methylpiperazin-1-yl)methanone (2.88 g, 8 mmol), K$_3$PO$_4$ (3.4 g, 2 mmol) in 1,4-dioxane (30 mL) and water (6 mL) was degassed with argon for 30 min. Pd(PPh$_3$)$_4$ (462 mg, 0.4 mmol) was added and again degassed with argon for 30 min and the reaction mixture was heated at 90° C. for 1 h. The reaction mixture was diluted with water and extracted with EtOAc, washed with water and brine solution. The organic layer was dried over anhydrous Na$_2$SO$_4$ and concentrated under reduced pressure to obtain the crude product. The crude product was purified by column chromatography to obtain 4-(6-(2-methoxy-4-(4-methylpiperazine-1-carbonyl)phenyl)imidazo[1,2-a]pyridin-3-yl)benzonitrile (1 g, 28%, AUC 99.3%) as an off-white solid; m.p. 123-178° C. $^1$H NMR (400 MHz, CD$_3$OD) δ (ppm): 8.72 (s, 1H), 7.92-7.86 (m, 5H), 7.70-7.52 (m, 3H), 7.17 (s, 1H), 7.10 (d, J=8.0 Hz, 1H), 3.90 (s, 3H), 3.81-3.56 (br. m, 4H), 2.60 (bs, 4H), 2.41 (s, 3H); MS (ESI) m/z 452.36 [C$_{27}$H$_{25}$N$_5$O$_2$+H]$^+$.

Step 2: A solution of 4-(6-(2-methoxy-4-(4-methylpiperazine-1-carbonyl)phenyl)imidazo[1,2-a]pyridin-3-yl)benzonitrile (500 mg, 1.1086 mmol) in CH$_2$Cl$_2$ (10 mL) was cooled to 0° C. followed by addition of BBr$_3$ (1.72 g, 6.87 mmol). The reaction mixture was stirred at rt for 2 h and heated to 40° C. for 30 min. After completion, the reaction mixture was cooled to 0° C. and quenched by drop wise addition of a saturated aqueous solution of NaHCO$_3$ (100 mL) followed by extraction with EtOAc (3×100 mL). The organic layer was washed with water and brine, dried over anhydrous Na$_2$SO$_4$, filtered and concentrated under reduced pressure. The crude compound was purified by column chromatography (silica gel, eluent CHCl$_3$/MeOH 99:1 to 97:3) to afford 4-(6-(2-hydroxy-4-(4-methylpiperazine-1-carbonyl)phenyl)imidazo[1,2-a]pyridin-3-yl)benzonitrile (100 mg, 20%, AUC HPLC 96.8) as an off white solid; m.p. 263-272° C. $^1$H NMR (400 MHz, CD$_3$OD) δ (ppm): 10.20 (s, 1H), 8.81 (s, 1H), 8.00-7.93 (m, 5H), 7.76-7.73 (m, 1H), 7.63-7.60 (m, 1H), 7.53-7.50 (m, 1H), 6.96-6.89 (m, 2H), 3.70-3.35 (m, 4H), 2.34 (bs, 4H), 2.21 (s, 3H); MS (ESI) m/z 438 [C$_{26}$H$_{23}$N$_5$O$_2$+H]$^+$.

Example 145: 4-(6-(4-(4-methylpiperazine-1-carbonyl)-3-(trifluoromethyl)phenyl)imidazo[1,2-a]pyridin-3-yl)benzonitrile

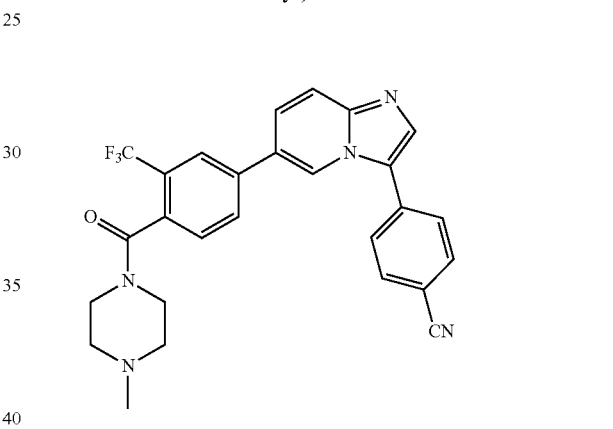

Step 1: To a solution of 2-trifluoromethyl-4-bromobenzoic acid (1 g, 3.74 mmol) in DMF (15 mL) was added NMM (755 mg, 7.41 mmol) followed by addition of HATU (2.14 g, 5.61 mmol) at rt and stirred for 30 min. 1-Methylpiperazine (411 mg, 7.41 mmol) was added and stirred at rt for 16 h. The reaction mixture was diluted with EtOAc and washed with water and brine solution. The organic layer was dried over anhydrous Na$_2$SO$_4$ and concentrated under reduced pressure to obtain crude product. The crude product was purified by column chromatography (silica gel, eluent petroleum ether/EtOAc 100:0 to 60:40) to afford (4-bromo-2-(trifluoromethyl)phenyl)(4-methylpiperazin-1-yl)methanone (1.2 g, 91%) as a red liquid. $^1$H NMR (400 MHz, CDCl$_3$) δ 7.56 (d, J=8.1 Hz, 2H), 7.39 (s, 1H), 3.79 (bs, 2H), 3.58 (bs, 2H), 2.45 (bs, 4H), 2.32 (s, 3H); MS (ESI) m/z 352 [M+H]$^+$ Step 2: To a solution of 4-bromo-2-(trifluoromethyl)phenyl)(4-methylpiperazin-1-yl)methanone (1.2 g, 3.42 mmol), bis(pinacolato)diboron (1.04 g, 4.11 mmol), KOAc (1 g, 10.26 mmol) in 1,4-dioxane (20 mL), was added PdCl$_2$dppf (75 mg, 0.1 mmol), dppf (56 mg, 0.1 mmol) and the reaction mixture was heated at 90° C. for 16 h. The reaction mixture was diluted with EtOAc and washed with water, the organic layer was dried over anhydrous Na$_2$SO$_4$ and concentrated under reduced pressure to afford (4-methylpiperazin-1-yl)(4-(4,4,5,5-tetramethyl-1,3,2-dioxaborolan-2-yl)-2-(trifluoromethyl)phenyl)methanone (600 mg) as a brown liquid which was used in next step without purification.

Step 3: To a solution of 4-(6-bromoimidazo[1,2-a]pyridin-3-yl)benzonitrile (390 mg, 1.3 mmol), (4-methylpiperazin-1-yl)(4-(4,4,5,5-tetramethyl-1,3,2-dioxaborolan-2-yl)-2-(trifluoromethyl)phenyl)methanone (400 mg, 1 mmol), $K_3PO_4$ (636 mg, 3 mmol) in 1,4-dioxane (10 mL) and water (2 mL) was degassed with argon for 30 min. $Pd(PPh_3)_4$ (34 mg, 0.03 mmol), was added and again degassed with argon for 30 min and the reaction mixture was heated at 90° C. for 1 h. TLC indicated absence of SM. The reaction mixture was diluted with water and extracted with EtOAc and washed with water and brine solution. The organic layer was dried over anhydrous $Na_2SO_4$ and concentrated under reduced pressure. The crude product was purified by preparative HPLC to afford 4-(6-(4-(4-methylpiperazine-1-carbonyl)-3-(trifluoromethyl)phenyl)imidazo[1,2-a]pyridin-3-yl)benzonitrile (40 mg, 8%, AUC HPLC>99%) as a pale yellow solid; m.p. 126-131° C. $^1$H NMR (400 MHz, CDCl$_3$) δ (ppm): 8.49 (s, 1H), 7.86-7.83 (m, 5H), 7.76-7.72 (m, 3H), 7.51-7.44 (m, 2H), 3.89 (bs, 1H), 3.81 (bs, 1H), 3.26 (bs, 2H), 2.50 (bs, 2H), 2.33 (s, 5H); MS (ESI) m/z 490 $[C_{27}H_{22}F_3N_5O+H]^+$.

Example 146: 4-(6-(3-amino-4-(4-methylpiperazine-1-carbonyl)phenyl)imidazo[1,2-a]pyridin-3-yl)benzonitrile

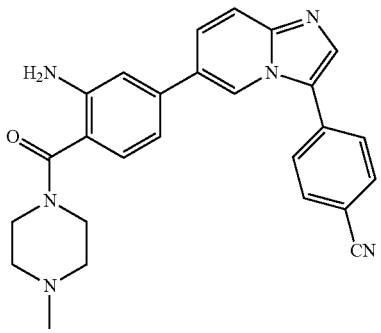 [SMILES: CN1CCN(C(=O)c2ccc(-c3ccc4ncc(-c5ccc(C#N)cc5)n4c3)cc2N)CC1]

Step 1: A solution of (4-bromo-2-nitrophenyl)(4-methylpiperazin-1-yl)methanone (750 mg, 2.29 mmol), bis(pinacolato)diboron (623 mg, 2.45 mmol), KOAc (675 mg, 6.87 mmol) in 1,4-dioxane (15 mL) was degassed with argon for 30 min. PdCl$_2$dppf (50 mg, 0.068 mmol), dppf (38 mg, 0.0687 mmol) was added and again degassed with argon for 30 min and the reaction mixture was heated at 90° C. for 16 h. The reaction mixture was diluted with EtOAc and washed with water, the organic layer was dried over anhydrous Na$_2$SO$_4$ and concentrated under reduced pressure to afford (4-methylpiperazin-1-yl)(2-nitro-4-(4,4,5,5-tetramethyl-1,3,2-dioxaborolan-2-yl)phenyl)methanone (400 mg) of as a brown liquid which direct-mass indicated the desired m/z. The crude product was used in the next step without purification.

Step 2: To a solution of (4-methylpiperazin-1-yl)(2-nitro-4-(4,4,5,5-tetramethyl-1,3,2-dioxaborolan-2-yl)phenyl)methanone (400 mg, 1.06 mmol), K$_3$PO$_4$ (451 mg, 2.13 mmol) in 1,4-dioxane (5 mL) and water (1 mL) was degassed with argon for 30 min. (A-Phos)$_2$PdCl$_2$ (61 mg, 0.053 mmol) was added and again degassed with argon for 30 min and the reaction mixture was heated at 90° C. for 1 h. Water was added to the reaction mixture to induce precipitation which was filtered to give crude product. The crude product was purified by column chromatography (silica gel, eluent CHCl$_3$/MeOH 96.5:3.5) to afford 4-(6-(4-(4-methylpiperazine-1-carbonyl)-3-nitrophenyl)imidazo[1,2-a]pyridin-3-yl)benzonitrile (340 mg, 68.5%, LC-MS 89%). $^1$H NMR (400 MHz, CDCl$_3$): δ 8.5 (s, 1H), 8.3 (s, 1H), 7.8 (s, 4H), 7.7 (d, J=8.3 Hz, 2H), 7.5 (d, J=7.9 Hz, 2H), 3.9 (bs, 1H), 3.7 (bs, 1H), 3.3 (s, 2H), 2.5 (bs, 2H), 2.3 (s, 5H).

Step 3: A solution of 4-(6-(4-(4-methylpiperazine-1-carbonyl)-3-nitrophenyl)imidazo[1,2-a]pyridin-3-yl)benzonitrile (340 mg, 0.73 mmol) in EtOH (10 mL) was added HCl (1 mL) and SnCl$_2$ (492 mg, 2.18 mmol). The reaction mixture was heated at 90° C. for 2 h. Work-up and purification by column chromatography gave 4-(6-(3-amino-4-(4-methylpiperazine-1-carbonyl)phenyl)imidazo[1,2-a]pyridin-3-yl)benzonitrile (120 mg, 99.2%, AUC HPLC>99%) as an off-white solid; m.p. 218-222° C. $^1$H NMR (400 MHz, DMSO-d$_6$) δ (ppm): 8.67 (s, 1H), 8.02-7.99 (m, 5H), 7.80 (d, J=8.0 Hz, 1H), 7.61 (d, J=8.0 Hz, 1H), 7.10 (d, J=8.0 Hz, 1H), 7.02 (s, 1H), 6.93 (d, J=8.0 Hz, 1H), 5.32 (s, 2H), 3.47 (bs, 4H), 2.31 (bs, 4H), 2.19 (s, 3H); MS (ESI) m/z 437 $[C_{26}H_{24}N_6O+H]^+$.

Example 147: 4-(6-(3-(diethylamino)-4-(4-methylpiperazine-1-carbonyl)phenyl)imidazo[1,2-a]pyridin-3-yl)benzonitrile

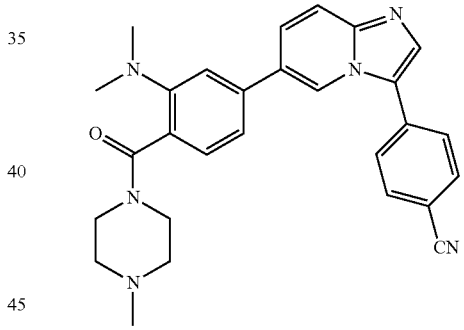

To a solution of 4-(6-(3-amino-4-(4-methylpiperazine-1-carbonyl)phenyl)imidazo[1,2-a]pyridin-3-yl)benzonitrile (200 mg) in methanol (20 mL) were added formaldehyde (6 mL), and acetic acid (2 mL) and the reaction mixture was stirred for 2 h at rt. NaCNBH$_3$ (4 eq) was added at 0° C. and the reaction mixture was stirred at rt for 6 h. The reaction mixture was basified with NaHCO$_3$ solution and extracted with EtOAc. The organic layer was dried over anhydrous Na$_2$SO$_4$ and concentrated under reduced pressure. The crude product was purified by column chromatography to obtain (150 mg, 75%) which further purified by preparative HPLC to afford 4-(6-(3-(dimethylamino)-4-(4-methylpiperazine-1-carbonyl)phenyl)imidazo[1,2-a]pyridin-3-yl)benzonitrile (90 mg, 45%, AUC HPLC 97.52%) as an off-white solid; m.p. 161-166° C. $^1$H NMR (400 MHz, CDCl$_3$) δ 8.47 (s, 1H), 7.84-7.74 (m, 6H), 7.51 (d, J=9.2 Hz, 1H), 7.31 (d, J=8.0 Hz, 1H), 7.05 (d, J=7.6 Hz, 1H), 3.85 (s, 2H), 3.40-3.27 (m, 2H), 2.87 (s, 6H), 2.51 (bs, 2H), 2.34 (bs, 6H); MS (ESI) m/z 465 $[C_{28}H_{28}N_6O+H]^+$.

Example 148: 4-(6-(3-(diethylamino)-4-(4-methyl-piperazine-1-carbonyl)phenyl)imidazo[1,2-a]pyridin-3-yl)benzonitrile

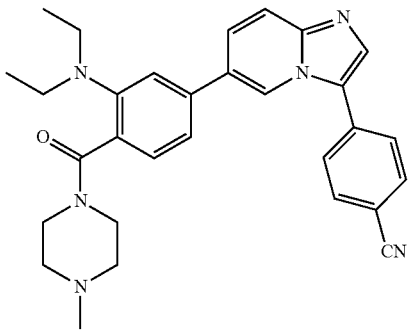 [SMILES: CCN(CC)c1cc(-c2ccc3ncc(-c4ccc(C#N)cc4)n3c2)ccc1C(=O)N1CCN(C)CC1]

To a solution of 4-(6-(3-amino-4-(4-methylpiperazine-1-carbonyl)phenyl)imidazo[1,2-a]pyridin-3-yl)benzonitrile (200 mg) in methanol (20 ml) were added acetaldehyde (4 mL) and acetic acid (2 mL) and the reaction mixture was stirred for 2 h at rt. NaCNBH$_3$ (4 eq) was added at 0° C. and the reaction mixture was stirred at rt for 6 h. The reaction mixture was basified with NaHSO$_4$ solution and extracted with EtOAc. The organic layer was dried over anhydrous Na$_2$SO$_4$ and concentrated under reduced pressure to afford the crude product which was purified by column chromatography to obtain the desired product (90 mg, 90%) which was purified further by preparative HPLC to give 4-(6-(3-(diethylamino)-4-(4-methylpiperazine-1-carbonyl)phenyl) imidazo[1,2-a]pyridin-3-yl)benzonitrile (70 mg, 31%, AUC HPLC 99.15%) as an off-white solid; m.p. 118-122° C. $^1$H NMR (400 MHz, CDCl$_3$) δ 8.48 (s, 1H), 7.83-7.73 (m, 6H), 7.50 (d, J=9.2 Hz, 1H), 7.33 (d, J=8.0 Hz, 1H), 7.11 (d, J=7.6 Hz, 1H), 7.05 (s, 1H), 4.00 (bs, 1H), 3.71 (bs, 1H), 3.39 (bs, 1H), 3.26-3.15 (m, 5H), 3.58 (bs, 1H), 2.42 (bs, 2H), 2.32 (s, 2H), 2.22 (bs, 2H), 1.11 (t, J=6.0 Hz, 6H); MS (ESI) m/z 493 [C$_{30}$H$_{32}$N$_6$O+H]$^+$.

Example 149: N-(5-(3-(4-cyanophenyl)imidazo[1,2-a]pyridin-6-yl)-2-(4-methylpiperazine-1-carbonyl)phenyl)acetamide

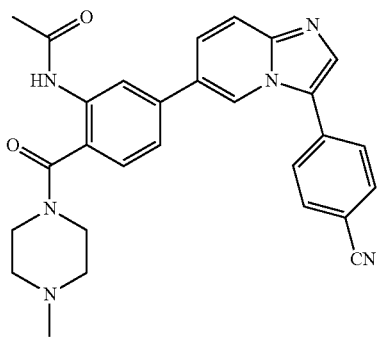 [SMILES: CC(=O)Nc1cc(-c2ccc3ncc(-c4ccc(C#N)cc4)n3c2)ccc1C(=O)N1CCN(C)CC1]

To a solution of 4-(6-(3-amino-4-(4-methylpiperazine-1-carbonyl)phenyl)imidazo[1,2-a]pyridin-3-yl)benzonitrile (200 mg, 0.45 mmol) in DCM (20 mL) were added acetic anhydride (70 mg, 0.68 mmol) and pyridine (72 mg, 0.91 mmol) at 0° C. and the reaction mixture was stirred at 0° C. to rt for 16 h. The reaction mixture was acidified with aq NaHSO$_4$ and extracted with EtOAc. The organic layer was dried over anhydrous Na$_2$SO$_4$ and concentrated under reduced pressure and purified by preparative HPLC to afford N-(5-(3-(4-cyanophenyl)imidazo[1,2-a]pyridin-6-yl)-2-(4-methylpiperazine-1-carbonyl)phenyl)acetamide (50 mg, 22%, AUC HPLC 96.7%) as an off-white solid; m.p. 156-172° C. $^1$H NMR (400 MHz, DMSO d$_6$) δ 9.68 (s, 1H), 8.73 (s, 1H), 7.99 (s, 5H), 7.81-7.80 (m, 2H), 7.65 (d, J=11.2 Hz, 1H), 7.58 (d, J=12.0 Hz, 1H), 7.34 (d, J=10.8 Hz, 1H), 3.6 (bs, 2H), 3.25 (bs, 2H), 2.39 (bs, 2H), 2.25 (bs, 2H), 2.20 (s, 3H), 2.00 (s, 3H); MS (ESI) m/z 479 [C$_{28}$H$_{26}$N$_6$O$_2$+H]$^+$

Example 150: 4-(6-(3-(methylamino)-4-(4-methyl-piperazine-1-carbonyl)phenyl)imidazo[1,2-a]pyridin-3-yl)benzonitrile

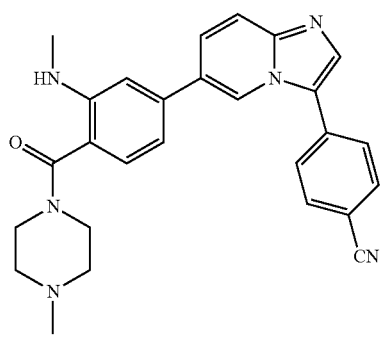 [SMILES: CNc1cc(-c2ccc3ncc(-c4ccc(C#N)cc4)n3c2)ccc1C(=O)N1CCN(C)CC1]

Step 1: To a solution of methylamine (2 M in THF, 128 mL, 255 mmol) in THF (23 mL) at 0° C. was added n-butyl lithium (2.5 M in hexanes, 80 mL, 201 mmol) slowly. The mixture was stirred for one hour at 0° C. and then it was transferred via cannula to a solution of 4-bromo-2-fluorobenzoic acid (5 g, 22.8 mmol) in THF (5 mL) at −78° C. The reaction was stirred for 30 minutes before it was quenched at −78° C. with 270 mL of 1N HCl. The aqueous layer was extracted ethyl acetate (4×200 mL) and the combined organic extracts were dried over Na$_2$SO$_4$, filtered, and concentrated. The crude product was purified by flash chromatography (silica, eluent 100% CH$_2$Cl$_2$ to CH$_2$Cl$_2$/MeOH 93:7) to give 4-bromo-2-(methylamino)benzoic acid (1.83 g, 35%, LC-MS 94%) as a light orange solid. $^1$H NMR (400 MHz, CDCl$_3$) δ 7.82 (d, J=8.8 Hz, 1H), 6.86 (d, J=1.2 Hz, 1H), 6.76 (dd, J=1.6, 8.4 Hz, 1H), 2.94 (s, 3H); LC-MS m/z 230 [M]+.

Step 2: To a solution of 4-bromo-2-(methylamino)benzoic acid (1 g, 4.38 mmol) in DMF (15 mL) was added NMM (664 mg, 6.57 mmol) followed by addition of HATU (2.49 g, 6.57 mmol) at rt and stirred for 30 min. 1-methylpiperazine (486 mg, 4.81 mmol) was added and stirred at rt for 16 h. The reaction mixture was diluted with EtOAc and washed with water and brine solution. The organic layer was dried over anhydrous Na$_2$SO$_4$ and concentrated under reduced pressure to obtain crude product. The crude product was purified by column chromatography (silica gel, eluent petroleum ether to petroleum ether/EtOAc 60/40) to afford (4-bromo-2-(trifluoromethyl)phenyl)(4-methylpiperazin-1-yl)methanone (0.8 g, 60%, LC-MS 68%) as an off-white solid. $^1$H NMR (400 MHz, CDCl$_3$) δ 8.01 (s, 1H), 6.91 (d, J=7.9 Hz, 2H), 6.79 (d, J=4.8 Hz, 1H), 5.3 (bs, 1H), 3.61 (bs, 4H), 2.54 (bs, 4H). LC-MS m/z 312 [M]+.

Step 3: To a solution of (4-bromo-2-(methylamino)phenyl)(4-methylpiperazin-1-yl)methanone (0.8 g, 2.564 mmol) 1,4-dioxane (20 mL), were sequentially added bis(pinacolato)diboron (716 mg, 2.82 mmol), KOAc (544 mg, 5.56 mmol), PdCl$_2$dppf (56 mg, 0.076 mmol) and dppf (42 mg, 0.076 mmol). The reaction mixture was heated at 90° C. for 16 h, then was diluted with EtOAc and washed with water. The organic layer was dried over anhydrous Na$_2$SO$_4$ and concentrated under reduced pressure to afford (2-(methylamino)-4-(4,4,5,5-tetramethyl-1,3,2-dioxaborolan-2-yl)phenyl)(4-methylpiperazin-1-yl)methanone as a brown liquid (700 mg) which was used in the next step without purification.

Step 4: A solution of (2-(methylamino)-4-(4,4,5,5-tetramethyl-1,3,2-dioxaborolan-2-yl)phenyl)(4-methylpiperazin-1-yl)methanone (300 mg, 1.01 mmol), (2-(methylamino)-4-(4,4,5,5-tetramethyl-1,3,2-dioxaborolan-2-yl)phenyl)(morpholino)methanone (400 mg, 1.1 mmol), K$_3$PO$_4$ (428 mg, 2.02 mmol) in 1,4-dioxane (20 mL) and water (4 mL) was degassed with argon for 30 min prior to the addition of Pd(PPh$_3$)$_4$ (34 mg, 0.03 mmol). The reaction mixture was heated at 90° C. for 1 h under argon atmosphere, then was diluted with water and extracted with EtOAc. The organic phase was washed with water and brine, was dried over anhydrous Na$_2$SO$_4$ and concentrated under reduced pressure. The crude residue was purified by column chromatography (silica gel, eluent CH$_2$Cl$_2$¦MeOH 95:5) followed by Preparative HPLC (C18, ACN/H$_2$O/10 mM NH$_4$HCO$_3$) to afford 4-(6-(3-(methylamino)-4-(4-methylpiperazine-1-carbonyl)phenyl)imidazo[1,2-a]pyridin-3-yl)benzonitrile (145 mg, 26%, AUC HPLC 99.2%) as a light brown solid; m.p. 128-133° C. $^1$H NMR (400 MHz, CDCl$_3$) δ (ppm): 8.5 (s, 1H), 7.84-7.54 (m, 6H), 7.54-7.52 (d, J=7.5 Hz, 1H), 7.15-7.13 (d, J=7.1 Hz, 1H), 6.80-6.76 (m, 2H), 5.04 (s, 1H), 3.67 (bs, 4H), 2.88 (d, J=0.08 Hz, 3H), 2.44 (bs, 4H), 2.33 (s, 3H); MS (ESI) m/z 451.1 [C$_{27}$H$_{26}$N$_6$O+H]$^+$.

Example 151: 4-(6-(3-(methylamino)-4-(morpholine-4-carbonyl)phenyl)imidazo[1,2-a]pyridin-3-yl)benzonitrile

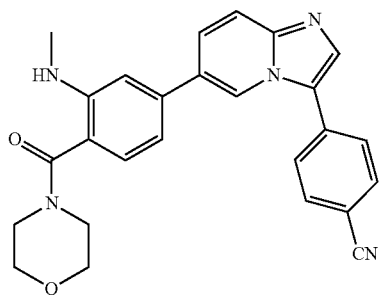 [SMILES: CNc1cc(-c2ccc3ncc(-c4ccc(C#N)cc4)n3c2)ccc1C(=O)N1CCOCC1]

Step 1: To a solution of methylamine (2M in THF, 128 mL, 255 mmol) in THF (23 mL) at 0° C. was slowly added n-butyl lithium (2.5M in hexanes, 80.3 mL, 201 mmol). The mixture was stirred for one hour at 0° C. and then it was transferred via cannula to a solution of 4-bromo-2-fluorobenzoic acid (5 g, 22.8 mmol) in THF (5 mL) at −78° C. The reaction was stirred for 30 minutes before it was quenched at −78° C. with 270 mL of 1N HCl. The aqueous layer was extracted with ethyl acetate (4×200 mL). The combined organic extracts were dried over Na$_2$SO$_4$, filtered and concentrated. The crude product was purified by flash column chromatography (silica gel, eluent 100% CH$_2$Cl$_2$ to CH$_2$Cl$_2$/MeOH 93:7) to give 4-bromo-2-(methylamino)benzoic acid (1.83 g, 35%, LC-MS 94%) as a light orange solid. $^1$H NMR (400 MHz, CDCl$_3$) δ 7.82 (d, J=8.8 Hz, 1H), 6.86 (d, J=1.2 Hz, 1H), 6.76 (dd, J=1.6, 8.4 Hz, 1H), 2.94 (s, 3H); LC-MS m/z 230.8 [M]+.

Step 2: To a solution of 4-bromo-2-(methylamino)benzoic acid (1 g, 4.38 mmol) in DMF (15 mL) was added NMM (664 mg, 6.57 mmol) followed HATU (2.49 g, 6.57 mmol) and the resulting mixture stirred at rt for 30 min. Morpholine (419 mg, 4.81 mmol) was added and stirred at rt for 16 h. The reaction mixture was diluted with EtOAc and washed with water and brine. The organic layer was dried over anhydrous Na$_2$SO$_4$ and concentrated under reduced pressure to obtain crude product. The crude product was purified by column chromatography (silica gel, eluent 100% Petroleum ether to petroleum ether/EtOAc 40:60) to afford (4-bromo-2-(trifluoromethyl)phenyl)(4-methylpiperazin-1-yl)methanone (1.2 g, 92%, AUC LC-MS 88%) as a solid. $^1$H NMR (400 MHz, CDCl$_3$) δ 7.82 (d, J=8.8 Hz, 1H), 6.86 (d, J=1.2 Hz, 1H), 6.76 (dd, J=8.4 Hz, 1H), 5.41 (bs, 1H), 3.84-3.61 (m, 8H), 2.94 (d, J=4.4 Hz, 3H). LC-MS m/z 299 [M]+.

Step 3: To a solution of (4-bromo-2-(methylamino)phenyl)(morpholino)methanone (1.2 g, 4.02 mmol), Bis(pinacolato)diboron (1.12 g, 4.42 mmol), KOAc (1.18 g, 12.06 mmol) in 1,4-dioxane (20 mL) was added PdCl$_2$(dppf) (87 mg, 0.12 mmol) and dppf (66 mg, 0.12 mmol) were added and again degassed with argon for 30 min and the reaction mixture was heated at 90° C. for 16 h. The reaction mixture was diluted with EtOAc and washed with water, the organic layer was dried over anhydrous Na$_2$SO$_4$ and concentrated under reduced pressure to afford (2-(methylamino)-4-(4,4,5,5-tetramethyl-1,3,2-dioxaborolan-2-yl)phenyl)(morpholino)methanone (800 mg) as a brown liquid which was used in the next step without purification.

Step 4: To a solution of 4-(6-bromoimidazo[1,2-a]pyridin-3-yl)benzonitrile (300 mg, 1.013 mmol), (2-(methylamino)-4-(4,4,5,5-tetramethyl-1,3,2-dioxaborolan-2-yl)phenyl)(morpholino)methanone (385 mg, 1.1 mmol), K$_3$PO$_4$ (428 mg, 2.02 mmol) in 1,4-dioxane (10 mL) and water (2 mL), was added Pd(PPh$_3$)$_4$ (58 mg, 0.05 mmol). The reaction mixture was heated at 90° C. for 1 h then, was diluted with water and extracted with EtOAc. The organic layer was washed with water and brine, dried over anhydrous Na$_2$SO$_4$ and concentrated under reduced pressure to obtain crude product. The crude residue was purified by column chromatography (silica gel, eluent CH$_2$Cl$_2$/MeOH 95:5) followed by preparative HPLC (C18, ACN/H$_2$O/10 mM NH$_4$HCO$_3$) to afford 4-(6-(3-(methylamino)-4-(morpholine-4-carbonyl)phenyl)imidazo[1,2-a]pyridin-3-yl)benzonitrile (4.5 mg, 10.2%, AUC HPLC 94.67%) as an off-White solid; m.p. 302-307° C. $^1$H NMR (400 MHz, CDCl$_3$) δ (ppm): 8.5 (s, 1H), 7.84-7.54 (m, 6H), 7.54-7.52 (d, J=7.5 Hz, 1H), 7.15-7.13 (d, J=7.1 Hz, 1H), 6.80-6.76 (m, 2H), 5.04 (s, 1H), 3.70-3.79 (m, 8H), 2.88 (d, J=2.8 Hz, 3H); MS (ESI) m/z 436.1 [C$_{26}$H$_{23}$N$_5$O$_2$+H]$^+$.

Example 152: 4-(6-(4-(2-(4-methylpiperazin-1-yl)acetyl)phenyl)imidazo[1,2-a]pyridin-3-yl)benzonitrile

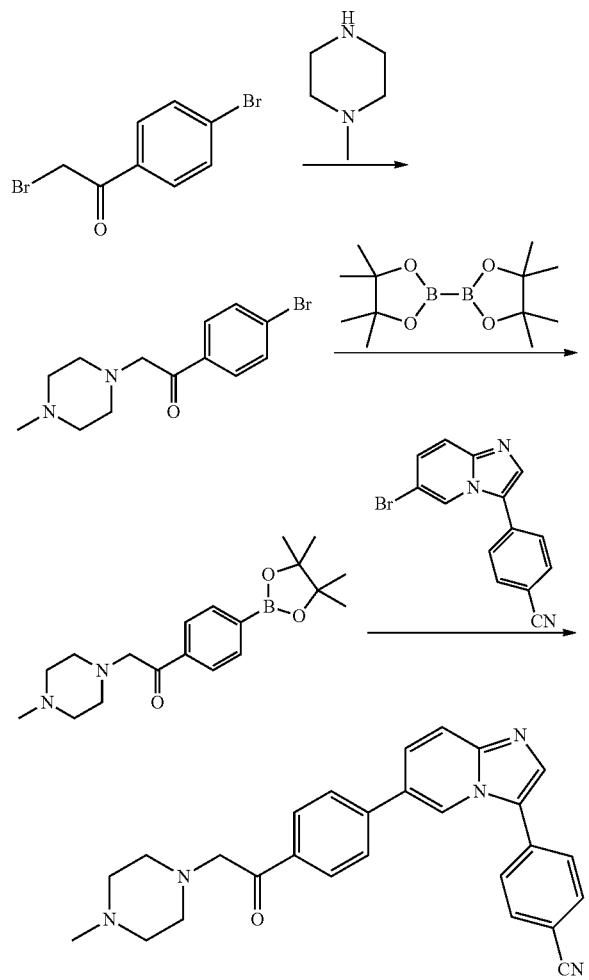

Step 1: To a solution of 2-bromo-1-(4-bromophenyl)ethanone (2.5 g, 8.99 mmol) in ACN (30 mL) was added $K_2CO_3$ (2.5 g, 173 mmol) followed by 1-methylpiperazine (1.17 g, 11.69 mmol) at rt and stirred for 16 h. The reaction mixture was filtered and the filtrate was concentrated under reduced pressure to obtain crude product. The crude product was passed through a plug of silica gel using 10% MeOH in $CHCl_3$ as eluent and concentrated to afford of 1-(4-bromophenyl)-2-(4-methylpiperazin-1-yl)ethanone 1 (500 mg, 40%, LC-MS-84%) as a yellow solid.

Step 2: To a mixture of 1-(4-bromophenyl)-2-(4-methylpiperazin-1-yl)ethanone (250 mg, 0.84 mmol), bis(pinacolato)diboron (278 mg, 1.09 mmol), KOAc (323 mg, 3.29 mmol) in 1,4-dioxane (10 mL) were added $PdCl_2$(dppf) (18.5 mg, 0.02 mmol) and dppf (14 mg, 0.02 mmol) and the reaction mixture was heated at 90° C. for 16 h. The direct mass indicated desired m/z. The reaction mixture was used in the next step without isolation.

Step 3: To a mixture of (4-methylpiperazin-1-yl)-1-(4-(4,4,5,5-tetramethyl-1,3,2-dioxaborolan-2-yl)phenyl)ethanone (1.2 g, 3.48 mmol), 4-(6-bromoimidazo[1,2-a]pyridin-3-yl)benzonitrile (1.24 g, 4.18 mmol), $K_3PO_4$ (2.21 g, 10.44 mmol) in 1,4-dioxane (20 mL) and water (3 mL) was added $Pd(PPh_3)_4$ (120 mg, 0.1 mmol) and the reaction mixture was heated at 90° C. for 4 h. The reaction mixture was diluted with EtOAc and washed with water and brine solution. The organic layer was dried over anhydrous $Na_2SO_4$ and concentrated under reduced pressure to obtain the crude product. The crude product was purified by preparative HPLC to afford 4-(6-(4-(2-(4-methylpiperazin-1-yl)acetyl)phenyl)imidazo[1,2-a]pyridin-3-yl)benzonitrile (150 mg, 15%, AUC HPLC 95.07%) as a yellow solid, m.p: 93-98° C. $^1$HNMR (400 MHz, $CDCl_3$) δ (ppm): 8.53 (s, 1H), 8.12 (d, J=10.8 Hz, 2H), 7.85-7.77 (m, 6H), 7.62 (d, J=10.8 Hz, 2H), 7.54 (d, J=12.8 Hz, 1H), 3.82 (s, 2H), 2.67-2.62 (m, 8H), 2.32 (s, 3H); MS (ESI) m/z 436 $[C_{27}H_{25}N_5O+H]^+$.

The following compounds in the table below were prepared following a procedure similar to that used in step 3 of example 152

| Ex. # | Boronate ester | Compound | Characterization |
|---|---|---|---|
| 153 | ![boronate] | ![compound] | (200 mg, 22.9%, AUC HPLC 99.03%) as an off-white solid, m.p: 215-218° C. $^1$H NMR (400 MHz, DMSO-$d_6$) δ (ppm): 8.67 (s, 1H), 7.96-8.03 (m, 5H), 7.79 (d, J = 9.4 Hz, 1H), 7.78-7.61 (m, 2H), 7.56-7.40 (m, 2H), 3.65 (bs, 2H), 3.31 (bs, 2H), 2.32 (bs, 4H), 2.20 (s, 3H); MS (ESI) m/z 456 $[C_{26}H_{22}ClN_5O + H]^+$. |

-continued

| Ex. # | Boronate ester | Compound | Characterization |
|---|---|---|---|
| 154 | | | (150 mg, 16.9%, AUC HPLC 98.91%) as a off-white solid, m.p: 188-191° C. $^1$H NMR (400 MHz, DMSO-$d_6$) δ (ppm): 8.51 (s, 1H), 8.01 (s, 1H), 7.95 (s, 4H), 7.76 (d, J = 9.2 Hz, 1H), 7.42 (d, J = 8.2 Hz, 2H), 7.34 (bs, 2H), 3.31 (bs, 4H), 2.31 (s, 7H), 2.20 (s, 3H); MS (ESI) m/z 436 [$C_{27}H_{25}N_5O$ + H]$^+$ |
| 155 | | | (100 mg, 23.5%, AUC HPLC 99.85%) as an off-white solid, m.p: 195-197° C. $^1$H NMR (400 MHz, CDCl$_3$) δ (ppm): 8.31 (s, 1H), 7.86 (s, 3H), 7.80-7.75 (m, 2H), 7.69-7.63 (m, 3H), 7.44 (d, J = 7.9 Hz, 1H), 7.26 (s, 1H), 3.86 (bs, 2H), 3.54 (bs, 2H), 2.60-2.34 (m, 4H), 2.39 (s, 3H); MS (ESI) m/z 490 [$C_{27}H_{22}F_3N_5O$ + H]$^+$ |
| 156 | | | (120 mg, 37.7%, AUC HPLC 98.77%) as an off-white solid, m.p: 140° C. $^1$H NMR (400 MHz, CDCl$_3$) δ (ppm) 8.46 (s, 1H), 7.84-7.72 (m, 6H), 7.51 (dd, J = 1.6 Hz, 1H), 7.38 (bs, 2H), 7.29 (s,1H), 3.84 (d, J = 4.81 Hz, 4H), 3.60 (s, 2H), 3.30 (s, 2H), 2.40 (s, 3H); MS (ESI) m/z 423 [$C_{26}H_{22}N_4O_2$ + H]$^+$ |
| 157 | | | (45 mg, 50%, AUC HPLC 96.9%) as a white solid; m.p. 109-113° C. $^1$H NMR (400 MHz, CDCl$_3$) δ 8.47 (s, 1H), 7.85-7.71 (m, 6H), 7.50-7.43 (m, 4H), 4.92-4.75 (m, 2H), 3.35 (bs, 2H), 2.50 (bs, 2H), 2.39 (bs, 2H), 2.30 (s, 3H); MS (ESI) m/z 506 [$C_{27}H_{22}F_3N_5O_2$ + H]$^+$ |

| Ex. # | Boronate ester | Compound | Characterization |
|---|---|---|---|
| 158 | | | (120 mg, 20%, AUC HPLC 95.96%) as an off-white solid; m.p. 169-174° C. $^1$H NMR (400 MHz, CDCl$_3$) S (ppm): 8.46 (s, 1H), 7.84-7.71 (m, 6H), 7.49 (d, J = 15.0 Hz, 1H), 7.34 (d, J = 10.4 Hz, 1H), 7.13 (d, J = 10.4 Hz, 1H), 7.01 (s, 1H), 3.90 (s, 3H), 3.85 (br. s, 4H), 3.42 (br. s, 2H), 3.35 (m, 2H); MS (ESI) m/z 437 [C$_{26}$H$_{22}$N$_4$O$_3$ – H]$^+$ |

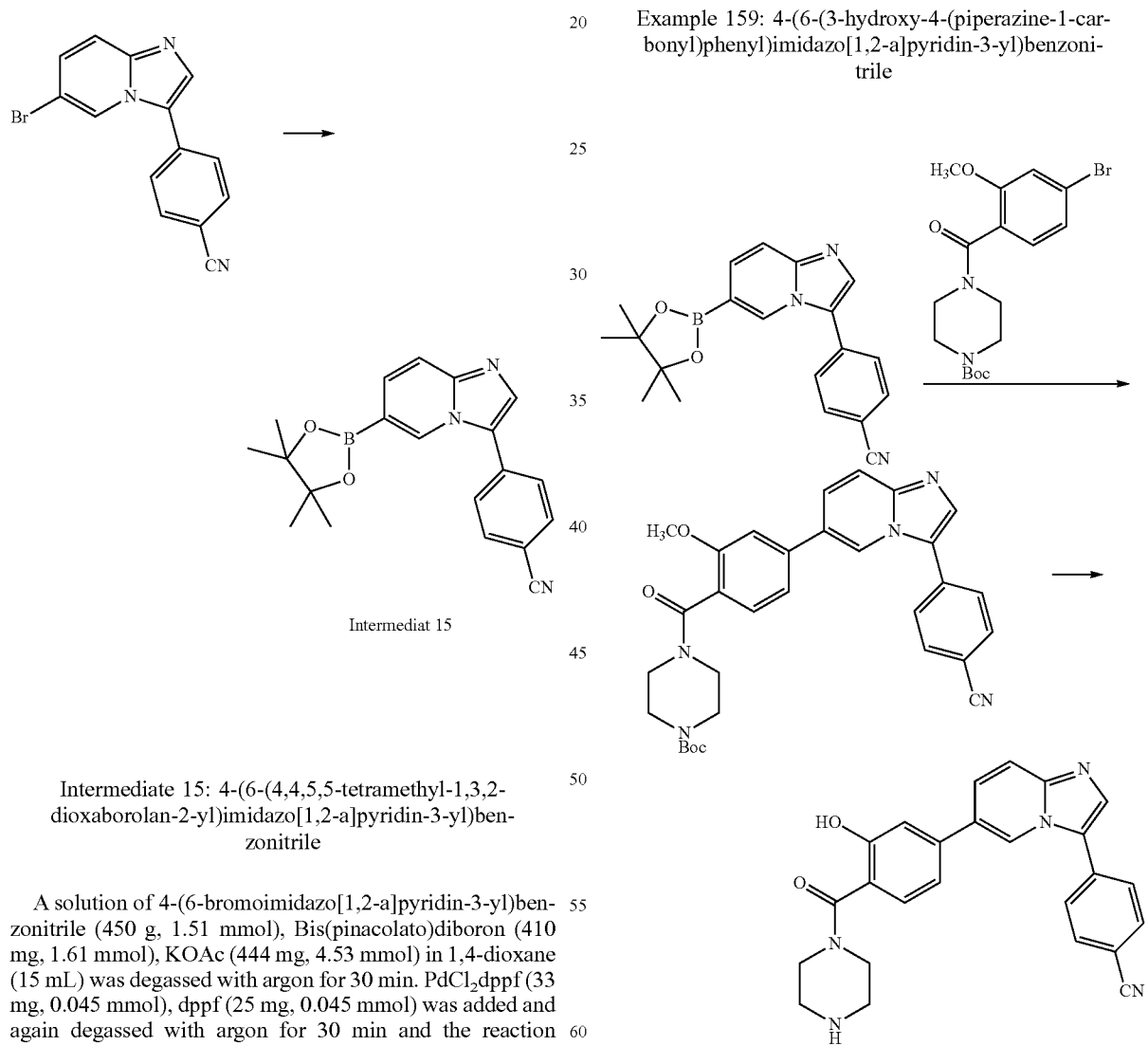

Intermediat 15

Intermediate 15: 4-(6-(4,4,5,5-tetramethyl-1,3,2-dioxaborolan-2-yl)imidazo[1,2-a]pyridin-3-yl)benzonitrile A solution of 4-(6-bromoimidazo[1,2-a]pyridin-3-yl)benzonitrile (450 g, 1.51 mmol), Bis(pinacolato)diboron (410 mg, 1.61 mmol), KOAc (444 mg, 4.53 mmol) in 1,4-dioxane (15 mL) was degassed with argon for 30 min. PdCl$_2$dppf (33 mg, 0.045 mmol), dppf (25 mg, 0.045 mmol) was added and again degassed with argon for 30 min and the reaction mixture was heated at 90° C. for 16 h. The reaction mixture was diluted with EtOAc and washed with water, the organic layer was dried over anhydrous Na$_2$SO$_4$ and concentrated under reduced pressure to afford 4-(6-(4,4,5,5-tetramethyl-1,3,2-dioxaborolan-2-yl)imidazo[1,2-a]pyridin-3-yl)benzonitrile as a brown liquid which was used in next step without purification. MS (ESI) m/z 346 [M+H]$^+$.

Example 159: 4-(6-(3-hydroxy-4-(piperazine-1-carbonyl)phenyl)imidazo[1,2-a]pyridin-3-yl)benzonitrile Step 1: To a solution of 2-methoxy-4-bromobenzoic acid (1 g, 4.32 mmol) in DMF (5 mL) was added NMM (0.97 mL, 8.65 mmol) followed by HATU (2.46 g, 6.49 mmol) at rt and stirred for 30 min. N-Boc-piperazine (886 mg, 4.76 mmol) was added and stirred at rt for 16 h. The reaction mixture was diluted with EtOAc and washed with water and brine solution. The organic layer was dried over anhydrous Na$_2$SO$_4$ and concentrated under reduced pressure to obtain tert-butyl 4-(4-bromo-2-methoxybenzoyl)piperazine-1-carboxylate (1.7 g, 95%, LC-MS 92%) as a solid. $^1$H NMR (400 MHz, DMSO-d$_6$) δ (ppm): 7.29 (s, 1H), 7.17 (q, J=11.6 Hz, 2H), 3.82 (s, 3H), 3.5 (bs, 2H), 3.31-3.26 (m, 2H), 3.25-3.09 (m, 4H), 1.40 (s, 9H); MS (ESI) m/z 398/401 [C$_{17}$H$_{23}$BrN$_2$O$_4$]$^+$.

Step 2: A mixture of tert-butyl 4-(4-bromo-2-methoxybenzoyl)piperazine-1-carboxylate (649 mg, 1.62 mmol), 4-(6-(4,4,5,5-tetramethyl-1,3,2-dioxaborolan-2-yl)imidazo[1,2-a]pyridin-3-yl)benzonitrile (468 mg, 1.35 mmol), K$_3$PO$_4$ (862 mg, 4.06 mmol) in 1,4-dioxane (10 mL) and water (2 mL) was added Pd(PPh$_3$)$_4$ (78 mg, 0.06 mmol) and the reaction mixture was heated at 90° C. for 1 h. The reaction mixture was diluted with water and extracted with EtOAc and washed with water and brine solution. The organic layer was dried over anhydrous Na$_2$SO$_4$ and concentrated under reduced pressure to obtain crude product. The crude product was purified by column chromatography to obtain tert-butyl 4-(4-(3-(4-cyanophenyl)imidazo[1,2-a]pyridin-6-yl)-2-methoxybenzoyl)piperazine-1-carboxylate (500 mg, 50%, LC-MS 87%) as a solid.

Step 3: To a solution of tert-butyl 4-(4-(3-(4-cyanophenyl)imidazo[1,2-a]pyridin-6-yl)-2-methoxybenzoyl)piperazine-1-carboxylate (100 mg, 0.18 mmol) in CH$_2$Cl$_2$ (5 mL) cooled to 0° C., was added BBr$_3$ (2 mL). The reaction mixture was stirred at rt for 2 h. The reaction mixture was cooled to 0° C. and quenched by drop wise addition of saturated aq. NaHCO$_3$ (50 mL) and extracted with EtOAc (3×50 mL). The organic layer was washed with water, brine, dried over anhydrous Na$_2$SO$_4$, filtered and concentrated under reduced pressure. The crude compound was purified by column chromatography (silica gel, eluent MeOH/CHCl$_3$ 5:95) followed by preparative HPLC to give 4-(6-(3-hydroxy-4-(piperazine-1-carbonyl)phenyl)imidazo[1,2-a]pyridin-3-yl)benzonitrile (50 mg, 63%, AUC HPLC 96.65%) as a white solid, m.p: 170-175° C. $^1$H NMR (400 MHz, DMSO-d$_6$) δ (ppm): 10.0 (bs, 1H), 8.69 (s, 1H), 7.99 (s, 5H), 7.80 (d, J=9.3 Hz, 1H), 7.62 (d, J=7.9 Hz, 1H), 7.19 (s, 2H), 7.12 (s, 1H), 3.51 (bs, 2H), 3.21 (bs, 2H), 2.63 (s, 4H); MS (ESI) m/z 422.0 [C$_{25}$H$_{21}$N$_5$O$_2$—H].

Example 160: 4-(6-[3-(morpholin-4-yl)-4-(morpholin-4-ylcarbonyl)phenyl]imidazo[1,2-a]pyridin-3-yl)benzonitrile

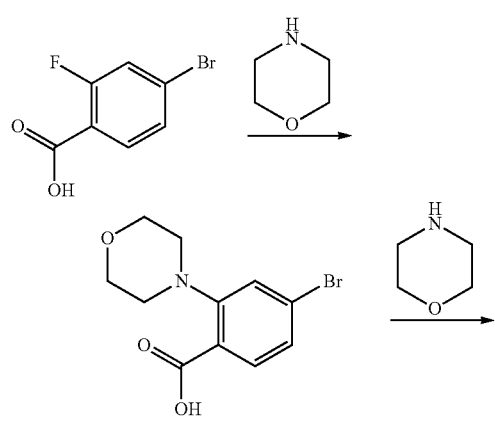

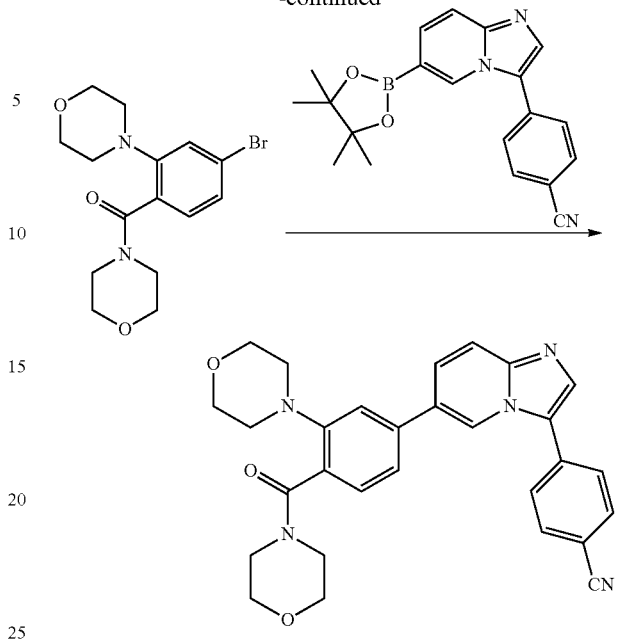

Step 1: To a solution of 2-fluororo-4-bromobenzoic acid (1 g, 4.56 mmol) in DMF (6 mL) was added K$_2$CO$_3$ (1.26 g, 9.13 mmol) followed by morpholine (0.47 g, 5.47 mmol) at rt and reaction was heated to reflux and stirred for 20 h at the same temperature. The reaction mixture was cooled to rt, and water (20 mL) was added and acidified with 1N HCl (5 mL). The reaction mixture was extracted with EtOAc and washed with water and brine solution. The organic layer was dried over anhydrous Na$_2$SO$_4$ and concentrated under reduced pressure to obtain 4-bromo-2-(morpholin-4-yl)benzoic acid (700 mg, 90%, LC-MS 95%).

Step 2: To a solution of 4-bromo-2-morpholinobenzoic acid (700 mg, 2.46 mmol) in DMF (6 mL) was added NMM (0.49 g, 4.91 mmol) followed by HATU (1.39 g, 3.68 mmol) at rt and stirred for 30 min. Morpholine (0.25 g, 2.94 mmol) was added to the reaction mixture and stirring was continued at rt for 16 h. The reaction mixture was diluted with EtOAc and washed with water and brine solution. The organic layer was dried over anhydrous Na$_2$SO$_4$ and concentrated under reduced pressure to obtain (4-bromo-2-morpholinophenyl)(morpholino)methanone (600 mg, LC-MS 86%).

Step 3: To a mixture of (4-bromo-2-morpholinophenyl)(morpholino)methanone (400 mg, 1.12 mmol), 4-(6-(4,4,5,5-tetramethyl-1,3,2-dioxaborolan-2-yl)imidazo[1,2-a]pyridin-3-yl)benzonitrile (470 mg, 1.35 mmol), K$_3$PO$_4$ (478 mg, 2.25 mmol) in 1,4-dioxane (5 mL), and water (1 mL) was added Pd(PPh$_3$)$_4$ (50 mg) and the reaction mixture was heated at 90° C. for 16 h. The reaction mixture was concentrated to give the crude product. The crude product was purified by preparative HPLC to obtain 4-(6-[3-(morpholin-4-yl)-4-(morpholin-4-ylcarbonyl)phenyl]imidazo[1,2-a]pyridin-3-yl)benzonitrile (50 mg, 20%, AUC HPLC 99.20%) as an off-white solid; m.p. 237-240° C. $^1$H NMR (400 MHz, CDCl$_3$) δ 8.46 (s, 1H), 7.84-7.79 (m, 4H), 7.73 (d, J=8.4 Hz, 2H), 7.51 (t, J=5.6 Hz, 1H), 7.37 (d, J=8.0 Hz, 1H), 7.24 (s, 1H), 7.11 (s, 1H), 3.99-3.95 (m, 1H), 3.85-3.66 (m, 8H), 3.55-3.40 (m, 1H), 3.42-3.32 (m, 3H), 3.21-3.18 (m, 1H), 2.90-2.89 (m, 2H); MS (ESI) m/z 494 [C$_{29}$H$_{27}$N$_5$O$_3$+H].

235

Examples 161 a and b: 4-(6-(3-hydroxy-4-(piperazine-1-carbonyl)phenyl)imidazo[1,2-a]pyridin-3-yl)benzonitrile

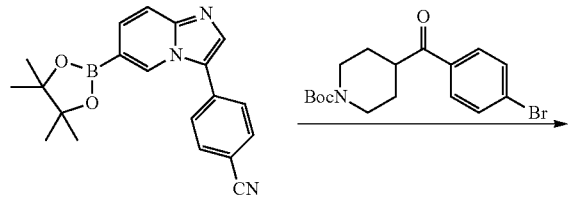

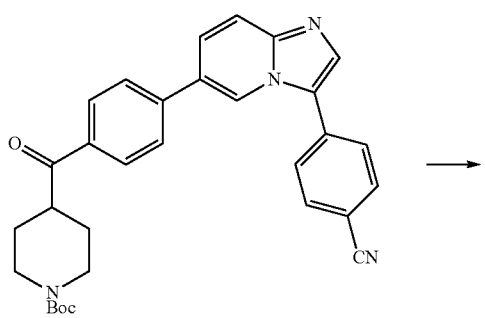

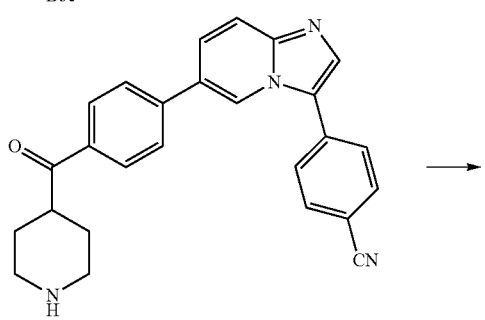

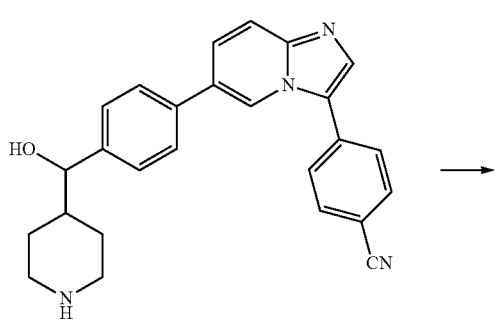

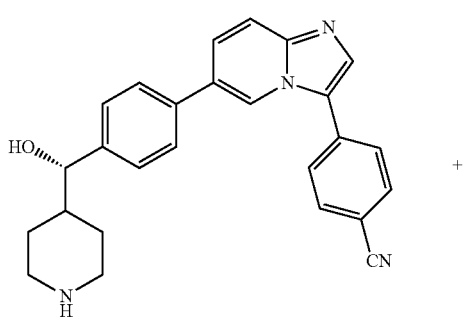

+

236

-continued

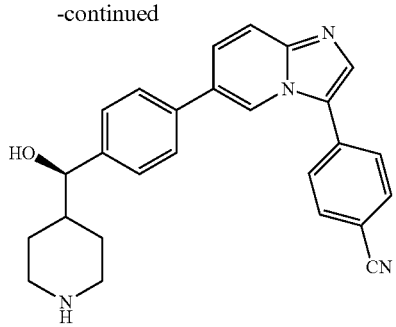

Step 1: To a solution of (4-bromophenyl)(piperidin-4-yl)methanone (600 mg, 2.23 mmol) in MeOH (5 mL) was added (Boc)$_2$O (561 mg, 2.57 mmol). The reaction mixture was stirred for 2 h at rt and concentrated. The residues was recrystallized from methanol to give tert-butyl 4-(4-bromobenzoyl)piperidine-1-carboxylate (650 mg, 74.5%, LC-MS 98%) as a solid. $^1$H NMR (400 MHz, DMSO-d$_6$) δ (ppm): 7.94 (d, J=8.4 Hz, 2H), 7.78 (d, J=8.8 Hz, 2H), 3.82-3.59 (m, 3H), 3.02 (bs, 2H), 1.92 (bs, 2H), 1.75 (bm, 2H), 1.46 (bs, 9H); MS (ESI) m/z 370 [C$_{17}$H$_{22}$BrNO$_3$+2]$^+$.

Step 2: A mixture of tert-butyl 4-(4-bromobenzoyl)piperidine-1-carboxylate (599 mg, 1.62 mmol), 4-(6-(4,4,5,5-tetramethyl-1,3,2-dioxaborolan-2-yl)imidazo[1,2-a]pyridin-3-yl)benzonitrile (468 mg, 1.35 mmol), K$_3$PO$_4$ (862 mg, 4.06 mmol) in 1,4-dioxane (10 mL) and water (2 mL) was added Pd(PPh$_3$)$_4$ (78 mg, 0.06 mmol) and the reaction mixture was heated at 90° C. for 16 h. The reaction mixture was diluted with water and extracted with EtOAc. The organic layer was washed with water and brine solution then dried over anhydrous Na$_2$SO$_4$ and concentrated under reduced pressure to give the crude product, which was purified by column chromatography to afford tert-butyl 4-(4-(3-(4-cyanophenyl)imidazo[1,2-a]pyridin-6-yl)benzoyl)piperidine-1-carboxylate (250 mg, 28%, LC-MS 39.6%) as a solid.

Step 3: tert-butyl 4-(4-(3-(4-cyanophenyl)imidazo[1,2-a]pyridin-6-yl)benzoyl)piperidine-1-carboxylate (250 mg) was treated with HCl in 1,4-dioxane (5 mL) at 0° C. for 2 h. The reaction mixture was cooled to 0° C. and quenched by drop wise addition of a saturated aqueous solution of NaHCO$_3$ (50 mL) and the mixture was extracted with EtOAc (3×50 mL). The organic layer was washed with water and brine, dried over anhydrous Na$_2$SO$_4$, filtered and concentrated under reduced pressure. The crude compound was purified by column chromatography (silica gel, eluent MeOH/CHCl$_3$ 5:95) followed by preparative HPLC to furnish 4-(6-(4-(piperidine-4-carbonyl)phenyl)imidazo[1,2-a]pyridin-3-yl)benzonitrile (50 mg, 25%, AUC HPLC 98.84%) as a white solid, m.p: 129-133° C. $^1$H NMR (400 MHz, DMSO-d$_6$) δ (ppm): 8.87 (s, 1H), 8.59 (bs, 1H), 8.30 (bs. 1H), 8.11 (d, J=8.4 Hz, 1H), 8.07 (s, 1H), 8.04-7.97 (m, 4H), 7.95-7.87 (m, 4H), 3.80 (bs, 1H), 3.34 (d, J=12.7 Hz, 2H), 3.10 (t, J=11.2 Hz, 2H), 1.97 (d, J=13.2 Hz, 2H), 1.76 (q, J=10.8 Hz, 2H); MS (ESI) m/z 407 [C$_{26}$H$_{22}$N$_4$O+H].

Step 4: To a solution of 4-(6-(4-(piperidine-4-carbonyl)phenyl)imidazo[1,2-a]pyridin-3-yl) (20 mg, 0.04 mmol) in MeOH (5 mL) cooled to 0° C. was added NaBH$_4$ (37 mg, 0.09 mmol) and the reaction mixture was stirred at rt for 2 h. The reaction mixture was extracted with EtOAc and the organic layer was washed with water and brine, dried over Na$_2$SO$_4$, filtered and concentrated under reduced pressure. The crude compound was purified by column chromatography (silica gel, eluent MeOH/CHCl$_3$ 5:95) followed by preparative HPLC to give 4-(6-(4-(hydroxy(piperidin-4-yl)methyl)phenyl)imidazo[1,2-a]pyridin-3-yl)benzonitrile (50 mg, 25%, AUC HPLC 97%) as a white solid. The racemic compound was resolved by chiral HPLC to afford both enantiomers as white solids. First enantiomer (example 161a) (10 mg, 30%, AUC HPLC 98%, chiral HPLC 99.6%) and second enantiomer (example 161b) (15 mg, AUC HPLC 98%, chiral HPLC 95.3%). $^1$HNMR (400 MHz, CDCl$_3$) δ (ppm): 8.48 (s, 1H), 7.83-7.71 (m, 6H), 7.53-7.50 (m, 3H), 7.41 (d, J=7.6 Hz, 2H), 4.48 (d, J=6.8 Hz, 1H), 3.20 (dd, J=12.48 Hz, 2H), 2.60 (q, J=9.6 Hz, 3H), 2.10 (d, J=13.2 Hz, 2H), 1.80 (bs, 2H), 1.40 (d, J=12.8 Hz, 2H); MS (ESI) m/z 409 [C$_{26}$H$_{24}$N$_4$O+H]$^+$.

Example 162: 4-(6-(3-fluoro-4-(morpholine-4-carbonyl)phenyl)imidazo[1,2-a]pyridin-3-yl)benzonitrile

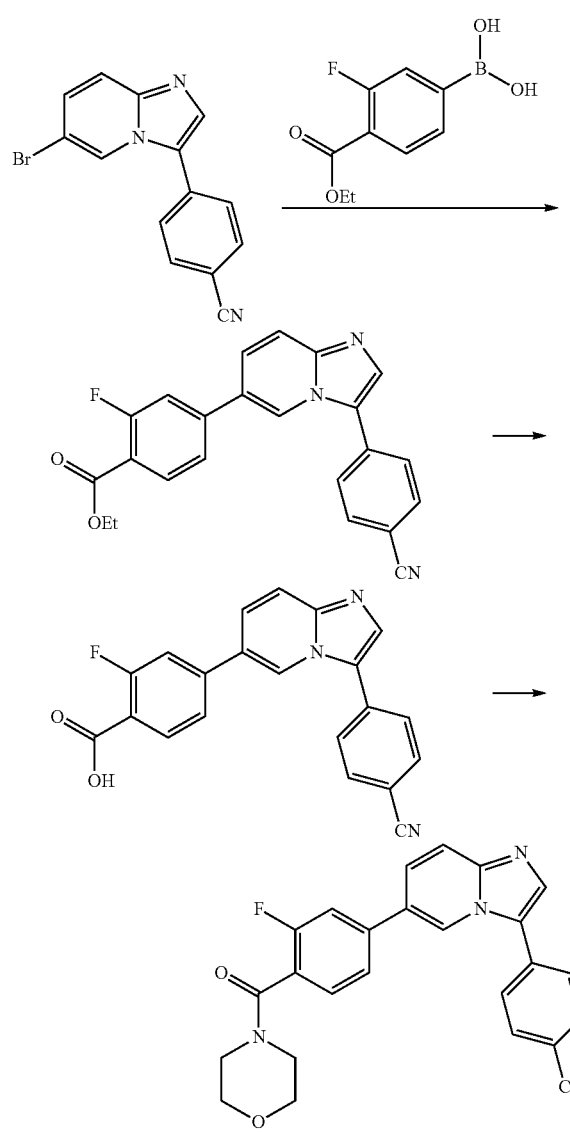

Step 1: To a mixture of 4-(ethoxycarbonyl)-3-fluorophenylboronic acid (400 mg, 1.34 mmol), 4-6-bromoimidazo[1,2a]pyridin3yl)benzonitrile (313 mg, 1.47 mmol), K$_3$PO$_4$ (853 mg, 4.02 mmol) in 1,4-dioxane (5 mL) and water was added (A-Phos)$_2$PdCl$_2$ (77 mg, 0.06 mmol) and the reaction mixture was heated at 100° C. for overnight under argon. The reaction mixture was washed with water and extracted with ethylacetate and concentrated. The crude product was purified by column chromatography (silica gel, eluent MeOH/CHCl$_3$ 10:90) to afford ethyl 4-(3-(4-cyanophenyl)imidazo[1,2-a]pyridin-6-yl)-2-fluorobenzoate (350 mg, 67.8%, LC-MS 98.5%). $^1$H NMR; (400 MHz, DMSO-d$_6$) δ (ppm): 8.91 (s, 1H), 7.99-8.02 (m, 6H), 7.83-7.79 (m, 4H), 4.3 (q, J=7 Hz, 2H), 1.3 (t, J=7.4 Hz, 3H); MS (ESI) m/z 386 [C$_{23}$H$_{16}$FN$_3$O$_2$+H]$^+$.

Step 2: To a solution of ethyl 4-(3-(4-cyanophenyl)imidazo[1,2-a]pyridin-6-yl)-2-fluorobenzoate (350 mg, 0.90 mmol) in 15 mL of THF/H$_2$O/EtOH 1:1:1 was added LiOH (76 mg, 1.81 mmol) and the reaction mixture was stirred at rt for 3 h. The reaction mixture was quenched with citric acid, washed with water and extracted with EtOAc (3×25 mL). The organic layer was washed with water and brine, dried over anhydrous Na$_2$SO$_4$, filtered and concentrated under reduced pressure. The crude product was purified by recrystallization to afford 4-(3-(4-cyanophenyl)imidazo[1,2-a]pyridin-6-yl)-2-fluorobenzoic acid (200 mg, 61.7%, LC-MS 95.7%).

Step 3: To a solution of 4-(3-(4-cyanophenyl)imidazo[1,2-a]pyridin-6-yl)-2-fluorobenzoic acid (200 mg, 0.56 mmol) in DMF (5 mL) was added NMM (0.12 mL, 1.12 mmol) followed by HATU (319 g, 0.84 mmol) and stirred for 20 min. To the reaction mixture, morpholine (0.05 g, 0.61 mmol) was added and stirred at rt for 16 h. The reaction mixture was diluted with EtOAc and washed with water and brine solution. The organic layer was dried over anhydrous Na$_2$SO$_4$ and concentrated under reduced pressure to obtain 4-(6-(3-fluoro-4-(morpholine-4-carbonyl)phenyl)imidazo[1,2-a]pyridin-3-yl)benzonitrile (100 mg, 42%, AUC HPLC 99.33%) as a white solid, m.p: 115-135° C. $^1$H NMR (400 MHz, CDCl$_3$) δ (ppm): 8.48 (s, 1H), 7.85-7.80 (m, 4H), 7.72 (d, J=8.3 Hz, 2H), 7.54-7.45 (m, 2H), 7.47 (dd, J=3.0 Hz, 1H), 7.29 (d, J=1.2 Hz, 1H), 3.83 (d, J=4.3 Hz, 4H), 3.79 (s, 2H), 3.39 (s, 2H); MS (ESI) m/z 427.35 [C$_{25}$H$_{19}$FN$_4$O$_2$+H]$^+$.

Example 163: 4-(6-(4-(4-methyl-4-morpholinopiperidine-1-carbonyl)phenyl)imidazo[1,2-a]pyridin-3-yl)benzonitrile

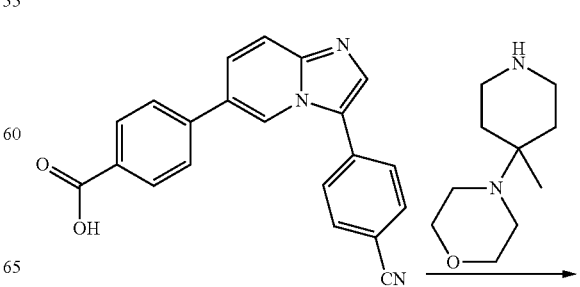

-continued

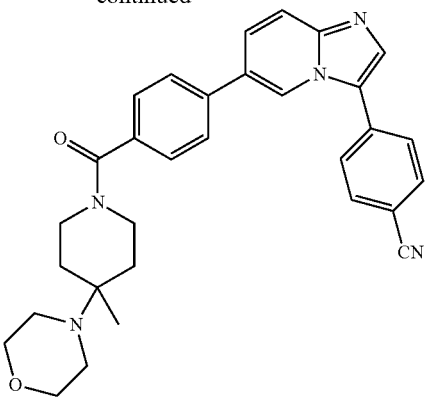

A mixture of 4-(3-(4-cyanophenyl)imidazo[1,2-a]pyridin-6-yl)benzoic acid (250 mg, 0.73 mmol), 4-(4-methylpiperidin-4-yl)morpholine (149 mg, 0.81 mmol) in DMF (10 mL) was added HATU (41 mg, 1.10 mmol) and NMM (0.16 mL, 1.47 mmol) and the reaction mixture was stirred at rt for 16 h. The reaction mixture was diluted with EtOAc and washed with water and brine solution. The organic layer was dried over anhydrous $Na_2SO_4$ and concentrated under reduced pressure to afford of 4-(6-(4-(4-methyl-4-morpholinopiperidine-1-carbonyl)phenyl)imidazo[1,2-a]pyridin-3-yl)benzonitrile (60 mg, 16%, AUC HPLC 97.67%) as an off-white solid, m.p: 238-242° C. $^1$H NMR (400 MHz, DMSO-$d_6$) δ 8.79 (s, 1H), 8.00 (s, 5H), 7.82-7.72 (m, 4H), 7.49 (d, J=7.4 Hz, 2H), 3.92 (bs, 1H), 3.58 (s, 4H), 3.41 (s, 2H), 3.31 (s, 1H), 2.44 (s, 4H), 1.82 (bs, 1H), 1.75 (bs, 1H), 1.39 (bs, 2H), 0.90 (s, 3H); MS (ESI) m/z 506.46 $[C_{31}H_{31}N_5O_2+H]$.

Example 164: 4-(6-(4-(4-methyl-4-(4-methylpiperazin-1-yl)piperidine-1-carbonyl)phenyl)imidazo[1,2-a]pyridin-3-yl)benzonitrile

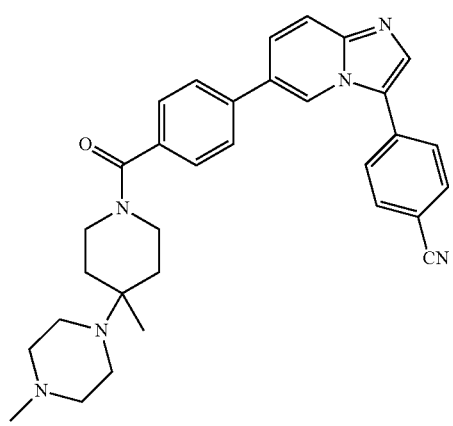 [SMILES: CN1CCN(C2(C)CCN(C(=O)c3ccc(-c4ccc5ncc(-c6ccc(C#N)cc6)n5c4)cc3)CC2)CC1]

To a mixture of 4-(3-(4-cyanophenyl)imidazo[1,2-a]pyridin-6-yl)benzoic acid (250 mg, 0.73 mmol), 1-methyl-4-(4-methylpiperidin-4-yl)piperazine (159 mg, 0.81 mmol) in DMF (5 mL) was added HATU (419 mg, 1.10 mmol), followed by NMM (0.16 mL, 1.47 mmol) and the reaction mixture was stirred at rt for 16 h. The reaction mixture was diluted with EtOAc and washed with water and brine solution. The organic layer was dried over anhydrous $Na_2SO_4$ and concentrated under reduced pressure to afford 4-(6-(4-(4-methyl-4-(5-methyl-1,3,4-oxadiazol-2-yl)piperidine-1-carbonyl)phenyl)imidazo[1,2-a]pyridin-3-yl)benzonitrile (100 mg, 26%, AUC HPLC 98.77%) as a white solid, m.p: 262-267° C. $^1$H NMR (400 MHz, CDCl$_3$): δ (ppm): 8.49 (s, 1H), 7.84-7.72 (m, 6H), 7.57-7.50 (m, 5H), 4.01 (bs, 1H), 3.55 (bs, 2H), 3.37 (bs, 1H), 2.55-2.45 (m, 8H), 2.28 (s, 3H), 1.93 (bs, 1H), 1.77 (bs, 1H), 1.51 (bs, 1H), 1.42 (bs, 1H), 0.97 (s, 3H); MS (ESI) m/z 519 $[C_{32}H_{34}N_6O+H]$.

Example 165: 4-(6-(4-(piperazine-1-carbonyl)phenyl)imidazo[1,2-a]pyridin-3-yl)benzonitrile

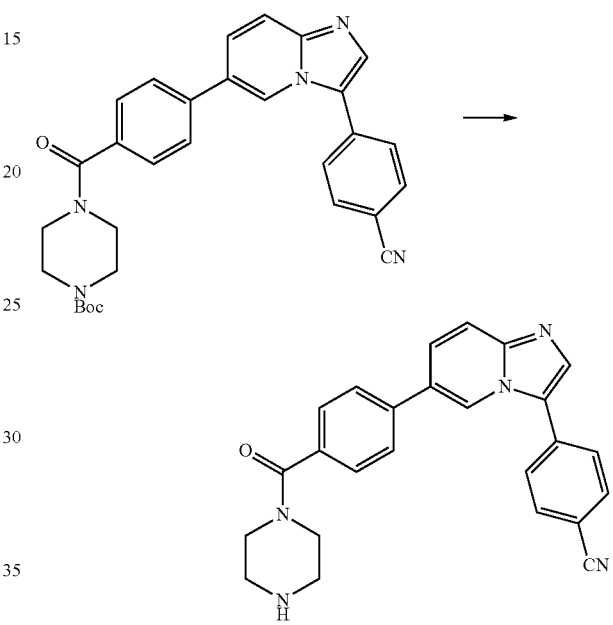

Step 1: To a solution of 4-(3-(4-cyanophenyl)imidazo[1,2-a]pyridin-6-yl)benzoic acid (0.25 g, 0.74 mmol) in DMF (5 mL) were added HATU (0.419 g, 1.1 mmol), N-methyl morpholine (0.15 g, 1.47 mmol) and tert-butyl piperidine-4-carboxylate A (0.15 g, 0.81 mmol). The reaction mixture was stirred at 0° C. to rt under inert atmosphere for 16 h, then was diluted with H$_2$O (15 mL) and extracted with EtOAc (3×25 mL). The combined organic layer was dried over Na$_2$SO$_4$ and was concentrated under reduced pressure. The crude product was purified by column chromatography (silica gel, eluent CH$_2$Cl$_2$/MeOH 97:3) to afford tert-butyl 4-(4-(3-(4-cyanophenyl)imidazo[1,2-a]pyridin-6-yl)benzoyl)piperazine-1-carboxylate (0.23 g, LC-MS 92%). $^1$HNMR (400 MHz, CDCl$_3$); δ 8.48 (s, 1H), 7.87-7.83 (m, 4H), 7.72 (d, J=8 Hz, 2H), 7.59-7.51 (m, 5H), 3.7-3.46 (m, 8H), 1.43 (s, 9H); MS (ESI) m/z 508 $[C_{30}H_{29}N_5O_3+H]^+$.

Step 2: A solution of hydrochloric acid in Ether was added drop wise to tert-butyl 4-(4-(3-(4-cyanophenyl)imidazo[1,2-a]pyridin-6-yl)benzoyl) piperazine-1-carboxylate (0.23 g, 0.45 mmol) at 0° C. Reaction mixture was stirred at rt for 2 h. Ether was evaporated under reduced pressure and basified with saturated NaHCO$_3$ solution. The solid thus formed was filtered to afford 4-(6-(4-(piperazine-1-carbonyl)phenyl)imidazo[1,2-a]pyridin-3-yl)benzonitrile (80 mg, 43.3%, AUC HPLC 95.22%) as an off-white solid, m.p: 88-98° C. $^1$H NMR: (400 MHz, CDCl$_3$) δ (ppm) 8.50 (s, 1H), 7.84-7.73 (m, 6H), 7.59-7.51 (m, 5H), 3.84 (bs, 2H), 3.25 (bs, 2H), 3.05-2.8 (m, 4H), 1.62 (s, 1H); MS (ESI) m/z 408.2 $[C_{25}H_{21}N_5O+H]^+$

Example 166: N-(5-(3-(4-cyanophenyl)imidazo[1,2-a]pyridin-6-yl)-2-(morpholine-4-carbonyl)phenyl) acetamide

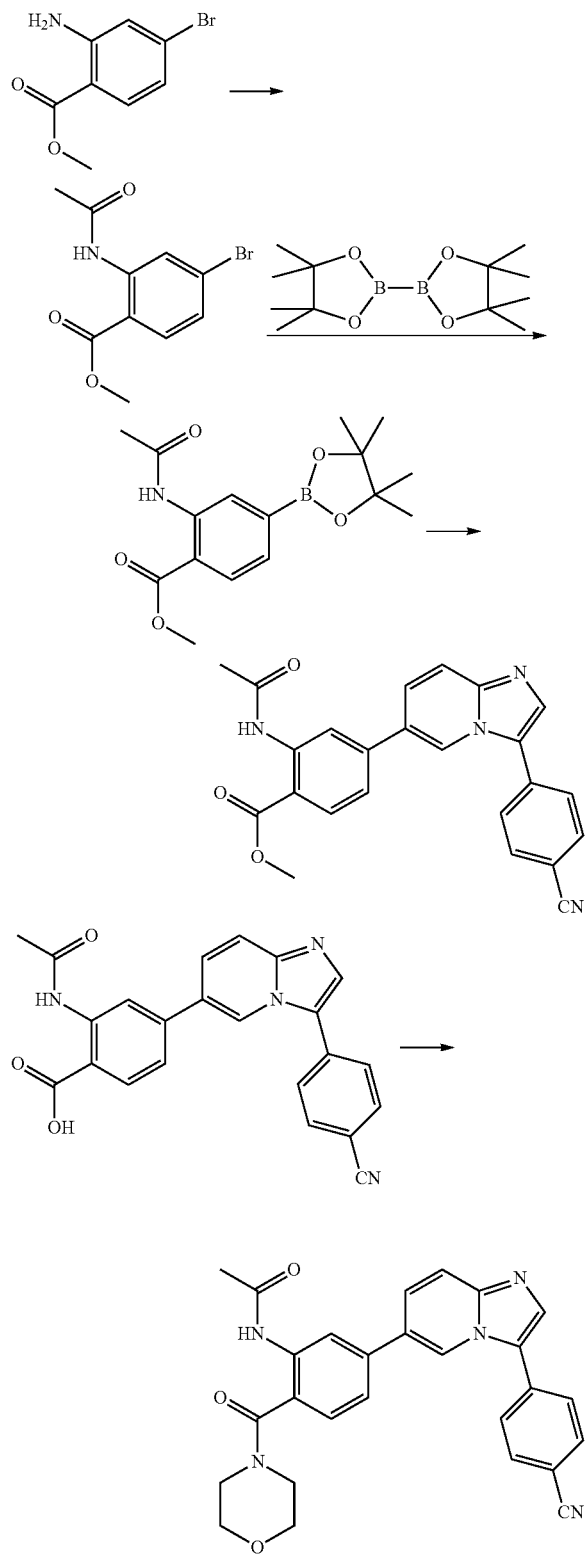

Step 1: To a solution of methyl 2-acetamido-4-bromobenzoate (1 g, 4.37 mmol) in DCM (15 mL) was added TEA (0.873 g, 8.6 mmol) followed by acetyl chloride (0.406 g, 5.21 mmol) at 0° C. and stirred for 4 h. The reaction mixture was diluted with DCM and washed with water and brine solution. The organic layer was dried over anhydrous $Na_2SO_4$ and concentrated under reduced pressure to obtain methyl 2-acetamido-4-bromobenzoate (600 mg, 51%) as a white solid.

Step 2: To a solution of methyl 2-acetamido-4-bromobenzoate (0.6 g, 2.21 mmol), bis(pinacolato)diboron (0.61 g, 2.435 mmol), KOAc (0.65 g, 6.64 mmol) in 1,4-dioxane (15 mL) were added $Pd_2(dba)_3$ (60 mg, 0.066 mmol), $P(Cy)_3$ (60 mg, 0.066 mmol) and the reaction mixture was heated at 90° C. for 16 h under argon. The reaction mixture was diluted with ethyl acetate and washed with water. The organic layer was dried over anhydrous $Na_2SO_4$ and concentrated under reduced pressure to afford methyl 2-acetamido-4-(4,4,5,5-tetramethyl-1,3,2-dioxaborolan-2-yl)benzoate (600 mg, LC-MS 70%) as a green solid which was used in the next step without purification.

Step 3: To a mixture of methyl 2-acetamido-4-(4,4,5,5-tetramethyl-1,3,2-dioxaborolan-2-yl)benzoate (0.6 g, 1.87 mmol), 4-(6-bromoimidazo[1,2-a]pyridin-3-yl)benzonitrile (0.4 g, 1.34 mmol), $K_3PO_4$ (0.57 g, mmol) in 1,4-dioxane (5 mL), and water (1 mL) was added $Pd(PPh_3)_4$ (40 mg) and the reaction mixture was heated at 90° C. for overnight and concentrated to give crude product. The crude product was purified by column chromatography (silica gel, eluent $MeOH/CHCl_3$ 3.5:96.5) to afford methyl 2-acetamido-4-(3-(4-cyanophenyl)imidazo[1,2-a]pyridin-6-yl)benzoate (350 mg, 63%, LC-MS 85%)

Step 4: To a solution of methyl 4-(3-(4-cyanophenyl)imidazo[1,2-a]pyridin-6-yl)-2-formamidobenzoate (350 mg, 0.85 mmol) in 10 mL of $THF: H_2O: EtOH$ (1:1:1) was added LiOH (72 mg, 1.723 mmol) at 0° C. and stirred at rt for 2 h. The reaction mixture was concentrated under reduced pressure then water (10 mL) was added to the reaction mixture, the resulting solid was filtered to give 2-acetamido-4-(3-(4-cyanophenyl)imidazo[1,2-a]pyridin-6-yl)benzoic acid (200 mg, LC-MS 92%) as a white solid.

Step 5: To a solution of 2-acetamido-4-(3-(4-cyanophenyl)imidazo[1,2-a]pyridin-6-yl)benzoic acid (200 mg) in DMF (6 mL) was added NMM (0.178 g, 1.76 mmol) followed by HATU (0.59 g, 1.56 mmol) at rt and stirred for 30 min. Morpholine (92 mg, 1.06 mmol) was added and the stirring was continued at rt for overnight. The reaction mixture was diluted with EtOAc and washed with water and brine solution. The organic layer was dried over anhydrous $Na_2SO_4$ and concentrated under reduced pressure to obtain crude compound which was purified by preparative HPLC to give N-(5-(3-(4-cyanophenyl)imidazo[1,2-a]pyridin-6-yl)-2-(morpholine-4-carbonyl)phenyl)acetamide (151 mg, AUC HPLC 96.2%) of as a pale yellow solid: mp 150-153° C. $^1H$ NMR (400 MHz, $CDCl_3$) δ 9.10 (s, 1H), 8.57 (s, 1H), 8.53 (s, 1H), 7.84-7.73 (m, 6H), 7.53 (d, J=9.6 Hz, 1H), 7.31 (d, J=8.0 Hz, 2H), 3.73 (bs, 8H), 2.21 (s, 3H); MS (ESI) m/z 466 [M+1]

Example 167: 4-(6-(3-hydroxy-4-(morpholine-4-carbonyl)phenyl)imidazo[1,2-a]pyridin-3-yl)benzonitrile

Example 168: 4-(6-(3-((1,3-dioxoisoindolin-2-yl)methyl)-4-(morpholine-4-carbonyl)phenyl)imidazo[1,2-a]pyridin-3-yl)benzonitrile

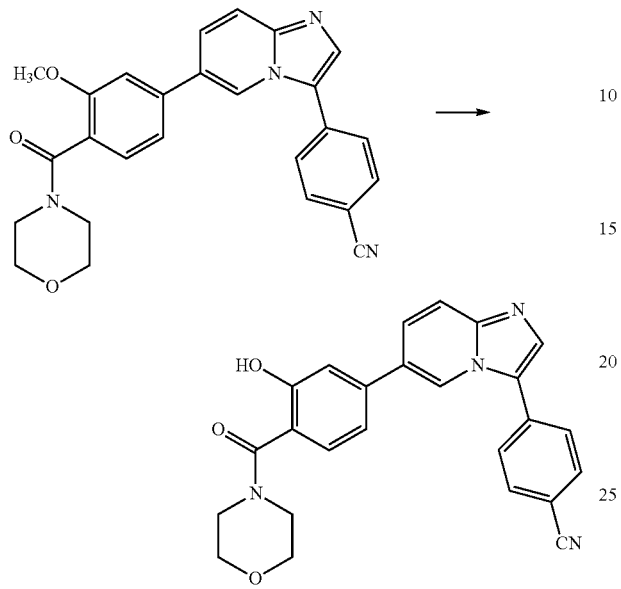

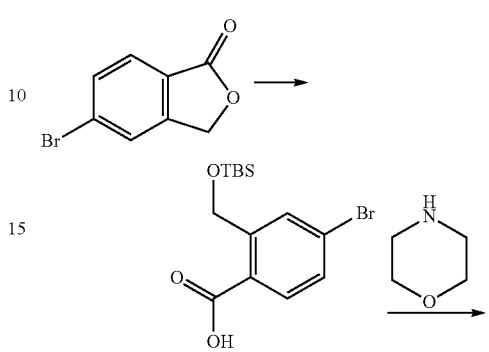

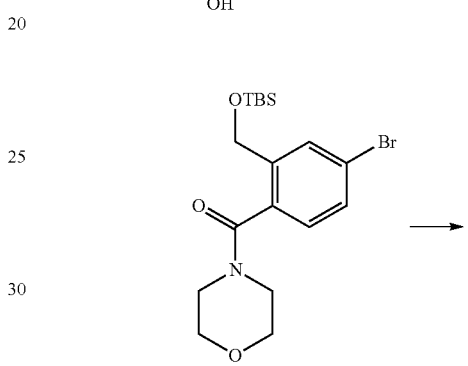

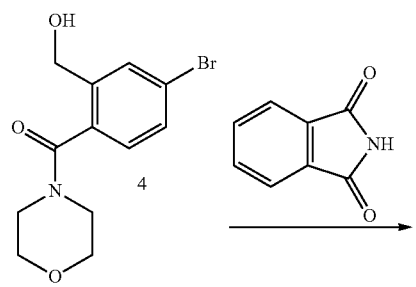

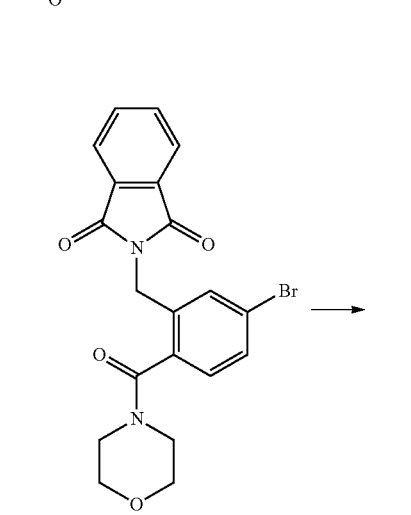

Step 1: To a mixture of 4-(6-bromoimidazo[1,2-a]pyridin-3-yl)benzonitrile (400 mg, 1.35 mmol), (2-methoxy-4-(4,4,5,5-tetramethyl-1,3,2-dioxaborolan-2-yl)phenyl)(morpholino)methanone (562 mg, 1.62 mmol), $K_3PO_4$ (572 mg, 2.7 mmol) in 1,4-dioxane (80 mL) and water (20 mL) was added Pd(PPh$_3$)$_4$ (77 mg, 0.068 mmol) and the reaction mixture was heated at 90° C. for 16 h. The reaction mixture was diluted with water and extracted with EtOAc and washed with water and brine solution. The organic layer was dried over anhydrous $Na_2SO_4$ and concentrated under reduced pressure to obtain crude product. The crude product was purified by preparative HPLC to give 4-(6-(3-methoxy-4-(morpholine-4-carbonyl)phenyl)imidazo[1,2-a]pyridin-3-yl)benzonitrile (120 mg, 20%, AUC HPLC 95.96%) as an off-white solid; m.p. 169-174° C. $^1$H NMR (400 MHz, CDCl$_3$) δ (ppm): 8.46 (s, 1H), 7.84-7.71 (m, 6H), 7.49 (d, J=15.0 Hz, 1H), 7.34 (d, J=10.4 Hz, 1H), 7.13 (d, J=10.4 Hz, 1H), 7.01 (s, 1H), 3.90 (s, 3H), 3.85 (bs, 4H), 3.42 (b s, 2H), 3.35 (m, 2H); MS (ESI) m/z 437 [C$_{26}$H$_{22}$N$_4$O$_3$—H.]$^+$.

Step 2: To a solution of 4-(6-(3-methoxy-4-(morpholine-4-carbonyl)phenyl)imidazo[1,2-a]pyridin-3-yl)benzonitrile (120 mg, 0.273 mmol) in CH$_2$Cl$_2$ (10 mL) cooled to 0° C. was added BBr$_3$ (136 mg, 0.547 mmol). The reaction mixture was stirred at rt for 2 h. The reaction mixture was cooled to 0° C. and quenched by drop wise addition of saturated aq. NaHCO$_3$ (100 mL) and extracted with EtOAc (3×100 mL). The organic layer was washed with water, brine, dried over anhydrous Na$_2$SO$_4$, filtered and concentrated under reduced pressure. The crude compound was purified by preparative HPLC to give 4-(6-(3-hydroxy-4-(morpholine-4-carbonyl)phenyl)imidazo[1,2-a]pyridin-3-yl)benzonitrile (80 mg, 72%, AUC HPLC 98.42%) as an off-white solid. mp 104-106° C. $^1$H NMR (400 MHz, DMSO-d$_6$) δ (ppm): 10.06 (s, 1H), 8.69 (s, 1H), 7.99 (m, 5H), 7.80 (d, J=9.2 Hz, 1H), 7.62 (d, J=9.2 Hz, 1H), 7.27-7.54 (m, 2H), 7.13 (s, 1H), 3.59-3.26 (m, 8H); MS (ESI) m/z 425 [C$_{25}$H$_{20}$N$_4$O$_3$+H]$^+$.

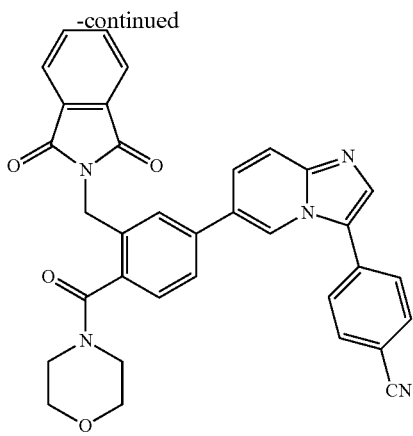

Step 1: A solution of 5-bromoisobenzofuran-1(3H)-one (5 g, 23.47 mmol) and KOH (1.58 g, 28.17 mmol) in MeOH (100 mL) was refluxed for 4 h. MeOH was removed and the residue was dissolved in DMF (30 mL) and treated with imidazole (4.79 g, 70.41 mmol) and tert-butyl dimethyl silyl chloride (7.07 g, 46.94 mmol) at 0° C. and reaction was stirred for 16 h at rt. The reaction mixture was poured into water and extracted with $Et_2O$ (3×100 mL). The combined organic layer was washed with brine solution, dried over anhydrous $Na_2SO_4$ and concentrated in vacuo. The crude residue was dissolved in MeOH (15 mL) and THF (15 mL) and then treated with aqueous solution of $K_2CO_3$ (6.47 g, 46.94 mmol). The mixture was stirred for 16 h at rt and diluted with water (60 mL). The mixture was cooled to 0° C. and pH was adjusted to 5-6 with saturated solution of citric acid. The two phases were separated and the aqueous layer was extracted with $Et_2O$ (3×50 mL). The combined organic layer was washed with brine solution, dried over anhydrous $Na_2SO_4$ and concentrated in vacuum to afford 4-bromo-2-((tert-butyldimethylsilyloxy)methyl)benzoic acid (4 g, 49%, LC-MS 90.5%). $^1$H NMR (400 MHz, DMSO-$d_6$) δ 13.21 (s, 1H), 7.88-7.81 (m, 2H), 7.62 (d, J=8 Hz, 1H), 5.08 (s, 2H), 0.97 (s, 9H), 0.48 (s, 6H); MS (ESI) m/z 346 $[C_{14}H_{21}BrSiO_3+H]^+$.

Step 2: To a solution of 4-bromo-2-((tert-butyldimethylsilyloxy)methyl)benzoic acid (3 g, 8.69 mmol) in DMF (20 mL) were added HATU (4.95 g, 13.03 mmol), N-methyl morpholine (1.75 g, 17.38 mmol) and morpholine (0.9 g, 10.43 mmol). The reaction mixture was stirred at 0° C. to rt for 16 h, then was diluted with $H_2O$ (50 mL) and extracted with EtOAc (3×150 mL). The combined organic layer was dried over $Na_2SO_4$ and was concentrated under reduced pressure. The crude residue was purified by column chromatography (silica gel, eluent hexane/EtOAc 70:30) to afford (4-bromo-2-((tert-butyldimethylsilyloxy)methyl)phenyl)(morpholino) methanone (1 g, 28%, LC-MS 98.56%). $^1$H NMR (400 MHz, CDCl$_3$) δ 7.70 (s, 1H), 7.43 (d, J=1.6 Hz, 1H), 7.02 (d, J=8 Hz, 1H), 4.69 (bs, 2H), 3.77 (bs, 4H), 3.58 (bs, 2H), 3.26 (bs, 2H), 0.94 (s, 9H), 0.11 (s, 6H); MS (ESI) m/z 415 $[C_{18}H_{22}BrNSiO_3+H]^+$.

Step 3: To a solution of (4-bromo-2-((tert-butyldimethylsilyloxy)methyl)phenyl)(morpholino) methanone (1 g, 2.41 mmol) in THF (10 mL) was added tetrabutylammonium fluoride in THF (1M solution in THF, 4.83 mL, 4.83 mmol) drop wise at 0° C. The reaction mixture was stirred at rt for 1 h and was diluted with $H_2O$ (20 mL) and extracted with EtOAc (3×50 mL). The combined organic layer was dried over $Na_2SO_4$ and concentrated under reduced pressure. The crude product was purified by column chromatography (silica gel, eluent hexane/EtOAc 30:70) to afford (4-bromo-2-(hydroxymethyl)phenyl)(morpholino)methanone (570 mg, 79%, LC-MS 90%). $^1$H NMR (400 MHz, CDCl$_3$) δ 7.62 (s, 1H), 7.47 (d, J=8.0 Hz, 1H), 7.09 (d, J=8 Hz, 1H), 4.55 (bs, 2H), 3.78 (bs, 4H), 3.60 (bs, 2H), 3.35 (bs, 2H); MS (ESI) m/z 301.15 $[C_{12}H_{14}BrNO_3+H]^+$.

Step 4: To a solution of (4-bromo-2-(hydroxymethyl)phenyl)(morpholino)methanone (2.8 g, 9.33 mmol), phthalimide (1.5 g, 10.26 mmol) and triphenyl phosphine (3.66 g, 13.99 mmol) in THF (30 mL) was added DEAD (2.43 g, 13.99 mmol) drop wise at 0° C. The reaction mixture was stirred at rt for 2 h then was diluted with $H_2O$ (50 mL) and extracted with EtOAc (3×150 mL). The combined organic layer was dried over $Na_2SO_4$ and was concentrated under reduced pressure. The crude product was purified by column chromatography (silica gel, eluent hexane/EtOAc 70:30) to afford 2-(5-bromo-2-(morpholine-4-carbonyl)benzyl)isoindoline-1,3-dione (2 g, LC-MS 39%) which was used in the next step without purification.

Step 5: To a mixture of 2-(5-bromo-2-(morpholine-4-carbonyl)benzyl)isoindoline-1,3-dione 5 (540 mg, 1.26 mmol), 4-(6-(4,4,5,5-tetramethyl-1,3,2-dioxaborolan-2-yl)imidazo[1,2-a]pyridin-3-yl)benzonitrile (521 mg, 1.51 mmol), $K_3PO_4$ (534 mg, 2.52 mmol) in 1,4-dioxane (15 mL) and water (3 mL) was added Pd(PPh$_3$)$_4$ (72.7 mg, 0.06 mmol) and the reaction mixture was heated at 90° C. for 16 h under argon. The reaction mixture was diluted with water and extracted with EtOAc and washed with water and brine solution. The organic layer was dried over anhydrous $Na_2SO_4$ and concentrated under reduced pressure to obtain the crude product. The crude product was purified by column chromatography (silica gel, eluent $CH_2Cl_2$/MeOH 97:3) to afford 4-(6-(3-((1,3-dioxoisoindolin-2-yl)methyl)-4-(morpholine-4-carbonyl)phenyl)imidazo[1,2-a]pyridin-3-yl)benzonitrile (250 mg, 35%, AUC HPLC 98%) as an light yellow solid; $^1$H NMR (400 MHz, CDCl$_3$) δ (ppm): 8.44 (s, 1H), 7.86-7.64 (m, 10H), 7.46 (d, J=8.4 Hz, 2H), 7.31 (d, J=8.2 Hz, 2H), 5.03-4.97 (m, 2H), 3.85-3.66 (m, 6H), 3.40 (s, 2H); MS (ESI) m/z 568 $[C_{34}H_{25}N_5O_4+H]^+$;

Example 169: N-(5-(3-(4-cyanophenyl)imidazo[1,2-a]pyridin-6-yl)-2-(4-(methylamino)piperidine-1-carbonyl)phenyl)acetamide

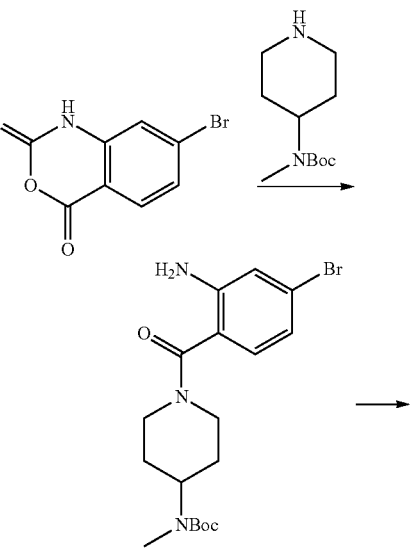

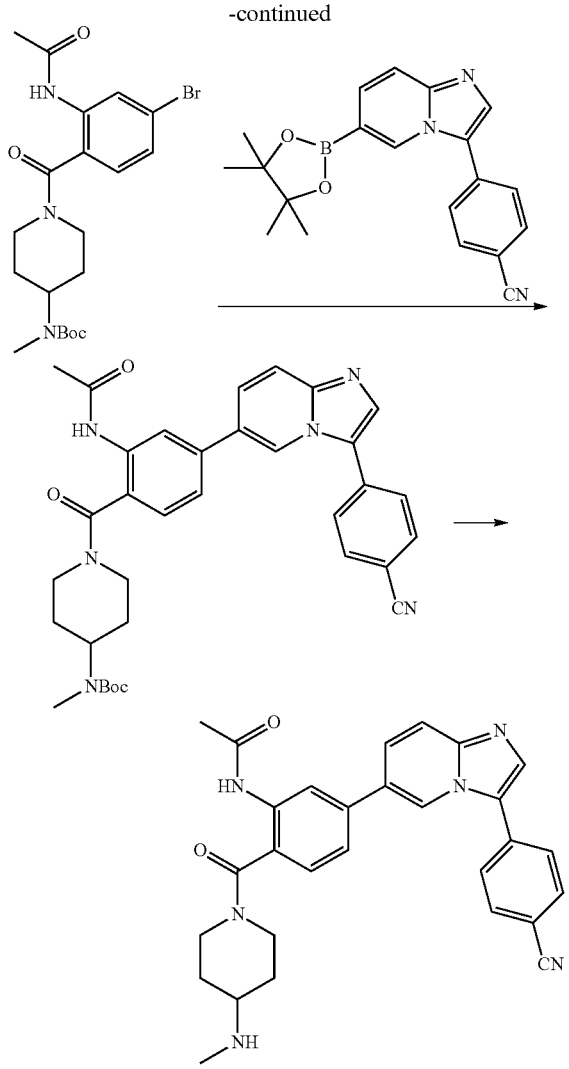

Step: 1 To a solution of 2-amino-4-bromobenzoic acid (2.5 g, 11.57 mmol) in 1,4-dioxane (10 mL) was added bis(trichloromethyl) carbonate at 0° C. and the reaction mixture was heated at 110° C. for 16 h. The reaction mixture was concentrated, filtered and washed with hexane to afford 7-bromo-1H-benzo[d][1,3]oxazine-2,4-dione (2.3 g, 82%, LC-MS 99%) as an off white solid. $^1$H NMR (400 MHz, DMSO-$d_6$) δ 11.8 (s, 1H), 7.83 (d, J=8.4 Hz, 1H), 7.43 (d, J=8.4 Hz, 2H); MS (ESI) m/z 242 [$C_8H_4BrNO_3$+H]$^+$.

Step 2: To a solution of 7-bromo-1H-benzo[d][1,3]oxazine-2,4-dione (400 mg, 1.65 mmol), tert-butyl methyl (piperidin-4-yl)carbamate (389 mg, 1.81 mmol) in DMF (5 mL) was added DMAP (20 mg, 0.16 mmol) at rt and stirred at same temperature for 16 h. The reaction mixture was added ice cooled water and extracted with EtOAc (3×30 mL). The combined organic layer was washed with water, brine solution and dried over Na$_2$SO$_4$ and was concentrated under reduced pressure to obtain the crude product. The crude product was washed with n-pentane to afford tert-butyl 1-(2-amino-4-bromobenzoyl)piperidin-4-yl(methyl) carbamate (670 mg, 98%, LC-MS 94%). $^1$H NMR (400 MHz, CDCl$_3$) δ 6.93 (d, J=8.4 Hz, 1H), 6.88 (s, 1H), 6.83 (d, J=6.8 Hz, 1H), 4.42 (s, 3H), 4.21 (br s, 2H), 2.95 (s, 2H), 2.88 (s, 3H), 1.72-1.62 (m, 4H), 1.46 (s, 9H); MS (ESI) m/z 412/414 [$C_{18}H_{26}BrN_3O_3$]$^+$.

Step 3: To a solution of tert-butyl 1-(2-amino-4-bromobenzoyl)piperidin-4-yl(methyl)carbamate (0.73 g, 1.78 mmol) in DCM (10 mL) was added triethylamine (0.74 mL, 5.34 mmol). Acetyl chloride (0.19 mL, 2.67 mmol) was added to the reaction mixture at 0° C. and stirred at rt for 2 h. The reaction mixture was added water and extracted with EtOAc (3×30 mL). The combined organic layer was washed with water, brine solution and dried over Na$_2$SO$_4$ and was concentrated under reduced pressure to obtain the crude product. The crude product was washed with n-pentane to afford tert-butyl 1-(2-acetamido-4-bromobenzoyl)piperidin-4-yl(methyl)carbamate (650 mg, 80.5%, LC-MS 92.5%). $^1$H NMR (400 MHz, CDCl$_3$) δ 9.01 (s, 1H), 8.55 (s, 1H), 7.25 (d, J=8.4 Hz, 1H), 7.01 (d, J=6.8 Hz, 1H), 4.18 (s, 2H), 2.95 (s, 3H), 2.74 (s, 4H), 2.18 (s, 3H), 1.82-1.65 (m, 3H), 1.46 (s, 9H); MS (ESI) m/z 554/556 [$C_{20}H_{28}BrN_3O_4$]$^+$.

Step 4: To a mixture of tert-butyl 1-(2-acetamido-4-bromobenzoyl)piperidin-4-yl(methyl)carbamate (215 mg, 0.47 mmol), 4-(6-(4,4,5,5-tetramethyl-1,3,2-dioxaborolan-2-yl)imidazo[1,2-a]pyridin-3-yl)benzonitrile (196.8 mg, 0.57 mmol), K$_3$PO$_4$ (201 mg, 0.95 mmol) in 1,4-dioxane (10 mL) and water (2 mL) was added Pd(PPh$_3$)$_4$ (27.4 mg, 0.02 mmol) and the reaction mixture was heated at 90° C. for 16 h. The reaction mixture was filtered through celite bed and washed with 10% MeOH in CHCl$_3$ and the filtrate was dried over anhydrous Na$_2$SO$_4$ and concentrated under reduced pressure to obtain the crude product. The crude product was purified by column chromatography (silica gel, eluent CHCl$_3$/MeOH 97:3) to afford tert-butyl 1-(2-acetamido-4-(3-(4-cyanophenyl)imidazo[1,2-a]pyridin-6-yl)benzoyl)piperidin-4-yl(methyl)carbamate (210 mg, 75%, LC-MS 61%) as a light yellow solid.

Step 5: To a solution of tert-butyl 1-(2-acetamido-4-(3-(4-cyanophenyl)imidazo[1,2-a]pyridin-6-yl)benzoyl)piperidin-4-yl(methyl)carbamate (200 mg, 0.33 mmol) in DCM (10 mL) was added TFA (1.2 mL) at 0° C. The reaction mixture was stirred at rt for 3 h, concentrated under reduced pressure and basified with saturated NaHCO$_3$ solution. The precipitated was isolated by filtration and was dried. The crude product was purified by preparative HPLC to afford N-(5-(3-(4-cyanophenyl)imidazo[1,2-a]pyridin-6-yl)-2-(4-(methylamino)piperidine-1-carbonyl)phenyl)acetamide (30 mg, 18%, AUC HPLC 95.9%) as a pale yellow solid. m.p. 147-151° C. $^1$H NMR (400 MHz, CDCl$_3$) δ 9.07 (s, 1H), 8.53 (s, 2H), 7.84-7.73 (m, 6H), 7.76 (d, J=7.6 Hz, 1H), 7.73 (s, 1H), 7.31 (d, J=8.0 Hz, 1H), 4.60 (s, 1H), 3.95 (s, 1H), 3.15 (s, 2H), 2.77 (s, 1H), 2.49 (s, 3H), 2.19 (s, 3H), 2.05 (s, 3H), 1.44 (s, 2H); MS (ESI) m/z 493.05 [$C_{29}H_{28}N_6O_2$+H]$^+$.

Example 170: N-(5-(3-(4-cyanophenyl)imidazo[1,2-a]pyridin-6-yl)-2-(piperazine-1-carbonyl)phenyl) acetamide

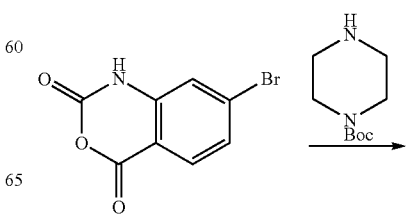

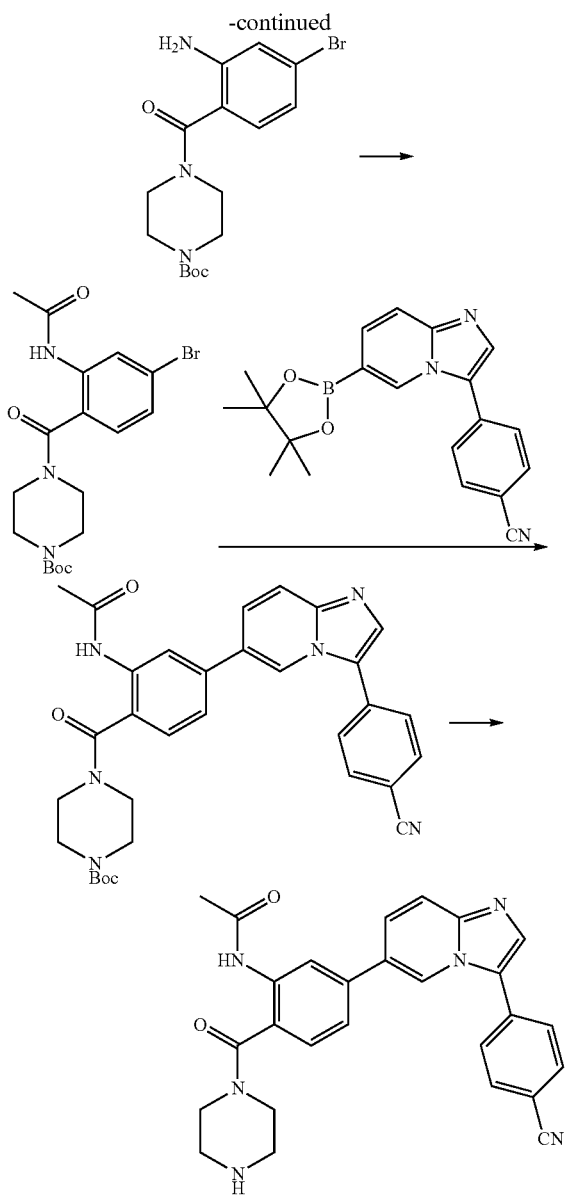

Step: 1 To a solution of 2-amino-4-bromobenzoicacid (2.5 g, 11.57 mmol) in 1,4-dioxane (10 mL) was added bis (trichloromethyl) carbonate at 0° C. and the reaction mixture was heated at 110° C. for 16 h. The reaction mixture was concentrated, filtered and washed with hexane to afford 7-bromo-1H-benzo[d][1,3]oxazine-2,4-dione (2.3 g, 82%, LC-MS 99%) as an off white solid. $^1$H NMR (400 MHz, DMSO-$d_6$) δ 11.8 (s, 1H), 7.83 (d, J=8.4 Hz, 1H), 7.43 (d, J=8.4 Hz, 2H); MS (ESI) m/z 242 $[C_8H_4BrNO_3+H]^+$.

Step 2: To a solution of 7-bromo-1H-benzo[d][1,3]oxazine-2,4-dione (400 mg, 1.65 mmol), tert-butyl methyl (piperidin-4-yl)carbamate (389 mg, 1.81 mmol) in DMF (5 mL) was added DMAP (20 mg, 0.16 mmol) at rt and the mixture was stirred for 16 h. To the reaction mixture was added ice cooled water and the solid thus precipitated was filtered and washed in turn with water, n-pentane and dried to afford tert-butyl 4-(2-amino-4-bromobenzoyl)piperazine-1-carboxylate (910 mg, 57%, LC-MS 64.6). MS (ESI) m/z 384/386 $[C_{16}H_{22}BrN_3O_3+H]^+$.

Step 3: To a solution of tert-butyl 4-(2-amino-4-bromobenzoyl)piperazine-1-carboxylate (0.9 g, 2.35 mmol) in dichloromethane (10 mL) was added TEA (0.98 mL, 7.05 mmol). Acetyl chloride (0.25 mL, 3.53 mmol) was added to the reaction mixture at 0° C. and stirred at rt for 2 h. To the reaction mixture was added water and the mixture was extracted with EtOAc (3×50 mL). The combined organic layer was washed in turn with water and brine. The organic solution and dried over $Na_2SO_4$, filtered and was concentrated under reduced pressure to obtain the crude product. The crude product was purified by column chromatography (silica gel, eluent $CHCl_3$/MeOH 97:3) to afford tert-butyl 4-(2-acetamido-4-bromobenzoyl)piperazine-1-carboxylate (600 mg, 60%, LC-MS 96.3%) as a light yellow solid. $^1$H NMR (400 MHz, $CDCl_3$) δ 8.96 (s, 1H), 8.54 (s, 1H), 7.24 (d, J=10 Hz, 1H), 7.04 (d, J=8.0 Hz, 1H), 3.58-3.41 (m, 8H), 2.15 (s, 3H), 1.47 (s, 9H); MS (ESI) m/z 426/428 $[C_{18}H_{24}BrN_3O_4]^+$.

Step 4: To a mixture of tert-butyl 4-(2-acetamido-4-bromobenzoyl)piperazine-1-carboxylate (373 mg, 0.87 mmol), 4-(6-(4,4,5,5-tetramethyl-1,3,2-dioxaborolan-2-yl)imidazo[1,2-a]pyridin-3-yl)benzonitrile C (364 mg, 1.05 mmol), $K_3PO_4$ (372.7 mg, 1.76 mmol) in 1,4-dioxane (10 mL) and water (2 mL) was added $Pd(PPh_3)_4$ (50.7 mg, 0.04 mmol) and the reaction mixture was heated at 90° C. for 16 h under argon. The reaction mixture was filtered through celite bed and washed with 10% MeOH in $CHCl_3$ and the filtrate was dried over anhydrous $Na_2SO_4$ and concentrated under reduced pressure to obtain the crude product. The crude product was purified by column chromatography (silica gel, eluent $CHCl_3$/MeOH 97:3) to afford tert-butyl 4-(2-acetamido-4-(3-(4-cyanophenyl)imidazo[1,2-a]pyridin-6-yl)benzoyl)piperazine-1-carboxylate (310 mg, 62%, LC-MS 76%) as a light yellow solid. MS (ESI) m/z 565 $[C_{32}H_{32}N_6O_4+H]^+$.

Step 5: To a solution of tert-butyl 4-(2-acetamido-4-(3-(4-cyanophenyl)imidazo[1,2-a]pyridin-6-yl)benzoyl)piperazine-1-carboxylate (250 mg, 0.44 mmol) in dichloromethane (10 mL) was added TFA (1.2 mL) at 0° C. The reaction mixture was stirred at rt for 3 h. Reaction mixture was diluted with water and basified with saturated $NaHCO_3$ solution and extracted with 10% MeOH in $CHCl_3$. The combined organic layer was washed with water, brine solution and dried over $Na_2SO_4$ and was concentrated under reduced pressure to obtain the crude product. The compound was further purified by preparative HPLC to afford N-(5-(3-(4-cyanophenyl)imidazo[1,2-a]pyridin-6-yl)-2-(piperazine-1-carbonyl)phenyl)acetamide (30 mg, 14.6%, AUC HPLC 98.3%) as an off-white solid. mp 160-165° C. $^1$H NMR (400 MHz, $CDCl_3$) δ 9.08 (s, 1H), 8.56-8.53 (m, 2H), 7.84-7.77 (m, 6H), 7.75-7.73 (m, 1H), 7.55-7.30 (m, 3H), 3.62 (s, 4H), 2.93 (s, 4H), 2.20 (s, 3H); MS (ESI) m/z 465 $[C_{27}H_{24}N_6O_2+H]^+$.

Example 171: 4-(6-(3-(piperazin-1-yl)-4-(piperazine-1-carbonyl)phenyl)imidazo[1,2-a]pyridin-3-yl)benzonitrile

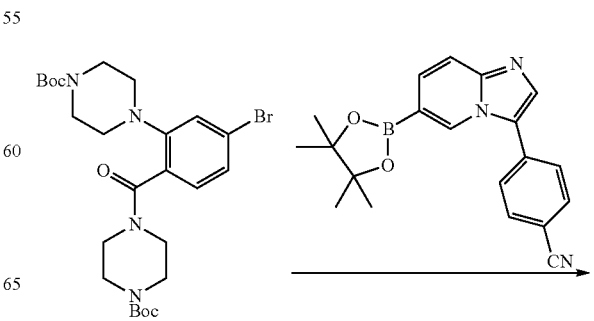

251

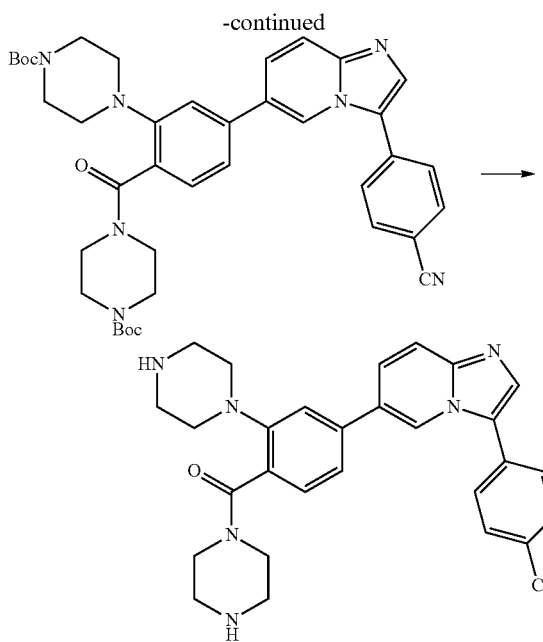

-continued

Step 1: To a solution of 4-bromo-2-(4-(tert-butoxycarbonyl)piperazin-1-yl)benzoic acid (0.8 g, 2.08 mmol) in DMF (6 mL) was added NMM (0.41 g, 4.16 mmol) followed by HATU (1.18 g, 3.12 mmol) at rt and the reaction mixture was stirred for 30 min. tert-butyl piperazine-1-carboxylate (0.46 g, 2.49 mmol) was added and stirred was continued at rt for 16 h. The reaction mixture was diluted with EtOAc and washed with water, brine solution. The organic layer was dried over anhydrous $Na_2SO_4$ and concentrated under reduced pressure to obtain tert-butyl 4-(4-bromo-2-(4-(tert-butoxycarbonyl)piperazin-1-yl)benzoyl)piperazine-1-carboxylate (600 mg, 52%, LC-MS-80%) as an off white solid.

Step 2: To a mixture of tert-butyl 4-(4-bromo-2-(4-(tert-butoxycarbonyl)piperazin-1-yl)benzoyl)piperazine-1-carboxylate (612 mg, 1.10 mmol), 4-(6-(4,4,5,5-tetramethyl-1,3,2-dioxaborolan-2-yl)imidazo[1,2-a]pyridin-3-yl)benzonitrile (470 mg, 1.00 mmol), $K_3PO_4$ (427 mg, 2.01 mmol) in 1,4-dioxane (15 mL) and water (1 mL) was added $Pd(PPh_3)_4$ (40 mg, 0.01 mmol) and the reaction mixture was heated at 90° C. for 16 h. The reaction mixture was diluted with EtOAc and washed with water and brine solution. The organic layer was dried over anhydrous $Na_2SO_4$ and concentrated under reduced pressure to obtain the crude product. The crude product was purified by column chromatography (silica gel, eluent methanol/dichloromethane 10:90) to afford tert-butyl 4-(2-(4-(tert-butoxycarbonyl)piperazin-1-yl)-4-(3-(4-cyanophenyl)imidazo[1,2-a]pyridin-6-yl)benzoyl)piperazine-1-carboxylate (200 mg, 29%, LC-MS 52%) as a light brown solid.

Step 3: To a solution of tert-butyl-4-(2-(4-(tert-butoxycarbonyl)piperazin-1-yl)-4-(3-(4-cyanophenyl)imidazo[1,2-a]pyridin-6-yl)benzoyl)piperazine-1-carboxylate (200 mg) in DCM (5 mL) was a HCl solution in ether (5 mL) at 0° C. and stirred at rt for 2 h. The reaction mixture was concentrated basified with $NaHCO_3$, diluted with EtOAc and washed with water and brine solution. The organic layer was dried over anhydrous $Na_2SO_4$ and concentrated under reduced pressure to obtain the crude product. The crude product was purified by column chromatography (silica gel, eluent methanol/dichloromethane 10:90) to afford 4-(6-(3-(piperazin-1-yl)-4-(piperazine-1-carbonyl)phenyl)imidazo

252

[1,2-a]pyridin-3-yl)benzonitrile (100 mg, 70%, AUC HPLC 94.35%) as an off-white solid; mp 170-174° C. $^1$H NMR (400 MHz, DMSO $d_6$) δ 8.76 (s, 1H), 8.02 (s, 5H), 7.80 (d, J=9.2 Hz, 1H), 7.71 (d, J=8.0 Hz, 1H), 7.39 (d, J=8.0 Hz, 1H), 7.28 (s, 1H), 7.25 (d, J=8.0 Hz, 2H), 3.67-3.64 (m, 1H), 3.51-3.47 (m, 1H), 3.16-3.13 (m, 3H), 3.01 (s, 1H), 2.97-2.67 (m, 9H), 2.5 (s, 1H); MS (ESI) m/z 492.31 $[C_{29}H_{29}N_7O+H]^+$.

Example 172: Synthesis of 4-(6-(4-(4-methoxy-4-methylpiperidine-1-carbonyl)phenyl)imidazo[1,2-a]pyridin-3-yl)benzonitrile

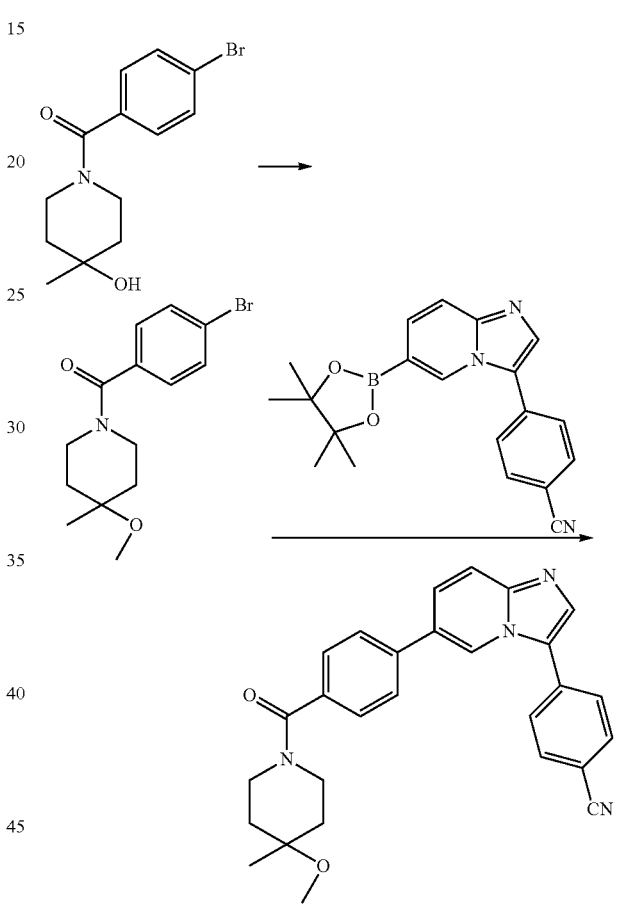

Step 1: To a solution of 4-bromobenzoic acid (500 mg, 4.97 mmol) in DMF (10 mL) were added HATU (1.41 g, 7.46 mmol), N-methyl morpholine (0.69 mL, 12.44 mmol) and 4-methylpiperidin-4-ol hydrochloride (452 mg, 5.97 mmol). The reaction mixture was stirred at 0° C. to room temperature under inert atmosphere for 16 h, then was diluted with $H_2O$ (30 mL) and extracted with EtOAc (3×30 mL). The combined organic layer was washed with water, brine and dried over $Na_2SO_4$ and was concentrated under reduced pressure. The crude residue was purified by column chromatography (silica gel, eluent $CH_2Cl_2$/MeOH 97:3) to afford (4-bromophenyl)(4-hydroxy-4-methylpiperidin-1-yl)methanone (435 mg, 58%, LC-MS 92.2%) as a pale yellow solid. MS (ESI) m/z 298/300 $[C_{13}H_{16}BrNO_2+H]^+$.

Step 2: A solution of (4-bromophenyl)(4-hydroxy-4-methylpiperidin-1-yl)methanone (375 mg, 1.26 mmol) in anhydrous DMF (8 mL) was added to sodium hydride (120.8 mg, 50%, 5.03 mmol) that was prewashed with n-hexane, cooled to 0° C. Methyl iodide (2.5 mL, 40.14 mmol) was added to the reaction mixture and stirred at rt for 16 h. The reaction mixture was quenched with ice-cold water and extracted with EtOAc (3×30 mL). The combined organic layer was washed with water, brine solution and dried over Na$_2$SO$_4$, filtered and was concentrated under reduced pressure to afford (4-bromophenyl)(4-methoxy-4-methylpiperidin-1-yl)methanone (250 mg) as a green solid. MS (ESI) m/z 312/314 [C$_{14}$H$_{18}$BrNO$_2$+H]$^+$.

Step 3: To a mixture of (4-bromophenyl)(4-methoxy-4-methylpiperidin-1-yl)methanone (240 mg, 0.77 mmol), 4-(6-(4,4,5,5-tetramethyl-1,3,2-dioxaborolan-2-yl)imidazo[1,2-a]pyridin-3-yl)benzonitrile (318.4 mg, 0.92 mmol), K$_3$PO$_4$ (326 mg, 1.54 mmol) in 1,4-dioxane (15 mL) and water (2 mL) was added Pd(PPh$_3$)$_4$ (44 mg, 0.04 mmol) and the reaction mixture was heated at 100° C. for 16 h. The reaction mixture was diluted with EtOAc and washed in turn with water and brine solution. The organic layer was dried over anhydrous Na$_2$SO$_4$, filtered and concentrated under reduced. The residue was purified by column chromatography (silica gel, eluent MeOH/DCM/MeOH 97:3) to afford 4-(6-(4-(4-methoxy-4-methylpiperidine-1-carbonyl)phenyl)imidazo[1,2-a]pyridin-3-yl)benzonitrile (70 mg, 29%, AUC HPLC 96.73%) as an off white solid. mp 159-163° C. $^1$H NMR (400 MHz, CDCl$_3$) δ (ppm): 8.50 (s, 1H), 7.84-7.72 (m, 6H), 7.58-7.50 (m, 5H), 4.40 (s, 1H), 3.55-3.40 (m, 2H), 3.33-312 (m, 4H), 1.92 (s, 1H), 1.75 (s, 1H), 1.45 (s, 2H), 1.20 (s, 3H); MS (ESI) m/z 451 [C$_{28}$H$_{26}$N$_4$O$_2$+H]$^+$.

Example 173: (4-amino-4-methylpiperidin-1-yl)(4-(3-(4-chlorophenyl)imidazo[1,2-a]pyridin-6-yl)phenyl)methanone

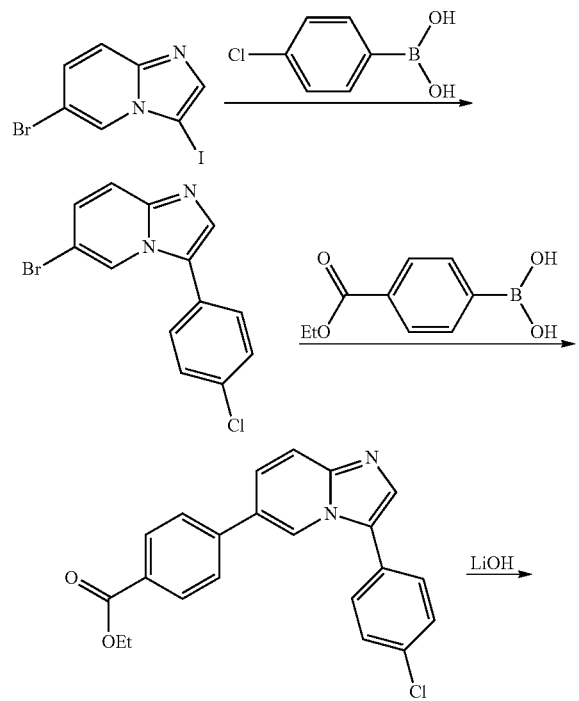

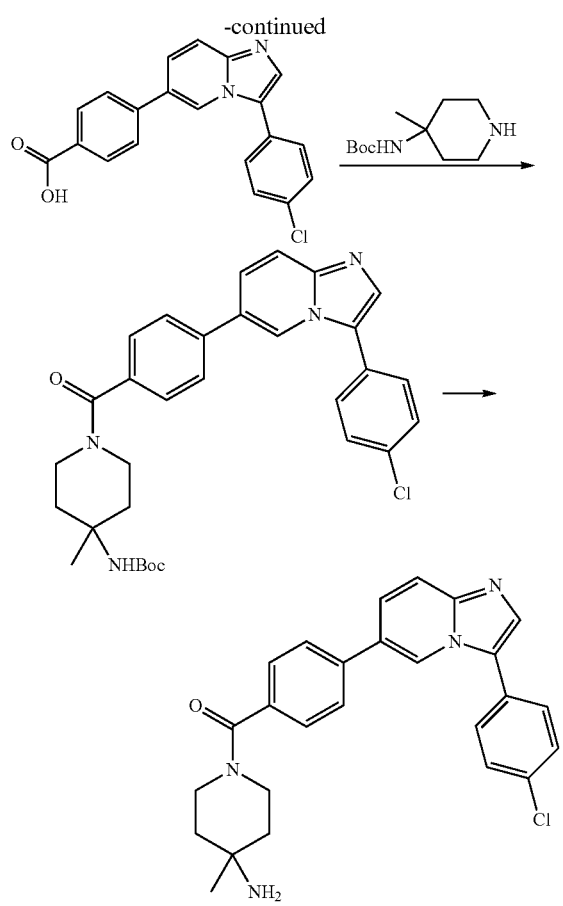

Step: 1 To a solution of 6-bromoimidazo[1,2-a]pyridine (20 g, 101.5 mmol) in ACN (300 mL) was added N-iodosuccinimide (22.8 g, 101.5 mmol) at rt and stirred for 5 h. The reaction mixture was filtered and washed with hot acetonitrile to afford 6-bromo-3-iodoimidazo[1,2-a]pyridine (22 g, 67%) as a pale yellow solid. $^1$H NMR (400 MHz, CDCl$_3$) δ 8.29 (s, 1H), 7.58 (d, J=9.2 Hz, 1H), 7.35 (d, J=7.6 Hz, 1H), 7.27 (s, 1H).

Step 2: A mixture of 6-bromo-3-iodoimidazo[1,2-a]pyridine (21 g, 65.4 mmol), 4-chlorophenylboronic acid (11.22 g, 71.9 mmol), K$_3$PO$_4$ (27.7 g, 130.8 mmol) in DMF (100 mL), and water (15 mL) was degassed with argon for 30 min. Pd(PPh$_3$)$_4$ (3.77 g, 3.27 mmol) was added and again degassed with argon for 30 min and the reaction mixture was heated at 90° C. for 6 h. TLC indicated absence of SM and formation of two polar spots. Water (2×100 ml) was added to the reaction mixture to induce precipitation which was filtered to give crude product. The crude product was purified by column chromatography (silica gel, eluent (CHCl$_3$/MeOH 95:5) to afford 6-bromo-3-(4-chlorophenyl)imidazo[1,2-a]pyridine (10.6 g, 52%) as a yellowish green solid. $^1$H NMR (400 MHz, CDCl$_3$) δ 8.38 (s, 1H), 7.69 (s, 1H), 7.60 (d, J=8.0 Hz, 2H), 7.82 (t, J=9.2 Hz, 1H), 7.58 (q, J=5.2 Hz, 4H), MS (ESI) m/z 309 [C$_{13}$H$_8$BrN$_2$Cl+2H]$^+$ Step 3: 4-(ethoxycarbonyl)phenylboronic acid (3.81 g, 19.67 mmol), K$_3$PO$_4$ (6.95 g, 32.78 mmol), and Pd(PPh$_3$)$_4$ (0.56 g, 0.49 mmol) were added sequentially to a solution of ethyl 6-bromo-3-(4-chlorophenyl)imidazo[1,2-a]pyridine (5 g, 16.39 mmol) in a mixture of 1,4-dioxane/H$_2$O (50:5 mL) at room temperature under argon atmosphere. The reaction mixture was refluxed for 6 h and was diluted with water (100 mL) and extracted with EtOAc (3×100 mL). The combined organic layer was dried over Na$_2$SO$_4$, filtered and concentrated under reduced pressure. The residue was purified by column chromatography (silica gel, eluent petroleum ether/EtOAc 1:1) to afford ethyl 4-(3-(4-chlorophenyl)imidazo[1,2-a]pyridin-6-yl)benzoate (2.7 mg, 58%) as an off-white solid. $^1$H NMR (400 MHz, CDCl$_3$) δ 9.21 (s, 1H), 8.95 (s, 1H), 8.21 (s, 1H), 8.17-8.12 (m, 5H), 8.08 (s, 1H), 7.91 (d, J=8.0 Hz, 2H), 7.82 (t, J=8.4 Hz, 1H), 4.03 (q, J=7.2 Hz, 2H), 1.42 (t, J=7.2 Hz, 3H); MS (ESI) m/z 378 [C$_{22}$H$_{17}$ClN$_2$O$_2$+H]$^+$ Step 4: To a solution of ethyl 4-(3-(4-chlorophenyl)imidazo[1,2-a]pyridin-6-yl)benzoate (2.7 g, 7.18 mmol) and LiOH (0.9 g, 21.54 mmol) in a mixture of THF (40 mL), water (10 mL) and MeOH (10 ml) was stirred for 5 h at rt. The reaction mixture was concentrated under reduced pressure to afford 4-(3-(4-chlorophenyl)imidazo[1,2-a]pyridin-6-yl)benzoic acid (900 mg, 37%) as an off white solid which was used in the next step without purification. $^1$H NMR (400 MHz, DMSO-d$_6$) δ (ppm): 8.87 (s, 1H), 8.14 (s, 1H), 8.12-8.02 (m, 5H), 7.95-7.87 (m, 5H); MS (ESI) m/z 349 [C$_{20}$H$_{13}$ClN$_2$O$_2$+H]$^+$.

Step 5: To a solution of 4-(3-(4-chlorophenyl)imidazo[1,2-a]pyridin-6-yl)benzoic acid (500 mg, 1.43 mmol) in DMF (15.0 mL) were added HATU (817 mg, 2.14 mmol), N-methyl morpholine (0.317 mL, 2.86 mmol) and tert-butyl 4-methylpiperidin-4-ylcarbamate (336 mg, 1.58 mmol). The reaction mixture was stirred at room temperature under inert atmosphere for 16 h, then was diluted with water (15 mL) and extracted with EtOAc (3×25 mL). The combined organic layer was dried over Na$_2$SO$_4$, filtered and was concentrated under reduced pressure. The residue was purified by column chromatography (silica gel, eluent CH$_2$Cl$_2$:MeOH 95:5) to afford tert-butyl 1-(4-(3-(4-chlorophenyl)imidazo[1,2-a]pyridin-6-yl)benzoyl)-4-methylpiperidin-4-ylcarbamate (410 mg, 52%, LC-MS 92%) as an off-white solid. $^1$H NMR (400 MHz, DMSO-d$_6$) δ (ppm): 8.68 (s, 1H), 7.85-7.77 (m, 6H), 7.70-7.66 (m, 1H), 7.61 (d, J=12.0 Hz, 2H), 7.46 (d, J=12.0 Hz, 2H), 3.79 (bs, 2H), 3.45 (bs, 3H), 1.45 (bs, 5H), 1.38 (s, 9H), 1.10 (s, 3H); MS (ESI) m/z 545 [C$_{31}$H$_{33}$ClN$_4$O$_3$+H]$^+$.

Step 6: To a solution of tert-butyl 1-(4-(3-(4-chlorophenyl)imidazo[1,2-a]pyridin-6-yl)benzoyl)-4-methylpiperidin-4-ylcarbamate (400 mg, 0.73 mmol) in dichloromethane (10 mL) was added TFA (3 mL) in dichloromethane (5 mL). The reaction mixture was stirred for 4 h at rt. The reaction mixture was diluted with water (100 mL), NaHCO$_3$ (100 mL) and extracted with CH$_2$Cl$_2$ (2×50 mL). The combined organic layer was concentrated to dryness under reduced pressure to afford crude compound. Crude compound was purified by prep-HPLC to afford (4-amino-4-methylpiperidin-1-yl)(4-(3-(4-chlorophenyl)imidazo[1,2-a]pyridin-6-yl)phenyl)methanone (80 mg, 16%, AUC HPLC 97.59%) as a yellow solid; m.p. 109-124° C. $^1$H NMR (400 MHz, DMSO-d$_6$) δ (ppm): 8.68 (s, 1H), 7.85-7.77 (m, 6H), 7.70-7.66 (m, 1H), 7.61 (d, J=12.0 Hz, 2H), 7.46 (d, J=12.0 Hz, 2H), 3.79 (bs, 2H), 3.45 (bs, 3H), 1.45 (bs, 5H), 1.10 (s, 3H); MS (ESI) m/z 445 [C$_{26}$H$_{25}$ClN$_4$O+H]$^+$.

Example 174: (4-aminopiperidin-1-yl)(4-(3-(4-chlorophenyl)imidazo[1,2-a]pyridin-6-yl)phenyl)methanone

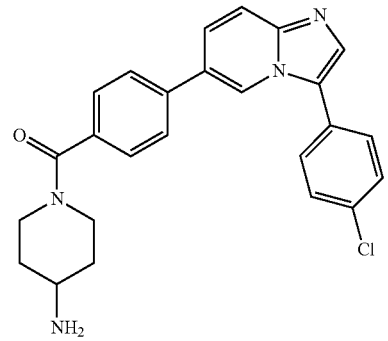

Step 1: To a solution of 4-(3-(4-chlorophenyl)imidazo[1,2-a]pyridin-6-yl)benzoic acid (400 mg, 1.14 mmol) in DMF (15.0 mL) were added HATU (651 mg, 1.71 mmol), N-methyl morpholine (0.253 mL, 2.28 mmol) and tert-butyl piperidin-4-ylcarbamate (251 mg, 1.26 mmol). The reaction mixture was stirred at room temperature under inert atmosphere for 16 h, then it was diluted with water (15 mL) and extracted with EtOAc (3×25 mL). The combined organic layer was dried over Na$_2$SO$_4$ and was concentrated under reduced pressure. The crude residue was purified by column chromatography (silica gel, eluent CH$_2$Cl$_2$/MeOH 95:5 to afford tert-butyl 1-(4-(3-(4-chlorophenyl)imidazo[1,2-a]pyridin-6-yl)benzoyl)-4-methylpiperidin-4-ylcarbamate (310 mg, 50%, LC-MS 91%) as an off-white solid. $^1$H NMR (400 MHz, DMSO-d$_6$) δ (ppm): 8.42 (s, 1H), 8.0 (s, 1H), 7.79 (d, J=9.2 Hz, 2H), 7.73 (s, 1H), 7.58-7.45 (m, 7H), 4.60 (bs, 1H), 4.45 (bs, 1H), 3.78 (bs, 2H), 3.18 (bs, 2H), 3.00 (bs, 2H), 2.18-1.89 (m, 2H), 1.44 (s, 9H); MS (ESI) m/z 531 [C$_{30}$H$_{31}$ClN$_4$O$_3$+H]$^+$.

Step 2: To a solution of tert-butyl 1-(4-(3-(4-chlorophenyl)imidazo[1,2-a]pyridin-6-yl)benzoyl)-4-methylpiperidin-4-ylcarbamate (310 g, 0.73 mmol) in DCM (15 mL) was added TFA (3 mL) and the reaction mixture was stirred at rt for 3 h. The reaction mixture was concentrated and poured into ice cold water, extracted with EtOAc (3×50 mL). The organic layer was washed with NaHCO$_3$ solution (2×20 mL), water (2×10 mL) and brine, dried over anhydrous Na$_2$SO$_4$, filtered and concentrated under reduced pressure. The crude compound was purified by preparative HPLC to afford (4-aminopiperidin-1-yl)(4-(3-(4-chlorophenyl)imidazo[1,2-a]pyridin-6-yl)phenyl)methanone (80 mg, 21%, AUC HPLC 97.7%) as a white solid; m.p. 85-89° C. $^1$H NMR (400 MHz, DMSO-d$_6$) δ (ppm): 8.69 (s, 1H), 7.85 (s, 1H), 7.82-7.78 (m, 5H), 7.70-7.61 (m, 3H), 7.46 (d, J=8.0 Hz, 2H), 4.28 (bs, 1H), 3.58 (s, 1H), 3.07 (bs, 1H), 2.94 (bs, 1H), 2.82 (m, 1H), 1.75-1.67 (m, 4H), 1.23 (s, 1H), 1.18 (bs, 1H); MS (ESI) m/z 431.44 [C$_{25}$H$_{23}$ClN$_4$O+H]$^+$.

Example 175: (4-(3-(4-hydroxyphenyl)imidazo[1,2-a]pyridin-6-yl)phenyl)(4-methylpiperazin-1-yl)methanone

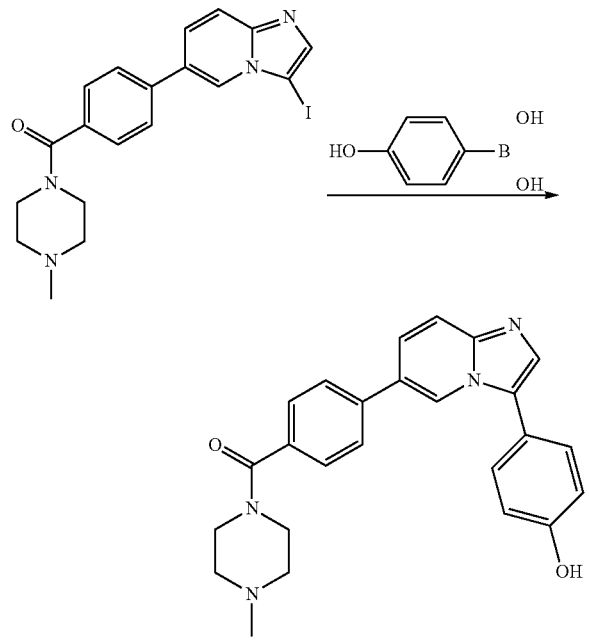

4-hydroxyphenylboronic acid (136 mg, 0.98 mmol), K₃PO₄ (380 mg, 1.79 mmol) and Pd(PPh₃)₄ (51 mg, 0.04 mmol) were added sequentially to a solution of 4-(3-iodoimidazo[1,2-a]pyridin-6-yl)phenyl)(4-methylpiperazin-1-yl)methanone (400 mg, 0.896 mmol) in a mixture of 1,4-dioxane/H₂O (15:1.5 mL) at room temperature under argon atmosphere. The reaction mixture was refluxed for 6 h and was diluted with water (50 mL) and extracted with EtOAc (3×50 mL). The combined organic layer was dried over Na₂SO₄, filtered and concentrated under reduced pressure. The residue was purified by column chromatography (silica gel, eluent CHCl₃/MeOH 95:5) and by preparative HPLC to afford of (4-(3-(4-hydroxyphenyl)imidazo[1,2-a]pyridin-6-yl)phenyl)(4-methylpiperazin-1-yl) (100 mg, 23%, AUC HPLC 98.3%) as an off-white solid; m.p. 151-217° C. $^1$H NMR (400 MHz, DMSO-d₆) δ (ppm): 9.79 (s, 1H), 8.55 (s, 1H), 7.78-7.72 (m, 3H), 7.67-7.46 (m, 6H), 6.94 (d, J=12.0 Hz, 2H), 3.62 (bs, 2H), 3.35 (bs, 2H), 2.31 (m, 4H), 2.20 (s, 3H); MS (ESI) m/z 413 [$C_{25}H_{24}N_4O$+H]$^+$.

Formula 5

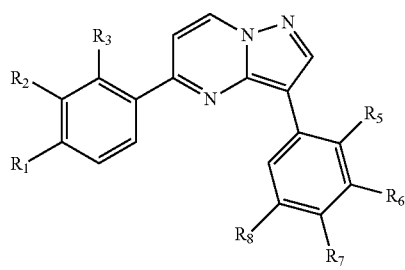

Example 176: 4-(5-(4-(4-methylpiperazine-1-carbonyl)phenyl)pyrazolo[1,5-a]pyrimidin-3-yl)benzonitrile

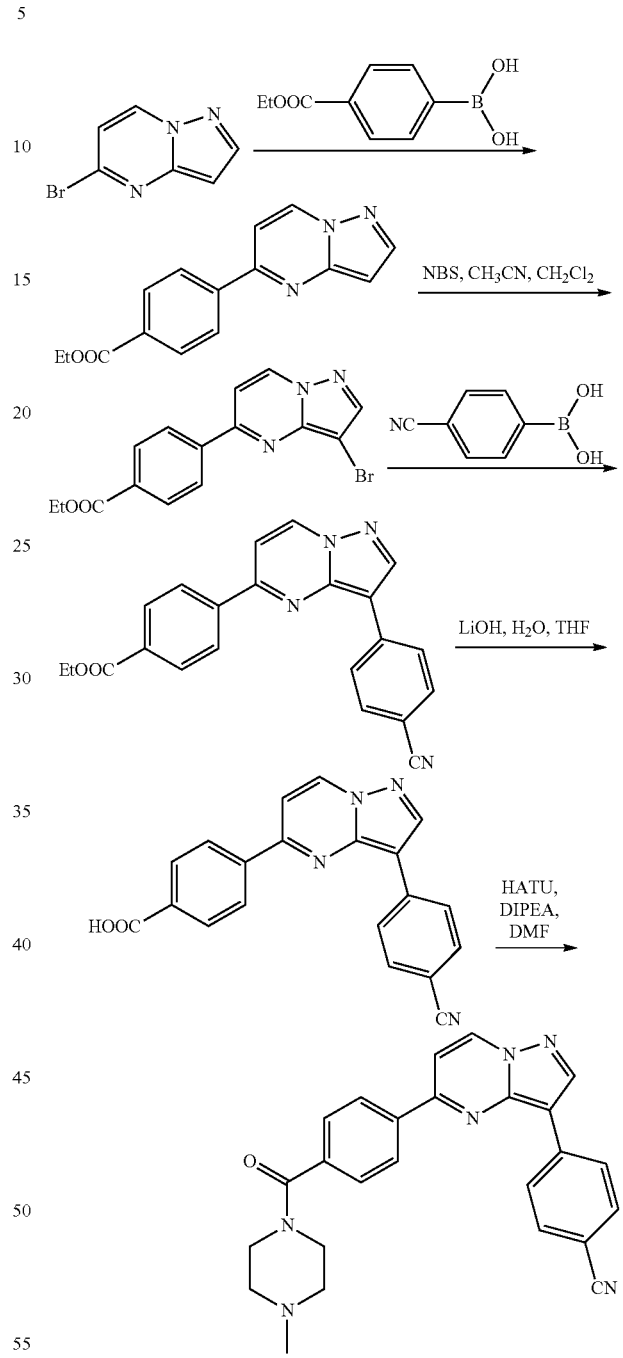

Step 1: To a solution of 5-bromopyrazolo[1,5-a]pyrimidine (300 mg, 1.5 mmol) in 1,4-dioxane (10 mL) and water (2 mL), were sequentially added 4-ethoxycarbonyl phenyl boronic acid (380 mg, 1.95 mmol), K₃PO₄ (955 mg, 4.5 mmol) and Pd(PPh₃)₄ (52 mg, 0.04 mmol). The reaction mixture was heated at 90° C. for 4 h under argon atmosphere then, was diluted with EtOAc and washed with water and brine solution. The organic layer was dried over anhydrous Na₂SO₄, filtered and concentrated under reduced pressure. The crude product was purified by column chromatography (silica gel, eluent petroleum ether/EtOAc 9:1 to 1:1) to afford ethyl 4-(pyrazolo[1,5-a]pyrimidin-5-yl)benzoate (200 mg, 49%) of as a yellow solid. $^1$H NMR (400 MHz, CDCl$_3$) δ (ppm): 8.77 (d, J=8.0, 1H), 8.18-8.15 (m, 4H), 7.33 (d, J=7.5 Hz, 2H), 7.12 (d, J=4.4 Hz, 1H), 6.77 (d, J=2.2 Hz, 1H), 4.45 (q, J=6.8 Hz, 2H), 1.44 (t, J=7.2 Hz, 3H); MS (ESI) m/z 268 $[C_{15}H_{13}N_3O_2+H]^+$.

Step 2: To a solution of ethyl 4-(pyrazolo[1,5-a]pyrimidin-5-yl)benzoate (2.3 g, 9.36 mmol) in DCM (15 mL) and ACN (35 mL) was added NBS (2.02 g, 11.23 mmol) at 0° C. and stirred at same temperature for 1 h. The reaction mixture was filtered and washed with water and dried to afford ethyl 4-(3-bromopyrazolo[1,5-a]pyrimidin-5-yl)benzoate (2.0 g, 67%) as a yellow solid. $^1$H NMR (400 MHz, CDCl$_3$) δ (ppm): 8.77 (d, J=8.0 Hz, 1H), 8.18-8.15 (m, 4H), 8.14 (s, 1H), 7.38 (d, J=4.4 Hz, 1H), 4.40 (q, J=6.8 Hz, 2H), 1.44 (t, J=7.2 Hz, 3H); MS (ESI) m/z 346 $[C_{15}H_{12}BrN_3O_2]^+$.

Step 3: A solution of ethyl 4-(3-bromopyrazolo[1,5-a]pyrimidin-5-yl)benzoate (120 mg, 0.34 mmol), 4-cyanophenylboronic acid (66 mg, 0.44 mmol), K$_3$PO$_4$ (220 mg, 1.03 mmol) in 1,4-dioxane (3 mL) and water (1 mL) was degassed with argon for 30 min prior to the addition of Pd(PPh$_3$)$_4$ (12 mg, 0.01 mmol). The reaction mixture was heated at 90° C. for 3 h under argon then, was diluted with EtOAc and washed with water and brine solution. The organic layer was dried over anhydrous Na$_2$SO$_4$ and concentrated under reduced pressure. The crude product was purified by column chromatography (silica gel, eluent petroleum ether/EtOAc 90/10 to 50/50) to afford of ethyl 4-(3-(4-cyanophenyl)pyrazolo[1,5-a]pyrimidin-5-yl)benzoate (80 mg, 61%) as a yellow solid. $^1$H NMR (400 MHz, CDCl$_3$) δ (ppm): 8.80 (d, J=7.5 Hz, 1H), 8.58 (s, 1H), 8.30-8.20 (m, 6H), 7.79 (d, J=12.0 Hz, 2H), 7.45 (d, J=12.0 Hz, 1H), 4.40 (q, J=6.8 Hz, 2H), 1.44 (t, J=7.2 Hz, 3H); MS (ESI) m/z 369 $[C_{22}H_{16}N_4O_2+H]^+$.

Step 4: To a solution of 4-(3-(4-cyanophenyl)pyrazolo[1,5-a]pyrimidin-5-yl)benzoate (500 mg, 1.35 mmol) in THF (20 mL) was added LiOH (228 mg, 5.43 mmol) in water (4 mL) at rt and stirred for 16 h. TLC indicated absence of SM and formation of a polar spot. The reaction mixture was concentrated under reduced pressure to afford 700 mg of 4-(3-(4-cyanophenyl)pyrazolo[1,5-a]pyrimidin-5-yl)benzoic acid as a yellow solid which was used in the next step without purification. $^1$H NMR (400 MHz, CDCl$_3$) δ (ppm): $^1$H NMR (400 MHz, DMSO-d$_6$) δ (ppm): 12.2 (bs, 1H), 9.35 (d, J=6.8 Hz, 1H), 8.97 (s, 1H), 8.48-8.44 (m, 2H), 8.34 (d, J=8.0 Hz, 2H), 8.14 (d, J=8.4 Hz, 2H), 8.09 (d, J=8.0 Hz, 2H), 7.93 (d, J=8.0 Hz, 1H), 7.86 (d, J=8.0 Hz, 1H); MS (ESI) m/z 340 $[C_{20}H_{12}N_4O_2+H]^+$.

Step 5: To a solution of 4-(3-(4-cyanophenyl)pyrazolo[1,5-a]pyrimidin-5-yl)benzoic acid (460 mg, 1.35 mmol) in DMF (5 mL) was added NMM (348 mg, 2.7 mmol) followed by addition of HATU (775 mg, 2.03 mmol) at rt and stirred for 30 min. 1-Methylpiperazine (270 mg, 2.7 mmol) was added and stirred at rt for 16 h. The reaction mixture was diluted with EtOAc and washed with water and brine. The organic layer was dried over anhydrous Na$_2$SO$_4$ and concentrated under reduced pressure to obtain crude product. The crude product was purified by column chromatography (silica gel, eluent CHCl$_3$/MeOH 90:10) and followed by preparative HPLC to afford 4-(5-(4-(4-methylpiperazine-1-carbonyl)phenyl)pyrazolo[1,5-a]pyrimidin-3-yl)benzonitrile, (50 mg, 9%, AUC HPLC 97.6%) as a yellow solid; m.p. 111-124° C. $^1$H NMR (400 MHz, CDCl$_3$) δ (ppm): 8.78 (d, J=8.0 Hz, 1H), 8.52 (s, 1H), 8.29 (d, J=16.0 Hz, 2H), 8.23 (d, J=16.0 Hz, 2H), 7.75 (d, J=16.0 Hz, 2H), 7.61 (d, J=16.0 Hz, 1H), 7.41 (d, J=12.0 Hz, 1H), 3.84 (bs, 2H), 3.49 (bs, 2H), 2.53 (bs, 2H), 2.39 (bs, 2H), 2.34 (s, 3H); MS (ESI) m/z 423 $[C_{25}H_{22}N_6O+H]^+$.

Example 177: 4-(5-(4-(4-isopropylpiperazine-1-carbonyl)phenyl)pyrazolo[1,5-a]pyrimidin-3-yl)benzonitrile

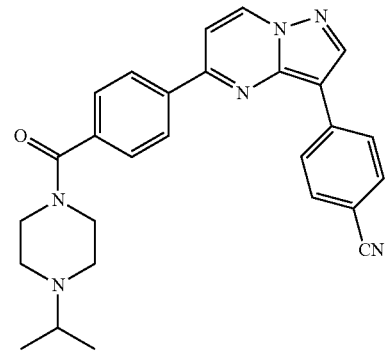 [SMILES: CC(C)N1CCN(C(=O)c2ccc(-c3ccn4ncc(-c5ccc(C#N)cc5)c4n3)cc2)CC1]

To a solution of 4-(3-(4-cyanophenyl)pyrazolo[1,5-a]pyrimidin-5-yl)benzoic (400 mg, 1.17 mmol) in DMF (5 mL) was added NMM (303 mg, 2.3 mmol) followed by HATU (670 mg, 1.76 mmol) at rt and the reaction mixture was stirred for 30 min. 1-isopropylpiperazine (196 mg, 1.52 mmol) was added to the reaction mixture and stirred was continued at rt for 16 h. The reaction mixture was diluted with EtOAc and washed with water and brine solution. The organic layer was dried over anhydrous Na$_2$SO$_4$ and concentrated under reduced pressure to obtain crude product. The crude product was purified by Prep-HPLC to afford 4-(5-(4-(4-methylpiperazine-1-carbonyl)phenyl)pyrazolo[1,5-a]pyrimidin-3-yl)benzonitrile (45 mg, 8%, AUC HPLC>99%) as a yellow solid; m.p. 106-116° C. $^1$H NMR (400 MHz, CDCl$_3$) δ (ppm): 8.77 (d, J=8.0 Hz, 1H), 8.51 (m, 1H), 8.30 (d, J=12 Hz, 2H), 8.22 (d, J=12 Hz, 2H), 7.75 (d, J=8.0 Hz, 2H), 7.61 (d, J=8.0 Hz, 2H), 7.40 (d, J=8.0 Hz, 1H), 3.83 (s, 2H), 3.47 (bs, 2H), 2.75 (m, 1H), 2.63 (bs, 2H), 2.49 (bs, 2H), 1.06 (d, J=8.0 Hz, 6H); MS (ESI) m/z 451 $[C_{27}H_{26}N_6O+H]^+$.

Example 178: 4-(5-(4-(4-ethylpiperazine-1-carbonyl)phenyl)pyrazolo[1,5-a]pyrimidin-3-yl)benzonitrile

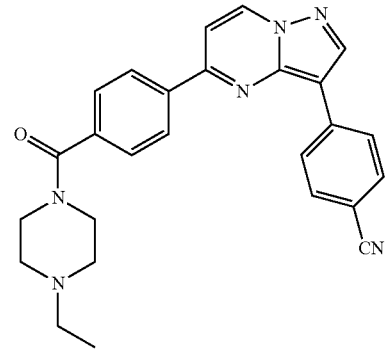 [SMILES: CCN1CCN(C(=O)c2ccc(-c3ccn4ncc(-c5ccc(C#N)cc5)c4n3)cc2)CC1]

To a solution of 4-(3-(4-cyanophenyl)pyrazolo[1,5-a]pyrimidin-5-yl)benzoic acid (400 mg, 1.17 mmol) in DMF (5 mL) was added NMM (303 mg, 2.35 mmol) followed by HATU (670 mg, 1.76 mmol) at rt and the solution was stirred for 30 min. 1-methylpiperazine (270 mg, 2.7 mmol) was added to the reaction mixture and stirring was continued for 16 h. The reaction mixture was diluted with EtOAc and washed with water and brine solution. The organic layer was dried over anhydrous Na$_2$SO$_4$ and concentrated under reduced pressure to obtain crude product. The crude product was purified by preparative HPLC to afford 4-(5-(4-(4-ethylpiperazine-1-carbonyl)phenyl)pyrazolo[1,5-a]pyrimidin-3-yl)benzonitrile (15 mg, AUC HPLC 97.4%) as a yellow solid; m.p. 200-202° C. $^1$H NMR (400 MHz, CDCl$_3$) δ (ppm): 8.77 (d, J=8.0 Hz, 1H), 8.51 (s, 1H), 8.30-8.20 (m, 4H), 7.75 (d, J=12.0 Hz, 2H), 7.61 (d, J=12.0 Hz, 2H), 7.40 (d, J=8.0 Hz, 1H), 3.85 (bs, 2H), 3.50 (bs, 2H), 2.56 (bs, 4H), 2.47 (q, J=8.0 Hz, 2H), 1.11 (t, J=8.0 Hz, 3H); MS (ESI) m/z 437 [C$_{26}$H$_{24}$N$_6$O+H]$^+$.

Example 179: 4-(5-(4-(4-(4-methylpiperazin-1-yl)piperidine-1-carbonyl)phenyl)pyrazolo[1,5-a]pyrimidin-3-yl)benzonitrile

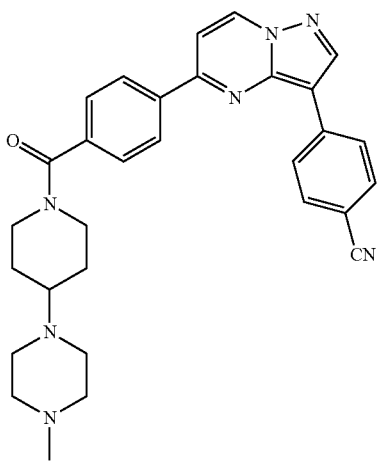 [SMILES: CN1CCN(C2CCN(C(=O)c3ccc(-c4ccn5ncc(-c6ccc(C#N)cc6)c5n4)cc3)CC2)CC1]

To a solution of 4-(3-(4-cyanophenyl)pyrazolo[1,5-a]pyrimidin-5-yl)benzoic acid (200 mg, 0.588 mmol) in DMF (5 mL), was added NMM (117 mg, 1.17 mmol) followed by HATU (667 mg, 0.88 mmol) and the solution was stirred at room temperature for 30 min. 1-methyl-4-(piperidin-4-yl)piperazine (118 mg, 0.646 mmol) was added to the reaction mixture and stirring was maintained for 16 h. The reaction mixture was diluted with EtOAc and washed with water and brine. The organic layer was dried over anhydrous Na$_2$SO$_4$, filtered and concentrated under reduced pressure. The residue was purified by Preparative HPLC (C18, ACN/H$_2$O/0.075% NH$_4$HCO$_3$) to afford 4-(5-(4-(4-(4-methylpiperazin-1-yl)piperidine-1-carbonyl)phenyl)pyrazolo[1,5-a]pyrimidin-3-yl)benzonitrile (30 mg, 10%, AUC HPLC 98.6%) as a yellow solid; $^1$H NMR (400 MHz, CDCl$_3$) δ (ppm): 8.78 (d, J=8.7 Hz, 1H), 8.52 (s, 1H), 8.30 (d, J=8.2 Hz, 2H), 8.23 (d, J=8.2 Hz, 2H), 7.768 (d, J=7.7 Hz, 2H), 7.62 (d, J=7.6 Hz, 2H), 7.41 (d, J=7.4 Hz, 1H), 5.6 (bs, 1H), 3.8 (bs, 1H), 3.19 (bs, 1H), 2.6 (bs, 4H), 2.4 (bs, 4H), 2.3 (bs, 3H), 2.06-1.82 (m, 2H), 1.45 (bs, 3H); MS (ESI) m/z 506 [C$_{30}$H$_{31}$N$_7$O+H]$^+$.

Example 180: 4-(5-(4-(4-(dimethylamino)piperidine-1-carbonyl)phenyl)pyrazolo[1,5-a]pyrimidin-3-yl)benzonitrile

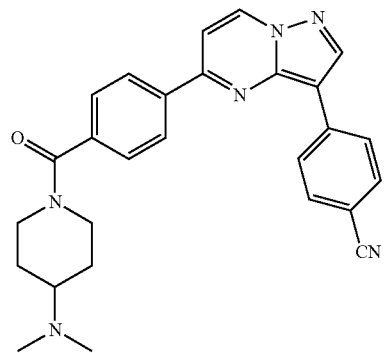 [SMILES: CN(C)C1CCN(C(=O)c2ccc(-c3ccn4ncc(-c5ccc(C#N)cc5)c4n3)cc2)CC1]

To a solution of 4-(3-(4-cyanophenyl)pyrazolo[1,5-a]pyrimidin-5-yl)benzoic acid (200 mg, 0.588 mmol) in DMF (5 mL) was added NMM (117 mg, 1.17 mmol) followed by HATU (667 mg, 0.88 mmol) and the solution was stirred at rt for 30 min. N,N-dimethylpiperidin-4-amine (82 mg, 0.646 mmol) was added to the reaction mixture and stirring was continued for 16 h. The reaction mixture was diluted with EtOAc and washed with water and brine solution. The organic layer was dried over anhydrous Na$_2$SO$_4$ and concentrated under reduced pressure to obtain crude product. The crude product was purified by column chromatography (silica gel, eluent CH$_2$Cl$_2$/MeOH 95:5) followed by preparative HPLC (C18, ACN/H$_2$O/10 mM NH$_4$HCO$_3$) to afford 4-(5-(4-(4-(dimethylamino)piperidine-1-carbonyl)phenyl) pyrazolo[1,5-a]pyrimidin-3-yl)benzonitrile (50 mg, 19%, AUC HPLC 99.8%) as a yellow solid; $^1$H NMR (400 MHz, CDCl$_3$); δ (ppm): 8.78 (d, J=8.7 Hz, 1H), 8.52 (s, 1H), 8.30 (d, J=8.2 Hz, 2H), 8.23 (d, J=8.2 Hz, 2H), 7.76 (d, J=7.7 Hz, 2H), 7.62 (d, J=7.6 Hz, 2H), 7.41 (d, J=7.4 Hz, 1H), 4.9 (bs, 1H), 3.90 (bs, 1H), 3.17 (bs, 1H), 2.91 (bs, 1H), 2.45 (bs, 1H), 2.38 (bs, 6H), 2.08 (bs, 1H), 1.95 (bs, 1H), 1.52 (bs, 2H); MS (ESI) m/z 451 [C$_{27}$H$_{26}$N$_6$O+H]$^+$.

Example 181: 4-(5-(4-(1,4-oxazepane-4-carbonyl)phenyl)pyrazolo[1,5-a]pyrimidin-3-yl)benzonitrile

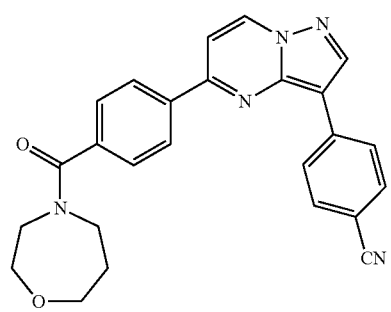 [SMILES: N#Cc1ccc(-c2cnn3ccc(-c4ccc(C(=O)N5CCCOCC5)cc4)nc23)cc1]

To a solution of 4-(3-(4-cyanophenyl)pyrazolo[1,5-a]pyrimidin-5-yl)benzoic acid (200 mg, 0.58 mmol) in DMF (5 mL) was added NMM (117 mg, 1.17 mmol) followed by HATU (667 mg, 0.88 mmol) and the solution was stirred for 30 min. 1,4-oxazepane (65 mg, 0.646 mmol) was added to the reaction mixture and stirring was continued for 16 h.

The reaction mixture was diluted with EtOAc and washed with water and brine solution. The organic layer was dried over anhydrous Na$_2$SO$_4$ and concentrated under reduced pressure to obtain crude product. The crude product was purified by column chromatography (silica gel, eluent CH$_2$Cl$_2$/MeOH 95:5) followed by Preparative HPLC (C18, ACN/H$_2$O/0.075% NH$_4$HCO$_3$) to afford 4-(5-(4-(morpholine-4-carbonyl)phenyl)pyrazolo[1,5-a]pyrimidin-3-yl)benzonitrile (20 mg, 8%, AUC HPLC 99%) as a yellow solid; $^1$H NMR (400 MHz, CDCl$_3$) δ (ppm): 8.78 (d, J=8.7 Hz, 1H), 8.52 (s, 1H), 8.30 (d, J=8.3 Hz, 2H), 8.23 (d, J=8.2 Hz, 2H), 7.768 (d, J=7.7 Hz, 2H), 7.62 (d, J=7.6 Hz, 2H), 7.41 (d, J=7.4 Hz, 1H) 4.09-3.80 (m, 5H), 3.7 (bs, 1H), 3.67 (bs, 2H), 2.1 (bs, 1H); 1.9 (bs, 1H); MS (ESI) m/z 424 [C$_{25}$H$_{21}$N$_5$O$_2$+H]$^+$.

Example 182: N-(1-(4-(3-(4-cyanophenyl)pyrazolo [1,5-a]pyrimidin-5-yl)benzoyl)-4-methylpiperidin-4-yl)acetamide

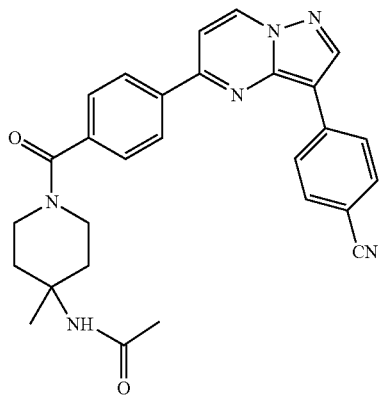 [SMILES: CC(=O)NC1(C)CCN(C(=O)c2ccc(-c3ccn4ncc(-c5ccc(C#N)cc5)c4n3)cc2)CC1]

Step 1: To a solution of 4-(3-(4-cyanophenyl)pyrazolo[1,5-a]pyrimidin-5-yl)benzoic acid (600 mg, 1.76 mmol) in DMF (5 mL) was added NMM (266 mg, 2.64 mmol) followed by HATU (1.0 g, 2.64 mmol) at rt and the solution was stirred for 30 min. tert-butyl 4-methylpiperidin-4-ylcarbamate (414.3 mg, 1.93 mmol) was added to the reaction mixture and stirring was continued for 16 h. The reaction mixture was diluted with EtOAc and washed with water and brine. The organic layer was dried over anhydrous Na$_2$SO$_4$, filtered and concentrated under reduced pressure to obtain crude product to afford tert-butyl 1-(4-(3-(4-cyanophenyl)pyrazolo[1,5-a]pyrimidin-5-yl)benzoyl)-4-methylpiperidin-4-ylcarbamate as a yellow solid (400 mg, 42.5%). $^1$H NMR (400 MHz, DMSO-d$_6$) δ (ppm): 8.77 (d, J=7.5 Hz, 1H), 8.52 (s, 1H), 8.30 (d, J=8.3 Hz, 2H), 8.22 (d, J=7.9 Hz, 2H), 7.75 (d, J=8.4 Hz, 2H), 7.59 (d, J=8.0 Hz, 2H), 7.41 (d, J=8.8 Hz, 1H), 4.39 (bs, 1H), 4.1 (s, 1H), 3.41-3.32 (m, 3H), 2.3 (m, 2H), 1.67-1.44 (m, 2H), 1.44 (s, 3H), 1.25 (s, 9H); MS (ESI) m/z 537 [C$_{31}$H$_{32}$N$_6$O$_3$+H]$^+$.

Step 2: To a solution of tert-butyl 1-(4-(3-(4-cyanophenyl)pyrazolo[1,5-a]pyrimidin-5-yl)benzoyl)-4-methylpiperidin-4-ylcarbamate (400 mg, 0.73 mmol) in dichloromethane (10 mL) was added TFA (3 mL) in dichloromethane (5 mL). The reaction mixture was stirred for 4 h at rt. The reaction mixture was diluted with water (100 mL), NaHCO$_3$ (100 mL) and extracted with CH$_2$Cl$_2$ (2×50 mL). The combined organic layer was concentrated to dryness under reduced pressure to afford 4-(5-(4-(4-amino-4-methylpiperidine-1-carbonyl)phenyl)pyrazolo[1,5-a]pyrimidin-3-yl)benzonitrile as a crude product (300 mg, 93%) as a yellow solid; $^1$H NMR (400 MHz, DMSO-d$_6$) δ (ppm): 9.33 (d, J=7.2 Hz, 1H), 8.96 (s, 1H), 8.46 (d, J=8.4 Hz, 2H), 8.41 (d, J=8.4 Hz, 2H), 7.93 (d, J=8.0 Hz, 2H), 7.84 (d, J=7.2 Hz, 2H), 7.60 (d, J=8.4 Hz, 1H), 5.20 (bs, 2H), 3.44-3.35 (m, 4H), 1.90-1.60 (m, 4H), 1.38 (s, 3H); MS (ESI) m/z 437 [C$_{26}$H$_{24}$N$_6$O+H]$^+$; MS (ESI) m/z 437 [C$_{26}$H$_{24}$N$_6$O+H]$^+$.

Step 3: To a solution of 4-(5-(4-(4-amino-4-methylpiperidine-1-carbonyl)phenyl)pyrazolo[1,5-a]pyrimidin-3-yl)benzonitrile 7 (300 mg, 0.73 mmol) in dichloromethane (10 mL) were added TEA (3 mL) and acetyl chloride in dichloromethane (63 mg, 0.825 mmol). The reaction mixture was stirred for 2 h at rt. The reaction mixture was diluted with water (100 mL), NaHCO$_3$ (100 mL) and extracted with CH$_2$Cl$_2$ (2×50 mL). The combined organic layer was concentrated to dryness under reduced pressure to afford crude compound. The crude residue was purified by preparative HPLC (C18, ACN/H$_2$O/10 mM NH$_4$HCO$_3$) to afford N-(1-(4-(3-(4-cyanophenyl)pyrazolo[1,5-a]pyrimidin-5-yl)benzoyl)-4-methylpiperidin-4-yl)acetamide (180 mg, 56%, AUC HPLC 99.48%) as a yellow solid; $^1$H NMR (400 MHz, CDCl$_3$) δ (ppm): 8.78 (d, J=7.6 Hz, 1H), 8.52 (s, 1H), 8.30 (d, J=8.4 Hz, 2H), 8.23 (d, J=8.4 Hz, 2H), 7.76 (d, J=8.4 Hz, 2H), 7.62 (d, J=8.0 Hz, 2H), 7.41 (d, J=7.6 Hz, 1H), 5.19 (s, 1H), 4.1 (bs, 1H), 3.54-3.25 (m, 3H), 2.3-2.10 (m, 2H), 2.0 (s, 3H), 1.6-1.70 (m, 2H), 1.42 (s, 3H); MS (ESI) m/z 479.35 [C$_{28}$H$_{26}$N$_6$O$_2$+H]; MS (ESI) m/z 479 [C$_{28}$H$_{26}$N$_6$O$_2$+H]$^+$.

Example 183: 4-(5-(4-(piperazine-1-carbonyl)phenyl)pyrazolo[1,5-a]pyrimidin-3-yl)benzonitrile

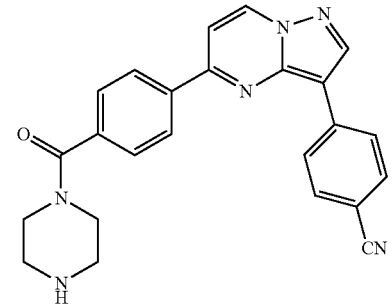 [SMILES: N#Cc1ccc(-c2cnn3ccc(-c4ccc(C(=O)N5CCNCC5)cc4)nc23)cc1]

Step 1: To a solution of 4-(3-(4-cyanophenyl)pyrazolo[1,5-a]pyrimidin-5-yl)benzoic acid (400 mg, 1.17 mmol) in DMF (5 mL) was added NMM (234 mg, 2.35 mmol) followed by HATU (667 mg, 1.76 mmol) at rt and the solution was stirred for 30 min. tert-butyl piperazine-1-carboxylate (239 mg, 1.28 mmol) was added to the reaction mixture and stirring was continued for 16 h. The reaction mixture was diluted with EtOAc and washed with water and brine solution. The organic layer was dried over anhydrous Na$_2$SO$_4$ and concentrated under reduced pressure to obtain crude product to afford tert-butyl 4-(4-(3-(4-cyanophenyl)pyrazolo[1,5-a]pyrimidin-5-yl)benzoyl)piperazine-1-carboxylate (250 mg, 42%); $^1$H NMR (400 MHz, CDCl$_3$) δ (ppm): 8.78 (d, J=7.6 Hz, 1H), 8.52 (s, 1H), 8.30 (d, J=8.0 Hz, 2H), 8.23 (d, J=8.4 Hz, 2H), 7.75 (d, J=8.4 Hz, 2H), 7.62 (d, J=8.0 Hz, 2H), 7.41 (d, J=7.6 Hz, 1H) 3.90-3.40 (m, 8H), 1.48 (s, 9H); MS (ESI) m/z 509 [C$_{29}$H$_{28}$N$_6$O$_3$+H]$^+$; MS (ESI) m/z 509 [C$_{29}$H$_{28}$N$_6$O$_3$+H]$^+$.

Step 2: To a solution of tert-butyl 4-(4-(3-(4-cyanophenyl)pyrazolo[1,5-a]pyrimidin-5-yl)benzoyl)piperazine-1-carboxylate (250 mg, 0.492 mmol) in dichloromethane (10 mL)

were added TFA (3 mL) in dichloromethane (5 mL). The reaction mixture was stirred for 4 h at rt. The reaction mixture was diluted with water (100 mL), NaHCO₃ (100 mL) and extracted with CH₂Cl2 (2×50 mL). The combined organic layer was concentrated to dryness under reduced pressure to afford crude compound. The crude product was purified by preparative HPLC (C18, ACN/H₂O/10 mM NH₄HCO₃) to afford 4-(5-(4-(piperazine-1-carbonyl)phenyl)pyrazolo[1,5-a]pyrimidin-3-yl)benzonitrile (120 mg, 38%, AUC HPLC 97.14%) as a yellow solid; 8.78 (d, J=7.6 Hz, 1H), 8.52 (s, 1H), 8.30 (d, J=8.4 Hz, 2H), 8.23 (d, J=8.4 Hz, 2H), 7.76 (d, J=8.4 Hz, 2H), 7.6 (d, J=8.0 Hz, 2H), 7.42 (d, J=7.6 Hz, 1H), 3.8 (bs, 2H), 3.43 (bs, 2H), 3.00-2.80 (m, 4H); MS (ESI) m/z 409 [C₂₄H₂₀N₆O+H]⁺.

Example 184: 4-(5-(4-(4-methylpiperazine-1-carbonyl)phenyl)pyrazolo[1,5-a]pyrimidin-3-yl)benzonitrile

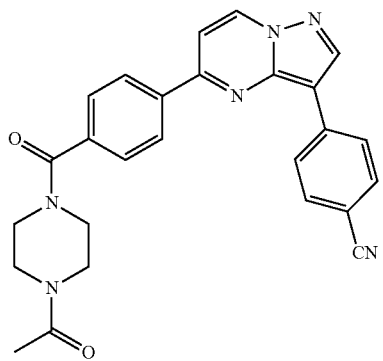 [SMILES: CC(=O)N1CCN(C(=O)c2ccc(-c3ccn4ncc(-c5ccc(C#N)cc5)c4n3)cc2)CC1]

To a solution of 4-(3-(4-cyanophenyl)pyrazolo[1,5-a]pyrimidin-5-yl)benzoic acid 6 (400 mg, 1.17 mmol) in DMF (5 mL) was added NMM (234 mg, 2.35 mmol) followed by HATU (667 mg, 1.76 mmol) at rt and the solution was stirred for 30 min. 1-(piperazin-1-yl)ethanone (164.7 mg, 1.28 mmol) was added to the reaction mixture and stirring was continued for 16 h. The reaction mixture was diluted with EtOAc and washed with water and brine solution. The organic layer was dried over anhydrous Na₂SO₄ and concentrated under reduced pressure to obtain crude product. The crude residue was purified by column chromatography (silica gel, eluent CH₂Cl₂/MeOH 95:5) to afford 4-(5-(4-(4-acetylpiperazine-1-carbonyl)phenyl)pyrazolo[1,5-a]pyrimidin-3-yl)benzonitrile (220 mg, 42%, AUC HPLC 98.4%) as a yellow solid; ¹H NMR (400 MHz, CDCl₃) δ (ppm): 8.78 (d, J=8.7 Hz, 1H), 8.52 (s, 1H), 8.30 (d, J=8.2 Hz, 2H), 8.23 (d, J=8.2 Hz, 2H), 7.76 (d, J=7.7 Hz, 2H), 7.62 (d, J=7.6 Hz, 2H), 7.41 (d, J=7.4 Hz, 1H) 3.9-3.4 (m, 8H), 2.16 (bs, 3H); MS (ESI) m/z 451.1 [C₂₆H₂₂N₆O₂+H]⁺.

Example 185: 4-(5-(4-(morpholine-4-carbonyl)phenyl)pyrazolo[1,5-a]pyrimidin-3-yl)benzonitrile

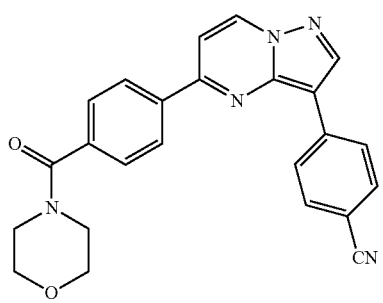 [SMILES: N#Cc1ccc(-c2cnn3ccc(-c4ccc(C(=O)N5CCOCC5)cc4)nc23)cc1]

To a solution of 4-(3-(4-cyanophenyl)pyrazolo[1,5-a]pyrimidin-5-yl)benzoic acid (200 mg, 0.58 mmol) in DMF (5 mL) was added NMM (117 mg, 1.17 mmol) followed by HATU (667 mg, 0.88 mmol) at rt and the solution was stirred for 30 min. Morpholine (56 mg, 0.646 mmol) was added to the reaction mixture and stirring was continued for 16 h. The reaction mixture was diluted with EtOAc and washed with water and brine. The organic layer was dried over anhydrous Na₂SO₄ and concentrated under reduced pressure to obtain crude product. The crude product was purified by column chromatography (silica gel, eluent CH₂Cl₂/MeOH 95:5) to afford 4-(5-(4-(morpholine-4-carbonyl)phenyl)pyrazolo[1,5-a]pyrimidin-3-yl)benzonitrile (120 mg, 75%, AUC HPLC 97.6%) as a yellow solid; ¹H NMR (400 MHz, CDCl₃) δ (ppm): 8.78 (d, J=8.7 Hz, 1H), 8.52 (s, 1H), 8.30 (d, J=8.2 Hz, 2H), 8.23 (d, J=8.2 Hz, 2H), 7.76 (d, J=7.7 Hz, 2H), 7.62 (d, J=7.6 Hz, 2H), 7.41 (d, J=7.4 Hz, 1H) 3.9-3.4 (m, 8H); MS (ESI) m/z 410 [C₂₄H₁₉N₅O₂+H]⁺.

Example 186: N-(1-(4-(3-(4-cyanophenyl)pyrazolo[1,5-a]pyrimidin-5-yl)benzoyl)piperidin-4-yl)acetamide

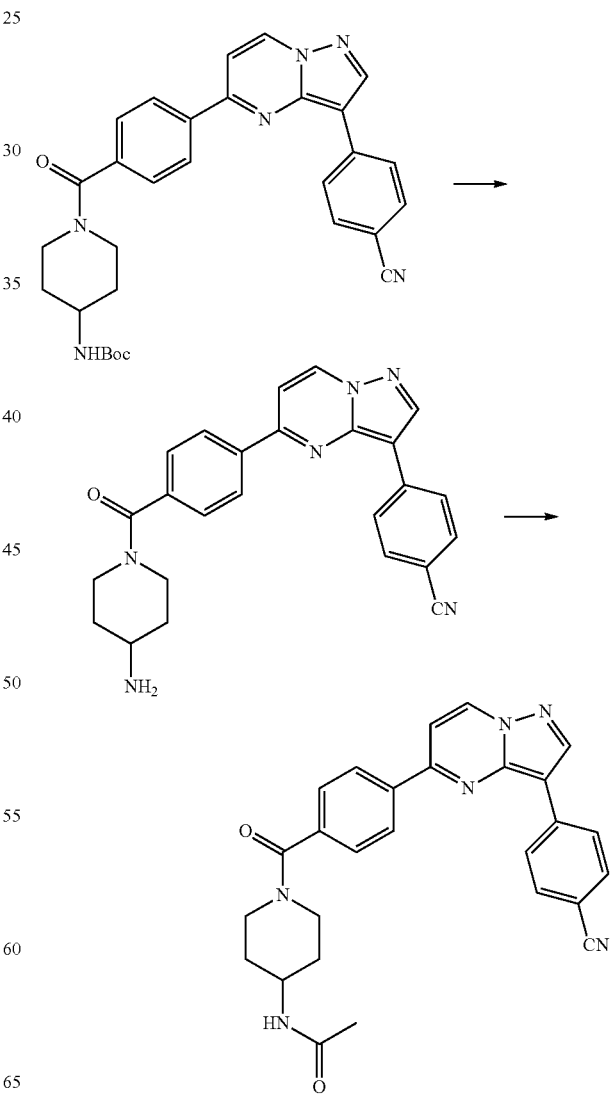

Step 1: To a solution of tert-butyl 1-(4-(3-(4-cyanophenyl)pyrazolo[1,5-a]pyrimidin-5-yl)benzoyl)piperidin-4-ylcarbamate (450 mg, 0.865 mmol) in DCM (10 mL) was added HCl in 1,4 dioxane (7 mL) at 0° C. and stirred at 0° C. to rt for 4 h. The reaction mixture was basified with an aqueous solution of NaHCO$_3$ and then extracted with DCM (60 mL). The organic layer was dried over anhydrous Na$_2$SO$_4$ and concentrated under reduced pressure to afford of 4-(5-(4-(4-aminopiperidine-1-carbonyl)phenyl)pyrazolo[1,5-a]pyrimidin-3-yl)benzonitrile (300 mg, 80%, LC-MS 91%) as a yellow solid which was used in the next step without purification.

Step 2: To a solution of 4-(5-(4-(4-aminopiperidine-1-carbonyl)phenyl)pyrazolo[1,5-a]pyrimidin-3-yl)benzonitrile (300 mg, 0.71 mmol) in DCM (5 mL) were added TEA (0.25 mL, 2.13 mmol) and acetyl chloride (0.07 g, 0.855 mmol). The reaction mixture was stirred at 0° C. to room temperature under inert atmosphere for 1 h, and was diluted with ice-cold water (10 mL) and extracted with DCM (25 mL). The organic layer was dried over Na$_2$SO$_4$ and was concentrated under reduced pressure. The crude product was purified by column chromatography (silica gel, eluent MeOH/DCM 5:95) to afford N-(1-(4-(3-(4-cyanophenyl)pyrazolo[1,5-a]pyrimidin-5-yl)benzoyl)piperidin-4-yl)acetamide (61 mg, 18%, AUC HPLC 96.26%) as a yellow solid; mp. 295-297° C.; $^1$H NMR (400 MHz, CDCl$_3$) δ (ppm): 8.77 (d, J=7.6 Hz, 1H), 8.52 (s, 1H), 8.29 (d, J=8.0 Hz, 2H), 8.22 (d, J=8.4 Hz, 2H), 7.75 (d, J=8.4 Hz, 2H), 7.60 (d, J=8.4 Hz, 2H), 7.40 (d, J=7.2 Hz, 1H), 5.37 (d, J=8.0 Hz, 1H), 4.71 (bs, 1H), 4.09-4.06 (m, 1H), 3.78 (bs, 1H), 3.19 (bs, 1H), 2.98 (bs, 1H), 2.10 (bs, 2H), 2.00 (s, 3H), 1.37 (bs, 2H); MS (ESI) m/z 465 [C$_{27}$H$_{24}$N$_6$O$_2$+H]$^+$.

Example 187: 4-(5-(3-hydroxy-4-(morpholine-4-carbonyl)phenyl)pyrazolo[1,5-a]pyrimidin-3-yl)benzonitrile

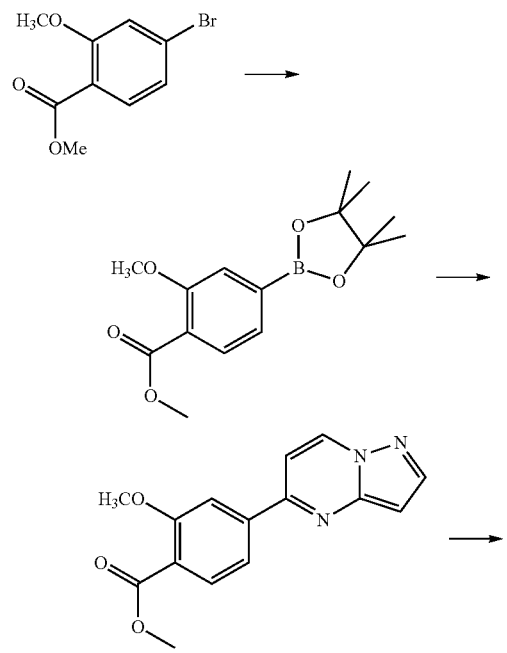

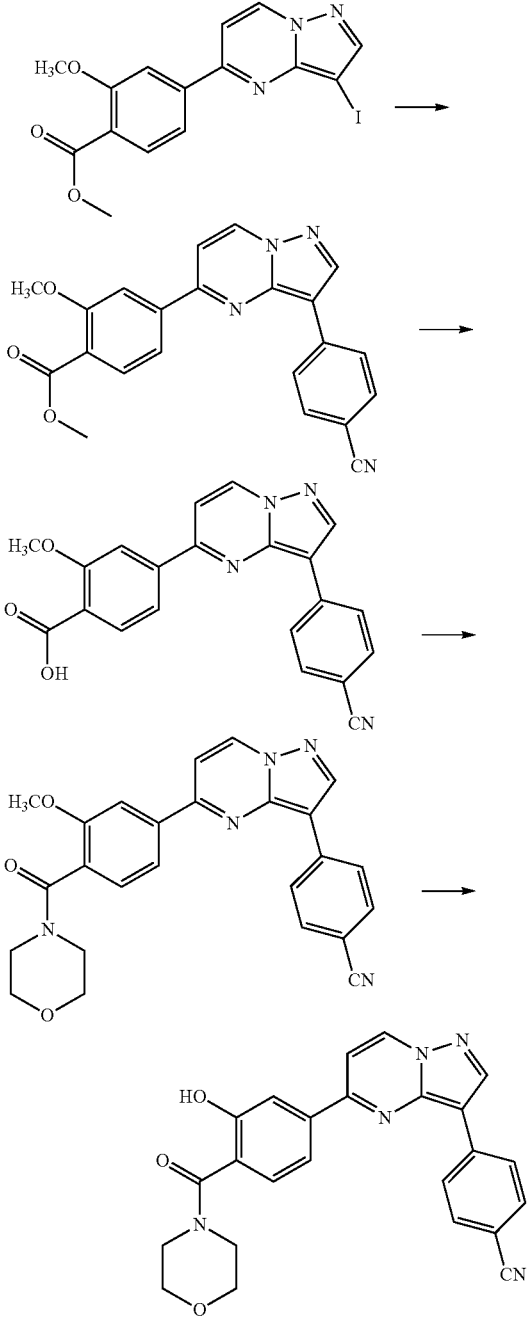

Step 1: To a mixture of methyl-4-bromo-2-methoxybenzoate (3 g, 12.24 mmol), bis(pinacolato)diboron (3.42 g, 13.46 mmol), KOAc (3.59 g, 36.72 mmol) in 1,4-dioxane (15 mL) was added PdCl$_2$(PPh$_3$)$_2$ (300 mg), and the reaction mixture was heated at 90° C. for 16 h under argon. The reaction mixture was used in next step without isolation.

Step 2: To a mixture methyl 2-methoxy-4-(4,4,5,5-tetramethyl-1,3,2-dioxaborolan-2-yl)benzoate (3.2 g, 11.04 mmol), 5-chloropyrazolo[1,5-a]pyrimidine (1.3 g, 8.49 mmol), K$_3$PO$_4$ (3.6 g, 16.99 mmol) in 1,4-dioxane (20 mL) and water (2 mL) was added Pd(PPh$_3$)$_4$ (150 mg) and the reaction mixture was heated at 90° C. for 16 h under argon. The reaction mixture was diluted with EtOAc and washed with water and brine solution. The organic layer was dried over anhydrous Na$_2$SO$_4$ and concentrated under reduced pressure to obtain Preparation of methyl 2-methoxy-4-(pyrazolo[1,5-a]pyrimidin-5-yl)benzoate (850 mg, LC-MS 83%) as a crude product which was used in the next step without purification.

Step 3: To a solution of methyl 2-methoxy-4-(pyrazolo[1,5-a]pyrimidin-5-yl)benzoate (850 mg, 3.00 mmol) in ACN (30 mL) was added N-iodosuccinimide (810 mg, 3.60 mmol) at rt and stirred for 2 h. Water was added to the reaction mixture and the resulting solid was filtered and washed with water to afford methyl 4-((4-iodo-1-methyl-1H-pyrazol-5-ylimino)methyl)-2-methoxybenzoate (1.1 g, 90%, LC-MS 70%).

Step 4: To a mixture of (E)-methyl 4-((4-iodo-1-methyl-1H-pyrazol-5-ylimino)methyl)-2-methoxybenzoate (1.1 g, 2.68 mmol), 4-cyanophenylboronic acid (0.51 g, 3.49 mmol), $K_3PO_4$ (1.14 g, 5.37 mmol) in 1,4-dioxane (20 mL) and water (3 mL) was added $Pd(PPh_3)_4$ (150 mg) and the reaction mixture was heated at 90° C. for 16 h under argon. The reaction mixture was diluted with EtOAc and washed with water and brine solution. The organic layer was dried over anhydrous $Na_2SO_4$ and concentrated under reduced pressure to obtain the crude product. The crude product was purified by column chromatography (silica gel, eluent $CHCl_3$/MeOH 95:5) to afford methyl 4-(3-(4-cyanophenyl)pyrazolo[1,5-a]pyrimidin-5-yl)-2-methoxybenzoate (1 g, 90%, LC-MS 44%) as a yellow solid.

Step 5: To a solution of ethyl 4-(3-(4-cyanophenyl)imidazo[1,2-a]pyridin-6-yl)benzoate (2.7 g, 7.18 mmol) in THF (40 mL) was added LiOH (0.9 g, 21.54 mmol) in water (10 mL) and MeOH (10 ml) at rt and the reaction mixture was stirred for 5 h. The reaction mixture was concentrated under reduced pressure to give crude compound which was washed with EtOAc and water was added to the reaction mixture then diluted with EtOAc. The aqueous layer was acidified with sat. $KHSO_4$ solution then solid thus formed was filtered and dried to afford 4-(3-(4-cyanophenyl)pyrazolo[1,5-a]pyrimidin-5-yl)-2-methoxybenzoic acid (600 mg, 64%, LC-MS 51%) which was used in the next step without purification.

Step 6: To a solution of 4-(3-(4-cyanophenyl)pyrazolo[1,5-a]pyrimidin-5-yl)-2-methoxybenzoic acid (300 mg, 0.81 mmol) in DMF (6 mL) was added NMM (0.163 g, 1.62 mmol) followed by HATU (0.42 g, 1.21 mmol) at rt and stirred for 30 min. Morpholine (84 mg, 0.97 mmol) was added and stirring was continued at rt for 16 h. The reaction mixture was diluted with EtOAc and washed with water and brine solution. The organic layer was dried over anhydrous $Na_2SO_4$ and concentrated under reduced pressure to obtain crude product which was purified by column chromatography (silica gel, eluent MeOH/DCM 10:90) to afford 4-(5-(3-methoxy-4-(morpholine-4-carbonyl)phenyl)pyrazolo[1,5-a]pyrimidin-3-yl)benzonitrile (300 mg, 84%, LC-MS 27%) as a yellow solid.

Step 7: To a solution of 4-(5-(3-methoxy-4-(morpholine-4-carbonyl)phenyl)pyrazolo[1,5-a]pyrimidin-3-yl)benzonitrile (300 mg) in DCM was added $BBr_3$ (3 mL) at 0° C. and stirred for 2 h at rt. The reaction mixture was basified with aq $NaHSO_4$ and extracted with DCM. The organic layer was dried over anhydrous $Na_2SO_4$ and concentrated under reduced pressure to obtain crude product which purified by column chromatography (silica gel, eluent MeOH-DCM 10:90) followed by preparative HPLC to afford 4-(5-(3-hydroxy-4-(morpholine-4-carbonyl)phenyl)pyrazolo[1,5-a]pyrimidin-3-yl)benzonitrile (25 mg, 8%, AUC HPLC 98.06%)) as a yellow solid; mp. 290-295° C.; $^1$H NMR (400 MHz, $CDCl_3$) δ (ppm): 9.81 (s, 1H), 8.77 (d, J=7.2 Hz, 1H), 8.52 (s, 1H), 8.29 (d, J=8.0 Hz, 2H), 7.78-7.72 (m, 4H), 7.44 (d, J=7.6 Hz, 1H), 7.38 (d, J=7.6 Hz, 1H), 3.81-3.79 (m, 8H); MS (ESI) m/z 426 $[C_{24}H_{19}N_5O_3+H]^+$.

Example 188: N-(5-(3-(4-cyanophenyl)pyrazolo[1,5-a]pyrimidin-5-yl)-2-(morpholine-4-carbonyl)phenyl)acetamide

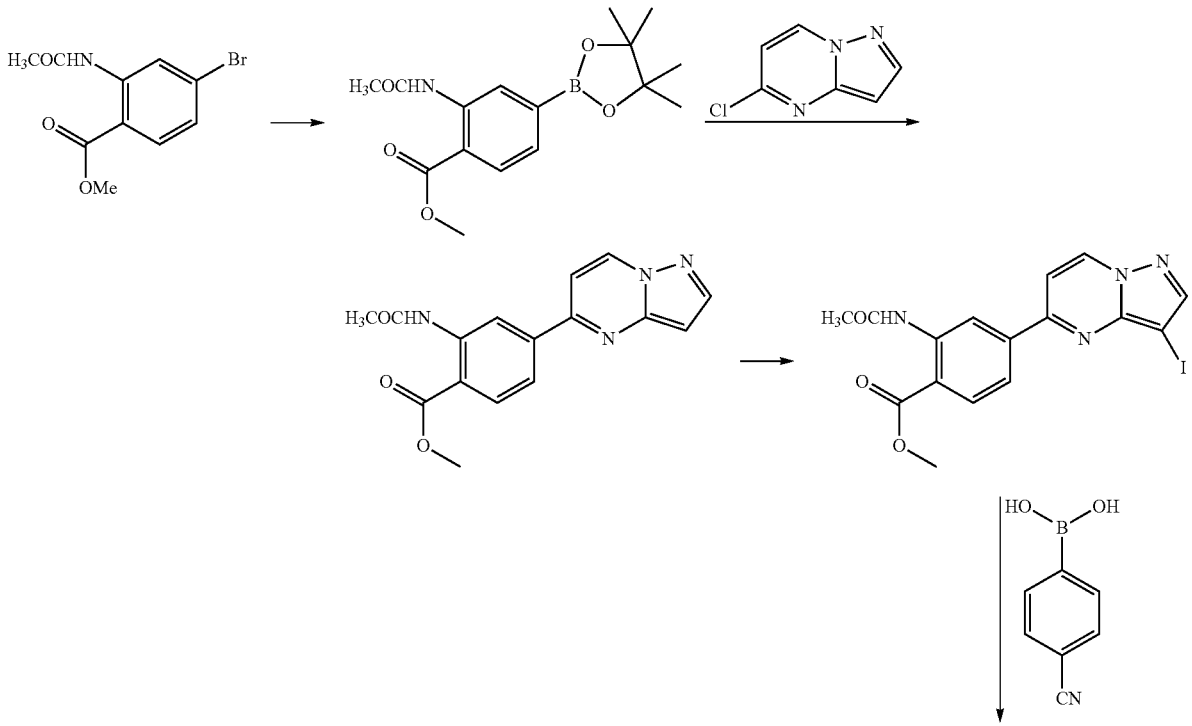

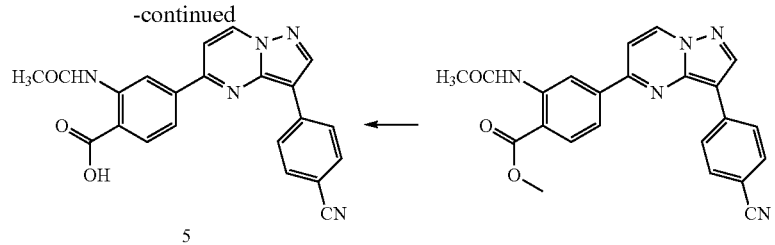

Step 1: To a solution of methyl-2-acetamido-4-bromobenzoate (2 g, 7.38 mmol), bis(pinacolato)diboron (2.06 g, 8.11 mmol), KOAc (2.16 g, 22.14 mmol) in 1,4-dioxane (15 mL) was added Pd$_2$(dba)$_3$ (200 mg) and P(Cy)$_3$ (200 mg) and the reaction mixture was heated at 90° C. for 16 h. The reaction mixture was used in next step without isolation.

Step 2: To a mixture of methyl 2-acetamido-4-(4,4,5,5-tetramethyl-1,3,2-dioxaborolan-2-yl)benzoate (2.3 g, 7.18 mmol), 5-chloropyrazolo[1,5-a]pyrimidine (1 g, 6.53 mmol), K$_3$PO$_4$ (2.77 g, 13.07 mmol) in 1,4-dioxane (20 mL) and water (2 mL) was added Pd(PPh$_3$)$_4$ (150 mg) and the reaction mixture was heated at 90° C. for 16 h. The reaction mixture was diluted with EtOAc and washed with water and brine solution. The organic layer was dried over anhydrous Na$_2$SO$_4$ and concentrated under reduced pressure to obtain the crude product. The crude product was purified by column chromatography (silica gel, eluent EtOAc/petroleum ether 50:50) to afford methyl 2-acetamido-4-(pyrazolo[1,5-a]pyrimidin-5-yl)benzoate (600 mg, 30%, LC-MS 98%) as a pale yellow solid. $^1$H NMR (400 MHz, CDCl$_3$) δ 11.14 (s, 1H), 9.43 (s, 1H), 8.74 (d, J=7.6 Hz, 1H), 8.17 (d, J=8.1 Hz, 1H), 7.94 (d, J=1.6 Hz, 1H), 7.93-7.92 (m, 1H), 7.38 (d, J=7.6 Hz, 1H), 6.76 (s, 1H), 3.97 (s, 3H), 2.29 (s, 3H); MS (ESI) m/z 311 [M+H]$^+$.

Step 3: To a solution of methyl 2-acetamido-4-(pyrazolo[1,5-a]pyrimidin-5-yl)benzoate (600 mg, 1.93 mmol) in ACN (30 mL) was added N-iodosuccinimide (522 mg, 2.32 mmol) at rt and stirred for 2 h. Water was added to the reaction mixture and the resulting solid was filtered and washed with water to afford methyl 2-acetamido-4-(3-iodopyrazolo[1,5-a]pyrimidin-5-yl)benzoate (0.7 g, 83%, LC-MS 87%) as a light brown solid. $^1$H NMR (400 MHz, CDCl$_3$) δ 11.15 (s, 1H), 9.46 (s, 1H), 8.70 (d, J=7.6 Hz, 1H), 8.18 (d, J=8.8 Hz, 2H), 8.09 (d, J=8.4 Hz, 1H), 7.43 (d, J=7.6 Hz, 1H), 3.98 (s, 3H), 2.29 (s, 3H); MS (ESI) m/z 437 [C$_{16}$H$_{13}$IN$_4$O$_3$+H]$^+$.

Step 4: To a mixture of methyl 2-acetamido-4-(3-iodopyrazolo[1,5-a]pyrimidin-5-yl)benzoate (0.7 g, 1.60 mmol), 4-cyanophenylboronic acid (0.3 g, 2.08 mmol), K$_3$PO$_4$ (0.68 g, 3.21 mmol) in 1,4-dioxane (20 mL), and water (3 mL) was added Pd(PPh$_3$)$_4$ (100 mg) and the reaction mixture was heated at 90° C. for 16 h. The reaction mixture was diluted with EtOAc and washed with water and brine solution. The organic layer was dried over anhydrous Na$_2$SO$_4$ and concentrated under reduced pressure to obtain the crude product. The crude product was purified by column chromatography (silica gel, eluent CHCl$_3$/MeOH 95:5) to afford methyl 2-acetamido-4-((E)-1-(4-cyanostyrylimino)allyl)benzoate (550 mg, 85%, LC-MS 30%) as a yellow solid. The intermediate was used in the next step without purification.

Step 5: To a solution of methyl 2-acetamido-4-((E)-1-(4-cyanostyrylimino)allyl)benzoate (0.55 g, 1.33 mmol) in THF (6 mL) was added LiOH (0.11 g, 2.67 mmol) in water (2 mL) and MeOH (4 mL) at rt and stirred for 5 h. The reaction mixture was concentrated under reduced pressure to 2-acetamido-4-(3-(4-cyanophenyl)pyrazolo[1,5-a]pyrimidin-5-yl)benzoicacid (350 mg, lithium salt, LC-MS 30%) as a yellow solid which was used in the next step without purification.

Step 6: To a solution of 2-acetamido-4-(3-(4-cyanophenyl)pyrazolo[1,5-a]pyrimidin-5-yl)benzoic acid 5 (350 mg, 0.88 mmol) in DMF (6 mL) was added NMM (0.17 g, 1.76 mmol) followed by HATU (0.44 g, 1.16 mmol) at rt and stirred for 30 min. Morpholine (92 mg, 1.05 mmol) was added and stirred at rt for 16 h. The reaction mixture was diluted with EtOAc and washed with water and brine solution. The organic layer was dried over anhydrous Na$_2$SO$_4$ and concentrated under reduced pressure to obtain crude compound which was purified by column chromatography (silica gel, eluent MeOH/DCM 10:90) followed by preparative HPLC to afford N-(5-(3-(4-cyanophenyl)pyrazolo[1,5-a]pyrimidin-5-yl)-2-(morpholine-4-carbonyl)phenyl)acetamide (28 mg, 7%, AUC HPLC 95.24%) as a yellow solid. m.p 151-155° C. $^1$H NMR (400 MHz, CDCl$_3$) δ 9.16 (s, 1H), 9.10 (s, 1H), 8.76 (d, J=7.6 Hz, 1H), 8.52 (s, 1H), 8.31 (d, J=8.0 Hz, 1H), 8.04 (d, J=1.2 Hz, 1H), 7.76 (d, J=8.4 Hz, 2H), 7.46-7.41 (m, 2H), 3.76 (bs, 8H), 2.25 (s, 2H); MS (ESI) m/z 465 [M−1].

Formula 6

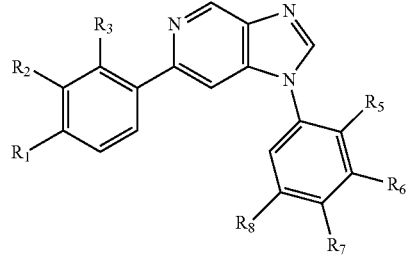

Example 189: 4-(6-(4-(4-methylpiperazine-1-carbonyl)phenyl)-1H-imidazo[4,5-c]pyridin-1-yl)benzonitrile

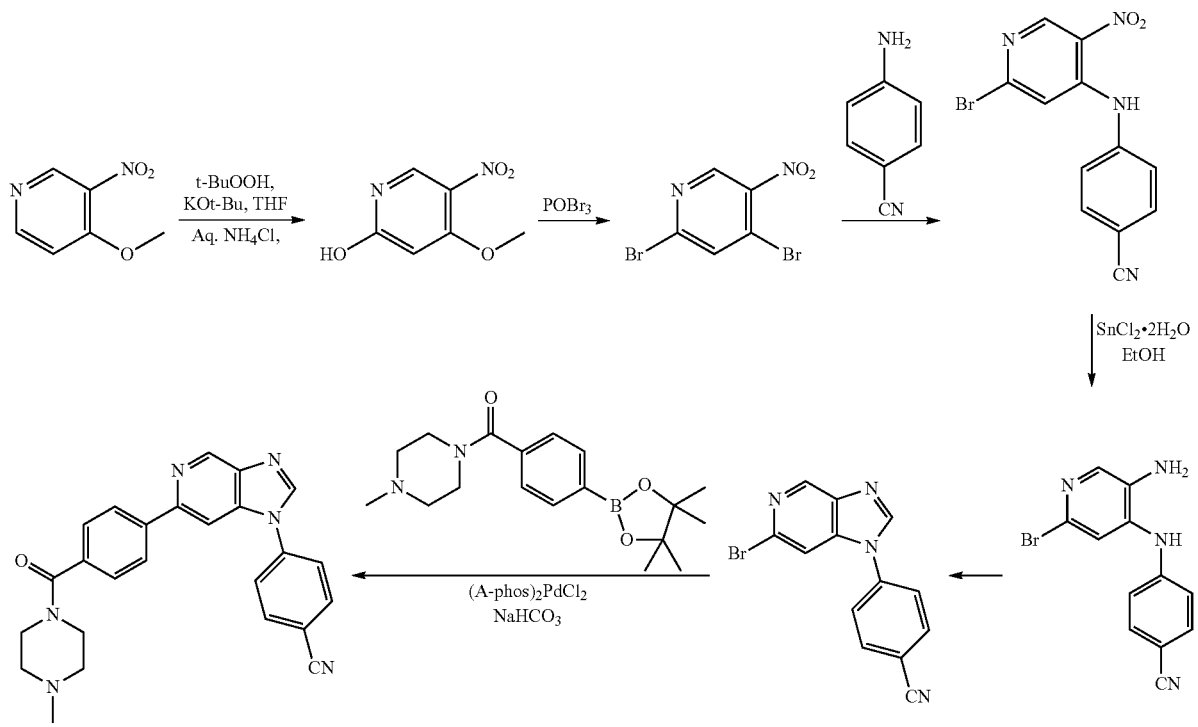

Step: 1 To a solution of anhydrous NH₃ (150 mL) in THF (50 mL) at −78° C. was Potassium t-butoxide (19.1 g, 170 mmol) and the reaction mixture was allowed to warm to −35° C. A solution of 4-Methoxy-3-nitropyridine (10.5 g, 68.2 mmol) in 100 mL of THF was cooled to 0° C. and 15 mL of t-BuOOH (5 M in decane, 75 mmol) was added slowly over 5 min. The resulting solution was then added dropwise to the t-BuOK solution prepared above over 1 h, then stirred for 2 h at −35° C. and then carefully quenched with 50 mL of sat. aqueous solution of NH₄Cl. The reaction mixture was allowed to vent and warm to rt overnight, then the organics were concentrated and the residue was acidified with NH₄Cl solution and filtered. The resulting solid was washed with cold water and dried under vacuum to give the title compound as a brown solid (10.6 g, 91%). $^1$H NMR (400 MHz, CDCl₃) δ 8.48 (s, 1H), 5.58 (s, 1H), 3.84 (s, 3H); MS (ESI) m/z 171 [M+H]⁺.

Step 2: Phosphorous oxybromide (5.73 g, 20 mmol) was added to a suspension of 4-methoxy-5-nitro-1H-pyridin-2-one (1.70 g, 10 mmol) in acetonitrile (20 mL) at rt and heated at reflux for 3 h. The reaction mixture was cooled and carefully poured on to icy saturated aqueous solution of K₂CO₃ then extracted with EtOAc. The organic extracts were combined, washed with water and brine, dried over MgSO₄, filtered and concentrated to give 2,4-dibromo-5-nitropyridine (2.1 g, 75%) as a black solid. $^1$H NMR (400 MHz, CDCl₃) δ 8.87 (s, 1H), 7.94 (s, 1H), MS (ESI) m/z 285 [M+H]⁺.

Step 3: A solution of 2,4-dibromo-5-nitropyridine (3 g, 7.16 mmol) in ethanol (25 mL) was cooled to 0° C. followed by addition of 4-cyanoaniline (0.845 g, 7.16 mmol) and triethylamine (1.52 ml, 10.75 mmol). The reaction mixture was stirred at rt for 24 h. After completion, the reaction mixture was cooled to 0° C., filtered and dried with vacuum to afford 4-(2-bromo-5-nitropyridin-4-ylamino)benzonitrile (1.7 g, 38.8%) as a yellow solid. $^1$H NMR (400 MHz, CDCl₃) δ 9.73 (bs, 1H), 9.09 (s, 1H), 7.82 (d, J=7.80 Hz, 2H), 7.43 (d, J=7.42 Hz, 2H); MS (ESI) m/z 317 [M]⁺.

Step 4: A solution of 4-(2-bromo-5-nitropyridin-4-ylamino)benzonitrile (1 g, 3.15 mmol) in ethanol (25 mL) was cooled to 0° C. followed by addition of SnCl₂.H₂O (2.13 g, 9.46 mmol). The reaction mixture was stirred at 80° C. for 4 h. After completion, the reaction mixture was cooled to 0° C. and quenched by drop wise addition of saturated NaHCO₃ (100 mL) followed by extraction with EtOAc (3×100 mL). The organic layer was washed with water, brine, dried over anhydrous Na₂SO₄, filtered and concentrated under reduced pressure to afford 4-(5-amino-2-bromopyridin-4-ylamino)benzonitrile (0.8 g). MS (ESI) m/z 288 [M]⁺. Crude product was used without purification in the next step.

Step 5: A solution of 4-(5-amino-2-bromopyridin-4-ylamino)benzonitrile (0.8 g, 2.77 mmol) in triethylorthoformate (15 mL) was stirred at 100° C. for 16 h. After completion, the reaction mixture was cooled to 0° C. and quenched by drop wise addition of saturated aqueous solution of NaHCO₃ (100 mL) followed by extraction with EtOAc (3×100 mL). The organic layer was washed with water, brine, dried over anhydrous Na₂SO₄, filtered and concentrated under reduced pressure. The crude compound was purified by column chromatography (silica gel, eluent petroleum ether/EtOAc 70:30) to afford 4-(6-bromo-1H-imidazo[4,5-c]pyridin-1-yl)benzonitrile (0.4 g, 48%); $^1$H NMR (400 MHz, DMSO-d$_6$) δ 8.9 (d, J=8.9 Hz, 2H), 8.15 (d, J=8.1 Hz, 2H), 7.9 (t, J=7.9 Hz, 3H), MS (ESI) m/z 297 [M]$^+$.

Step 6: To a mixture of 4-(6-bromo-1H-imidazo[4,5-c]pyridin-1-yl)benzonitrile (300 mg, 1.0 mmol), (4-methyl-piperazin-1-yl)(4-(4,4,5,5-tetramethyl-1,3,2-dioxaborolan-2-yl)phenyl)methanone (366 mg, 1.11 mmol), NaHCO$_3$ (169 mg, 2.02 mmol) in DMF (15 mL) and water (5 mL), was added (A-Phos)$_2$PdCl$_2$ (35 mg, 0.05 mmol) and the reaction mixture was heated at 90° C. for 1 h. The reaction mixture was diluted with water and extracted with EtOAc, the organic phase was washed with water and brine, dried over Na$_2$SO$_4$ and concentrated under reduced pressure to obtain crude product. The crude product was purified by Preparative TLC to afford of 4-(6-(4-(4-methylpiperazine-1-carbonyl)phenyl)-1H-imidazo[4,5-c]pyridin-1-yl)benzonitrile (60 mg, 15%, AUC HPLC 99.6%) as an off white solid. $^1$H NMR (400 MHz, CDCl$_3$) δ (ppm): 9.32 (s, 1H), 8.23 (s, 1H), 8.05 (d, J=8.0 Hz, 2H), 7.97 (d, J=8.8 Hz, 2H), 7.86 (s, 1H), 7.72 (d, J=8.8 Hz, 2H), 7.53 (d, J=8.4 Hz, 2H), 3.83 (bs, 2H), 3.48 (bs, 2H), 2.51 (bs, 2H), 2.34 (bs, 2H), 2.33 (s, 3H); MS (ESI) m/z 423.24 [C$_{25}$H$_{22}$N$_6$O+H]$^+$.

Formula 7

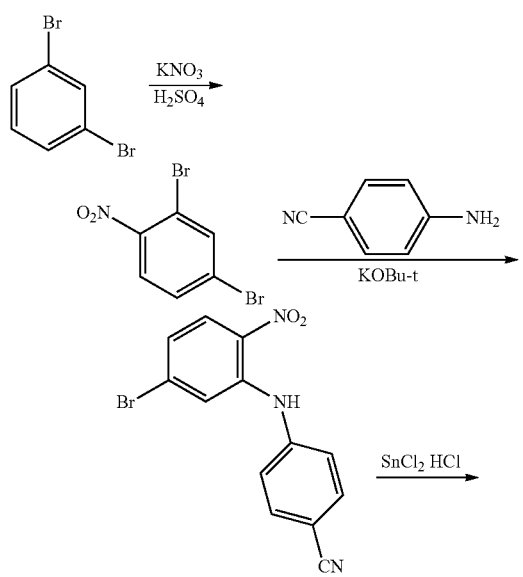

Example 190: Synthesis of 4-(6-(4-(morpholine-4-carbonyl)phenyl)-1H-benzo[d]imidazol-1-yl)benzonitrile

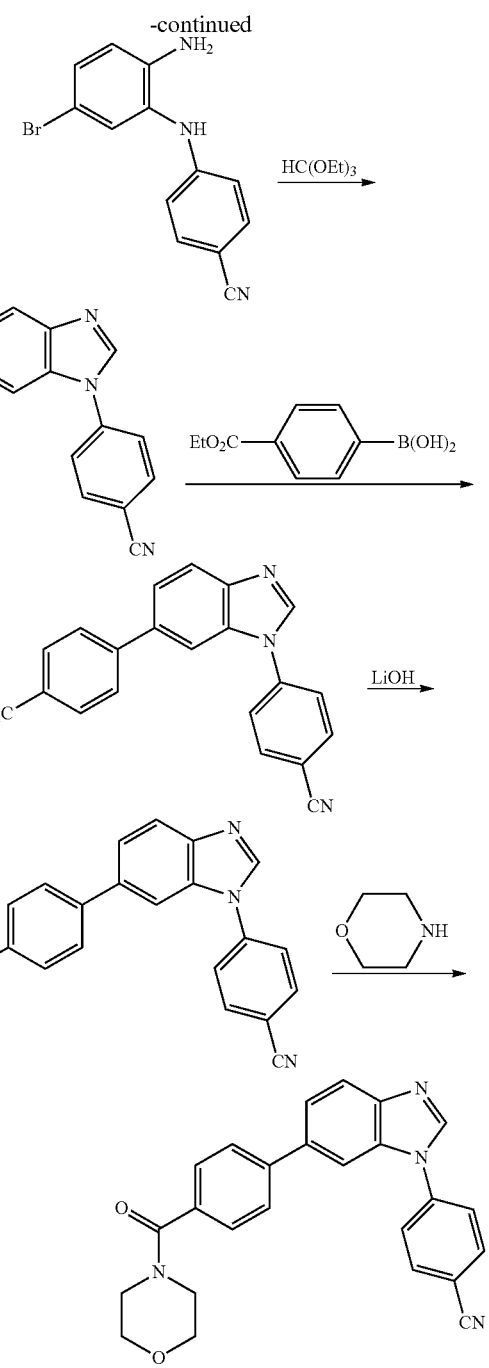

Step 1: To an ice-bath cooled solution of 1,3-dibromobenzene (8.2 mL, 34.7 mmol) in concentrated sulfuric acid (80 mL) was slowly added KNO$_3$ (6.8 g, 34.7 mmol) so as to maintain the internal reaction temperature below 10° C. The reaction mixture was stirred for an additional 1 h and then poured into crushed ice (500 mL). The yellow precipitate isolated by filtration, washed with water and dried under reduced pressure to afford 2,4-dibromo-1-nitrobenzene (8.4 g, 90%) as a yellow solid. $^1$H NMR (400 MHz, CDCl$_3$) δ (ppm): 7.92 (s, 1H), 7.75 (d, J=8.4 Hz, 1H), 7.61 (d, J=1.6 Hz, 1H); MS (ESI) m/z 280.9 [C$_6$H$_3$Br$_2$NO$_2$]$^+$.

Step 2: To a solution of 2,4-dibromonitrobenzene (8 g, 28.47 mmol) and 4-aminobenzonitrile (3.69 g, 28.79 mmol) in DMF (100 mL) was slowly added t-BuOK (6.38 g, 56.94 mmol) while maintaining temperature between 0° C. to 5° C. The reaction mixture was stirred at rt for 1 h then, was poured into ice-water and pH was adjusted to 6 with 5% aqueous HCl. The solid was collected, washed with water, and purified by recrystallization from EtOH to afford 4-(5-bromo-2-nitrophenylamino)benzonitrile (7.0 g, 77%) as a pale yellow solid. $^1$H NMR (400 MHz, CDCl$_3$) δ (ppm): 9.54 (s, 1H), 8.19 (d, J=9.2, 1H), 7.71 (d, J=8.4 Hz, 2H), 7.35 (d, J=8.8 Hz, 2H), 6.91 (d, J=2.0 Hz, 1H); MS (ESI) m/z 318 [C$_{13}$H$_8$BrN$_3$O$_2$]$^+$.

Step 3: To a solution of 4-(5-bromo-2-nitrophenylamino) benzonitrile (7 g, 22 mmol) in ethanol (70 mL) cooled at 0° C. was added SnCl$_2$.H$_2$O (14.9 g, 66.0 mmol). The reaction mixture was stirred at 80° C. for 4 h. The reaction mixture was cooled to 0° C. and quenched by drop wise addition of saturated aqueous solution of NaHCO$_3$ (100 mL) and extracted with EtOAc (3×100 mL). The organic layer was washed with water, brine, dried over anhydrous Na$_2$SO$_4$, filtered and concentrated under reduced pressure to afford 4-(2-amino-5-bromophenylamino)benzonitrile (5.0 g, 79%, LC-MS 60%). The crude product was used in the next step without purification. MS (ESI) m/z 288 [C$_{13}$H$_{10}$BrN$_3$]$^+$.

Step 4: A solution of 4-(2-amino-5-bromophenylamino) benzonitrile (5 g, 17.36 mmol) in triethylorthoformate (25 mL) was stirred at 100° C. for 16 h. The reaction mixture was cooled to 0° C. and quenched by drop wise addition of saturated aqueous solution of NaHCO$_3$ (100 mL) then, extracted with EtOAc (3×100 mL). The organic layer was washed with water, brine, dried over anhydrous Na$_2$SO$_4$, filtered and concentrated under reduced pressure. The crude product was purified by column chromatography (silica gel, eluent EtOAc/petroleum ether 30:70) to afford 4-(6-bromo-1H-benzo[d]imidazol-1-yl)benzonitrile (3.5 g, 68%, LC-MS 80%); $^1$H NMR (400 MHz, CDCl$_3$) δ 8.11 (s, 1H), 7.92 (d, J=4.0 Hz, 2H), 7.76 (d, J=8.8 Hz, 1H), 7.71 (s, 1H), 7.66 (d, J=8.0 Hz, 2H), 7.51 (d, J=1.6 Hz, 1H); MS (ESI) m/z 298 [C$_{14}$H$_8$BrN$_3$]$^+$ Step 5: A mixture of 4-(6-bromo-1H-benzo[d]imidazol-1-yl)benzonitrile (3.5 g, 11.74 mmol), 4-ethoxycarbonyl phenylboronic acid (2.5 g, 12.94 mmol), K$_3$PO$_4$ (4.97 g, 23.48 mmol), Pd(PPh$_3$)$_4$ (0.67 g, 0.587 mmol) in 1,4-dioxane (100 mL) and water (20 mL) was heated at 90° C. for 4 h under argon. The reaction mixture was diluted with EtOAc (2×100 mL) and washed with water (2×50 mL), brine solution (2×50 mL). The organic layer was dried over anhydrous Na$_2$SO$_4$ and concentrated under reduced pressure to obtain crude product. The crude product was purified by column chromatography (silica gel, eluent EtOAc/petroleum ether 10:90 to 50:50) to afford ethyl 4-(1-(4-cyanophenyl)-1H-benzo[d]imidazol-6-yl)benzoate (2.8 g, 65%) as an off-white solid. $^1$H NMR (400 MHz, CDCl$_3$) δ (ppm): 8.19 (s, 1H), 8.12 (d, J=8.4 Hz, 2H), 7.99-7.92 (m, 3H), 7.75-7.65 (m, 6H), 4.41 (d, J=7.2 Hz, 2H), 1.44 (t, J=7.6 Hz, 3H); MS (ESI) m/z 368 [C$_{23}$H$_{17}$N$_3$O$_2$+H]$^+$.

Step 6: To a solution of 4-(3-(4-cyanophenyl)pyrazolo[1,5-a]pyrimidin-5-yl)benzoate 5 (2.5 g, 6.8 mmol) in THF (20 mL) was added LiOH (571 mg, 13.6 mmol) in water (4 mL) and stirred for 16 h at rt. The reaction mixture was worked up and concentrated under reduced pressure to afford 4-(1-(4-cyanophenyl)-1H-benzo[d]imidazol-6-yl)benzoic acid (2 g, 86%, LC-MS 65%) as an off-white solid. $^1$H NMR (400 MHz, DMSO-d$_6$) δ (ppm): 8.77 (s, 1H), 8.14 (d, J=8.0 Hz, 2H), 8.10-7.95 (m, 5H), 7.95-7.83 (m, 3H), 7.72 (d, J=8.4 Hz, 1H); MS (ESI) m/z 340.13 [C$_{21}$H$_{13}$N$_3$O$_2$+H]$^+$.

Step 7: To a solution of 4-(1-(4-cyanophenyl)-1H-benzo[d]imidazol-6-yl)benzoic acid 6 (300 mg, 0.88 mmol) in DMF (5 mL) was added NMM (0.178 mL, 1.76 mmol) followed by HATU (501 mg, 1.32 mmol) at rt and the solution was stirred for 30 min. Morpholine (0.84 mL, 0.968 mmol) was added to the reaction mixture and stirring was continued for 16 h. The reaction mixture was diluted with EtOAc and washed with water and brine solution. The organic layer was dried over anhydrous Na$_2$SO$_4$ and concentrated under reduced pressure to obtain crude product. The crude product was purified by preparative HPLC to afford 4-(6-(4-(morpholine-4-carbonyl)phenyl)-1H-benzo [d]imidazol-1-yl)benzonitrile (100 mg, 27%, AUC HPLC 95.9%) as an off-white solid; m.p. 207-210° C.; $^1$H NMR (400 MHz, CDCl$_3$) δ (ppm): 8.18 (s, 1H), 7.98-7.92 (m, 3H), 7.72 (d, J=6.6 Hz, 3H), 7.66-7.61 (m, 3H), 7.51 (d, J=7.9 Hz, 2H), 3.90-3.40 (m, 8H); MS (ESI) m/z 409.15 [C$_{25}$H$_{20}$N$_4$O$_2$+H]$^+$.

Annexure

Enzymatic and Cellular IC$_{50}$ table:

| Examples | IC50 (μM) | | |
| --- | --- | --- | --- |
|  | Mnk1 | Mnk2 | Hela |
| 1 | <0.1 | <0.1 | <1.0 |
| 2 | <1.0 | <1.0 | <1.0 |
| 3 | <1.0 | <0.1 | <1.0 |
| 4 | <0.1 | <0.1 | <1.0 |
| 5 | <0.1 | <0.1 | <1.0 |
| 6 | <1.0 | <1.0 | <1.0 |
| 7 | <1.0 | <1.0 | <1.0 |
| 9 | <1.0 | <1.0 | <1.0 |
| 14 | <1.0 | <1.0 | <1.0 |
| 15 | <1.0 | <1.0 | <1.0 |
| 17 | <1.0 | <1.0 | <1.0 |
| 21 | <1.0 | <1.0 | <1.0 |
| 23 | <1.0 | <0.1 | <1.0 |
| 24 | <1.0 | <1.0 | <1.0 |
| 26 | <1.0 | <1.0 | <1.0 |
| 27 | <0.1 | <0.1 | <1.0 |
| 28 | <0.1 | <0.1 | <1.0 |
| 29 | <1.0 | <1.0 | <1.0 |
| 30 | <1.0 | <1.0 | <1.0 |
| 31 | <1.0 | <1.0 | <1.0 |
| 32 | <0.1 | <1.0 | <1.0 |
| 38 | <1.0 | <1.0 | <1.0 |
| 39 | <1.0 | <1.0 | <1.0 |
| 41 | <1.0 | <1.0 | <1.0 |
| 42 | <1.0 | <1.0 | <1.0 |
| 43 | <1.0 | <1.0 | <1.0 |
| 45 | <1.0 | <1.0 | <1.0 |
| 46 | <1.0 | <1.0 | <1.0 |
| 47 | <1.0 | <0.1 | <1.0 |
| 48 | <1.0 | <1.0 | <1.0 |
| 49 | <1.0 | <1.0 | <1.0 |
| 54 | <0.1 | <0.1 | <1.0 |
| 55 | <0.1 | <0.1 | <1.0 |
| 56 | <0.1 | <0.1 | <1.0 |
| 57 | <0.1 | <0.1 | <1.0 |
| 58 | <0.1 | <0.1 | <1.0 |
| 59 | <0.1 | <0.1 | <1.0 |
| 60 | <0.1 | <0.1 | <1.0 |
| 61 | <0.1 | <0.1 | <1.0 |
| 62 | <0.1 | <0.1 | <1.0 |
| 63 | <0.1 | <0.1 | <1.0 |
| 64 | <0.1 | <0.1 | <1.0 |
| 65 | <0.1 | <0.1 | <1.0 |
| 66 | <0.1 | <0.1 | <1.0 |
| 68 | <0.1 | <0.1 | <1.0 |
| 69 | <0.1 | <0.1 | <1.0 |
| 70 | <0.1 | <0.1 | <1.0 |
| 71 | <0.1 | <0.1 | <1.0 |
| 72 | <0.1 | <0.1 | <1.0 |
| 73 | <0.1 | <0.1 | <1.0 |
| 74 | <0.1 | <0.1 | <1.0 |
| 78 | <0.1 | <0.1 | <1.0 |

-continued

| Examples | IC50 (µM) Mnk1 | Mnk2 | Hela |
|---|---|---|---|
| 79 | <0.1 | <0.1 | <1.0 |
| 80 | <0.1 | <0.1 | <1.0 |
| 81 | <0.1 | <0.1 | <1.0 |
| 85 | <0.1 | <0.1 | <1.0 |
| 86 | <0.1 | <0.1 | <1.0 |
| 87 | <0.1 | <0.1 | <1.0 |
| 89 | <0.1 | <0.1 | <1.0 |
| 94 | <0.1 | <0.1 | <1.0 |
| 95 | <0.1 | <0.1 | <1.0 |
| 96 | <0.1 | <0.1 | <1.0 |
| 97 | <0.1 | <0.1 | <1.0 |
| 98 | <0.1 | <0.1 | <1.0 |
| 99 | <0.1 | <0.1 | <1.0 |
| 100 | <0.1 | <0.1 | <1.0 |
| 101 | <0.1 | <0.1 | <1.0 |
| 102 | <0.1 | <0.1 | <1.0 |
| 103 | <0.1 | <0.1 | <1.0 |
| 105 | <0.1 | <0.1 | <1.0 |
| 106 | <0.1 | <0.1 | <1.0 |
| 107 | <0.1 | <0.1 | <1.0 |
| 109 | <0.1 | <0.1 | <1.0 |
| 111 | <0.1 | <0.1 | <1.0 |
| 112 | <0.1 | <0.1 | <1.0 |
| 113 | <0.1 | <0.1 | <1.0 |
| 115 | <1.0 | <1.0 | <1.0 |
| 116 | <1.0 | <1.0 | <1.0 |
| 117 | <0.1 | <0.1 | <1.0 |
| 118 | <0.1 | <0.1 | <1.0 |
| 119 | <0.1 | <0.1 | <1.0 |
| 122 | <1.0 | <1.0 | <1.0 |
| 123 | <0.1 | <0.1 | <1.0 |
| 124 | <0.1 | <0.1 | <1.0 |
| 125 | <0.1 | <0.1 | <1.0 |
| 126 | <0.1 | <0.1 | <1.0 |
| 129 | <1.0 | <0.1 | <1.0 |
| 130 | <0.1 | <0.1 | <1.0 |
| 133 | <0.1 | <0.1 | <1.0 |
| 134 | <0.1 | <0.1 | <1.0 |
| 135 | <0.1 | <0.1 | <1.0 |
| 137 | <1.0 | <0.1 | <1.0 |
| 138 | <1.0 | <1.0 | <1.0 |
| 139 | <1.0 | <0.1 | <1.0 |
| 140 | <0.1 | <0.1 | <1.0 |
| 141 | <0.1 | <0.1 | <1.0 |
| 142 | <1.0 | <0.1 | <1.0 |
| 143 | <0.1 | <0.1 | <1.0 |
| 144 | <0.1 | <0.1 | <1.0 |
| 145 | <0.1 | <1.0 | <1.0 |
| 146 | <0.1 | <0.1 | <1.0 |
| 147 | <0.1 | <0.1 | <1.0 |
| 149 | <1.0 | <1.0 | <1.0 |
| 150 | <0.1 | <0.1 | <1.0 |
| 151 | <1.0 | <0.1 | <1.0 |
| 153 | <1.0 | <1.0 | <1.0 |
| 156 | <1.0 | <1.0 | <1.0 |
| 157 | <1.0 | <1.0 | <1.0 |
| 158 | <1.0 | <0.1 | <1.0 |
| 159 | <0.1 | <0.1 | <1.0 |
| 160 | <0.1 | <0.1 | <1.0 |
| 162 | <1.0 | <1.0 | <1.0 |
| 163 | <0.1 | <0.1 | <1.0 |
| 164 | <0.1 | <0.1 | <1.0 |
| 165 | <0.1 | <0.1 | <1.0 |
| 166 | <0.1 | <0.1 | <1.0 |
| 167 | <0.1 | <0.1 | <1.0 |
| 169 | <0.1 | <0.1 | <1.0 |
| 170 | <0.1 | <0.1 | <1.0 |
| 172 | <0.1 | <0.1 | <1.0 |
| 173 | <0.1 | <0.1 | <1.0 |
| 174 | <0.1 | <0.1 | <1.0 |
| 175 | <1.0 | <0.1 | <1.0 |
| 176 | <0.1 | <0.1 | <1.0 |
| 179 | <0.1 | <0.1 | <1.0 |
| 181 | <0.1 | <0.1 | <1.0 |
| 183 | <0.1 | <0.1 | <1.0 |
| 184 | <0.1 | <0.1 | <1.0 |
| 185 | <0.1 | <0.1 | <1.0 |
| 186 | <0.1 | <0.1 | <1.0 |
| 187 | <0.1 | <0.1 | <1.0 |
| 188 | <0.1 | <0.1 | <1.0 |
| 190 | <1.0 | <1.0 | <1.0 |

REFERENCE LIST (1) Buxade, M.; Parra-Palau, J. L.; Proud, C. G. *Front Biosci.* 2008, 13, 5359-5373.

(2) Fukunaga, R.; Hunter, T. *EMBO J.* 1997, 16, 1921-1933.

(3) Waskiewicz, A. J.; Flynn, A.; Proud, C. G.; Cooper, J. A. *EMBO J.* 1997, 16, 1909-1920.

(4) Worch, J.; Tickenbrock, L.; Schwable, J.; Steffen, B.; Cauvet, T.; Mlody, B.; Buerger, H.; Koeffler, H. P.; Berdel, W. E.; Serve, H.; Muller-Tidow, C. *Oncogene* 2004, 23, 9162-9172.

(5) Pellagatti, A.; Esoof, N.; Watkins, F.; Langford, C. F.; Vetrie, D.; Campbell, L. J.; Fidler, C.; Cavenagh, J. D.; Eagleton, H.; Gordon, P.; Woodcock, B.; Pushkaran, B.; Kwan, M.; Wainscoat, J. S.; Boultwood, J. *Br. J. Haematol.* 2004, 125, 576-583.

(6) Bredel, M.; Bredel, C.; Juric, D.; Harsh, G. R.; Vogel, H.; Recht, L. D.; Sikic, B. I. *Cancer Res.* 2005, 65, 4088-4096.

(7) Hendrix, N. D.; Wu, R.; Kuick, R.; Schwartz, D. R.; Fearon, E. R.; Cho, K. R. *Cancer Res.* 2006, 66, 1354-1362.

(8) Culjkovic, B.; Topisirovic, I.; Borden, K. L. *Cell Cycle* 2007, 6, 65-69.

(9) Culjkovic, B.; Tan, K.; Orolicki, S.; Amri, A.; Meloche, S.; Borden, K. L. *J. Cell Biol.* 2008, 181, 51-63.

(10) Nathan, C. O.; Carter, P.; Liu, L.; Li, B. D.; Abreo, F.; Tudor, A.; Zimmer, S. G.; De Benedetti, A. *Oncogene* 1997, 15, 1087-1094.

(11) Bianchini, A.; Loiarro, M.; Bielli, P.; Busa, R.; Paronetto, M. P.; Loreni, F.; Geremia, R.; Sette, C. *Carcinogenesis* 2008, 29, 2279-2288.

(12) Topisirovic, I.; Guzman, M. L.; McConnell, M. J.; Licht, J. D.; Culjkovic, B.; Neering, S. J.; Jordan, C. T.; Borden, K. L. *Mol. Cell Biol.* 2003, 23, 8992-9002.

(13) Graff, J. R.; Zimmer, S. G. *Clin. Exp. Metastasis* 2003, 20, 265-273.

(14) Ruggero, D.; Montanaro, L.; Ma, L.; Xu, W.; Londei, P.; Cordon-Cardo, C.; Pandolfi, P. P. *Nat. Med.* 2004, 10, 484-486.

(15) Kevil, C.; Carter, P.; Hu, B.; DeBenedetti, A. *Oncogene* 1995, 11, 2339-2348.

(16) Kevil, C. G.; De Benedetti, A.; Payne, D. K.; Coe, L. L.; Laroux, F. S.; Alexander, J. S. *Int. J. Cancer* 1996, 65, 785-790.

(17) Scott, P. A.; Smith, K.; Poulsom, R.; De Benedetti, A.; Bicknell, R.; Harris, A. L. *Br. J. Cancer* 1998, 77, 2120-2128.

(18) Rosenwald, I. B.; Lazaris-Karatzas, A.; Sonenberg, N.; Schmidt, E. V. *Mol. Cell Biol.* 1993, 13, 7358-7363.

(19) Abid, M. R.; Li, Y.; Anthony, C.; De Benedetti, A. *J. Biol. Chem.* 1999, 274, 35991-35998.

(20) De Benedetti, A.; Rhoads, R. E. *Proc. Natl. Acad. Sci. U.S.A* 1990, 87, 8212-8216.

(21) Lazaris-Karatzas, A.; Montine, K. S.; Sonenberg, N. *Nature* 1990, 345, 544-547.
(22) Rinker-Schaeffer, C. W.; Graff, J. R.; De Benedetti, A.; Zimmer, S. G.; Rhoads, R. E. *Int. J. Cancer* 1993, 55, 841-847.
(23) Rousseau, D.; Gingras, A. C.; Pause, A.; Sonenberg, N. *Oncogene* 1996, 13, 2415-2420.
(24) Crew, J. P.; Fuggle, S.; Bicknell, R.; Cranston, D. W.; De Benedetti, A.; Harris, A. L. *Br. J. Cancer* 2000, 82, 161-166.
(25) DeFatta, R. J.; Turbat-Herrera, E. A.; Li, B. D.; Anderson, W.; De Benedetti, A. *Int. J. Cancer* 1999, 80, 516-522.
(26) Kerekatte, V.; Smiley, K.; Hu, B.; Smith, A.; Gelder, F.; De Benedetti, A. *Int. J. Cancer* 1995, 64, 27-31.
(27) Turbat-Herrera, E. A. T. A. B. D. L. S. d. A. B. M. a. M.-G. *Southwest Assoc. Clin. Microbiol* 1999, 8.
(28) Franklin, S.; Pho, T.; Abreo, F. W.; Nassar, R.; De Benedetti, A.; Stucker, F. J.; Nathan, C. O. *Arch. Otolaryngol. Head Neck Surg.* 1999, 125, 177-182.
(29) Nathan, C. O.; Liu, L.; Li, B. D.; Abreo, F. W.; Nandy, I.; De Benedetti, A. *Oncogene* 1997, 15, 579-584.
(30) Villar, H. O.; Yan, J.; Hansen, M. R. *Curr. Opin. Chem. Biol.* 2004, 8, 387-391.
(31) Williams, B. J.; Eastham, J. A.; Venables, D.; DeBenedetti, A.; Acree, D. T. *AACR Special Conference on Angiogenesis and Cancer* 1998, B69-B70.
(32) Raught, B.; Gingras, A. C. *Int. J. Biochem. Cell Biol.* 1999, 31, 43-57.
(33) Topisirovic, I.; Ruiz-Gutierrez, M.; Borden, K. L. *Cancer Res.* 2004, 64, 8639-8642.
(34) Wendel, H. G.; Silva, R. L.; Malina, A.; Mills, J. R.; Zhu, H.; Ueda, T.; Watanabe-Fukunaga, R.; Fukunaga, R.; Teruya-Feldstein, J.; Pelletier, J.; Lowe, S. W. *Genes Dev.* 2007, 21, 3232-3237.
(35) Ueda, T.; Watanabe-Fukunaga, R.; Fukuyama, H.; Nagata, S.; Fukunaga, R. *Mol. Cell Biol.* 2004, 24, 6539-6549.
(36) Scheper, G. C.; Proud, C. G. *Eur. J. Biochem.* 2002, 269, 5350-5359.
(37) Sharon Lim, Tzuen Yih Saw, Sandy Chang, Min Zhang, Matthew Robert Janes, David A Fruman, David A. Rizzieri, Soo-Yong Tan, Charles Chuah, and S. Tiong Ong. Targeting of a Novel MNK-eIF4E-b-Catenin Axis in Blast Crisis Chronic Myelogenous Leukemia Inhibits Leukemia Stem Cell Function. 2011. 53$^{st}$ ASH Annual Meeting and Exposition. Oral Session: Chronic Myeloid Leukemia—Biology and Pathophysiology, excluding Therapy: Extrinsic and Intrinsic Survival Mechanisms. Dec. 10, 2011. Ref Type: Conference Proceeding
(38) Ly, C.; Arechiga, A. F.; Melo, J. V.; Walsh, C. M.; Ong, S. T. *Cancer Res.* 2003, 63, 5716-5722.
(39) Prabhu, S.; Saadat, D.; Zhang, M.; Halbur, L.; Fruehauf, J. P.; Ong, S. T. *Oncogene* 2007, 26, 1188-1200.
(40) Zhang, M.; Fu, W.; Prabhu, S.; Moore, J. C.; Ko, J.; Kim, J. W.; Druker, B. J.; Trapp, V.; Fruehauf, J.; Gram, H.; Fan, H. Y.; Ong, S. T. *Mol. Cell Biol.* 2008, 28, 6496-6509.
(41) Hay, N. *Proc. Natl. Acad. Sci. U.S.A* 2010, 107, 13975-13976.
(42) Marzec, M.; Liu, X.; Wysocka, M.; Rook, A. H.; Odum, N.; Wasik, M. A. *PLoS. One.* 2011, 6, e24849.
(43) Jimenez-Rivera, C.; Avitzur, Y.; Fecteau, A. H.; Jones, N.; Grant, D.; Ng, V. L. *Pediatr. Transplant.* 2004, 8, 243-248.
(44) Zaltzman, J. S.; Prasad, R.; Chun, K.; Jothy, S. *Nephrol. Dial. Transplant.* 2005, 20, 1748-1751.
(45) Campistol, J. M.; Gutierrez-Dalmau, A.; Torregrosa, J. V. *Transplantation* 2004, 77, 760-762.
(46) Stallone, G.; Schena, A.; Infante, B.; Di Paolo, S.; Loverre, A.; Maggio, G.; Ranieri, E.; Gesualdo, L.; Schena, F. P.; Grandaliano, G. *N. Engl. J. Med.* 2005, 352, 1317-1323.
(47) Franz, D. N.; Leonard, J.; Tudor, C.; Chuck, G.; Care, M.; Sethuraman, G.; Dinopoulos, A.; Thomas, G.; Crone, K. R. *Ann. Neurol.* 2006, 59, 490-498.
(48) Hess, G.; Smith, S. M.; Berkenblit, A.; Coiffier, B. *Semin. Oncol.* 2009, 36 *Suppl* 3, S37-S45.
(49) Chan, H. Y.; Grossman, A. B.; Bukowski, R. M. *Adv. Ther.* 2010, 27, 495-511.
(50) Hudes, G.; Carducci, M.; Tomczak, P.; Dutcher, J.; Figlin, R.; Kapoor, A.; Staroslawska, E.; Sosman, J.; McDermott, D.; Bodrogi, I.; Kovacevic, Z.; Lesovoy, V.; Schmidt-Wolf, I. G.; Barbarash, O.; Gokmen, E.; O'Toole, T.; Lustgarten, S.; Moore, L.; Motzer, R. J. *N. Engl. J. Med.* 2007, 356, 2271-2281.
(51) Gibbons, J. J.; Abraham, R. T.; Yu, K. *Semin. Oncol.* 2009, 36 *Suppl* 3, S3-S17.
(52) Beuvink, I.; Boulay, A.; Fumagalli, S.; Zilbermann, F.; Ruetz, S.; O'Reilly, T.; Natt, F.; Hall, J.; Lane, H. A.; Thomas, G. *Cell* 2005, 120, 747-759.
(53) Teachey, D. T.; Sheen, C.; Hall, J.; Ryan, T.; Brown, V. I.; Fish, J.; Reid, G. S.; Seif, A. E.; Norris, R.; Chang, Y. J.; Carroll, M.; Grupp, S. A. *Blood* 2008, 112, 2020-2023.
(54) Wang, X.; Yue, P.; Chan, C. B.; Ye, K.; Ueda, T.; Watanabe-Fukunaga, R.; Fukunaga, R.; Fu, H.; Khuri, F. R.; Sun, S. Y. *Mol. Cell Biol.* 2007, 27, 7405-7413.
(55) HEMMINGS, Brian, GRZMIL, Michal, MORIN, Pier, and MERLO, Adrian. Treating Cancer by Modulating a Mnk. (WO2010055072A2). 2010. Ref Type: patent
(56) Hou, L.; Sasaki, H.; Stashenko, P. *Infect. Immun.* 2000, 68, 4681-4687.
(57) Andersson, K.; Sundler, R. *Cytokine* 2006, 33, 52-57.
(58) Rowlett, R. M.; Chrestensen, C. A.; Nyce, M.; Harp, M. G.; Pelo, J. W.; Cominelli, F.; Ernst, P. B.; Pizarro, T. T.; Sturgill, T. W.; Worthington, M. T. *Am. J. Physiol Gastrointest. Liver Physiol* 2008, 294, G452-G459.
(59) Buxade, M.; Parra, J. L.; Rousseau, S.; Shpiro, N.; Marquez, R.; Morrice, N.; Bain, J.; Espel, E.; Proud, C. G. *Immunity.* 2005, 23, 177-189.
(60) Guil, S.; Long, J. C.; Caceres, J. F. *Mol. Cell Biol.* 2006, 26, 5744-5758.
(61) Buxade, M.; Morrice, N.; Krebs, D. L.; Proud, C. G. *J. Biol. Chem.* 2008, 283, 57-65.
(62) Hefner, Y.; Borsch-Haubold, A. G.; Murakami, M.; Wilde, J. I.; Pasquet, S.; Schieltz, D.; Ghomashchi, F.; Yates, J. R., III; Armstrong, C. G.; Paterson, A.; Cohen, P.; Fukunaga, R.; Hunter, T.; Kudo, I.; Watson, S. P.; Gelb, M. H. *J. Biol. Chem.* 2000, 275, 37542-37551.
(63) DaSilva, J.; Xu, L.; Kim, H. J.; Miller, W. T.; Bar-Sagi, D. *Mol. Cell Biol.* 2006, 26, 1898-1907.
(64) Ushigome, M.; Ubagai, T.; Fukuda, H.; Tsuchiya, N.; Sugimura, T.; Takatsuka, J.; Nakagama, H. *Int. J. Oncol.* 2005, 26, 635-640.
(65) Boukakis, G.; Patrinou-Georgoula, M.; Lekarakou, M.; Valavanis, C.; Guialis, A. *BMC. Cancer* 2010, 10, 434.
(66) Soni, A.; Akcakanat, A.; Singh, G.; Luyimbazi, D.; Zheng, Y.; Kim, D.; Gonzalez-Angulo, A.; Meric-Bernstam, F. *Mol. Cancer Ther.* 2008, 7, 1782-1788.
(67) Berkel, H. J.; Turbat-Herrera, E. A.; Shi, R.; De Benedetti, A. *Cancer Epidemiol. Biomarkers Prev.* 2001, 10, 663-666.
(68) Wendel, H. G.; De Stanchina, E.; Fridman, J. S.; Malina, A.; Ray, S.; Kogan, S.; Cordon-Cardo, C.; Pelletier, J.; Lowe, S. W. *Nature* 2004, 428, 332-337.

(69) De Benedetti, A.; Graff, J. R. *Oncogene* 2004, 23, 3189-3199.
(70) Santini, E., et al. Exaggerated translation causes synaptic and behavioural aberrations associated with autism, *Nature* 2013, 493(7432), 411-415.
(71) Bozdagi, O., et al., Haploinsufficiency of Cyfip1 produces fragile X-like phenotypes in mice, *PLoS One* 2012, 7(8), e42422.
(72) Gkogkas, C. G., et al., Autism-related deficits via dysregulated eIF4E-dependent translational control, *Nature* 2013, 493(7432), 371-377.
(73) Baudouin, S. J., et al., Shared synaptic pathophysiology in syndromic and nonsyndromic rodent models of autism, *Science* 2012, 338(6103), 128-132.
(74) Radyushkin, K., et al. Neuroligin-3-deficient mice: model of a monogenic heritable form of autism with an olfactory deficit, *Genes Brain Behav* 2009, 8(4), 416-425.
(75) Scattoni, M. L., et al. Ultrasonic vocalizations: a tool for behavioural phenotyping of mouse models of neurodevelopmental disorders, *Neurosci Biobehav Rev* 2009, 33(4), 508-515.
(76) Neves-Pereira, M., et al., *Deregulation of EIF4E: a novel mechanism for autism.* J Med Genet, 2009. 46(11): p. 759-65.
(77) Waltes, R., et al., *Common EIF4E variants modulate risk for autism spectrum disorders in the high-functioning range.* J Neural Transm, 2014. 121(9): p. 1107-16.
(78) Tam, G. W., et al., *Confirmed rare copy number variants implicate novel genes in schizophrenia.* Biochem Soc Trans, 2010. 38(2): p. 445-51.
(79) Jamieson, C. H., et al., *Granulocyte-macrophage progenitors as candidate leukemic stem cells in blast-crisis CML.* N Engl J Med, 2004. 351(7): p. 657-67.
(80) Huntly, B. J., et al., *MOZ-TIF2, but not BCR-ABL, confers properties of leukemic stem cells to committed murine hematopoietic progenitors.* Cancer Cell, 2004. 6(6): p. 587-96.

What is claimed is:
1. A compound of Formula (Ia):

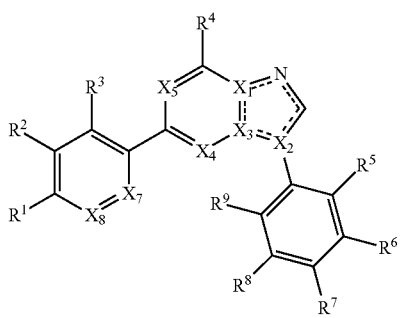

(Ia)

or a pharmaceutically acceptable form thereof, wherein
$X_1$, $X_2$, and $X_3$ are independently N or C;
$X_4$ and $X_5$ are independently N or $CR^4$;
wherein at least one of $X_1$, $X_2$, $X_3$, $X_4$, and $X_5$ is N;
$X_7$ is $CR^{10}$;
$X_8$ is $CR^{11}$;
----- is a single or double bond, as valency allows;
$R^2$, $R^3$, $R^5$, $R^6$, $R^7$, $R^8$, and $R^9$, are independently hydrogen, halogen, optionally substituted aliphatic, —CN, —OR, —SR, —N(R)$_2$, —NO$_2$, —C(O)R, —CO$_2$R, —C(O)NROR, —OC(O)R, —C(O)NH$_2$;

$R^1$ is independently —C(O)R, —CO$_2$(optionally substituted C$_{1-6}$ aliphatic), —CO$_2$(optionally substituted heteroaryl), —CO$_2$(optionally substituted heterocyclyl), or —OC(O)(optionally substituted C$_{1-6}$ aliphatic);
$R^{10}$ and $R^{11}$ are each independently hydrogen, halogen, optionally substituted aliphatic, —CN, —OR, SR, —N(R)$_2$, —NO$_2$, —C(O)R, —CO$_2$R, or —C(O)NROR;
each R is independently hydrogen or optionally substituted C$_{1-6}$ aliphatic optionally substituted heteroaryl, or optionally substituted heterocyclyl; and
each $R^4$ is independently hydrogen, halogen, or optionally substituted C$_{1-6}$ aliphatic; and
$R^6$ and $R^7$, or $R^7$ and $R^8$, may be optionally taken together to form an optionally substituted 5-6 membered fused heterocyclic or 5-6 membered fused heteroaryl ring.

2. The compound of claim 1, wherein the compound is of Formula (Ia-i):

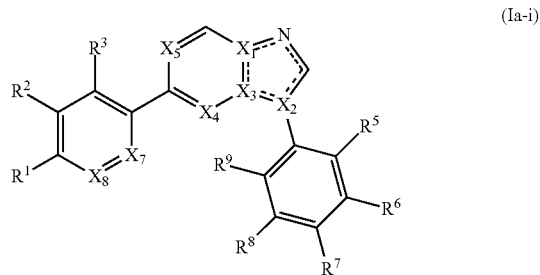

(Ia-i)

or a pharmaceutically acceptable form thereof.

3. The compound of claim 1, wherein the compound is of Formula (Ib-i) or (Ib-ii):

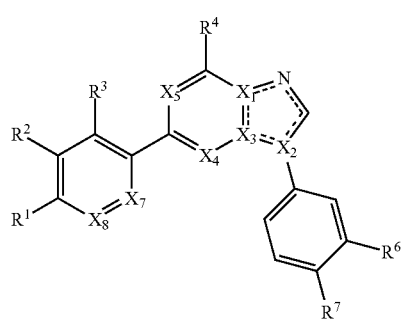

(Ib-i)

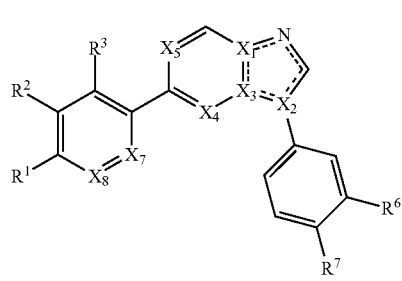

(Ib-ii)

or a pharmaceutically acceptable form thereof, wherein
$X_1$, $X_2$, and $X_3$ are independently N or C;
$X_4$ and $X_5$ are independently N or $CR^4$;

wherein at least one of $X_1$, $X_2$, $X_3$, $X_4$, and $X_5$ is N;

$X_7$ is CH;

$X_8$ is CH;

----- is a single or double bond, as valency allows;

$R^1$ is —C(O)R, wherein R is an optionally substituted heterocyclyl;

$R^2$, $R^3$, $R^6$, and $R^7$ are independently —H, —F, —Cl, —CN, —CH$_3$, —CF$_3$, —CHF$_2$, —C(O)NH$_2$, —OH, —OC$_{1-4}$alkyl, or —OCF$_3$; or $R^6$ and $R^7$ are taken together to form a 5-6 membered fused heterocyclyl or 5-6 membered fused heteroaryl; and each $R^4$ is independently hydrogen or $C_{1-6}$ alkyl.

4. The compound of claim 1, wherein $R^7$ is —CN.

5. The compound of claim 1, wherein $R^2$, $R^3$, or $R^6$ is hydrogen.

6. The compound of claim 1, wherein both $R^2$ and $R^3$ are hydrogen.

7. The compound of claim 1, wherein $R^2$ is —N(R$^N$)$_2$ and $R^3$ is hydrogen, wherein each instance of $R^N$ is independently hydrogen, or optionally substituted $C_{1-6}$ aliphatic.

8. The compound of claim 1, wherein $R^2$ is —OR$^O$ and $R^3$ is hydrogen, wherein $R^O$ is hydrogen, or optionally substituted $C_{1-6}$ aliphatic.

9. The compound of claim 1, wherein $R^1$ is —C(O)R, wherein R is one of the following:

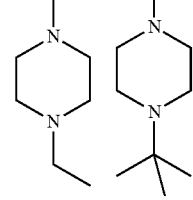
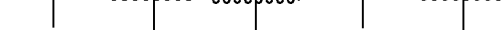
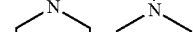
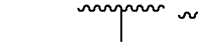
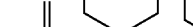
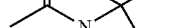
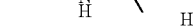
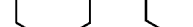

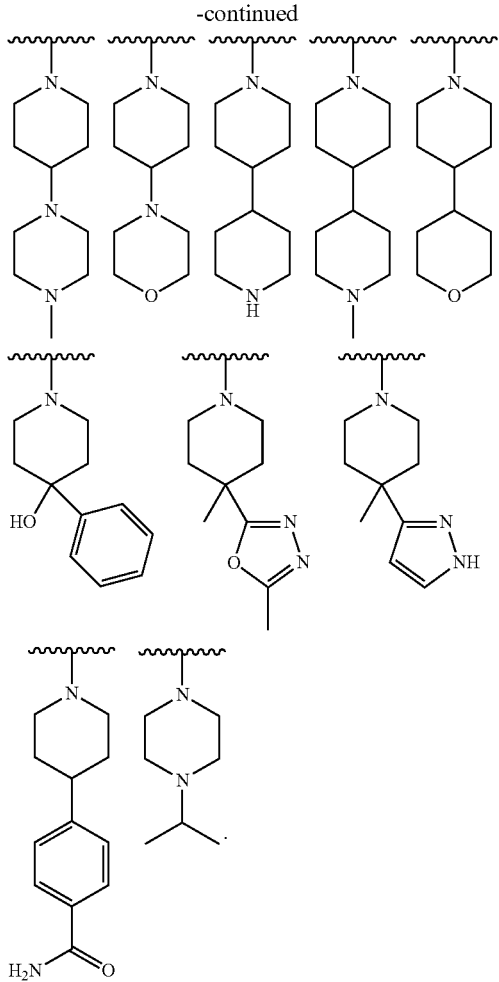
10. The compound of claim 1, wherein the compound is of Formula (II), (III), (IV), (V), (VI), or (VII):
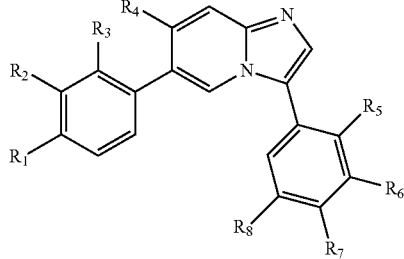
Formula II
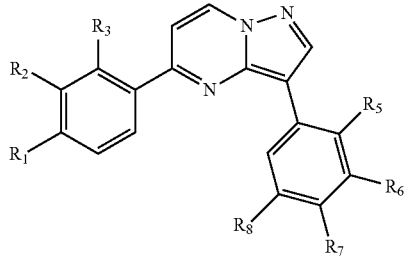
Formula III
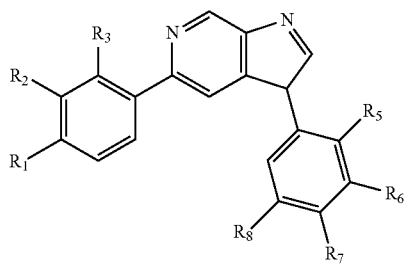
Formula IV
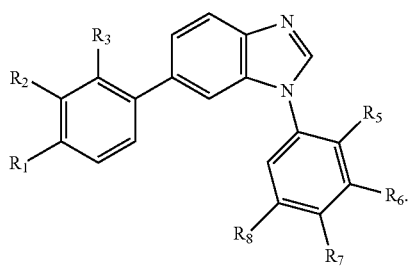
Formula V
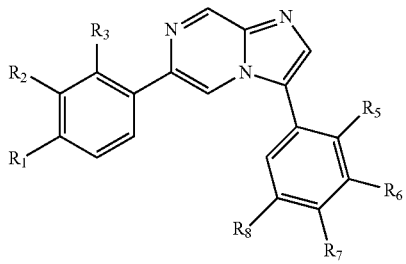
Formula VI
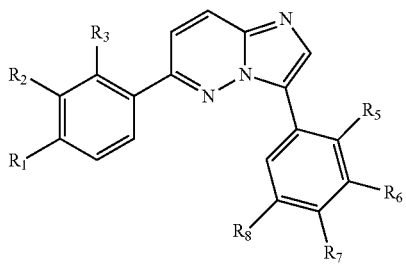
Formula VII
11. The compound of claim 1, wherein the compound is selected from the group consisting of:
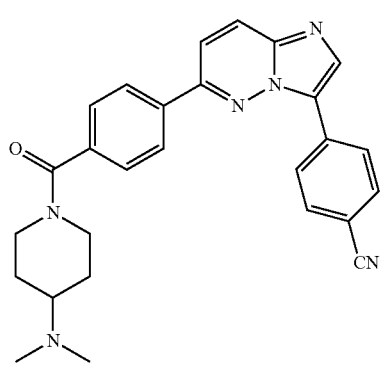

-continued
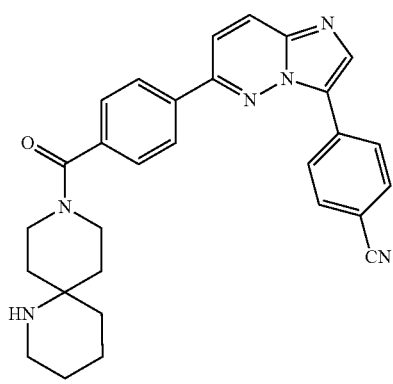
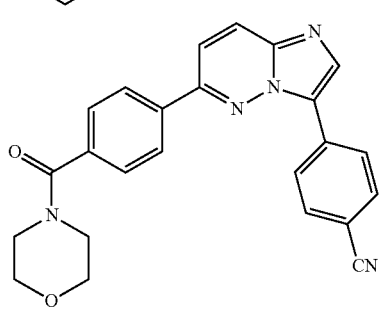
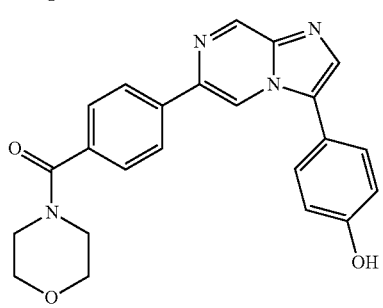
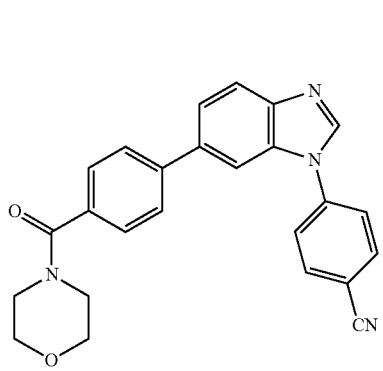
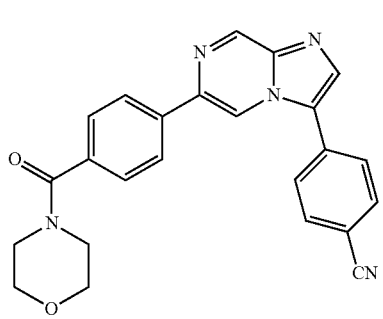
-continued
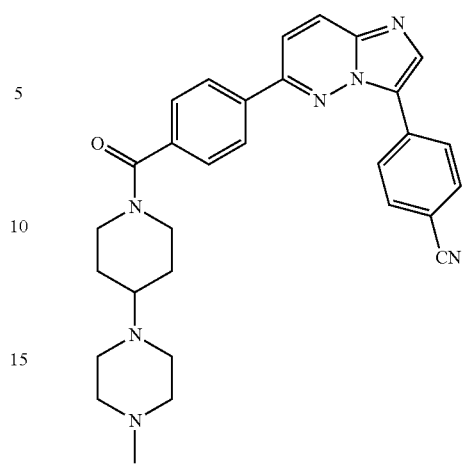
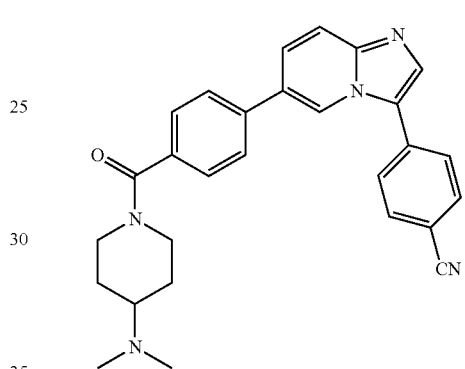
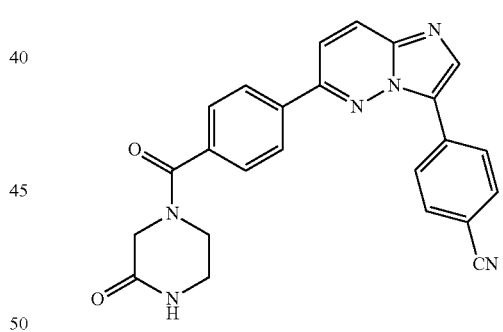
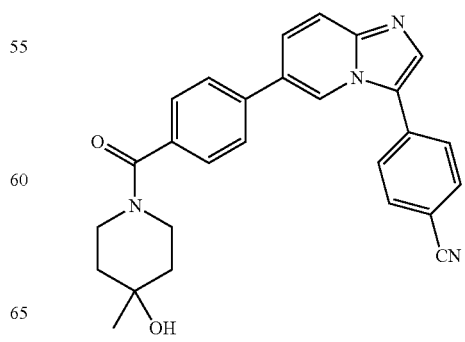

291
-continued
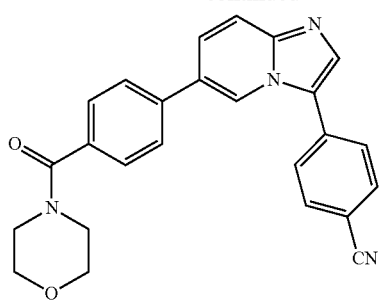
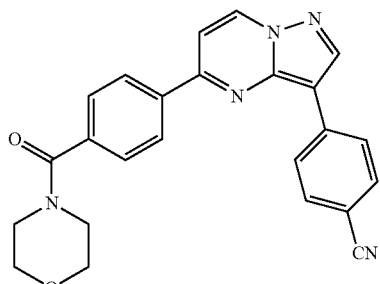
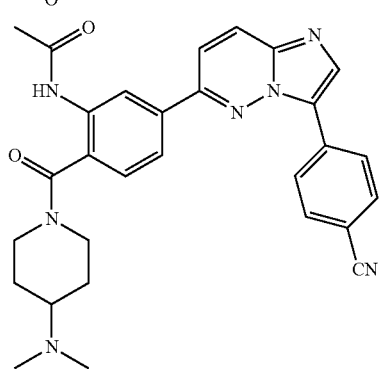
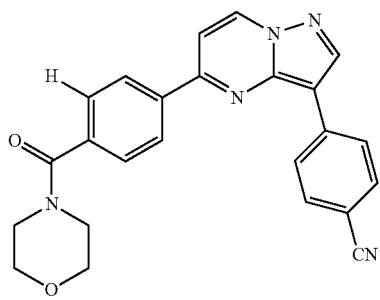 [SMILES: N#Cc1ccc(-c2cnn3ccc(-c4ccc(C(=O)N5CCOCC5)c(O)c4)nc23)cc1]
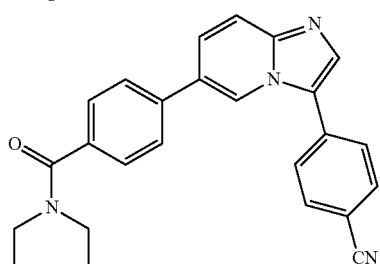
292
-continued
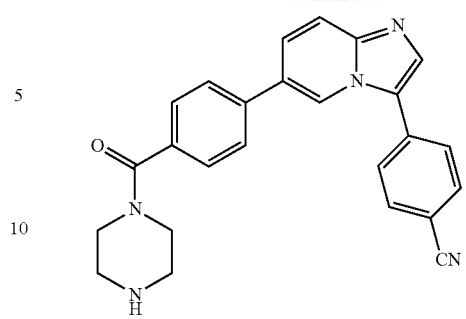
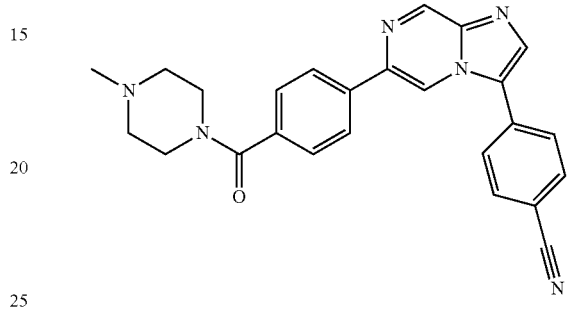
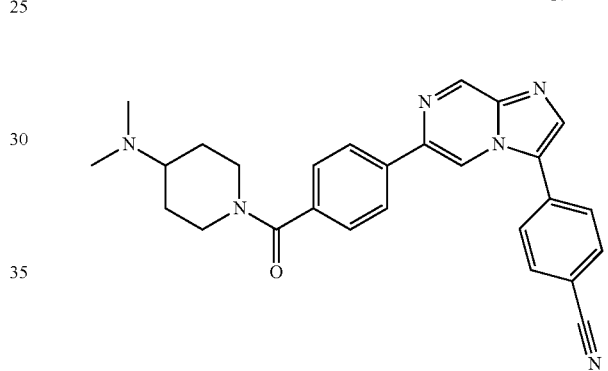
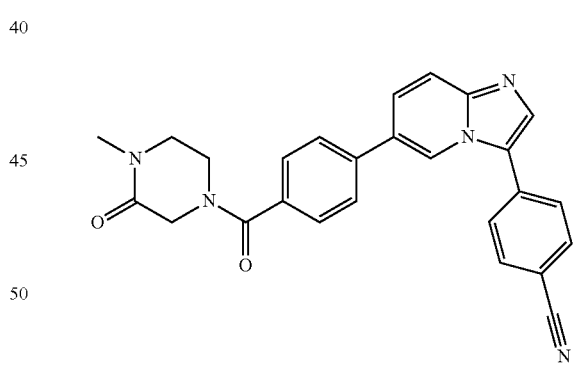
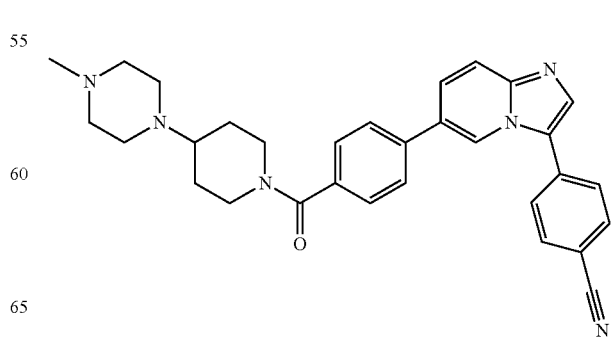

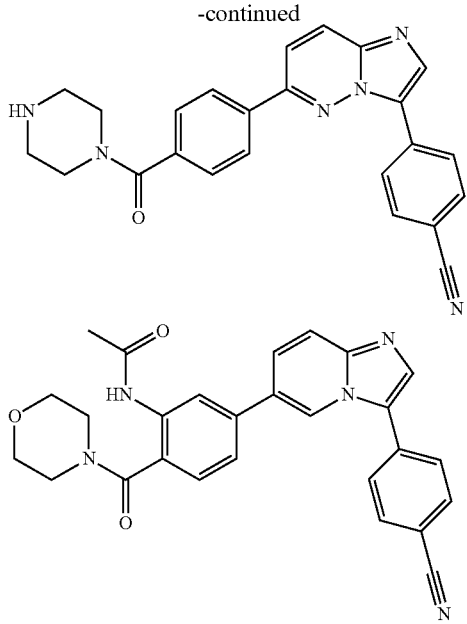

and pharmaceutically acceptable forms thereof.

12. A composition comprising a compound of claim 1, or a pharmaceutically acceptable form thereof, and a pharmaceutically acceptable excipient.

13. The composition of claim 12, wherein the composition comprises a kinase inhibitor selected from a PI3K inhibitor and an mTOR inhibitor.

14. A method of inhibiting MNK1 and/or MNK2 in a cell comprising administering to a cell a compound of claim 1, or a pharmaceutically acceptable form thereof.

15. A method of treating leukemia comprising administering to a subject in need of treatment a compound of claim 1.

16. The method of claim 15, wherein the compound is administered in combination with a kinase inhibitor selected from a PI3K inhibitor and an mTOR inhibitor.

17. The method of claim 15, wherein the compound is administered at a dosage level sufficient to deliver from about 0.001 mg/kg to about 100 mg/kg to a subject in need thereof.

18. A method of treating leukemia comprising administering to a subject in need of treatment a composition of claim 12.

* * * * *